United States Patent
Altman et al.

(10) Patent No.: US 12,320,060 B2
(45) Date of Patent: Jun. 3, 2025

(54) SILK COATED FABRICS AND PRODUCTS AND METHODS OF PREPARING THE SAME

(71) Applicant: EVOLVED BY NATURE, INC., Needham, MA (US)

(72) Inventors: Gregory H. Altman, Providence, RI (US); Enrico Mortarino, Hickory, NC (US); Sara Ann Johnson, Cambridge, MA (US); Maria L. Ufret, Grafton, MA (US); Markrete Krikorian, Arlington, MA (US); Rebecca L Lacouture, Needham, MA (US)

(73) Assignee: EVOLVED BY NATURE, INC., Needham, MA (US)

( * ) Notice: Subject to any disclaimer, the term of this patent is extended or adjusted under 35 U.S.C. 154(b) by 0 days.

(21) Appl. No.: 18/753,686

(22) Filed: Jun. 25, 2024

(65) Prior Publication Data

US 2025/0101676 A1    Mar. 27, 2025

Related U.S. Application Data

(63) Continuation of application No. 17/732,107, filed on Apr. 28, 2022, now Pat. No. 12,129,596, which is a (Continued)

(51) Int. Cl.
*C09D 189/00* (2006.01)
*D06M 15/15* (2006.01)
(Continued)

(52) U.S. Cl.
CPC ........... *D06M 15/15* (2013.01); *C09D 189/00* (2013.01); *D06M 15/643* (2013.01); *D06P 5/08* (2013.01);
(Continued)

(58) Field of Classification Search
CPC ............... D06M 15/15; D06M 15/643; D06M 2101/12; D06M 2101/32; D06M 2101/34;
(Continued)

(56) References Cited

U.S. PATENT DOCUMENTS

| 3,424,164 A | 1/1969 | Bloch et al. |
| 4,233,211 A | 11/1980 | Ohtomo et al. |

(Continued)

FOREIGN PATENT DOCUMENTS

| AU | 2015358537 A1 | 7/2017 |
| BR | 112017011641 A2 | 3/2018 |

(Continued)

OTHER PUBLICATIONS

US 8,979,992 B2, 03/2015, Sugahara et al. (withdrawn)
(Continued)

*Primary Examiner* — Eisa B Elhilo
(74) *Attorney, Agent, or Firm* — Morgan, Lewis & Bockius LLP

(57) ABSTRACT

Silk coated and/or infused performance materials, apparel, and methods of preparing the same are disclosed herein. In some embodiments, silk performance apparel includes textiles, fabrics, consumer products, and other materials that are coated with aqueous solutions of pure silk fibroin-based protein fragments having low, medium, and/or high molecular weight in various ratios.

15 Claims, 248 Drawing Sheets

Related U.S. Application Data continuation of application No. 16/651,611, filed as application No. PCT/US2018/053163 on Sep. 27, 2018, now Pat. No. 11,390,988.

(60) Provisional application No. 62/564,228, filed on Sep. 27, 2017, provisional application No. 62/564,233, filed on Sep. 27, 2017, provisional application No. 62/564,239, filed on Sep. 27, 2017, provisional application No. 62/597,898, filed on Dec. 12, 2017.

(51) Int. Cl.
  *D06M 15/643* (2006.01)
  *D06P 5/08* (2006.01)
  *D06M 101/12* (2006.01)
  *D06M 101/32* (2006.01)
  *D06M 101/34* (2006.01)

(52) U.S. Cl.
  CPC .... *D06M 2101/12* (2013.01); *D06M 2101/32* (2013.01); *D06M 2101/34* (2013.01); *D06M 2200/12* (2013.01); *D06M 2200/35* (2013.01); *D06M 2200/45* (2013.01); *D06M 2200/50* (2013.01)

(58) Field of Classification Search
  CPC ......... D06M 2200/12; D06M 2200/35; D06M 2200/45; D06M 2200/50; C09D 189/00; D06P 5/08
  USPC .......................................................... 8/495
  See application file for complete search history.

(56) References Cited

U.S. PATENT DOCUMENTS

| | | |
|---|---|---|
| 4,521,458 A | 6/1985 | Nelson |
| 5,089,395 A | 2/1992 | Snyder et al. |
| 5,142,292 A | 8/1992 | Chang |
| 5,143,724 A | 9/1992 | Leshchiner et al. |
| 5,246,698 A | 9/1993 | Eshchiner et al. |
| 5,399,351 A | 3/1995 | Leshchiner et al. |
| 5,432,910 A | 7/1995 | Barker |
| 5,527,530 A | 6/1996 | Simmons et al. |
| 5,820,928 A | 10/1998 | Groshens |
| 5,902,932 A | 5/1999 | Bills et al. |
| 5,968,762 A | 10/1999 | Jadamec et al. |
| 5,984,974 A | 11/1999 | Shibata et al. |
| 6,034,220 A | 3/2000 | Stedronsky |
| 6,110,590 A | 8/2000 | Zarkoob et al. |
| 6,217,890 B1 | 4/2001 | Paul et al. |
| 6,228,132 B1 | 5/2001 | Prince et al. |
| 6,303,136 B1 | 10/2001 | Li et al. |
| 6,303,150 B1 | 10/2001 | Perrier et al. |
| 6,482,420 B2 | 11/2002 | Ozeki et al. |
| 6,491,931 B1 | 12/2002 | Collin |
| 6,497,893 B1 | 12/2002 | Everhart et al. |
| 6,565,863 B1 | 5/2003 | Guillou et al. |
| 6,607,714 B1 | 8/2003 | Dupuis et al. |
| 6,607,734 B1 | 8/2003 | Afriat |
| 6,627,422 B1 | 9/2003 | Li et al. |
| 6,733,859 B2 | 5/2004 | Yoneda et al. |
| 6,815,427 B2 | 11/2004 | Tsubouchi et al. |
| 6,858,168 B1 | 2/2005 | Vollrath et al. |
| 6,902,932 B2 | 6/2005 | Altman et al. |
| 6,997,960 B1 | 2/2006 | Sano et al. |
| 7,014,807 B2 | 3/2006 | O'Brien |
| 7,057,023 B2 | 6/2006 | Islam et al. |
| 7,060,260 B2 | 6/2006 | Fahnestock et al. |
| 7,115,388 B2 | 10/2006 | Tsubouchi |
| 7,335,739 B2 | 2/2008 | Mello et al. |
| 7,632,873 B2 | 12/2009 | Mougin |
| 7,635,755 B2 | 12/2009 | Kaplan et al. |
| 7,662,409 B2 | 2/2010 | Masters |
| 7,674,882 B2 | 3/2010 | Kaplan et al. |
| 7,682,539 B1 | 3/2010 | Phillips et al. |
| 7,727,542 B2 | 6/2010 | DiBenedetto et al. |
| 7,785,617 B2 | 8/2010 | Shakesheff et al. |
| 7,868,146 B2 | 1/2011 | Scheibel et al. |
| 7,901,668 B2 | 3/2011 | Tsubouchi et al. |
| 7,922,929 B2 | 4/2011 | Li et al. |
| 8,071,722 B2 | 12/2011 | Kaplan et al. |
| 8,153,591 B2 | 4/2012 | Masters et al. |
| 8,187,616 B2 | 5/2012 | Wang et al. |
| 8,192,760 B2 | 6/2012 | Hossainy et al. |
| 8,288,347 B2 | 10/2012 | Collette et al. |
| 8,348,974 B2 | 1/2013 | Asakura |
| 8,354,501 B2 | 1/2013 | Kaplan et al. |
| 8,357,795 B2 | 1/2013 | Lebreton |
| 8,372,436 B2 | 2/2013 | Scheibel et al. |
| 8,420,077 B2 | 4/2013 | Altman et al. |
| 8,450,475 B2 | 5/2013 | Lebreton |
| 8,465,772 B2 | 6/2013 | Hossainy et al. |
| 8,465,773 B2 | 6/2013 | Hossainy et al. |
| 8,501,172 B2 | 8/2013 | Kaplan et al. |
| 8,551,538 B2 | 10/2013 | Qian |
| 8,614,293 B2 | 12/2013 | Kaplan et al. |
| 8,623,398 B2 | 1/2014 | Altman et al. |
| 8,628,791 B2 | 1/2014 | Altman et al. |
| 8,633,027 B2 | 1/2014 | Altman et al. |
| 8,642,734 B2 | 2/2014 | Johansson et al. |
| 8,674,077 B2 | 3/2014 | Sutherland et al. |
| 8,685,426 B2 | 4/2014 | Altman et al. |
| 8,697,056 B2 | 4/2014 | Van Epps et al. |
| 8,715,740 B2 | 5/2014 | Wang et al. |
| 8,721,991 B2 | 5/2014 | Scheibel et al. |
| 8,728,498 B2 | 5/2014 | Zhang et al. |
| 8,741,281 B2 | 6/2014 | Van Epps et al. |
| 8,742,069 B2 | 6/2014 | Kaplan et al. |
| 8,822,676 B2 | 9/2014 | Lebreton |
| 8,828,436 B2 | 9/2014 | Hossainy et al. |
| 8,871,267 B2 | 10/2014 | Masters |
| 8,894,992 B2 | 11/2014 | Van Epps et al. |
| 8,900,571 B2 | 12/2014 | Van Epps et al. |
| 8,926,963 B2 | 1/2015 | Van Epps et al. |
| 9,051,453 B2 | 6/2015 | Sugahara et al. |
| 9,074,302 B2 | 7/2015 | Lo et al. |
| 9,084,840 B2 | 7/2015 | Kaplan et al. |
| 9,089,518 B2 | 7/2015 | Lebreton |
| 9,089,519 B2 | 7/2015 | Lebreton |
| 9,089,594 B2 | 7/2015 | Dyer et al. |
| 9,090,703 B2 | 7/2015 | Kobayashi et al. |
| 9,187,538 B2 | 11/2015 | Altman et al. |
| 9,217,017 B2 | 12/2015 | Leimer et al. |
| 10,287,728 B2 | 5/2019 | Allman et al. |
| 10,301,768 B2 | 6/2019 | Altman et al. |
| 11,453,975 B2 | 9/2022 | Altman et al. |
| 11,512,425 B2 | 11/2022 | Altman et al. |
| 11,649,585 B2 | 5/2023 | Altman et al. |
| 2001/0002417 A1 | 5/2001 | Akkara et al. |
| 2001/0051815 A1 | 12/2001 | Esplin |
| 2001/0053931 A1 | 12/2001 | Hess et al. |
| 2002/0077629 A1 | 6/2002 | Hoffman et al. |
| 2002/0082220 A1 | 6/2002 | Hoffman et al. |
| 2002/0111591 A1 | 8/2002 | McKinnon et al. |
| 2002/0114919 A1 | 8/2002 | Yoneda et al. |
| 2003/0099630 A1 | 5/2003 | DiBenedetto et al. |
| 2003/0139752 A1 | 7/2003 | Pasricha et al. |
| 2003/0206897 A1 | 11/2003 | O'Prey et al. |
| 2003/0208209 A1 | 11/2003 | Gambale et al. |
| 2003/0220646 A1 | 11/2003 | Thelen et al. |
| 2003/0229361 A1 | 12/2003 | Jackson |
| 2003/0236555 A1 | 12/2003 | Thornes |
| 2004/0005363 A1 | 1/2004 | Tsukada et al. |
| 2004/0063616 A1 | 4/2004 | Patt |
| 2004/0073176 A1 | 4/2004 | Utterberg |
| 2004/0127907 A1 | 7/2004 | Dakin et al. |
| 2004/0170590 A1 | 9/2004 | Fahnestock |
| 2004/0191199 A1 | 9/2004 | Mougin |
| 2004/0199241 A1 | 10/2004 | Gravell |
| 2004/0219630 A1 | 11/2004 | Tsubouchi et al. |
| 2004/0224406 A1 | 11/2004 | Altman et al. |
| 2004/0234609 A1 | 11/2004 | Collier et al. |
| 2004/0265260 A1 | 12/2004 | Tsubouchi et al. |

(56) References Cited

U.S. PATENT DOCUMENTS

| | | |
|---|---|---|
| 2004/0267317 A1 | 12/2004 | Higgins et al. |
| 2005/0004670 A1 | 1/2005 | Gebhardt et al. |
| 2005/0021148 A1 | 1/2005 | Gibbs et al. |
| 2005/0049598 A1 | 3/2005 | West, Jr. et al. |
| 2005/0090827 A1 | 4/2005 | Gedebou |
| 2005/0107882 A1 | 5/2005 | Stone et al. |
| 2005/0130301 A1 | 6/2005 | McKay et al. |
| 2005/0147690 A1 | 7/2005 | Masters et al. |
| 2005/0149118 A1 | 7/2005 | Koyfman et al. |
| 2005/0171804 A1 | 8/2005 | Michalow |
| 2005/0177237 A1 | 8/2005 | Shappley et al. |
| 2005/0251153 A1 | 11/2005 | Sakamoto et al. |
| 2005/0251209 A1 | 11/2005 | Saadat et al. |
| 2005/0261642 A1 | 11/2005 | Weston |
| 2006/0004364 A1 | 1/2006 | Green et al. |
| 2006/0178743 A1 | 8/2006 | Carter |
| 2006/0195106 A1 | 8/2006 | Jones et al. |
| 2006/0229676 A1 | 10/2006 | Doll et al. |
| 2006/0229623 A1 | 10/2006 | Bonutti et al. |
| 2006/0241776 A1 | 10/2006 | Brown et al. |
| 2006/0241781 A1 | 10/2006 | Brown et al. |
| 2008/0188152 A1 | 8/2008 | Tsai et al. |
| 2008/0188416 A1 | 8/2008 | Bernstein |
| 2009/0162439 A1 | 6/2009 | Gobin |
| 2009/0188152 A1 | 7/2009 | Davin |
| 2009/0209456 A1 | 8/2009 | Sweis |
| 2009/0234026 A1 | 9/2009 | Kaplan et al. |
| 2010/0112058 A1 | 5/2010 | Lim et al. |
| 2010/0172853 A1 | 7/2010 | Pavel et al. |
| 2011/0008406 A1 | 1/2011 | Altman et al. |
| 2011/0008436 A1 | 1/2011 | Altman et al. |
| 2011/0014287 A1 | 1/2011 | Altman et al. |
| 2011/0020409 A1 | 1/2011 | Altman et al. |
| 2011/0076384 A1 | 3/2011 | Cannizzaro et al. |
| 2011/0105402 A1 | 5/2011 | Kim et al. |
| 2011/0111031 A1 | 5/2011 | Jiang et al. |
| 2011/0136669 A1 | 6/2011 | Liebmann et al. |
| 2011/0189292 A1 | 8/2011 | Lebreton et al. |
| 2011/0223153 A1 | 9/2011 | Lu et al. |
| 2011/0240054 A1 | 10/2011 | Pratt et al. |
| 2012/0040907 A1 | 2/2012 | DiBenedetto et al. |
| 2012/0070427 A1 | 3/2012 | Kaplan et al. |
| 2012/0076771 A1 | 3/2012 | Vepari et al. |
| 2012/0123519 A1 | 5/2012 | Lovett et al. |
| 2012/0171770 A1 | 7/2012 | Numata et al. |
| 2012/0172317 A1 | 7/2012 | Altman et al. |
| 2012/0187591 A1 | 7/2012 | Wang et al. |
| 2012/0244143 A1 | 9/2012 | Lo et al. |
| 2012/0252294 A1 | 10/2012 | Leimer et al. |
| 2012/0265297 A1 | 10/2012 | Altman et al. |
| 2013/0045278 A1 | 2/2013 | Dian |
| 2013/0109762 A1 | 5/2013 | Lammel et al. |
| 2013/0165004 A1 | 6/2013 | Kaplan et al. |
| 2013/0240251 A1 | 9/2013 | Kaplan et al. |
| 2013/0243893 A1 | 9/2013 | Omenetto et al. |
| 2013/0287742 A1 | 10/2013 | Kaplan et al. |
| 2013/0287835 A1 | 10/2013 | Kaplan et al. |
| 2014/0058086 A1 | 2/2014 | Sekiyama et al. |
| 2014/0105995 A1 | 4/2014 | Kaplan et al. |
| 2014/0134240 A1 | 5/2014 | Kaplan et al. |
| 2014/0194025 A1 | 7/2014 | Klimov et al. |
| 2014/0206839 A1 | 7/2014 | Tman et al. |
| 2014/0222152 A1 | 8/2014 | Kaplan et al. |
| 2014/0264985 A1 | 9/2014 | Sutti et al. |
| 2014/0287043 A1 | 9/2014 | Kaplan et al. |
| 2014/0308362 A1 | 10/2014 | Bellas et al. |
| 2014/0315828 A1 | 10/2014 | Pavlovic et al. |
| 2014/0378661 A1 | 12/2014 | Lo et al. |
| 2015/0038043 A1 | 2/2015 | Kaplan et al. |
| 2015/0038456 A1 | 2/2015 | Gousse et al. |
| 2015/0045764 A1 | 2/2015 | Kaplan et al. |
| 2015/0047532 A1 | 2/2015 | Lewis et al. |
| 2015/0056256 A1 | 2/2015 | Essaidi |
| 2015/0056261 A1 | 2/2015 | Serban |
| 2015/0056293 A1 | 2/2015 | Wang et al. |
| 2015/0056294 A1 | 2/2015 | Kaplan et al. |
| 2015/0065686 A1 | 3/2015 | Stylios |
| 2015/0079012 A1 | 3/2015 | Bellas et al. |
| 2015/0093340 A1 | 4/2015 | Altman et al. |
| 2015/0094269 A1 | 4/2015 | Altman et al. |
| 2015/0164117 A1 | 6/2015 | Kaplan et al. |
| 2015/0165092 A1 | 6/2015 | Kaplan et al. |
| 2015/0183841 A1 | 7/2015 | Lo et al. |
| 2015/0202304 A1 | 7/2015 | Kaplan et al. |
| 2015/0238817 A1 | 8/2015 | Kaplan et al. |
| 2015/0273021 A1 | 10/2015 | Kaplan et al. |
| 2015/0284565 A1 | 10/2015 | Scheibel et al. |
| 2015/0307728 A1 | 10/2015 | Omenetto et al. |
| 2016/0022559 A1 | 1/2016 | Altman et al. |
| 2016/0022560 A1 | 1/2016 | Altman et al. |
| 2016/0022561 A1 | 1/2016 | Altman et al. |
| 2016/0022562 A1 | 1/2016 | Altman et al. |
| 2016/0022563 A1 | 1/2016 | Altman et al. |
| 2016/0046679 A1 | 2/2016 | Kluge et al. |
| 2016/0058685 A1 | 3/2016 | Dyer |
| 2016/0193130 A1 | 7/2016 | Altman et al. |
| 2016/0222579 A1 | 8/2016 | Altman et al. |
| 2016/0235889 A1 | 8/2016 | Pallotta et al. |
| 2016/0237128 A1 | 8/2016 | Omenetto et al. |
| 2016/0250831 A1* | 9/2016 | Gladish .................. D06M 15/15 428/137 |
| 2016/0256604 A1 | 9/2016 | Hanna et al. |
| 2016/0263046 A1 | 9/2016 | Kaplan et al. |
| 2016/0263228 A1 | 9/2016 | Kluge et al. |
| 2017/0156358 A1 | 6/2017 | Omenetto |
| 2017/0202995 A1 | 7/2017 | Gerhard |
| 2019/0003113 A1 | 1/2019 | Altman |
| 2020/0256009 A1 | 8/2020 | Allman et al. |

FOREIGN PATENT DOCUMENTS

| | | |
|---|---|---|
| CA | 2969563 A1 | 6/2016 |
| CL | 2017001404 A1 | 2/2018 |
| CN | 1575188 A | 2/2002 |
| CN | 1518612 A | 8/2004 |
| CN | 1589764 A | 3/2005 |
| CN | 1732022 A | 2/2006 |
| CN | 1277584 C | 10/2006 |
| CN | 1920162 A | 2/2007 |
| CN | 102327644 A | 1/2012 |
| CN | 102605619 A | 7/2012 |
| CN | 102605619 B | 7/2012 |
| CN | 102965934 A | 3/2013 |
| CN | 103041440 A | 4/2013 |
| CN | 107405277 A | 11/2017 |
| CO | 2017006672 A2 | 1/2018 |
| EA | 201791221 A1 | 12/2017 |
| EP | 1118705 A2 | 7/2001 |
| EP | 1446169 | 5/2003 |
| EP | 1915436 | 2/2004 |
| EP | 2099509 | 6/2008 |
| EP | 2211876 | 12/2008 |
| EP | 2349366 | 4/2010 |
| EP | 2421549 | 10/2010 |
| EP | 2421550 | 10/2010 |
| EP | 2421551 | 10/2010 |
| EP | 3052203 | 8/2016 |
| EP | 3226835 A1 | 10/2017 |
| JP | 04100975 | 4/1992 |
| JP | H04100795 A | 4/1992 |
| JP | H04100975 A | 4/1992 |
| JP | H05-005275 A | 1/1993 |
| JP | H07300772 A | 11/1995 |
| JP | H08-27186 | 1/1996 |
| JP | H0816309 B2 | 2/1996 |
| JP | 091888972 | 7/1997 |
| JP | H09188972 A | 7/1997 |
| JP | H10-212456 A | 8/1998 |
| JP | H10212456 | 8/1998 |
| JP | 2000143472 A | 5/2000 |
| JP | 2000-328455 A | 11/2000 |
| JP | 2001-262470 A | 9/2001 |
| JP | 2002080498 A | 3/2002 |
| JP | 2002-302874 A | 10/2002 |

(56) References Cited

FOREIGN PATENT DOCUMENTS

| | | | |
|---|---|---|---|
| JP | 2002-363861 | A | 12/2002 |
| JP | 2003-171874 | A | 6/2003 |
| JP | 2003-171876 | A | 6/2003 |
| JP | 2003171875 | A | 6/2003 |
| JP | 2005510268 | A | 4/2005 |
| JP | 2009-074201 | A | 4/2009 |
| JP | 2010513266 | A | 4/2010 |
| JP | 2011-153389 | A | 8/2011 |
| JP | 2014518557 | A | 7/2014 |
| JP | 2016531943 | | 10/2016 |
| JP | 2018500470 | A | 1/2018 |
| KR | 20170099920 | | 9/2017 |
| PE | 20171791 | | 12/2017 |
| SG | 11201704494S | A | 6/2017 |
| WO | 199933899 | A1 | 7/1999 |
| WO | 2003/035124 | A2 | 5/2003 |
| WO | 03035124 | A2 | 5/2003 |
| WO | 2004/060424 | A2 | 7/2004 |
| WO | 2004/073644 | A2 | 9/2004 |
| WO | 2006/008163 | A2 | 1/2006 |
| WO | 2006033473 | A1 | 3/2006 |
| WO | 2007016524 | A2 | 2/2007 |
| WO | 2007/038837 | A1 | 4/2007 |
| WO | 2008069919 | A2 | 6/2008 |
| WO | 2008/083098 | A1 | 7/2008 |
| WO | 2008/083908 | A1 | 7/2008 |
| WO | 2008150861 | A1 | 12/2008 |
| WO | 2009031620 | A1 | 3/2009 |
| WO | 2010036992 | A2 | 4/2010 |
| WO | 2010123945 | A9 | 10/2010 |
| WO | 2010123946 | A2 | 10/2010 |
| WO | 2010123947 | A2 | 10/2010 |
| WO | 2011008842 | | 1/2011 |
| WO | 2011038401 | | 3/2011 |
| WO | 2011/069643 | A2 | 6/2011 |
| WO | 2011063990 | A2 | 6/2011 |
| WO | 2011160098 | A2 | 12/2011 |
| WO | 2012145739 | A2 | 10/2012 |
| WO | 2014037453 | | 3/2013 |
| WO | 2013070907 | A1 | 5/2013 |
| WO | 2013150258 | | 10/2013 |
| WO | 2014011644 | A1 | 1/2014 |
| WO | 2014012099 | A1 | 1/2014 |
| WO | 2014145002 | A2 | 9/2014 |
| WO | 2014183053 | | 11/2014 |
| WO | 2015023788 | | 2/2015 |
| WO | 2015048805 | | 4/2015 |
| WO | 2015061079 | A1 | 4/2015 |
| WO | 2015070108 | | 5/2015 |
| WO | 2015095407 | | 6/2015 |
| WO | 2015110656 | A1 | 7/2015 |
| WO | 2015190292 | A1 | 12/2015 |
| WO | 2016090055 | A1 | 6/2016 |
| WO | 2016110873 | A1 | 7/2016 |
| WO | 2017/011679 | A1 | 1/2017 |
| WO | 20170011679 | A1 | 1/2017 |

OTHER PUBLICATIONS

Second Office Action issued in corresponding Chinese Application No. 201880076685.4, dated Oct. 13, 2023, 15 pages.
European Search Report issued in corresponding European Application No. 18861347.5, dated Jun. 4, 2021, 10 pages.
Third Party Submission issued in corresponding Application No. EP 18861347.5, dated Dec. 14, 2021, 12 pages.
First Office Action issued in corresponding Chinese Patent Application No. 201880076685.4, dated Feb. 15, 2023, 37 pages.
Third-Party Submission under 37 CFR 1.290 filed Feb. 5, 2021 in U.S. Appl. No. 16/651,611.
Behera et al., "Size recipes for low-humidity weaving of cotton yarn", In J Fibre Textile Res 19:67-70, 1994.
Mizutani et al., "A New Apparatus for the Study of Fabric Drape", Textile Res J 75(1):81-87, 2005.
Yamada Hiromi et al., "Preparation of undegraded native molecular fibroin solution from silkworm cocoons", Materials Science and Engineering C, 2001, pp. 41-46.
Eurasia Patent Application No. 21791221/28 Official Action, dated May 29, 2018, 4 pages.
European Patent Application No. 15864424.5, Extended European Search Report dated Aug. 23, 2018, 30 pages.
Arai et al.; "Biodegradation of Bombyx mori Silk Fibroin Fibers and Films"; Journal of Applied Polymer Science, vol. 91, 2383-2390 (2004).
Chilean Patent Application No. 1404-2017 Office Action dated Nov. 5, 2018.
English translation of Chilean Patent Application No. 1404-2017 Office Action dated Nov. 5, 2018.
European Patent Application No. 16825194.0 Search Report and Written Opinion dated Dec. 10, 2018.
Eurasian Patent Application No. 201791221 Office Actions dated Dec. 12, 2018.
English translation of Eurasian Patent Application No. 201791221 Office Action dated Dec. 12, 2018.
Eurasian Patent Application No. 201890289 Office Action daled Dec. 21, 2018.
English translation of Eurasian Patent Application No. 201890289 Office Action dated Dec. 21, 2018.
Columbian Patent Application No. NC2017/0006672 Office Action dated Nov. 5, 2018.
English translation of Columbian Patent Application No. NC2017/0006672 Office Action dated Nov. 5, 2018.
Singapore Patent Application No. 11201800272U Search Report and Written Opinion dated Apr. 2, 2019.
Nakazawa et al.; "Development of Amall-Diameter Vascular Grafts Based on Silk Fibroin Fibers from Bombys mori for Vascular Regeneration"; Journal of Biomaterials Science 22 (2011) 195-206.
Hardy et al.; "Polymeric materials based on silk proteins"; Polymer 49 (2008) 4309-4327.
Hoffman et al.; "Silk fibroin as an organic polymer for controlled drug delivery"; Journal of Controlled Release 111 (2006) 219-227.
Sielc, "Separation of Potassium, Reverse Elution Order in Separation of Alkali Cation" (2012).
Singapore Patent Application No. 11201704494S Search Report and Written Opinion dated Apr. 23, 2018.
European Patent Application No. 15864424.5 Supplemental Search Report dated Aug. 23, 2018.
Cetinkaya et al.; "Silk Fiber Mechanics from Multiscale Force Distribution Analysis", Biophysical Journal, vol. 100, Mar. 2011, 1298-1305.
Cho et al.; "Molecular weight distribution and solution properties of silk fibroins with different dissolution conditions"; International Journal of Biological Macromolecules, 51 (2012) 336-341.
Fan et al.; "Vitamin C-reinforcing silk fibroin nanofibrous matrices for skin care application"; RSC Advances, 2012, 2, 4110-4119.
Fournier; "Quantitative data on the *Bombyx mori* L. silkworm: a review", Biochimie, 1979, 61, 293-320.
Gilbert et al.; "Dispersity in Polymer Science", Pure Appl. Chem., vol. 1, No. 2, pp. 351-353, 2009.
Dyde et al.; "Molecular Weight of Silk Fibroin"; Journal of Polymer Science, vol. 58, pp. 1082-1088 (1962).
Motta et al.; "Stabilization of Bombyx mori silk fibroin/sericin films by crosslinking with PEG-DE 600 and genipin"; Journal of Bioactive and Compatible Polymers, 26(2) 130-143 (2011).
Pandit et al.; "Studies on Silk Fibroin, I. molecular Weight, Sedimentation Coefficient, Viscosity and Optical Rotation of Silk Fibroin from Carbonate-Extracted Silk Fiber"; Archives of Biochemistry and Biophysics 149, 259-268 (1972).
Paula's Choice: "Jar Packaging: A Waste of Good Antioxidants & Money"; The Cosmetics Cop; 3 pages (2012).
Preda et al.; "Bioengineered Silk Proteins to Control Cell and Tissue Functions"; Protein Nanotechnology: Protocols, Instrumentation, and Applications, Methods Molecular Biology, vol. 996, (2013) DOI 10.1007/978-1-62703-354-1_2.
Rockwood et al.; "Materials fabrication from Bombyx mori silk fibroin"; Nature Protocols, vol. 6, No. 10, 2011, pp. 1612-1631.

(56) References Cited

OTHER PUBLICATIONS

Sah et al.; "Regenerated Silk Fibroin from B. mori Silk Cocoon for Tissue Engineering Applications"; International Journal of Environmental Science and Development, vol. 1, No. 5, Dec. 2010.
Wang et al.; "Design and engineering of silk fibroin scaffolds with biometric hierarchical structures"; Chem Commun, 2013, 49, 1431.
Wang et al.; "Effect of Various Dissolution Systems on the Molecular Weight of Regenerated Silk Fibroin"; American Chemical Society, BioMacromolecules 2013, 14, 285-289.
Wray et al.; "Effect of Processing on Silk-Based Biomaterials: Reproducibility and Biocompatibility"; J. Biomed Mater Res B Appl Biomater. Oct. 2011; 99(1): 89-101.
Zhang et al.; "Stabilization of vaccines and antibiotics in silk and eliminating the cold chain"; PNAS, Jul. 24, 2012, vol. 109, No. 30, 11881-11986.
International Patent Application No. PCT/US14/58462, International Search Report, dated Mar. 2, 2015.
International Patent Application No. PCT/US2015/063545 IPRP dated 2016.
International Patent Application No. PCT/US15/63545, International Search Report, dated Jan. 28, 2016.
International Patent Application No. PCT/US2016/042316 IPRP dated Aug. 16, 2017.
International Patent Application No. PCT/US2016/042316 ISR and WO daled Dec. 15, 2016.
European Patent Application No. 15864424.5 Search opinion dated Aug. 23, 2018.
European Patent Application No. 16825194 supplemental search report and written opinion dated Dec. 10, 2018.
European Patent Application No. 16825194 supplemental search report dated Nov. 30, 2018.
European Patent Application No. 201791221 office action dated May 28, 2018.
English translation of European Patent Application No. 201791221 office action dated May 28, 2018.
Eurasian Patent Application No. 201890289 Office Action dated Sep. 6, 2019.
English translation of Eurasian Patent Application No. 201890289 Office Action dated Sep. 6, 2019.
Brazil Patent Application No. 112017011641 Office Action dated Aug. 27, 2019.
English translation of Brazil Patent Application No. 112017011641 Office Action dated Aug. 27, 2019.
Singapore Patent Application No. 11201704494S Search Report and Written Opinion dated Feb. 18, 2019.
Singapore Patent Application No. 11201704494S Search Report dated Apr. 23, 2018.
Singapore Patent Application No. 11201800272SRNT dated Apr. 2, 2019.
Written Opinion dated Dec. 20, 2019 for Singapore Patent Application No. 11201704494S.
Yasumoto Nakazawa et al. "Development of Small-Diameter Vascular Grafts Based on Silk Fibroin Fibers from Bombyx mori for Vascular Regeneration." Journal of Biomaterials Science 22 (2011) 195-206.
Office Action dated May 28, 2019 for Indonesian Patent Application No. P-00201704289.
Notice of Reasons for Rejection dated Dec. 24, 2019 for Japanese Patent Application No. 2017-529648.
Office Action dated Dec. 17, 2019 for Chinese Patent Application No. 201580075200.6.
First Office Action for Colombian Patent Application No. NC2017/0006672.
Second Office Action for Colombian Patent Application No. NC2017/0006672.
Takayuki Arai et al. "Biodegredation of Bombyx mori Silk Fibroin Fibers and Films." Journal of Applied Polymer Science, vol. 91, 2383-2390 (2004).
Office Action dated Sep. 6, 2019 for Eurasian Patent Application No. 201890289.
Office Action dated Apr. 29, 2020 for Eurasian Patent Application No. 201890289.
Office Action dated Jun. 3, 2019 for Chilean Patent Application No. 2017-001404.
CL 198200371—AKZO NV. Pub. Feb. 4, 1983 (registro 33669).
Third Party Observations filed Jun. 10, 2020 in European Patent Application No. 15864424.5.
Third Party Observations filed Jun. 10, 2020 in European Patent Application No. 16825194.0.
Notice of Reasons for Rejection dated Jul. 28, 2020 for Japanese Patent Application No. 2018-501372.
Yamada et al., "AFM observation of silk fibroin on mica substrates: morphologies refelecting the secondary structure", Thin Solid Films, 440 (2003) pp. 208-216.
Examination Report dated Aug. 10, 2020 for Australian Patent Application No. 2015358537.
Examination Report dated Aug. 21, 2020 for Indian Patent Application No. 201717022753.
Search Report daled Sep. 11, 2020 for Eurasian Patent Application No. 202090772.
Examination Report dated Sep. 17, 2020 for Saudi Arabian Patent Application No. 517381633 (with partial English summary).
Notice of Reasons for Rejection dated Oct. 20, 2020 for Japanese Patent Application No. 2017-529648 (with English translation).
Wang et al., "Nanolayer Biomaterial Coatings of Silk Fibroin for Controlled Release," J. Control Release, Aug. 28, 2007; 121 (3): 190-199.
Office Action dated Nov. 2, 2020 for Chinese Patent Application No. 201580075200.6 (English translation).
Office Action dated Nov. 9, 2020 for Brazilian Patent Application No. BR112018000699-8 (English translation).
Office Action dated Nov. 24, 2020 for Indonesian Patent Application No. P00201801017 (with partial English summary).
Office Action dated Dec. 29, 2020 for Eurasian Patent Application No. 201890289 (with English translation).
Office Action dated Nov. 18, 2020 for Costa Rican Patent Application No. 2017-0000302 (with English translation).
Office Action dated Jan. 11, 2021 for Chinese Patent Application No. 201680053476.9 (w/ translation).
Xu Yunhui et al. "Preparation and controlled release effect of soybean protein/multicarboxylic acids modified cotton fabric." Chinese Journal of Textile Research, vol. 34, No. 6, pp. 73-78, Jun. 2013 (w/ English abstract).
Wu Huiying. "Study on Modification of Silk Fibroin Solution to Cotton Fabric." Cotton Textile Technology, vol. 42, No. 3, pp. 1-4, Mar. 2014 (w/ English abstract).
Examination Report, mailed Jun. 18, 2021, for Singapore Patent Application No. 11201704494S.
Examination Report, mailed Jun. 18, 2021, for Singapore Patent Application No. 11201800272U.
Examination Report, mailed Jul. 2, 2021, for Indian Patent Application No. 201817005205.
Examination Report, mailed Jul. 16, 2021, for Peruvian Patent Application No. 000958-2017 (w/ partial translation).
Examination Report, mailed Aug. 31, 2021, for Australian Patent Application No. 2016294611.
Office Action, dated Sep. 3, 2021, for Chinese Patent Application No. 201680053476.9 (w/ translation).
Search Report for European Patent Application No. 18861347.5 dated Jun. 4, 2021.
International Search Report for PCT International Application No. PCT/2018/05163 dated Nov. 30, 2018.
Written Opinion for PCT International Application No. PCT/2018/05163 dated Nov. 30, 2018.
IPRP for PCT International Application No. PCT/2018/05163 dated Nov. 30, 2018.
Office Action issued in corresponding Chinese Application No. 201880076685.4, dated Mar. 7, 2024, 23 pages.

* cited by examiner

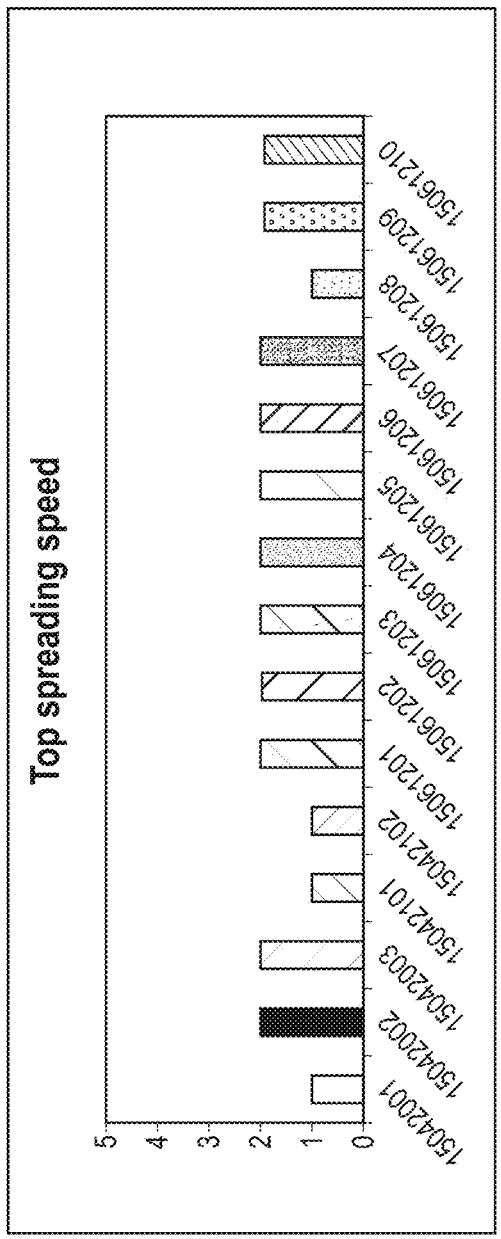
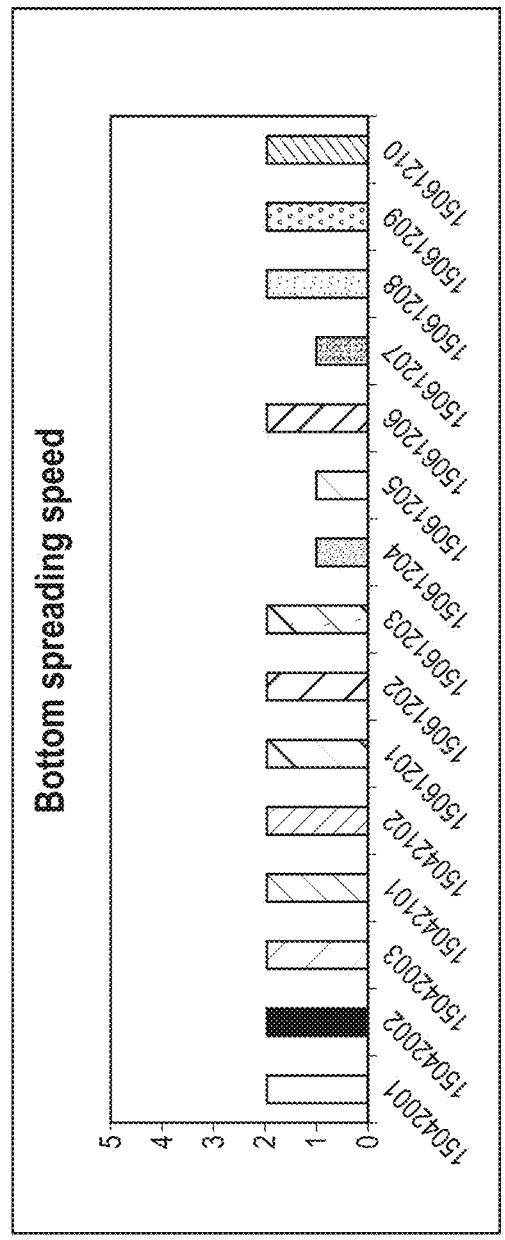

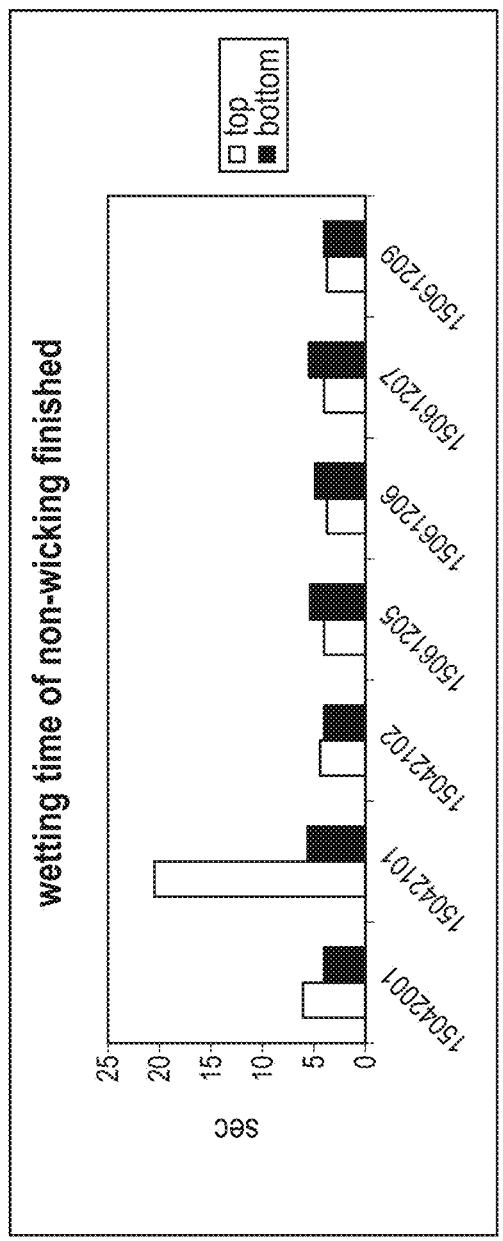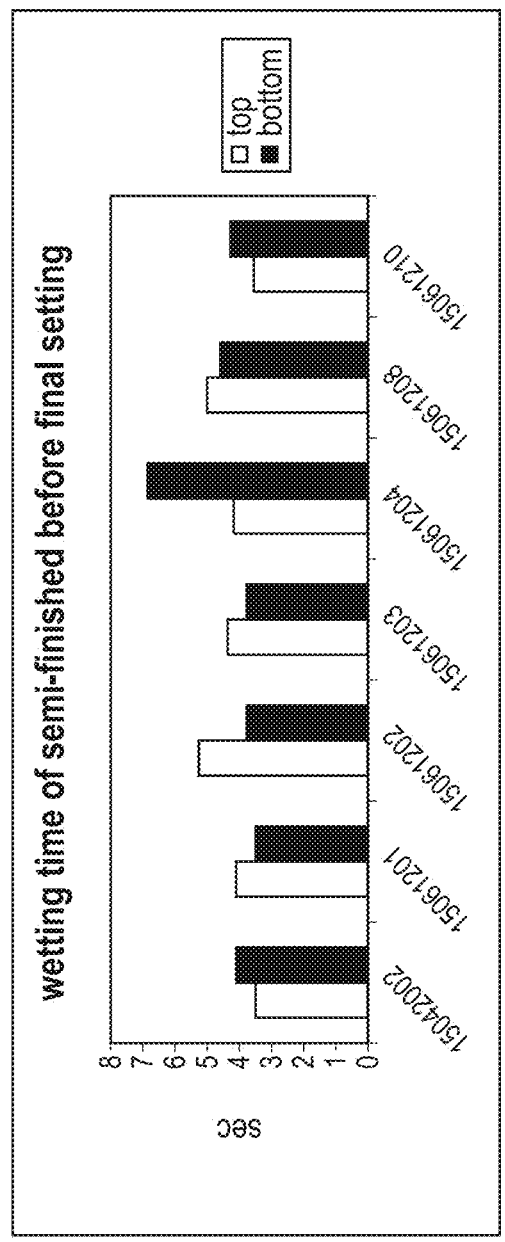

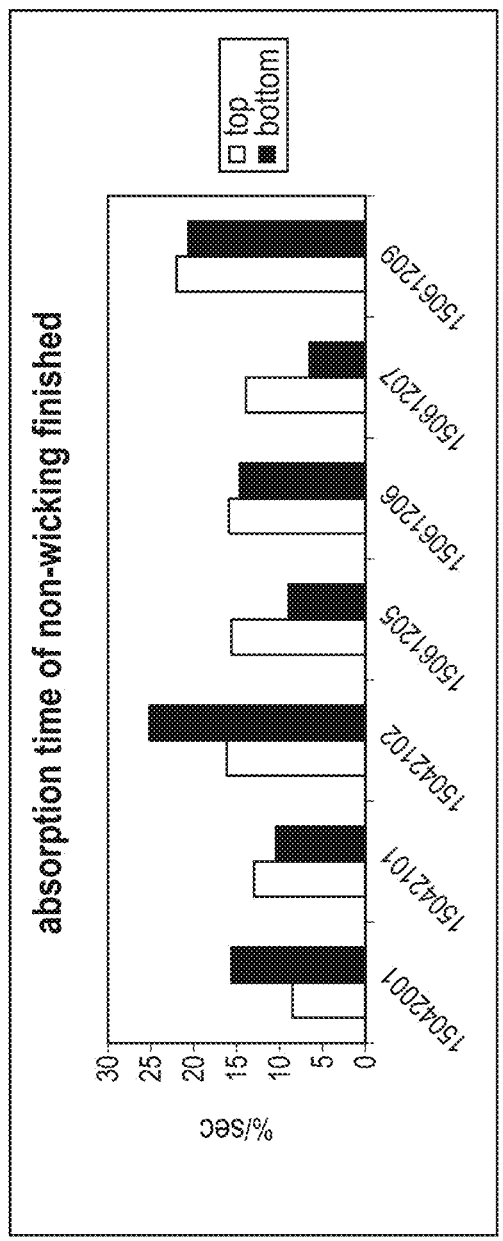
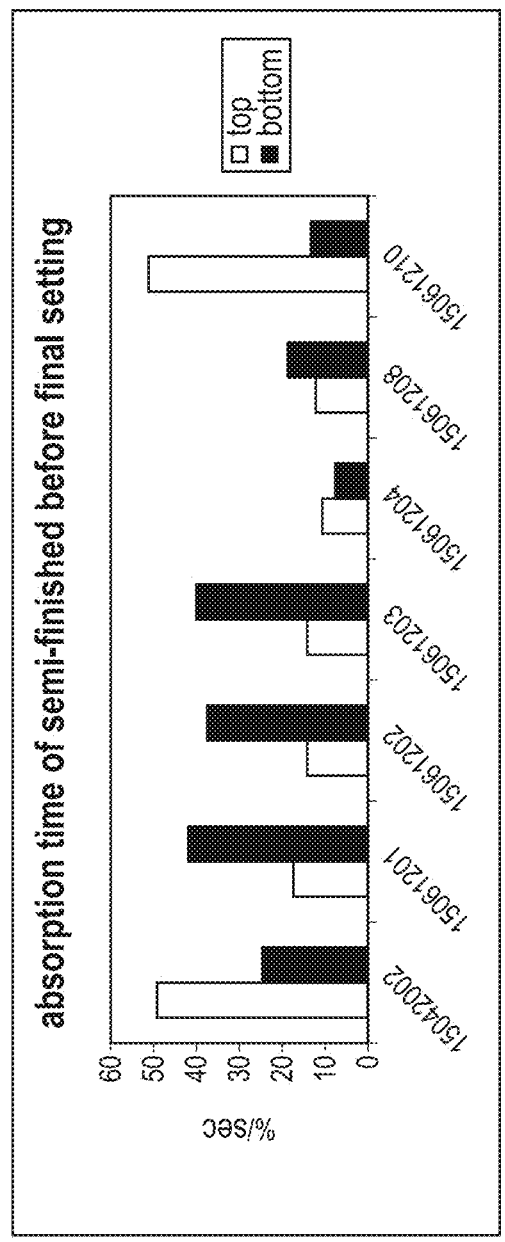
FIG. 44A
FIG. 44B

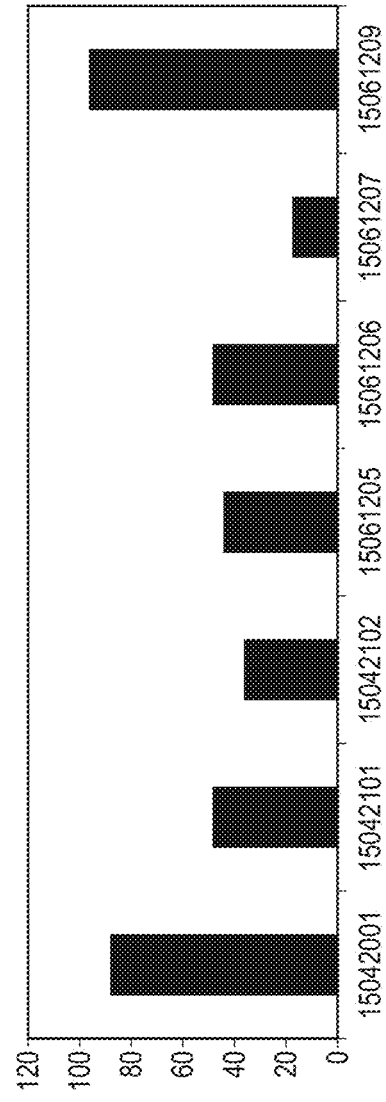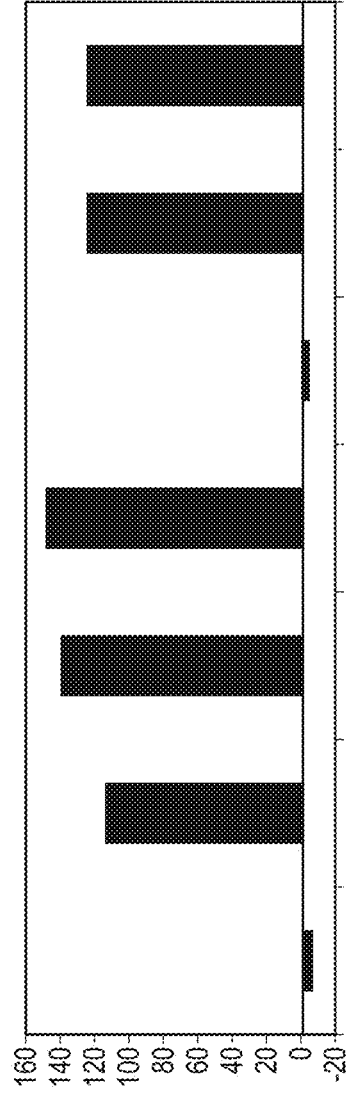
FIG. 46A
FIG. 46B

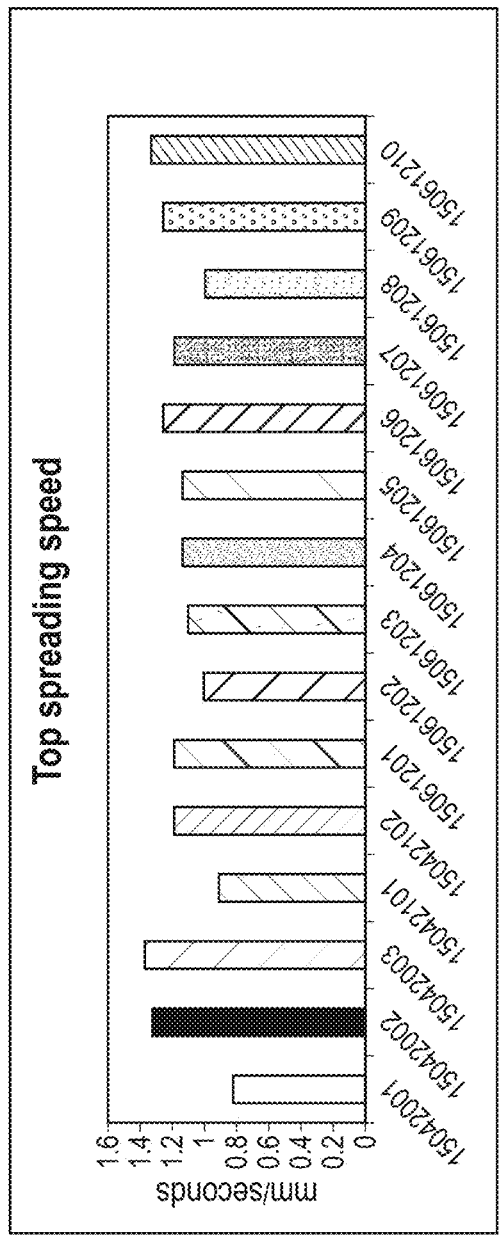
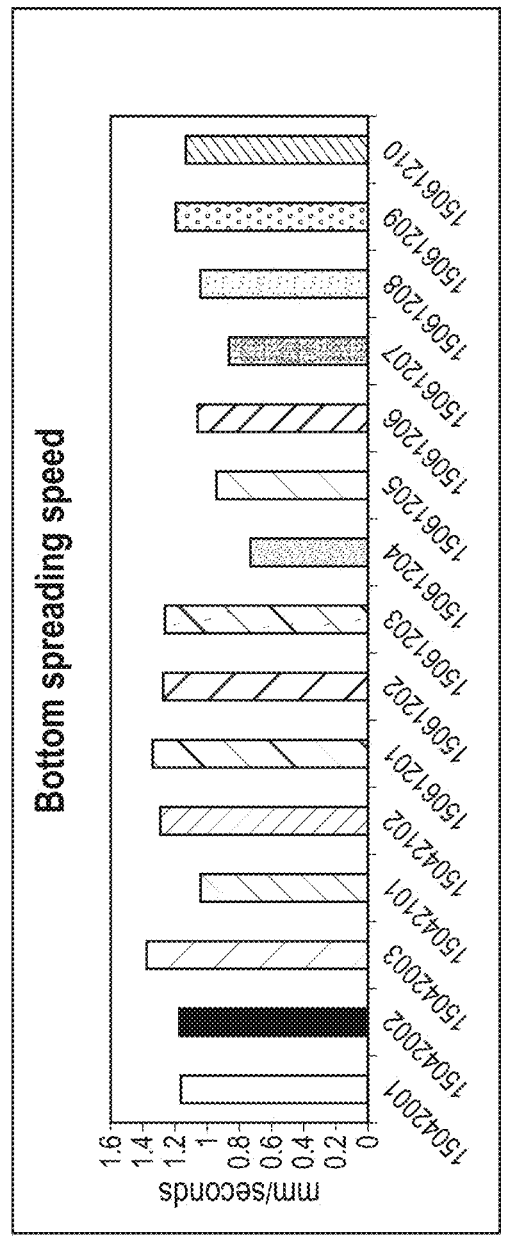
FIG. 61A
FIG. 61B

Testing Results:

| | | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|---|
| 16040101 | Mean | 6.2062 | 7.2188 | 8.7689 | 5.1279 | 5 | 5 | 0.8888 | 0.7830 | 599.4741 | 0.5028 |
| 16040102 | Mean | | | | | | | | | | |
| 16040103 | Mean | 4.5005 | 6.6565 | 6.4329 | 5.6507 | 5 | 5 | 1.0684 | 0.8066 | 613.2260 | 0.5019 |
| 16040106 | Mean | 4.2000 | 5.4564 | 12.7828 | 8.5878 | 5 | 5 | 1.1428 | 0.9071 | 374.3193 | 0.4723 |
| 16040105 | Mean | 4.3310 | 4.8936 | 11.8091 | 10.4725 | 5 | 5 | 1.1096 | 0.9923 | 364.2011 | 0.4650 |
| 16040104 | Mean | 4.9498 | 4.1248 | 14.0804 | 17.1970 | 5 | 5 | 1.1247 | 1.2175 | 287.8853 | 0.4207 |
| 15042001 | Mean | 6.103 | 4.2124 | 8.6855 | 15.8154 | 5 | 5 | 0.8041 | 1.1509 | 88.4355 | 0.1827 |

FIG. 193

Testing Results:

| | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Overall Moisture Management Capability OMMC |
|---|---|---|---|---|---|---|---|---|---|---|
| Grade | | | | | | | | | | |
| 16040101 | 3 | 3 | 1 | 1 | 1 | 1 | 1 | 1 | 5 | 3 |
| 16040102 | | | | | | | | | | |
| 16040103 | 4 | 3 | 1 | 1 | 1 | 1 | 2 | 1 | 5 | 3 |
| 16040104 | 4 | 4 | 2 | 2 | 1 | 1 | 2 | 2 | 4 | 3 |
| 16040105 | 4 | 4 | 2 | 2 | 1 | 1 | 2 | 1 | 4 | 3 |
| 16040106 | 4 | 3 | 2 | 1 | 1 | 1 | 2 | 1 | 4 | 3 |
| 15042001 | 3 | 4 | 1 | 2 | 1 | 1 | 1 | 2 | 2 | 1 |

FIG. 194

Testing Results:

| | | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|---|
| 16040801 | Mean | 32.5310 | 6.5620 | 3.8394 | 2.8465 | 5 | 5 | 0.1528 | 0.7407 | 461.1657 | 0.5000 |
| 16040802 | Mean | 4.5652 | 4.8466 | 8.201 | 5.7837 | 5 | 5 | 1.0535 | 0.9992 | 437.2409 | 0.5028 |
| 16040803 | Mean | 3.9938 | 4.6312 | 13.3611 | 9.2254 | 5 | 7 | 1.1942 | 1.0736 | 433.6376 | 0.5097 |
| 16040804 | Mean | 4.2 | 4.5754 | 12.5656 | 7.9578 | 5 | 5 | 1.1412 | 1.0528 | 432.1879 | 0.5052 |
| 16040805 | Mean | 4.3310 | 4.8936 | 11.8091 | 10.4725 | 5 | 5 | 1.1096 | 0.9923 | 364.2011 | 0.4650 |
| 16040806 | Mean | 4.2936 | 4.425 | 10.4676 | 11.8023 | 5 | 5 | 1.1238 | 1.0855 | 443.8888 | 0.5125 |
| 16040807 | Mean | 4.406 | 4.5936 | 10.4972 | 8.7678 | 5 | 5 | 1.1101 | 1.0603 | 436.9568 | 0.5097 |
| 16040808 | Mean | 5.6434 | 4.256 | 9.4582 | 11.9617 | 5 | 5 | 1.0143 | 1.1318 | 437.3739 | 0.5201 |
| 15042001 | Mean | 6.103 | 4.2124 | 8.6855 | 15.8154 | 5 | 5 | 0.8041 | 1.1509 | 88.4355 | 0.1827 |

FIG. 195

Testing Results:

| | Wetting Time | | Absorption Rate | | Max Wetted Radius | | Spreading Speed | | Accumulative One-Way Transport index(%) | Over all Moisture Management Capability |
|---|---|---|---|---|---|---|---|---|---|---|
| | Top | Bottom | Top | Bottom | Top | Bottom | Top | Bottom | | |
| Grade | (sec) | (sec) | (%/sec) | (%/sec) | (mm) | (mm) | (mm/sec) | (mm/sec) | | OMMC |
| 16040801 | 2 | 1 | 1 | 1 | 1 | 1 | 1 | 1 | 5 | 3 |
| 16040802 | 4 | 4 | 1 | 1 | 1 | 1 | 2 | 1 | 5 | 3 |
| 16040803 | 4 | 4 | 2 | 1 | 1 | 1 | 2 | 2 | 5 | 3 |
| 16040804 | 4 | 4 | 2 | 1 | 1 | 1 | 2 | 2 | 5 | 3 |
| 16040805 | 2 | 2 | 1 | 1 | 1 | 1 | 1 | 1 | 5 | 3 |
| 16040806 | 4 | 4 | 2 | 4 | 1 | 1 | 2 | 2 | 5 | 3 |
| 16040807 | 4 | 4 | 2 | 4 | 1 | 1 | 2 | 2 | 5 | 3 |
| 16040808 | 3 | 4 | 1 | 2 | 1 | 1 | 2 | 2 | 5 | 3 |
| 15042001 | 3 | 4 | 1 | 2 | 1 | 1 | 1 | 2 | 2 | 1 |

FIG. 196

Testing Results:

| | Mean Values | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Overall Moisture Management Capability OMMC |
|---|---|---|---|---|---|---|---|---|---|---|---|
| 16041201 | 1% low mw, 150C, 10 min | 4.9498 | 5.381 | 10.1284 | 7.8688 | 5 | 5 | 0.9978 | 0.9255 | 244.6475 | 0.3296 |
| 16041202 | 1% low mw, 200C, 10 min | 14.6560 | 15.8747 | 6.8175 | 3.3093 | 5 | 5 | 0.3982 | 0.3609 | 256.3562 | 0.3404 |
| 16041302 | 1% low mw, 150C, 5 min | 4.9594 | 4.65 | 8.9505 | 12.7455 | 5 | 5 | 1.117 | 1.1924 | 170.7486 | 0.2834 |
| 16041303 | 1% low mw, 200C, 5 min | 4.822 | 5.1782 | 11.3758 | 6.8097 | 5 | 5 | 1.0106 | 0.9397 | 250.1812 | 0.3364 |
| 16041203 | 1% medium mw, 200C, 10 min | 36.4377 | 48.9377 | 4.4255 | 3.0289 | 5 | 5 | 0.1758 | 0.1077 | 163.9531 | 0.2377 |
| 16041204 | 1% medium mw, 150C, 10 min | 7.0122 | 6.8058 | 12.668 | 12.0749 | 5 | 5 | 0.8715 | 0.9216 | 90.3758 | 0.1858 |
| 16041305 | 1% medium mw, 200C, 3 min | 6.469 | 63.703 | 7.32785 | 3.18745 | 10 | 2.5 | 0.87815 | 0.2614 | 561.1452 | 0.5 |
| 16041306 | 1% medium mw, 150C, 5 min | 15.1498 | 11.2872 | 12.8199 | 5.54318 | 5 | 6 | 0.67668 | 0.782 | 151.81352 | 0.23198 |
| 16041301 | no coating, 150C, 5 min | 4.1906 | 4.0594 | 13.16422 | 9.1083 | 5 | 5 | 1.1456 | 0.9716 | 219.342 | 0.30542 |
| 16041304 | no coating, 200C, 3 min | 5.4375 | 2.64825 | 7.775525 | 10.8061 | 5 | 5 | 0.922975 | 1.021225 | 219.26975 | 0.391575 |

FIG. 197

| Testing Results: | | | | | | | | | |
|---|---|---|---|---|---|---|---|---|---|
| | Wetting Time | Wetting Time | Top Absorption Rate | Bottom Absorption Rate | Top Max Wetted Radius | Bottom Max Wetted Radius | Top Spreading Speed | Bottom Spreading Speed | Accumulative One-Way Transport | Over all Moisture Management Capability |
| | Top (sec) | Bottom (sec) | (%/sec) | (%/sec) | (mm) | (mm) | (mm/sec) | (mm/sec) | index(%) | OMMC |
| Grade | | | | | | | | | | |
| 16041201 | 3 | 3 | 2 | 1 | 1 | 1 | 1 | 1 | 4 | 2 |
| 16041202 | 3 | 3 | 1 | 1 | 1 | 1 | 1 | 1 | 4 | 2 |
| 16041302 | 4 | 4 | 1 | 2 | 1 | 1 | 2 | 2 | 3 | 2 |
| 16041303 | 4 | 3 | 2 | 1 | 1 | 1 | 2 | 1 | 4 | 2 |
| 16041203 | 2 | 2 | 1 | 1 | 1 | 1 | 1 | 1 | 3 | 2 |
| 16041204 | 3 | 3 | 2 | 2 | 1 | 1 | 1 | 1 | 2 | 1 |
| 16041305 | 3 | 2 | 1 | 1 | 2 | 1 | 1 | 1 | 5 | 3 |
| 16041306 | 3 | 3 | 2 | 1 | 1 | 1 | 2 | 1 | 4 | 2 |
| 16041301 | 4 | 4 | 2 | 1 | 1 | 1 | 1 | 1 | 4 | 2 |
| 16041304 | 3 | 5 | 1 | 2 | 1 | 1 | 1 | 1 | 4 | 2 |

FIG. 198

Testing Results:

| | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|
| 16041301 Mean | 4.1906 | 4.0594 | 13.16422 | 9.1083 | 5 | 5 | 1.1456 | 0.9716 | 219.342 | 0.30542 |
| 16041302 Mean | 4.9594 | 4.65 | 8.9505 | 12.7455 | 5 | 5 | 1.117 | 1.1924 | 170.7486 | 0.2834 |
| 16041303 Mean | 4.822 | 5.1782 | 11.3758 | 6.8097 | 5 | 5 | 1.0106 | 0.9397 | 250.1812 | 0.3364 |
| 16041304 Mean | 5.4375 | 2.6483 | 7.7755 | 10.8061 | 5 | 5 | 0.9230 | 1.0212 | 291.2698 | 0.3916 |
| 16041305 Mean | 6.4690 | 63.7030 | 7.3279 | 3.1875 | 5 | 3 | 0.8782 | 0.2614 | 561.1452 | 0.5000 |
| 16041306 Mean | 15.1498 | 11.2872 | 12.8199 | 5.5432 | 10 | 6 | 0.6767 | 0.7820 | 151.8135 | 0.2320 |
| 15042001 Mean | 6.103 | 4.2124 | 8.6855 | 15.8154 | 5 | 5 | 0.8041 | 1.1509 | 88.4355 | 0.1827 |
| 16040101 Mean | 6.2062 | 7.2188 | 8.7689 | 5.1279 | 5 | 5 | 0.8888 | 0.7830 | 599.4741 | 0.5028 |
| 16040106 Mean | 4.2 | 5.4564 | 12.7828 | 8.5878 | 5 | 5 | 1.1428 | 0.9071 | 374.3193 | 0.4723 |

FIG. 199

Testing Results:

| | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|
| | Grade | | | | | | | | | |
| 16041301 | 4 | 4 | 2 | 1 | 1 | 1 | 2 | 1 | 4 | 2 |
| 16041302 | 4 | 4 | 1 | 2 | 1 | 1 | 2 | 2 | 3 | 2 |
| 16041303 | 4 | 3 | 2 | 1 | 1 | 1 | 2 | 1 | 4 | 2 |
| 16041304 | 3 | 5 | 1 | 2 | 1 | 1 | 1 | 1 | 4 | 2 |
| 16041305 | 3 | 2 | 1 | 1 | 2 | 1 | 1 | 1 | 5 | 3 |
| 16041306 | 3 | 3 | 2 | 2 | 1 | 1 | 1 | 2 | 4 | 2 |
| 15042001 | 3 | 4 | 1 | 1 | 1 | 1 | 1 | 1 | 2 | 1 |
| 16040101 | 3 | 3 | 1 | 1 | 1 | 1 | 1 | 1 | 5 | 3 |
| 16040106 | 4 | 3 | 2 | 1 | 1 | 1 | 2 | 1 | 4 | 3 |

FIG. 200

| | Low Molecular Weight (MW) Silk | | | | | | | Medium Molecular Weight (MW) Silk | | | | | | |
|---|---|---|---|---|---|---|---|---|---|---|---|---|---|---|
| | 65C | | 150C | | | 200C (385F = 196C) | | 65C | | 150C | | | 200C (385F = 196C) | |
| Silk conc (%) | 10min | 3min | 5min | 10min | 3min | 5min | 10 | 10 | 3 | 5 | 10 | 3 | 5 | 10 |
| 1.000 | 599.5, 0.5028 | | 151.8, 0.2319 | 90.4, 0.1858 | 613.2, 0.5019 | | 250.2, 0.3364 | 374.3, 0.4723 | | 364.2, 0.4650 | 244.6, 0.3296 | 287.9, 0.4207 | | 256.4, 0.3404 |
| 0.750 | | | 461.2, 0.500 | | | | | | | | | | | |
| 0.500 | | | | | | | | | | 364.2, 0.4650 | | | | |
| 0.250 | 40.6, 0.1327 | | 437.3, 0.5028 | | 188.0, 0.2805 | | | 97.0, 0.1635 | | 106.3, 0.1778 | | 141.6, 0.2236 | | |
| 0.100 | 138.0, 0.2532 | | 112.9, 0.2116 | | 63.4, 0.1260 | | | 134.9, 0.2250 | | 443.9, 0.5125 | | 91.2, 0.1599 | | |
| 0.075 | | | 456.3, 0.5052 | | | | | | | | | | | |
| 0.050 | | | 432.2, 0.5052 | | | | | | | 436.9, 0.5097 | | | | |
| 0.025 | | | | | | | | | | 437.4, 0.5201 | | | | |
| 0.001 | | | | | | | | | | | | | | |
| Fabric Controls (no heat setting) | non-finished | 88.4, 0.1827 | semi-finished | (-) 6.8, 0.1038 | finished | 62.4, 0.2854 | | | | | | | | |

FIG. 201

| test group | description | percentage change |
|---|---|---|
| 160511 | medium mw 0.1% | -0.29% |
| | medium mw 0.25% | -0.21% |
| | low mw 0.1% | -0.23% |
| | low mw 0.25% | -0.42% |
| 160520 | medium mw 1% - SI 2.2% | -0.36% |
| | medium mw 1% - SI 2.2% - acetic acid 0.05% | 0.16% |
| | medium mw 1% - CSP 5% - acetic acid 0.1% | -0.24% |
| | medium mw 1% - CSP 5% - acetic acid 0.1% | -0.29% |
| | medium mw 1% - citric acid 0.1% | -1.88% |
| | medium mw 15% - citric acid 0.05% | 0.61% |
| 160525 | 2.2% SI | -0.34% |
| | 2.2% SI - 0.05% acetic acid | -0.20% |
| | 5% CSP | -0.51% |
| | 5% CSP - 0.1% acetic acid | -0.38% |

FIG. 204

| sample # | variables | mass before coating | mass post coating | mass post 24hrs coating | coating mass % |
|---|---|---|---|---|---|
| 16050401 | 0.1%, medium mw, 65C 10min | 27.8998 | 27.8441 | 27.8797 | -0.07% |
| 16050402 | 0.1%, medium mw, 150C 5min | 27.4518 | 27.3692 | 27.4133 | -0.14% |
| 16050403 | 0.1%, medium mw, 200C 3min | 27.4786 | 27.3371 | 27.3965 | -0.30% |
| 16050404 | 0.25%, medium mw, 65C 10min | 27.4948 | 27.3842 | 27.4556 | -0.14% |
| 16050405 | 0.25%, medium mw, 150C 5min | 27.3981 | 27.3046 | 27.3693 | -0.11% |
| 16050406 | 0.25%, medium mw, 200C 3min | 27.5101 | 27.4633 | 27.5152 | 0.02% |
| 16050407 | 0.1%, low mw, 65C 10min | 27.4390 | 27.3486 | 27.3890 | -0.18% |
| 16050408 | 0.1%, low mw, 150C 5min | 27.7413 | 27.6189 | 27.6738 | -0.24% |
| 16050409 | 0.1%, low mw, 200C 3min | 28.4868 | 28.2885 | 28.3568 | -0.46% |
| 16050410 | 0.25%, low mw, 65C 10min | 27.7291 | 27.6048 | 27.6583 | -0.26% |
| 16050411 | 0.25%, low mw, 150C 5min | 27.7296 | 27.6167 | 27.6878 | -0.15% |
| 16050412 | 0.25%, low mw, 200C 3min | 27.6659 | 27.6153 | 27.6237 | -0.15% |
| 15042001 | no coating | | | | |

FIG. 205

| mean | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Overall Moisture Management Capability index(%) |
|---|---|---|---|---|---|---|---|---|---|---|
| 16050401 | 3.6562 | 3.9002 | 21.1783 | 19.132 | 5 | 5 | 1.3021 | 1.226 | 138.0962 | 0.2532 |
| 16050402 | 3.7876 | 3.994 | 19.1555 | 15.0486 | 5 | 5 | 1.2542 | 1.1981 | 112.9818 | 0.2116 |
| 16050403 | 4.5562 | 5.4936 | 7.5662 | 6.5758 | 5 | 5 | 1.0592 | 0.8944 | 63.4438 | 0.126 |
| 16050404 | 4.7814 | 5.2688 | 9.5862 | 13.4556 | 5 | 5 | 1.0693 | 1.0128 | 40.5577 | 0.1327 |
| 16050405 | 4.1436 | 4.7154 | 14.1859 | 9.356 | 5 | 5 | 1.1598 | 1.033 | 171.9273 | 0.2539 |
| 16050406 | 4.0502 | 4.481 | 15.0691 | 11.1372 | 5 | 5 | 1.1817 | 1.0909 | 188.01 | 0.2805 |
| 16050407 | 4.03876 | 4.51684 | 15.431 | 12.24992 | 5 | 5 | 1.1914 | 1.08848 | 134.89182 | 0.22504 |
| 16050408 | 4.05 | 4.8188 | 14.7362 | 11.2181 | 5 | 5 | 1.2453 | 1.1026 | 119.3349 | 0.2133 |
| 16050409 | 4.6122 | 5.625 | 14.8515 | 9.1391 | 5 | 5 | 1.0401 | 0.8718 | 91.2189 | 0.1599 |
| 16050410 | 4.3312 | 6.45 | 9.3714 | 7.5046 | 5 | 5 | 1.1074 | 0.7927 | 97.0366 | 0.1635 |
| 16050411 | 4.2002 | 5.0626 | 13.4135 | 8.2152 | 5 | 5 | 1.1403 | 0.9616 | 106.3481 | 0.1778 |
| 16050412 | 4.1436 | 4.6874 | 14.1363 | 11.1217 | 5 | 5 | 1.1583 | 1.0408 | 141.6139 | 0.2236 |
| 15042001 | 6.103 | 4.2124 | 8.6855 | 15.8154 | 5 | 5 | 0.8041 | 1.1509 | 88.4355 | 0.1827 |

FIG. 206

| sample # | variables | mass before coating | mass post coating | mass post 24hrs coating | coating mass % |
|---|---|---|---|---|---|
| 16051101 | no coating, 65C, 10min | 27.7959 | 27.7209 | 27.7958 | 0.00% |
| 16051102 | no coating, 150C, 5min | 27.5591 | 27.4186 | 27.5361 | -0.08% |
| 16051103 | no coating, 200C, 3min | 27.5610 | 27.3764 | 27.5184 | -0.15% |
| 16051104 | 0.1%, medium mw, 200C 3min | 27.6831 | 27.5328 | 27.6529 | -0.11% |
| 16051105 | 0.1%, medium mw, 150C 5min | 27.5614 | 27.4813 | 27.5808 | 0.07% |
| 16051106 | 0.1%, medium mw, 65C 10min | 27.7428 | 27.6970 | 27.7638 | 0.08% |
| 16051107 | 0.25%, medium mw, 65C 10min | 27.4758 | 27.4524 | 27.5281 | 0.19% |
| 16051108 | 0.25%, medium mw, 150C 5min | 28.0202 | 27.9299 | 28.0444 | 0.09% |
| 16051109 | 0.25%, medium mw, 200C 3min | 26.8532 | 26.7314 | 26.8612 | 0.03% |
| 16051110 | 0.1%, low mw, 200C 3min | 27.2731 | 27.1462 | 27.2458 | -0.10% |
| 16051111 | 0.1%, low mw, 150C 5min | 27.2532 | 27.1622 | 27.2574 | 0.02% |
| 16051112 | 0.1%, low mw, 65C 10min | 27.9193 | 27.8521 | 27.9375 | 0.07% |
| 16051113 | 0.25%, low mw, 65C 10min | 27.5451 | 27.5295 | 27.5999 | 0.20% |
| 16051114 | 0.25%, low mw, 150C 5min | 27.5025 | 27.4405 | 27.5743 | 0.26% |
| 16051115 | 0.25%, low mw, 200C 3min | 27.6829 | 27.5671 | 27.6922 | 0.03% |

FIG. 207

| mean | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|
| 16051101 | 3.9376 | 4.2564 | 13.2112 | 18.2272 | 5 | 5 | 1.2169 | 1.1411 | 103.023 | 0.2051 |
| 16051102 | 4.1526 | 4.5748 | 14.7715 | 16.11604 | 5 | 5 | 1.17186 | 1.0658 | 59.44466 | 0.14638 |
| 16051103 | 4.5128 | 5.7314 | 12.3379 | 10.5193 | 5 | 5 | 1.0869 | 0.8947 | 83.235 | 0.156 |
| 16051104 | 7.444 | 28.8754 | 6.5736 | 6.9355 | 5 | 5 | 0.8685 | 0.4821 | 72.883 | 0.1365 |
| 16051105 | 4.6498 | 4.6312 | 10.4792 | 11.2174 | 5 | 5 | 1.0467 | 1.0495 | 47.9845 | 0.1206 |
| 16051106 | 4.0688 | 4.5376 | 16.2767 | 17.2449 | 5 | 5 | 1.1941 | 1.1597 | 52.839 | 0.1533 |
| 16051107 | 19.6124 | 13.8564 | 6.996 | 7.9745 | 5 | 7 | 0.82 | 0.7765 | 127.3957 | 0.201 |
| 16051108 | 11.9688 | 26.2188 | 7.1779 | 5.1517 | 5 | 5 | 0.7964 | 0.8926 | 242.7475 | 0.3466 |
| 16051109 | 5.3816 | 10.425 | 8.4204 | 4.1142 | 5 | 5 | 0.9135 | 0.5415 | 223.8266 | 0.3043 |
| 16051110 | 4.4628 | 8.4376 | 7.849 | 4.4341 | 5 | 5 | 1.0764 | 0.6062 | 226.5862 | 0.3073 |
| 16051111 | 3.9752 | 5.2502 | 15.2155 | 11.2055 | 5 | 5 | 1.2513 | 1.1286 | 115.8167 | 0.2153 |
| 16051112 | 4.3346 | 4.5596 | 11.2951 | 12.7915 | 5 | 5 | 1.1111 | 1.0635 | 123.1502 | 0.207 |
| 16051113 | 4.2938 | 4.5376 | 10.8059 | 8.5425 | 5 | 5 | 1.1225 | 1.0614 | 107.2899 | 0.1815 |
| 16051114 | 4.5408 | 4.8404 | 8.6481 | 12.9761 | 5 | 8 | 1.0668 | 1.0496 | 124.2615 | 0.2094 |
| 16051115 | 5.328 | 7.6656 | 7.5532 | 4.8861 | 5 | 5 | 0.9082 | 0.6484 | 113.2722 | 0.1814 |

FIG. 208

| sample number | description | mass before coating | mass 24hrs after coating | coating mass % |
|---|---|---|---|---|
| 16052001 | 1% medium mw. + 2.2% SI | 16.7936 | 16.9149 | 0.72% |
| 16052002 | 1% medium mw. + 2.2% SI + acetic acid 0.5% | 16.0038 | 16.1727 | 1.06% |
| 16052003 | 1% medium mw. + 5% CSP | 17.2366 | 17.4209 | 1.07% |
| 16052004 | 1%, medium mw. + 5% CSP + acetic acid 1% | 16.0087 | 16.1993 | 1.19% |
| 16052005 | 1% medium mw. + 0.1% citric acid | 17.3912 | 17.5276 | 0.78% |
| 16052006 | 1% medium mw. + 0.05% citric acid | 15.4389 | 15.5261 | 0.56% |
| 16052501 | 2.2% SI | 16.5019 | 16.5885 | 0.52% |
| 16052502 | 2.2% SI + acetic acid 0.5% | 18.6291 | 18.7321 | 0.55% |
| 16052503 | 5% CSP | 17.0946 | 17.1797 | 0.50% |
| 16052504 | 5% CSP + acetic acid 1% | 15.2729 | 15.336 | 0.41% |

FIG. 209

| Raw Data: | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|
| 16052001 | 120 | 32.6251 | 0 | 11.4019 | 0 | 4.375 | 0 | 1.4944 | 396.8843 | 0.4432 |
| 16052002 | 120 | 25.0664 | 0 | 9.5604 | 0 | 6.875 | 0 | 2.5826 | 1084.6953 | 0.6414 |
| 16052003 | 120 | 20.5548 | 0 | 11.5085 | 0 | 6.25 | 0 | 2.4735 | 1157.5399 | 0.6303 |
| 16052004 | 120 | 6.4103 | 0 | 12.6385 | 0 | 5.625 | 0 | 2.1531 | 1182.457 | 0.6057 |
| 16052005 | 66.0589 | 34.5352 | 2.8804 | 5.0824 | 3.75 | 3.75 | 0.1023 | 1.7183 | 1165.2373 | 0.5832 |
| 16052006 | 107.4843 | 75.8671 | 1.0243 | 1.3469 | 1.25 | 1.875 | 0.0323 | 0.5417 | 1121.1284 | 0.5243 |
| 16052501 | 120 | 17.5666 | 0 | 12.0892 | 0 | 3.75 | 0 | 1.2849 | 639.587 | 0.56 |
| 16052502 | 120 | 17.1211 | 0 | 25.1403 | 0 | 5.625 | 0 | 2.1137 | 709.6938 | 0.6477 |
| 16052503 | 120 | 105.3281 | 0 | 3.6746 | 0 | 0.625 | 0 | 0.2222 | 845.16 | 0.5148 |
| 16052504 | 120 | 90.7149 | 0 | 3.4472 | 0 | 1.25 | 0 | 0.4365 | 865.4872 | 0.5198 |

FIG. 210

| sample # | variables | mass before coating (gr) | mass post coating (gr) | mass post coating 24 hrs (gr) | coating mass variation (%) |
|---|---|---|---|---|---|
| 16050301 | 1% low mw, 200C 3min | 27.3448 | 27.3546 | 27.4811 | 0.50% |
| 16050302 | 0.1% low mw, 200C, 3min | 27.2618 | 27.0759 | 27.2113 | -0.19% |
| 16050303 | 1% medium mw, 200C 3min | 27.6729 | 27.7292 | 27.8732 | 0.72% |
| 16050304 | 1% medium mw, 200C 3min | 27.3121 | 27.3775 | 27.5029 | 0.70% |
| 16050305 | 1% medium mw, 200C 3min | 27.5503 | 27.6099 | 27.7419 | 0.70% |
| 16050306 | 0.1% medium mw, 200C, 3min | 27.8158 | 27.6649 | 27.7825 | -0.12% |
| 16050307 | 15042001 non wicking finished, 200C, 3 min | 27.7029 | 27.5171 | 27.6341 | -0.25% |
| 16050308 | 15042001 non wicking finished, 200C, 3 min | 27.5277 | 27.3671 | 27.4566 | -0.26% |
| 16050309 | 15042001 non wicking finished, 200C, 3 min | 27.5404 | 27.4003 | 27.4746 | -0.24% |
| 16050310 | 15042001 non wicking finished, 150C, 5 min | 27.5235 | 27.3960 | 27.4786 | -0.16% |
| 16050311 | 15042001 non wicking finished, 150C, 5 min | 27.6228 | 27.5090 | 27.5840 | -0.14% |
| 16050312 | 15042001 non wicking finished, 150C, 5 min | 27.8506 | 27.7355 | 27.8059 | -0.16% |

FIG. 211

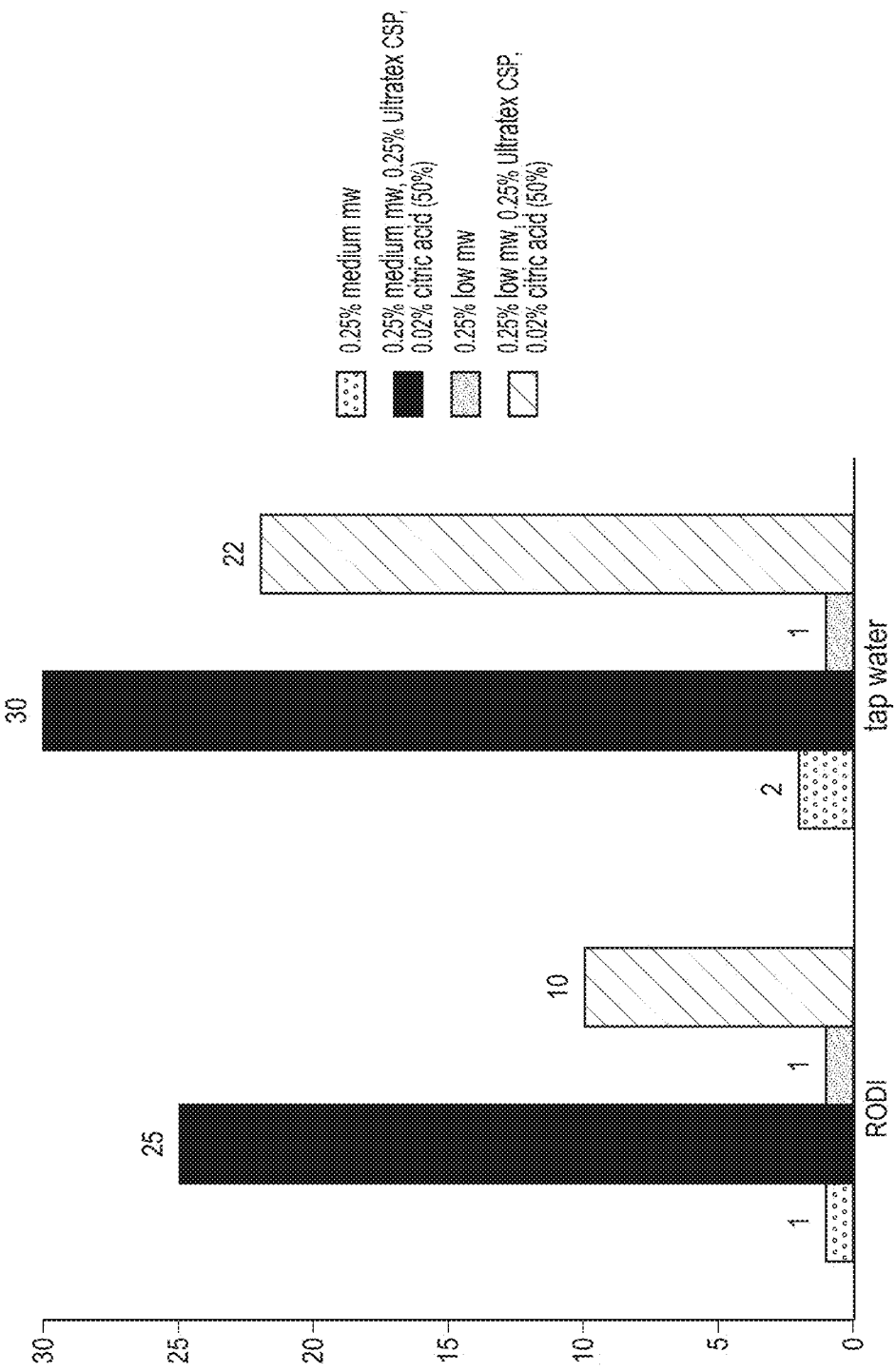

| | Step 1: Application | Step 2: Rinse (5 min) | Step 3: Rinse (5 min) | Step 4: Dry (10 min) |
|---|---|---|---|---|
| Silk Formulation A | 0.5% M silk | 20% GlyOH | 20% GlyOH | Oven, 60 °C |
| Silk Formulation B | 4.5% M silk | Water | Water | Oven, 60 °C |
| Silk Formulation C | 0.75% M silk | Water | Water | Oven, 60 °C |
| Silk Formulation D | 0.5% M silk | 20% MeOH | 20% MeOH | Oven, 60 °C |
| Silk Formulation E | 0.5% M silk | Water | Water | Oven, 60 °C |
| Silk Formulation F | 1% M silk | Water | Water | Oven, 60 °C |
| Silk Formulation G | 0.5% M silk | Water | Water | Oven, 60 °C |
| Silk Formulation H | 0.25% M silk | Water | Water | Oven, 60 °C |
| Silk Formulation I | 0.5% M silk | Water | 80% MeOH | Oven, 60 °C |
| Silk Formulation J | 4.5% M silk | 80% MeOH | 80% MeOH | Oven, 60 °C |
| Unfinished Control | Unfinished Control | | | |
| Water | Water | Water | Water | Oven, 60 °C |
| | 0.1% GTA-NaHSO3 only | | | |
| Silk Formulation K | 0.5% M silk | Water | Water | Oven, 60 °C |
| Silk Formulation L | 0.5% M silk | 50% MeOH | 50% MeOH | Oven, 60 °C |
| Silk Formulation M | 0.5% M silk | 80% IPA | 80% IPA | Oven, 60 °C |
| Silk Formulation N | 0.5% 3L1M silk | 80% MeOH | 80% MeOH | Oven, 60 °C |
| Silk Formulation O | 0.5% M silk | 80% MeOH | 80% MeOH | Oven, 60 °C |

FIG. 219

Control visible.

SILK COATED FABRICS AND PRODUCTS AND METHODS OF PREPARING THE SAME

CROSS-REFERENCE TO RELATED APPLICATIONS

This application is a continuation of U.S. patent application Ser. No. 17/732,107, which is a continuation of U.S. patent application Ser. No. 16/651,611 filed Mar. 27, 2020, now U.S. Pat. No. 11,390,988, which is a U.S. national stage of International Application No. PCT/US2018/053163, filed Sep. 27, 2018, which claims the benefit of U.S. Provisional Patent Application No. 62/564,228, filed on Sep. 27, 2017, U.S. Provisional Patent Application No. 62/564,233, filed on Sep. 27, 2017, U.S. Provisional Patent Application No. 62/564,239, filed on Sep. 27, 2017, and U.S. Provisional Patent Application No. 62/597,898, filed on Dec. 12, 2017, which are hereby incorporated by reference in their entirety.

FIELD OF THE INVENTION

In some embodiments, the invention relates to silk-coated performance materials, apparel, and products for use in home and automotive applications, such as fabrics coated with pure silk fibroin-based proteins or protein fragments thereof.

BACKGROUND OF THE INVENTION

Silk is a natural polymer produced by a variety of insects and spiders, and comprises a filament core protein, silk fibroin, and a glue-like coating consisting of a non-filamentous protein, sericin. Silk fibers are light weight, breathable, and hypoallergenic. Silk is comfortable when worn next to the skin and insulates very well; keeping the wearer warm in cold temperatures and is cooler than many other fabrics in warm temperatures.

SUMMARY OF THE INVENTION

In an embodiment, a method is provided for coating a material with silk fibroin that may include silk-based proteins or fragments thereof to provide a silk fibroin coated material, wherein the silk fibroin coated upon the silk fibroin coated material may be heat resistant to a selected temperature. In some embodiments, the method may include preparing a silk fibroin solution that may include a concentration of one or more of low molecular weight silk fibroin, medium molecular weight silk fibroin, and high molecular weight silk fibroin at less than about 1% by volume (v/v), or less than about 0.1% by volume (v/v), or less than about 0.01% by volume (v/v), or less than about 0.001% by volume (v/v). In some embodiments, the method may include, coating a surface of the material with the silk fibroin solution. In some embodiments, the method may include drying the surface of the material that has been coated with the silk fibroin solution to provide the silk fibroin coated material, wherein drying the surface of the material comprises heating the surface of the material without substantially decreasing silk fibroin coating performance.

In an embodiment, a method is provided for coating a textile with a silk fibroin solution that may include silk-based proteins or fragments thereof to provide a silk fibroin coated article, wherein the silk fibroin coated upon the silk fibroin coated article may be heat resistant to a selected temperature. In some embodiments, the method may include preparing the silk fibroin solution with one or more of low molecular weight silk fibroin, medium molecular weight silk fibroin, and high molecular weight silk fibroin. In some embodiments, the method may include acidically adjusting the pH of the silk fibroin solution with an acidic agent. In some embodiments, the method may include coating a surface of the textile with the silk fibroin solution. In some embodiments, the method may include drying the surface of the textile that has been coated with the silk fibroin solution to provide the silk fibroin coated article, wherein drying the surface of the textile comprises heating the surface of the textile without substantially decreasing silk fibroin coating performance.

In some embodiments, a method is provided for manufacturing a silk fibroin coated textile that may include selected fabric properties. In some embodiments, the method may include admixing silk-based proteins or fragments thereof with one or more chemical agents to provide a coating solution, wherein the one or more chemical agents may be selected to modify one or more of a first selected property and second selected property of the silk fibroin coated textile. In some embodiments, the method may include providing the coating solution to a textile to be coated with one or more of a bath coating process, a kiss rolling process, a spray process, and a two-sided rolling process. In some embodiments, the method may include removing excess coating solution from the silk fibroin coated textile. In some embodiments, the method may include heating the silk fibroin coated textile to modify a third selected property of the silk fibroin coated textile. In some embodiments, the first selected property may include one or more of an antimicrobial property, an antiodor property, a water repellant property, an oil repellant property, a flame retardant property, a coloring property, a fabric softening property, a stain repellant property, a pH adjusting property, an anticrocking property, an antipilling property, and an antifelting property. In some embodiments, the second selected property may include one or more of wetting time, absorption rate, spreading speed, accumulative one-way transport, drying rate, and overall moisture management capability. In some embodiments, the third selected property may include one or more of fabric hand, fabric stretch, fabric recovery, fabric stretch and recovery, and drapability.

In an embodiment, a selected property of the SFS coated articles that may be enhanced as compared to non-coated articles may include one or more of dimensional stability to laundering, dimensional stability to dry cleaning, appearance after laundering, appearance after dry cleaning, colorfastness to laundering, colorfastness to dry cleaning, colorfastness to non-chlorine bleach, seam torque/spirality (on knits), colorfastness to crocking, colorfastness to rubbing, colorfastness to water, colorfastness to light, colorfastness to perspiration, colorfastness to chlorinated pool water, colorfastness to sea water, tensile strength, seam slippage, tearing strength, seam breaking strength, abrasion resistance, pilling resistance, stretch recovery, bursting strength, colorfastness to die transfer in storage (labels), colorfastness to ozone, pile retention, bowing and skewing, colorfastness to saliva, snagging resistance, wrinkle resistance (e.g., appearance of apparel, retention of creases in fabrics, smooth appearance of fabrics), water repellency, water resistance, stain repellant (e.g., water repellency, oil repellency, water/alcohol repellency), vertical wicking, water absorption, dry rate, soil release, air permeability, wicking, antimicrobial properties, ultraviolet protection, resistance to torque, malodor resistant, biocompatibility, wetting time, absorption rate, spreading speed, accumulative one-way transport, flame retardant properties, coloring properties, fabric softening properties, a pH adjusting property, an antifelting property, and overall moisture management capability.

In an embodiment, the silk fibroin coated materials of the invention may be coated with one or more of low molecular weight silk, medium molecular weight silk, and high molecular weight silk to provide resulting coated materials having enhanced hydrophobic or hydrophilic properties.

In an embodiment, the silk fibroin coated materials of the invention, for example a fiber, a yarn, or a fabric, may be coated with compositions including one or more of low molecular weight silk, medium molecular weight silk, and high molecular weight silk, to provide resulting coated materials having enhanced hydrophobic or hydrophilic properties. In an embodiment, the silk fibroin coated materials of the invention, for example a fiber, a yarn, or a fabric, may be coated with compositions including low molecular weight silk and medium molecular weight silk. In an embodiment, the silk fibroin coated materials of the invention, for example a fiber, a yarn, or a fabric, may be coated with compositions including low molecular weight silk and high molecular weight silk. In an embodiment, the silk fibroin coated materials of the invention, for example a fiber, a yarn, or a fabric, may be coated with compositions including medium molecular weight silk and high molecular weight silk. In an embodiment, the silk fibroin coated materials of the invention, for example a fiber, a yarn, or a fabric, may be coated with compositions including low molecular weight silk, medium molecular weight silk, and high molecular weight silk.

In and embodiment, materials coated by silk fibroin coatings described herein may include one or more of textiles, woven materials, non-woven materials, knit materials, crochet materials, and leather materials.

In an embodiment, the invention provides an article comprising a fiber or yarn having a coating, wherein the coating comprises silk based proteins or fragments thereof having a weight average molecular weight range of about 5 kDa to about 144 kDa.

In an embodiment, the invention provides an article comprising a fiber or yarn having a coating, wherein the coating comprises silk based proteins or fragments thereof having an average number of amino acid residues of about 1 to 400 residues, or 1 to 300 residues, or 1 to 200 residues, or 1 to 100 residues, or 1 to 50 residues, or 5 to 25 residues, or 10 to 20 residues.

In an embodiment, the invention provides an article comprising a fiber or yarn having a coating, wherein the coating comprises silk based proteins or fragments thereof having a weight average molecular weight range of about 5 kDa to about 144 kDa, and wherein the article is a fabric.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments thereof comprise silk fibroin-based proteins or protein fragments having about 0.01% (w/w) to about 10% (w/w) sericin.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments thereof are selected from the group consisting of natural silk based proteins or fragments thereof, recombinant silk based proteins or fragments thereof, and combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments comprise silk and a copolymer.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and wherein the proteins or protein fragments, prior to coating the fabric, do not spontaneously or gradually gelate and do not visibly change in color or turbidity when in a solution for at least 10 days.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, silk, alpaca fleece, alpaca wool, lama fleece, lama wool, cotton, cashmere, sheep fleece, sheep wool, and combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, acrylic polymer or copolymer, rayon, i.e., semi-synthetic fiber made of modified cellulose, and combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the fabric exhibits an improved property, wherein the improved property is an accumulative one-way moisture transport index selected from the group consisting of greater than 40%, greater than 60%, greater than 80%, greater than 100%, greater than 120%, greater than 140%, greater than 160%, and greater than 180%. In an embodiment, the foregoing improved property is determined after a period of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the fabric exhibits an improved property, wherein the improved property is an accumulative one way transport capability increase relative to uncoated fabric selected from the group consisting of 1.2 fold, 1.5 fold, 2.0 fold, 3.0 fold, 4.0 fold, 5.0 fold, and 10 fold. In an embodiment, the foregoing improved property is determined after a period of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the fabric exhibits an improved property, wherein the improved property is an overall moisture management capability selected from the group consisting of greater than 0.05, greater than 0.10, greater than 0.15, greater than 0.20, greater than 0.25, greater than 0.30, greater than 0.35, greater than 0.40, greater than 0.50, greater than 0.60, greater than 0.70, and greater than 0.80. In an embodiment, the foregoing improved property is determined after a period of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric exhibits substantially no increase in microbial growth after a number of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the fabric exhibits substantially no increase in microbial growth after a number of machine washing cycles selected from the group consisting of 5 cycles, 10 cycles, 25 cycles, and 50 cycles, and wherein the microbial growth is microbial growth of a microbe selected from the group consisting of *Staphylococcus aureus*, *Klebsiella pneumoniae*, and combinations thereof.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the fabric exhibits substantially no increase in microbial growth after a number of machine washing cycles selected from the group consisting of 5 cycles, 10 cycles, 25 cycles, and 50 cycles, wherein the microbial growth is microbial growth of a microbe selected from the group consisting of *Staphylococcus aureus*, *Klebsiella pneumoniae*, and combinations thereof, wherein the microbial growth is reduced by a percentage selected from the group consisting of 50%, 100%, 500%, 1000%, 2000%, and 3000% compared to an uncoated fabric.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the coating is applied to the fabric at the fiber level prior to forming the fabric.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the coating is applied to the fabric at the fabric level.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, and wherein the fabric is bath coated.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, and wherein the fabric is spray coated.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, and wherein the fabric is coated with a stencil.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, wherein the coating is applied to at least one side of the fabric using a method selected from the group consisting of a bath coating process, a spray coating process, a stencil process, a silk-foam based, and a roller-based process.

In an embodiment, the invention provides an article comprising a fiber or yarn having a coating, wherein the coating comprises silk based proteins or fragments thereof having a weight average molecular weight range of about 5 kDa to about 144 kDa, and wherein the coating has a thickness of about one nanolayer.

In an embodiment, the invention provides an article comprising a fiber or yarn having a coating, wherein the coating comprises silk based proteins or fragments thereof having a weight average molecular weight range of about 5 kDa to about 144 kDa, and wherein the coating has a thickness selected from the group consisting of about 5 nm, about 10 nm, about 15 nm, about 20 nm, about 25 nm, about 50 nm, about 100 nm, about 200 nm, about 500 nm, about 1 µm, about 5 µm, about 10 µm, and about 20 µm.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the coating is adsorbed on the fabric.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the coating is attached to the fabric through chemical, enzymatic, thermal, or irradiative cross-linking.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, and wherein the hand of the coated fabric is improved relative to an uncoated fabric.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the coating is applied to the fabric at the fabric level, and wherein the hand of the coated fabric is improved relative to an uncoated fabric, wherein the hand of the coated fabric that is improved is selected from the group consisting of softness, crispness, dryness, silkiness, and combinations thereof.

According to aspects illustrated herein, an aqueous solution of pure silk fibroin-based protein fragments of the present disclosure is available for application to a product, including, but not limited to, apparel, padding, shoes, gloves, luggage, furs, jewelry and bags, or for directly spraying on the body of a consumer, to impart desired properties to the product.

Silk performance apparel and methods of preparing the same are disclosed herein. According to aspects illustrated herein, the present disclosure relates to apparel configured to be worn or carried on the body, that is at least partially surface treated with a solution of pure silk fibroin-based protein fragments of the present disclosure so as to result in a silk coating on the product. In some embodiments, the solutions of silk fibroin-based proteins or fragments thereof may be aqueous solutions, organic solutions, or emulsions. In an embodiment, the product is manufactured from a textile material. In an embodiment, the product is manufactured from a non-textile material. In an embodiment, desired additives can be added to an aqueous solution of pure silk fibroin-based protein fragments of the present disclosure so as to result in a silk coating having desired additives.

In an embodiment, a textile comprising a silk coating of the present disclosure is sold to a consumer. In an embodiment, a textile of the present disclosure is used in constructing action sportswear apparel. In an embodiment, a textile of the present disclosure is used in constructing fitness apparel. In an embodiment, a textile of the present disclosure is used in constructing performance apparel. In an embodiment, a textile of the present disclosure is used in constructing golf apparel. In an embodiment, a textile of the present disclosure is used in constructing lingerie. In an embodiment, a silk coating of the present disclosure is positioned on the underlining of action sportswear/apparel. In an embodiment, a silk coating of the present disclosure is positioned on the shell, the lining, or the interlining of action sportswear/apparel. In an embodiment, action sportswear/apparel is partially made from a silk coated textile of the present disclosure and partially made from an uncoated textile. In an embodiment, action sportswear/apparel partially made from a silk coated textile and partially made from an uncoated textile combines an uncoated inert synthetic material with a silk coated inert synthetic material. Examples of inert synthetic material include, but are not limited to, polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, LYCRA (polyester-polyurethane copolymer, also known as SPANDEX and elastomer), and mixtures thereof. In an embodiment, action sportswear/apparel partially made from a silk coated textile and partially made from an uncoated textile combines an elastomeric material at least partially covered with a silk coating of the present disclosure. In an embodiment, the percentage of silk to elastomeric material can be varied to achieve desired shrink or wrinkle resistant properties and desired moisture content against the skin surface. In an embodiment, a silk coating of the present disclosure is positioned on an internal layer of a shoe (textile or non-textile based). In an embodiment, a silk coating of the present disclosure positioned on an internal layer of a shoe helps maintain optimal feet microenvironment, such as temperature and humidity while reducing any excessive perspiration.

In an embodiment, a silk coating of the present disclosure is visible. In an embodiment, a silk coating of the present disclosure is transparent. In an embodiment, a silk coating of the present disclosure positioned on action sportswear/apparel helps control skin temperature of a person wearing the apparel. In an embodiment, a silk coating of the present disclosure positioned on action sportswear/apparel helps control fluid transfer away from the skin of a person wearing the apparel. In an embodiment, a silk coating of the present disclosure positioned on action sportswear/apparel has a soft feel against the skin decreasing abrasions from fabric on the skin. In an embodiment, a silk coating of the present disclosure positioned on a textile has properties that confer at least one of wrinkle resistance, shrinkage resistance, or machine washability to the textile. In an embodiment, a silk coated textile of the present disclosure is 100% machine washable and dry cleanable. In an embodiment, a silk coated textile of the present disclosure is 100% waterproof. In an embodiment, a silk coated textile of the present disclosure is wrinkle resistant. In an embodiment, a silk coated textile of the present disclosure is shrink resistant. In an embodiment, a silk coated fabric improves the health of the skin. In an embodiment, healthy skin can be determined by visibly seeing an even skin tone. In an embodiment, healthy skin can be determined by visibly seeing a smooth, glowing complexion. In an embodiment, a silk coated fabric decreases irritation of the skin. In an embodiment, a decrease in irritation of the skin can result in a decrease in skin bumps or sores. In an embodiment, a decrease in irritation of the skin can result in a decrease in scaly or red skin. In an embodiment, a decrease in irritation of the skin can result in a decrease in itchiness or burning. In an embodiment, a silk coated fabric decreases inflammation of the skin. In an embodiment, a silk coated textile of the present disclosure has the qualities of being waterproof, breathable, and elastic and possess a number of other qualities which are highly desirable in action sportswear. In an embodiment, a silk coated textile of the present disclosure manufactured from a silk fabric of the present disclosure further includes LYCRA brand spandex fibers (polyester-polyurethane copolymer).

In an embodiment, a textile at least partially coated with an aqueous solution of pure silk fibroin-based protein fragments of the present disclosure is a breathable fabric. In an embodiment, a textile at least partially coated with an aqueous solution of pure silk fibroin-based protein fragments of the present disclosure is a water-resistant fabric. In an embodiment, a textile at least partially coated with an aqueous solution of pure silk fibroin-based protein fragments of the present disclosure is a shrink-resistant fabric. In an embodiment, a textile at least partially coated with an aqueous solution of pure silk fibroin-based protein fragments of the present disclosure is a machine-washable fabric. In an embodiment, a textile at least partially coated with an aqueous solution of pure silk fibroin-based protein fragments of the present disclosure is a wrinkle resistant fabric. In an embodiment, textile at least partially coated with an aqueous solution of pure silk fibroin-based protein fragments of the present disclosure provides moisture and vitamins to the skin.

In an embodiment, the textile at least partially coated with an aqueous solution of pure silk fibroin-based protein fragments of the present disclosure has an accumulative one-way transport index of greater than 140. In an embodiment, the textile at least partially coated with an aqueous solution of pure silk fibroin-based protein fragments of the present disclosure has an accumulative one-way transport index of greater than 120. In an embodiment, the textile at least partially coated with an aqueous solution of pure silk fibroin-based protein fragments of the present disclosure has an accumulative one-way transport index of greater than 100. In an embodiment, the textile at least partially coated with an aqueous solution of pure silk fibroin-based protein fragments of the present disclosure has an accumulative one-way transport index of greater than 80.

In an embodiment, the textile at least partially coated with an aqueous solution of pure silk fibroin-based protein fragments of the present disclosure has an overall moisture management capability of greater than 0.4. In an embodiment, the textile at least partially coated with an aqueous solution of pure silk fibroin-based protein fragments of the present disclosure has an overall moisture management capability of greater than 0.35. In an embodiment, the textile at least partially coated with an aqueous solution of pure silk fibroin-based protein fragments of the present disclosure has an overall moisture management capability of greater than 0.3. In an embodiment, the textile at least partially coated with an aqueous solution of pure silk fibroin-based protein fragments of the present disclosure has an overall moisture management capability of greater than 0.25.

In an embodiment, the textile at least partially coated with an aqueous solution of pure silk fibroin-based protein fragments of the present disclosure has a wetting time of at least 3 seconds. In an embodiment, the textile at least partially coated with an aqueous solution of pure silk fibroin-based protein fragments of the present disclosure has a wetting time of at least 2.5 seconds. In an embodiment, the textile at least partially coated with an aqueous solution of pure silk fibroin-based protein fragments of the present disclosure has a wetting time of at least 2 seconds. In an embodiment, the textile at least partially coated with an aqueous solution of pure silk fibroin-based protein fragments of the present disclosure has a wetting time of at least 1.5 seconds.

In an embodiment, the textile at least partially coated with an aqueous solution of pure silk fibroin-based protein fragments of the present disclosure has a top absorption time of at least 50 seconds. In an embodiment, the textile at least partially coated with an aqueous solution of pure silk fibroin-based protein fragments of the present disclosure has a top absorption time of at least 40 seconds. In an embodiment, the textile at least partially coated with an aqueous solution of pure silk fibroin-based protein fragments of the present disclosure has a top absorption time of at least 30 seconds. In an embodiment, the textile at least partially coated with an aqueous solution of pure silk fibroin-based protein fragments of the present disclosure has a top absorption time of at least 29 seconds, 28 seconds, 27 seconds, 26 seconds, 25 seconds, 24 seconds, 23 seconds, 22 seconds, 21 seconds, 20 seconds, 19 seconds, 18 seconds, 17 seconds, 16 seconds, 15 seconds, 14 seconds, 13 seconds, 12 seconds, 11 seconds, 10 seconds, 9 seconds, 8 seconds, 7 seconds, 6 seconds, 5 seconds, 4 seconds, 3 seconds, 2 seconds, or 1 second.

In an embodiment, the textile at least partially coated with an aqueous solution of pure silk fibroin-based protein fragments of the present disclosure has a bottom absorption time of at least 80 seconds. In an embodiment, the textile at least partially coated with an aqueous solution of pure silk fibroin-based protein fragments of the present disclosure has a bottom absorption time of at least 70 seconds. In an embodiment, the textile at least partially coated with an aqueous solution of pure silk fibroin-based protein fragments of the present disclosure has a bottom absorption time of at least 60 seconds. In an embodiment, the textile at least partially coated with an aqueous solution of pure silk fibroin-based protein fragments of the present disclosure has a bottom absorption time of at least 50 seconds. In an embodiment, the textile at least partially coated with an aqueous solution of pure silk fibroin-based protein fragments of the present disclosure has a bottom absorption time of at least 40 seconds.

In an embodiment, the textile at least partially coated with an aqueous solution of pure silk fibroin-based protein fragments of the present disclosure has a spreading speed of at least 1.6 mm/second. In an embodiment, the textile at least partially coated with an aqueous solution of pure silk fibroin-based protein fragments of the present disclosure has a spreading speed of at least 1.4 mm/second. In an embodiment, the textile at least partially coated with an aqueous solution of pure silk fibroin-based protein fragments of the present disclosure has a spreading speed of at least 1.2 mm/second. In an embodiment, the textile at least partially coated with an aqueous solution of pure silk fibroin-based protein fragments of the present disclosure has a spreading speed of at least 1.0 mm/second. In an embodiment, the textile at least partially coated with an aqueous solution of pure silk fibroin-based protein fragments of the present disclosure has a spreading speed of at least 0.8 mm/second.

In an embodiment, the textile at least partially coated with an aqueous solution of pure silk fibroin-based protein fragments of the present disclosure shows less than 2000% microbial growth over 24 hours. In an embodiment, the textile at least partially coated with an aqueous solution of pure silk fibroin-based protein fragments of the present disclosure shows less than 1000% microbial growth over 24 hours. In an embodiment, the textile at least partially coated with an aqueous solution of pure silk fibroin-based protein fragments of the present disclosure shows less than 500% microbial growth over 24 hours. In an embodiment, the textile at least partially coated with an aqueous solution of pure silk fibroin-based protein fragments of the present disclosure shows less than 400% microbial growth over 24 hours. In an embodiment, the textile at least partially coated with an aqueous solution of pure silk fibroin-based protein fragments of the present disclosure shows less than 300% microbial growth over 24 hours. In an embodiment, the textile at least partially coated with an aqueous solution of pure silk fibroin-based protein fragments of the present disclosure shows less than 200% microbial growth over 24 hours. In some embodiments, as described herein, the reduction in microbial growth may be measured and provided after one or more wash cycles in non-chlorine bleach. In some embodiments, solutions that include silk fibroin-based protein fragments may include an additional chemical agent, as described herein, that may provide antimicrobial, antifungal, and/or antibacterial properties.

In an embodiment, the textile at least partially coated with an aqueous solution of pure silk fibroin-based protein fragments of the present disclosure shows less than 2000% bacterial growth over 24 hours. In an embodiment, the textile at least partially coated with an aqueous solution of pure silk fibroin-based protein fragments of the present disclosure shows less than 1000% bacterial growth over 24 hours. In an embodiment, the textile at least partially coated with an aqueous solution of pure silk fibroin-based protein fragments of the present disclosure shows less than 500% bacterial growth over 24 hours. In an embodiment, the textile at least partially coated with an aqueous solution of pure silk fibroin-based protein fragments of the present disclosure shows less than 400% bacterial growth over 24 hours. In an embodiment, the textile at least partially coated with an aqueous solution of pure silk fibroin-based protein fragments of the present disclosure shows less than 300% bacterial growth over 24 hours. In an embodiment, the textile at least partially coated with an aqueous solution of pure silk fibroin-based protein fragments of the present disclosure shows less than 200% bacterial growth over 24 hours.

In an embodiment, the textile at least partially coated with an aqueous solution of pure silk fibroin-based protein fragments of the present disclosure shows less than 2000% fungal growth over 24 hours. In an embodiment, the textile at least partially coated with an aqueous solution of pure silk fibroin-based protein fragments of the present disclosure shows less than 1000% fungal growth over 24 hours. In an embodiment, the textile at least partially coated with an aqueous solution of pure silk fibroin-based protein fragments of the present disclosure shows less than 500% fungal growth over 24 hours. In an embodiment, the textile at least partially coated with an aqueous solution of pure silk fibroin-based protein fragments of the present disclosure shows less than 400% fungal growth over 24 hours. In an embodiment, the textile at least partially coated with an aqueous solution of pure silk fibroin-based protein fragments of the present disclosure shows less than 300% fungal growth over 24 hours. In an embodiment, the textile at least partially coated with an aqueous solution of pure silk fibroin-based protein fragments of the present disclosure shows less than 200% fungal growth over 24 hours.

In an embodiment, the textile at least partially coated with an aqueous solution of pure silk fibroin-based protein fragments of the present disclosure shows less than 2000% growth of *Staphylococcus aureus* over 24 hours. In an embodiment, the textile at least partially coated with an aqueous solution of pure silk fibroin-based protein fragments of the present disclosure shows less than 1000% growth of *Staphylococcus aureus* over 24 hours. In an embodiment, the textile at least partially coated with an aqueous solution of pure silk fibroin-based protein fragments of the present disclosure shows less than 500% growth of *Staphylococcus aureus* over 24 hours. In an embodiment, the textile at least partially coated with an aqueous solution of pure silk fibroin-based protein fragments of the present disclosure shows less than 400% growth of *Staphylococcus aureus* over 24 hours. In an embodiment, the textile at least partially coated with an aqueous solution of pure silk fibroin-based protein fragments of the present disclosure shows less than 300% growth of *Staphylococcus aureus* over 24 hours. In an embodiment, the textile at least partially coated with an aqueous solution of pure silk fibroin-based protein fragments of the present disclosure shows less than 200% growth of *Staphylococcus aureus* over 24 hours.

In an embodiment, the textile at least partially coated with an aqueous solution of pure silk fibroin-based protein fragments of the present disclosure shows less than 2000% growth of *Klebsiella pneumoniae* over 24 hours. In an embodiment, the textile at least partially coated with an aqueous solution of pure silk fibroin-based protein fragments of the present disclosure shows less than 1000% growth of *Klebsiella pneumoniae* over 24 hours. In an embodiment, the textile at least partially coated with an aqueous solution of pure silk fibroin-based protein fragments of the present disclosure shows less than 500% growth of *Klebsiella pneumoniae* over 24 hours. In an embodiment, the textile at least partially coated with an aqueous solution of pure silk fibroin-based protein fragments of the present disclosure shows less than 400% growth of *Klebsiella pneumoniae* over 24 hours. In an embodiment, the textile at least partially coated with an aqueous solution of pure silk fibroin-based protein fragments of the present disclosure shows less than 300% growth of *Klebsiella pneumoniae* over 24 hours. In an embodiment, the textile at least partially coated with an aqueous solution of pure silk fibroin-based protein fragments of the present disclosure shows less than 200% growth of *Klebsiella pneumoniae* over 24 hours.

In an embodiment, an aqueous solution of pure silk fibroin-based protein fragments of the present disclosure is used to coat a textile. In an embodiment, the concentration of silk in the solution ranges from about 0.001% to about 20.0%. In an embodiment, the concentration of silk in the solution ranges from about 0.01% to about 15.0%. In an embodiment, the concentration of silk in the solution ranges from about 0.5% to about 10.0%. In an embodiment, the concentration of silk in the solution ranges from about 1.0% to about 5.0%. In an embodiment, an aqueous solution of pure silk fibroin-based protein fragments of the present disclosure is applied directly to a fabric. Alternatively, silk microsphere and any additives may be used for coating a fabric. In an embodiment, additives can be added to an aqueous solution of pure silk fibroin-based protein fragments of the present disclosure before coating (e.g., alcohols) to further enhance material properties. In an embodiment, a silk coating of the present disclosure can have a pattern to optimize properties of the silk on the fabric. In an embodiment, a coating is applied to a fabric under tension and/or lax to vary penetration in to the fabric.

In an embodiment, a silk coating of the present disclosure can be applied at the yarn level, followed by creation of a fabric once the yarn is coated. In an embodiment, an aqueous solution of pure silk fibroin-based protein fragments of the present disclosure can be spun into fibers to make a silk fabric and/or silk fabric blend with other materials known in the apparel industry.

In an embodiment, a method for silk coating a fabric includes immersion of the fabric in any of the aqueous solutions of pure silk fibroin-based protein fragments of the present disclosure. In an embodiment, a method for silk coating a fabric includes spraying. In an embodiment, a method for silk coating a fabric includes chemical vapor deposition. In an embodiment, a method for silk coating a fabric includes electrochemical coating. In an embodiment, a method for silk coating a fabric includes knife coating to spread any of the aqueous solutions of pure silk fibroin-based protein fragments of the present disclosure onto the fabric. The coated fabric may then be air dried, dried under heat/air flow, or cross-linked to the fabric surface. In an embodiment, a drying process includes curing with additives and/or ambient condition.

According to aspects illustrated herein, methods for preparing aqueous solutions of pure silk fibroin-based protein fragments are disclosed. In an embodiment, at least one pure silk fibroin-based protein fragment (SPF) mixture solution having a specific average weight average molecular weight (MW) range and polydispersity is created. In an embodiment, at least SPF mixture solution having a MW range between about 6 kDa and 17 kDa and a polydispersity range between about 1.5 and about 3.0 is created. In an embodiment, at least one SPF mixture solution having a MW between about 17 kDa and 39 kDa and a polydispersity range between about 1.5 and about 3.0 is created. In an embodiment, at least one SPF mixture solution having a MW range between about 39 kDa and 80 kDa and a polydispersity range between about 1.5 and about 3.0 is created.

In one embodiment, the invention relates to a material including one or more fibers including a protein, wherein a substantial portion of fibers are coated with silk fibroin-based protein fragments. In some embodiments, the material includes one or more of a woven material, a non-woven material, a knit material, and a crochet material. In some embodiments, the material includes fabric, thread, yarn, fiber, or a combination thereof. In some embodiments, the material includes wool. In some embodiments, the material includes cashmere. In some embodiments, the wool includes one or more of natural wool, synthetic wool, alpaca fleece, alpaca wool, lama fleece, lama wool, cashmere, sheep fleece, sheep wool, mohair wool, camel hair, or angora wool. In some embodiments, the silk fibroin-based protein fragments include one or more of low molecular weight silk fibroin-based protein fragments, medium molecular weight silk fibroin-based protein fragments, and high molecular weight silk fibroin-based protein fragments. In some embodiments, the silk fibroin-based protein fragments have an average molecular weight from about 1 kDa to about 350 kDa. In some embodiments, the silk fibroin-based protein fragments have a polydispersity from about 1.0 to about 5.0.

In one embodiment, the invention relates to coating a material including one or more proteinaceous fibers, wherein a substantial portion of the proteinaceous fibers are coated with silk fibroin-based protein fragments. In some embodiments, the proteinaceous fibers include keratin. In some embodiments, the proteinaceous fibers include hair. In some embodiments, the proteinaceous fibers include human hair or animal hair. In some embodiments, the silk fibroin-based protein fragments include one or more of low molecular weight silk fibroin-based protein fragments, medium molecular weight silk fibroin-based protein fragments, and high molecular weight silk fibroin-based protein fragments. In some embodiments, the silk fibroin-based protein fragments have an average molecular weight from about 1 kDa to about 350 kDa. In some embodiments, the silk fibroin-based protein fragments have a polydispersity from about 1.0 to about 5.0.

In one embodiment, the invention relates to a method of making a silk fibroin coated material, the method including preparing a silk fibroin solution including low molecular weight silk fibroin-based protein fragments, coating a surface of the material with the silk fibroin solution, and drying the surface of the material that has been coated with the silk fibroin solution to provide the silk fibroin coated material. In one embodiment, the invention relates to a method of improving hand in a material, the method including preparing a silk fibroin solution including low molecular weight silk fibroin-based protein fragments, coating a surface of the material with the silk fibroin solution, and drying the surface of the material that has been coated with the silk fibroin solution, wherein the resulting coated material has an improved hand compared to the uncoated material. In one embodiment, the invention relates to a method of improving hand retention on laundering in a material, the method including preparing a silk fibroin solution including low molecular weight silk fibroin-based protein fragments, coating a surface of the material with the silk fibroin solution, and drying the surface of the material that has been coated with the silk fibroin solution, wherein upon laundering, the coated material retains a substantial portion of its initial hand prior to laundering. In one embodiment, the invention relates to a method of improving size and/or shape retention on laundering in a material, the method including preparing a silk fibroin solution including low molecular weight silk fibroin-based protein fragments, coating a surface of the material with the silk fibroin solution, and drying the surface of the material that has been coated with the silk fibroin solution, wherein upon laundering, the coated material substantially retains its initial size and/or shape prior to laundering. In one embodiment, the invention relates to a method of improving pilling resistance in a material, the method including preparing a silk fibroin solution including low molecular weight silk fibroin-based protein fragments, coating a surface of the material with the silk fibroin solution, and drying the surface of the material that has been coated with the silk fibroin solution, wherein the coated material has an improved pilling resistance compared to a similar material which was not so coated. In one embodiment, the invention relates to a method of improving water repellency in a material, the method including preparing a silk fibroin solution comprising low molecular weight silk fibroin-based protein fragments, coating a surface of the material with the silk fibroin solution, and drying the surface of the material that has been coated with the silk fibroin solution, wherein the coated material has an improved water repellency compared to a similar material which was not so coated. In some embodiments, the methods further include an additional treatment step. In some embodiments, the additional treatment step is a pre-treatment step (e.g., preparation of an article surface before treatment or coating), a post treatment step, or a final treatment step. In some embodiments, the additional treatment step comprises an acidic treatment or an alcohol treatment. In some embodiments, the silk fibroin solution further includes medium molecular weight silk fibroin-based protein fragments. In some embodiments, the w/w ratio between low molecular weight silk fibroin-based protein fragments and medium molecular weight silk fibroin-based protein fragments is about 90:10, about 80:20, about 75:25, about 70:30, about 66:34, about 60:40, about 50:50, about 40:60, about 34:66, about 30:70, about 25:75, about 20:80, or about 10:90. In some embodiments, the w/w ratio between low molecular weight silk fibroin-based protein fragments and medium molecular weight silk fibroin-based protein fragments is about 3:1. In some embodiments, the silk fibroin solution further includes high molecular weight silk fibroin-based protein fragments. In some embodiments, the silk fibroin solution further includes medium molecular weight silk fibroin-based protein fragments, and high molecular weight silk fibroin-based protein fragments. In some embodiments, drying the surface of the material includes heating the surface of the material without substantially modifying silk fibroin coating performance. In some embodiments, the silk fibroin solution includes silk fibroin-based protein fragments at less than about 0.001% by volume (v/v), less than about 0.1% v/v, less than about 1% v/v, less than about 2.5% v/v, or less than about 5% v/v. In some embodiments, the silk fibroin solution includes silk fibroin-based protein fragments at about 0.5% by v/v, weight/weight (w/w), or weight/volume (w/v). In some embodiments, the silk fibroin solution includes a Brønsted acid. In some embodiments, the silk fibroin solution includes one or more of citric acid and acetic acid. In some embodiments, the material includes one or more of a woven material, a non-woven material, a knit material, and a crochet material. In some embodiments, the material includes fabric, thread, yarn, fiber, or a combination thereof. In some embodiments, the material includes wool. In some embodiments, the material includes cashmere. In some embodiments, the wool includes one or more of natural wool, synthetic wool, alpaca fleece, alpaca wool, lama fleece, lama wool, cashmere, sheep fleece, sheep wool, mohair wool, camel hair, angora wool.

According to aspects illustrated herein, there is disclosed a composition that includes pure silk fibroin-based protein fragments that are substantially devoid of sericin, wherein the composition has an average weight average molecular weight ranging from about 6 kDa to about 17 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.01 wt % to about 30.0 wt % pure silk fibroin-based protein fragments. In some embodiments, the pure silk fibroin-based protein fragments are stable in the solution for at least 30 days. In some embodiments, the pure silk fibroin-based protein fragments are stable in the solution for at least 30 days at about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., or about 25° C. In some embodiments, the pure silk fibroin-based protein fragments are stable in the solution for at least 30 days at room temperature. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a composition that includes pure silk fibroin-based protein fragments that are substantially devoid of sericin, wherein the composition has an average weight average molecular weight ranging from about 17 kDa to about 39 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.01 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a composition that includes pure silk fibroin-based protein fragments that are substantially devoid of sericin, wherein the composition has an average weight average molecular weight ranging from about 39 kDa to about 80 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.01 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a gel that includes pure silk fibroin-based protein fragments substantially devoid of sericin and comprising: an average weight average molecular weight ranging from about 17 kDa to about 39 kDa; and a polydispersity of between about 1.5 and about 3.0; and water from about 20 wt. % to about 99.9 wt. %, wherein the gel includes between 0 ppm and 500 ppm of inorganic residuals, and wherein the gel includes between 0 ppm and 500 ppm of organic residuals. In an embodiment, the gel includes between about 1.0% and about 50.0% crystalline protein domains. In an embodiment, the gel includes from about 0.1 wt. % to about 6.0 wt. % of pure silk fibroin-based protein fragments. In an embodiment, the gel has a pH from about 1.0 to about 7.0. In an embodiment, the gel further includes from about 0.5 wt. % to about 20.0 wt. % of vitamin C or a derivative thereof. In an embodiment, the vitamin C or a derivative thereof remains stable within the gel for a period of from about 5 days to about 5 years. In an embodiment, the vitamin C or a derivative thereof is stable within the gel so as to result in release of the vitamin C in a biologically active form. In an embodiment, the gel further includes an additive selected from the group consisting of vitamin E, rosemary oil, rose oil, lemon juice, lemon grass oil and caffeine. In an embodiment, the gel is packaged in an airtight container. In an embodiment, the pure silk fibroin-based protein fragments are hypoallergenic. In an embodiment, the gel has less than 10 colony forming units per milliliter.

According to aspects illustrated herein, there is disclosed a method for preparing an aqueous solution of pure silk fibroin-based protein fragments having an average weight average molecular weight ranging from about 6 kDa to about 17 kDa, the method including the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 17 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, there is disclosed a method for preparing an aqueous solution of pure silk fibroin-based protein fragments having an average weight average molecular weight ranging from about 17 kDa to about 39 kDa, the method including the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 39 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, there is disclosed a method for preparing an aqueous solution of pure silk fibroin-based protein fragments having an average weight average molecular weight ranging from about 39 kDa to about 80 kDa, the method including the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, a method is disclosed for producing silk gels having entrapped molecules or therapeutic agents such as those listed in the following paragraphs. In an embodiment, at least one molecule or therapeutic agent of interest is physically entrapped into a SPF mixture solution of the present disclosure during processing into aqueous gels. An aqueous silk gel of the present disclosure can be used to release at least one molecule or therapeutic agent of interest.

In some embodiments, the w/w ratio between low molecular weight silk and medium molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and medium molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and medium molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. In an embodiment, the w/w ratio between low molecular weight silk and medium molecular weight silk is about 3:1. In an embodiment, the w/w ratio between low molecular weight silk and medium molecular weight silk is about 1:3.

In some embodiments, the w/w ratio between low molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the silk fibroin coated materials of the invention, for example a fiber, a yarn, or a fabric, may be coated with compositions including medium molecular weight silk and high molecular weight silk. In some embodiments, the w/w ratio between medium molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between medium molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between medium molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the silk fibroin coated materials of the invention, for example a fiber, a yarn, or a fabric, may be coated with compositions including low molecular weight silk, medium molecular weight silk, and high molecular weight silk. In an embodiment, the w/w ratio between low molecular weight silk, medium molecular weight silk, and high molecular weight silk is about 1:1:8, 1:2:7, 1:3:6, 1:4:5, 1:5:4, 1:6:3, 1:7:2, 1:8:1, 2:1:7, 2:2:6, 2:3:5, 2:4:4, 2:5:3, 2:6:2, 2:7:1, 3:1:6, 3:2:5, 3:3:4, 3:4:3, 3:5:2, 3:6:1, 4:1:5, 4:2:4, 4:3:3, 4:4:2, 4:5:1, 5:1:4, 5:2:3, 5:3:2, 5:4:1, 6:1:3, 6:2:2, 6:3:1, 7:1:2, 7:2:1, or 8:1:1. In an embodiment, the w/w ratio between low molecular weight silk, medium molecular weight silk, and high molecular weight silk is about 3:0.1:0.9, 3:0.2:0.8, 3:0.3:0.7, 3:0.4:0.6, 3:0.5:0.5, 3:0.6:0.4, 3:0.7:0.3, 3:0.8:0.2, or 3:0.9:0.1.

According to aspects illustrated herein, pure silk fibroin-based protein fragments from aqueous solutions of the present disclosure can be formed into yarns and fabrics including for example, woven or weaved fabrics, and these fabrics can be used in textiles, as described above.

According to aspects illustrated herein, silk fabric manufactured from SPF mixture solutions of the present disclosure are disclosed. In an embodiment, at least one molecule or therapeutic agent of interest is physically entrapped into a SPF mixture solution of the present disclosure. A silk film of the present disclosure can be used to release at least one molecule or therapeutic agent of interest.

In some embodiments, the invention may include an article having a fiber or yarn having a coating, wherein the coating may include silk based proteins or fragments thereof having a weight average molecular weight range of about 5 kDa to about 144 kDa. In some embodiments, the article may be a fabric. In some embodiments, the silk based proteins or fragments thereof may include silk fibroin-based proteins or protein fragments having about 0.01% (w/w) to about 10% (w/w) sericin.

In some embodiments, the silk based proteins or fragments thereof may be selected from the group consisting of natural silk based proteins or fragments thereof that may be selected from the group consisting of spider silk based proteins or fragments thereof, silkworm silk based proteins or fragments thereof, and combinations thereof.

In some embodiments, the silk based proteins or fragments thereof may be natural silk based proteins or fragments thereof that may be selected from the group consisting of spider silk based proteins or fragments thereof, silkworm silk based proteins or fragments thereof, and combinations thereof.

In some embodiments, the natural silk based proteins or fragments may be silkworm silk based proteins or fragments thereof, and the silkworm silk based proteins or fragments thereof may be *Bombyx mori* silk based proteins or fragments thereof.

In some embodiments, the silk based proteins or fragments may include silk and a copolymer.

In some embodiments, the silk based proteins or protein fragments thereof may have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof may have a polydispersity of between about 1.5 and about 3 In some embodiments, the natural silk based proteins or fragments may be silkworm silk based proteins or fragments thereof, and the silkworm silk based proteins or fragments thereof may be *Bombyx mori* silk based proteins or fragments thereof.

In some embodiments, the silk based proteins or fragments may include silk and a copolymer.

In some embodiments, the silk based proteins or protein fragments thereof may have an average weight average molecular weight range of about 1 kDa to about 350 kDa, wherein the silk based proteins or fragments thereof may have a polydispersity of between about 1.0 and about 5.0, and wherein the proteins or protein fragments, prior to coating the fabric, do not spontaneously or gradually gelate and do not visibly change in color or turbidity when in a solution for at least 10 days.

In some embodiments, the fiber or yarn may be selected from the group consisting of natural fiber or yarn, synthetic fiber or yarn, or combinations thereof.

In some embodiments, the fiber or yarn may be natural fiber or yarn selected from the group consisting of cotton, alpaca fleece, alpaca wool, lama fleece, lama wool, cotton, cashmere, sheep fleece, sheep wool, and combinations thereof. In some embodiments, the fiber or yarn may be natural fiber or yarn comprising wool, and combinations thereof. In some embodiments, the fiber or yarn may be natural fiber or yarn comprising cashmere, and combinations thereof.

In some embodiments, the fiber or yarn may be synthetic fiber or yarn selected from the group consisting of polyester, nylon, polyester-polyurethane copolymer, and combinations thereof.

In some embodiments, the fabric may exhibit an improved property, wherein the improved property may be an accumulative one-way moisture transport index selected from the group consisting of greater than 40%, greater than 60%, greater than 80%, greater than 100%, greater than 120%, greater than 140%, greater than 160%, and greater than 180%.

In some embodiments, the fabric may exhibit an improved property, wherein the improved property may be an accumulative one-way transport capability increase relative to uncoated fabric selected from the group consisting of 1.2 fold, 1.5 fold, 2.0 fold, 3.0 fold, 4.0 fold, 5.0 fold, and 10 fold.

In some embodiments, the fabric may exhibit an improved property, wherein the improved property may be an overall moisture management capability selected from the group consisting of greater than 0.05, greater than 0.10, greater than 0.15, greater than 0.20, greater than 0.25, greater than 0.30, greater than 0.35, greater than 0.40, greater than 0.50, greater than 0.60, greater than 0.70, and greater than 0.80. In some embodiments, the improved property may be determined after a period of machine washing cycles selected from the group consisting of 5 cycles, 10 cycles, 25 cycles, and 50 cycles.

In some embodiments, the fabric may exhibit substantially no increase in microbial growth after a number of machine washing cycles selected from the group consisting of 5 cycles, 10 cycles, 25 cycles, and 50 cycles. In some embodiments, the microbial growth may be microbial growth of a microbe selected from the group consisting of *Staphylococcus aureus, Klebsiella pneumoniae*, and combinations thereof. In some embodiments, the microbial growth may be reduced by a percentage selected from the group consisting of 50%, 100%, 500%, 1000%, 2000%, and 3000% compared to an uncoated fabric.

In some embodiments, the coating may be applied to the fabric at the fiber level prior to forming the fabric.

In some embodiments, the coating may be applied to the fabric at the fabric level. In some embodiments, the fabric may be bath coated. In some embodiments, the fabric may be spray coated. In some embodiments, the fabric may be coated with a stencil. In some embodiments, the coating may be applied to at least one side of the fabric using a method selected from the group consisting of a bath coating process, a spray coating process, a stencil process, a silk-foam based process, and a roller-based process.

In some embodiments, the coating may have a thickness of about one nanolayer.

In some embodiments, the coating may have a thickness selected from the group consisting of about 5 nm, about 10 nm, about 15 nm, about 20 nm, about 25 nm, about 50 nm, about 100 nm, about 200 nm, about 500 nm, about 1 μm, about 5 μm, about 10 μm, and about 20 μm.

In some embodiments, the coating may be adsorbed on the fabric.

In some embodiments, the coating may be attached to the fabric through chemical, enzymatic, thermal, or irradiative cross-linking.

In some embodiments, the hand of the coated fabric may be improved relative to an uncoated fabric.

In some embodiments, the hand of the coated fabric that may be improved may be selected from the group consisting of softness, crispness, dryness, silkiness, and combinations thereof.

In some embodiments, a flame retardation property of the coated fabric may be improved relative to an uncoated fabric.

In some embodiments, a flame retardation property of an uncoated fabric may not be adversely affected by the coating.

In some embodiments, the abrasion resistance may be improved relative to an uncoated fabric.

In an embodiment, the invention may include an article comprising a textile or leather having a coating, wherein the coating comprises silk based proteins or fragments thereof having a weight average molecular weight range of about 5 kDa to about 144 kDa, or about 1 kDa to about 350 kDa.

In some embodiments, the silk based proteins or protein fragments thereof have an average weight average molecular weight range of about 1 kDa to about 350 kDa, wherein the silk based proteins or fragments thereof have a polydispersity of between about 1.0 and about 5.0, and wherein the proteins or protein fragments, prior to coating the fabric, do not spontaneously or gradually gelate and do not visibly change in color or turbidity when in a solution for at least 10 days.

In some embodiments, at least one property of the article may be improved, wherein the property that may be improved may be selected from the group consisting of color retention, resistance to microbial growth, resistance to bacterial growth, resistance to fungal growth, resistance to the buildup of static electrical charge, resistance to the growth of mildew, transparency of the coating, resistance to freeze-thaw cycle damage, resistance from abrasion, blocking of ultraviolet (UV) radiation, regulation of the body temperature of a wearer, resistance to tearing, elasticity of the article, rebound dampening, tendency to cause itching in the wearer, thermal insulation of the wearer, wrinkle resistance, stain resistance, stickiness to skin, and flame resistance.

In some embodiments, the article may be a textile used for apparel.

In some embodiments, the article may be fabricated as an item selected from the group consisting of an item of athletic apparel, an item of outdoor gear, a jacket, an overcoat, a shoe, a sneaker, a glove, an umbrella, a chair, a blanket, a towel, a surgical drape, a surgical gown, a laboratory coat, a wound dressing, a sterilization wrap, a surgical face mask, a surgical sleeve, a laboratory sleeve, a retention bandage, a support device, a compression bandage, a shoe cover, and a surgical blanket.

In some embodiments, the article may be a textile used to fabricate an automotive product.

In an embodiment, the invention may include a method of coating a fabric that may include the step of optionally applying a pretreatment selected from the group consisting of a wetting agent, a detergent, a sequestering or dispersing agent, an enzyme, a bleaching agent, an antifoaming agent, an anti-creasing agent, a dye dispersing agent, a dye leveling agent, a dye fixing agent, a dye special resin agent, a dye anti-reducing agent, a pigment dye system anti-migrating agent, a pigment dye system binder, a delave agent, a wrinkle free treatment, a softener, a handle modifier, a waterborne polyurethane dispersion, a finishing resin, an oil or water repellant, a flame retardant, a crosslinker, a thickener for technical finishing, or any combination thereof. In an embodiment, the method may include the step of applying a coating that may include a solution of silk based proteins or fragments thereof that may have an average molecular weight range of about 1 kDa to about 350 kDa, using a process selected from the group consisting of a continuous spray process, a continuous screen or stencil process, a continuous bath process, a batch spray process, a batch screen or stencil process, and a batch bath process. In an embodiment, the method may include the step of drying and optionally curing the coating.

In an embodiment, the silk based proteins or protein fragments thereof may have an average weight average molecular weight range of about 1 kDa to about 350 kDa, wherein the silk based proteins or fragments thereof may have a polydispersity of between about 1.0 and about 5.0, and optionally wherein the proteins or protein fragments, prior to coating the fabric, do not spontaneously or gradually gelate and do not visibly change in color or turbidity when in a solution for at least 10 days.

In one embodiment, the invention relates to a method of making a silk fibroin coated material, the method including preparing a silk fibroin solution comprising low molecular weight silk fibroin-based protein fragments, coating a surface of a material with the silk fibroin solution, and drying the surface of the material that has been coated with the silk fibroin solution to provide the silk fibroin coated material. In some embodiments, the silk fibroin solution further includes medium molecular weight silk fibroin-based protein fragments. In some embodiments, the w/w ratio between low molecular weight silk fibroin-based protein fragments and medium molecular weight silk fibroin-based protein fragments is about 90:10, about 80:20, about 75:25, about 70:30, about 66:34, about 60:40, about 50:50, about 40:60, about 34:66, about 30:70, about 25:75, about 20:80, or about 10:90. In some embodiments, the w/w ratio between low molecular weight silk fibroin-based protein fragments and medium molecular weight silk fibroin-based protein fragments is about 3:1. In some embodiments, the silk fibroin solution further includes high molecular weight silk fibroin-based protein fragments. In some embodiments, the silk fibroin solution further includes medium molecular weight silk fibroin-based protein fragments, and high molecular weight silk fibroin-based protein fragments. In some embodiments, drying the surface of the material includes heating the surface of the material without substantially modifying silk fibroin coating performance. In some embodiments, the silk fibroin solution includes silk fibroin-based protein fragments between 0.01% and 1% volume (v/v). In some embodiments, the silk fibroin solution includes silk fibroin-based protein fragments at about 0.25% by volume (v/v). In some embodiments, the polydispersity of the silk fibroin-based protein fragments is between 1.5 and 3. In some embodiments, the silk fibroin solution further includes a Brønsted acid. In some embodiments, the silk fibroin solution further includes one or more of citric acid and acetic acid. In some embodiments, the silk fibroin solution has an acidic pH. In some embodiments, the silk fibroin solution has a pH between 4 and 5. In some embodiments, the method further includes coating the material with a silicone solution. In some embodiments, the silicone solution has an acidic pH. In some embodiments, the silk fibroin solution coating precedes the silicone solution coating. In some embodiments, the material includes one or more of a woven material, a non-woven material, a knit material, and a crochet material. In some embodiments, the material includes fabric, thread, yarn, or a combination thereof. In some embodiments, the material includes one or more of polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, and/or LYCRA.

In one embodiment, the invention relates to a method of improving hand in a material, the method including coating a surface of the material with a silk fibroin solution including low molecular weight silk fibroin-based protein fragments, drying the material, and coating a surface of the material with a silicone solution, wherein the resulting coated material has an improved hand compared to the uncoated material. In one embodiment, the invention relates to a method of improving hand retention on laundering in a material, the method including coating a surface of the material with a silk fibroin solution including low molecular weight silk fibroin-based protein fragments, drying the material, and coating a surface of the material with a silicone solution, wherein upon laundering, the coated material retains at least about 80% of its initial hand prior to laundering. In one embodiment, the invention relates to a method of improving the water drop absorption time of a material, the method including coating a surface of the material with a silk fibroin solution including low molecular weight silk fibroin-based protein fragments, drying the material, and coating a surface of the material with a silicone solution, wherein the resulting coated material has an improved water drop absorption time compared to the uncoated material. In one embodiment, the invention relates to a method of improving the abrasion resistance of a material, the method including coating a surface of the material with a silk fibroin solution including low molecular weight silk fibroin-based protein fragments, drying the material, and coating a surface of the material with a silicone solution, wherein the resulting coated material has an improved abrasion resistance compared to the uncoated material. In some embodiments, the silk fibroin solution further includes medium molecular weight silk fibroin-based protein fragments. In some embodiments, the w/w ratio between low molecular weight silk fibroin-based protein fragments and medium molecular weight silk fibroin-based protein fragments is about 90:10, about 80:20, about 75:25, about 70:30, about 66:34, about 60:40, about 50:50, about 40:60, about 34:66, about 30:70, about 25:75, about 20:80, or about 10:90. In some embodiments, the w/w ratio between low molecular weight silk fibroin-based protein fragments and medium molecular weight silk fibroin-based protein fragments is about 3:1. In some embodiments, the silk fibroin solution further includes high molecular weight silk fibroin-based protein fragments. In some embodiments, the silk fibroin solution further includes medium molecular weight silk fibroin-based protein fragments, and high molecular weight silk fibroin-based protein fragments. In some embodiments, drying the surface of the material includes heating the surface of the material without substantially modifying silk fibroin coating performance. In some embodiments, the silk fibroin solution includes silk fibroin-based protein fragments between 0.01% and 1% volume (v/v). In some embodiments, the silk fibroin solution includes silk fibroin-based protein fragments at about 0.25% by volume (v/v). In some embodiments, the polydispersity of the silk fibroin-based protein fragments is between 1.5 and 3. In some embodiments, the silk fibroin solution further includes a Brønsted acid. In some embodiments, the silk fibroin solution further includes one or more of citric acid and acetic acid. In some embodiments, the silk fibroin solution has an acidic pH. In some embodiments, the silk fibroin solution has a pH between 4 and 5. In some embodiments, the silicone solution has an acidic pH. In some embodiments, the silk fibroin solution coating precedes the silicone solution coating. In some embodiments, the material includes one or more of a woven material, a non-woven material, a knit material, and a crochet material. In some embodiments, the material comprises fabric, thread, yarn, or a combination thereof. In some embodiments, the material includes one or more of polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, and/or LYCRA.

In an embodiment, the silk fibroin coated materials of the invention, for example a fiber, a yarn, or a fabric, may be coated with compositions including low molecular weight silk and medium molecular weight silk. In some embodiments, the w/w ratio between low molecular weight silk and medium molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and medium molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and medium molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. In an embodiment, the w/w ratio between low molecular weight silk and medium molecular weight silk is about 3:1. In an embodiment, the w/w ratio between low molecular weight silk and medium molecular weight silk is about 1:3.

In an embodiment, the silk fibroin coated materials of the invention, for example a fiber, a yarn, or a fabric, may be coated with compositions including low molecular weight silk and high molecular weight silk. In some embodiments, the w/w ratio between low molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the silk fibroin coated materials of the invention, for example a fiber, a yarn, or a fabric, may be coated with compositions including medium molecular weight silk and high molecular weight silk. In some embodiments, the w/w ratio between medium molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between medium molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between medium molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the silk fibroin coated materials of the invention, for example a fiber, a yarn, or a fabric, may be coated with compositions including low molecular weight silk, medium molecular weight silk, and high molecular weight silk. In an embodiment, the w/w ratio between low molecular weight silk, medium molecular weight silk, and high molecular weight silk is about 1:1:8, 1:2:7, 1:3:6, 1:4:5, 1:5:4, 1:6:3, 1:7:2, 1:8:1, 2:1:7, 2:2:6, 2:3:5, 2:4:4, 2:5:3, 2:6:2, 2:7:1, 3:1:6, 3:2:5, 3:3:4, 3:4:3, 3:5:2, 3:6:1, 4:1:5, 4:2:4, 4:3:3, 4:4:2, 4:5:1, 5:1:4, 5:2:3, 5:3:2, 5:4:1, 6:1:3, 6:2:2, 6:3:1, 7:1:2, 7:2:1, or 8:1:1. In an embodiment, the w/w ratio between low molecular weight silk, medium molecular weight silk, and high molecular weight silk is about 3:0.1:0.9, 3:0.2:0.8, 3:0.3:0.7, 3:0.4:0.6, 3:0.5:0.5, 3:0.6:0.4, 3:0.7:0.3, 3:0.8:0.2, or 3:0.9:0.1.

According to aspects illustrated herein, pure silk fibroin-based protein fragments from aqueous solutions of the present disclosure can be formed into yarns and fabrics including for example, woven or weaved fabrics, and these fabrics can be used in textiles, as described above.

In some embodiments, the fiber or yarn may be selected from the group consisting of synthetic fiber or yarn, or combinations thereof.

In some embodiments, the fabric may exhibit an improved property, wherein the improved property may be an accumulative one-way transport capability increase relative to uncoated fabric selected from the group consisting of 1.2 fold, 1.5 fold, 2.0 fold, 3.0 fold, 4.0 fold, 5.0 fold, and 10 fold.

In some embodiments, the fabric may exhibit an improved property, wherein the improved property may be an overall moisture management capability selected from the group consisting of greater than 0.05, greater than 0.10, greater than 0.15, greater than 0.20, greater than 0.25, greater than 0.30, greater than 0.35, greater than 0.40, greater than 0.50, greater than 0.60, greater than 0.70, and greater than 0.80. In some embodiments, the improved property may be determined after a period of machine washing cycles selected from the group consisting of 5 cycles, 10 cycles, 25 cycles, and 50 cycles.

In some embodiments, the fabric may exhibit substantially no increase in microbial growth after a number of machine washing cycles selected from the group consisting of 5 cycles, 10 cycles, 25 cycles, and 50 cycles. In some embodiments, the microbial growth may be microbial growth of a microbe selected from the group consisting of *Staphylococcus aureus, Klebsiella pneumoniae*, and combinations thereof. In some embodiments, the microbial growth may be reduced by a percentage selected from the group consisting of 50%, 100%, 500%, 1000%, 2000%, and 3000% compared to an uncoated fabric.

In some embodiments, the coating may be applied to the fabric at the fiber level prior to forming the fabric.

In some embodiments, the coating may be applied to the fabric at the fabric level. In some embodiments, the fabric may be bath coated. In some embodiments, the fabric may be spray coated. In some embodiments, the fabric may be coated with a stencil. In some embodiments, the coating may be applied to at least one side of the fabric using a method selected from the group consisting of a bath coating process, a spray coating process, a stencil process, a silk-foam based process, and a roller-based process.

In some embodiments, the coating may have a thickness of about one nanolayer.

In some embodiments, the coating may have a thickness selected from the group consisting of about 5 nm, about 10 nm, about 15 nm, about 20 nm, about 25 nm, about 50 nm, about 100 nm, about 200 nm, about 500 nm, about 1 µm, about 5 µm, about 10 µm, and about 20 µm.

In some embodiments, the coating may be adsorbed on the fabric.

In some embodiments, the coating may be attached to the fabric through chemical, enzymatic, thermal, or irradiative cross-linking.

In some embodiments, the hand of the coated fabric may be improved relative to an uncoated fabric.

In some embodiments, the hand of the coated fabric that may be improved may be selected from the group consisting of softness, crispness, dryness, silkiness, and combinations thereof.

In some embodiments, a flame retardation property of the coated fabric may be improved relative to an uncoated fabric.

In some embodiments, a flame retardation property of an uncoated fabric may not be adversely affected by the coating.

In some embodiments, the abrasion resistance may be improved relative to an uncoated fabric.

In an embodiment, the invention may include an article comprising a textile having a coating, wherein the coating comprises silk based proteins or fragments thereof having a weight average molecular weight range of about 1 kDa to about 350 kDa.

In some embodiments, the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, or between about 1.0 and about 5.0, and wherein the proteins or protein fragments, prior to coating the fabric, do not spontaneously or gradually gelate and do not visibly change in color or turbidity when in a solution for at least 10 days.

In some embodiments, at least one property of the article may be improved, wherein the property that may be improved may be selected from the group consisting of color retention, resistance to microbial growth, resistance to bacterial growth, resistance to fungal growth, resistance to the buildup of static electrical charge, resistance to the growth of mildew, transparency of the coating, resistance to freeze-thaw cycle damage, resistance from abrasion, blocking of ultraviolet (UV) radiation, regulation of the body temperature of a wearer, resistance to tearing, elasticity of the article, rebound dampening, tendency to cause itching in the wearer, thermal insulation of the wearer, wrinkle resistance, stain resistance, stickiness to skin, and flame resistance.

In some embodiments, the article may be a textile used for apparel.

In some embodiments, the article may be fabricated as an item selected from the group consisting of an item of athletic apparel, an item of outdoor gear, a jacket, an overcoat, a shoe, a sneaker, a glove, an umbrella, a chair, a blanket, a towel, a surgical drape, a surgical gown, a laboratory coat, a wound dressing, a sterilization wrap, a surgical face mask, a surgical sleeve, a laboratory sleeve, a retention bandage, a support device, a compression bandage, a shoe cover, and a surgical blanket.

In some embodiments, the article may be a textile, leather, or foam used to fabricate an automotive product.

In some embodiments, the article may be fabricated as an item selected from the group consisting of an upholstery, a foam cushion, a fabric cushion, a floor mat, a vehicle carpet, an automotive trim, a children's car seat, a seat belt, a safety harness, a headrest, an armrest, a dashboard, a sunvisor, a seat, an interior panel, an airbag, an airbag cover, a wiring harness, or an insulation.

In an embodiment, the invention may include a method of coating a fabric that may include the step of optionally applying a pretreatment selected from the group consisting of a wetting agent, a detergent, a sequestering or dispersing agent, an enzyme, a bleaching agent, an antifoaming agent, an anti-creasing agent, a dye dispersing agent, a dye leveling agent, a dye fixing agent, a dye special resin agent, a dye anti-reducing agent, a pigment dye system anti-migrating agent, a pigment dye system binder, a delave agent, a wrinkle free treatment, a softener, a handle modifier, a waterborne polyurethane dispersion, a finishing resin, an oil or water repellant, a flame retardant, a crosslinker, a thickener for technical finishing, or any combination thereof. In an embodiment, the method may include the step of applying a coating that may include a solution of silk based proteins or fragments thereof that may have an average molecular weight range of about 5 kDa to about 144 kDa, or about 1 kDa to about 350 kDa, using a process selected from the group consisting of a continuous spray process, a continuous screen or stencil process, a continuous bath process, a batch spray process, a batch screen or stencil process, and a batch bath process. In an embodiment, the method may include the step of drying and optionally curing the coating.

In an embodiment, the silk based proteins or protein fragments thereof may have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof may have a polydispersity of between about 1.0 and about 5.0, or between about 1.5 and about 3.0, and optionally wherein the proteins or protein fragments, prior to coating the fabric, do not spontaneously or gradually gelate and do not visibly change in color or turbidity when in a solution for at least 10 days.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 41A is a graph illustrating top spreading speed; FIG. 41B is a graph illustrating bottom spreading speed.

FIG. 43A is a graph illustrating wetting time of non-wicking finished; FIG. 43B is a graph illustrating wetting time of semi-finished before final setting.

FIG. 44A is a graph illustrating absorption time of non-wicking finished; FIG. 44B is a graph illustrating absorption time of semi-finished before final setting.

FIG. 46A is a graph illustrating accumulative one-way transport index of non-wicking finished; FIG. 46B is a graph illustrating accumulative one way transport index of semi-finished before final setting.

FIG. 61A is a graph illustrating summary of top spreading speed. FIG. 61B is a graph illustrating summary of bottom spreading speed.

FIG. 111 illustrates a scanning electron microscopy image of fabric sample FAB-10-SPRAY-B (seventh view).

FIG. 112 illustrates a scanning electron microscopy image of fabric sample FAB-10-SPRAY-C.

FIG. 113 illustrates a scanning electron microscopy image of fabric sample FAB-10-STEN-B (first view).

FIG. 114 illustrates a scanning electron microscopy image of fabric sample FAB-10-STEN-B (third view).

FIG. 115 illustrates a scanning electron microscopy image of fabric sample FAB-10-STEN-B (fifth view).

FIG. 116 illustrates a scanning electron microscopy image of fabric sample FAB-10-STEN-B (sixth view).

FIG. 117 illustrates a scanning electron microscopy image of fabric sample FAB-10-STEN-B (seventh view).

FIG. 118 illustrates a scanning electron microscopy image of a fabric control sample (first view).

FIG. 119 illustrates a scanning electron microscopy image of a fabric control sample (second view).

FIG. 120 illustrates a scanning electron microscopy image of a fabric control sample (third view).

FIG. 121 shows results from optical profiling measurements on the Mylar Control sample taken at the top, location 1 (shiny side).

FIG. 122 shows results from optical profiling measurements on the Mylar Control sample taken at the bottom, location 2 (more matte side).

Figure 123:
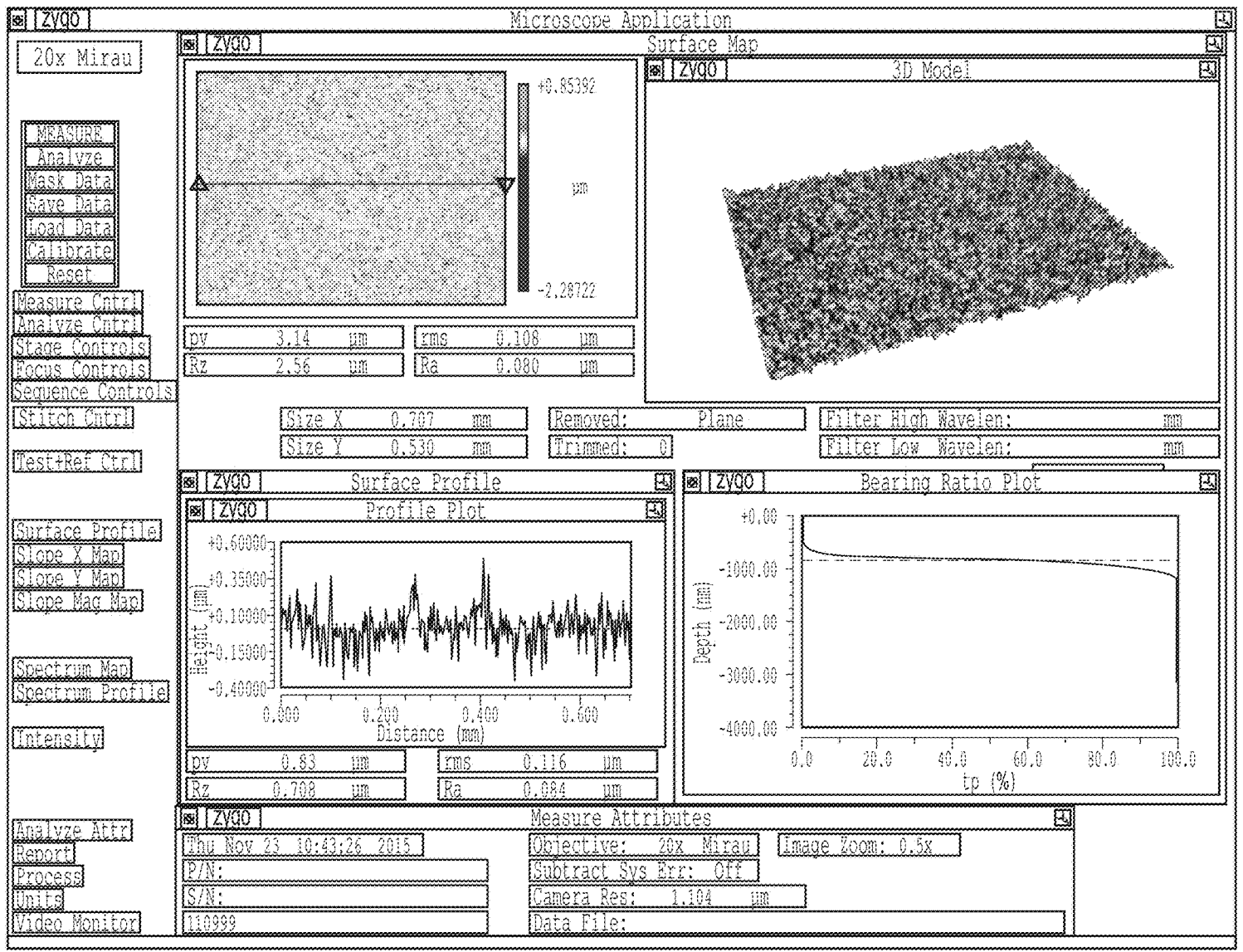

FIG. 123 shows results from optical profiling measurements on the Melinex Control sample taken at the top, location 1.

Figure 124:
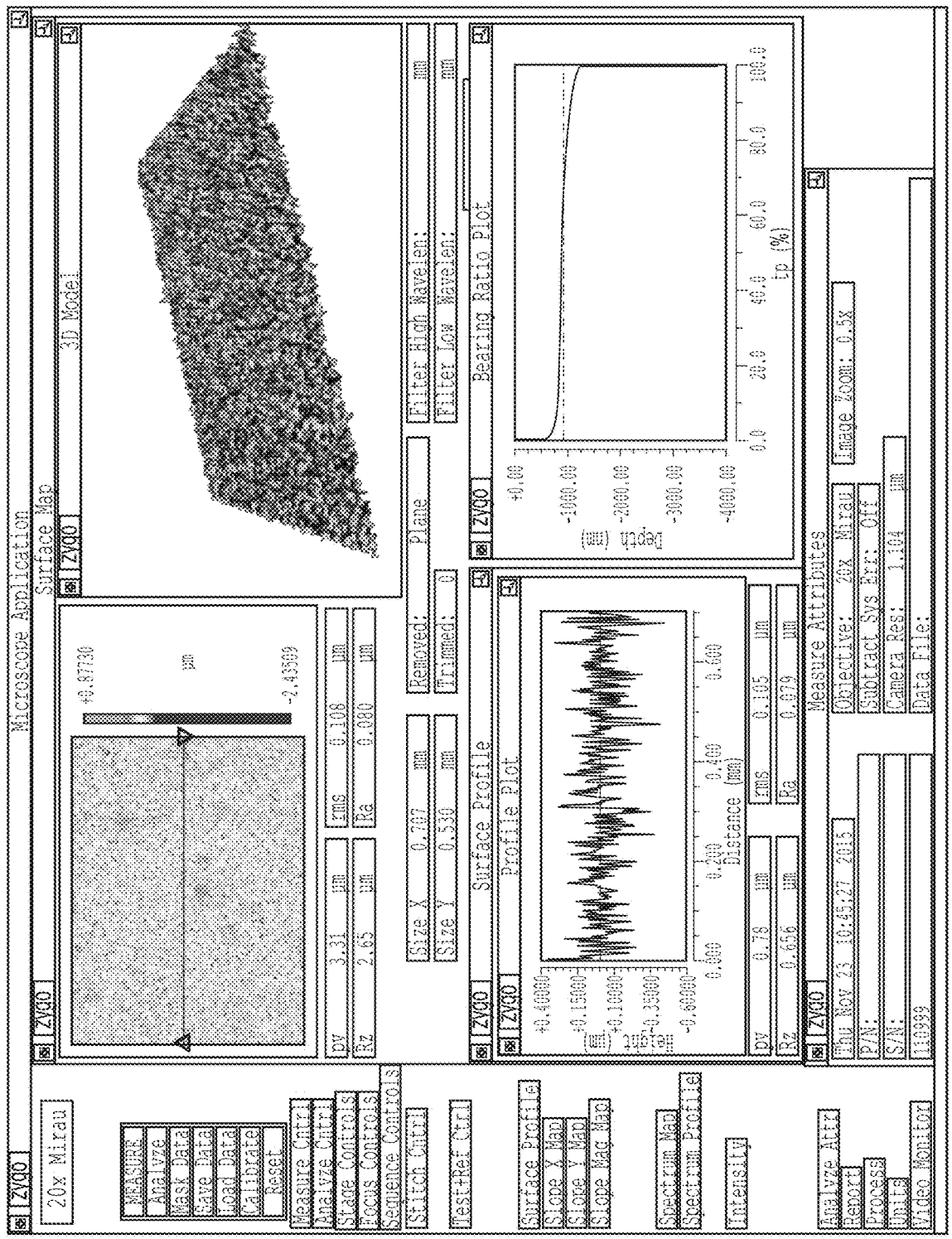

FIG. 124 shows results from optical profiling measurements on the Melinex Control sample taken at the bottom, location 2.

Figure 125:
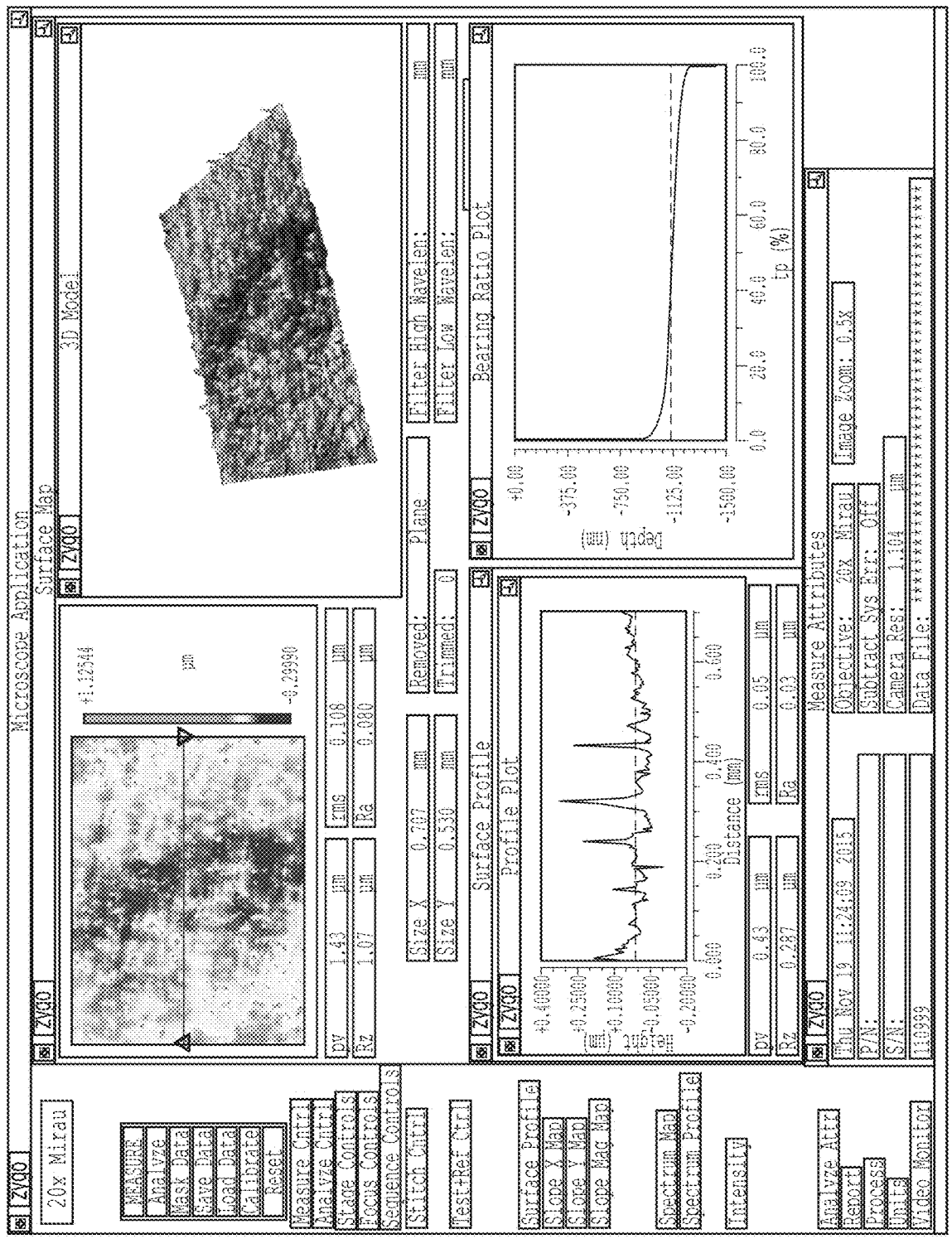

FIG. 125 shows results from optical profiling measurements on sample FIL-10-SPRAY-B-01MYL taken at the top, location 1.

Figure 126:
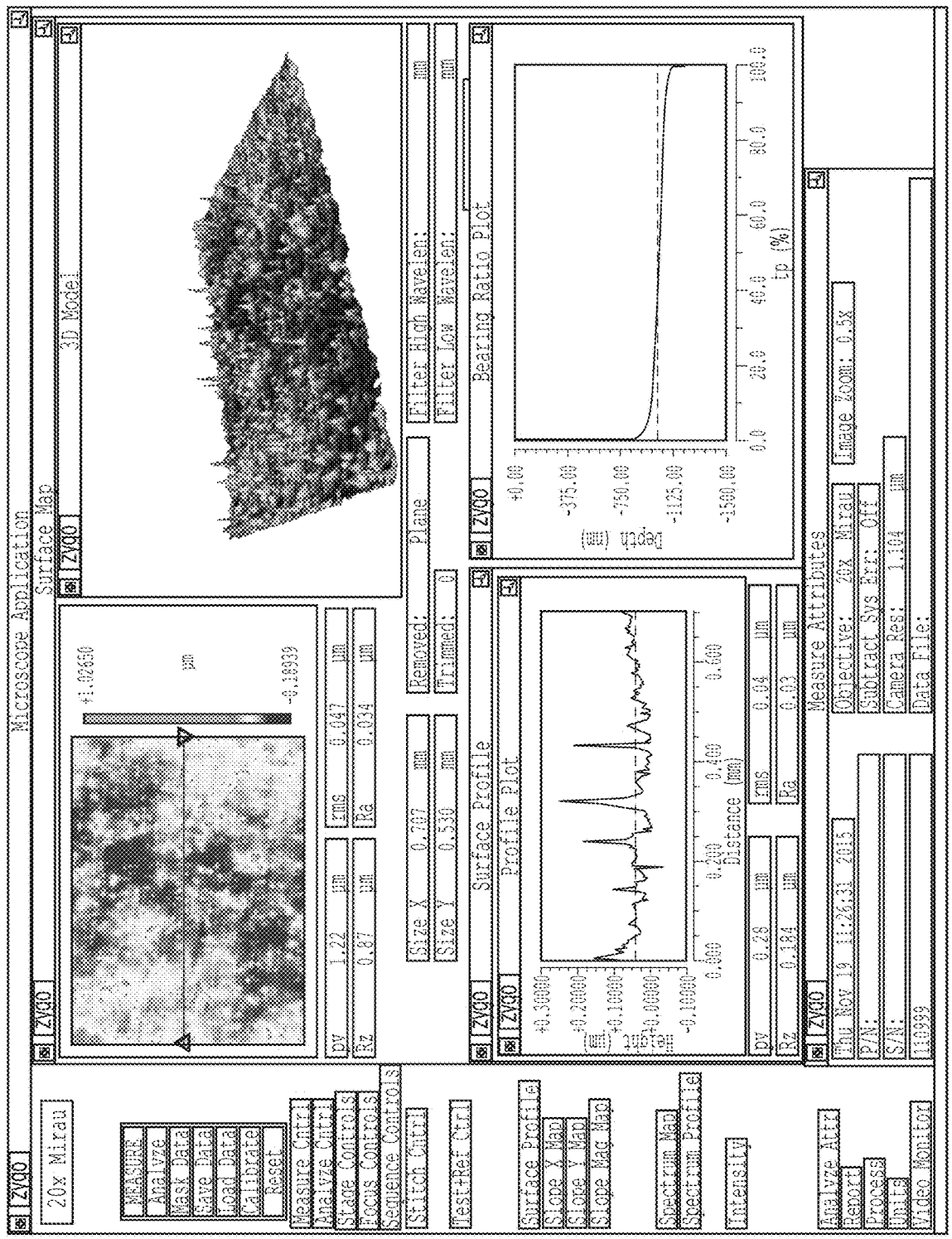

FIG. 126 shows results from optical profiling measurements on sample FIL-10-SPRAY-B-01MYL taken at the bottom, location 2.

Figure 127:
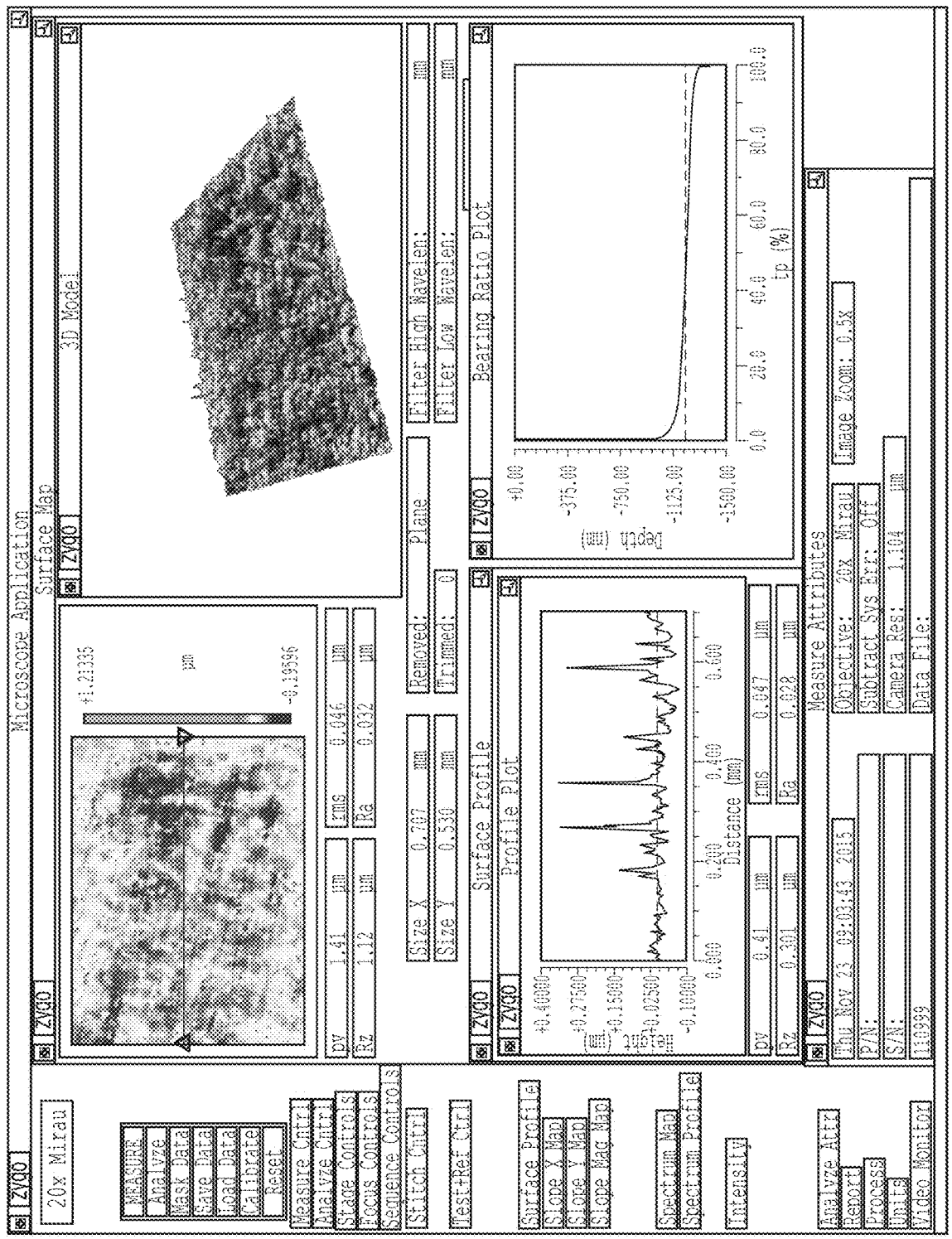

FIG. 127 shows results from optical profiling measurements on sample FIL-01-SPRAY-B-01MYL taken at the top, location 1.

Figure 128:

FIG. 128 shows results from optical profiling measurements on sample FIL-01-SPRAY-B-01MYL taken at the bottom, location 2.

Figure 129:

FIG. 129 shows results from optical profiling measurements on sample FIL-01-SPRAY-B-007MEL taken the top, location 1.

Figure 130:
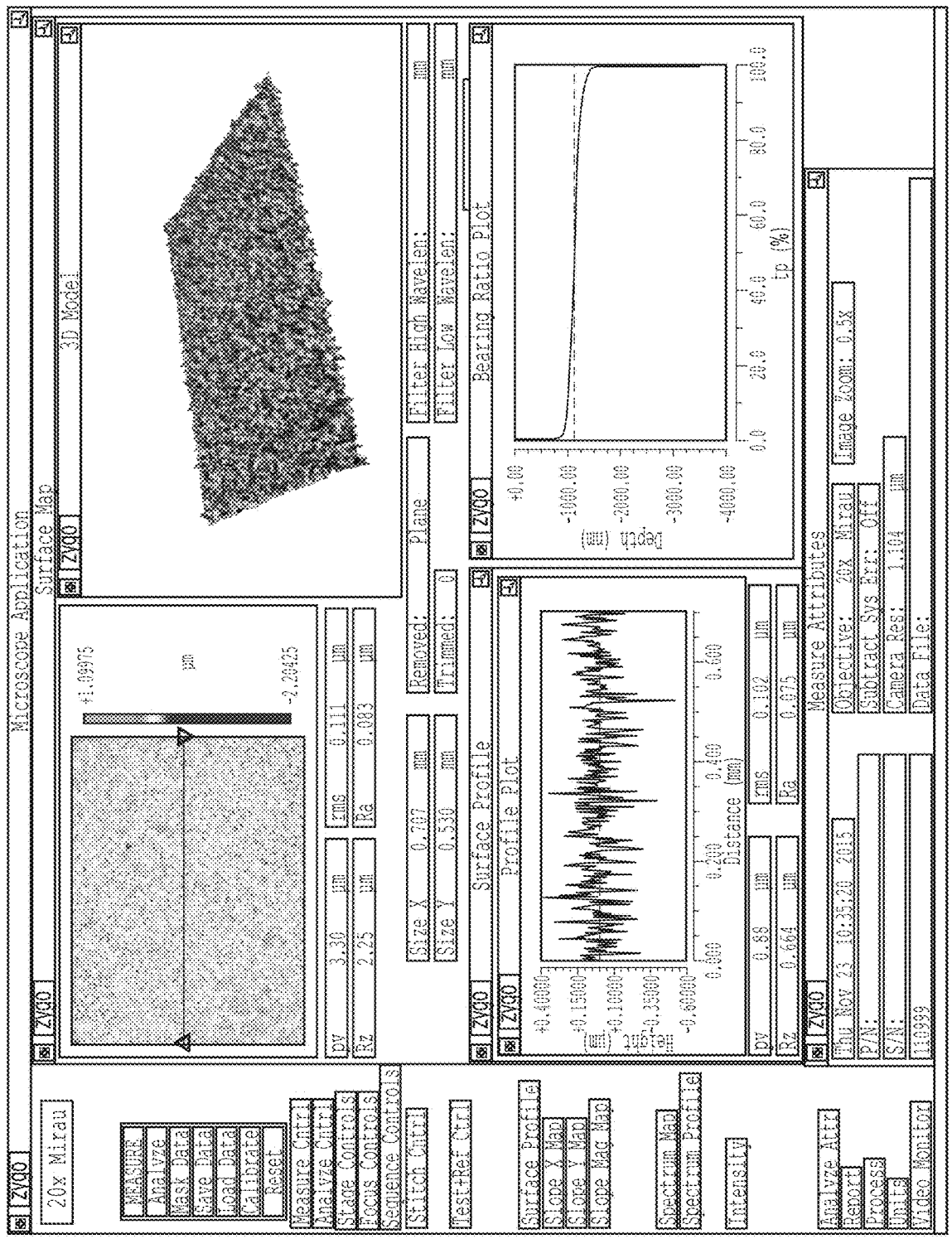

FIG. 130 shows results from optical profiling measurements on sample FIL-01-SPRAY-B-007MEL taken at the bottom, location 2.

Figure 131:
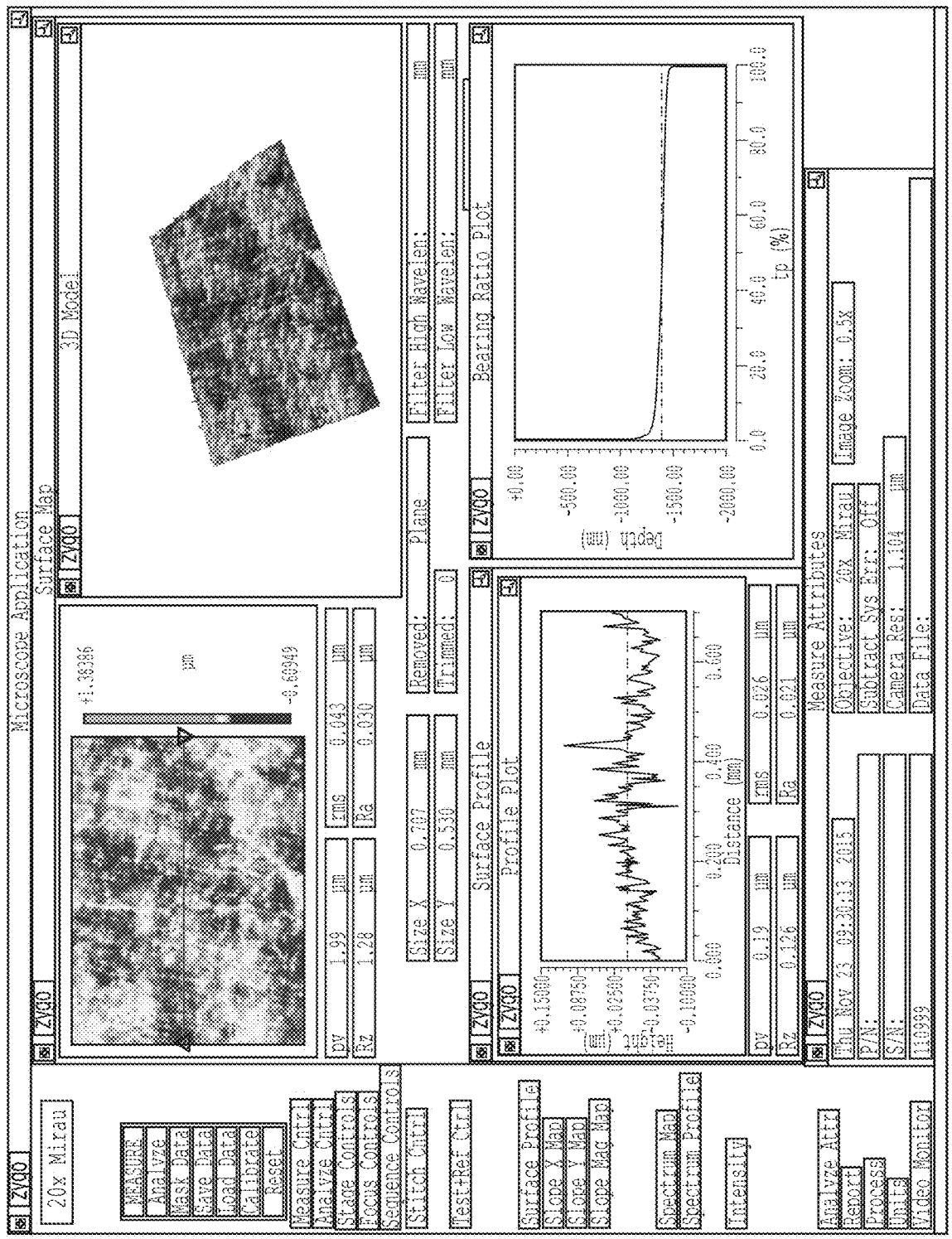

FIG. 131 shows results from optical profiling measurements on sample FIL-01-SPRAY-C-01MYL taken at the top, location 1.

Figure 132:
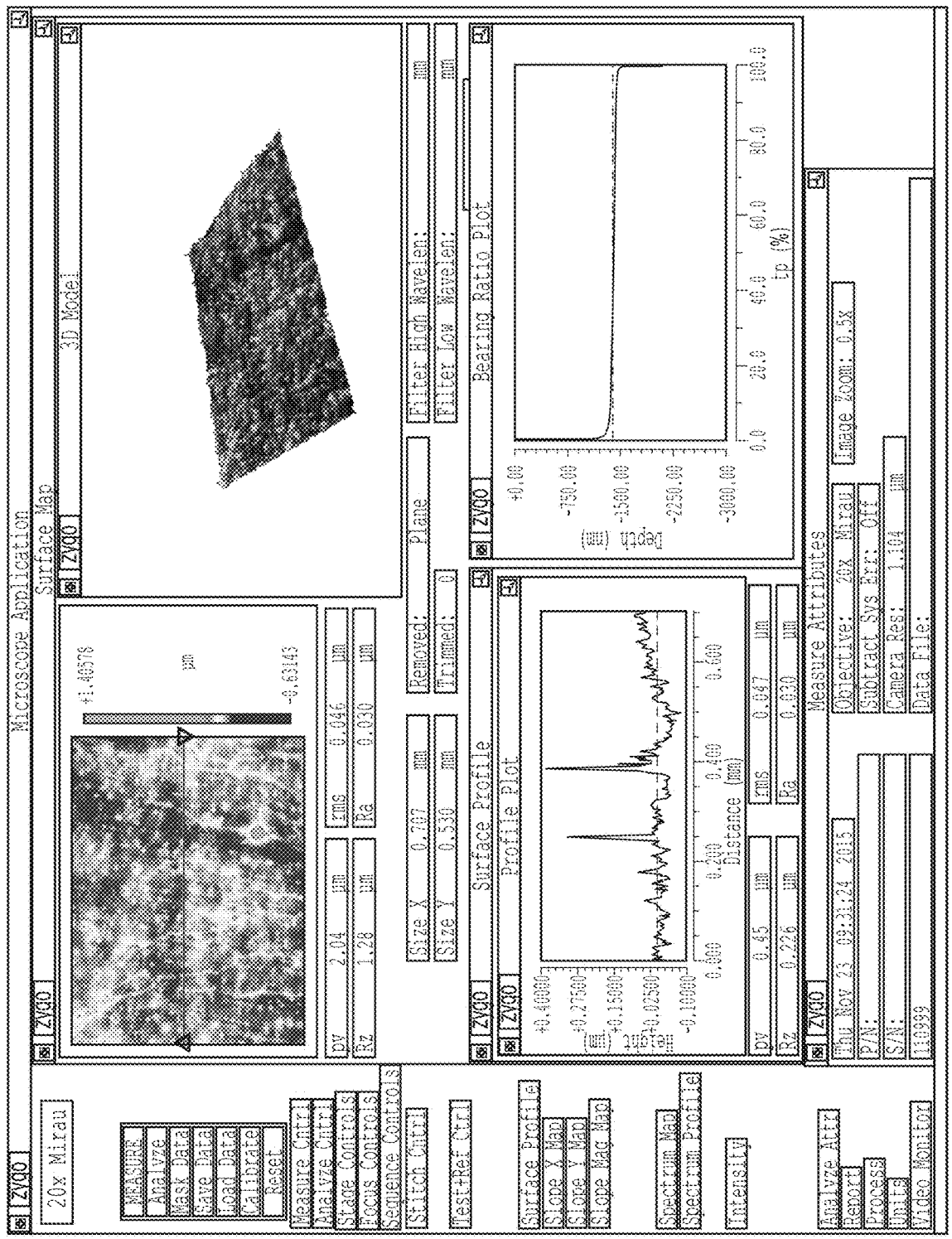

FIG. 132 shows results from optical profiling measurements on sample FIL-01-SPRAY-C-01MYL taken at bottom, location 2

Figure 133:
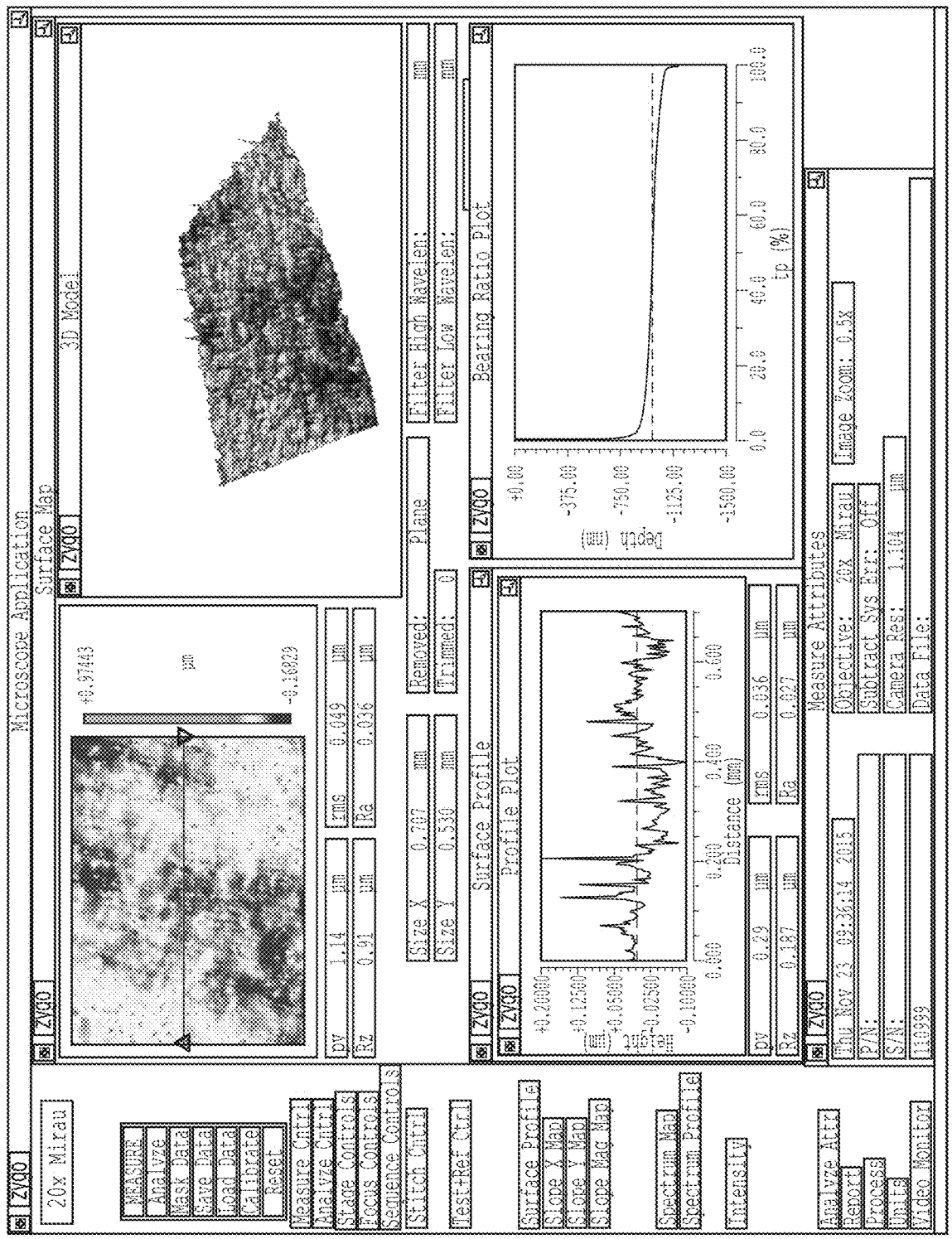

FIG. 133 shows results from optical profiling measurements on sample FIL-01-STEN-B-01MYL taken at the top, location 1.

Figure 134:
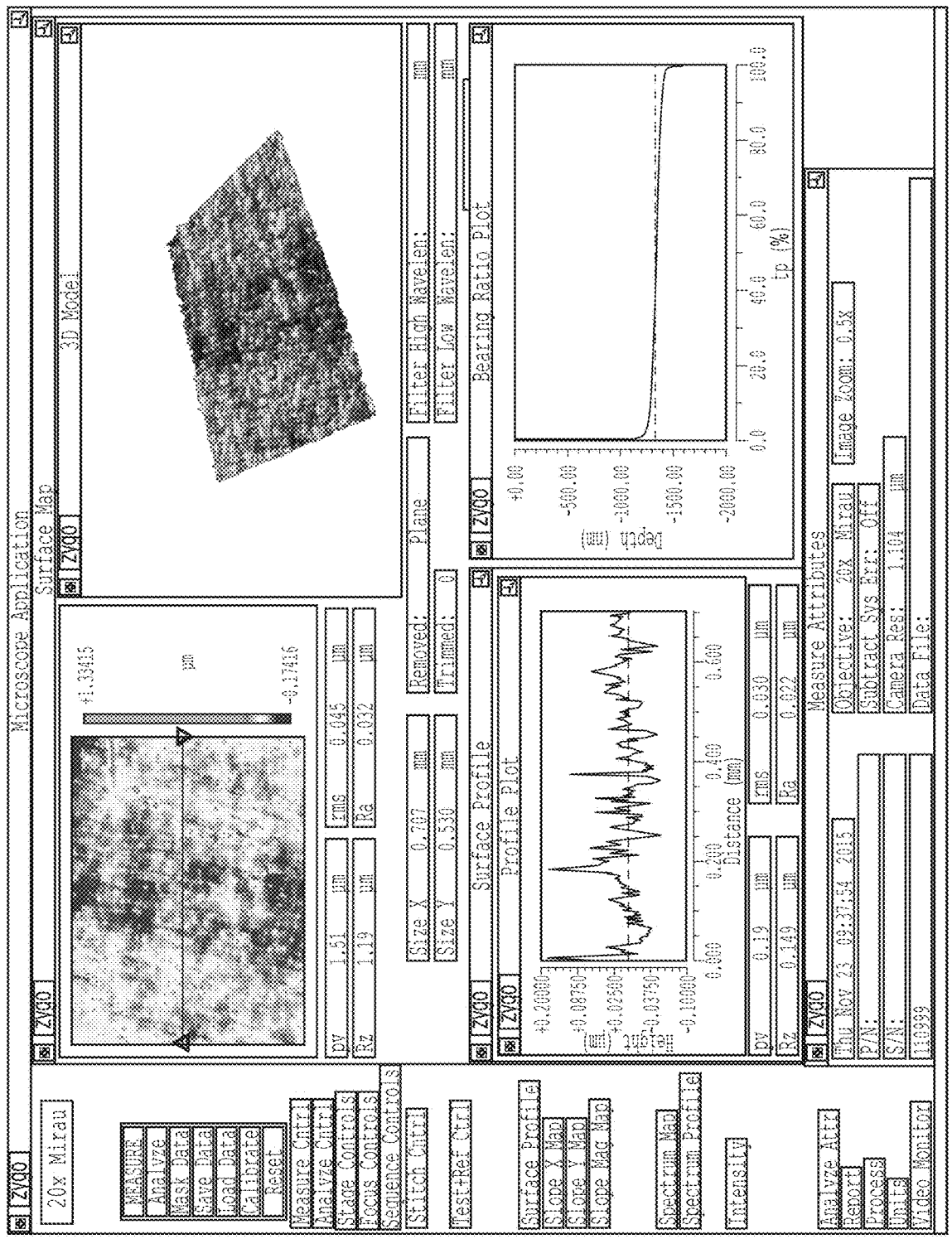

FIG. 134 shows results from optical profiling measurements on sample FIL-01-STEN-B-01MYL taken at the bottom, location 2.

Figure 135:
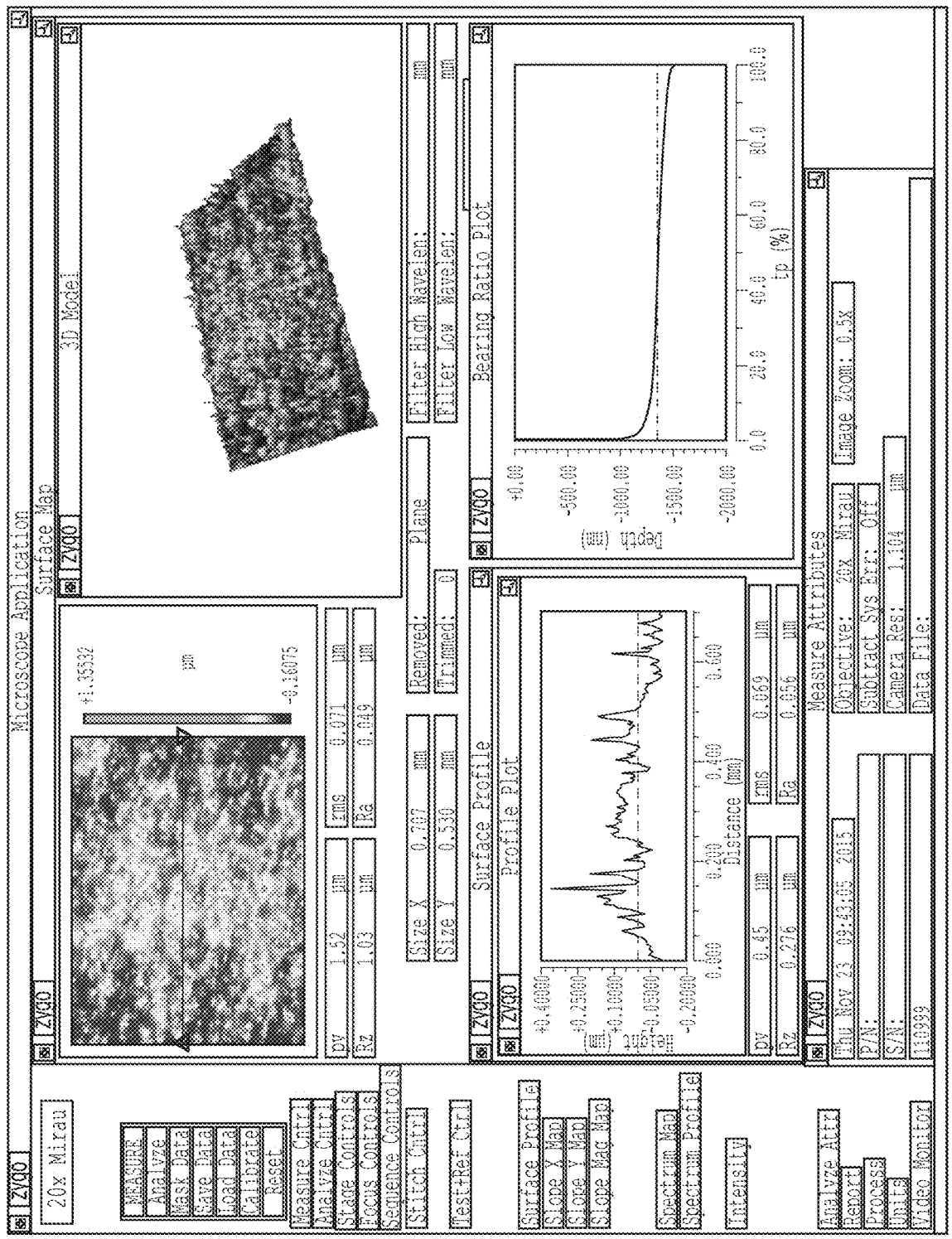

FIG. 135 shows results from optical profiling measurements on sample FIL-01-STEN-C-01MYL taken at the top, location 1.

Figure 136:
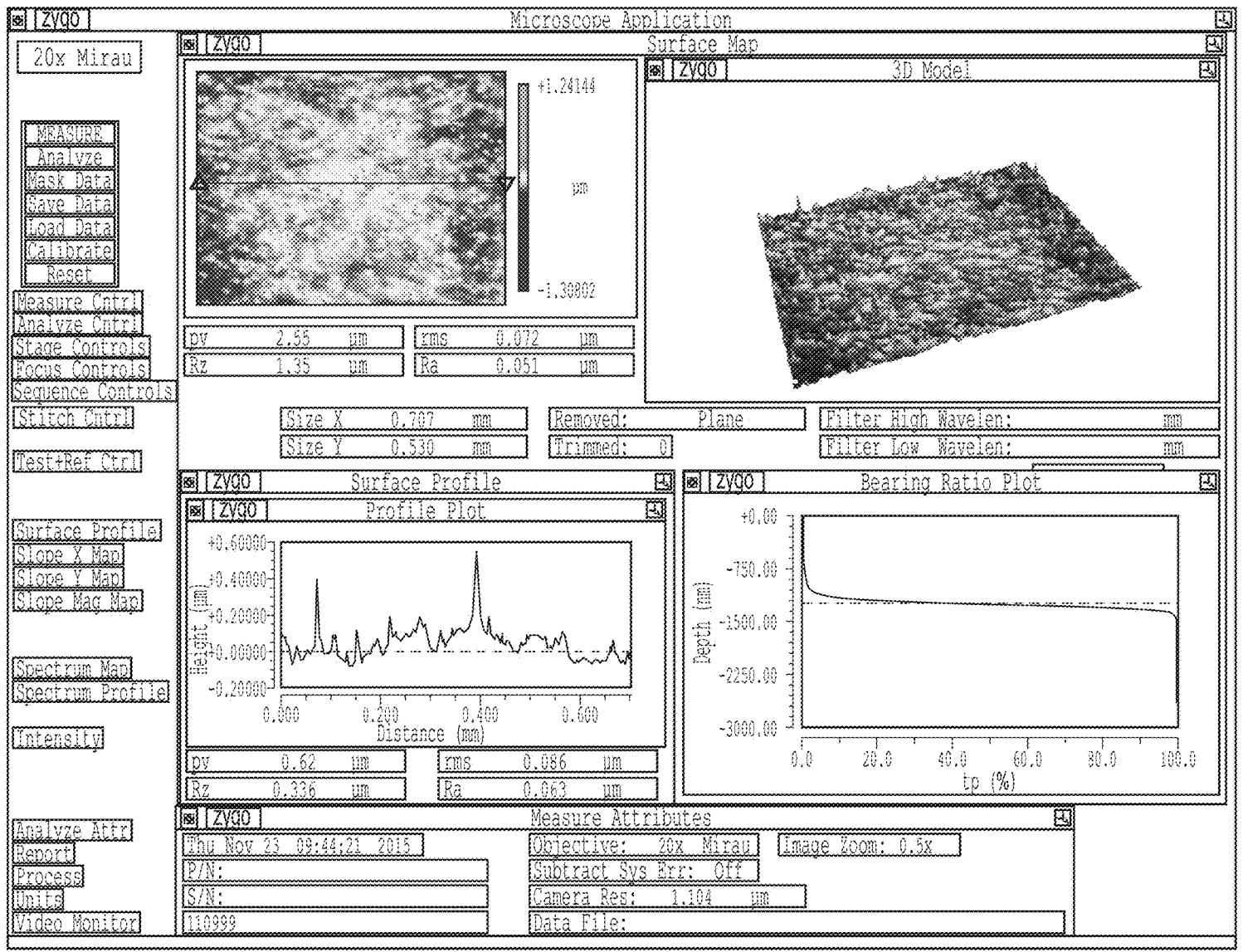

FIG. 136 shows results from optical profiling measurements on sample FIL-01-STEN-C-01MYL taken at the bottom, location 2.

Figure 137:
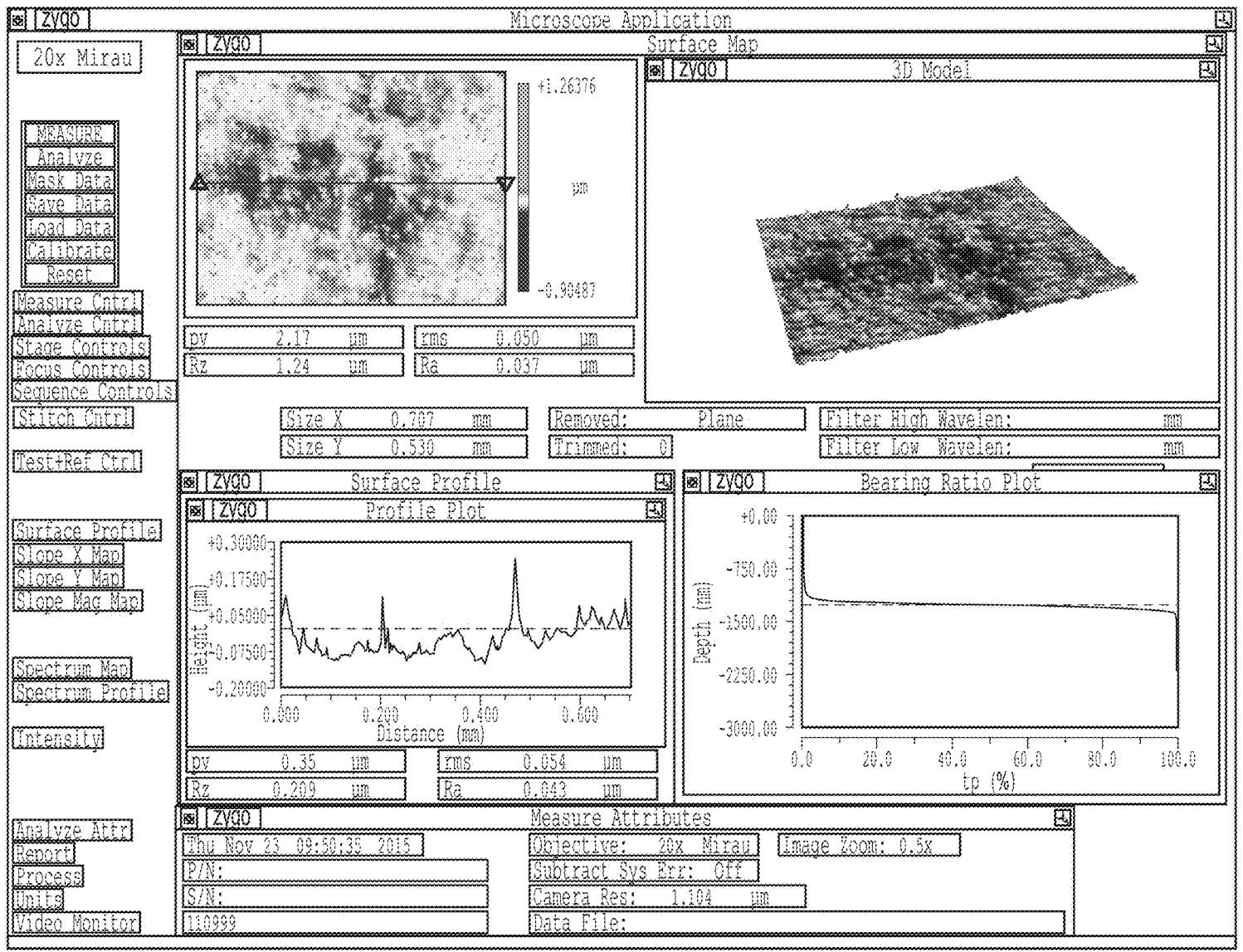

FIG. 137 shows results from optical profiling measurements on sample FIL-10-BATH-B-01MYL taken at the top, location 1.

Figure 138:
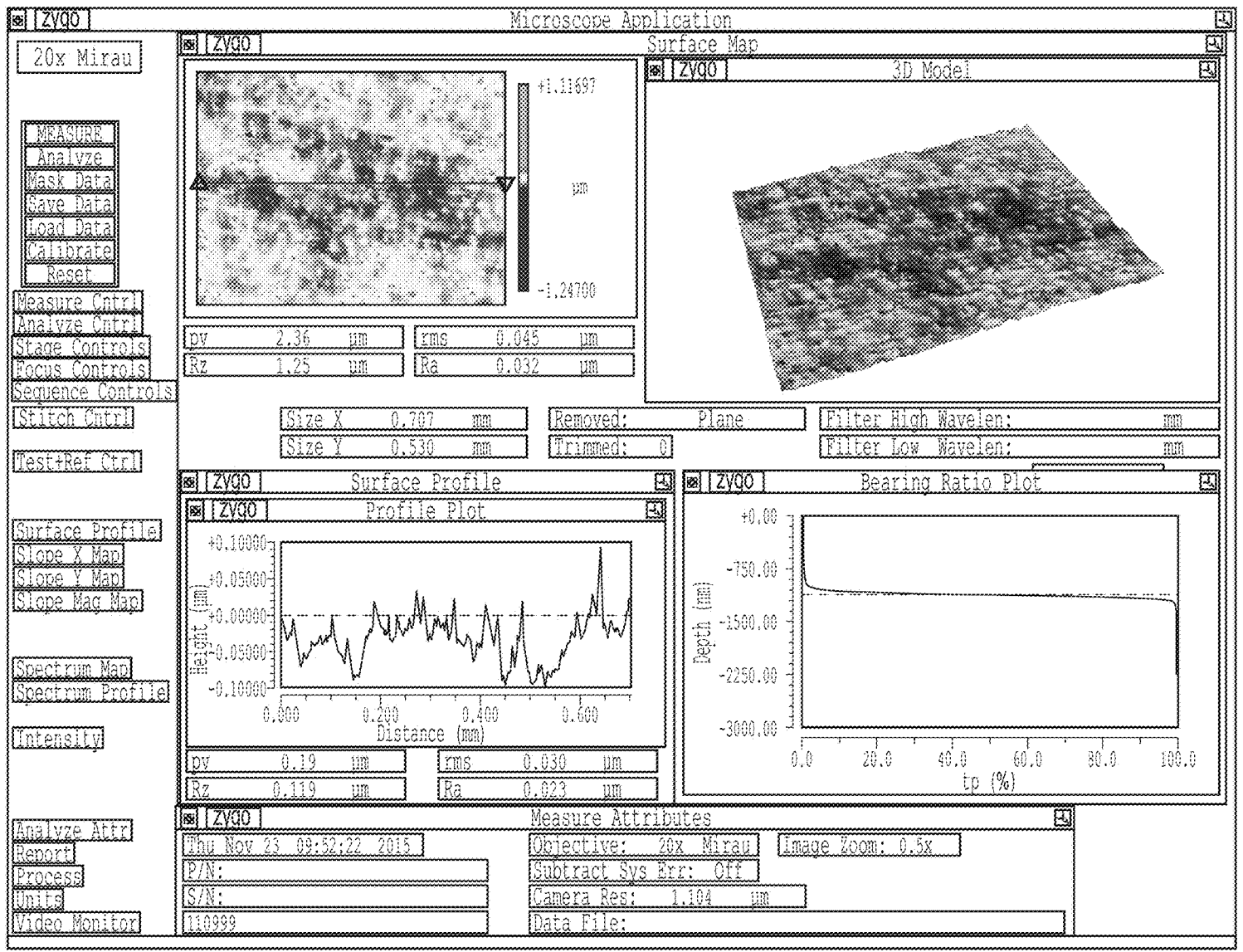

FIG. 138 shows results from optical profiling measurements on sample FIL-10-BATH-B-01MYL taken at the bottom, Location 2.

Figure 139:
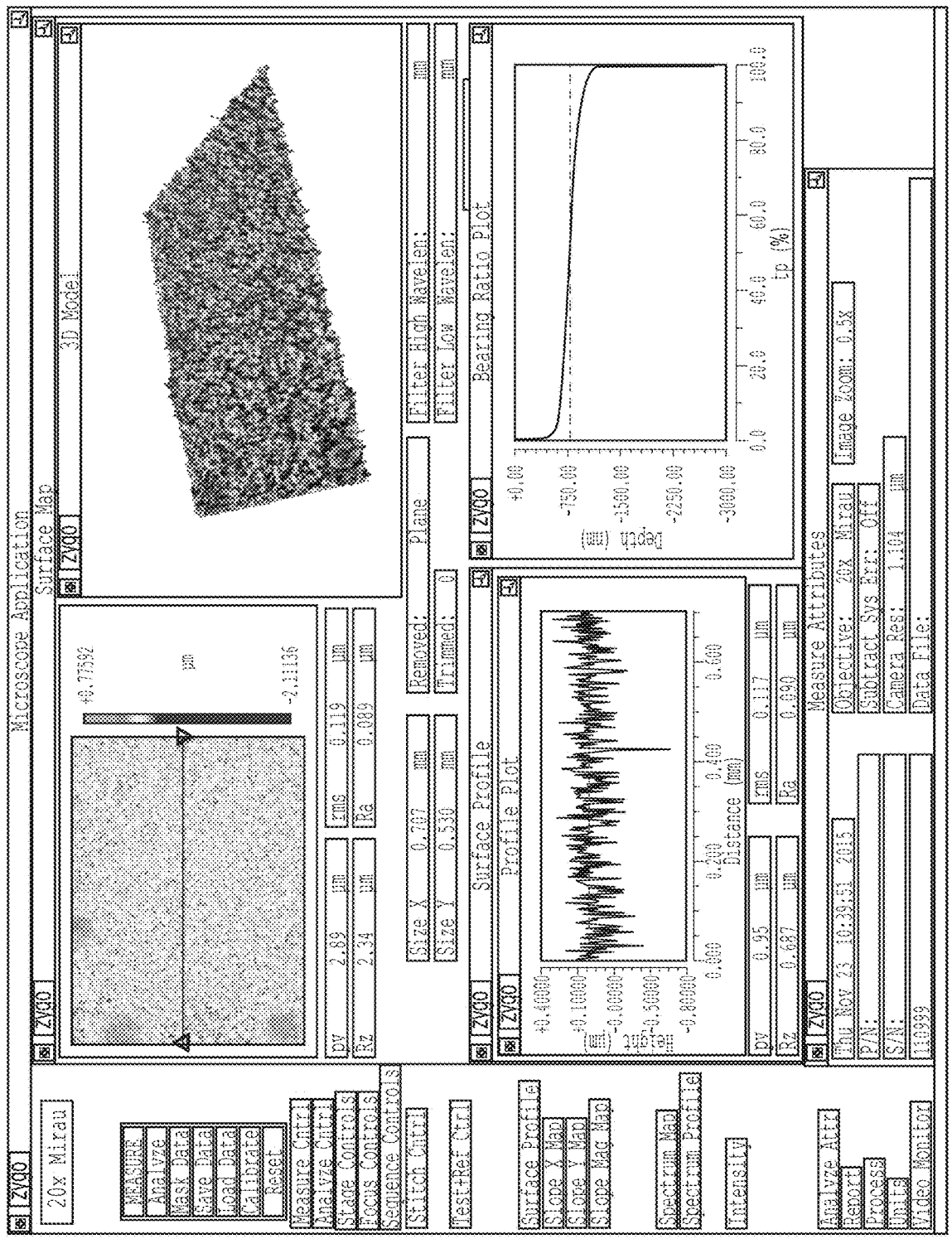

FIG. 139 shows results from optical profiling measurements on sample FIL-10-BATH-B-007MEL taken at the top, location 1.

Figure 140:
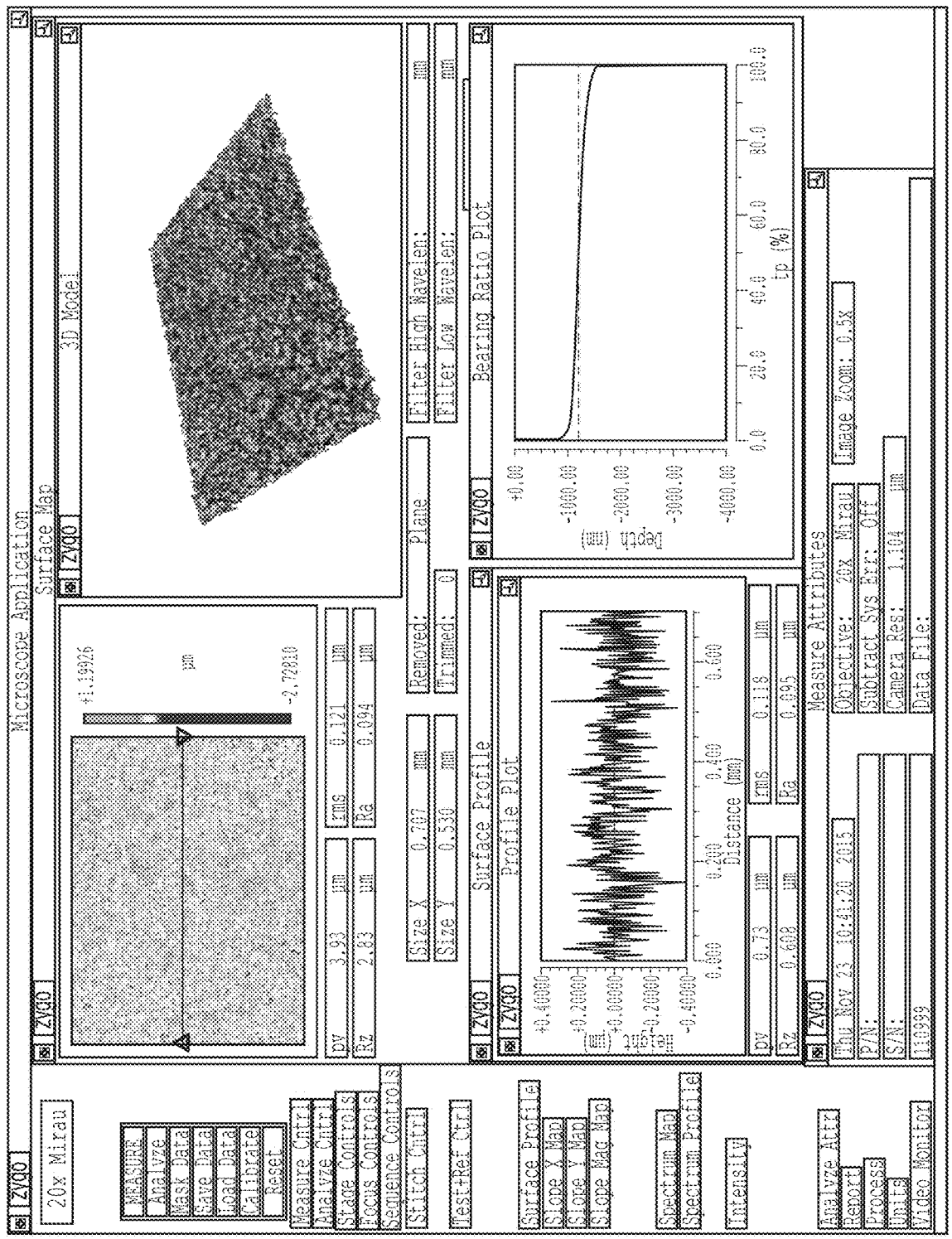

FIG. 140 shows results from optical profiling measurements on sample FIL-10-BATH-B-007MEL taken at the bottom, location 2.

Figure 141:
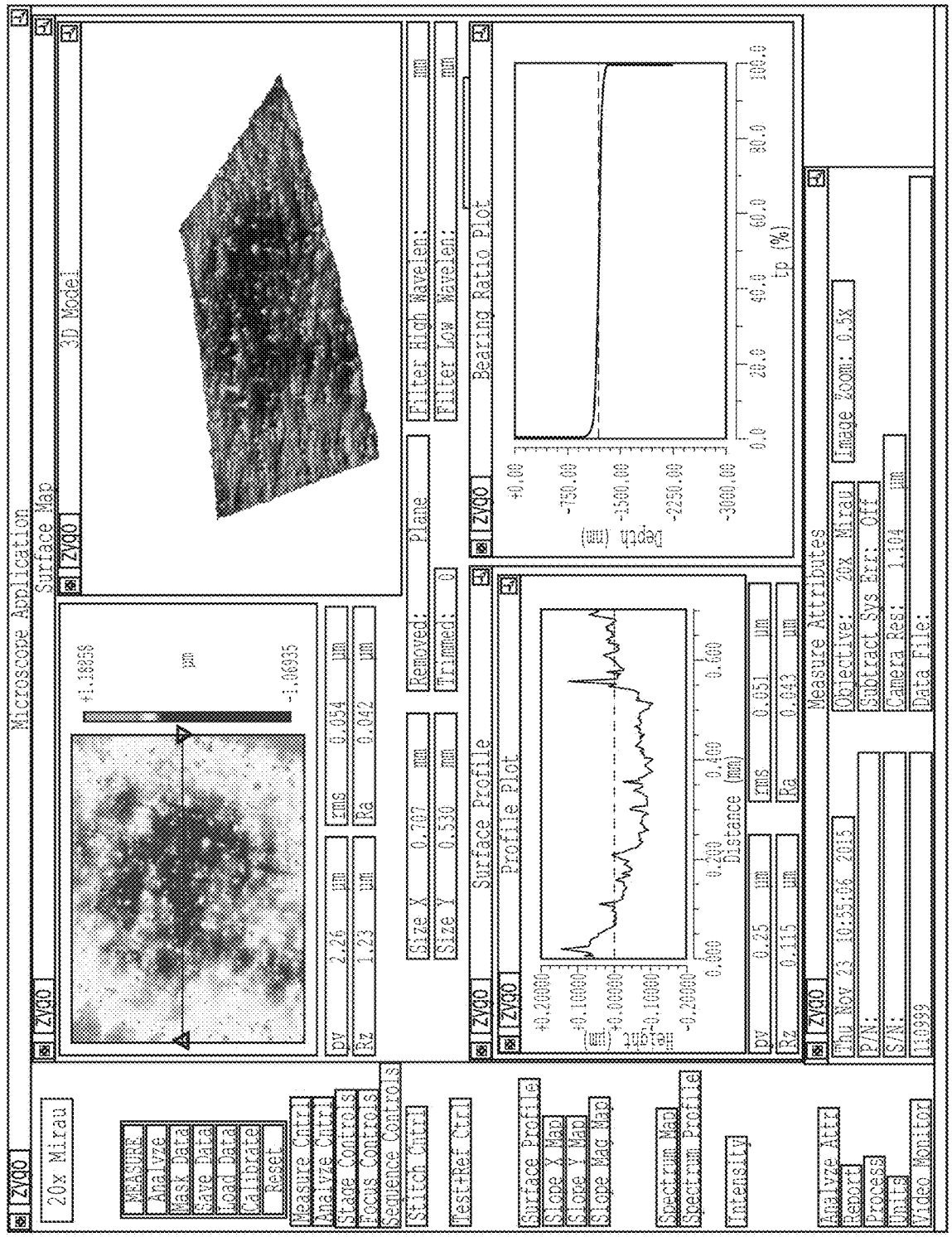

FIG. 141 shows results from optical profiling measurements on sample FIL-10-BATH-C-01MYL taken at top, location 1.

Figure 142:
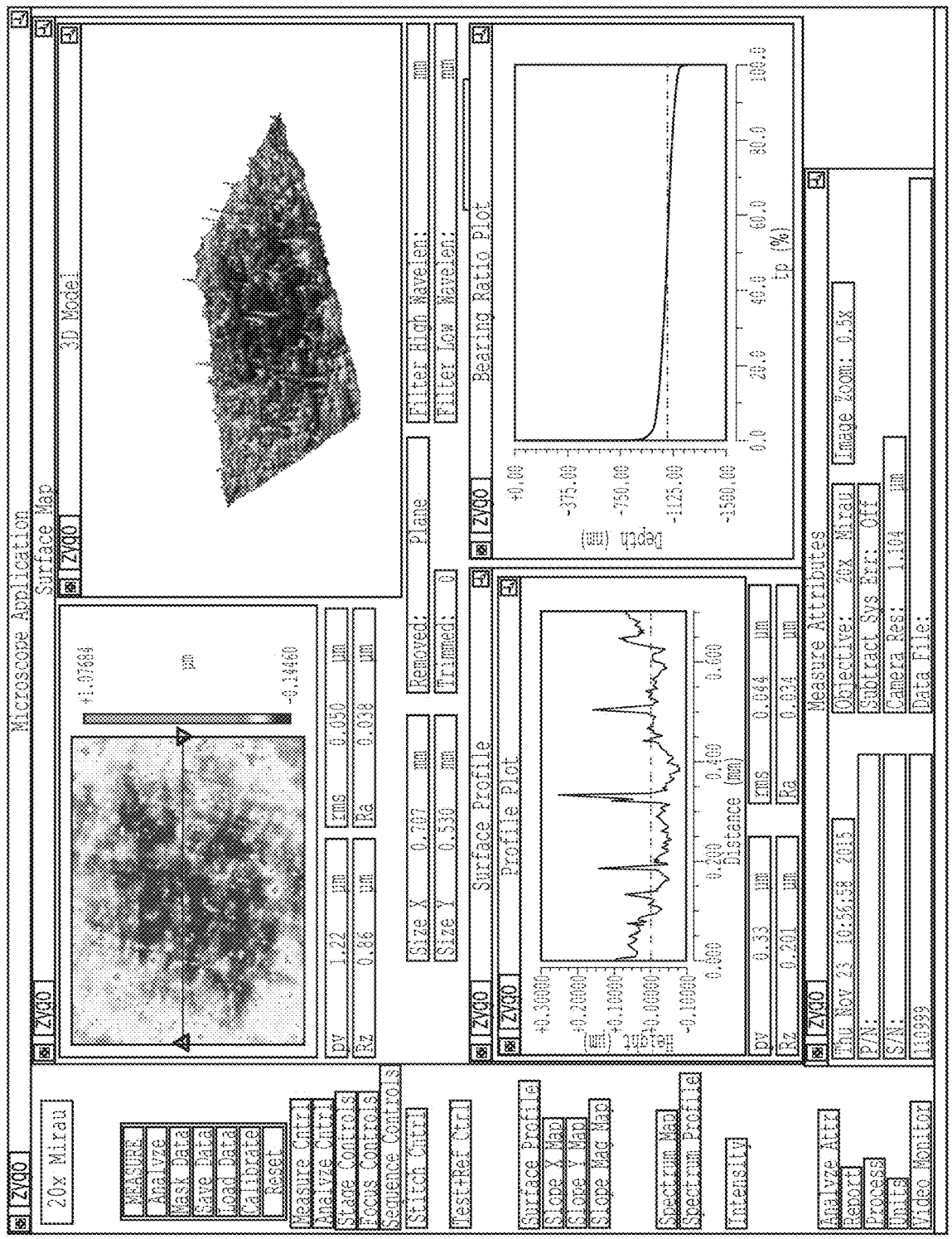

FIG. 142 shows results from optical profiling measurements on sample FIL-10-BATH-C-01MYL taken at the bottom, location 2.

Figure 143:
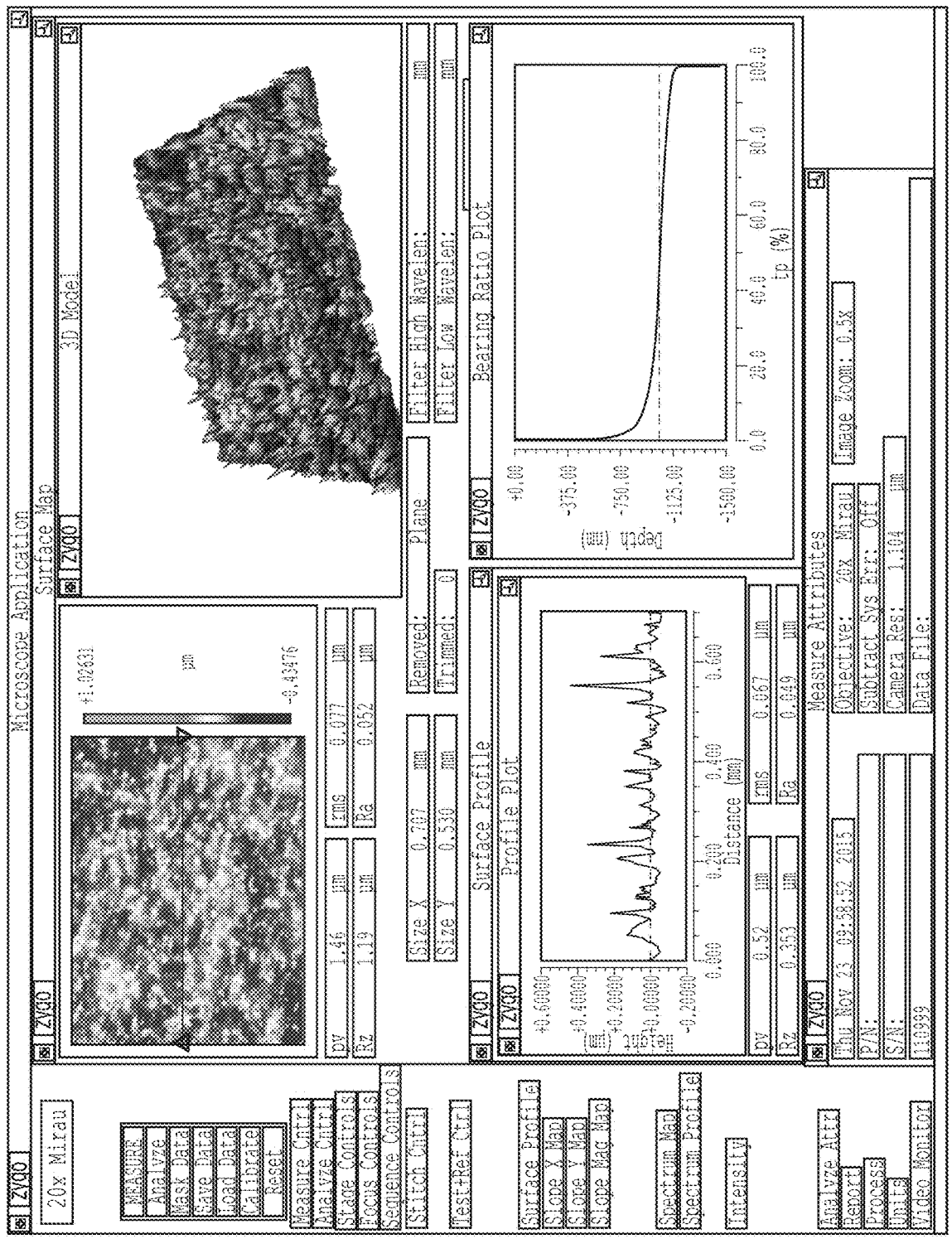

FIG. 143 shows results from optical profiling measurements on sample FIL-01-BATH-B-01MYL taken at the top, location 1.

Figure 144:
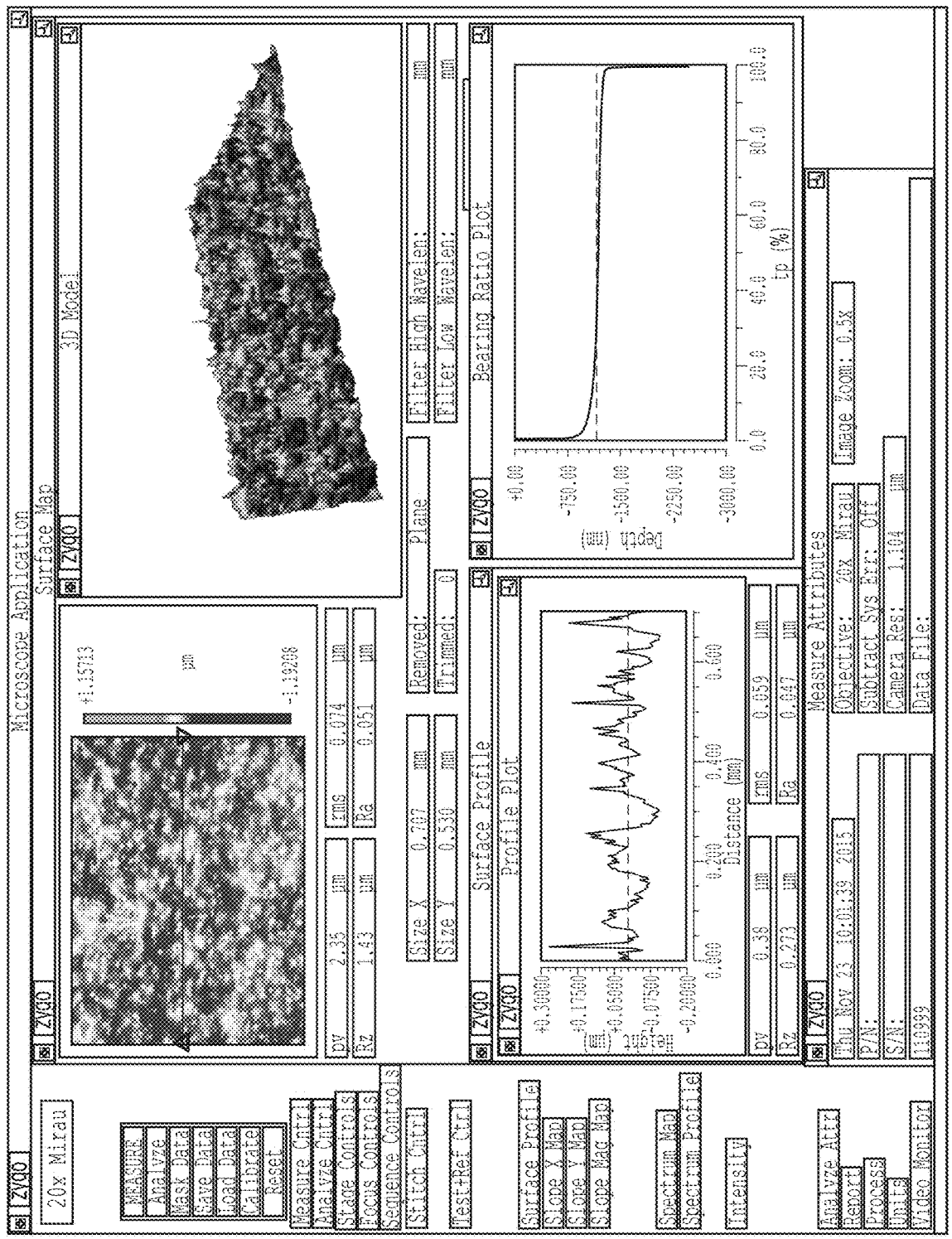

FIG. 144 shows results from optical profiling measurements on sample FIL-01-BATH-B-01MYL taken at the bottom, location 2.

Figure 145:
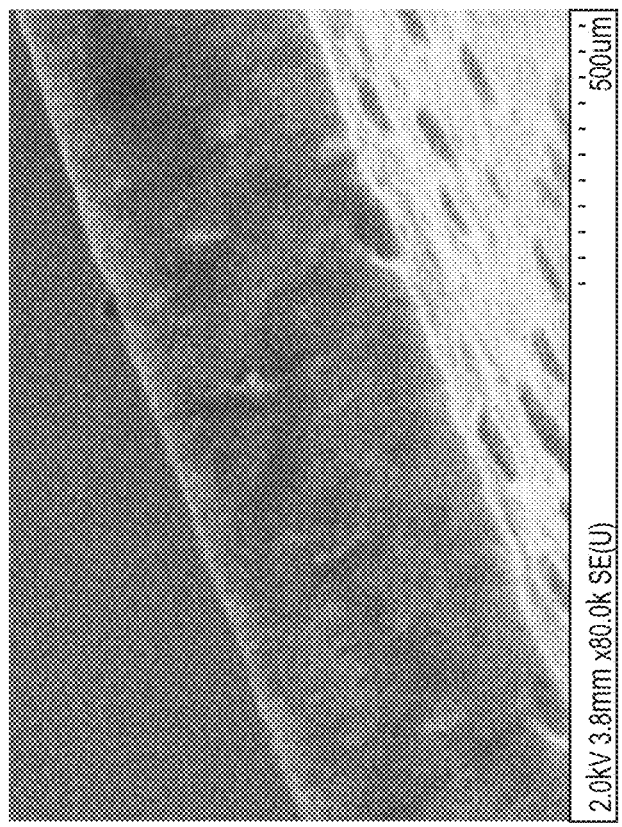

FIG. 145 illustrates a scanning electron microscopy image of film sample FIL-01-SPRAY-B-01MYL cross-section.

Figure 146:
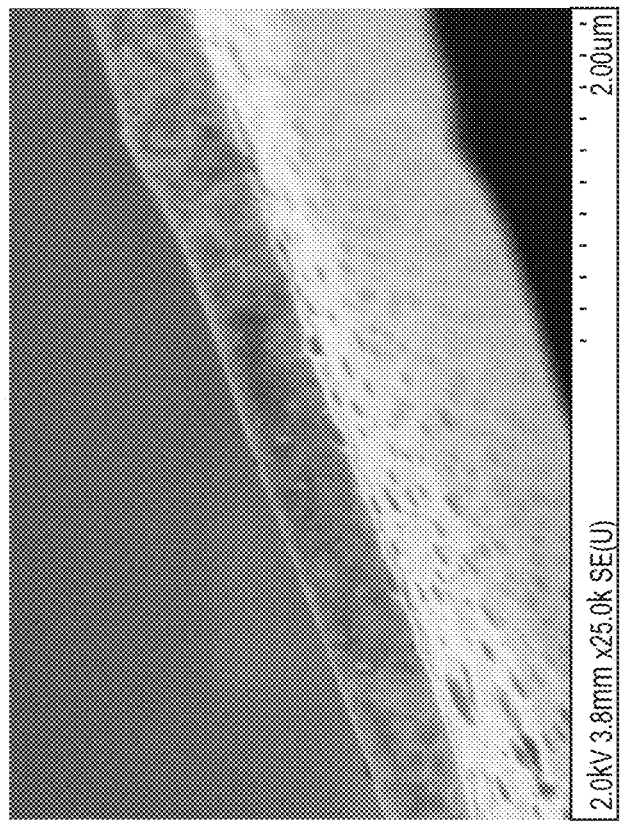

FIG. 146 illustrates a scanning electron microscopy image of film sample FIL-01-SPRAY-B-01MYL cross-section.

Figure 147:
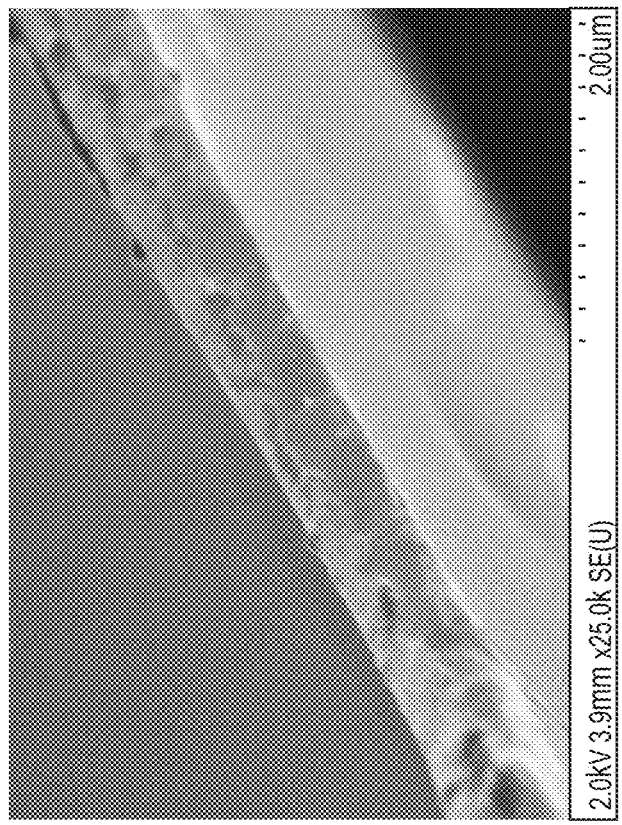

FIG. 147 illustrates a scanning electron microscopy image of film sample FIL-01-SPRAY-B-01MYL cross-section.

Figure 148:
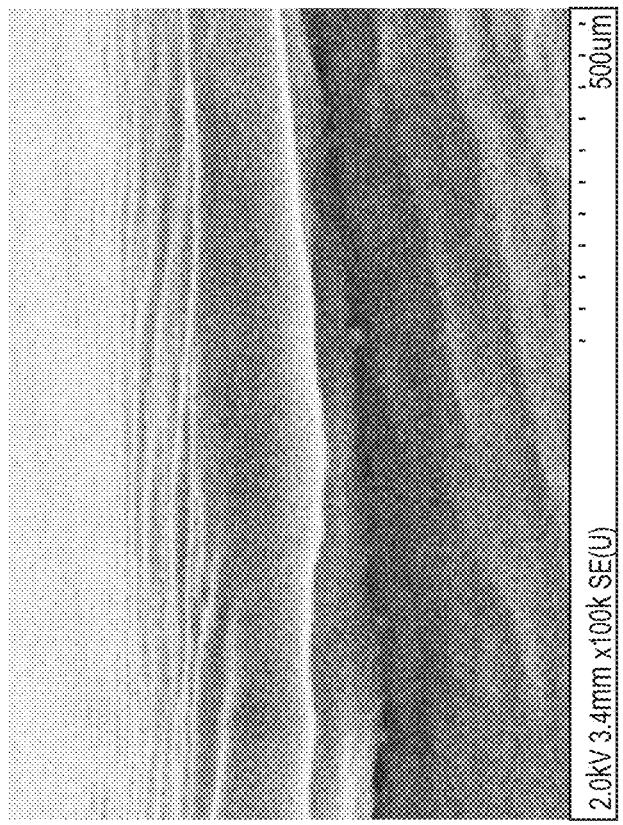

FIG. 148 illustrates a scanning electron microscopy image of film sample FIL-10-BATH-C-01MYL cross-section.

Figure 149:
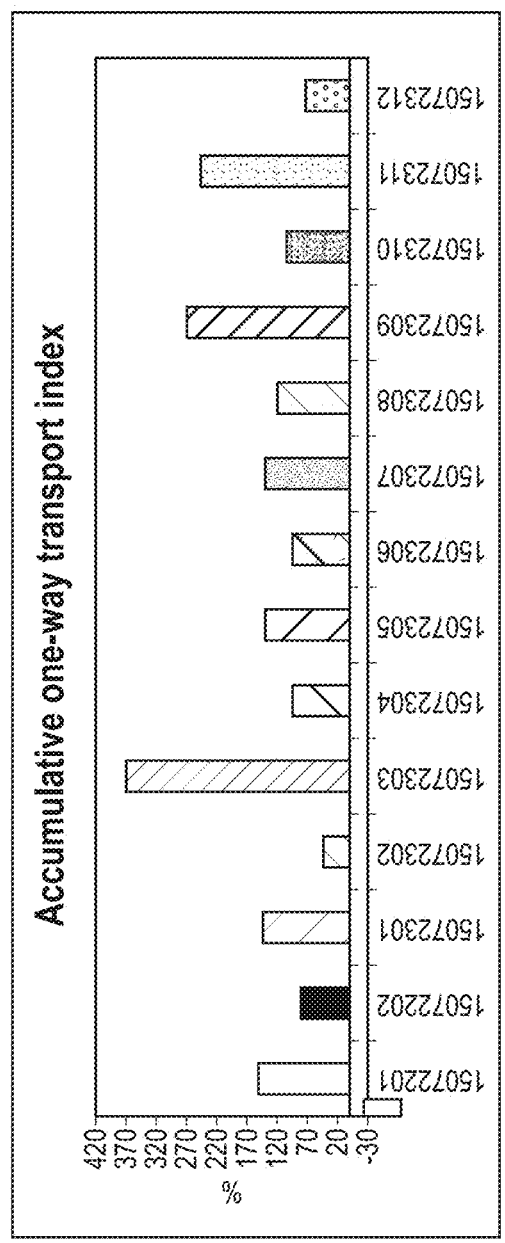

FIG. 149 illustrates accumulative one-way transport index results for natural fibers.

Figure 150:
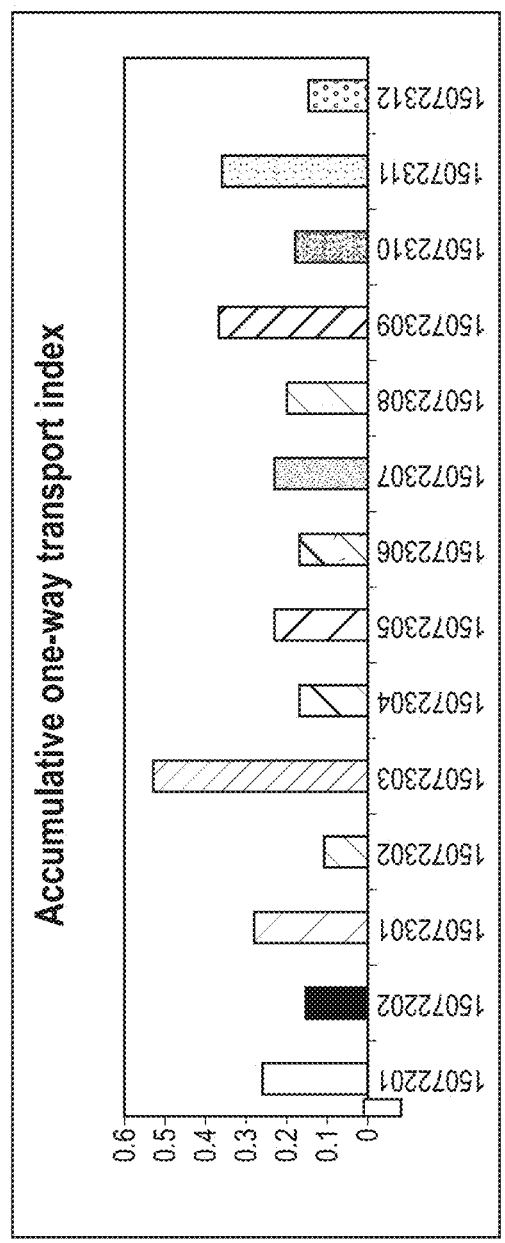

FIG. 150 illustrates overall moisture management capability for natural fibers.

Figure 151:
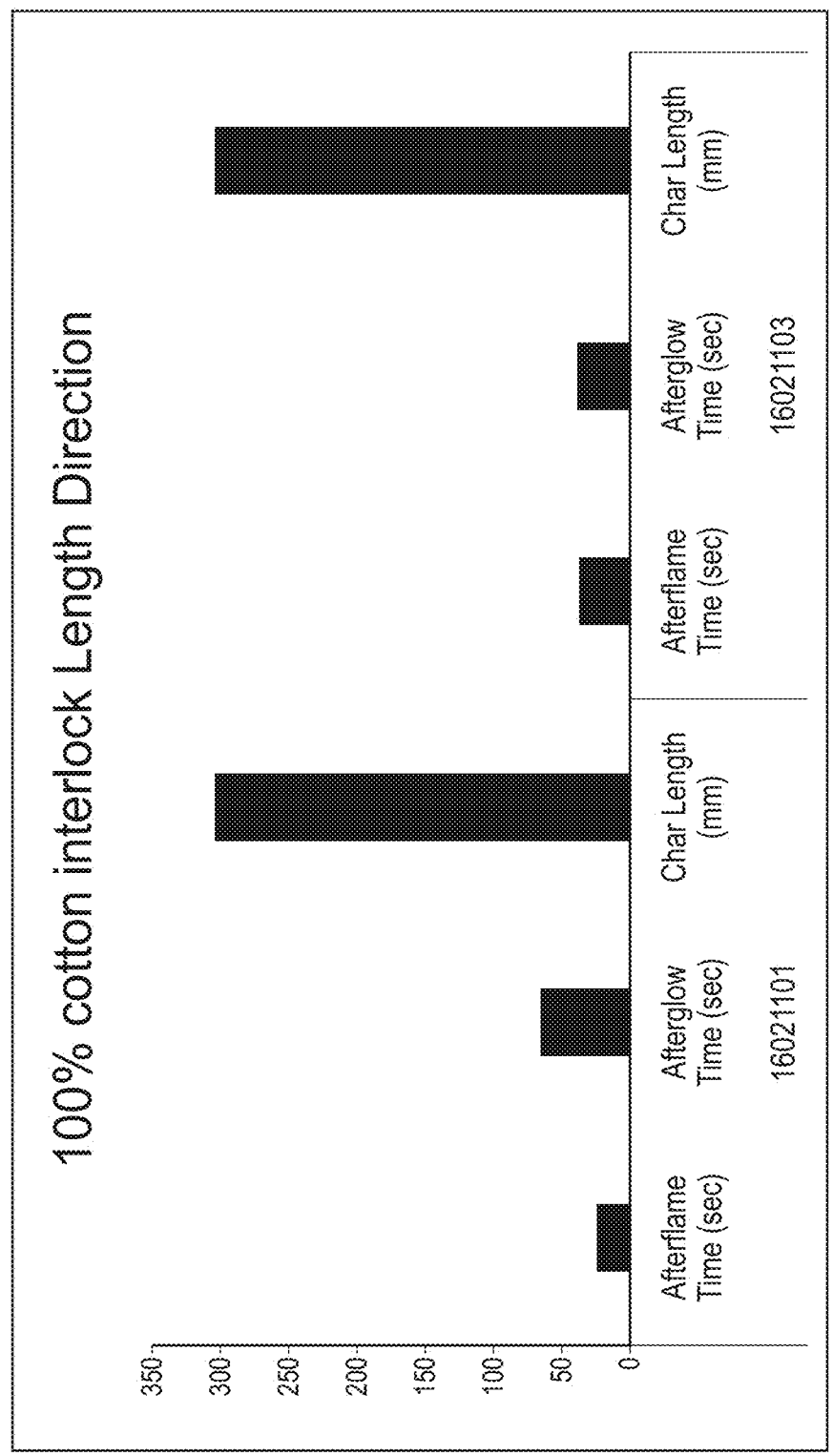

FIG. 151 illustrates flammability test results for a cotton interlock fabric with (16021103) and without (16021101) coating with 1% silk fibroin solution.

Figure 152:
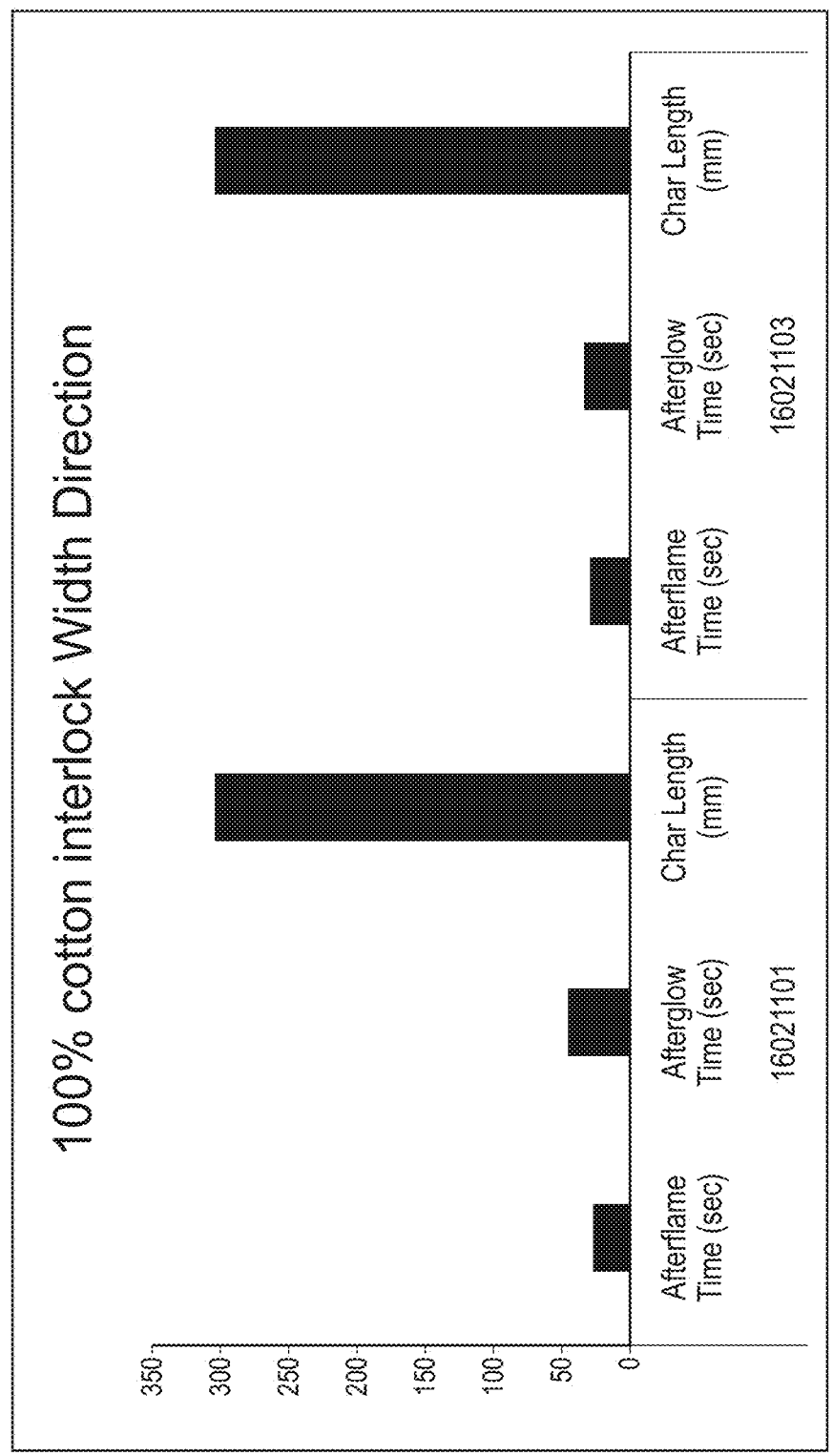

FIG. 152 illustrates flammability test results for a cotton interlock fabric with (16021103) and without (16021101) coating with 1% silk fibroin solution.

Figure 153:
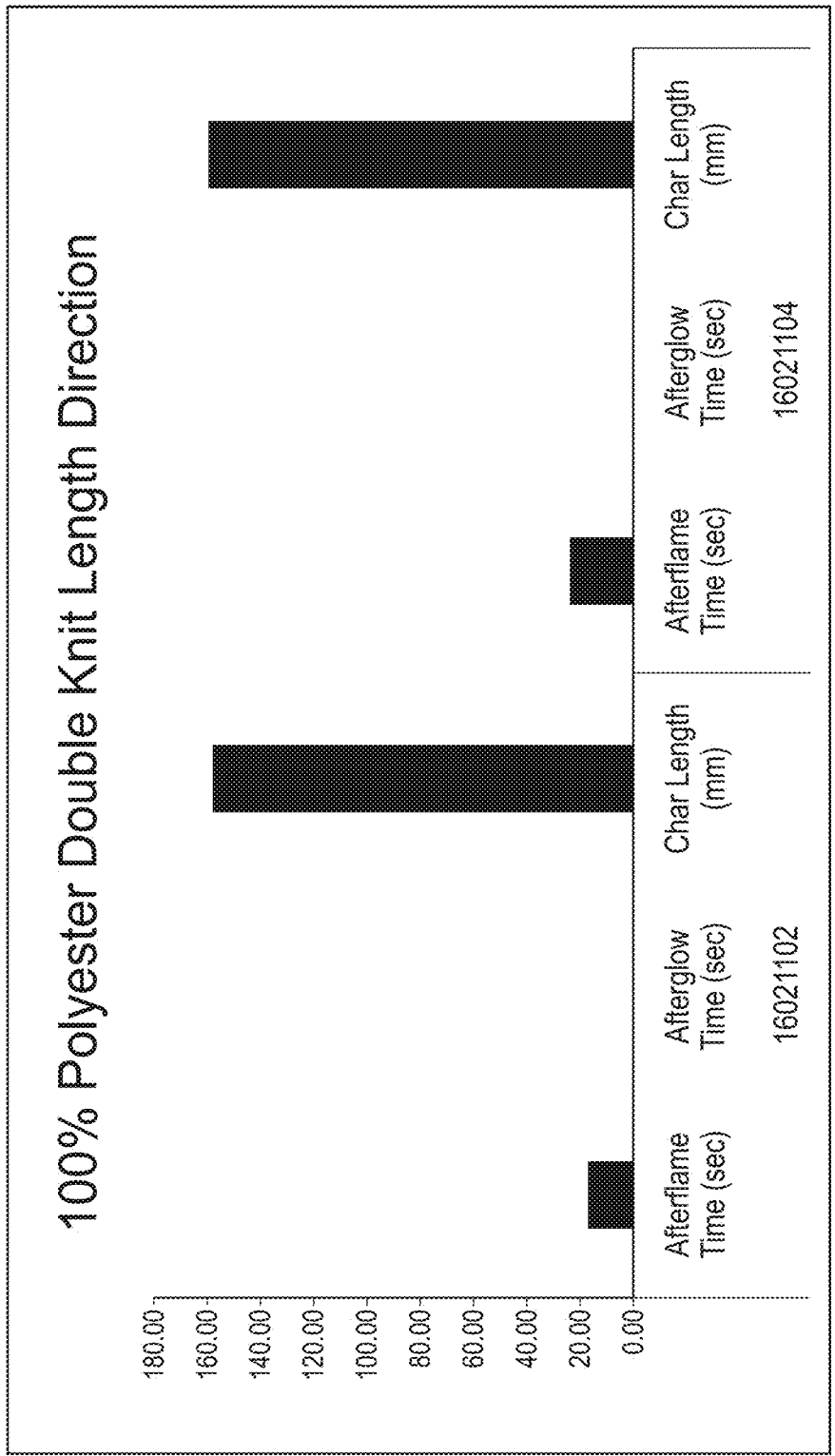

FIG. 153 illustrates flammability test results for a polyester double knit fabric with (16021104) and without (16021102) coating with 1% silk fibroin solution.

Figure 154:
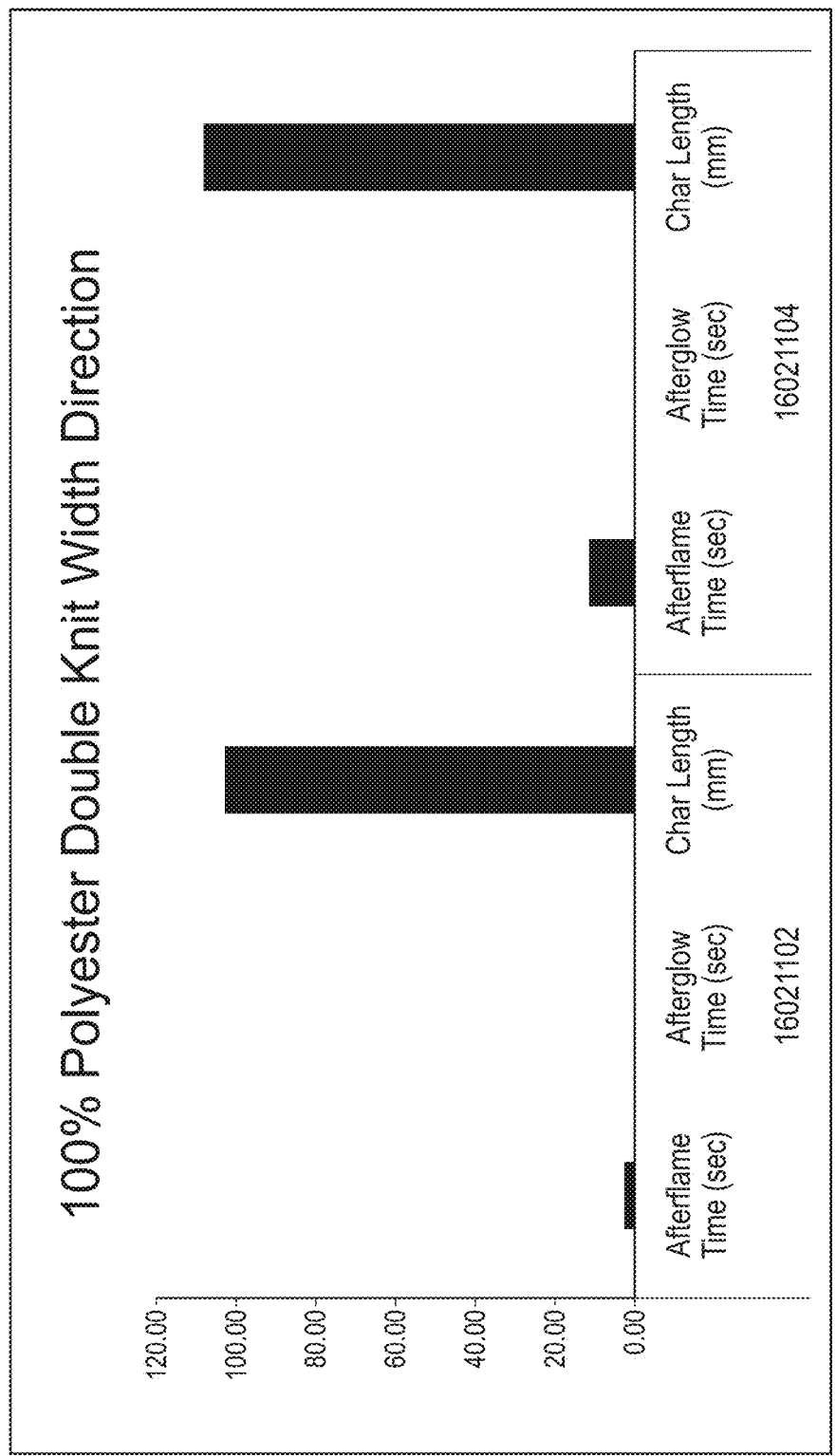

FIG. 154 illustrates flammability test results for a polyester double knit fabric with (16021104) and without (16021102) coating with 1% silk fibroin solution.

Figure 155:
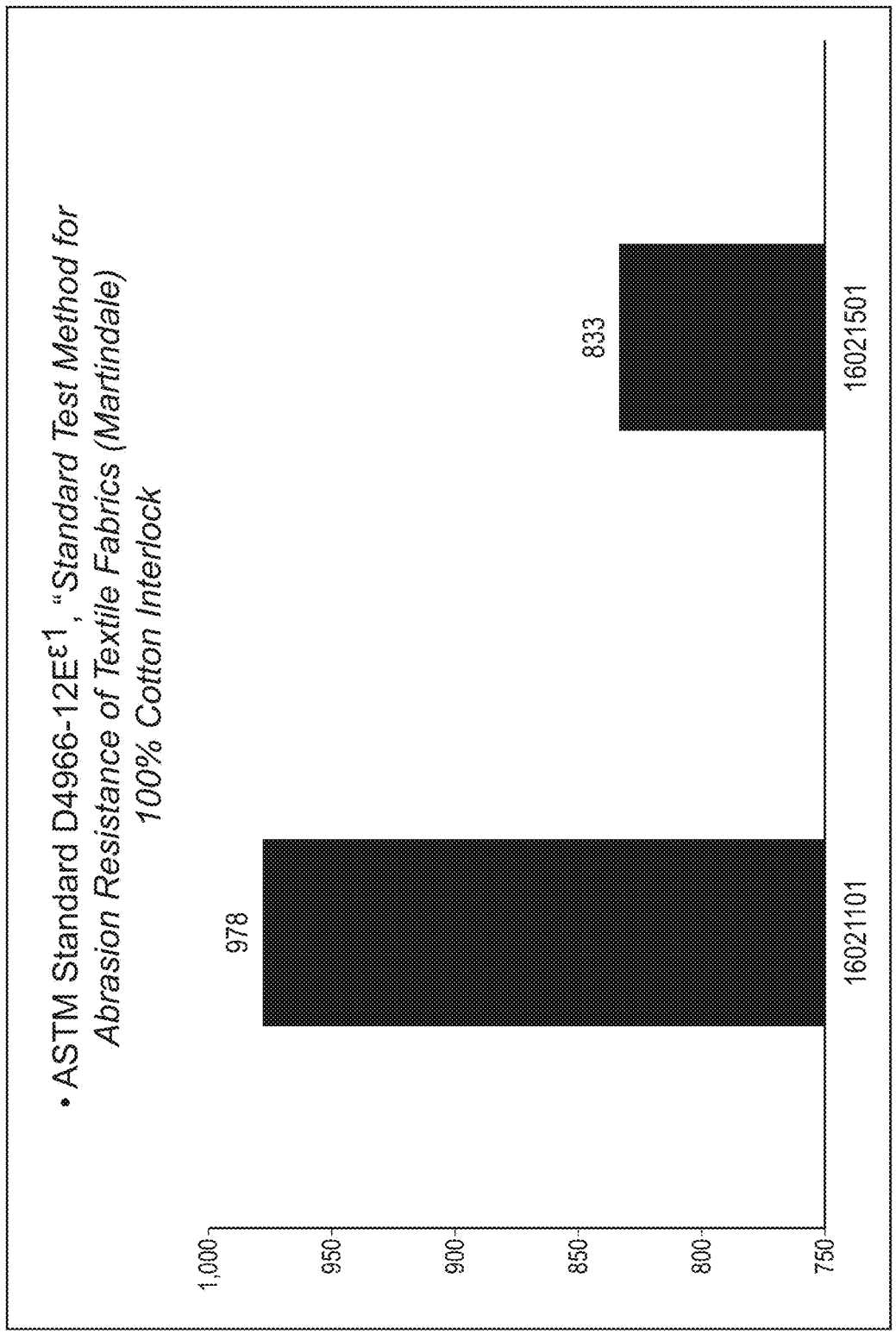

FIG. 155 illustrates abrasion test results for a cotton interlock fabric with (16021501) and without (16021101) coating with 1% silk fibroin solution.

Figure 156:
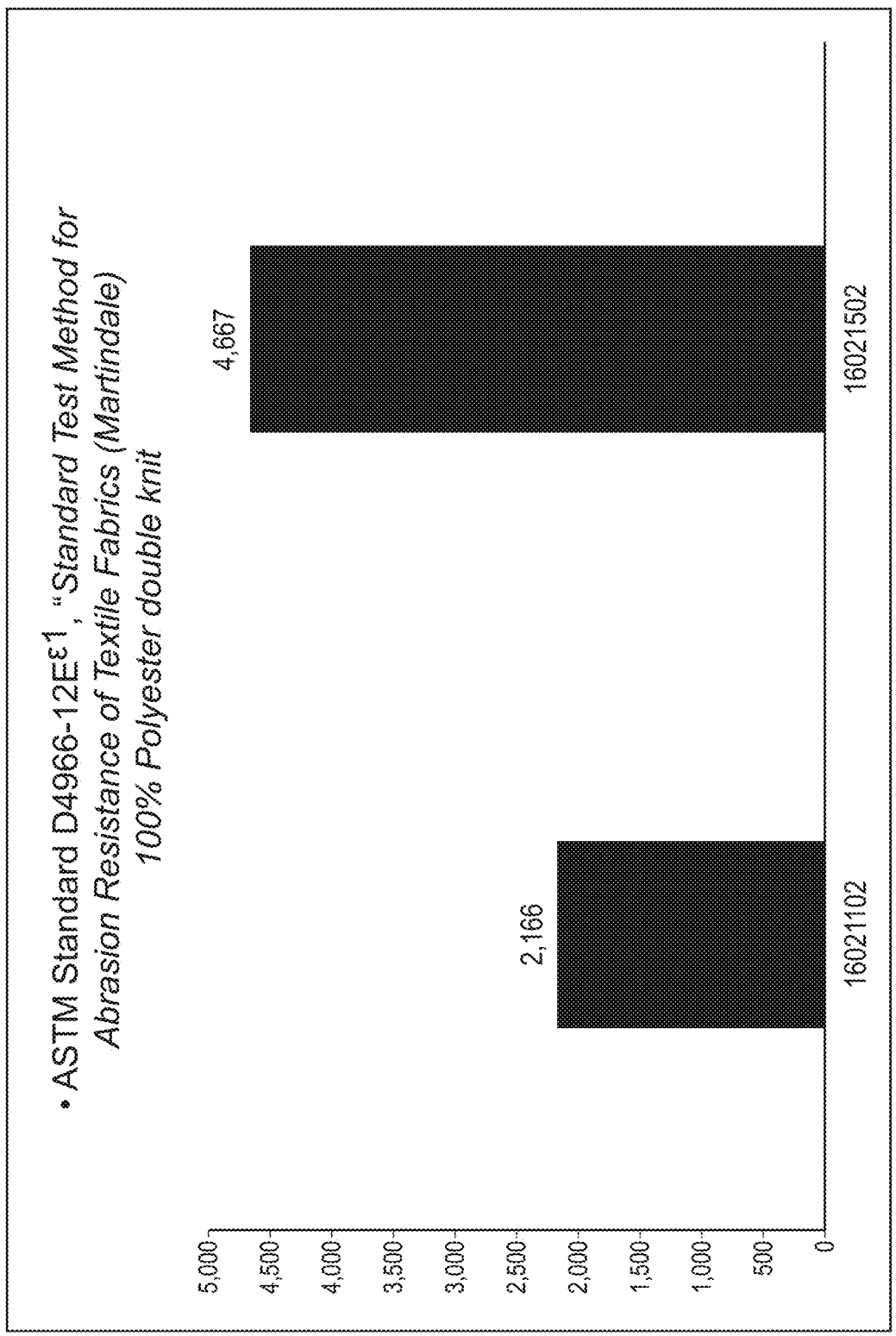

FIG. 156 illustrates abrasion test results for a polyester double knit fabric with (16021502) and without (16021102) coating with 1% silk fibroin solution.

Figure 157:
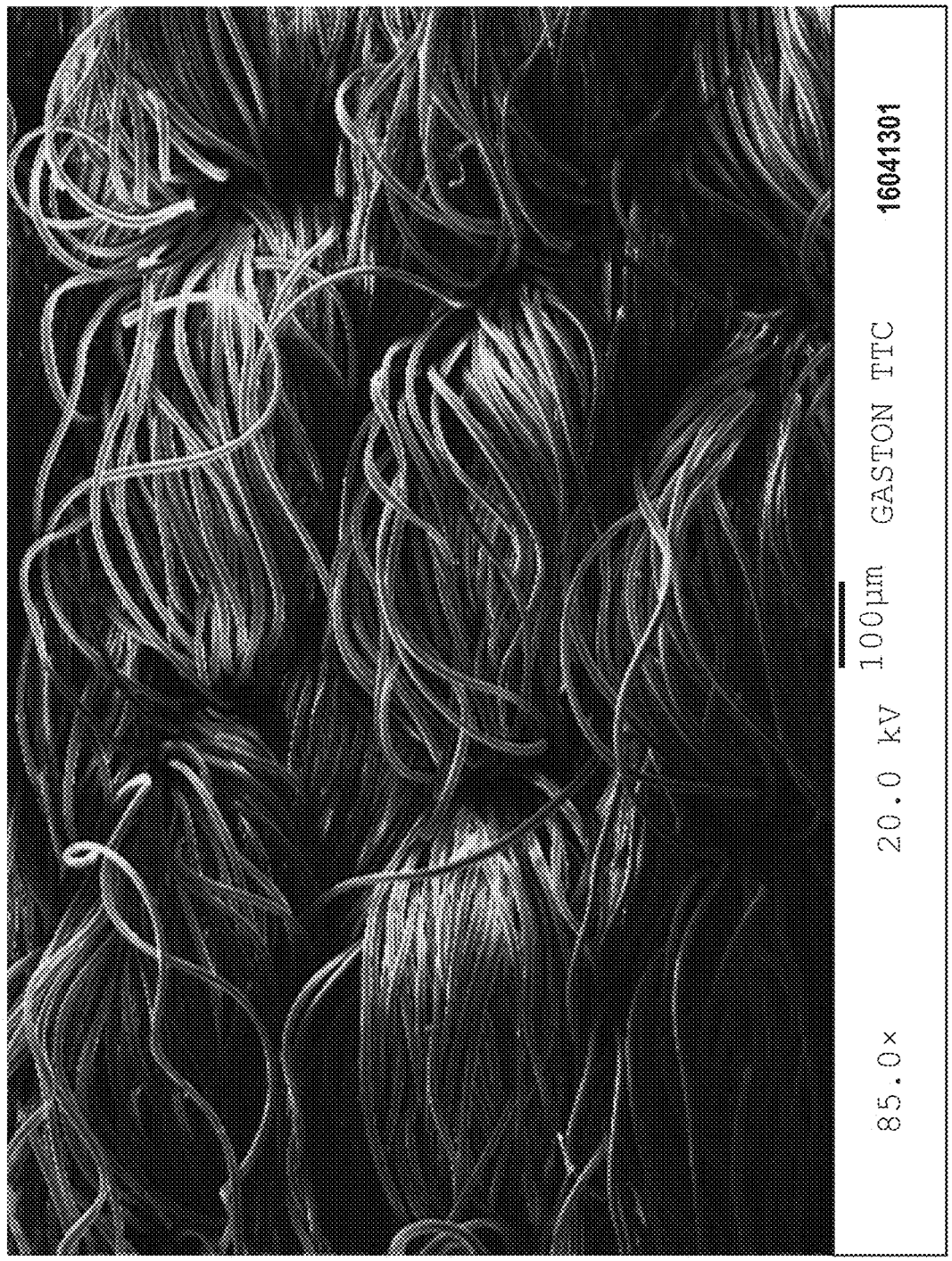

FIG. 157 illustrates a scanning electron microscope image of sample 16041301.

Figure 158:
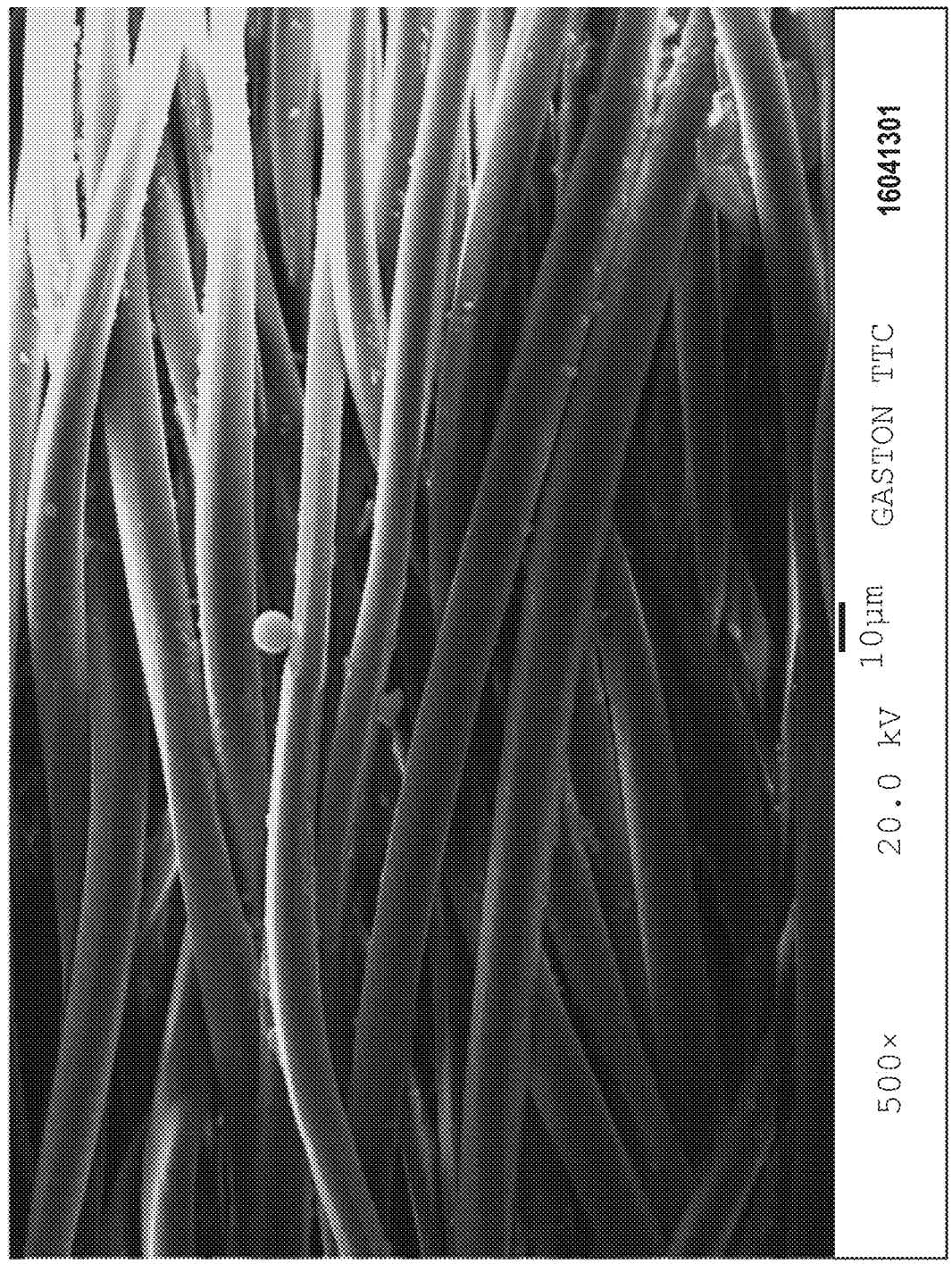

FIG. 158 illustrates a scanning electron microscope image of sample 16041301.

Figure 159:
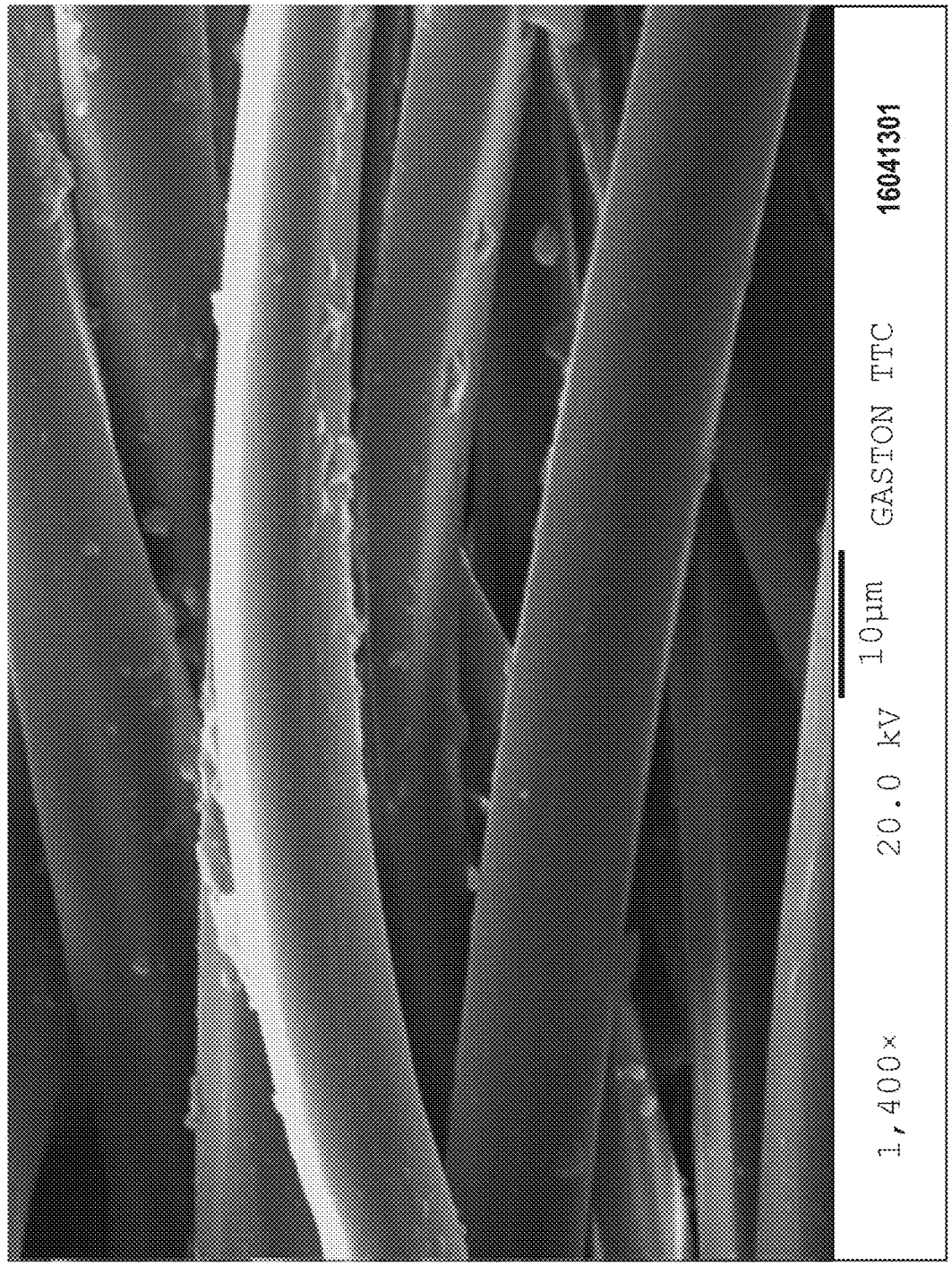

FIG. 159 illustrates a scanning electron microscope image of sample 16041301.

Figure 160:
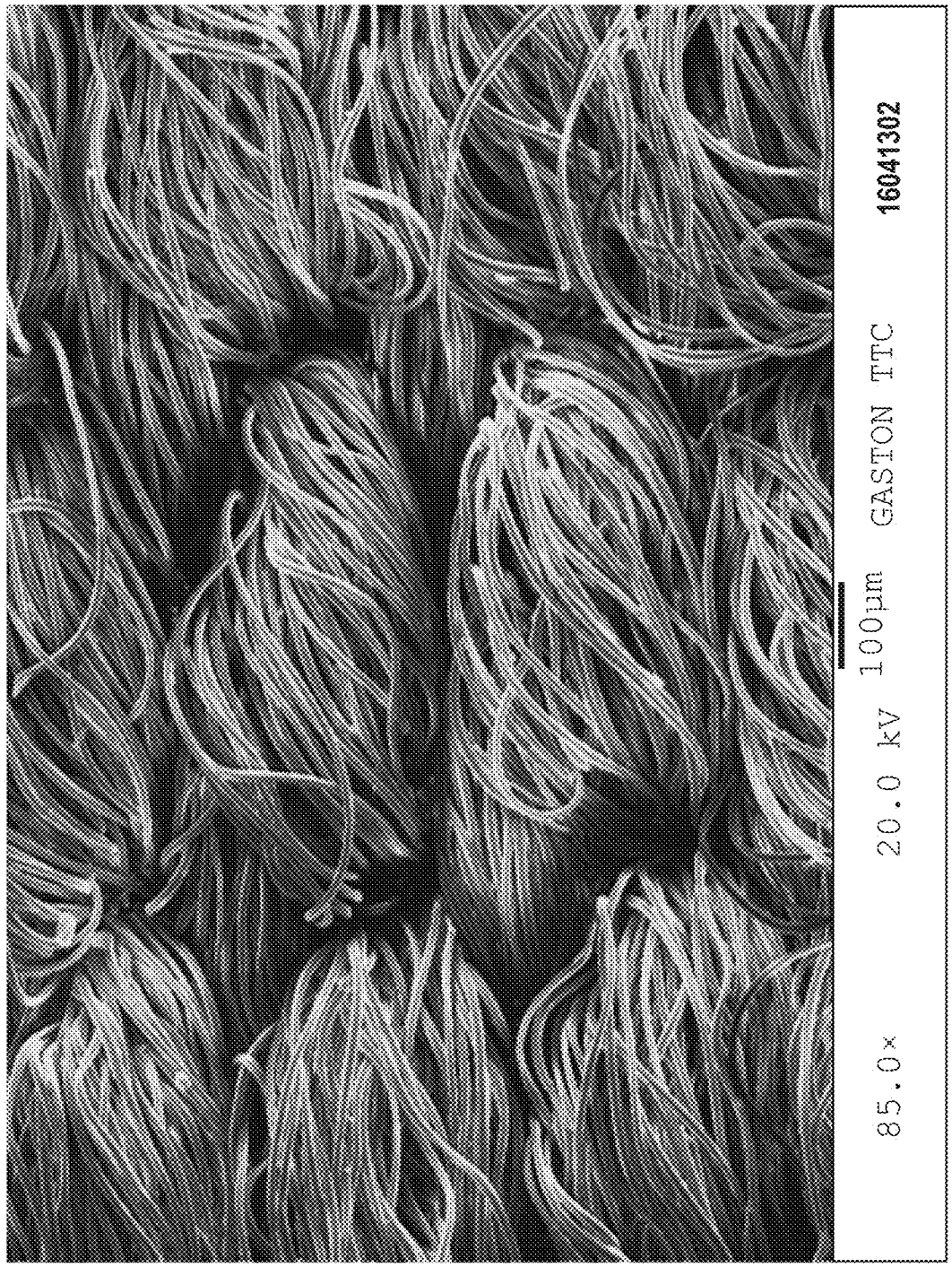

FIG. 160 illustrates a scanning electron microscope image of sample 16041302.

Figure 161:
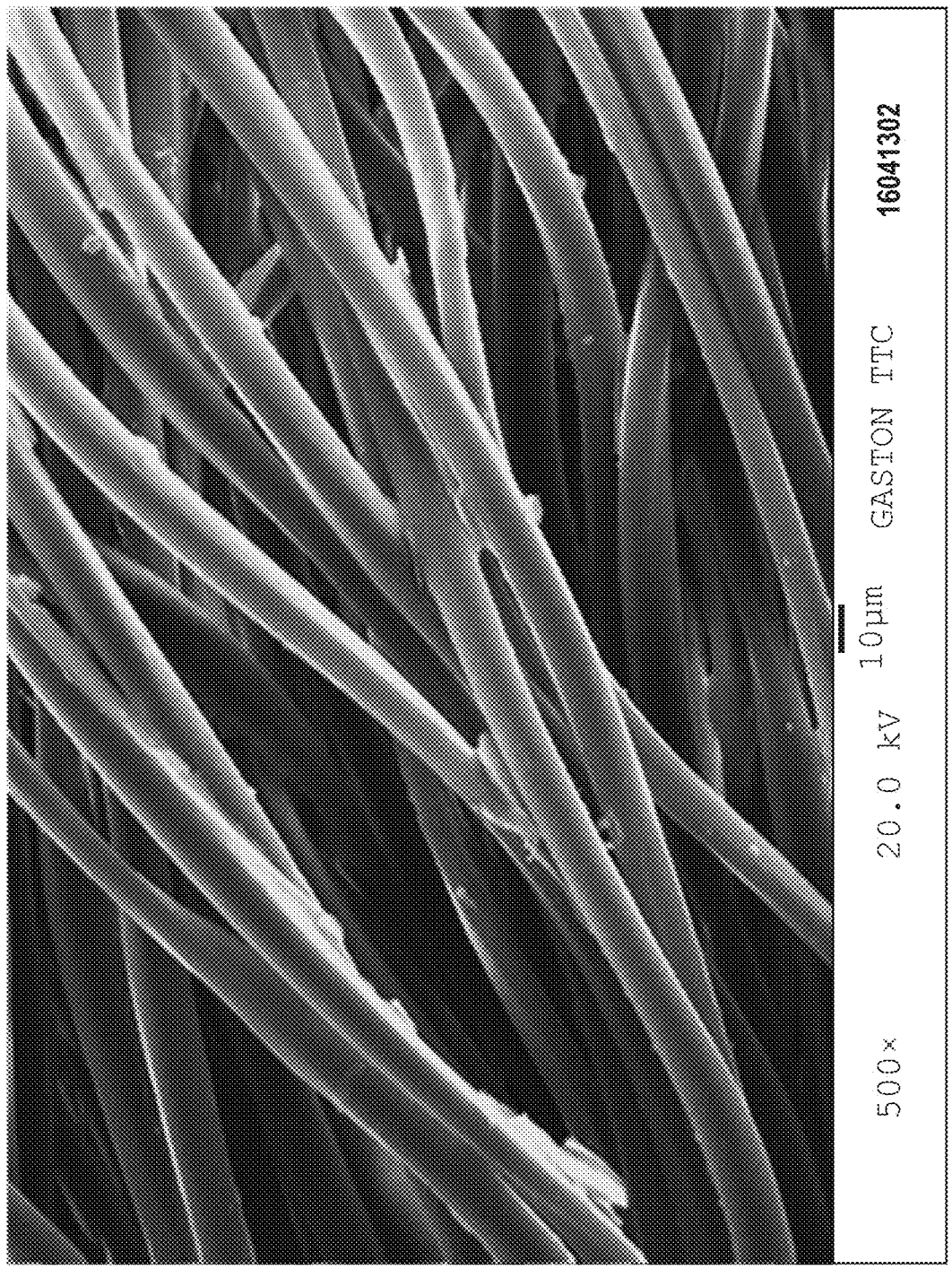

FIG. 161 illustrates a scanning electron microscope image of sample 16041302.

Figure 162:
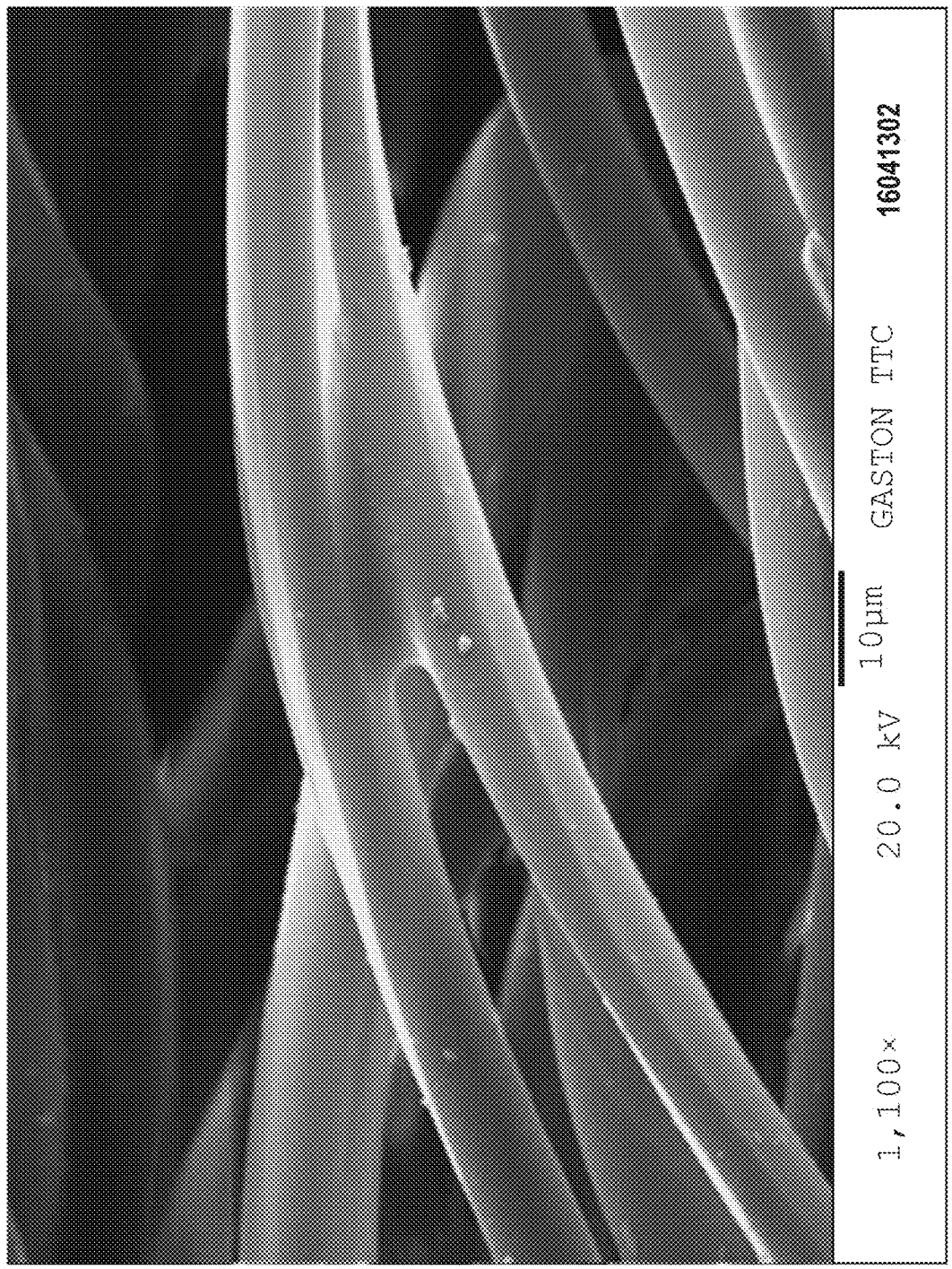

FIG. 162 illustrates a scanning electron microscope image of sample 16041302.

Figure 163:

FIG. 163 illustrates a scanning electron microscope image of sample 16041303.

Figure 164:
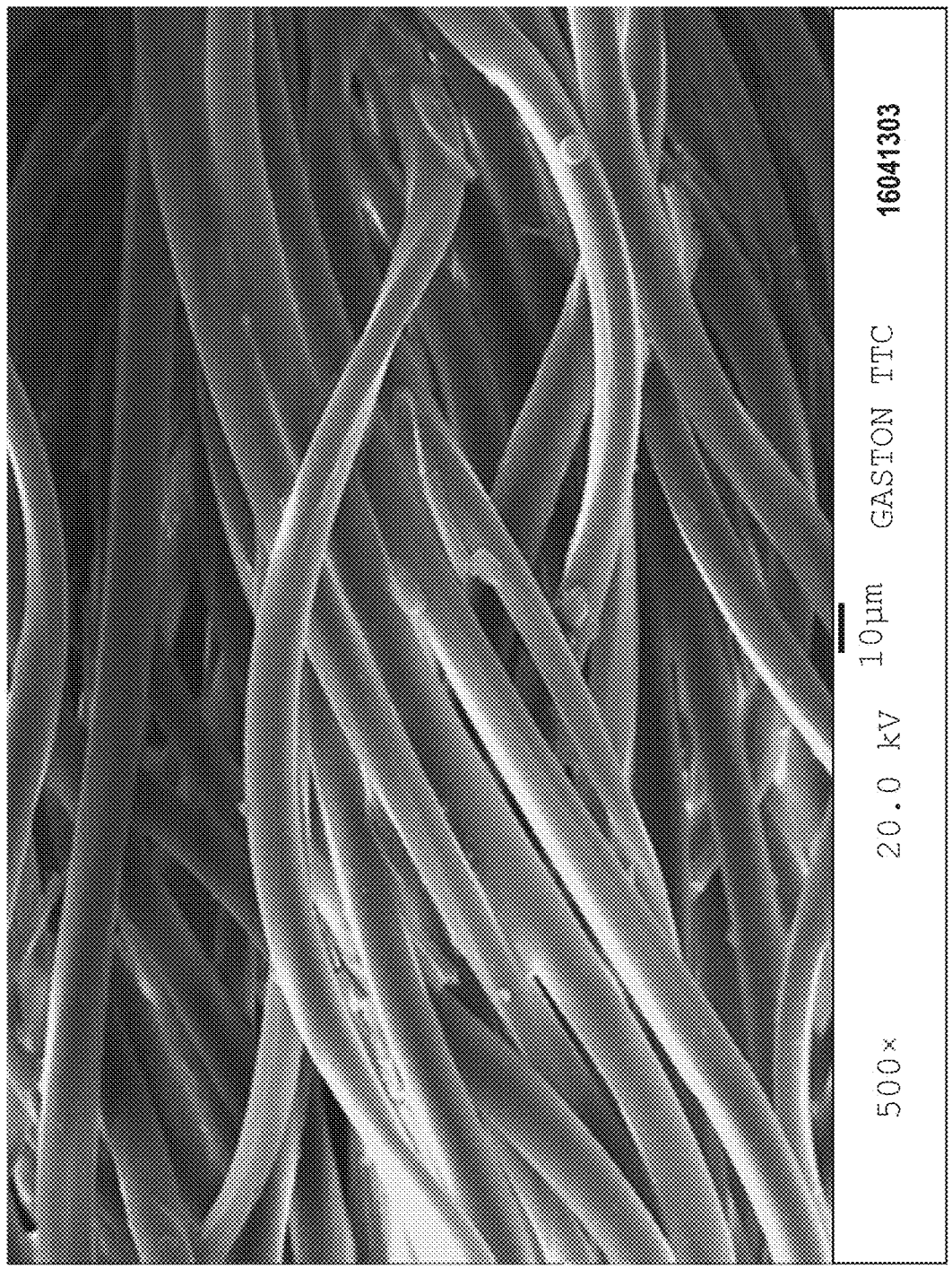

FIG. 164 illustrates a scanning electron microscope image of sample 16041303.

Figure 165:
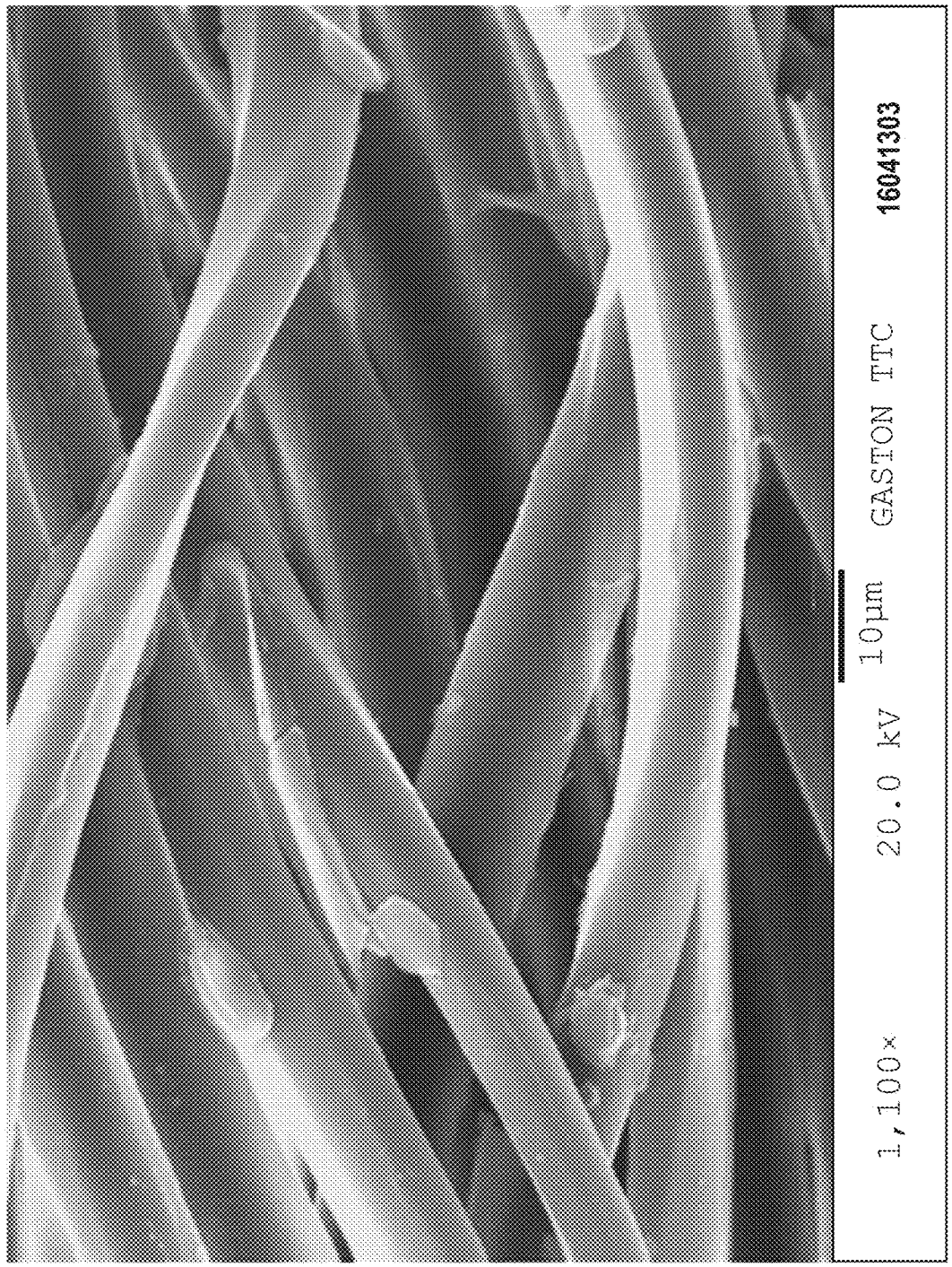

FIG. 165 illustrates a scanning electron microscope image of sample 16041303.

Figure 166:
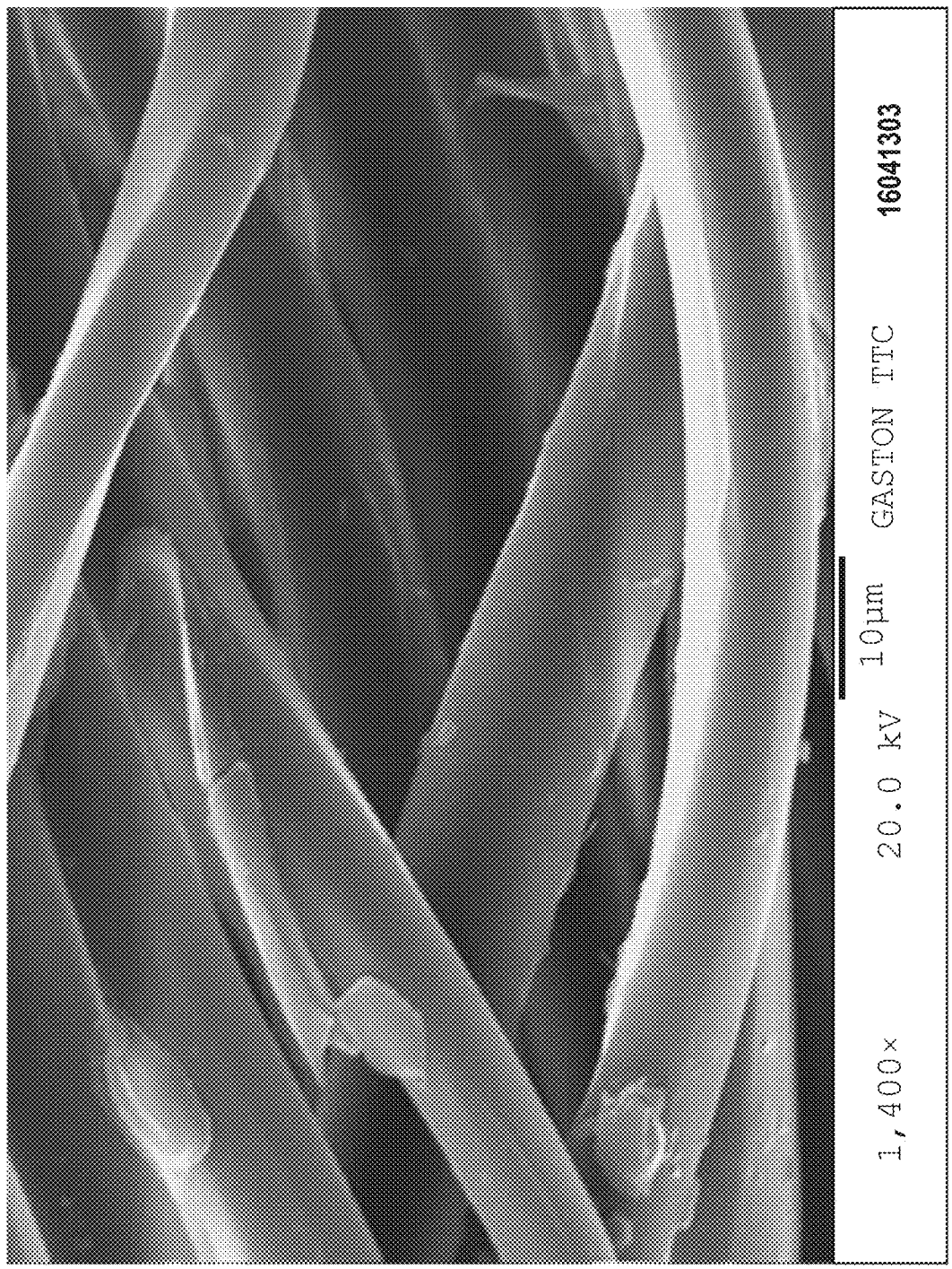

FIG. 166 illustrates a scanning electron microscope image of sample 16041303.

Figure 167:

FIG. 167 illustrates a scanning electron microscope image of sample 16041304.

Figure 168:
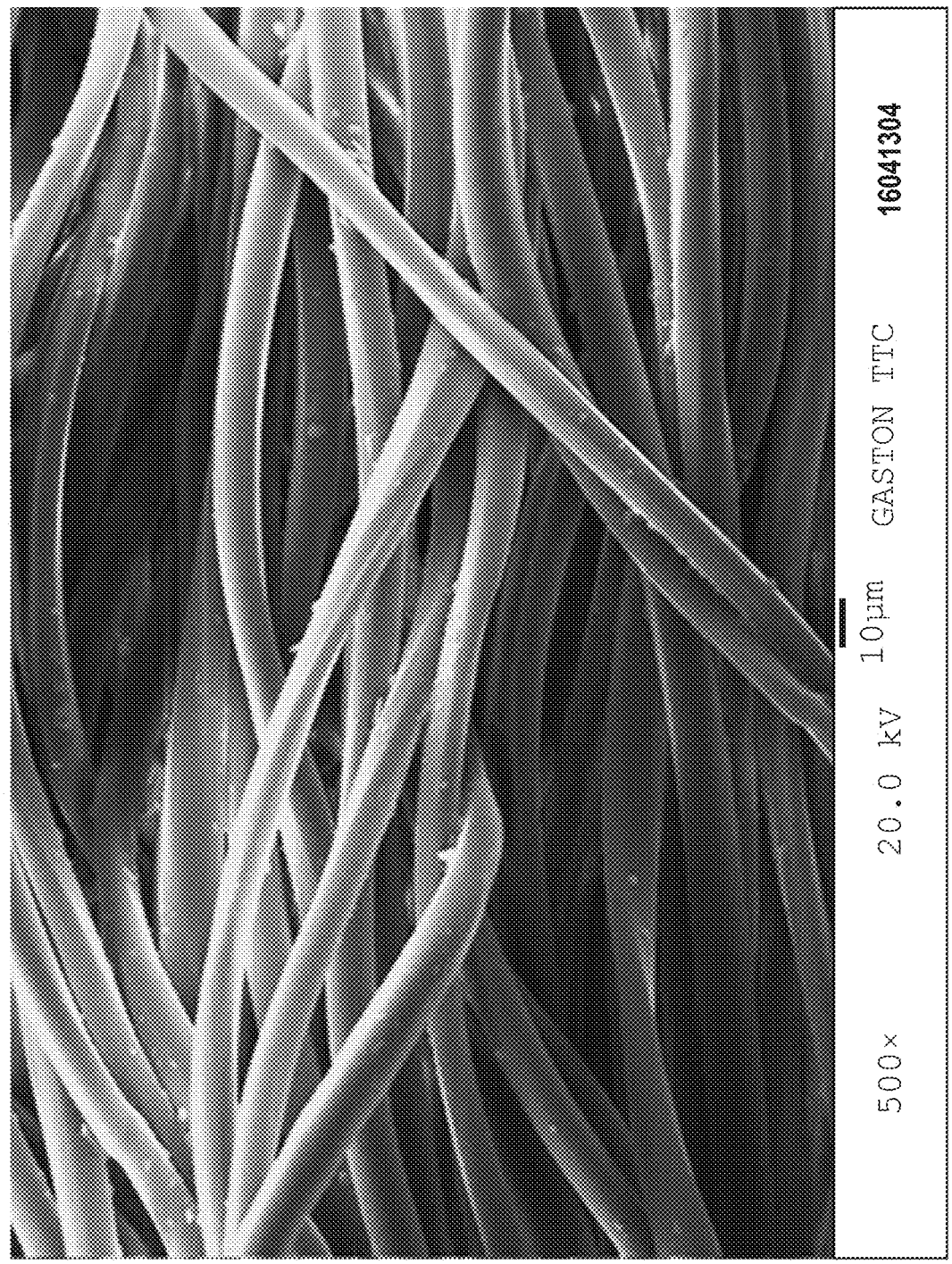

FIG. 168 illustrates a scanning electron microscope image of sample 16041304.

Figure 169:
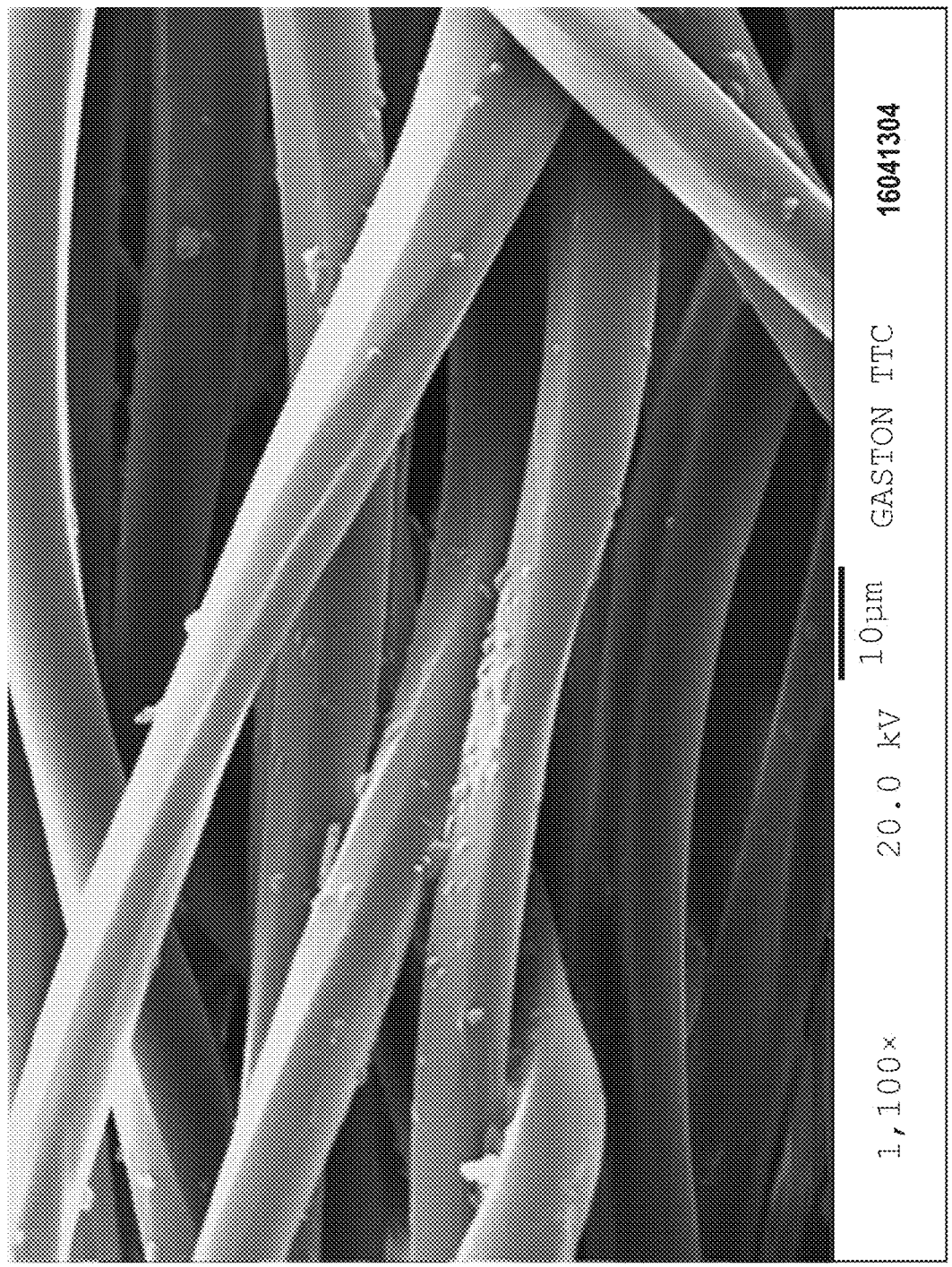

FIG. 169 illustrates a scanning electron microscope image of sample 16041304.

Figure 170:
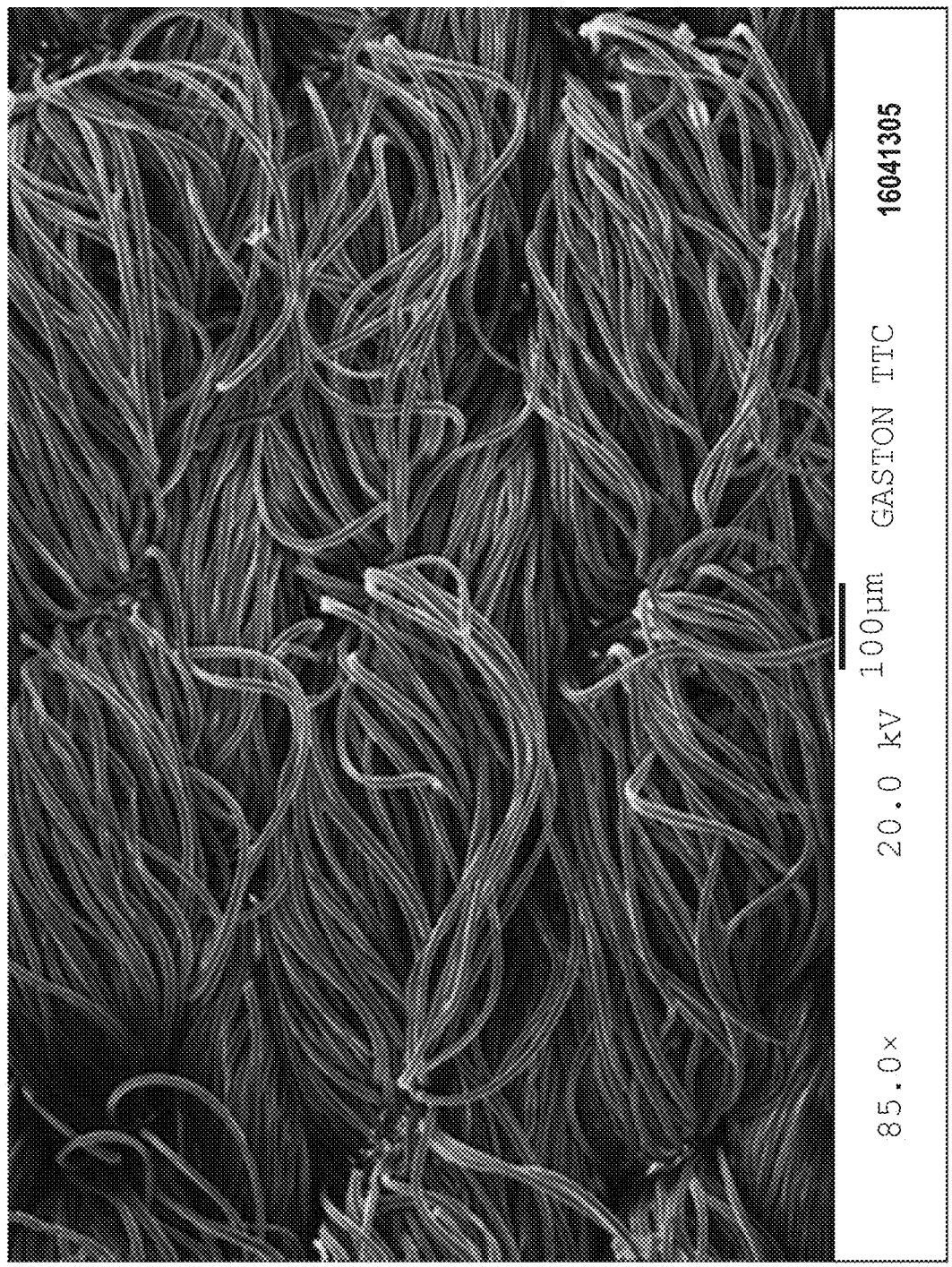

FIG. 170 illustrates a scanning electron microscope image of sample 16041305.

Figure 171:
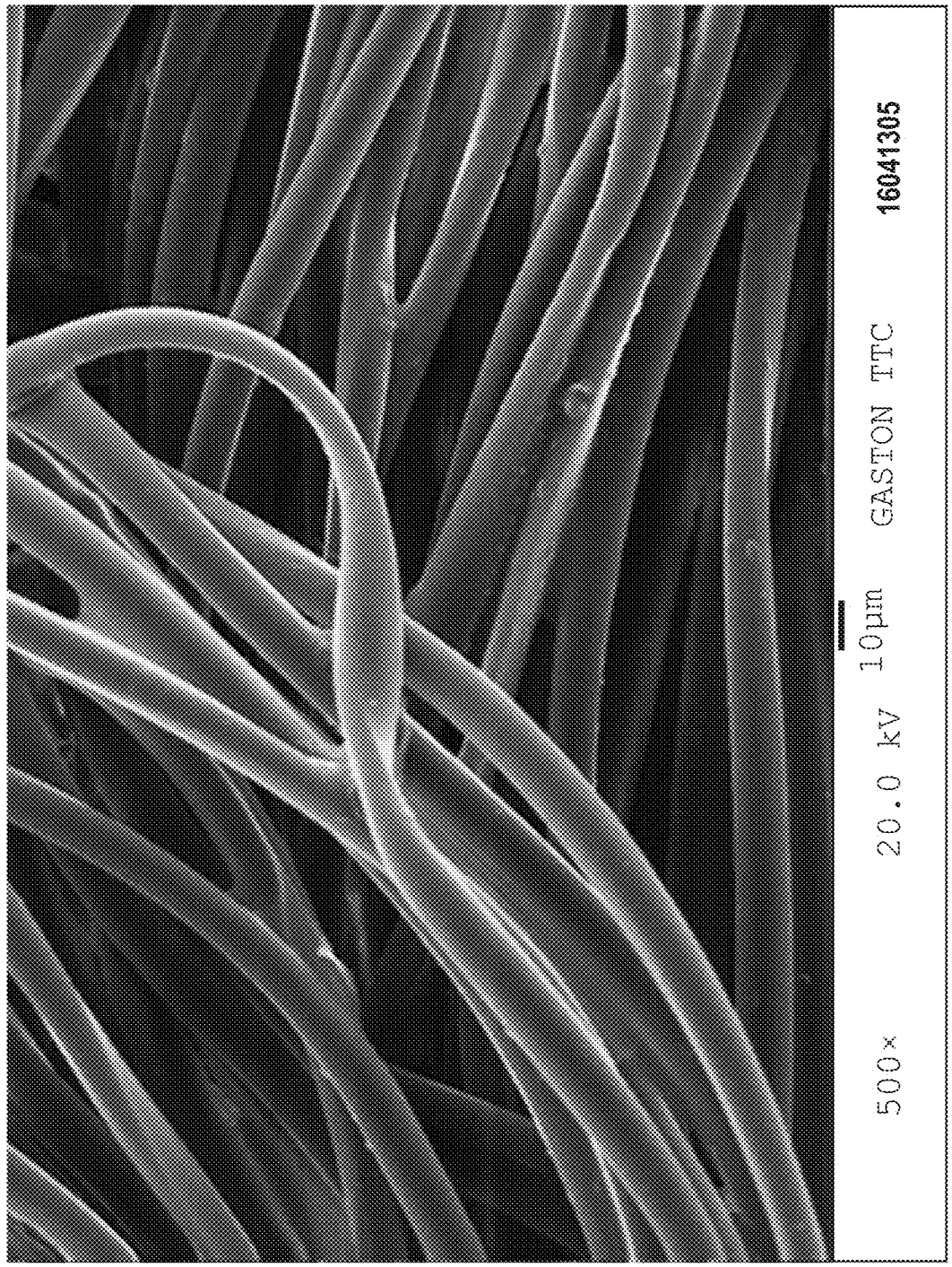

FIG. 171 illustrates a scanning electron microscope image of sample 16041305.

Figure 172:
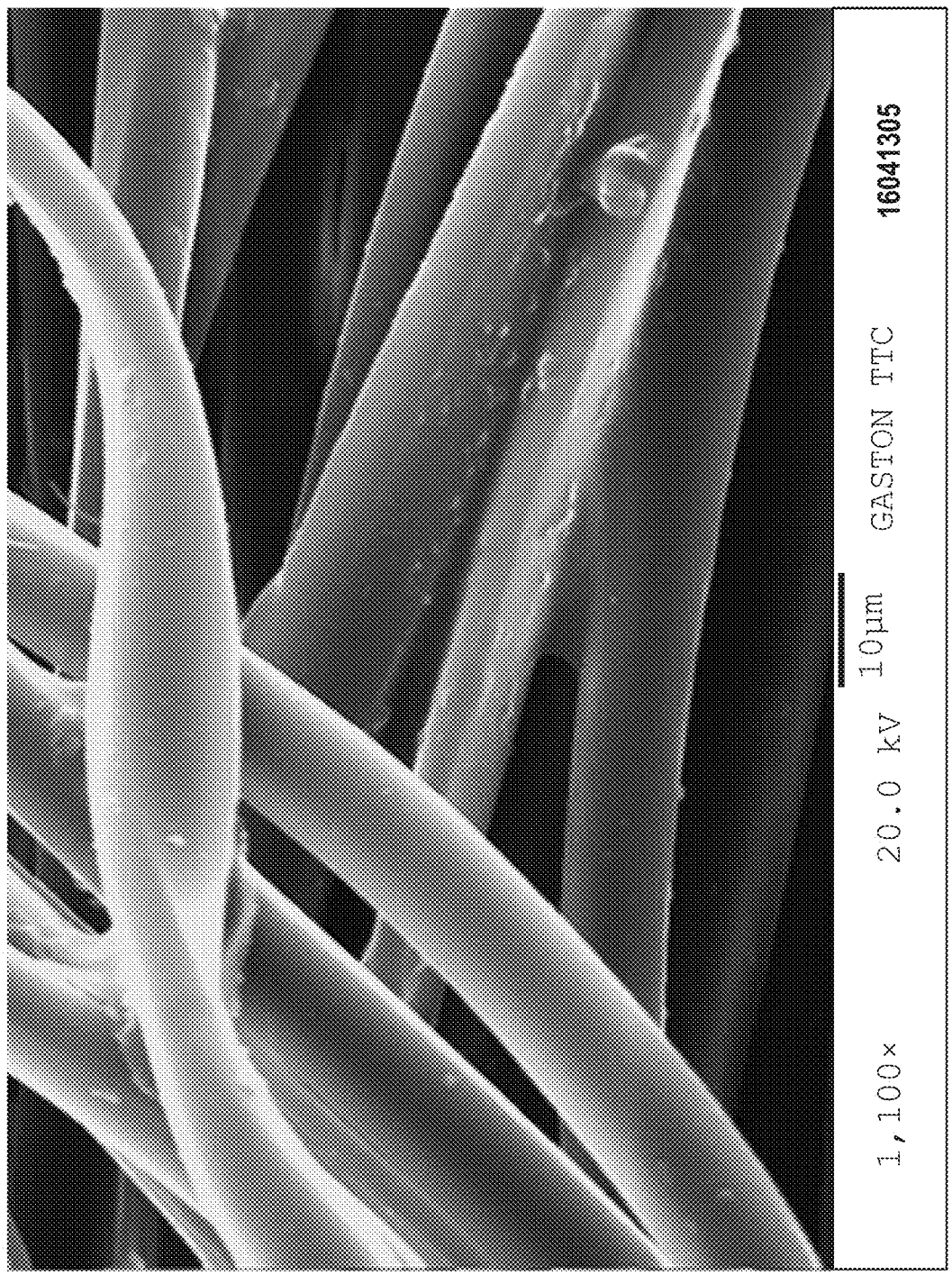

FIG. 172 illustrates a scanning electron microscope image of sample 16041305.

Figure 173:
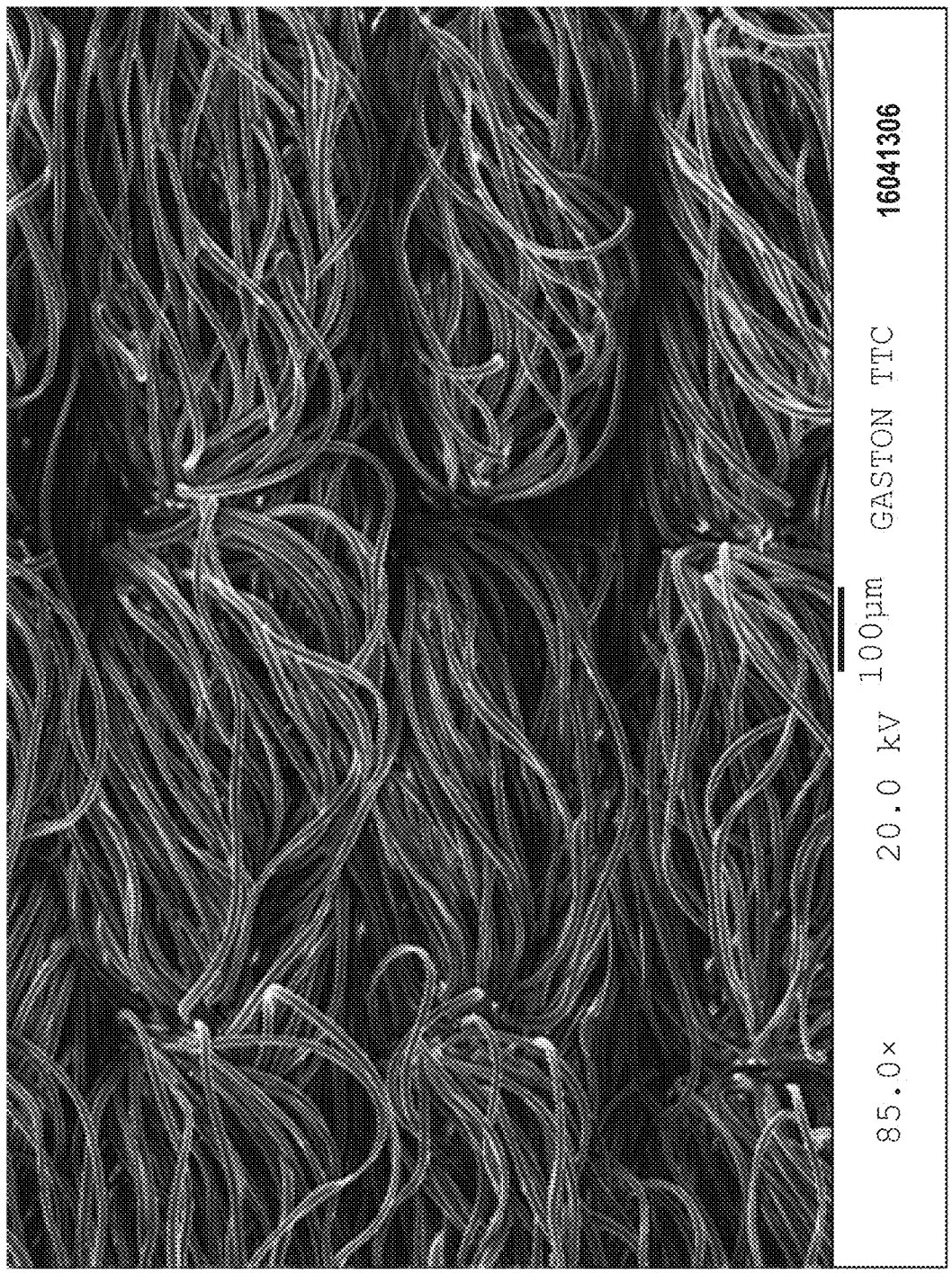

FIG. 173 illustrates a scanning electron microscope image of sample 16041306.

Figure 174:

FIG. 174 illustrates a scanning electron microscope image of sample 16041306.

Figure 175:
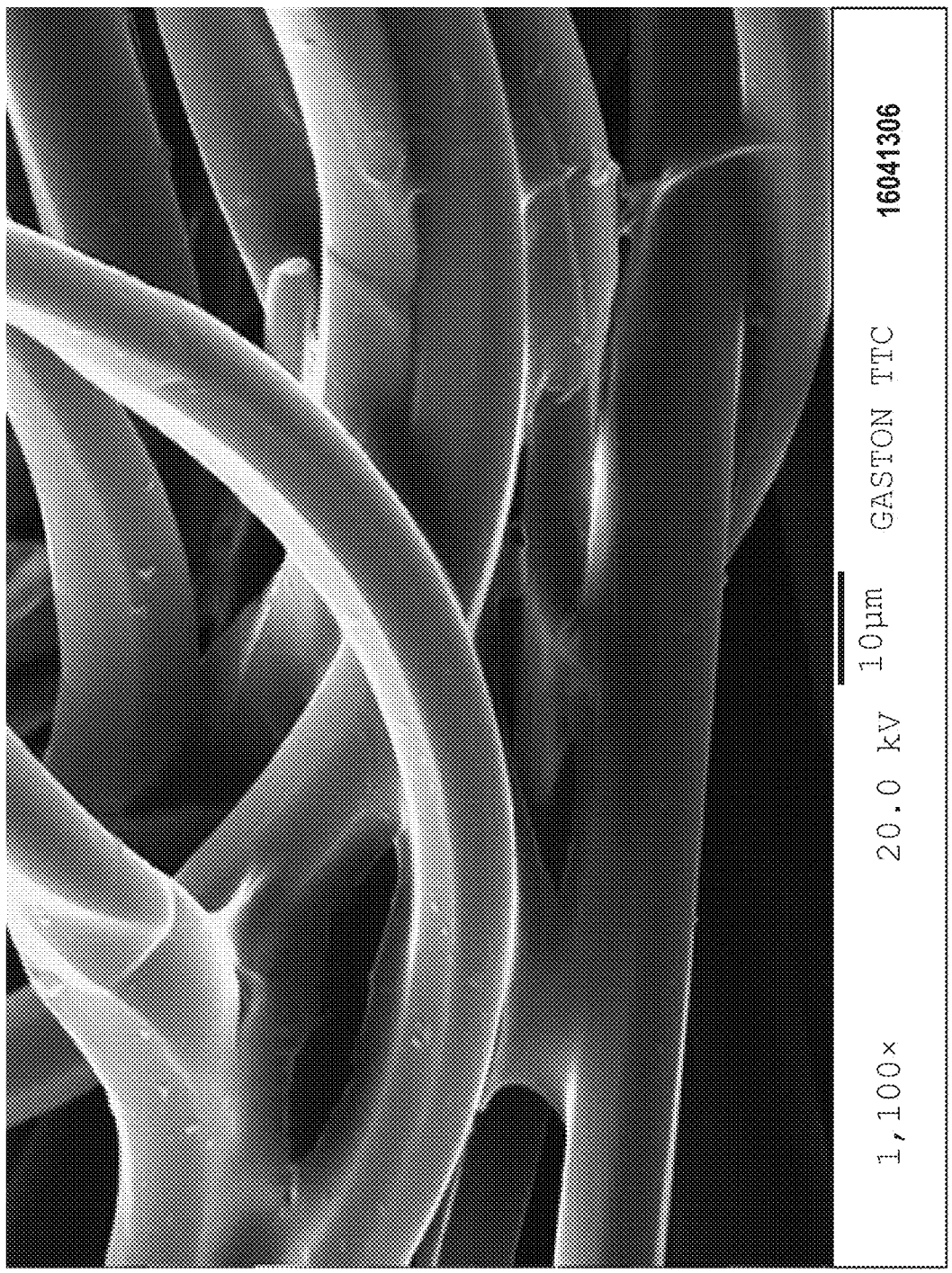

FIG. 175 illustrates a scanning electron microscope image of sample 16041306.

Figure 176:
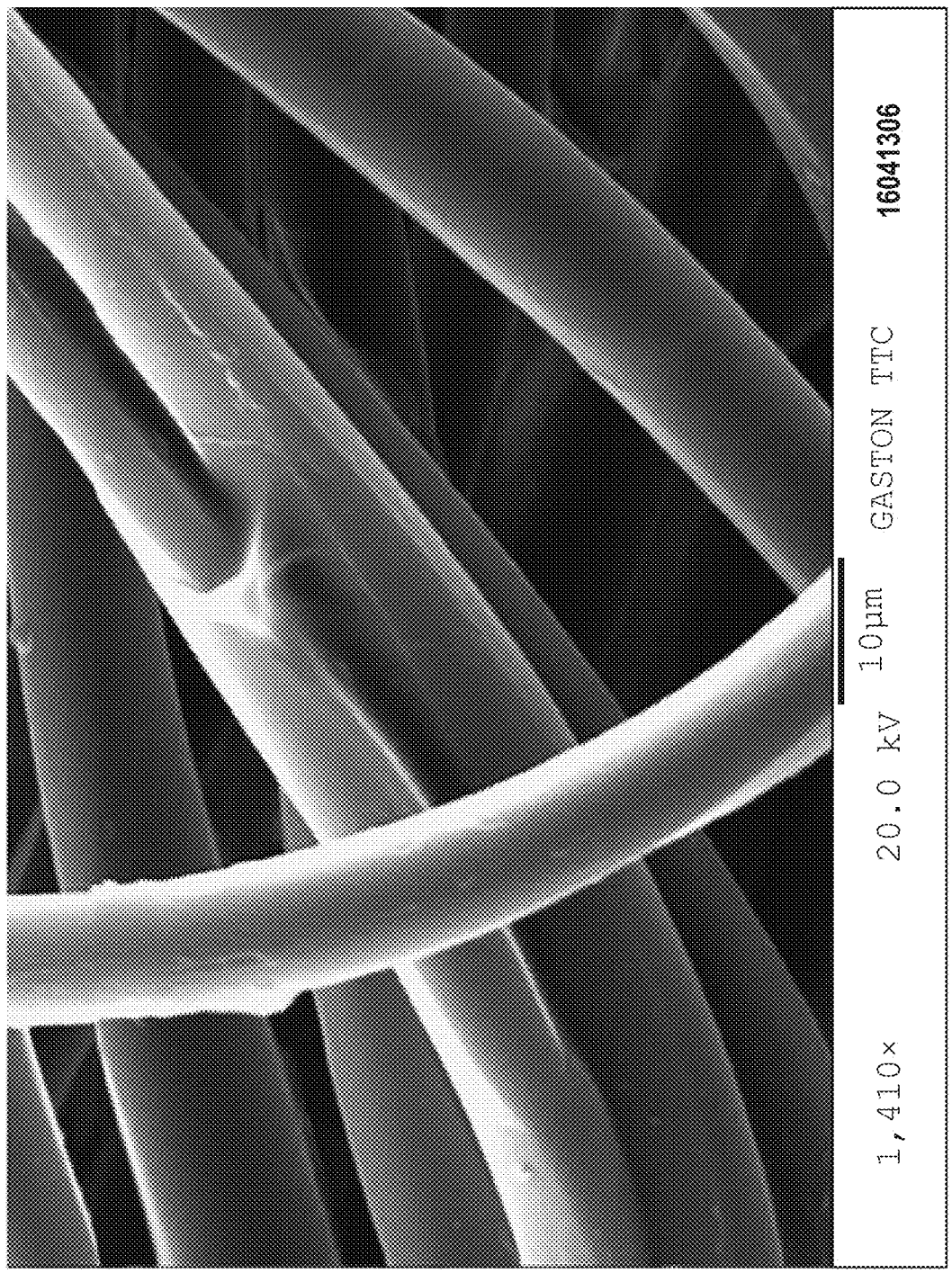

FIG. 176 illustrates a scanning electron microscope image of sample 16041306.

Figure 177:

FIG. 177 illustrates a scanning electron microscope image of sample 16040803.

Figure 178:
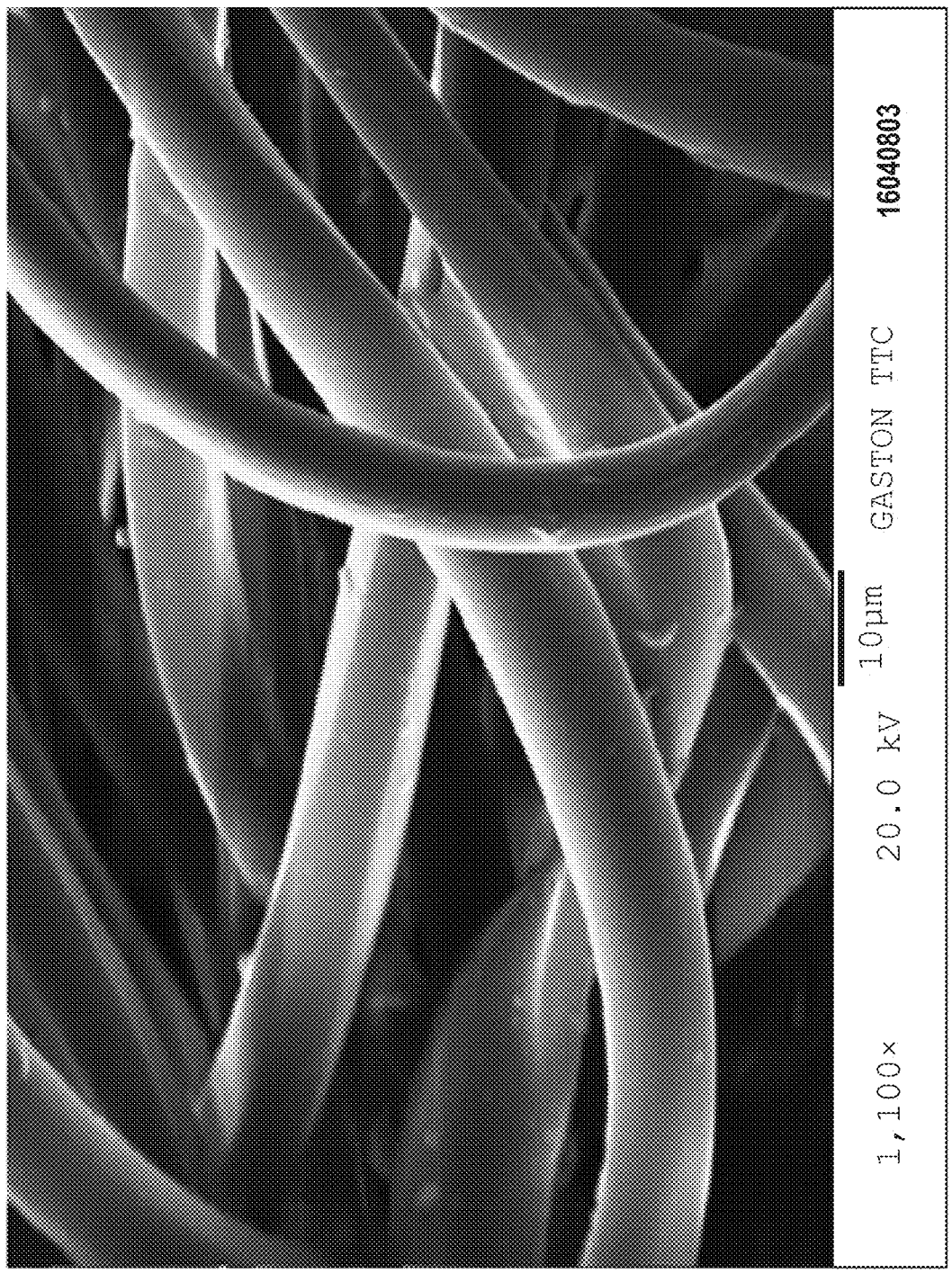

FIG. 178 illustrates a scanning electron microscope image of sample 16040803.

Figure 179:
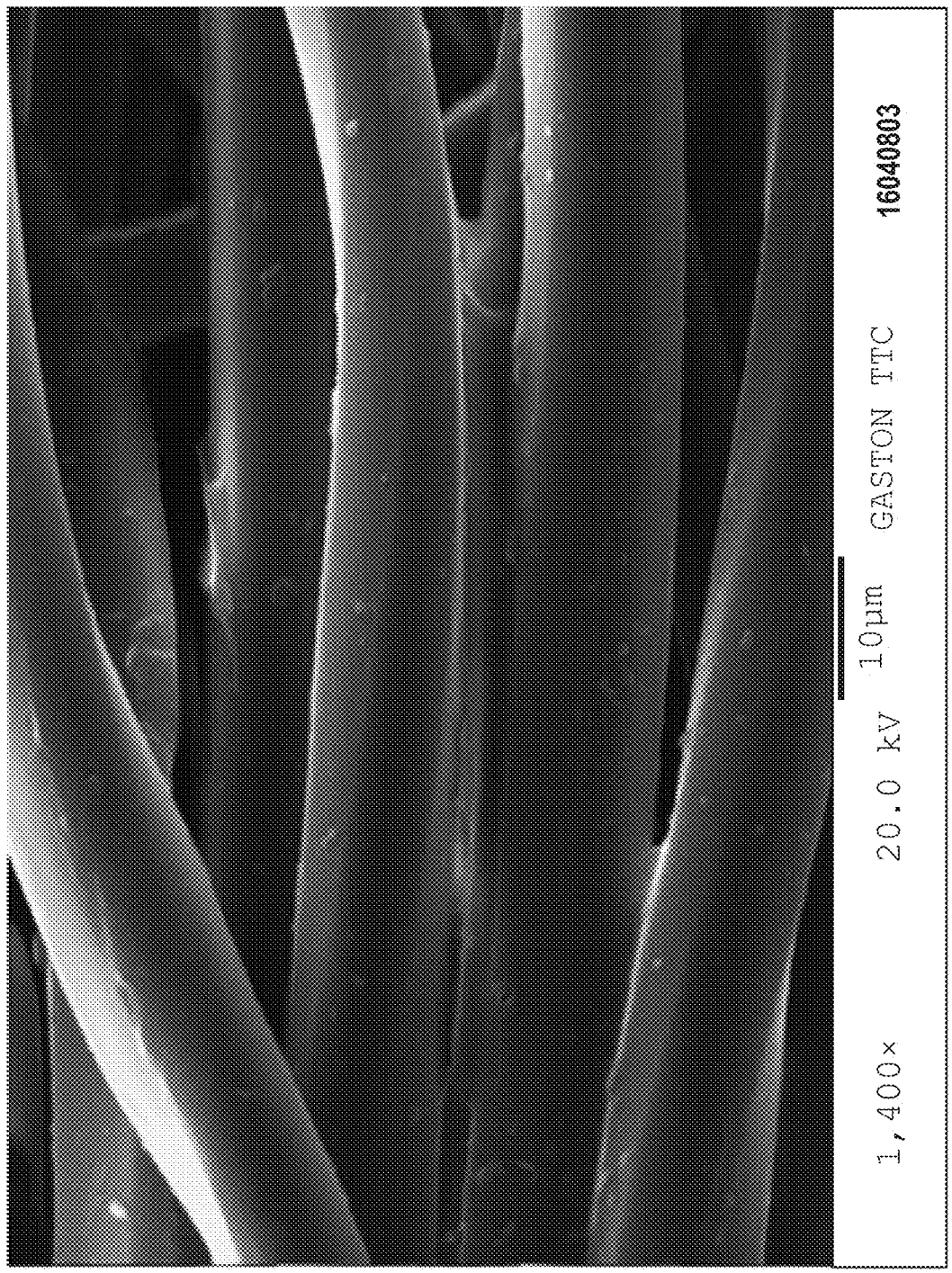

FIG. 179 illustrates a scanning electron microscope image of sample 16040803.

Figure 180:

FIG. 180 illustrates a scanning electron microscope image of sample 16040808.

Figure 181:

FIG. 181 illustrates a scanning electron microscope image of sample 16040808.

Figure 182:
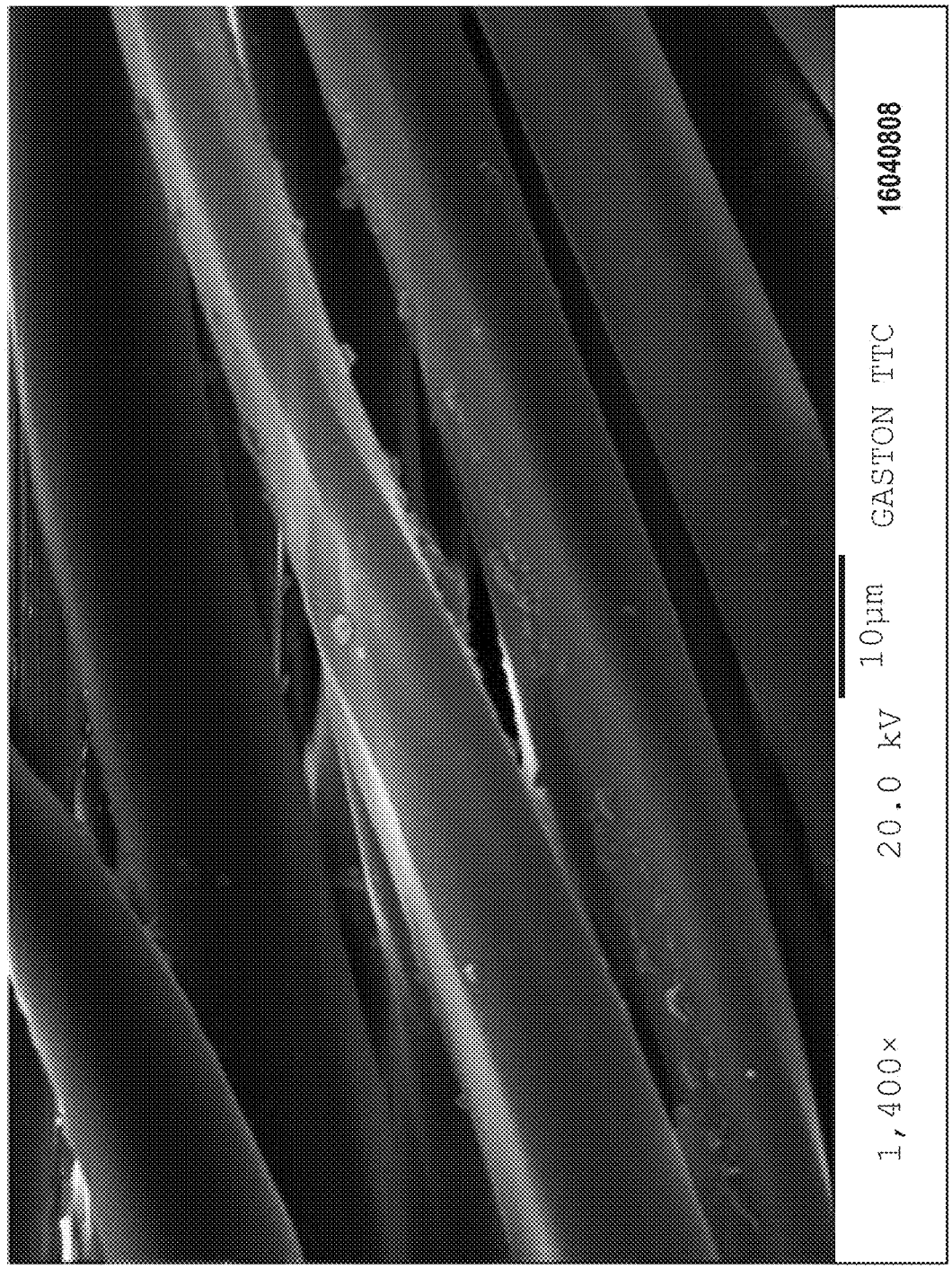

FIG. 182 illustrates a scanning electron microscope image of sample 16040808.

Figure 183:
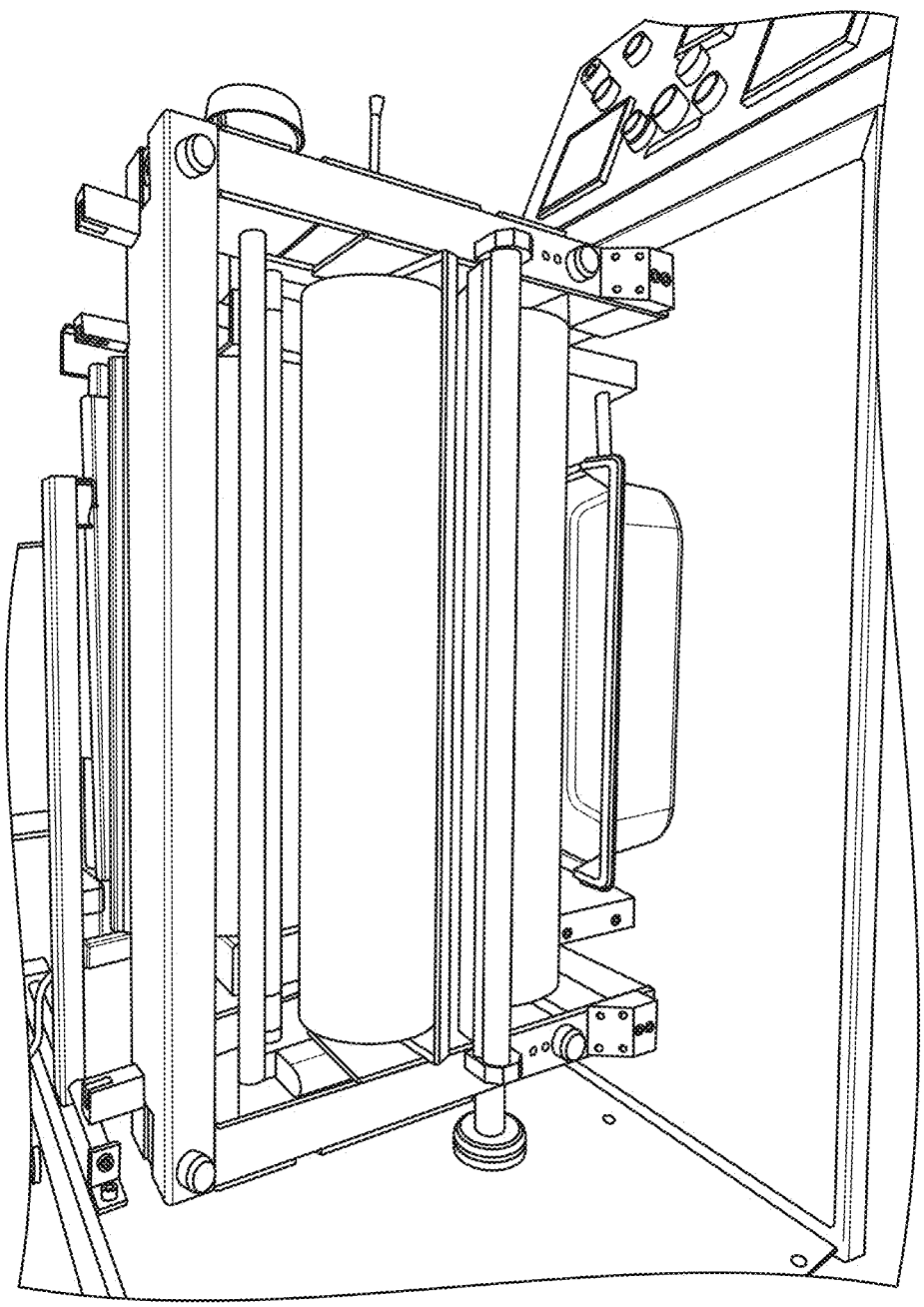

FIG. 183 illustrates an exemplary padder roller.

Figure 184:
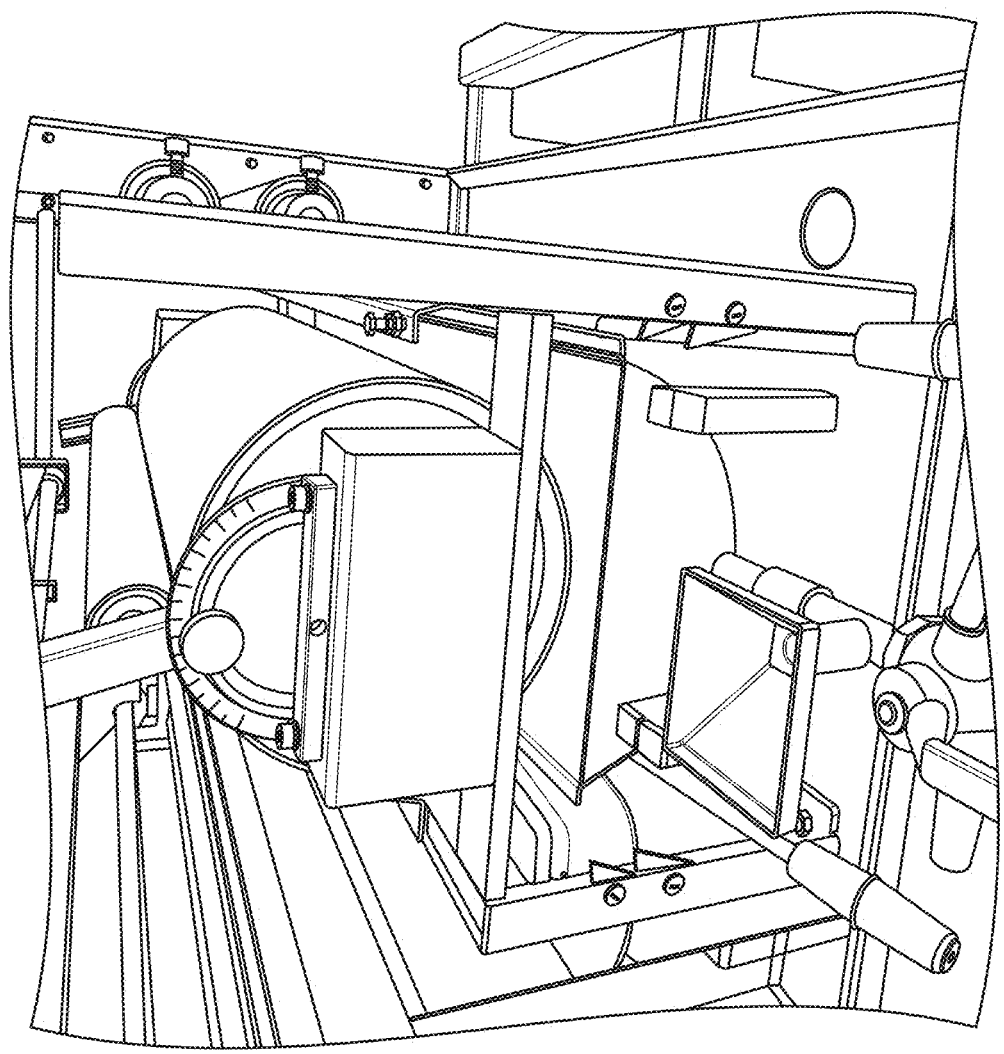

FIG. 184 illustrates an exemplary kiss roller.

Figure 185:
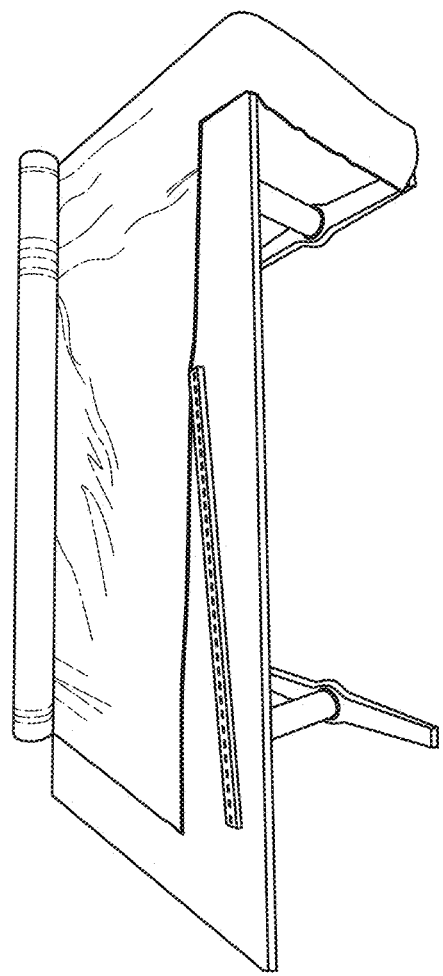

FIG. 185 illustrates the process of unrolling an exemplary fabric roller.

Figure 186:
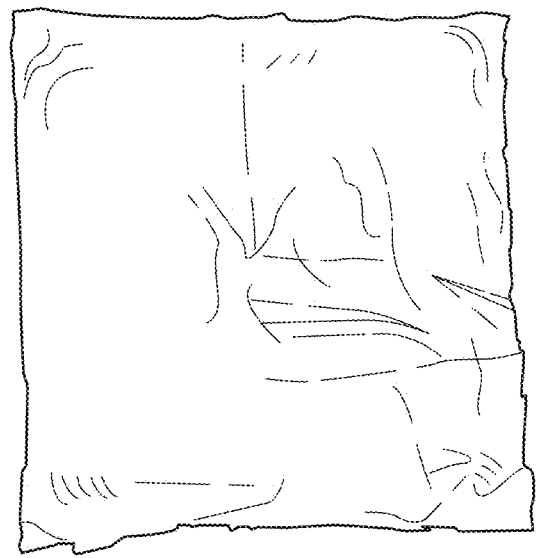

FIG. 186 illustrates a square of sample fabric to be coated.

Figure 187:
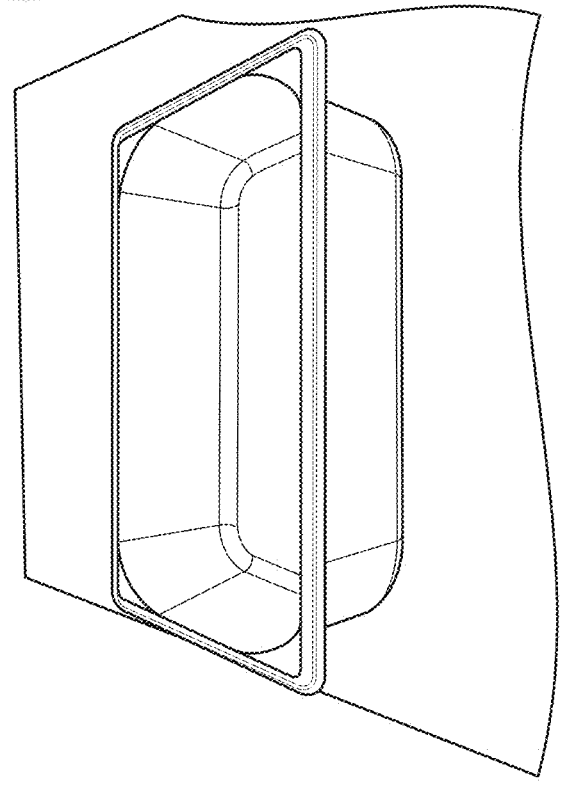

FIG. 187 illustrates an exemplary stainless steel bath.

Figure 188:
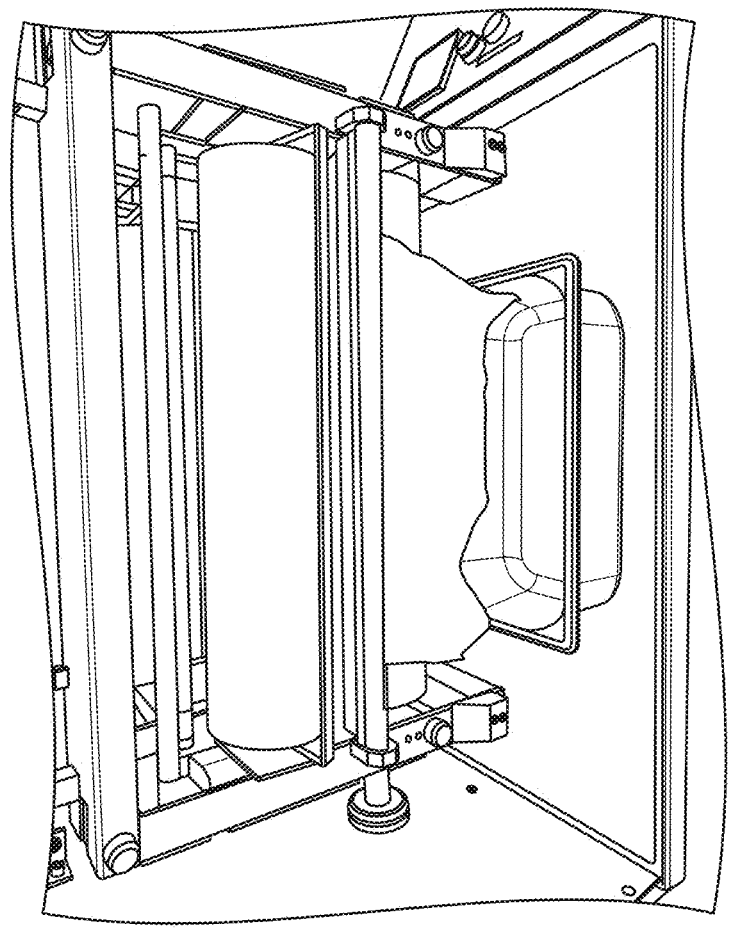

FIG. 188 illustrates a padder unit having two rollers.

Figure 189:
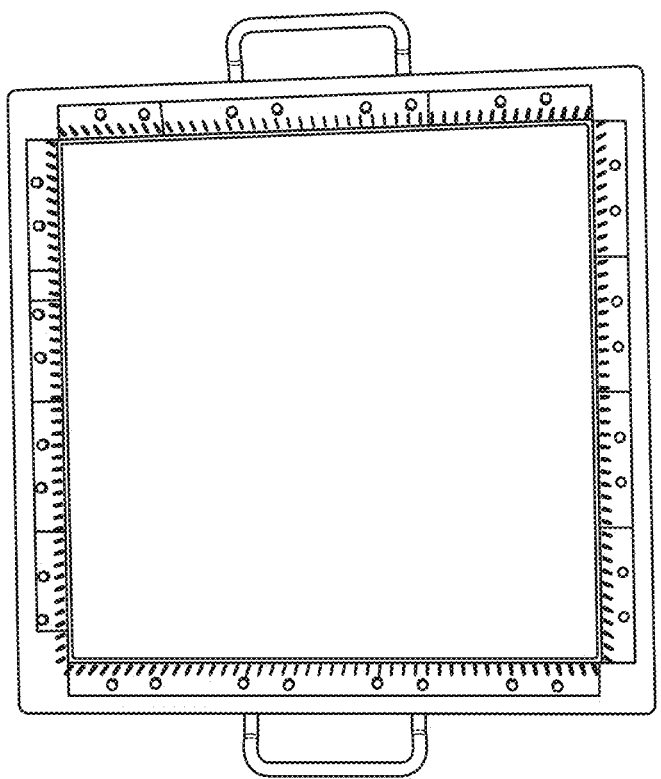

FIG. 189 illustrates a curing frame without fabric provided thereon.

Figure 190:
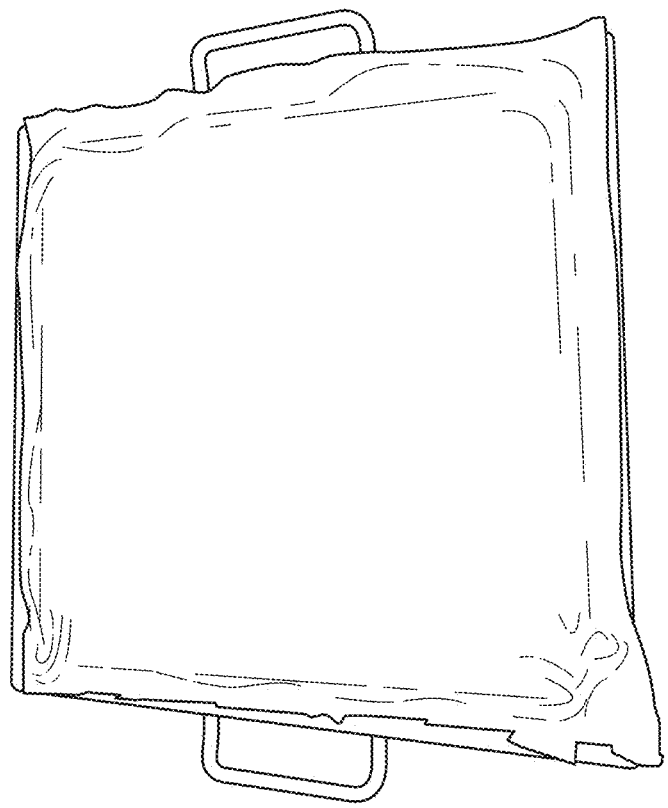

FIG. 190 illustrates a curing frame with fabric provided thereon.

Figure 191:
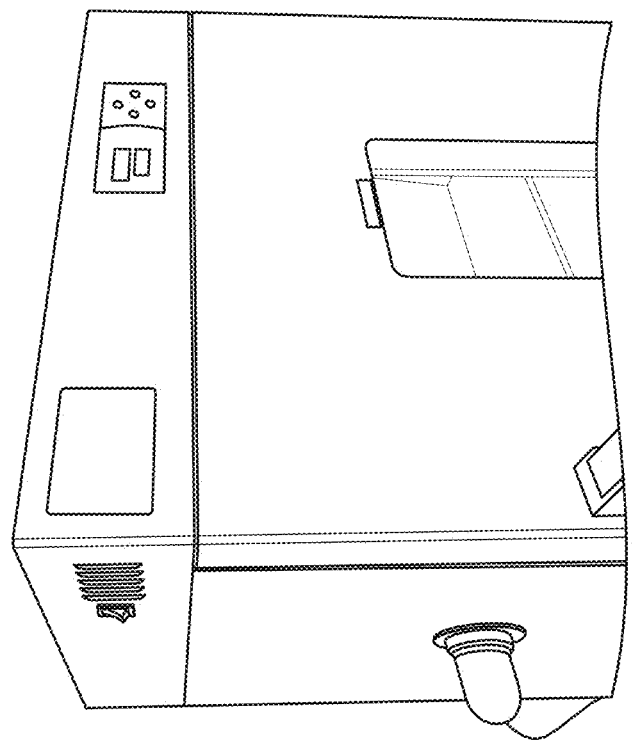

FIG. 191 illustrates an exemplary curing oven.

Figure 192:
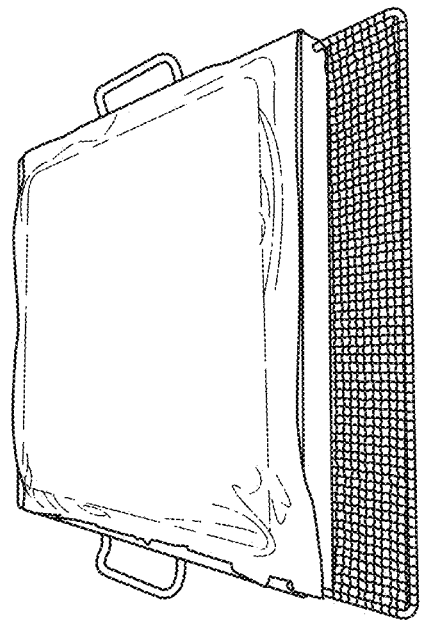

FIG. 192 illustrates a cooling rack with a curing frame and fabric provided thereon.

FIG. 193 illustrates a table that provides testing results for wetting time, absorption rate, wetted radius, spreading speed, accumulative one-way transport, and overall moisture management capability (OMMC) for sample nos. 16040101, 16040102, 16040103, 16040104, 16040105, and 16040106.

FIG. 194 illustrates testing results in grades for wetting time, absorption rate, wetted radius, spreading speed, accumulative one-way transport, and OMMC for 16040101, 16040102, 16040103, 16040104, 16040105, and 16040106.

FIG. 195 illustrates testing results for wetting time, absorption rate, wetted radius, spreading speed, accumulative one-way transport, and OMMC for 16040801, 16040802, 16040803, 16040804, 16040805, 16040806, 16040807, and 16040808.

FIG. 196 illustrates testing results in grades for wetting time, absorption rate, wetted radius, spreading speed, accumulative one-way transport, and OMMC for 16040801, 16040802, 16040803, 16040804, 16040805, 16040806, 16040807, and 16040808.

FIG. 197 illustrates testing results for wetting time, absorption rate, wetted radius, spreading speed, accumulative one-way transport, and OMMC for 16041201, 16041202, 16041302, 16041303, 16041203, 16041204, 16041305, 16041306, 16041301, and 16041304.

FIG. 198 illustrates testing results in grades for wetting time, absorption rate, wetted radius, spreading speed, accumulative one-way transport, and OMMC for 16041201, 16041202, 16041302, 16041303, 16041203, 16041204, 16041305, 16041306, 16041301, and 16041304.

FIG. 199 illustrates testing results for wetting time, absorption rate, wetted radius, spreading speed, accumulative one-way transport, and OMMC for 16041301, 16041302, 16041303, 16041304, 16041305, 16041306, 16042001, 16040101, and 16040106.

FIG. 200 illustrates testing results in grades for wetting time, absorption rate, wetted radius, spreading speed, accumulative one-way transport, and OMMC for 16041301, 16041302, 16041303, 16041304, 16041305, 16041306, 16042001, 16040101, and 16040106.

Figure 202:
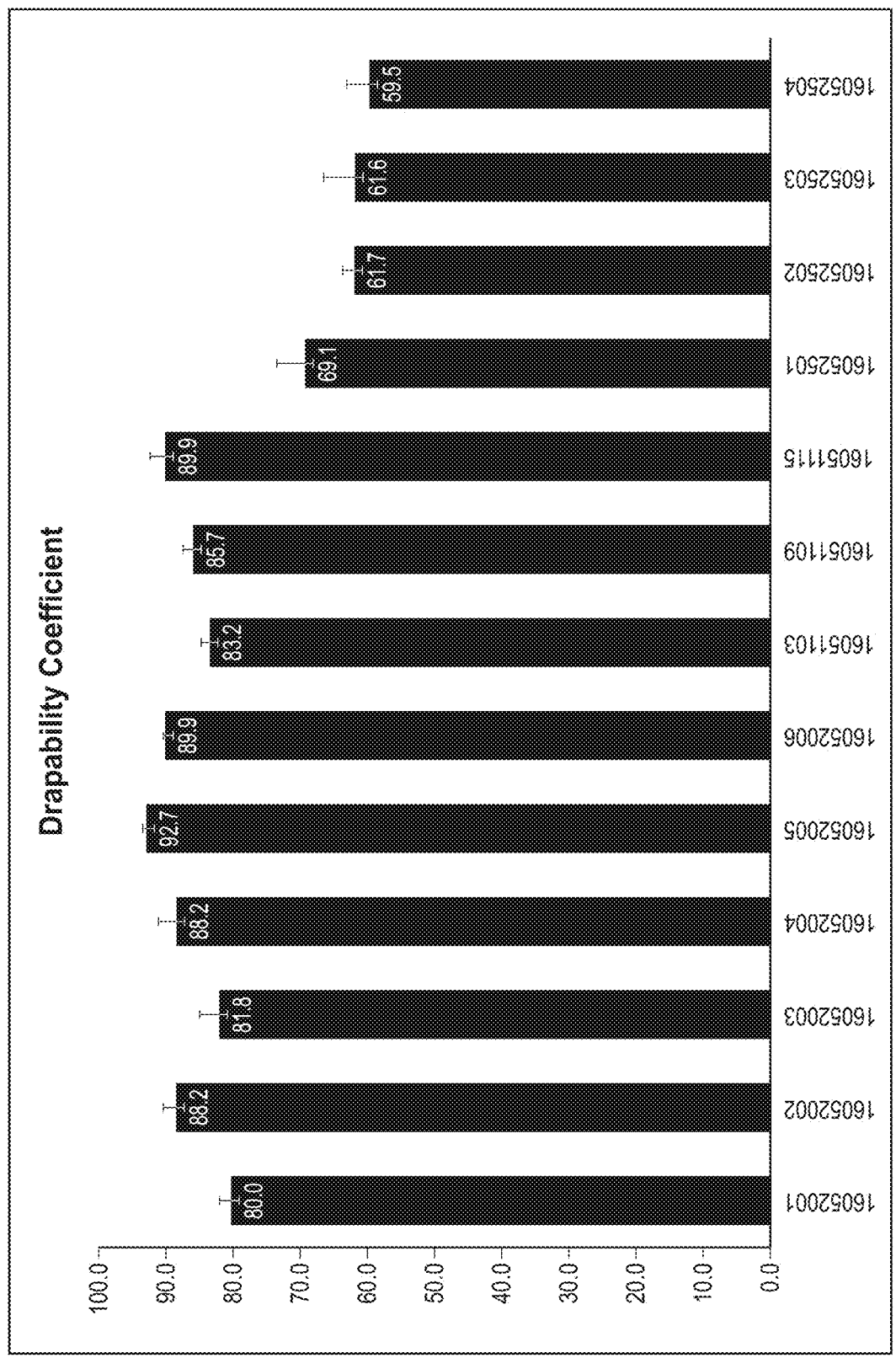

FIG. 201 illustrates a map of Liquid Moisture Management Test results for various coated fabrics described herein FIG. 202 illustrates drapability coefficient testing results for various SFS coated fabrics.

Figure 203:
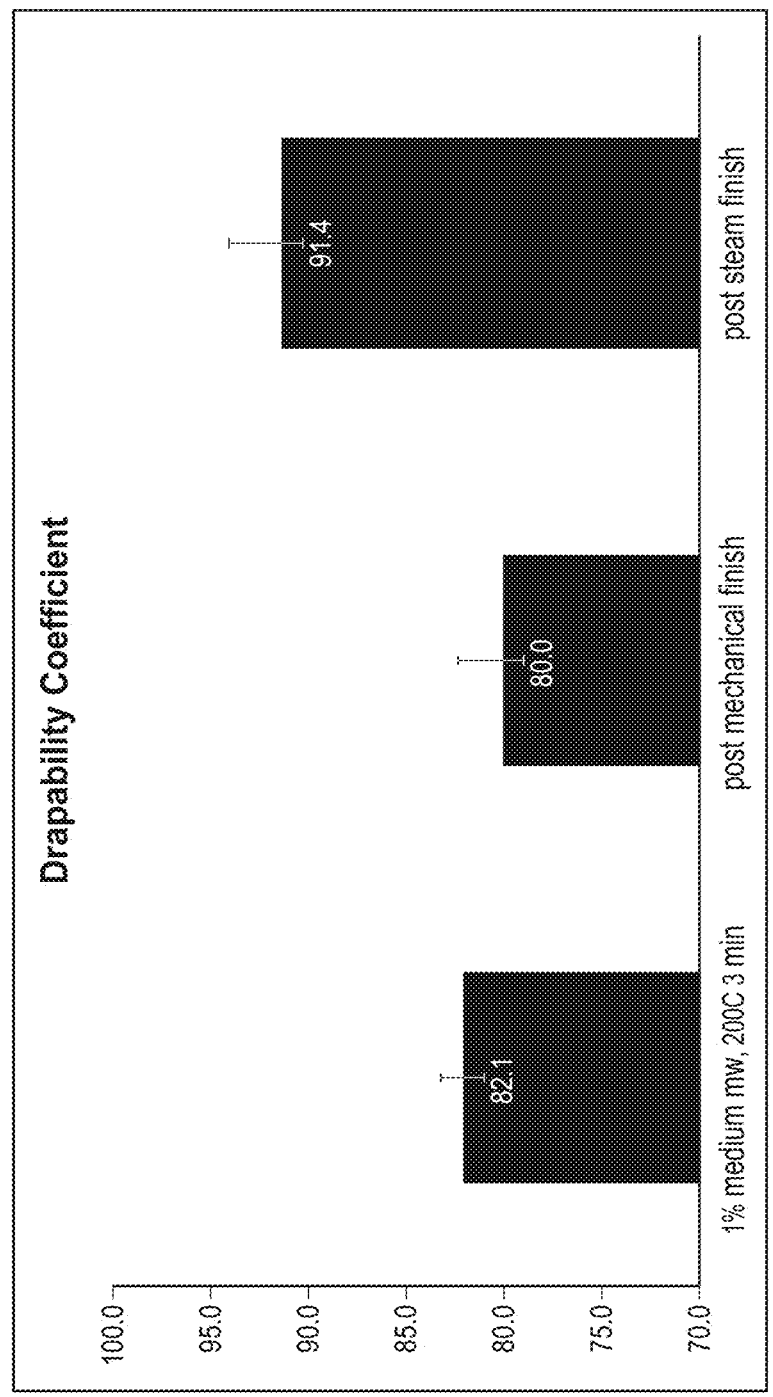

FIG. 203 illustrates drapability coefficient testing results for an SFS coated fabric after mechanical and steam finishing.

FIG. 204 illustrates the results of a solution depletion calculation during coating.

FIG. 205 illustrates samples used in moisture management testing.

FIG. 206 illustrates the results of moisture management testing.

FIG. 207 illustrates samples used in moisture management testing.

FIG. 208 illustrates the results of moisture management testing.

FIG. 209 illustrates samples used in moisture management testing.

FIG. 210 illustrates the results of moisture management testing.

FIG. 211 illustrates samples used in antimicrobial testing.

Figure 212:
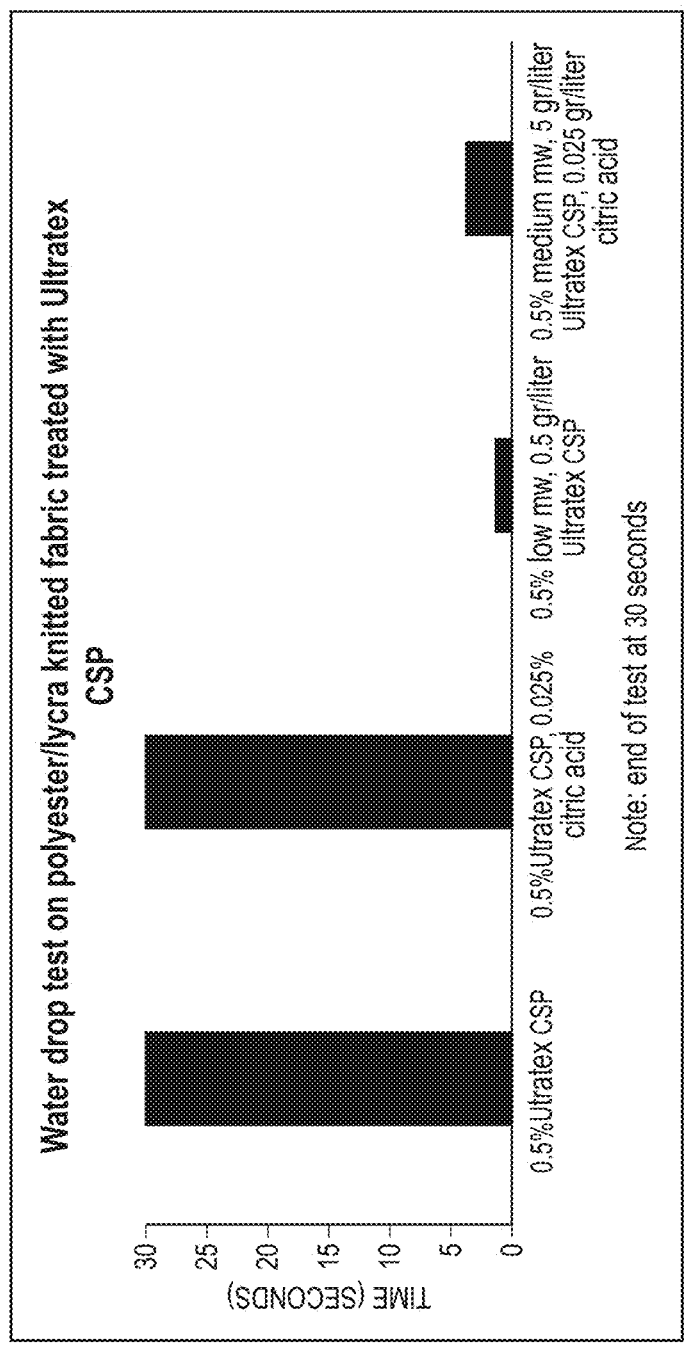

FIG. 212 illustrates the results of a water drop test on polyester/lycra knitted fabric treated with Ultratex CSP.

Figure 213:
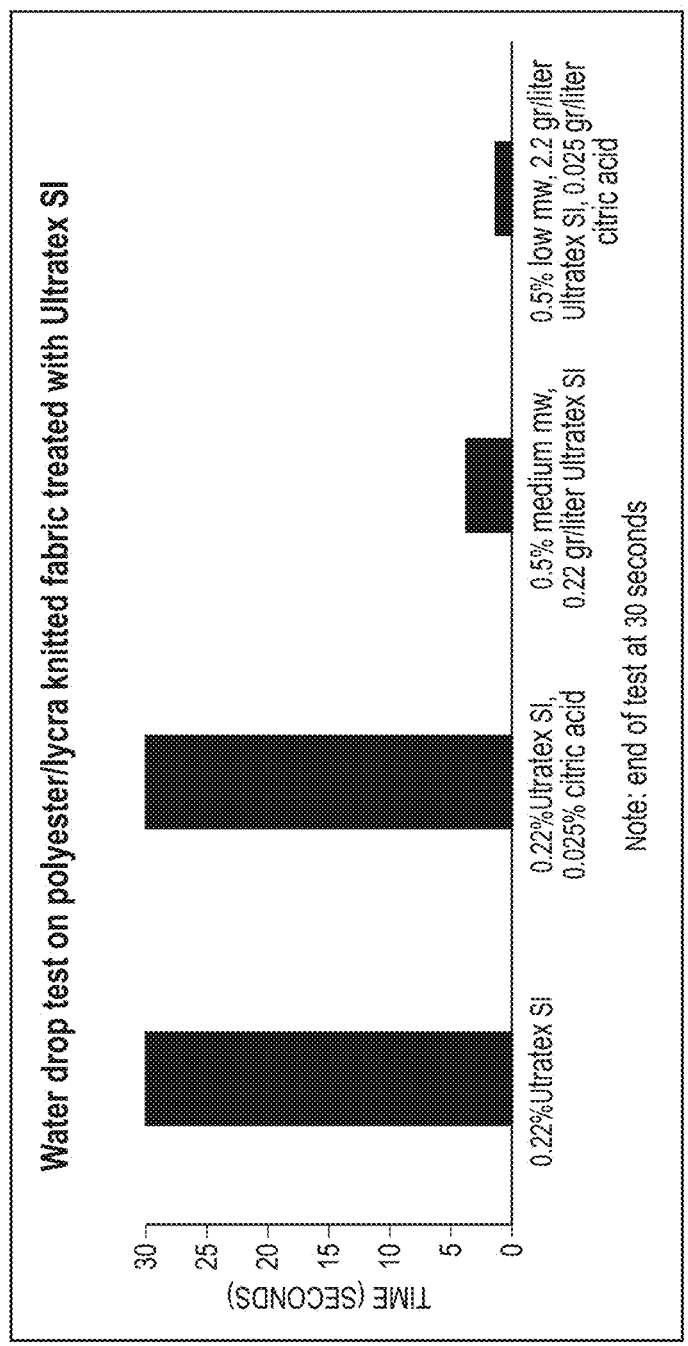

FIG. 213 illustrates the results of a water drop test on polyester/lycra knitted fabric treated with Ultratex SI.

Figure 214:
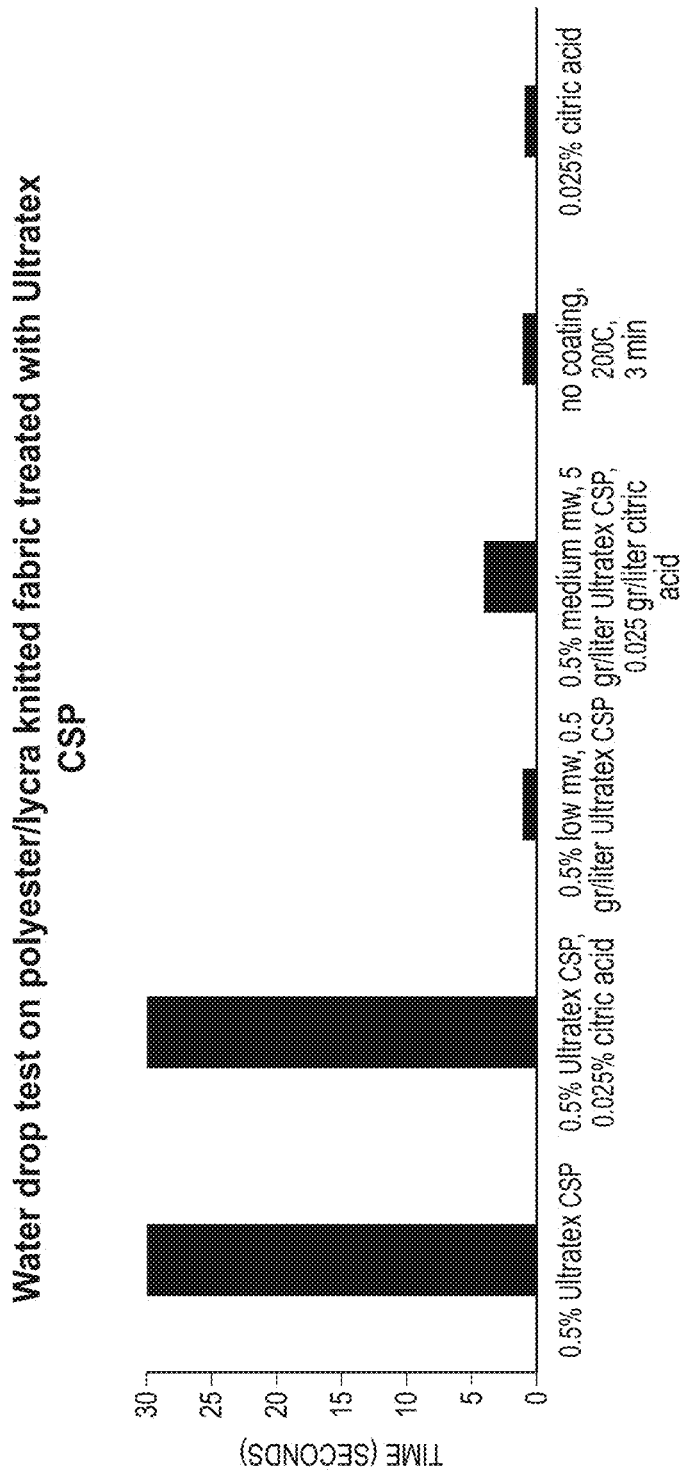

FIG. 214 illustrates the results of a water drop test on polyester/lycra knitted fabric treated with Ultratex CSP.

Figure 215:
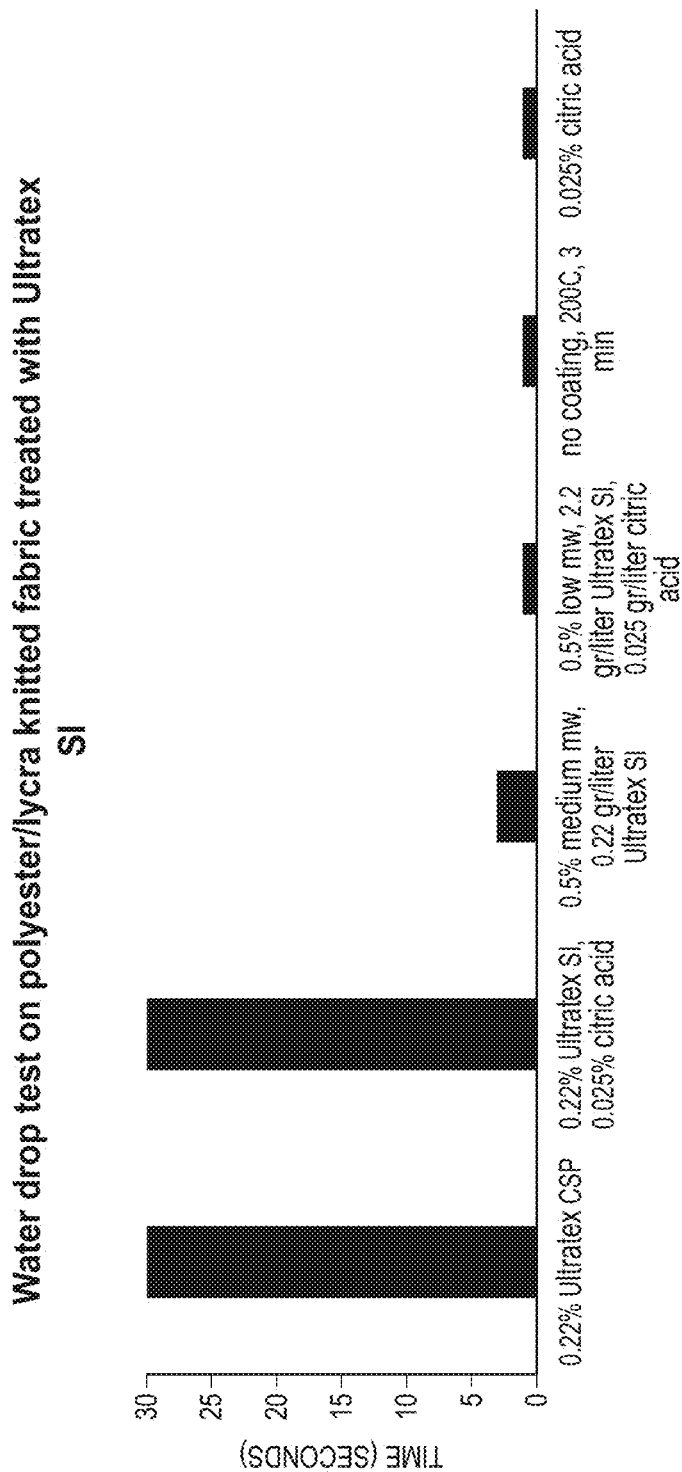

FIG. 215 illustrates the results of a water drop test on polyester/lycra knitted fabric treated with Ultratex SI.

FIG. 216 illustrates the results of a water drop test on polyester/lycra knitted fabric treated with RODI water or tap water.

Figure 217A:
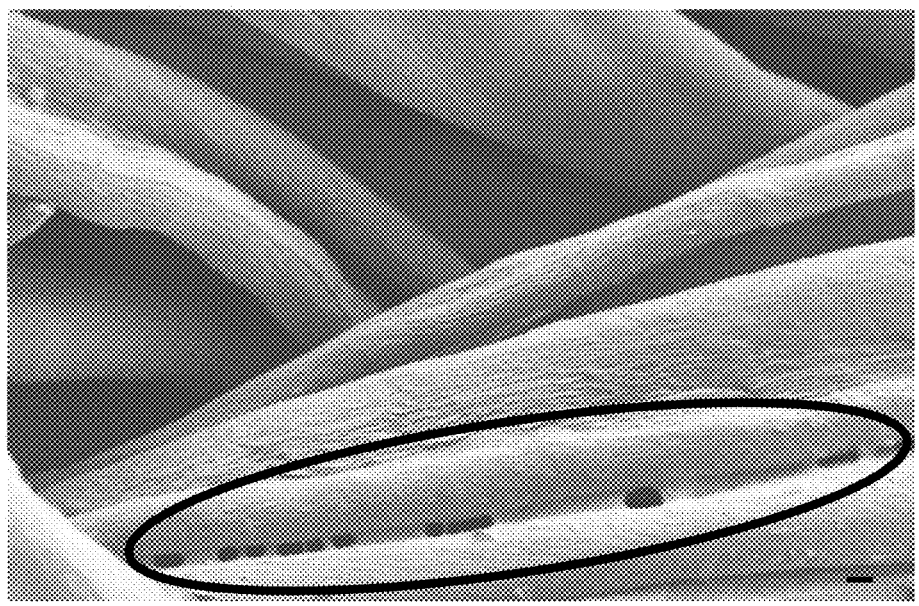

FIG. 217A illustrates a silk-coated cotton SEM image; scalebar represents 2 µm.

Figure 217B:
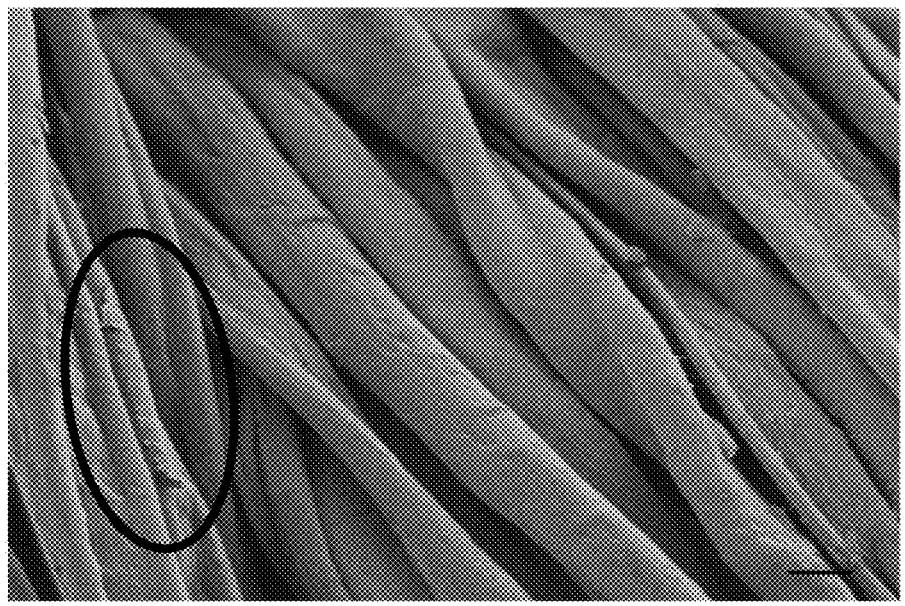

FIG. 217B illustrates a silk-coated cotton SEM image; scalebar represents 10 µm.

Figure 218:
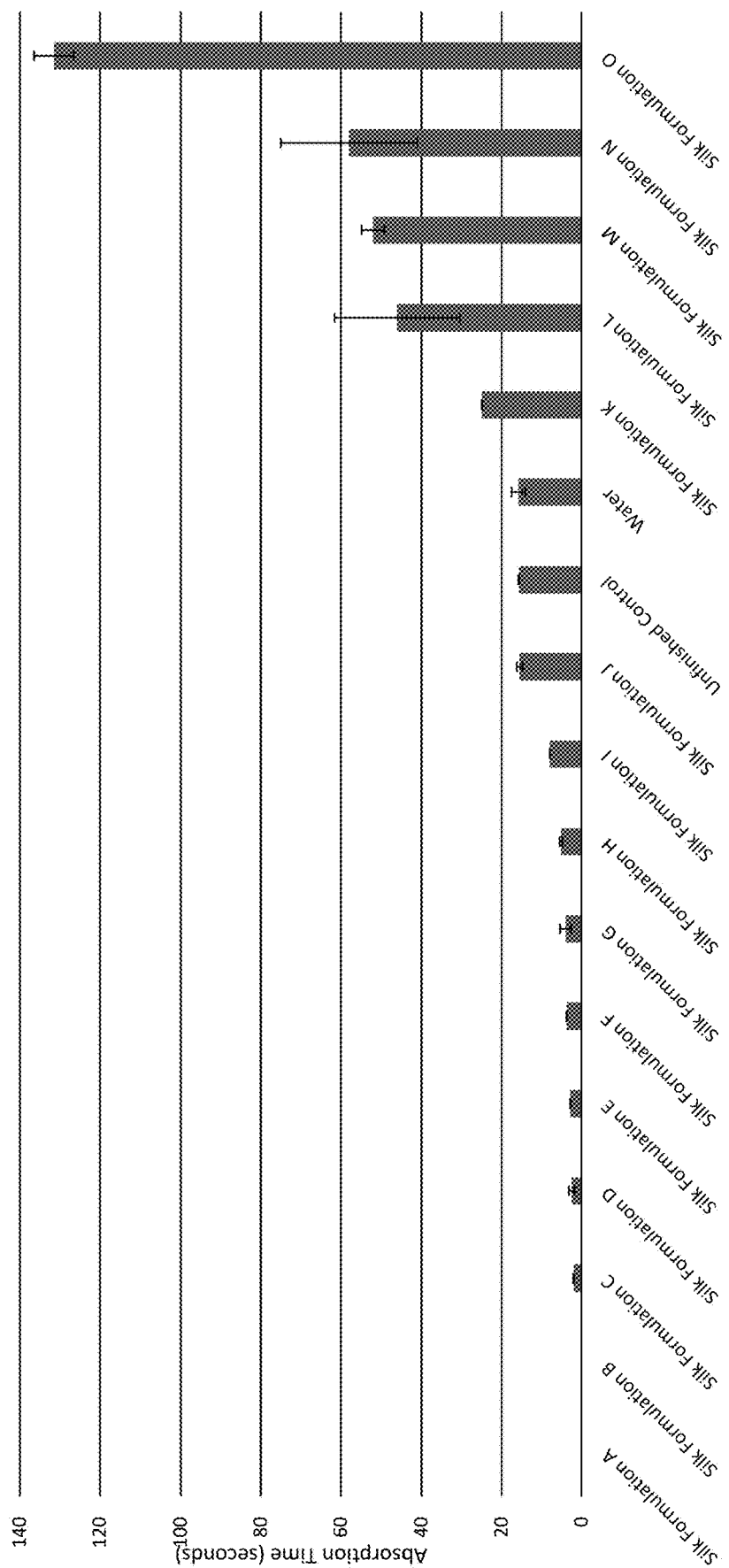

FIG. 218 illustrates manipulating water absorbency of liquid silk coated fabric. The time needed for a standard water drop to fully absorb into the fabric is recorded, and varies according to the silk treatment.

FIG. 219 illustrates various process parameters for coating fabrics.

Figure 220:
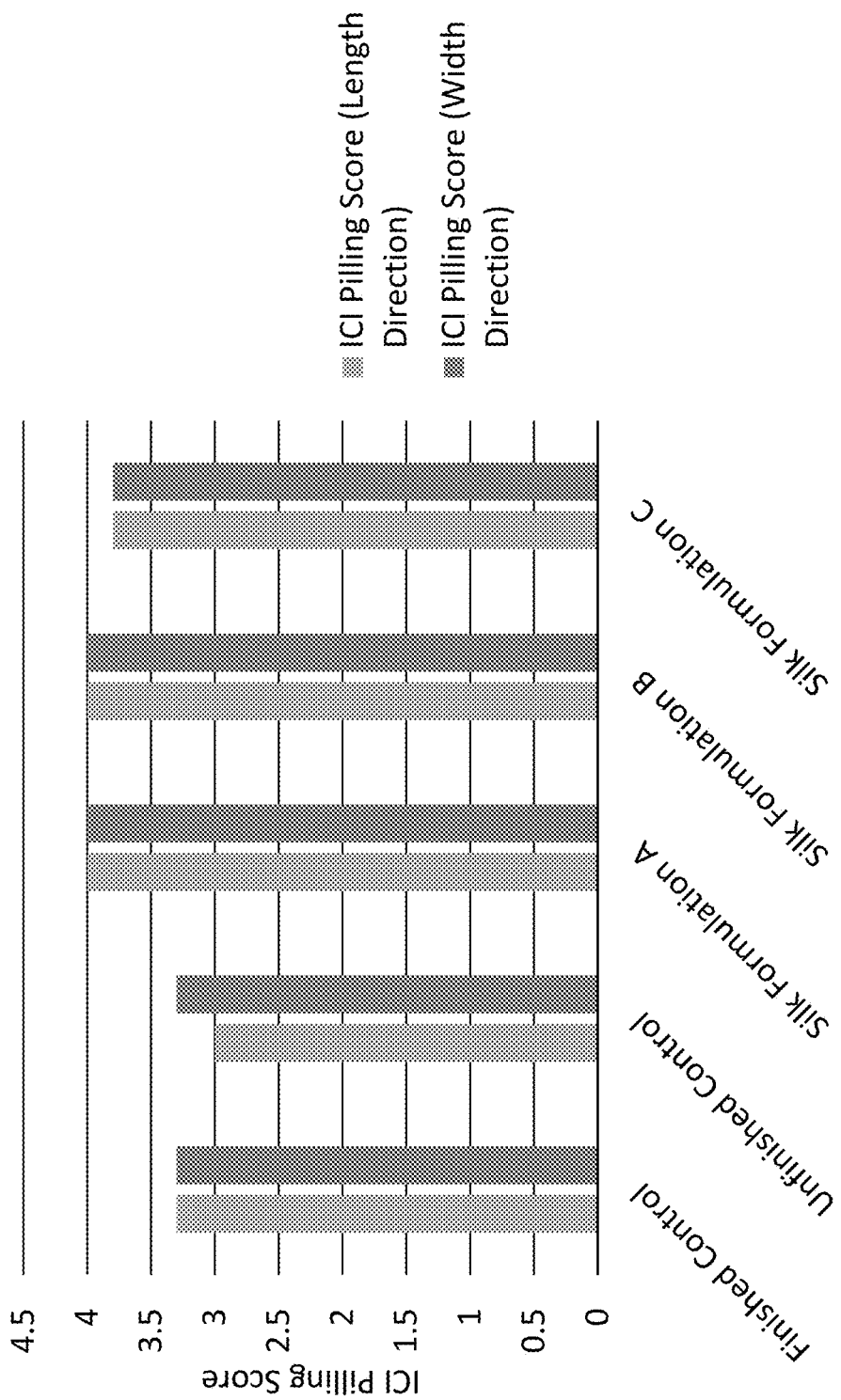

FIG. 220 illustrates that liquid silk application significantly reduces pilling on cashmere; the pilling score of each cashmere panel, as measured according to ISO 12945-1: Score 5=No change; Score 4=Slight surface fuzzing and/or partially formed pills; Score 3=Moderate surface fuzzing and/or moderate pilling, pills of varying size and density partially covering the specimen surface; Score 2=Distinct surface fuzzing and/or severe pilling, pills of varying size and density covering a large proportion of the specimen; Score 1=Dense surface fuzzing and/or severe pilling, pills of varying size and density covering the whole of the specimen surface. Silk Formulation A: 0.05% M Silk; pH unadjusted, STI-18050801-T004. Silk Formulation B: 0.25% M Silk; pH 9.25, STI-18050801-T009. Silk Formulation C: 0.25% 3L1M Silk, pH unadjusted, STI-18050801-T005.

Figure 221B:
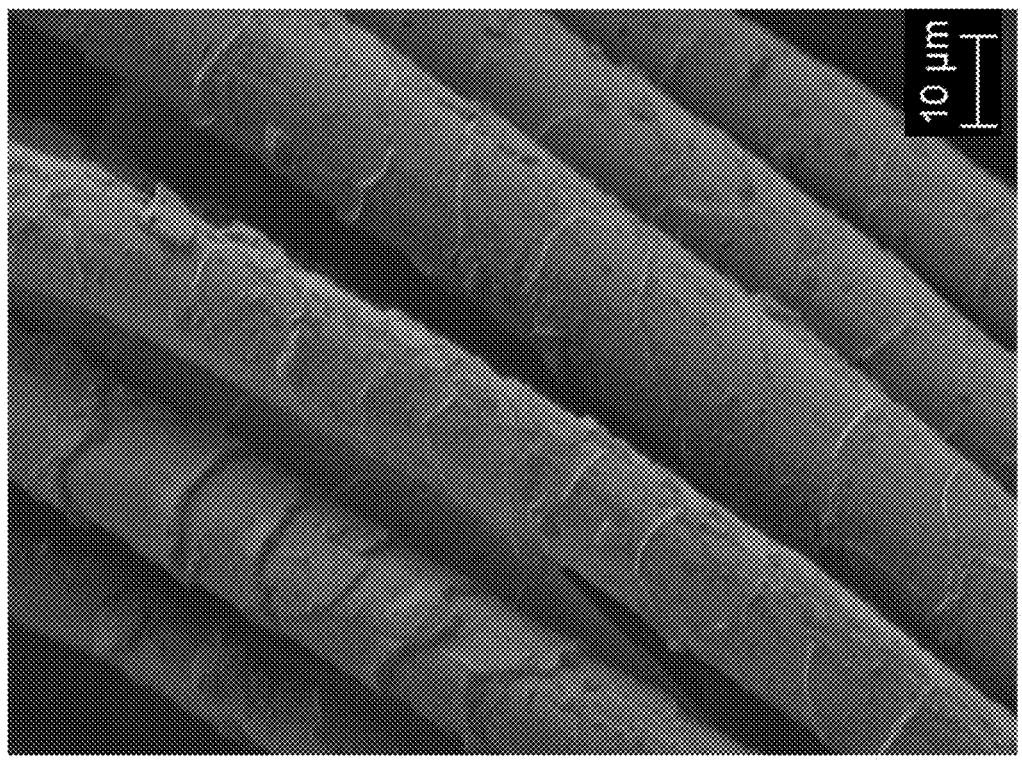
Figure 221A:
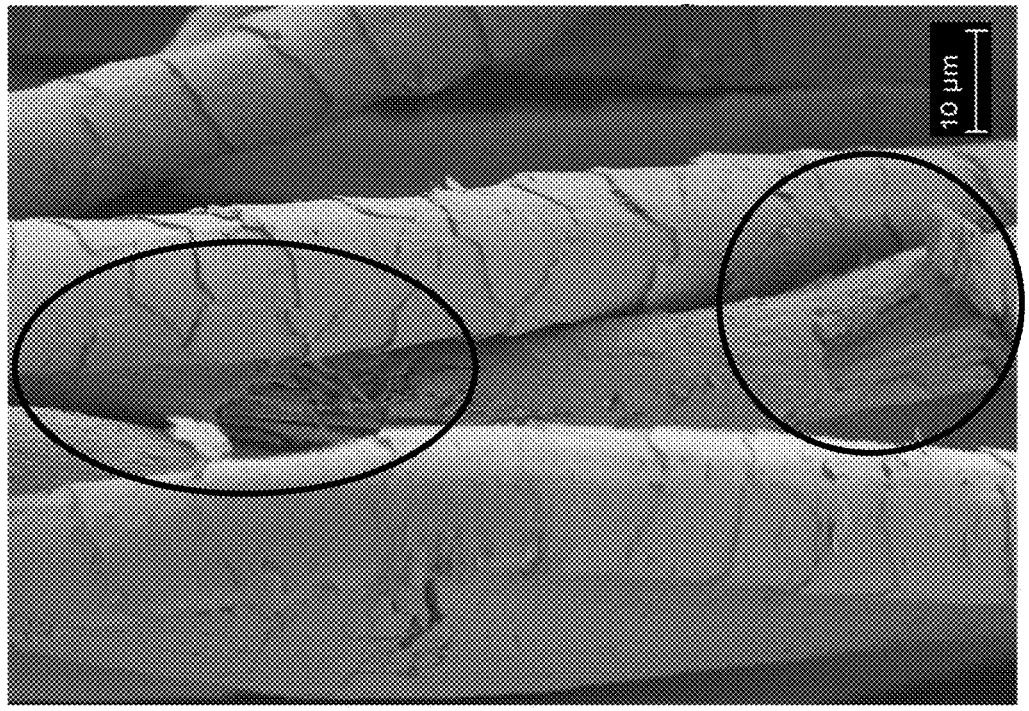

FIG. 221A (control) and FIG. 221B (cashmere treated with silk) illustrate cashmere coating coverage by scanning electron microscopy (SEM); as liquid silk and cashmere bond naturally, SEM demonstrates that liquid silk smooths and refines cashmere fibers.

Figures 222A, 222B:
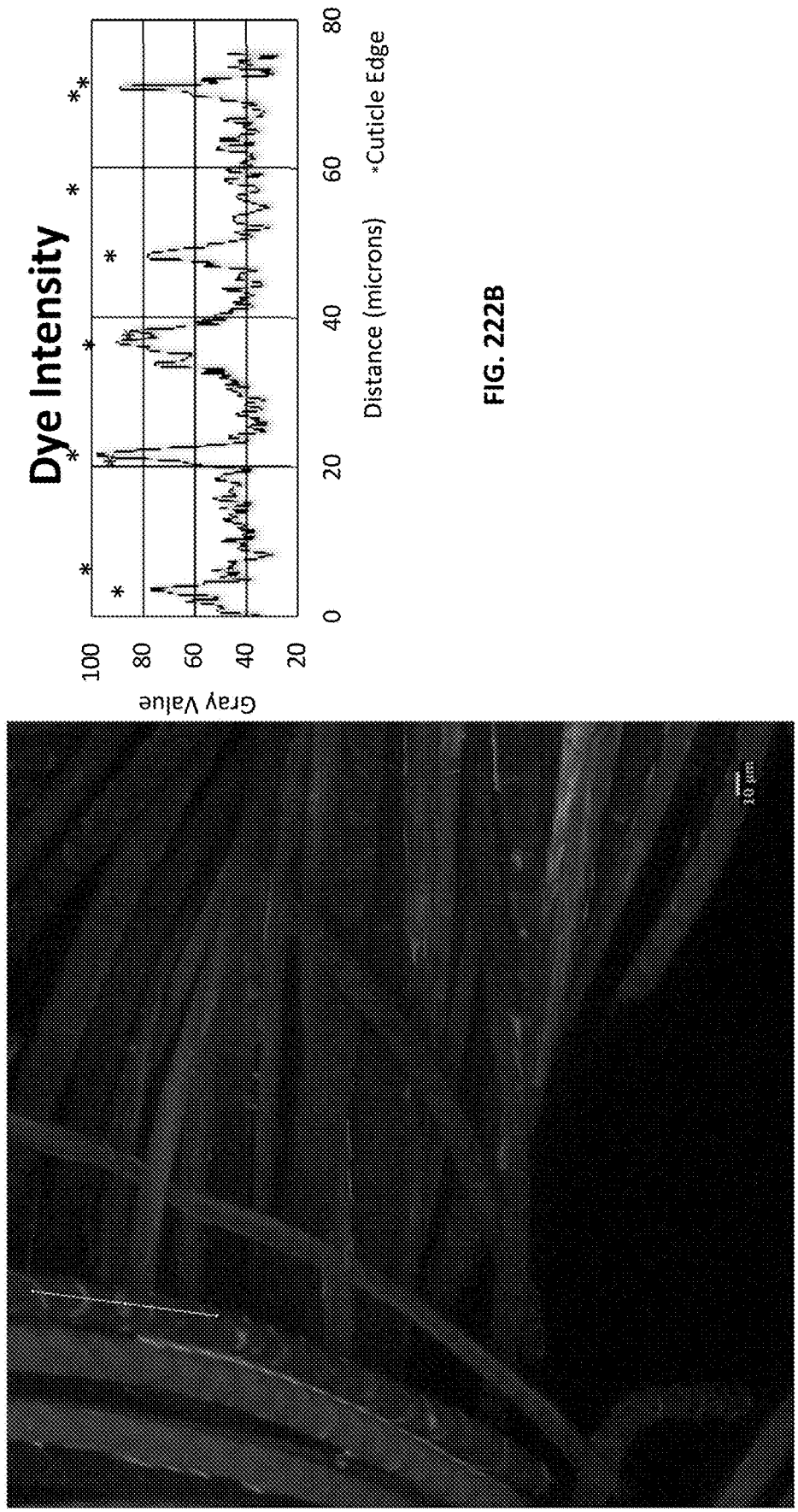

FIG. 222A (microscopic image) and FIG. 222B (dye intensity chart) illustrate deposition of FITC labeled silk fragments preferentially on cashmere cuticles; cuticle edges are 15-20 microns apart, and exhibit more fluorescence than the cuticle faces. (20× objective; laser power: 12%; gain: 600; gamma: 0.45).

Figure 223:
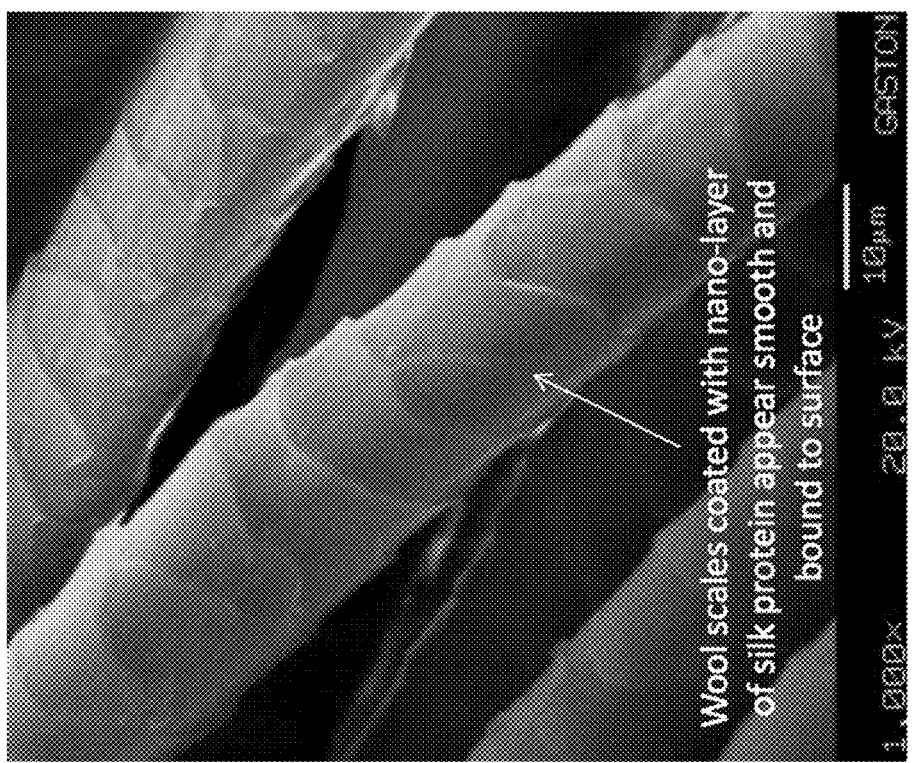
Figure 225B:
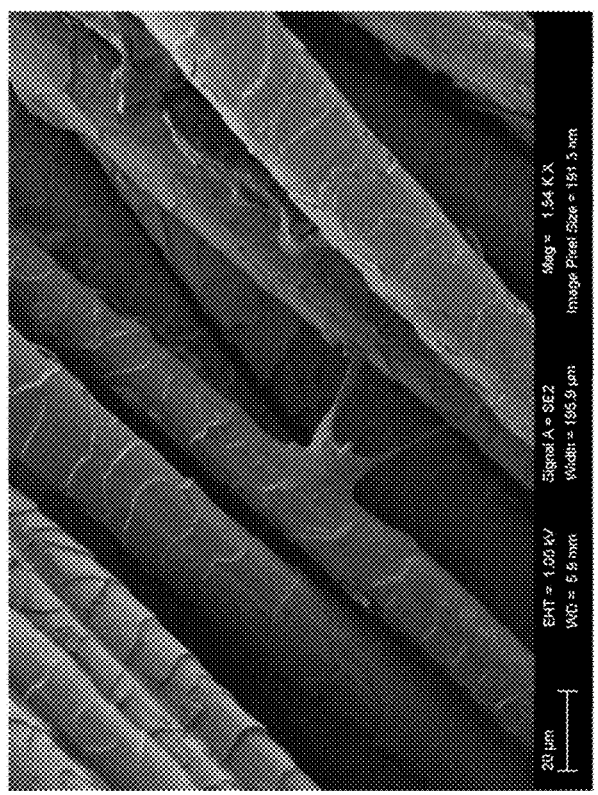
Figure 225A:
Figure 225D:
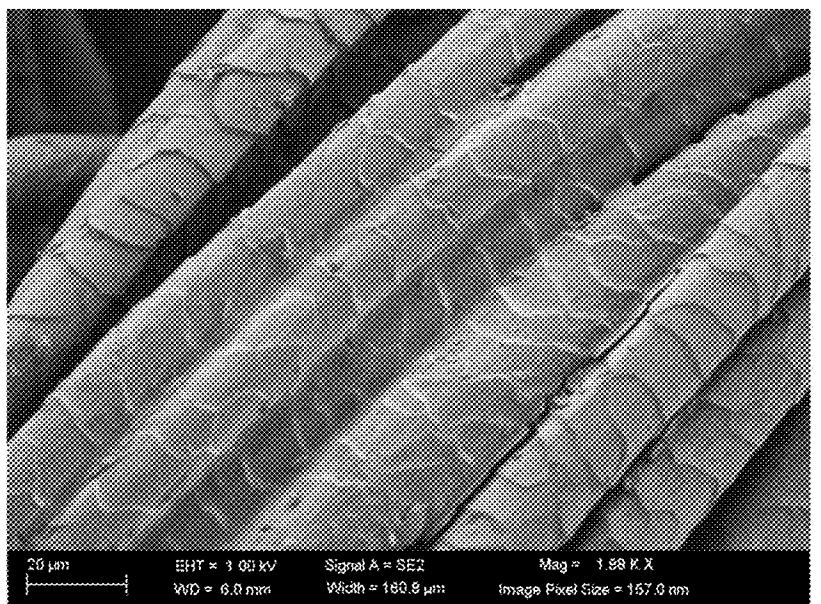
Figure 225C:
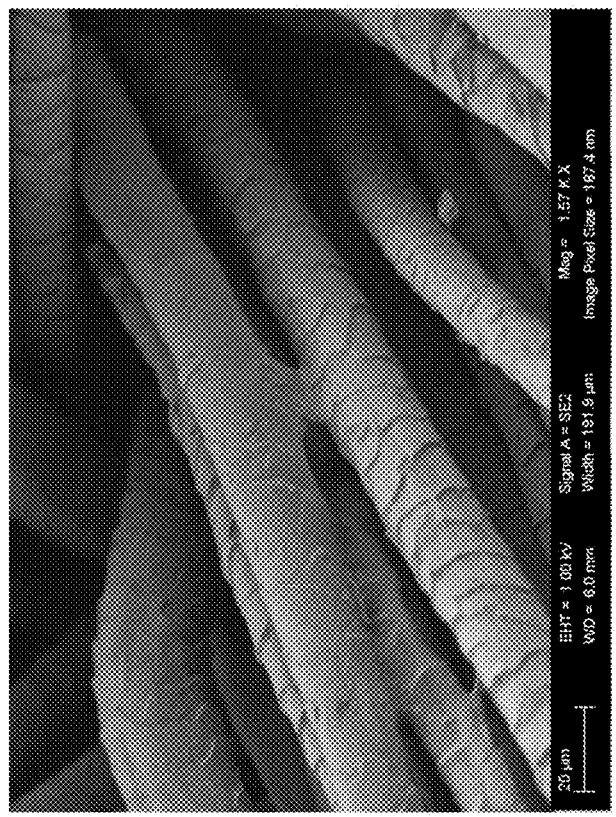

FIG. 223 illustrate silk protein binding and smoothing the "scales" of wool to the core fiber, preventing the "Velcro-like" effect that is responsible for wool's shrinkage and inability to withstand washing; additional data shows wool+ liquid silk is water resistant, stable and shrink-resistant following washing while matching or improving pilling.

Figure 224:
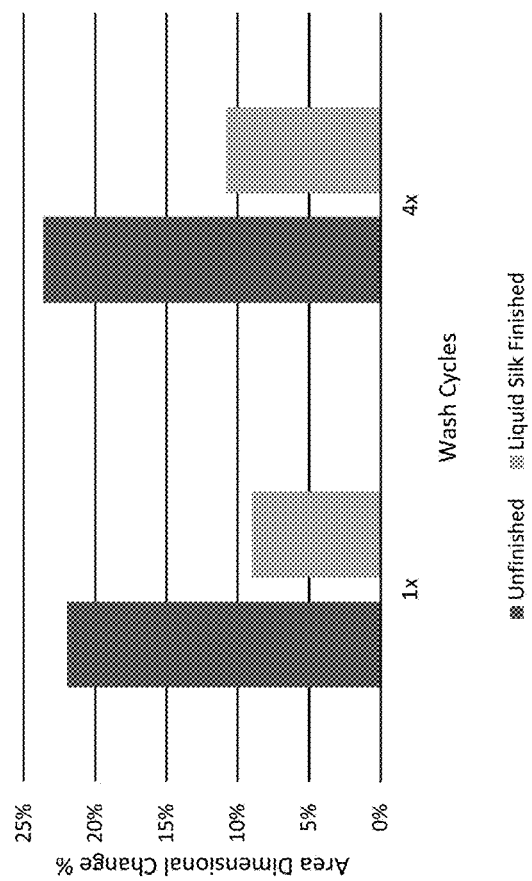

FIG. 224 illustrates improved washability of wool by area dimensional change on wool tubes finished with liquid silk compared to untreated wool tubes. Liquid silk improves area dimensional change about twofold.

FIG. 225A-225D illustrates SEM images of silk coated wool.

Figure 226B:
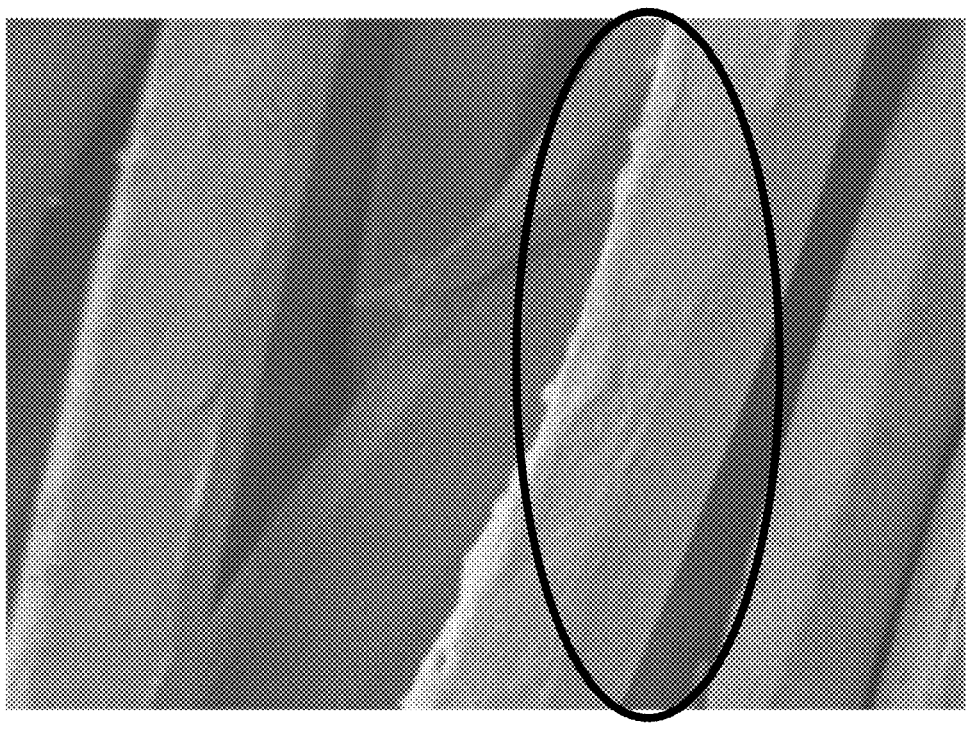
Figure 226A:
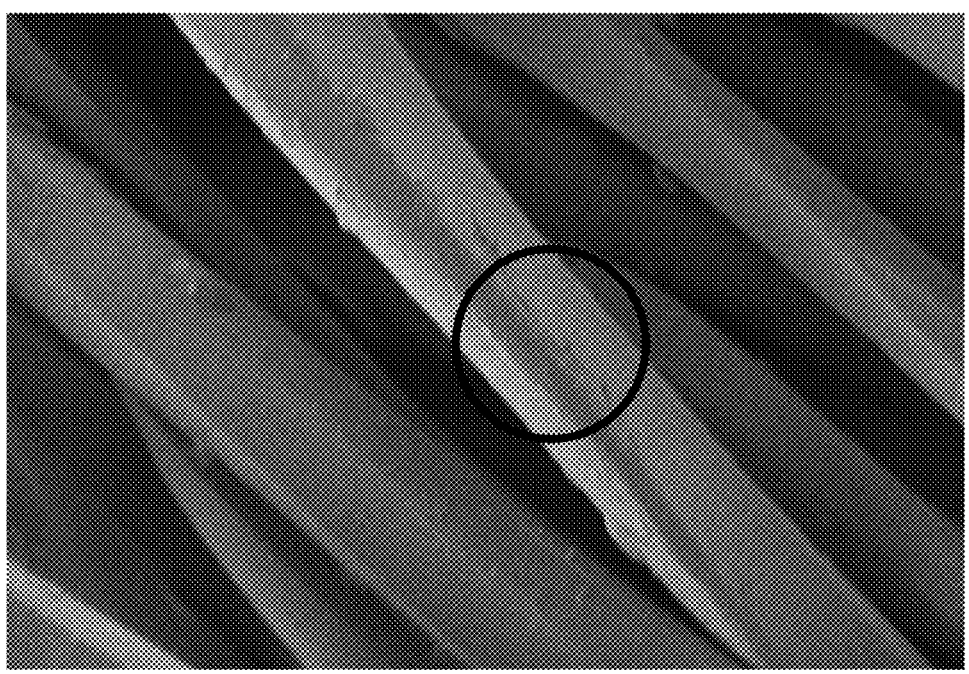

FIG. 226A-226B illustrates the coating coverage of silk fragments on polyester as shown by scanning electron microscopy (SEM); SEM confirms that after application of liquid silk, coating coverage is similar or greater than other commercial coatings for polyester. FIG. 226A illustrates polyester unfinished control sample, showing fibers with no coating. FIG. 226B illustrates polyester finished with silk, showing coated layers on the polyester fibers.

Figure 227A:
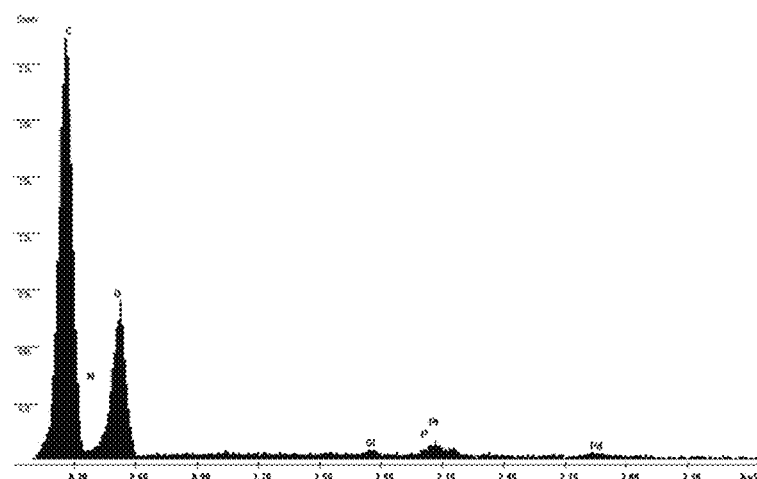
Figure 227B:
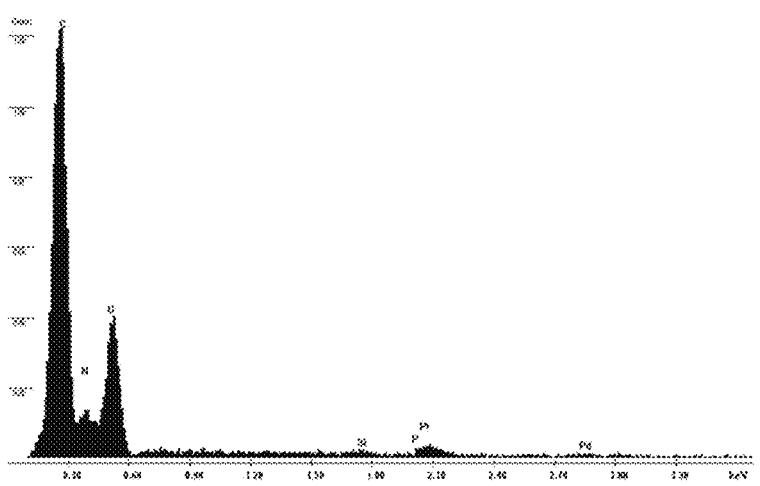
Figure 227C:
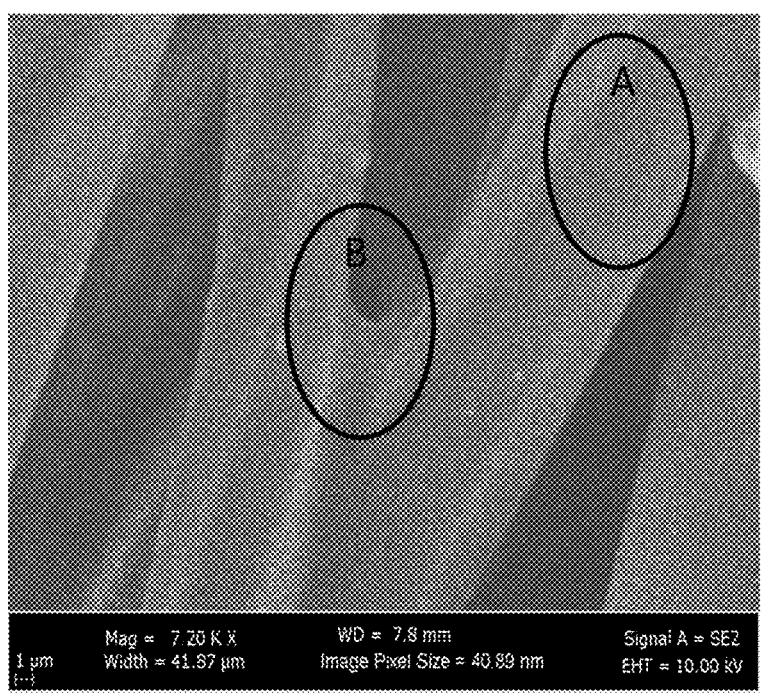

FIG. 227A-227C illustrates EDS Data on Polyester Related Experiments; polyester fabric was coated in 6% silk (FIG. 227C) and energy-dispersive X-ray spectroscopy (EDS) was used to determine chemical content (FIG. 227A and FIG. 227B); EDS suggests regions between fibers (FIG. 227B) show nitrogen content due to silk depositions regions.

Figure 228:
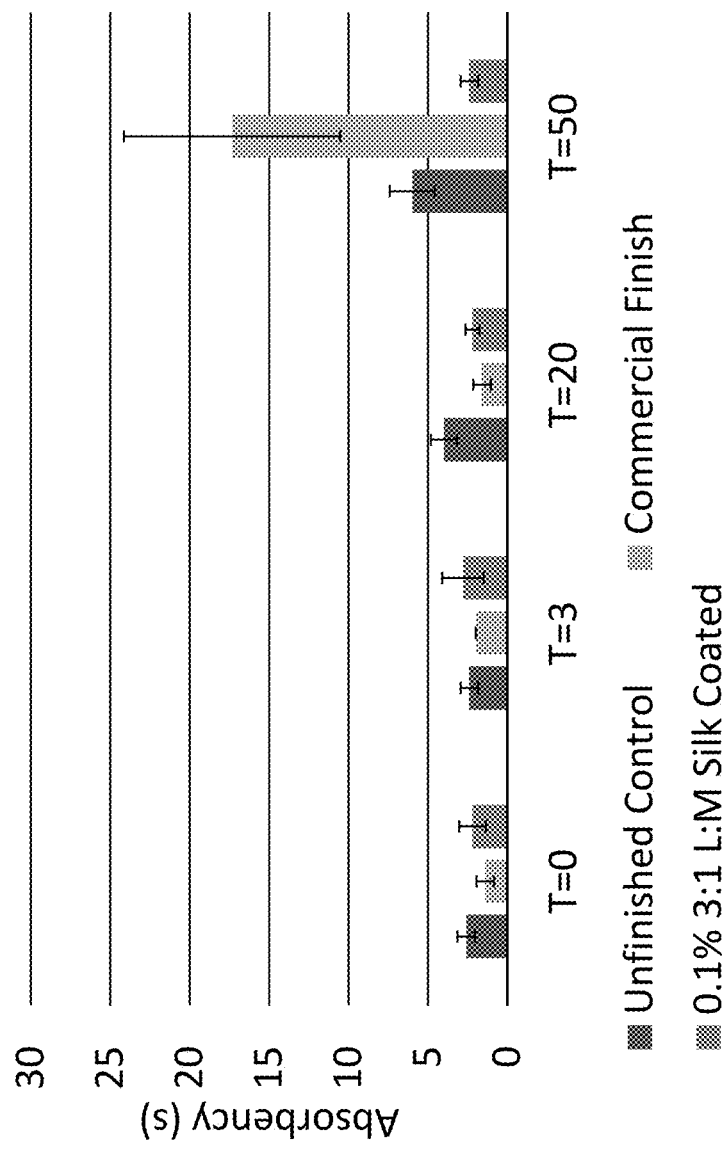

FIG. 228 illustrates liquid silk coated polyester absorbency; the results indicate that the coated material exceeds commonly accepted industry criteria for absorbency, and outperformed commercial counterparts after 50 laundering cycles.

Figure 229:
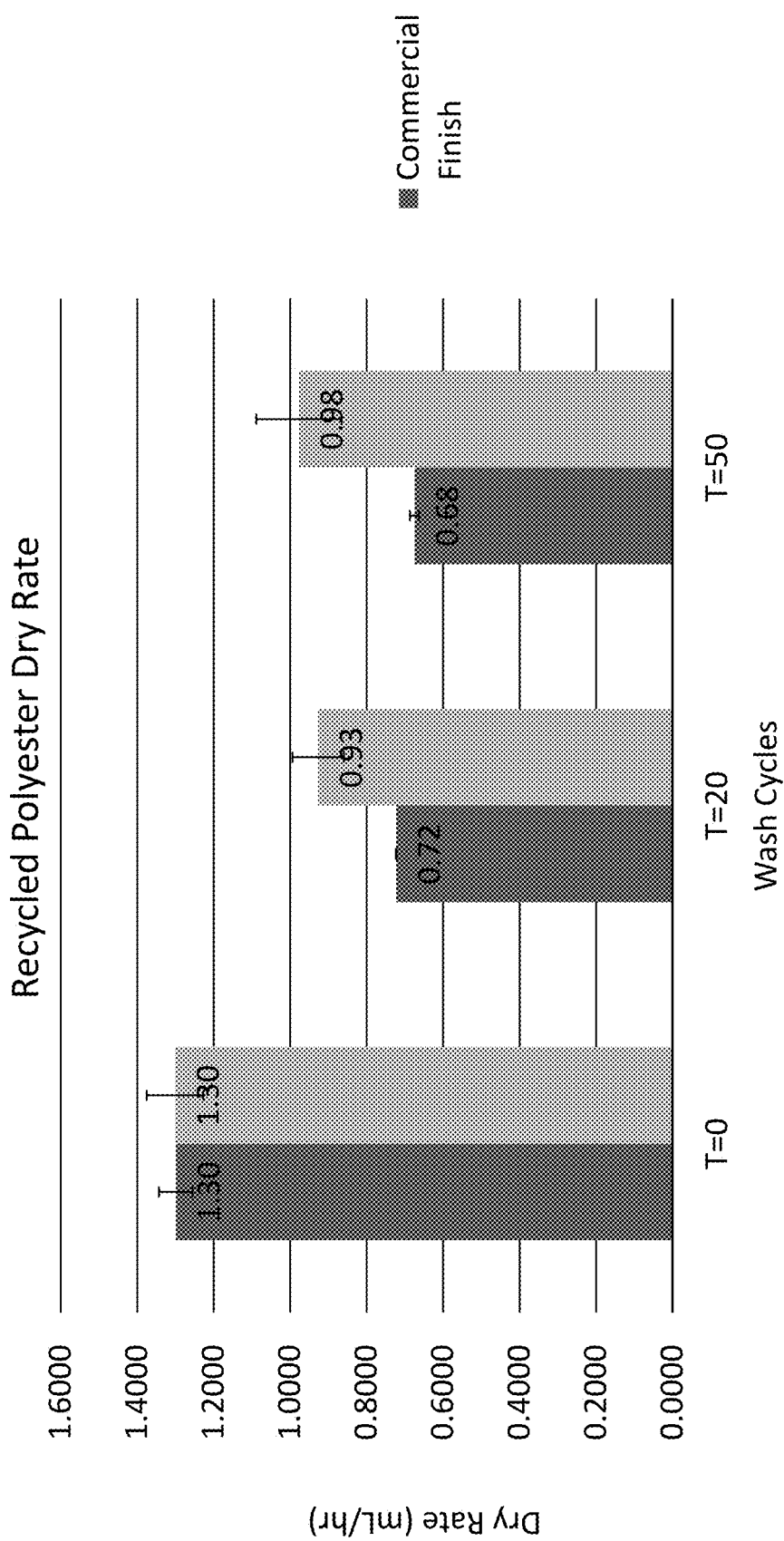

FIG. 229 illustrates dry rate in polyester samples; in general liquid silk coated polyester dried faster than commercial control before laundering and after multiple laundering cycles; AATCC Test Method 201-1013 Heated Plate Method; higher values indicate faster dry rate (silk+mechanical denotes a second water pass and drying process).

Figure 230B:
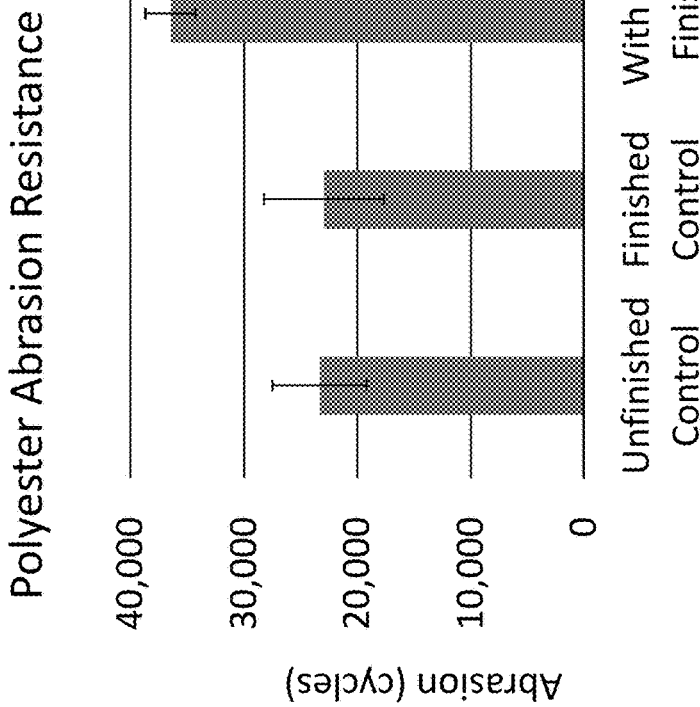
Figure 230A:
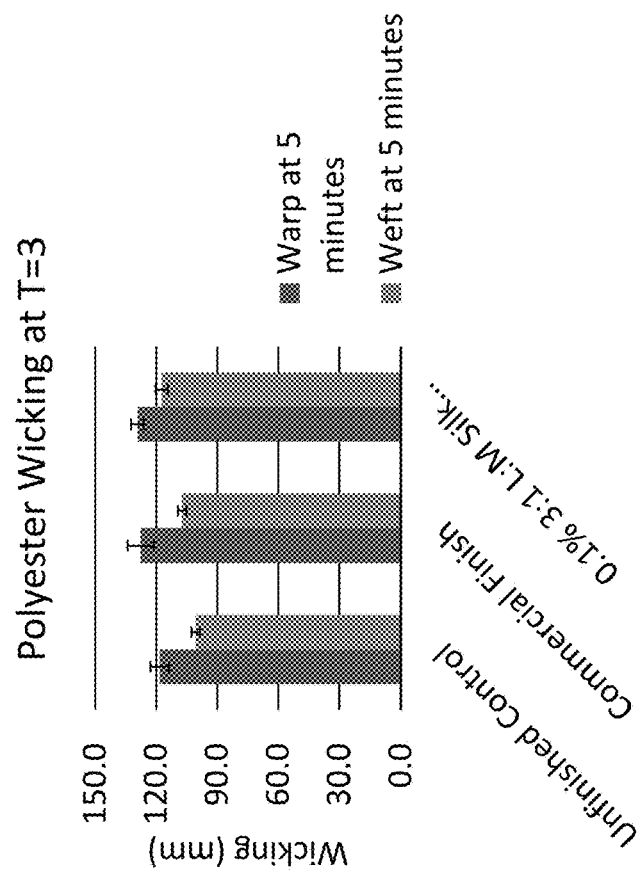

FIG. 230A-230B illustrates vertical wicking and abrasion resistance in polyester samples. FIG. 230A: liquid silk coated polyester demonstrated improved wicking at 5 minutes vs. unfinished fabric after 3 laundering cycles. FIG. 230B: liquid silk improves abrasion resistance of polyester fabrics, and outperformed the commercial standard.

Figure 231:
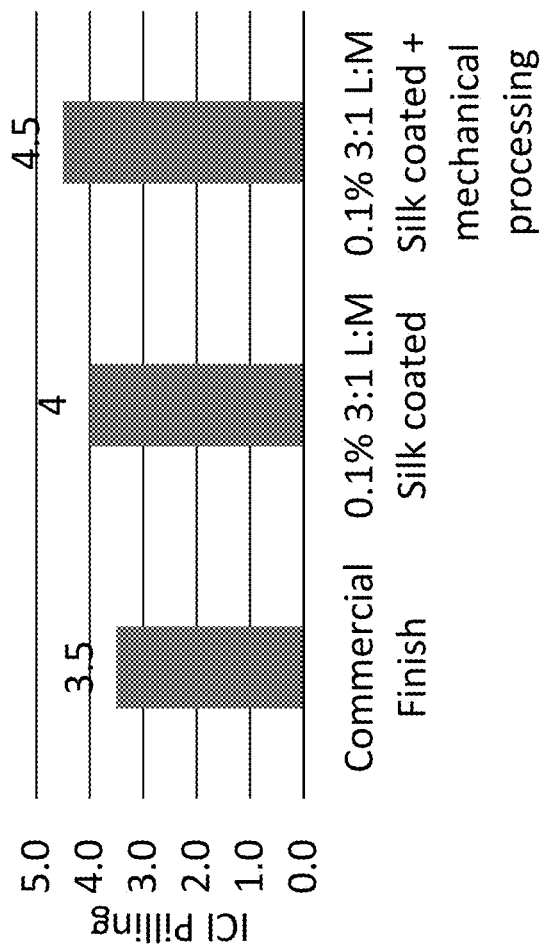

FIG. 231 illustrates pilling resistance in polyester liquid silk coated fabric which outperforms the commercial standard.

Figure 232B:
Figure 232A:
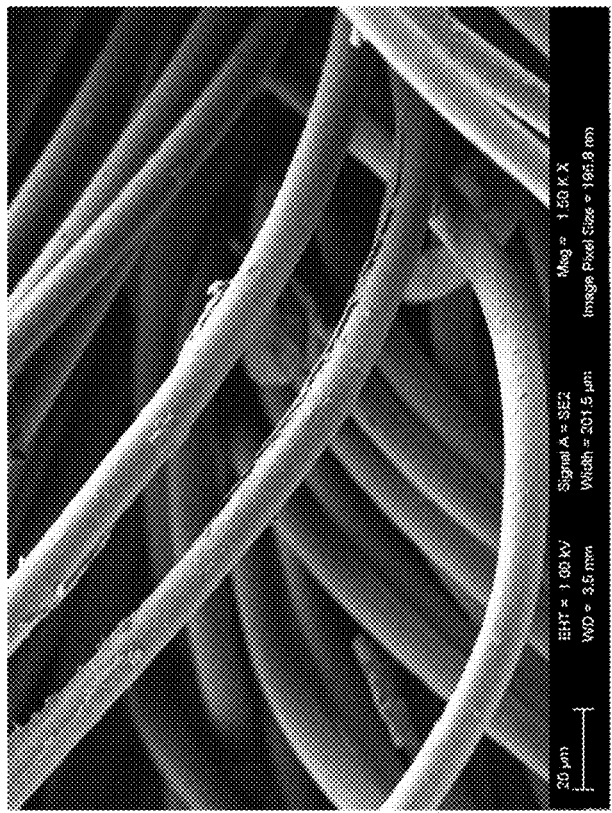

FIG. 232A and FIG. 232B illustrates silk-coated Nylon SEM images.

Figure 233B:
Figure 233A:

FIG. 233A-233B illustrates fluorescence microscopy images for silk-coated vs. control; FIG. 233A: FITC-Silk Coated Nylon; scale bars represent 107 µm. FIG. 233B: Uncoated Nylon Control; scale bars represent 53 µm. Nylon coated in FITC-Silk showed increased fluorescence due to the FITC-silk coating; 5% enhancement.

Figure 234B:
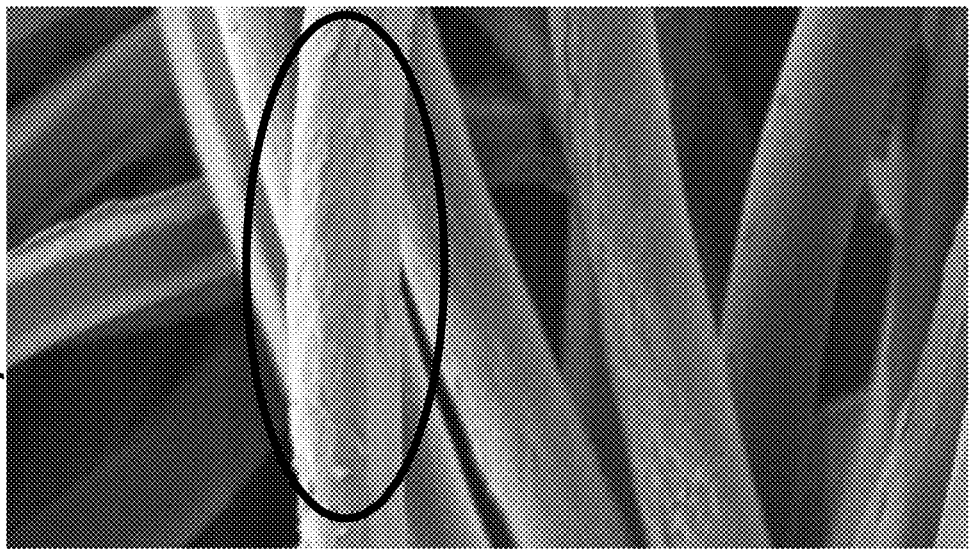
Figure 234A:
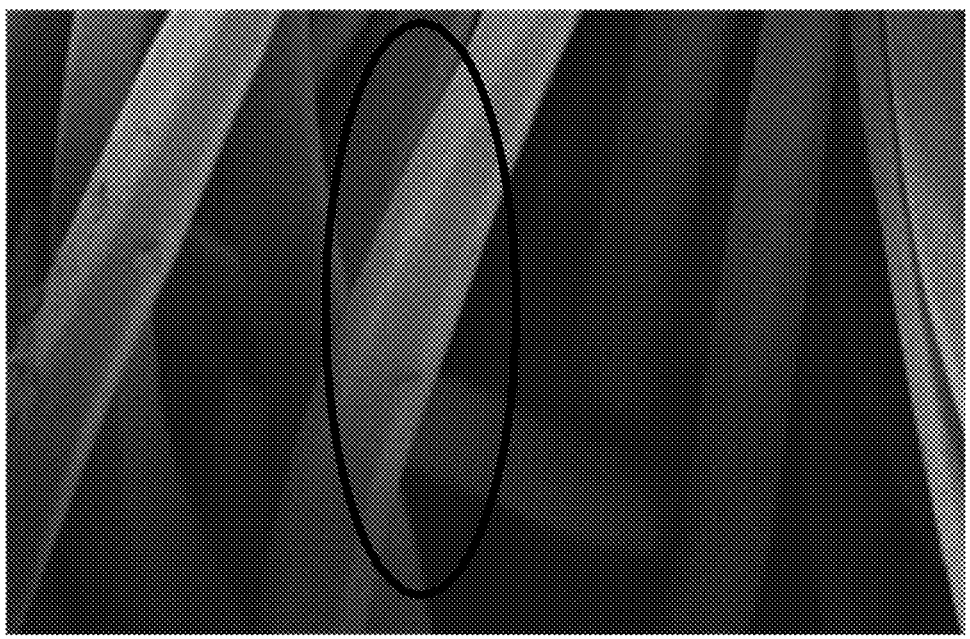

FIG. 234A-234B illustrates coating coverage on Nylon: scanning electron microscopy (SEM) confirms application of liquid silk. FIG. 234A: Nylon unfinished control. FIG. 234B: Nylon with silk finish—coated silk layers also adopt clear surface features.

Figure 235B:
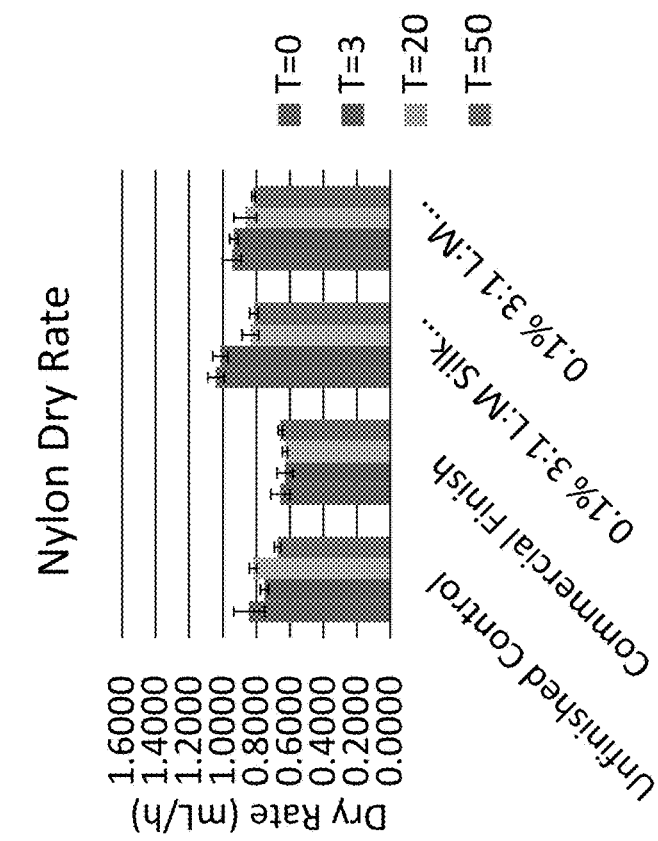
Figure 235A:
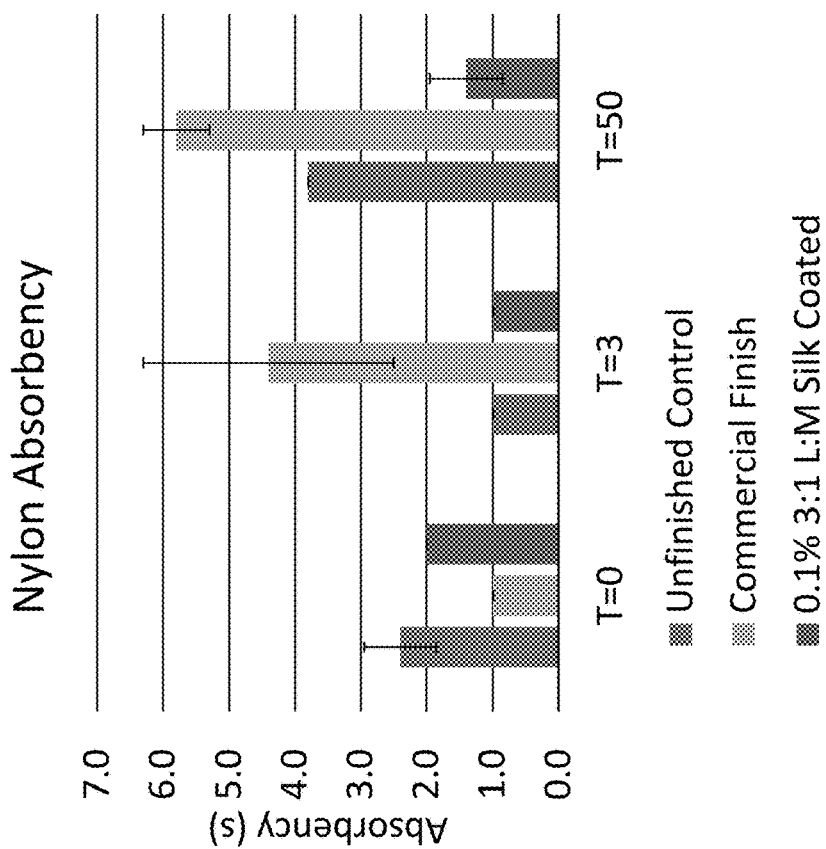

FIG. 235A illustrates absorbency performance of coated Nylon; liquid silk coated nylon exceeded commonly accepted industry criteria for absorbency, and outperformed commercial counterparts after 50 laundering cycles (AATCC Test Method 79-2013; smaller values indicate faster absorbency, silk+mechanical denotes a second water pass and drying process). FIG. 235B illustrates dry rate performance in coated nylon; liquid silk coated nylon dried faster than commercial control before laundering and after multiple laundering cycles (AATCC Test Method 201-1013 Heated Plate Method; higher values indicate faster dry rate; silk+mechanical denotes a second water pass and drying process).

Figures 236A, 236B:
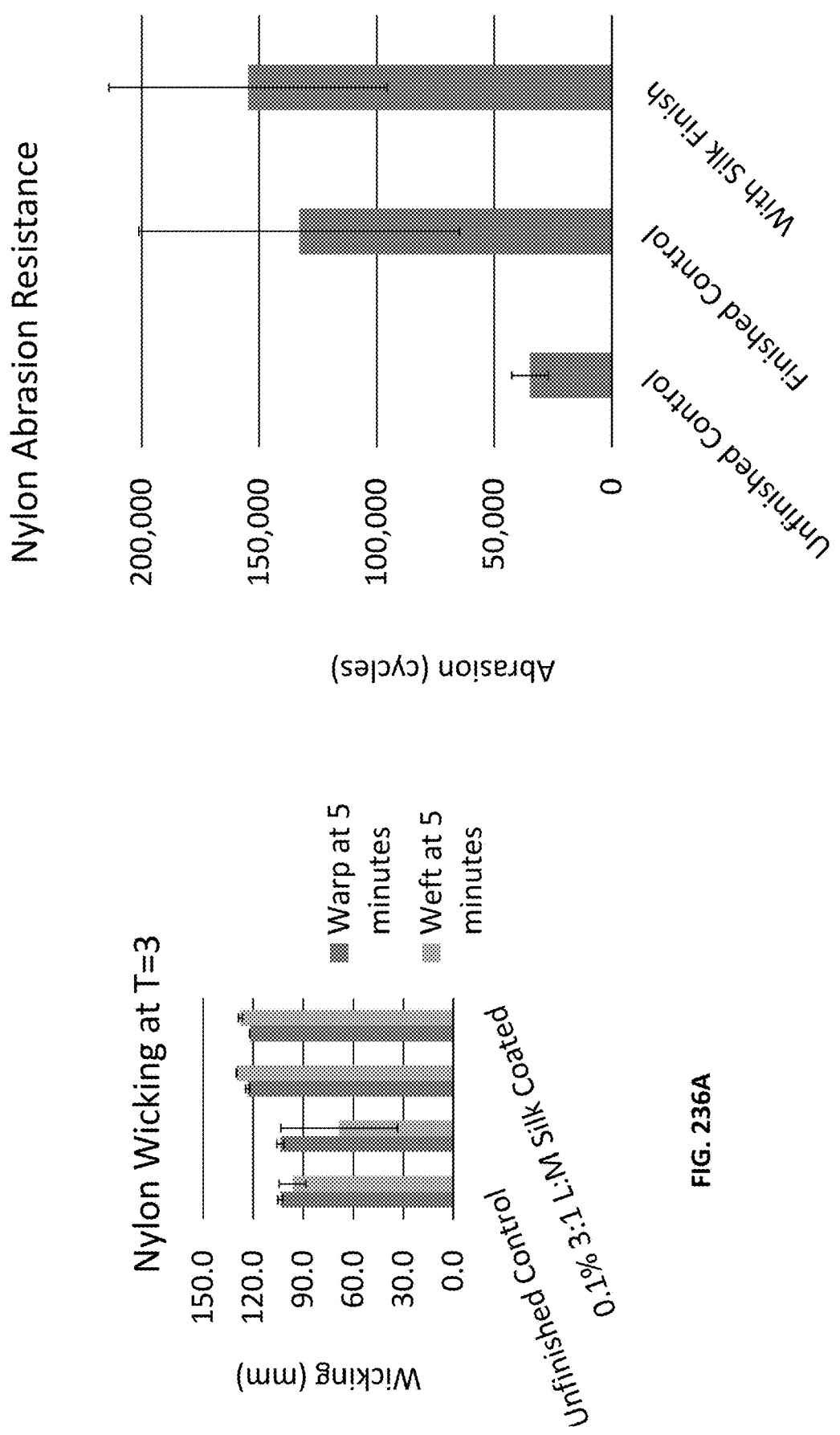

FIG. 236A illustrates vertical wicking performance; Nylon liquid silk coated nylon demonstrated improved wicking at 5 minutes vs. commercial finish after 3 laundering cycles (AATCC Test Method 197 (modified); higher values indicate better wicking; silk+mechanical denotes a second water pass and drying process). FIG. 236B illustrates abrasion resistance performance; Nylon liquid silk coated improves abrasion resistance of nylon; liquid silk coated nylon matched the commercial standard Abrasion Resistance—ASTM Standard D4966-12Eε1 (accelerated); testing ended when fabric first demonstrated abrasion or broke, whichever happened first; instead of wool, Trizact was used.

Figure 237:
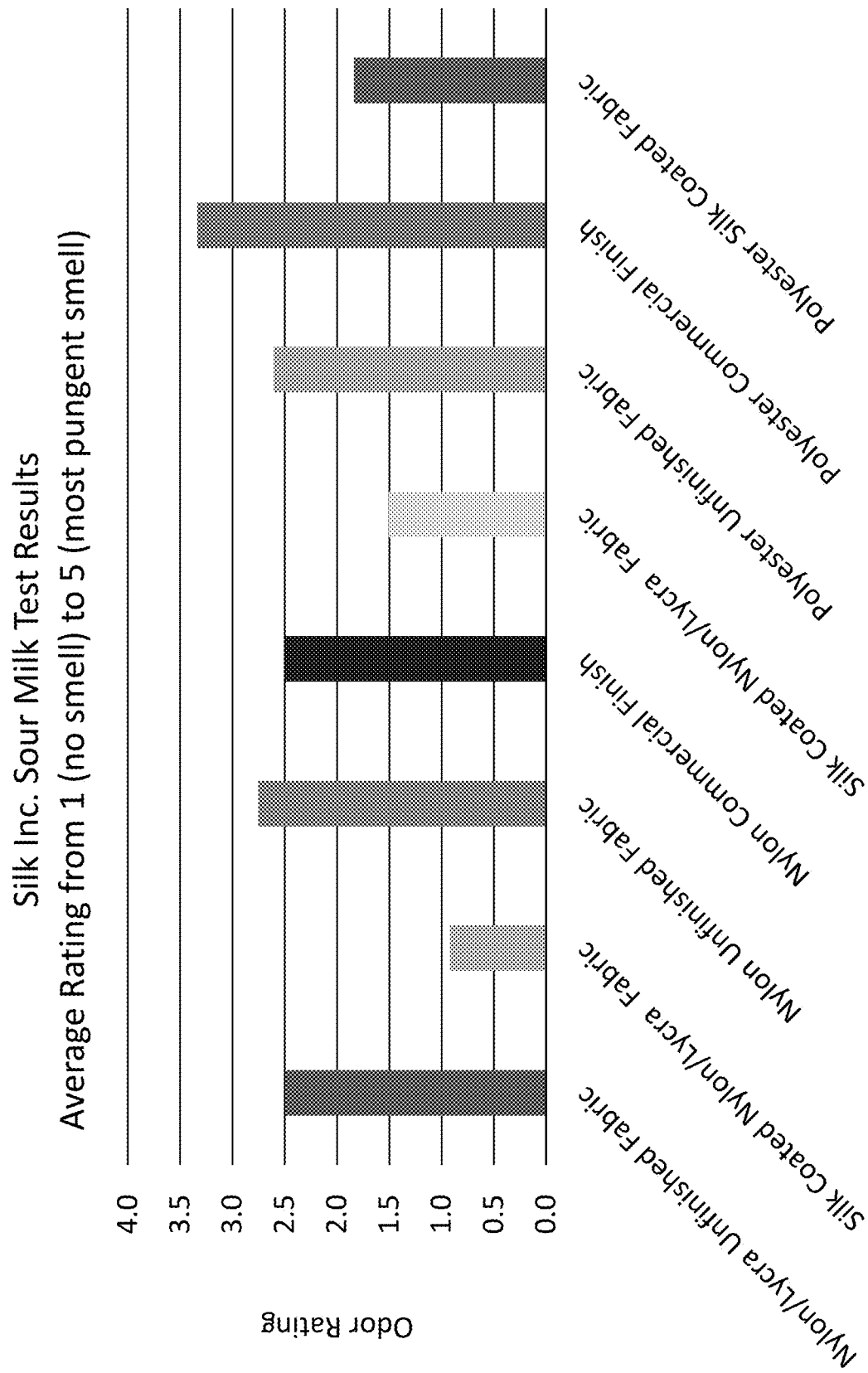

FIG. 237 illustrates the Sour Milk Test Experimental Results; liquid silk coated fabrics reduced odor more than both finished and unfinished fabrics.

Figures 238A, 238B:

FIG. 238A and FIG. 238B illustrates Sour Milk Test Experimental Results; liquid silk coated fabrics reduced odor more than both finished and unfinished fabrics.

Figure 239:
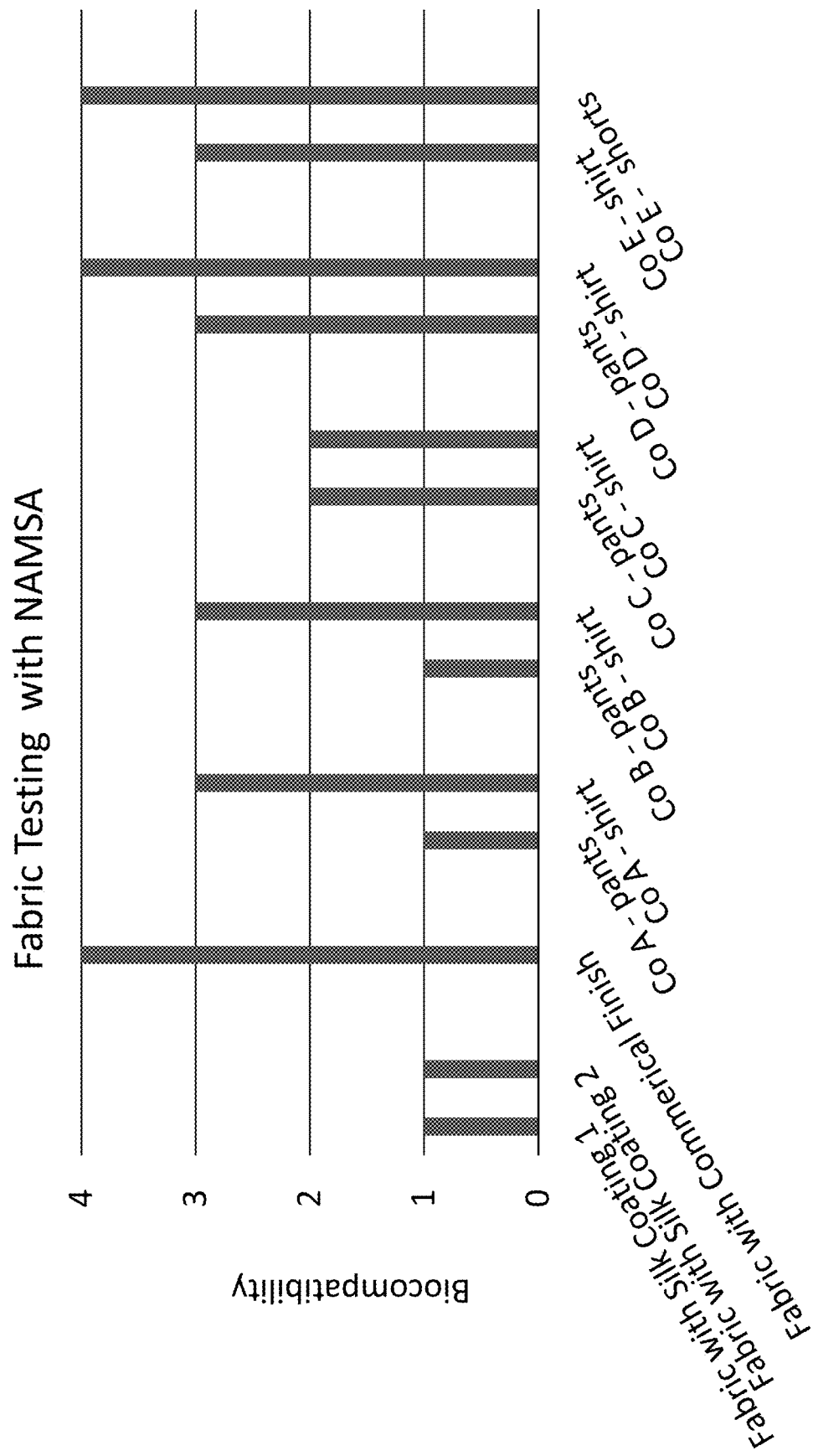

FIG. 239 illustrates biocompatibility of liquid silk coated fabrics (by the FDA standard test to show compatibility for contact with human skin); liquid silk coated fabrics demonstrated no reactivity; multiple commercial performance fabrics failed biocompatibility testing (0=No reactivity around or under specimen (passed); 1=Slight reactivity, some degenerated cell under test article (passed); 2=Mild reactivity, zone limited to area under the test article (passed); 3=Moderate reactivity, zone of lysis extending specimen size up to 1 cm (failed); 4=Severe, zone of lysis extending farther than 1 cm beyond specimen (failed)).

Figure 240B:
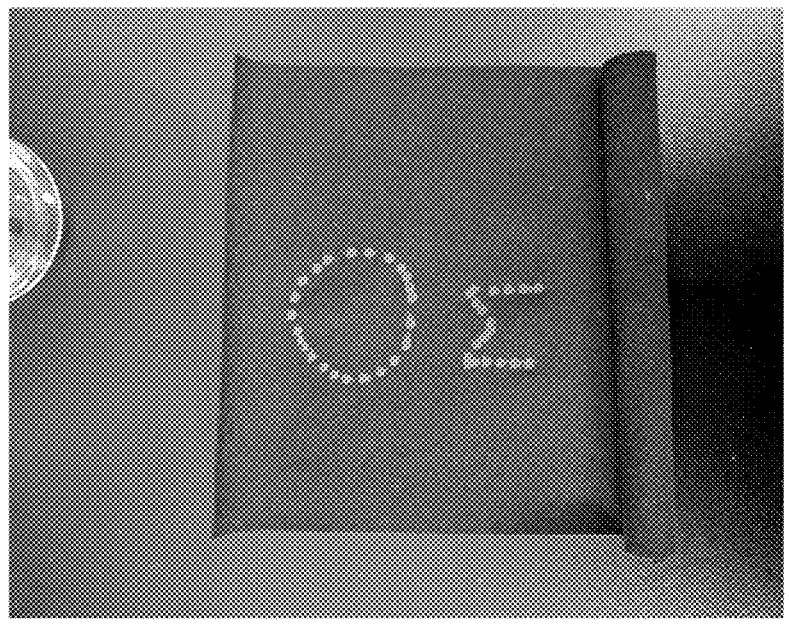
Figure 240A:
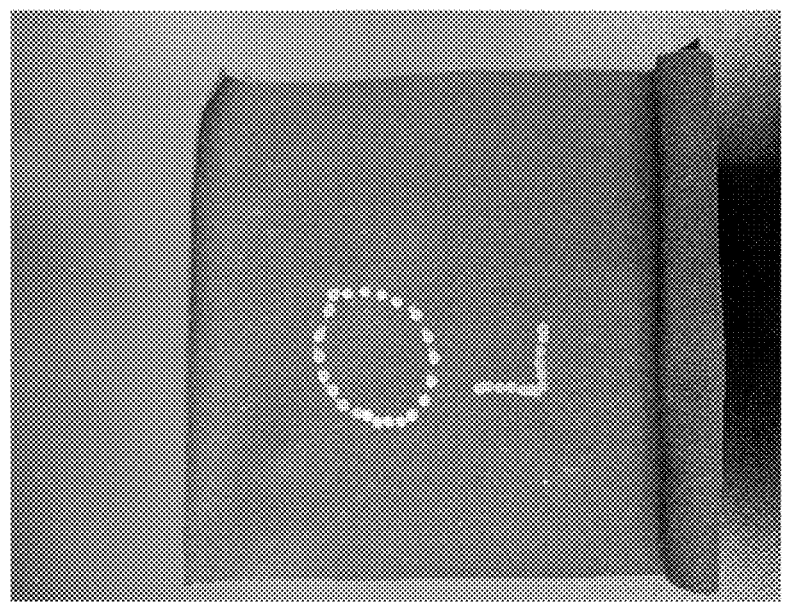
Figure 240D:
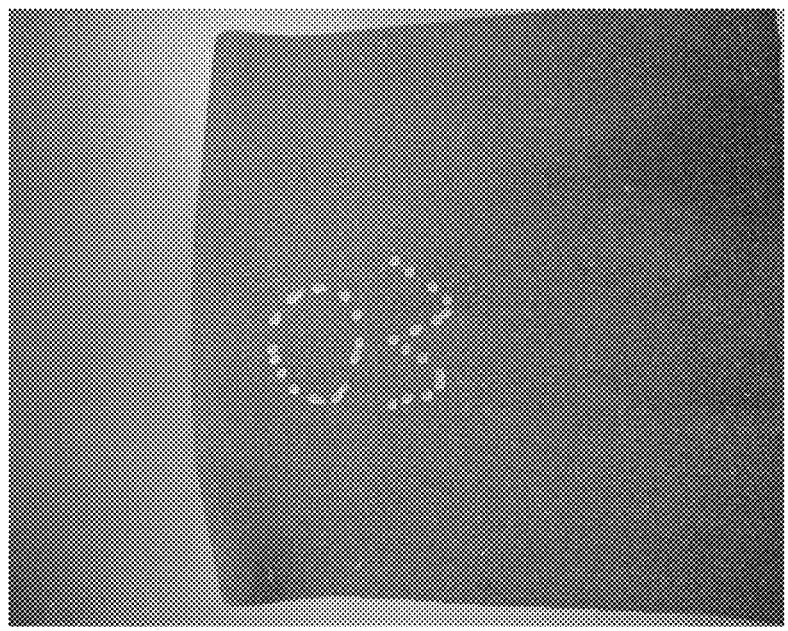
Figure 240C:
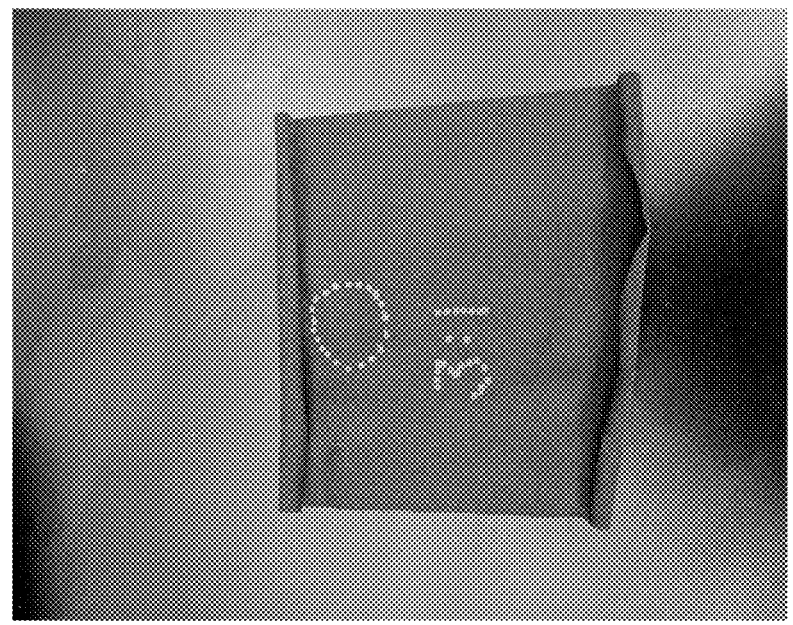
Figure 240F:
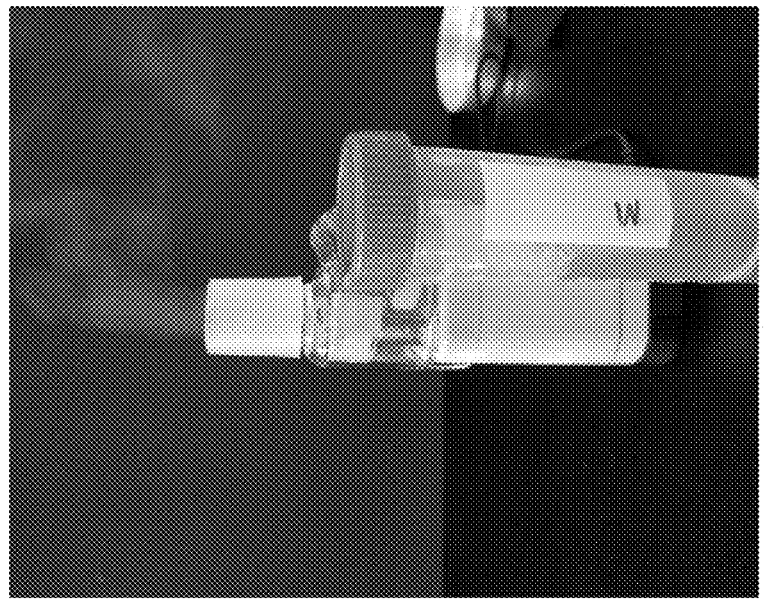
Figure 240E:
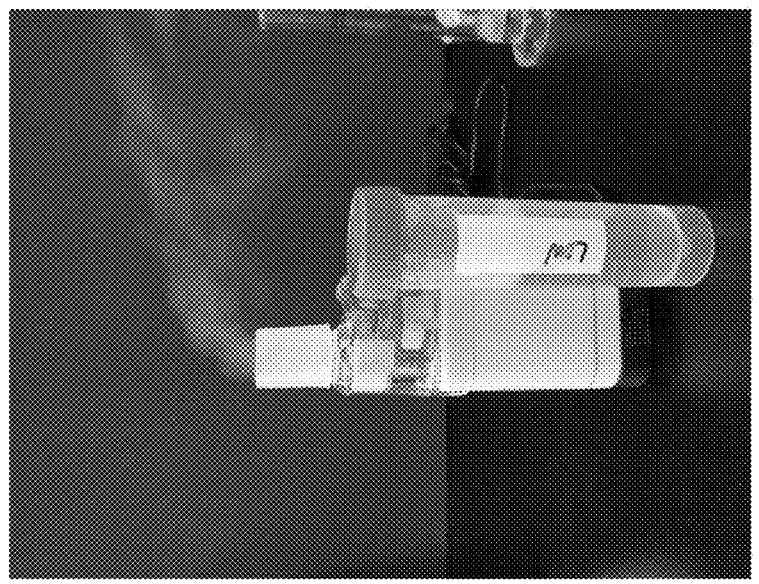
Figure 240H:
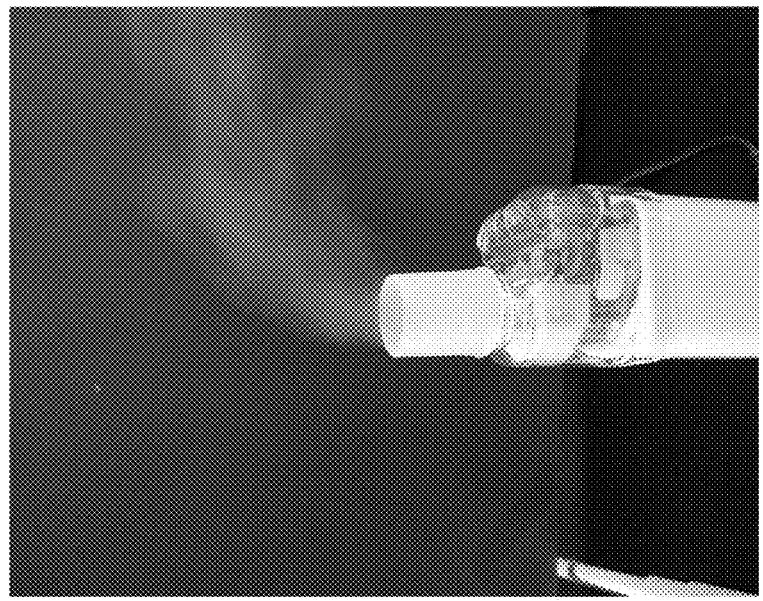
Figure 240G:
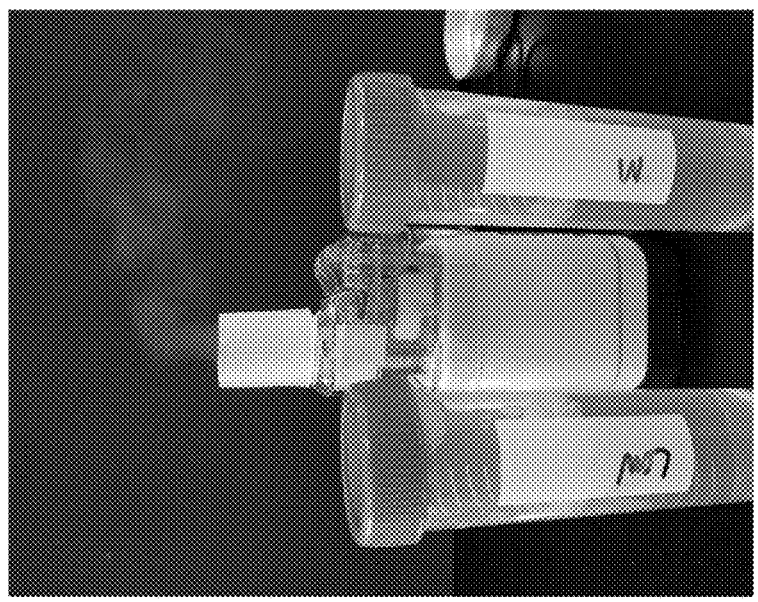

FIGS. 240A-240D illustrate samples of fabric coated with silk formulations using a nebulizer applicator. FIG. 240A: low MW silk; FIG. 240B: medium MW silk;

FIG. 240C: low MW to medium MW 3:1; FIG. 240D: control.

FIGS. 240E-240H illustrate nebulizers and the silk solutions, and control, respectively.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Silk Fibroin-Based Protein Fragments and Solutions Thereof

Provided herein are methods for producing pure and highly scalable silk protein fragment (SPF) mixture solutions that may be used to coat at least a portion of textiles or may be formed into usable fibers for weaving into yarn. In some embodiments, SPF mixture solutions may also refer to silk fibroin solutions (SFS), and vice versa. The solutions are generated from raw pure intact silk protein material and processed in order to remove any sericin and achieve the desired weight average molecular weight (MW) and polydispersity of the fragment mixture. Select method parameters may be altered to achieve distinct final silk protein fragment characteristics depending upon the intended use. The resulting final fragment solution is pure silk protein fragments and water with PPM to non-detectable levels of process contaminants. The concentration, size and polydispersity of silk protein fragments in the solution may further be altered depending upon the desired use and performance requirements. In an embodiment, the pure silk fibroin-based protein fragments in the solution are substantially devoid of sericin, have an average weight average molecular weight ranging from about 1 kDa to about 350 kDa, and have a polydispersity ranging from about 1.0 and about 5.0. In an embodiment, the pure silk fibroin-based protein fragments in the solution are substantially devoid of sericin, have an average weight average molecular weight ranging from about 6 kDa to about 17 kDa, and have a polydispersity ranging from about 1.5 and about 3.0, or from about 1.0 and about 5.0. In an embodiment, the pure silk fibroin-based protein fragments in the solution are substantially devoid of sericin, have an average weight average molecular weight ranging from about 17 kDa to about 39 kDa, and have a polydispersity ranging from about 1.5 and about 3.0, or from about 1.0 and about 5.0. In an embodiment, the pure silk fibroin-based protein fragments in the solution are substantially devoid of sericin, have an average weight average molecular weight ranging from about 39 kDa to about 80 kDa, and have a polydispersity ranging from about 1.5 and about 3.0, or from about 1.0 and about 5.0. In an embodiment, the solutions may be used to generate articles, such as silk gels of varying gel and liquid consistencies by varying water content/concentration, or sold as a raw ingredient into the consumer market. As used herein, the term "silk solution" may refer to solutions of silk proteins, including solutions of silk fibroin-based protein fragments. Methods of making silk fibroin-based protein fragments and solutions thereof are described for example in U.S. Pat. Nos. 9,187,538, 9,511,012, 9,517,191, 9,522,107, 9,522,108, and 9,545,369.

As used herein, the term "leather" refers to natural leather and synthetic leather. Natural leather includes chrome-tanned leather (e.g., tanned using chromium sulfate and other chromium salts), vegetable-tanned leather (e.g., tanned using tannins), aldehyde-tanned leather (also known as wet-white leather, e.g., tanned using glutaraldehyde or oxazolidine compounds), brain-tanned leather, formaldehyde-tanned leather, Chamois leather (e.g., tanned using cod oils), rose-tanned leather (e.g., tanned using rose otto oils), synthetic-tanned leather (e.g., tanned using aromatic polymers), alum-tanned leather, patent leather, Vachetta leather, nubuck leather, and rawhide leather. Natural leather also includes split leather, full-grain leather, top-grain leather, and cor-rected-grain leather, the properties and preparation of which are known to those of skill in the art.

As used herein, "silk based proteins or fragments thereof" includes silk fibroin-based proteins or fragments thereof, natural silk based proteins or fragments thereof, recombinant silk based proteins or fragments thereof, and combinations thereof. Natural silk based proteins or fragments thereof include spider silk based proteins or fragments thereof, silkworm silk based proteins or fragments thereof, and combinations thereof. Silkworm based proteins or fragments thereof may include *Bombyx mori* silk based proteins or fragments thereof. The SPF mixture solutions described herein may include silk based proteins or fragments thereof. Moreover, SFS, as described herein, may be replaced with SPF mixture solutions.

As used herein, "low molecular weight" silk fibroin solutions may include those SFS solutions that include silk fibroin-based protein fragments having a molecular weight in a range of about 5 kDa to 20 kDa. In some embodiments, a target low molecular weight for certain silk fibroin-based protein fragments may be about 11 kDa.

As used herein, "medium molecular weight" silk fibroin solutions may include those SFS solutions that include silk-fibroin based protein fragments having a molecular weight in a range of about 20 kDa to about 55 kDa. In some embodiments, a target medium molecular weight for certain silk fibroin-based protein fragments may be about 40 kDa.

As used herein, "high molecular weight" silk fibroin solutions may include those SFS solutions that include silk-fibroin based protein fragments having a molecular weight that is in a range of about 55 kDa to about 150 kDa. In some embodiments, a target high molecular weight for certain silk fibroin-based protein fragments may be about 100 kDa to about 145 kDa.

In some embodiments, the molecular weights described herein (e.g., low molecular weight silk, medium molecular weight silk, high molecular weight silk) may be converted to the approximate number of amino acids contained within the respective natural or recombinant proteins, such as natural or recombinant silk proteins, as would be understood by a person having ordinary skill in the art. For example, the average weight of an amino acid may be about 110 daltons (i.e., 110 g/mol). Therefore, in some embodiments, dividing the molecular weight of a linear protein by 110 daltons may be used to approximate the number of amino acid residues contained therein.

As used herein, the terms "substantially sericin free" or "substantially devoid of sericin" refer to silk fibers in which a majority of the sericin protein has been removed. In an embodiment, silk fibroin that is substantially devoid of sericin refers to silk fibroin having between about 0.01% (w/w) and about 10.0% (w/w) sericin. In an embodiment, silk fibroin that is substantially devoid of sericin refers to silk fibroin having between about 0.01% (w/w) and about 9.0% (w/w) sericin. In an embodiment, silk fibroin that is substantially devoid of sericin refers to silk fibroin having between about 0.01% (w/w) and about 8.0% (w/w) sericin. In an embodiment, silk fibroin that is substantially devoid of sericin refers to silk fibroin having between about 0.01% (w/w) and about 7.0% (w/w) sericin. In an embodiment, silk fibroin that is substantially devoid of sericin refers to silk fibroin having between about 0.01% (w/w) and about 6.0% (w/w) sericin. In an embodiment, silk fibroin that is substantially devoid of sericin refers to silk fibroin having between about 0.01% (w/w) and about 5.0% (w/w) sericin. In an embodiment, silk fibroin that is substantially devoid of sericin refers to silk fibroin having between about 0% (w/w)

and about 4.0% (w/w) sericin. In an embodiment, silk fibroin that is substantially devoid of sericin refers to silk fibroin having between about 0.05% (w/w) and about 4.0% (w/w) sericin. In an embodiment, silk fibroin that is substantially devoid of sericin refers to silk fibroin having between about 0.1% (w/w) and about 4.0% (w/w) sericin. In an embodiment, silk fibroin that is substantially devoid of sericin refers to silk fibroin having between about 0.5% (w/w) and about 4.0% (w/w) sericin. In an embodiment, silk fibroin that is substantially devoid of sericin refers to silk fibroin having between about 1.0% (w/w) and about 4.0% (w/w) sericin. In an embodiment, silk fibroin that is substantially devoid of sericin refers to silk fibroin having between about 1.5% (w/w) and about 4.0% (w/w) sericin. In an embodiment, silk fibroin that is substantially devoid of sericin refers to silk fibroin having between about 2.0% (w/w) and about 4.0% (w/w) sericin. In an embodiment, silk fibroin that is substantially devoid of sericin refers to silk fibroin having between about 2.5% (w/w) and about 4.0% (w/w) sericin. In an embodiment, silk fibroin that is substantially devoid of sericin refers to silk fibroin having a sericin content between about 0.01% (w/w) and about 0.1% (w/w). In an embodiment, silk fibroin that is substantially devoid of sericin refers to silk fibroin having a sericin content below about 0.1% (w/w). In an embodiment, silk fibroin that is substantially devoid of sericin refers to silk fibroin having a sericin content below about 0.05% (w/w). In an embodiment, when a silk source is added to a boiling (100° C.) aqueous solution of sodium carbonate for a treatment time of between about 30 minutes to about 60 minutes, a degumming loss of about 26 wt. % to about 31 wt. % is obtained.

As used herein, the term "substantially homogeneous" may refer to pure silk fibroin-based protein fragments that are distributed in a normal distribution about an identified molecular weight. As used herein, the term "substantially homogeneous" may refer to an even distribution of additive, for example vitamin C, throughout a composition of the present disclosure.

As used herein, the term "substantially free of inorganic residuals" means that the composition exhibits residuals of 0.1% (w/w) or less. In an embodiment, substantially free of inorganic residuals refers to a composition that exhibits residuals of 0.05% (w/w) or less. In an embodiment, substantially free of inorganic residuals refers to a composition that exhibits residuals of 0.01% (w/w) or less. In an embodiment, the amount of inorganic residuals is between 0 ppm ("non-detectable" or "ND") and 1000 ppm. In an embodiment, the amount of inorganic residuals is ND to about 500 ppm. In an embodiment, the amount of inorganic residuals is ND to about 400 ppm. In an embodiment, the amount of inorganic residuals is ND to about 300 ppm. In an embodiment, the amount of inorganic residuals is ND to about 200 ppm. In an embodiment, the amount of inorganic residuals is ND to about 100 ppm. In an embodiment, the amount of inorganic residuals is between 10 ppm and 1000 ppm.

As used herein, the term "substantially free of organic residuals" means that the composition exhibits residuals of 0.1% (w/w) or less. In an embodiment, substantially free of organic residuals refers to a composition that exhibits residuals of 0.05% (w/w) or less. In an embodiment, substantially free of organic residuals refers to a composition that exhibits residuals of 0.01% (w/w) or less. In an embodiment, the amount of organic residuals is between 0 ppm ("non-detectable" or "ND") and 1000 ppm. In an embodiment, the amount of organic residuals is ND to about 500 ppm. In an embodiment, the amount of organic residuals is ND to about 400 ppm. In an embodiment, the amount of organic residuals is ND to about 300 ppm. In an embodiment, the amount of organic residuals is ND to about 200 ppm. In an embodiment, the amount of organic residuals is ND to about 100 ppm. In an embodiment, the amount of organic residuals is between 10 ppm and 1000 ppm.

Compositions of the present disclosure are "biocompatible" or otherwise exhibit "biocompatibility" meaning that the compositions are compatible with living tissue or a living system by not being toxic, injurious, or physiologically reactive and not causing immunological rejection or an inflammatory response. Such biocompatibility can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely. For example, in some embodiments, the coatings described herein are biocompatible coatings.

In some embodiments, compositions described herein, which may be biocompatible compositions (e.g., biocompatible coatings that include silk), may be evaluated and comply with International Standard ISO 10993-1, titled the "Biological evaluation of medical devices—Part 1: Evaluation and testing within a risk management process." In some embodiments, compositions described herein, which may be biocompatible compositions, may be evaluated under ISO 106993-1 for one or more of cytotoxicity, sensitization, hemocompatibility, pyrogenicity, implantation, genotoxicity, carcinogenicity, reproductive and developmental toxicity, and degradation.

In some embodiments, compositions and articles described herein, and methods of preparing the same, include silk coated fabrics and textiles wherein the silk coating is partially dissolved in the fabric or textile. The fabric or textile may be a polymeric material such as those described elsewhere herein. The term "partially dissolved" includes mixing to form a dispersion of, e.g., a portion of a polymeric fabric or textile with a portion of the silk based coating. In some embodiments, the dispersion may be a solid suspension (i.e., a dispersion comprising domains on the order of 10 nm) or a solid solution (i.e., a molecular dispersion) of silk in the polymeric fabric or textile. In some embodiments, the dispersion may be localized at the surface interface between the silk coating and the polymeric fabric or textile, and may have a depth of 1 nm, 2 nm, 5 nm, 10 nm, 25 nm, 50 nm, 75 nm, 100 nm, or greater than 100 nm, depending on the method of preparation. In some embodiments, the dispersion may be a layer sandwiched between the polymeric fabric or textile and the silk coating. In some embodiments, the dispersion may be prepared by coating silk, including silk fibroin with the characteristics described herein, onto the polymeric fabric or textile, and then performing an additional process to form the dispersion, including heating at a temperature of 100° C., 125° C., 150° C., 175° C., 200° C., 225° C., or 250° C. for a time period selected from the group consisting of 1 minute, 2 minutes, 5 minutes, 10 minutes, 15 minutes, 20 minutes, 30 minutes, 1 hour, 2 hours, 4 hours, 8 hours, 16 hours, or 24 hours. In some embodiments, heating may be performed at or above the glass transition temperature ($T_g$) of silk and/or the polymeric fabric or textile, which may be assessed by methods known in the art. In some embodiments, the dispersion may be formed by coating silk, including silk fibroin with the characteristics described herein, onto the polymeric fabric or textile, and then performing an additional process to impregnate the silk coating into the polymeric fabric or textile, including treatment with an organic solvent. Methods for characterizing the properties of polymers dissolved in one another are well known in the art and include differential scanning calorimetry and surface analysis methods capable of depth profiling, including spectroscopic methods.

Compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

In some embodiments, where aqueous solutions are used to prepare SPF compositions or SPF containing coatings, the aqueous solutions may be prepared with DI water or tap water. As used herein, "tap water" refers to potable water provided by public utilities and water of comparable quality, regardless of the source, without further refinement such as by reverse osmosis, distillation, and/or deionization. Therefore, the use of "DI water," "RODI water," or "water," as set forth herein, may be understood to be interchangeable with "tap water" according to the processes described herein without deleterious effects to such processes.

Textiles and Materials Coated with Silk Fibroin-Based Protein Fragments

As used herein, the term "washable" and "exhibiting washability" means that a silk coated fabric of the present disclosure is capable of being washed without shrinking, fading, or the like.

As used herein, the term "textile" refers to a flexible woven or non-woven material consisting of a network of natural or artificial fibers often referred to as fabric, thread, or yarn. In an embodiment, textiles can be used to fabricate clothing, apparel, shoes, and bags. In an embodiment, textiles can be used to fabricate carpeting, upholstered furnishings, window shades, towels, and coverings for tables, beds, and other flat surfaces. In an embodiment, textiles can be used to fabricate flags, backpacks, tents, nets, handkerchiefs, balloons, kites, sails, and parachutes.

As used herein, the term "hand" refers to the feel of a fabric, which may be further described as the feeling of softness, crispness, dryness, silkiness, and combinations thereof. Fabric hand is also referred to as "drape." A fabric with a hard hand is coarse, rough, and generally less comfortable for the wearer. A fabric with a soft hand is fluid and smooth, such as fine silk, wool, or cashmere, and generally more comfortable for the wearer. Fabric hand can be determined by comparison to collections of fabric samples, or by use of methods such as the Kawabata Evaluation System (KES) or the Fabric Assurance by Simple Testing (FAST) methods. Behera and Hari, *Ind. J. Fibre & Textile Res.*, 1994, 19, 168-71.

As used herein, the term "yarn" refers to a single or multi-fiber construct.

As used herein, a "coating" refers to a material, or combination of materials, that form a substantially continuous layer or film on an exterior surface of a substrate, such as a textile. In some embodiments, a portion of the coating may penetrate at least partially into the substrate. In some embodiments, the coating may penetrate at least partially into the interstices of a substrate. In some embodiments, the coating may be infused into a surface of the substrate such that the application of the coating, or coating process, may include infusing (at the melting temperature of the substrate) at least one coating component at least partially into a surface of the substrate. A coating may be applied to a substrate by one or more of the processes described herein.

In embodiments described where the coating may be infused into a surface of the substrate, the coating may be codissolved in a surface of the substrate such that a component of the coating may be intermixed in the surface of the substrate to a depth of at least about 1 nm, or at least about 2 nm, or at least about 3 nm, or at least about 4 nm, or at least about 5 nm, or at least about 6 nm, or at least about 7 nm, or at least about 8 nm, or at least about 9 nm, or at least about 10 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm. In some embodiments, the coating may be infused into a surface of the substrate where the substrate includes one or more polymers including, but not limited to, polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, and LYCRA.

As used herein, the term "bath coating" encompasses coating a fabric in a batch, immersing a fabric in a bath, and submerging a fabric in a bath. Concepts of bath coating are set forth in U.S. Pat. No. 4,521,458, the entirety of which is incorporated by reference.

As used herein, and unless more specifically described, the term "drying" may refer to drying a coated material as described herein at a temperature greater than room temperature (i.e., 20° C.).

In one embodiment, the invention relates to coating a material including one or more proteinaceous fibers, wherein a substantial portion of the proteinaceous fibers are coated with silk fibroin-based protein fragments. In some embodiments, the proteinaceous fibers include keratin. In some embodiments, the proteinaceous fibers include hair. In some embodiments, the proteinaceous fibers include human hair or animal hair. In some embodiments, the silk fibroin-based protein fragments include one or more of low molecular weight silk fibroin-based protein fragments, medium molecular weight silk fibroin-based protein fragments, and high molecular weight silk fibroin-based protein fragments. In some embodiments, the silk fibroin-based protein fragments have an average molecular weight from about 1 kDa to about 350 kDa. In some embodiments, the silk fibroin-based protein fragments have a polydispersity from about 1.0 to about 5.0.

Synthetic leather includes poromeric imitation leathers (e.g., polyurethane on polyester), vinyl and polyamide felt fibers, polyurethane, polyvinyl chloride, polyethylene (PE), polypropylene (PP), vinyl acetate copolymer (EVA), polyamide, polyester, textile-polymer composite microfibers, corfan, koskin, leatherette, BIOTHANE®, BIRKIBUC®, BIRKO-FLOR®, CLARINO®, ECOLORICA®, KYDEX®, LORICA®, NAUGAHYDE®, REXINE®, VEGETAN®, FABRIKOID®, or combinations thereof.

In an embodiment, the invention provides a textile or leather product coated with silk fibroin-based proteins or fragments thereof. In an embodiment, the invention provides a textile or leather product coated with silk fibroin-based proteins or fragments thereof, wherein the textile is a textile used for human apparel, including performance and/or athletic apparel. In an embodiment, the invention provides a textile or leather product coated with silk fibroin-based proteins or fragments thereof, and wherein the textile or leather product exhibits improved moisture management properties and/or resistance to microbial growth. In an embodiment, the invention provides a textile or leather product coated with silk fibroin-based proteins or fragments thereof, wherein the textile is a textile or leather product used for home upholstery. In an embodiment, the invention provides a textile or leather product coated with silk fibroin-based proteins or fragments thereof, wherein the textile or leather product is used for automobile upholstery. In an embodiment, the invention provides a textile or leather product coated with silk fibroin-based proteins or fragments thereof, wherein the textile or leather product is used for aircraft upholstery. In an embodiment, the invention provides a textile or leather product coated with silk fibroin-based proteins or fragments thereof, wherein the textile or leather product is used for upholstery in transportation vehicles for public, commercial, military, or other use, including buses and trains. In an embodiment, the invention provides a textile or leather product coated with silk fibroin-based proteins or fragments thereof, wherein the textile or leather product is used for upholstery of a product that requires a high degree of resistance to wear as compared to normal upholstery.

In an embodiment, the invention provides a textile or leather product coated with silk fibroin-based proteins or fragments thereof, wherein the textile is a textile or leather product fabricated as trim on automobile upholstery. In an embodiment, the invention provides a textile or leather product coated with silk fibroin-based proteins or fragments thereof, wherein the textile is a textile or leather product fabricated as a steering wheel. In an embodiment, the invention provides a textile or leather product coated with silk fibroin-based proteins or fragments thereof, wherein the textile is a textile or leather product fabricated as a headrest. In an embodiment, the invention provides a textile or leather product coated with silk fibroin-based proteins or fragments thereof, wherein the textile is a textile or leather product fabricated as an armrest. In an embodiment, the invention provides a textile or leather product coated with silk fibroin-based proteins or fragments thereof, wherein the textile is a textile or leather product fabricated as an automobile floor mat. In an embodiment, the invention provides a textile or leather product coated with silk fibroin-based proteins or fragments thereof, wherein the textile is a textile or leather product fabricated as automobile or vehicle carpet. In an embodiment, the invention provides a textile or leather product coated with silk fibroin-based proteins or fragments thereof, wherein the textile is a textile or leather product fabricated as automotive trim. In an embodiment, the invention provides a textile or leather product coated with silk fibroin-based proteins or fragments thereof, wherein the textile is a textile or leather product fabricated as a children's car seat. In an embodiment, the invention provides a textile or leather product coated with silk fibroin-based proteins or fragments thereof, wherein the textile is a textile or leather product fabricated as a seat belt or safety harness. In an embodiment, the invention provides a textile or leather product coated with silk fibroin-based proteins or fragments thereof, wherein the textile is a textile or leather product fabricated as a dashboard. In an embodiment, the invention provides a textile or leather product coated with silk fibroin-based proteins or fragments thereof, wherein the textile is a textile or leather product fabricated as a seat. In an embodiment, the invention provides a textile or leather product coated with silk fibroin-based proteins or fragments thereof, wherein the textile is a textile or leather product fabricated as a seat panel. In an embodiment, the invention provides a textile or leather product coated with silk fibroin-based proteins or fragments thereof, wherein the textile is a textile or leather product fabricated as an interior panel. In an embodiment, the invention provides a textile or leather product coated with silk fibroin-based proteins or fragments thereof, wherein the textile is a textile or leather product fabricated as an airbag cover. In an embodiment, the invention provides a textile or leather product coated with silk fibroin-based proteins or fragments thereof, wherein the textile is a textile or leather product fabricated as an airbag. In an embodiment, the invention provides a textile or leather product coated with silk fibroin-based proteins or fragments thereof, wherein the textile is a textile or leather product fabricated as a sunvisor. In an embodiment, the invention provides a textile or leather product coated with silk fibroin-based proteins or fragments thereof, wherein the textile is a textile or leather product fabricated as a wiring harness. In an embodiment, the invention provides a product coated with silk fibroin-based proteins or fragments thereof, wherein the product is a cushion. In an embodiment, the invention provides a product coated with silk fibroin-based proteins or fragments thereof, wherein the product is automotive, aircraft, or other vehicular insulation. The coating comprises silk based proteins or fragments thereof having a weight average molecular weight range of about 1 kDa to about 350 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, or about 1.0 and about 5.0, and optionally wherein the proteins or protein fragments, prior to coating the fabric, do not spontaneously or gradually gelate and do not visibly change in color or turbidity when in a solution for at least 10 days. The coating comprises silk based proteins or fragments thereof having a weight average molecular weight range of about 5 kDa and about 144 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and optionally wherein the proteins or protein fragments, prior to coating the fabric, do not spontaneously or gradually gelate and do not visibly change in color or turbidity when in a solution for at least 10 days.

In an embodiment, the invention provides an article comprising a textile or leather coated with silk fibroin-based proteins or fragments thereof. In an embodiment, the textile or leather is a textile or leather used in the manufacture of tents, sleeping bags, ponchos, and soft-walled coolers. In an embodiment, the textile or leather is a textile or leather used in the manufacture of athletic equipment. In an embodiment, the textile or leather is a textile or leather used in the manufacture of outdoor gear. In an embodiment, the textile or leather is a textile or leather used in the manufacture of hiking gear, such as harnesses and backpacks. In an embodiment, the textile or leather is a textile or leather used in the manufacture of climbing gear. In an embodiment, the textile or leather is canvass. In an embodiment, the textile or leather is a textile or leather used in the manufacture of a hat. In an embodiment, the textile or leather is a textile or leather used in the manufacture of an umbrella. In an embodiment, the textile or leather is a textile or leather used in the manufacture of a tent. In an embodiment, the textile or leather is a textile or leather used in the manufacture of a baby sleeper, a baby blanket, or a baby pajama. In an embodiment, the textile or leather is a textile or leather used in the manufacture of a glove, such as a driving glove or an athletic glove. In an embodiment, the textile or leather is a textile or leather used in the manufacture of athletic pants, such as sweat pants, jogging pants, yoga pants, or pants for use in competitive sports. In an embodiment, the textile or leather is a textile or leather used in the manufacture of athletic shirts, such as sweat shirts, jogging shirts, yoga shirts, or shirts for use in competitive sports. In an embodiment, the textile or leather is a textile or leather used in the manufacture of beach equipment, such as beach umbrellas, beach chairs, beach blankets, and beach towels. In an embodiment, the textile or leather is a textile or leather used in the manufacture of jackets or overcoats. In an embodiment, the textile or leather is a textile or leather used in the manufacture of medical garments, such as surgical drapes, surgical gowns, surgical sleeves, laboratory sleeves, laboratory coats, wound dressings, sterilization wraps, surgical face masks, retention bandages, support devices, compression bandages, shoe covers, surgical blankets, and the like. The coating comprises silk based proteins or fragments thereof having a weight average molecular weight range of about 5 kDa to about 144 kDa.

In an embodiment, the invention provides an article comprising a textile coated with silk fibroin-based proteins or fragments thereof. In an embodiment, the textile is a textile used in the manufacture of tents, sleeping bags, ponchos, and soft-walled coolers. In an embodiment, the textile is a textile used in the manufacture of athletic equipment. In an embodiment, the textile is a textile used in the manufacture of outdoor gear. In an embodiment, the textile is a textile used in the manufacture of hiking gear, such as harnesses and backpacks. In an embodiment, the textile is a textile used in the manufacture of climbing gear. In an embodiment, the textile is canvass. In an embodiment, the textile is a textile used in the manufacture of a hat. In an embodiment, the textile is a textile used in the manufacture of an umbrella. In an embodiment, the textile is a textile used in the manufacture of a tent. In an embodiment, the textile is a textile used in the manufacture of a baby sleeper, a baby blanket, or a baby pajama. In an embodiment, the textile is a textile used in the manufacture of a glove, such as a driving glove or an athletic glove. In an embodiment, the textile is a textile used in the manufacture of athletic pants, such as sweat pants, jogging pants, yoga pants, or pants for use in competitive sports. In an embodiment, the textile is a textile used in the manufacture of athletic shirts, such as sweat shirts, jogging shirts, yoga shirts, or shirts for use in competitive sports. In an embodiment, the textile is a textile used in the manufacture of beach equipment, such as beach umbrellas, beach chairs, beach blankets, and beach towels. In an embodiment, the textile is a textile used in the manufacture of jackets or overcoats. In an embodiment, the textile is a textile used in the manufacture of medical garments, such as surgical drapes, surgical gowns, surgical sleeves, laboratory sleeves, laboratory coats, wound dressings, sterilization wraps, surgical face masks, retention bandages, support devices, compression bandages, shoe covers, surgical blankets, and the like. The coating comprises silk based proteins or fragments thereof having a weight average molecular weight range of about 1 kDa to about 350 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.0 and about 5.0, and optionally wherein the proteins or protein fragments, prior to coating the fabric, do not spontaneously or gradually gelate and do not visibly change in color or turbidity when in a solution for at least 10 days.

In an embodiment, the invention provides a shoe coated with silk fibroin-based proteins or fragments thereof. In an embodiment, the invention provides a shoe coated with silk fibroin-based proteins or fragments thereof, wherein the shoe exhibits an improved property relative to an uncoated shoe. In an embodiment, the invention provides a shoe coated with silk fibroin-based proteins or fragments thereof, wherein the shoe exhibits an improved property relative to an uncoated shoe, and wherein the improved property is stain resistance. In an embodiment, the invention provides a shoe coated with silk fibroin-based proteins or fragments thereof, wherein the shoe exhibits an improved property relative to an uncoated shoe, and wherein the shoe is made of natural leather or synthetic leather. The coating comprises silk based proteins or fragments thereof having a weight average molecular weight range of about 1 kDa to about 350 kDa, or about 5 kDa to about 144 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.0 and about 5.0, or about 1.5 and about 3.0, and optionally wherein the proteins or protein fragments, prior to coating the fabric, do not spontaneously or gradually gelate and do not visibly change in color or turbidity when in a solution for at least 10 days.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, and wherein the article is a textile or leather.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.0 and about 5.0, or about 1.5 and about 3.0, and wherein the proteins or protein fragments, prior to coating the fabric, do not spontaneously or gradually gelate and do not visibly change in color or turbidity when in a solution for at least 10 days.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, alpaca fleece, alpaca wool, lama fleece, lama wool, cotton, cashmere, sheep fleece, sheep wool, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of synthetic fiber or yarn, or combinations thereof.

In an embodiment, the invention provides an article comprising a fiber or yarn having a coating, wherein the coating comprises silk based proteins or fragments thereof having a weight average molecular weight range of about 1 kDa to about 350 kDa, wherein the fiber or yarn is selected from the group consisting of natural fiber or yarn, comprising for example wool, synthetic fiber or yarn, or combinations thereof, wherein the fiber or yarn is synthetic fiber or yarn selected from the group consisting of polyester, nylon, polyester-polyurethane copolymer and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is synthetic fiber or yarn selected from the group consisting of natural fiber or yarn, synthetic fiber or yarn, or combinations thereof, wherein the fiber or yarn comprises cashmere, nylon, polyester-polyurethane copolymer, polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, and combinations thereof, and/or LYCRA.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits an improved property, wherein the improved property is an accumulative one-way moisture transport index selected from the group consisting of greater than 40%, greater than 60%, greater than 80%, greater than 100%, greater than 120%, greater than 140%, greater than 160%, and greater than 180%. In an embodiment, the foregoing improved property is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits an improved property, wherein the improved property is an accumulative one way transport capability increase relative to uncoated fabric selected from the group consisting of 1.2 fold, 1.5 fold, 2.0 fold, 3.0 fold, 4.0 fold, 5.0 fold, and 10 fold. In an embodiment, the foregoing improved property is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits an improved property, wherein the improved property is an overall moisture management capability selected from the group consisting of greater than 0.05, greater than 0.10, greater than 0.15, greater than 0.20, greater than 0.25, greater than 0.30, greater than 0.35, greater than 0.40, greater than 0.50, greater than 0.60, greater than 0.70, and greater than 0.80. In an embodiment, the foregoing improved property is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits an improved property, wherein the improved property is dimensional stability. In some embodiments, dimensional stability refers to length stability, width stability, or an overall dimensional stability. In an embodiment, dimensional stability is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, and wherein the fabric exhibits substantially no increase in microbial growth after a number of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits substantially no increase in microbial growth after a number of machine washing cycles selected from the group consisting of 1 cycle, 2 cycles, 3 cycles, 4 cycles, 5 cycles, 10 cycles, 25 cycles, and 50 cycles, and wherein the microbial growth is microbial growth of a microbe selected from the group consisting of *Staphylococcus aureus, Klebsiella pneumoniae*, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits substantially no increase in microbial growth after a number of machine washing cycles selected from the group consisting of 1 cycle, 2 cycles, 3 cycles, 4 cycles, 5 cycles, 10 cycles, 25 cycles, and 50 cycles, wherein the microbial growth is microbial growth of a microbe selected from the group consisting of *Staphylococcus aureus, Klebsiella pneumoniae*, and combinations thereof, wherein the microbial growth is reduced by a percentage selected from the group consisting of 50%, 100%, 500%, 1000%, 2000%, and 3000% compared to an uncoated fabric.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits substantially no increase in microbial growth after a number of machine washing cycles selected from the group consisting of 5 cycles, 10 cycles, 25 cycles, and 50 cycles, and wherein the microbial growth is microbial growth of a microbe selected from the group consisting of *Staphylococcus aureus, Klebsiella pneumoniae*, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits substantially no increase in microbial growth after a number of machine washing cycles selected from the group consisting of 5 cycles, 10 cycles, 25 cycles, and 50 cycles, wherein the microbial growth is microbial growth of a microbe selected from the group consisting of *Staphylococcus aureus, Klebsiella pneumoniae*, and combinations thereof, wherein the microbial growth is reduced by a percentage selected from the group consisting of 50%, 100%, 500%, 1000%, 2000%, and 3000% compared to an uncoated fabric.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the coating is applied to the fabric at the fiber level prior to forming the fabric.

In some embodiments, the silk coated fibers and/or yarns included herein may have enhanced dye and/or color features due to application of dye and/or coloring agent at the liquid silk layer and/or the fabric or yarn layer of the silk coated fibers and/or yarns that may make up the articles described herein. In some embodiments, a liquid silk layer of the silk coated fibers and/or yarns included herein may affect, change, increase, decrease, or otherwise modulate the birefringence, reflectivity, and/or refractivity of the silk coated fibers and/or yarns as compared to uncoated fibers and/or yarns.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits a change in birefringence compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric exhibits an increase in birefringence compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a decrease in birefringence compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a modulation of birefringence compared to an uncoated fabric.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a change in reflectivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits an increase in reflectivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a decrease in reflectivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a modulation of reflectivity compared to an uncoated fabric.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a change in refractivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits an increase in refractivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a decrease in refractivity compared to an uncoated fabric. In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the fabric exhibits a modulation of refractivity compared to an uncoated fabric.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, and wherein the coating is applied to the fabric at the fiber level prior to forming the fabric.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, and wherein the coating is applied to the fabric at the fabric level or garment level (e.g., after manufacture of a garment from fabrics, leathers, and/or other materials).

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level or garment level, and wherein the fabric is bath coated.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level or garment level, and wherein the fabric is spray coated.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level or garment level, and wherein the fabric is coated with a stencil.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level or garment level, and wherein the coating is applied to at least one side of the fabric using a method selected from the group consisting of a bath coating process, a spray coating process, a stencil (i.e., screen) process, a silk-foam based process, a roller-based process, a magnetic roller process, a knife process, a transfer process, a foam process, a lacquering process, and a printing process. In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level, and wherein the coating is applied to both sides of the fabric using a method selected from the group consisting of a bath coating process, a spray coating process, a stencil (i.e., screen) process, a silk-foam based process, a roller-based process, a magnetic roller process, a knife process, a transfer process, a foam process, a lacquering process, and a printing process.

In any of the foregoing embodiments, the coating may be applied at the fabric garment level by any of the methods disclosed herein to recondition fabrics or garments. For example, such reconditioning using a coating comprising silk based proteins or fragments thereof may be performed as part of washing or cleaning a fabric or garment.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, and wherein the coating has a thickness of about one nanolayer.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, and wherein the coating has a thickness selected from the group consisting of about 5 nm, about 10 nm, about 15 nm, about 20 nm, about 25 nm, about 50 nm, about 100 nm, about 200 nm, about 500 nm, about 1 µm, about 5 µm, about 10 µm, and about 20 µm.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, and wherein the coating is adsorbed on the fabric.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, and wherein the coating is attached to the fabric through chemical, enzymatic, thermal, or irradiative cross-linking.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level, and wherein the hand of the coated fabric is improved relative to an uncoated fabric.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level, and wherein the hand of the coated fabric is improved relative to an uncoated fabric, wherein the hand of the coated fabric that is improved is selected from the group consisting of softness, crispness, dryness, silkiness, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level, and wherein the hand of the coated fabric is improved relative to an uncoated fabric, wherein the hand of the coated fabric that is improved is selected from the group consisting of softness, crispness, dryness, silkiness, and combinations thereof.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is applied to the fabric at the fabric level, and wherein the pilling of the fabric is improved relative to an uncoated fabric.

In an embodiment, the silk coating is applied using a bath process, a screen (or stencil) process, a spray process, a silk-foam based process, and a roller based process.

In an embodiment, a fiber or a yarn comprises a synthetic fiber or yarn (e.g., from animal or plant sources), including polyester, Mylar, cotton, nylon, polyester-polyurethane copolymer, rayon, acetate, aramid (aromatic polyamide), acrylic, ingeo (polylactide), lurex (polyamide-polyester), olefin (polyethylene-polypropylene), and combinations thereof.

In an embodiment, a fiber or a yarn comprises a natural fiber or yarn (e.g., from animal or plant sources), including alpaca fiber, alpaca fleece, alpaca wool, lama fiber, lama fleece, lama wool, cotton, cashmere and sheep fiber, sheep fleece, sheep wool, byssus, chiengora, qiviut, yak, rabbit, lambswool, mohair wool, tibetan wool, lopi, camel hair, pashmina, angora wool, spider silk, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber. In an embodiment, a fiber or a yarn comprises a natural fiber or yarn, including wool fiber. In an embodiment, a fiber or a yarn comprises a natural fiber or yarn, including cashmere fiber. In an embodiment, a fiber or a yarn comprises a natural fiber or yarn, including silk.

In an embodiment, a fiber or a yarn comprises a mineral fiber, also known as mineral wool, mineral cotton, or manmade mineral fiber, including fiberglass, glass, glasswool, stone wool, rock wool, slagwool, glass filaments, asbestos fibers, and ceramic fibers.

In an embodiment, a fiber or a yarn may include cashmere fiber or yarn component and non-cashmere fiber or yarn component. In some embodiments, the non-cashmere fiber or yarn component may comprise alpaca fiber, alpaca fleece, alpaca wool, lama fiber, lama fleece, lama wool, cotton, sheep fleece, sheep wool, byssus, chiengora, qiviut, yak, rabbit, lambswool, mohair wool, tibetan wool, lopi, camel hair, pashmina, angora wool, silkworm silk, spider silk, abaca fiber, coir fiber, flax fiber, jute fiber, kapok fiber, kenaf fiber, raffia fiber, bamboo fiber, hemp, modal fiber, pina, ramie, sisal, soy protein fiber, polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, LYCRA (polyester-polyurethane copolymer, also known as SPANDEX and elastomer), or a mixture thereof. In some embodiments, the non-cashmere fiber or yarn component may be wool. In some embodiments, the non-cashmere fiber or yarn component may be an inert synthetic material, such as polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, LYCRA (polyester-polyurethane copolymer, also known as SPANDEX and elastomer), rayon, or a mixture thereof.

In some embodiments, an article described herein may include a cashmere fiber or yarn component in an amount, by weight of the article (w/w), of greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%0, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein. In some embodiments, an article described herein may include a cashmere fiber or yarn component in an amount, by weight of the article (w/w), of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein. In some embodiments, an article described herein may include a cashmere fiber or yarn component in an amount, by weight of the article (w/w), of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein.

In some embodiments, the cashmere fiber or yarn component may be a silk coated cashmere fiber or yarn component, where the silk coating may be any silk coating provided herein. In some embodiments, the non-cashmere fiber or yarn component may be a silk coated non-cashmere fiber or yarn component, where the silk coating may be ay silk coating provided herein.

In some embodiments, an article described herein may include a silk coated cashmere fiber or yarn component in an amount, by weight of the article (w/w), of greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein. In some embodiments, an article described herein may include a silk coated cashmere fiber or yarn component in an amount, by weight of the article (w/w), of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein. In some embodiments, an article described herein may include a silk coated cashmere fiber or yarn component in an amount, by weight of the article (w/w), of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a non-cashmere fiber or yarn component, as described herein.

In some embodiments, an article described herein may include a silk coated cashmere fiber or yarn component in an amount, by weight of the article (w/w), of greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein. In some embodiments, an article described herein may include a silk coated cashmere fiber or yarn component in an amount, by weight of the article (w/w), of less than 1%, 2%, 3%, 4%, 5%, 6%, 7%, 8%, 9%, 10%, 11%, 2%, 3%, %14%, %15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein. In some embodiments, an article described herein may include a silk coated cashmere fiber or yarn component in an amount, by weight of the article (w/w), of about 1%, 2%, 3%, 4%, 5%, 6%, 7%, 8%, 9%, 10%, 11%, 12%, 13%, 14%, %, %16%, %$^{17}$%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein.

In some embodiments, an article described herein may include a cashmere fiber or yarn component in an amount, by weight of the article (w/w), of greater than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein. In some embodiments, an article described herein may include a cashmere fiber or yarn component in an amount, by weight of the article (w/w), of less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein. In some embodiments, an article described herein may include a cashmere fiber or yarn component in an amount, by weight of the article (w/w), of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, where the balance of the article, by weight (w/w), is a silk coated non-cashmere fiber or yarn component, as described herein.

In an embodiment, a water-soluble silk coating may be used as an adhesive or binder for binding particles to fabrics or for binding fabrics. In an embodiment, an article comprises a fabric bound to another fabric using a silk coating. In an embodiment, an article comprises a fabric with particles bound to the fabric using a silk adhesive.

In an embodiment, the coating is applied to an article including a fabric at the yarn level. In an embodiment, the coating is applied at the fabric level. In an embodiment, the coating has a thickness selected from the group consisting of about 5 nm, about 10 nm, about 15 nm, about 20 nm, about 25 nm, about 50 nm, about 100 nm, about 200 nm, about 500 nm, about 1 µm, about 5 µm, about 10 µm, and about 20 µm.

In an embodiment, the coating has a thickness range selected from the group consisting of about 5 nm to about 100 nm, about 100 nm to about 200 nm, about 200 nm to about 500 nm, about 1 µm to about 2 µm, about 2 µm to about 5 µm, about 5 µm to about 10 µm, and about 10 µm to about 20 µm.

In an embodiment, a fiber or a yarn is treated with a polymer, such as polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In an embodiment, the silk coating surface can be modified silk crystals that range in size from nm to µm.

The criterion for "visibility" is satisfied by any one of the following: a change in the surface character of the textile; the silk coating fills the interstices where the yarns intersect; or the silk coating blurs or obscures the weave.

In an embodiment, a silk based protein or fragment solution may be utilized to coat at least a portion of a fabric which can be used to create a textile. In an embodiment, a silk based protein or fragment solution may be weaved into yarn that can be used as a fabric in a textile. In an embodiment, a silk based protein or fragment solution may be used to coat a fiber. In an embodiment, the invention provides an article comprising a silk based protein or fragment solution coating at least a portion of a fabric or a textile. In an embodiment, the invention provides an article comprising a silk based protein or fragment solution coating a yarn. In an embodiment, the invention provides an article comprising a silk based protein or fragment solution coating a fiber.

There is disclosed a textile that is at least partially surface treated with an aqueous solution of pure silk fibroin-based protein fragments of the present disclosure so as to result in a silk coating on the textile. In an embodiment, the silk coating of the present disclosure is available in a spray can and can be sprayed on any textile by a consumer. In an embodiment, a textile comprising a silk coating of the present disclosure is sold to a consumer. In an embodiment, a textile of the present disclosure is used in constructing action sportswear/apparel. In an embodiment, a silk coating of the present disclosure is positioned on the underlining of apparel. In an embodiment, a silk coating of the present disclosure is positioned on the shell, the lining, or the interlining of apparel. In an embodiment, apparel is partially made from a silk coated textile of the present disclosure and partially made from an uncoated textile. In an embodiment, apparel partially made from a silk coated textile and partially made from an uncoated textile combines an uncoated inert synthetic material with a silk coated inert synthetic material. Examples of inert synthetic material include, but are not limited to, polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, and mixtures thereof. In an embodiment, apparel partially made from a silk coated textile and partially made from an uncoated textile combines an elastomeric material at least partially covered with a silk coating of the present disclosure. In an embodiment, the percentage of silk to elastomeric material can be varied to achieve desired shrink or wrinkle resistant properties.

In an embodiment, a silk coating of the present disclosure is visible. In an embodiment, a silk coating of the present disclosure positioned on apparel helps control skin temperature. In an embodiment, a silk coating of the present disclosure positioned on apparel helps control fluid transfer away from the skin. In an embodiment, a silk coating of the present disclosure positioned on apparel has a soft feel against the skin decreasing abrasions from fabric on skin. In an embodiment, a silk coating of the present disclosure positioned on a textile has properties that confer at least one of wrinkle resistance, shrinkage resistance, or machine washability to the textile. In an embodiment, a silk coated textile of the present disclosure is 100% machine washable and dry cleanable. In an embodiment, a silk coated textile of the present disclosure is 100% waterproof. In an embodiment, a silk coated textile of the present disclosure is wrinkle resistant. In an embodiment, a silk coated textile of the present disclosure is shrink resistant. In an embodiment, a silk coated textile of the present disclosure has the qualities of being waterproof, breathable, and elastic and possess a number of other qualities which are highly desirable in action sportswear. In an embodiment, a silk coated textile of the present disclosure manufactured from a silk fabric of the present disclosure further includes LYCRA® brand spandex fibers.

In an embodiment, a textile at least partially coated with an aqueous solution of pure silk fibroin-based protein fragments of the present disclosure is a breathable fabric. In an embodiment, a textile at least partially coated with an aqueous solution of pure silk fibroin-based protein fragments of the present disclosure is a water-resistant fabric. In an embodiment, a textile at least partially coated with an aqueous solution of pure silk fibroin-based protein fragments of the present disclosure is a shrink-resistant fabric. In an embodiment, a textile at least partially coated with an aqueous solution of pure silk fibroin-based protein fragments of the present disclosure is a machine-washable fabric. In an embodiment, a textile at least partially coated with an aqueous solution of pure silk fibroin-based protein fragments of the present disclosure is a wrinkle resistant fabric. In an embodiment, textile at least partially coated with an aqueous solution of pure silk fibroin-based protein fragments of the present disclosure provides moisture and vitamins to the skin.

In an embodiment, an aqueous solution of pure silk fibroin-based protein fragments of the present disclosure is used to coat a textile or leather. In an embodiment, the concentration of silk in the solution ranges from about 0.1% to about 20.0%. In an embodiment, the concentration of silk in the solution ranges from about 0.1% to about 15.0%. In an embodiment, the concentration of silk in the solution ranges from about 0.5% to about 10.0%. In an embodiment, the concentration of silk in the solution ranges from about 1.0% to about 5.0%. In an embodiment, an aqueous solution of pure silk fibroin-based protein fragments of the present disclosure is applied directly to a fabric. Alternatively, silk microsphere and any additives may be used for coating a fabric. In an embodiment, additives can be added to an aqueous solution of pure silk fibroin-based protein fragments of the present disclosure before coating (e.g., alcohols) to further enhance material properties. In an embodiment, a silk coating of the present disclosure can have a pattern to optimize properties of the silk on the fabric. In an embodiment, a coating is applied to a fabric under tension and/or lax to vary penetration in to the fabric.

In an embodiment, a silk coating of the present disclosure can be applied at the yarn level, followed by creation of a fabric once the yarn is coated. In an embodiment, an aqueous solution of pure silk fibroin-based protein fragments of the present disclosure can be spun into fibers to make a silk fabric and/or silk fabric blend with other materials known in the apparel industry.

Uses of Textiles and Leathers Coated with Silk Fibroin-Based Protein Fragments in Apparel and Garment Applications In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article exhibits an improved color retention property. Without being bound by any specific theory, it is postulated that the coating prevents the article from color degradation by separating the fiber or yarn from air or from detergents during washing.

Methods of testing the color retention property of an article are well within the knowledge of one skilled in the art. A specific method of testing of the color retention property of a fabric is described in U.S. Pat. No. 5,142,292, which is incorporated herein by reference in its entirety.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, alpaca fleece, alpaca wool, lama fleece, lama wool, cotton, cashmere, sheep fleece, sheep wool, and combinations thereof, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, and combinations thereof, wherein the article exhibits an improved color retention property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an improved color retention property. In an embodiment, the foregoing color retention property of the fabric is determined after a period of machine washing cycles selected from the group consisting of 5 cycles, 10 cycles, 25 cycles, and 50 cycles.

In an embodiment, a textile or leather of the present disclosure exhibits an improved color retention property. In an embodiment, the foregoing improved color retention property of the textile is determined after a period of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, wherein the silk based proteins or fragments comprise silk and a copolymer, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 5 kDa to about 144 kDa, wherein the silk based proteins or fragments comprise silk and a copolymer, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, alpaca fleece, alpaca wool, lama fleece, lama wool, cotton, cashmere, sheep fleece, sheep wool, and combinations thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, cotton, alpaca fleece, alpaca wool, lama fleece, lama wool, cotton, cashmere, sheep fleece, sheep wool, and combinations thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 5 kDa to about 144 kDa, or about 1 kDa to about 350 kDa, wherein the fiber or yarn is selected from the group consisting of synthetic fiber or yarn, or combinations thereof, wherein the fiber or yarn is natural fiber or yarn selected from the group consisting of polyester, nylon, polyester-polyurethane copolymer, and combinations thereof, wherein the article is resistant to microbial (including bacterial and fungal) growth.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the article is resistant to microbial (including bacterial and fungal) growth. In an embodiment, the foregoing resistant to microbial (including bacterial and fungal) growth property of the fabric is determined after a period of machine washing cycles selected from the group consisting of 5 cycles, 10 cycles, 25 cycles, and 50 cycles.

In an embodiment, a textile or leather of the present disclosure exhibits resistant to microbial (including bacterial and fungal) growth property. In an embodiment, the foregoing resistant to microbial (including bacterial and fungal) growth property of the textile is determined after a period of machine washing cycles selected from the group consisting of 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, alpaca fleece, alpaca wool, lama fleece, lama wool, cotton, cashmere, sheep fleece, sheep wool, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is natural fiber or yarn selected from the group consisting of synthetic fiber or yarn, or combinations thereof, wherein the fiber or yarn is synthetic fiber or yarn selected from the group consisting of polyester, nylon, polyester-polyurethane copolymer, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, wherein the fiber or yarn is selected from the group consisting of cotton, alpaca fleece, alpaca wool, lama fleece, lama wool, cotton, cashmere, sheep fleece, sheep wool, and combinations thereof, wherein the article is resistant to the buildup of static electrical charge.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the article is resistant to the buildup of static electrical charge. In an embodiment, the foregoing resistant to the buildup of static electrical charge property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits resistant to the buildup of static electrical charge property. In an embodiment, the foregoing resistant to the buildup of static electrical charge property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 5 kDa to about 144 kDa, wherein the article is mildew resistant.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, wherein the silk based proteins or fragments thereof are selected from the group consisting of natural silk based proteins or fragments thereof, recombinant silk based proteins or fragments thereof, and combinations thereof, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of cotton, alpaca fleece, alpaca wool, lama fleece, lama wool, cotton, cashmere, sheep fleece, sheep wool, and combinations thereof, wherein the article is mildew resistant.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, and combinations thereof, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is natural fiber or yarn selected from the group consisting of silk, cotton, alpaca fleece, alpaca wool, lama fleece, lama wool, cotton, cashmere, sheep fleece, sheep wool, or wherein the fiber or yarn is synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article is mildew resistant.

In an embodiment, the invention provides an article comprising a fiber or yarn having a coating, wherein the coating comprises silk based proteins or fragments thereof having a weight average molecular weight range of about 1 kDa to about 350 kDa, wherein the article is a fabric, wherein the article is mildew resistant. In an embodiment, the foregoing mildew resistant property of the fabric is determined after a period of machine washing cycles selected from the group consisting of 5 cycles, 10 cycles, 25 cycles, and 50 cycles.

In an embodiment, a textile or leather of the present disclosure exhibits mildew resistant property. In an embodiment, the foregoing mildew resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is natural fiber or yarn selected from the group consisting of natural fiber or yarn, silk, cotton, alpaca fleece, alpaca wool, lama fleece, lama wool, cotton, cashmere, sheep fleece, sheep wool, or synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the coating is transparent.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating is transparent. In an embodiment, the foregoing transparent property of the coating is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather comprises a silk coating of the present disclosure, wherein the silk coating is transparent. In an embodiment, the foregoing transparent property of the coating is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article is resistant to freeze-thaw cycle damage.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is resistant to freeze-thaw cycle damage. In an embodiment, the foregoing resistant to freeze-thaw cycle damage property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits resistant to freeze-thaw cycle damage. In an embodiment, the foregoing resistant to freeze-thaw cycle damage property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the coating provides protection from abrasion.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the coating provides protection from abrasion.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the coating provides protection from abrasion. In an embodiment, the foregoing abrasion resistant property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits abrasion resistant. In an embodiment, the foregoing abrasion resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, or synthetic fiber or yarn selected from the group consisting of polyester, nylon, polyester-polyurethane copolymer, rayon, and combinations thereof, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article exhibits the property of blocking ultraviolet (UV) radiation.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits the property of blocking ultraviolet (UV) radiation. In an embodiment, the foregoing UV blocking property of the fabric is determined after a period of machine washing cycles selected from the group consisting of 5 cycles, 10 cycles, 25 cycles, and 50 cycles.

In an embodiment, a textile or leather of the present disclosure exhibits UV blocking property. In an embodiment, the foregoing UV blocking property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, or synthetic fiber or yarn selected from the group consisting of polyester, nylon, polyester-polyurethane copolymer, rayon, and combinations thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the garment regulates the body temperature of a wearer.

In an embodiment, the invention provides a garment comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the garment regulates the body temperature of a wearer. In an embodiment, the foregoing temperature regulation property of the fabric is determined after a period of machine washing cycles selected from the group consisting of 5 cycles, 10 cycles, 25 cycles, and 50 cycles.

In an embodiment, a textile or leather of the present disclosure exhibits a temperature regulation property. In an embodiment, the foregoing temperature regulation property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, and wherein the article is tear resistant.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, and wherein the article is tear resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, and wherein the article is tear resistant. In an embodiment, the foregoing tear resistant property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits a tear resistant property. In an embodiment, the foregoing tear resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the elasticity of the article is improved.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the elasticity of the article is reduced.

In an embodiment, the invention provides an article comprising a fiber or yarn having a coating, wherein the coating comprises silk based proteins or fragments thereof having a weight average molecular weight range of about 1 kDa to about 350 kDa, wherein the silk based proteins or fragments thereof comprise silk fibroin-based proteins or protein fragments having about 0.01% (w/w) to about 10% (w/w) sericin, wherein the elasticity of the article is improved.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the elasticity of the article is improved.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the elasticity of the article is reduced.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article exhibits a rebound dampening property. Without being bound by any specific theory, it is postulated that the coating prevents the article from returning to the original shape or orientation, and results in the rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the article exhibits a rebound dampening property.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article exhibits a rebound dampening property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits a rebound dampening property. In an embodiment, the foregoing rebound dampening property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits a rebound dampening property. In an embodiment, the foregoing rebound dampening property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the article exhibits an anti-itch property.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article exhibits an anti-itch property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an anti-itch property. In an embodiment, the foregoing anti-itch property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits an anti-itch property. In an embodiment, the foregoing anti-itch property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article exhibits an improved insulation/warmth property.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article exhibits an improved insulation/warmth property. In an embodiment, the foregoing improved insulation/warmth property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits improved an insulation/warmth property. In an embodiment, the foregoing improved insulation/warmth property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments thereof are silkworm silk based proteins or fragments thereof, and the silkworm silk based proteins or fragments thereof is *Bombyx mori* silk based proteins or fragments thereof, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, or synthetic fiber or yarn selected from the group consisting of polyester, nylon, polyester-polyurethane copolymer, rayon, and combinations thereof, wherein the article is wrinkle resistant.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article is wrinkle resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is wrinkle resistant. In an embodiment, the foregoing wrinkle resistant property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits wrinkle resistant property. In an embodiment, the foregoing wrinkle resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, or synthetic fiber or yarn selected from the group consisting of polyester, nylon, polyester-polyurethane copolymer, rayon, and combinations thereof, wherein the article is stain resistant.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article is stain resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is stain resistant. In an embodiment, the foregoing stain resistant property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits stain resistant property. In an embodiment, the foregoing stain resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is sticky. Without being bound to any specific theory, it is postulated that the coating provides stickiness and maintains stickiness.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is sticky.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is sticky.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the article is sticky. In an embodiment, the foregoing sticky property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure exhibits sticky property. In an embodiment, the foregoing sticky property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides an article comprising a textile or leather coated with silk fibroin-based proteins or fragments thereof, wherein the article exhibits improved flame resistance relative to an uncoated textile. In an embodiment, the invention provides an article comprising a textile or leather coated with silk fibroin-based proteins or fragments thereof, wherein the article exhibits equal flame resistance relative to an uncoated textile or leather. In an embodiment, the invention provides an article comprising a textile or leather coated with silk fibroin-based proteins or fragments thereof, wherein the article exhibits equal flame resistance relative to an uncoated textile or leather, wherein an alternative textile or leather coating exhibits reduced flame resistance. In an embodiment, the invention provides an article comprising a textile or leather coated with silk fibroin-based proteins or fragments thereof, wherein the article exhibits improved resistance to fire relative to an uncoated textile or leather, wherein the improved resistance to fire is determined by a flammability test. In an embodiment, the flammability test measures afterflame time, afterglow time, char length, and the observation of fabric melting or dripping.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is flame resistant.

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, wherein the article is flame resistant.

In an embodiment, the invention provides an article comprising a polyester having a coating, wherein the coating comprises silk based proteins or fragments thereof having a weight average molecular weight range of about 1 kDa to about 350 kDa, or about 5 kDa to about 144 kDa, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is a fabric, and wherein the article is flame resistant.

In an embodiment, the invention provides an article comprising a polyester having a coating, wherein the coating comprises silk based proteins or fragments thereof having a weight average molecular weight range of about 1 kDa to about 350 kDa, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof comprise silk fibroin-based proteins or protein fragments having about 0.01% (w/w) to about 10% (w/w) sericin, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, wherein the silk based proteins or fragments thereof are selected from the group consisting of natural silk based proteins or fragments thereof, recombinant silk based proteins or fragments thereof, and combinations thereof, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments thereof are selected from the group consisting of natural silk based proteins or fragments thereof, recombinant silk based proteins or fragments thereof, and combinations thereof, wherein the silk based proteins or fragments thereof are natural silk based proteins or fragments thereof that are selected from the group consisting of spider silk based proteins or fragments thereof, silkworm silk based proteins or fragments thereof, and combinations thereof, wherein the natural silk based proteins or fragments are silkworm silk based proteins or fragments thereof, and the silkworm silk based proteins or fragments thereof is *Bombyx mori* silk based proteins or fragments thereof, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the silk based proteins or fragments comprise silk and a copolymer, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the fiber or yarn is selected from the group consisting of natural fiber or yarn, synthetic fiber or yarn, or combinations thereof, wherein the fiber or yarn is natural fiber or yarn selected from the group consisting of silk, cotton, alpaca fleece, alpaca wool, lama fleece, lama wool, cotton, cashmere, sheep fleece, sheep wool, and combinations thereof, wherein the article is flame resistant.

In an embodiment, the invention provides an article comprising a fiber or yarn having a coating, wherein the coating comprises silk based proteins or fragments thereof having a weight average molecular weight range of about 5 kDa to about 144 kDa, wherein the fiber or yarn is selected from the group consisting of natural fiber or yarn, synthetic fiber or yarn, or combinations thereof, wherein the fiber or yarn is synthetic fiber or yarn selected from the group consisting of polyester, nylon, polyester-polyurethane copolymer, rayon, and combinations thereof, wherein the article is flame resistant.

In an embodiment, the invention provides an article comprising a fiber or yarn having a coating, wherein the coating comprises silk based proteins or fragments thereof having a weight average molecular weight range of about 1 kDa to about 350 kDa, or about 5 kDa to about 144 kDa, wherein the article is a fabric, wherein the fabric is flame resistant. In an embodiment, the foregoing flame resistant property of the fabric is determined after a period of machine washing cycles selected from the group consisting of 1 cycle, 2 cycles, 3 cycles, 4 cycles, 5 cycles, 10 cycles, 25 cycles, and 50 cycles.

In an embodiment, a textile or leather of the present disclosure is flame resistant. In an embodiment, the foregoing flame resistant property of the textile is determined after a period of machine washing cycles selected from the group consisting of 1 cycle, 2 cycles, 3 cycles, 4 cycles, 5 cycles, 10 cycles, 25 cycles, and 50 cycles.

In an embodiment, the invention provides a leather coated with coating, wherein the coating comprises silk based proteins or fragments thereof having a weight average molecular weight range of about 5 kDa to about 144 kDa, wherein the leather exhibits an property selected from the group consisting of an improved color retention property, improved mildew resistance, improved resistance to freeze-thaw cycle damage, improved resistance to abrasion, improved blocking of ultraviolet (UV) radiation, improved regulation of the body temperature of a wearer, improved tear resistance, improved elasticity, improved rebound dampening, improved anti-itch properties, improved insulation, improved wrinkle resistance, improved stain resistance, and improved stickiness. In an embodiment, the invention provides a leather coated with coating, wherein the coating comprises silk based proteins or fragments thereof having a weight average molecular weight range of about 5 kDa to about 144 kDa, wherein the coating is transparent.

In any of the foregoing embodiments, at least one property of the article is improved, wherein the property that is improved is selected from the group consisting of color retention, resistance to microbial growth, resistance to bacterial growth, resistance to fungal growth, resistance to the buildup of static electrical charge, resistance to the growth of mildew, transparency of the coating, resistance to freeze-thaw cycle damage, resistance from abrasion, blocking of ultraviolet (UV) radiation, regulation of the body temperature of a wearer, resistance to tearing, elasticity of the article, rebound dampening, tendency to cause itching in the wearer, thermal insulation of the wearer, wrinkle resistance, stain resistance, stickiness to skin, and flame resistance, and wherein the property is improved by an amount relative to an uncoated article selected from the group consisting of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 125%, at least 150%, at least 200%, at least 300%, at least 400%, and at least 500%.

In any of the foregoing embodiments, the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.0 and about 5.0, or about 1.5 and about 3.0, and optionally wherein the proteins or protein fragments, prior to coating the fabric, do not spontaneously or gradually gelate and do not visibly change in color or turbidity when in a solution for at least 10 days.

Additional Agents for Use with Textiles Coated with Silk Fibroin-Based Protein Fragments In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with a wetting agent. In an embodiment, the wetting agent improves one or more coating properties. Suitable wetting agents are known to those of skill in the art. Exemplary, non-limiting examples of wetting agents from a representative supplier, Lamberti SPA, are given in the following table.

| | |
|---|---|
| Imbitex NDT | Non silicone low foaming with high wetting in both hot or cold conditions, with good detergency and good stability to alkalis. |
| Imbitex TBL | Wetting and de-aerating agent. |
| Imbitex MRC | Wetting and penetrating agent for mercerizing of cotton. |
| Tensolam Na liq. | Low foam, special wetting and dispersing agent for non-woven wet treatments. |
| Imbitex NRW3 | Wetting agent for water-and oil repellent finishing. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with a detergent. In an embodiment, the detergent improves one or more coating properties. Suitable detergents are known to those of skill in the art. Exemplary, non-limiting examples of detergents from a representative supplier, Lamberti SPA, are given in the following table.

| | |
|---|---|
| Biorol CPNN | Wetting and detergent agent with alkaline stability in NaOH up to 10° C. Recommended for continuous scouring, bleaching, and Jigger applications. |
| Biorol JK new | Wetting and detergent agent with extremely low foam properties, recommended for high bath turbulence machine (e.g., jet, overflow, etc.). |
| Biorol OW 60 | General-purpose wetting and detergent agent suitable for desizing, scouring, and bleaching processes. |
| Biorol OWK | Detergent/wetting agent, low foaming, high concentration, recommended for over-flow. Useful for removal of silicone oil on Lycra blends. |
| Cesapon Silk liq. | Specific scouring, de-gumming agent for silk. |
| Cesapon Extra | High detergent power product containing solvent. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with a sequestering or dispersing agent. Suitable sequestering or dispersing agents are known to those of skill in the art. Exemplary, non-limiting examples of sequestering or dispersing agents from a representative supplier, Lamberti SPA, are given in the following table.

| | |
|---|---|
| Lamegal DSP | Dispersing and anti-redepositing agent useful for preparation dyeing and after soaping of dyed and printed materials with reactive and vat dyes. This product is also useful as an anti-olygomer agent in reduction clearing of polyester, dyed or printed with disperse dyes. |
| Chelam TLW/T | Multi-purpose sequestring and dispersing agent for a wide variety of textile processes. No shade variation on dyestuff containing metals. |
| Lamegal TL5 | Multi-purpose sequestring and dispersing agent for a wide variety of textile processes. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with an enzyme. Suitable enzymes are known to those of skill in the art. Exemplary, non-limiting examples of enzymes from a representative supplier, Lamberti SPA, are given in the following table.

| | |
|---|---|
| Lazim HT | Thermo-stable amylase for rapid high temperature desizing. |
| Lazim PE | Specific enzyme for bioscouring; provides optimal wettability, it improves dyeing and color fastness without causing depolimerization and fabric strength loss. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with a bleaching agent. Suitable bleaching agents are known to those of skill in the art. Exemplary, non-limiting examples of bleaching agents from a representative supplier, Lamberti SPA, are given in the following table.

| | |
|---|---|
| Stabilox OTN conc. | Highly concentrated stabilizer for alkaline bleaching with hydrogen peroxide. Suitable for a wide variety of processes. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with an antifoaming agent. Suitable antifoaming agents are known to those of skill in the art. Exemplary, non-limiting examples of antifoaming agents from a representative supplier, Lamberti SPA, are given in the following table.

| | |
|---|---|
| Antifoam SE 47 | General purpose defoaming agent. |
| Defomex JET | Silicone defoamer effective up to 130° C. Recommended for HT and JET dyeing systems. |
| Defomex 2033 | Non-silicone defoamer. |
| Kollasol LOK | Silicone containing mixture of special surface active substances with higher alcohols. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is pretreated with an anti-creasing agent. Suitable anti-creasing agents are known to those of skill in the art. Exemplary, non-limiting examples of anti-creasing agents from a representative supplier, Lamberti SPA, are given in the following table.

| | |
|---|---|
| Lubisol AM | Lubricating and anti-creasing agent for rope wet operation on all kind of fibers and machines. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a dye dispersing agent. Suitable dye dispersing agents are known to those of skill in the art. Exemplary, non-limiting examples of dye dispersing agents from a representative supplier, Lamberti SPA, are given in the following table.

| | |
|---|---|
| Lamegal BO | Liquid dispersing agent (non-ionic), suitable for direct, reactive, disperse dyeing and PES stripping. |
| Lamegal DSP | Dispersing and anti back-staining agent in preparation, dyeing and soaping of dyed and printed materials. Antioligomer agent. |
| Lamegal 619 | Effective low foam dispersing leveling agent for dyeing of PES. |
| Lamegal TL5 | Multi-purpose sequestering and dispersing agent for a variety of textile processes. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a dye leveling agent. Suitable dye leveling agents are known to those of skill in the art. Exemplary, non-limiting examples of dye leveling agents from a representative supplier, Lamberti SPA, are given in the following table.

| | |
|---|---|
| Lamegal A 12 | Leveling agent for dyeing on wool, polyamide and its blends with acid or metal complex dyes. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a dye fixing agent. Suitable dye fixing agents are known to those of skill in the art. Exemplary, non-limiting examples of dye fixing agents from a representative supplier, Lamberti SPA, are given in the following table.

| | |
|---|---|
| Lamfix L | Fixing agent for direct and reactive dyestuffs, containing formaldehyde. |
| Lamfix LU conc. | Formaldehyde free cationic fixing agent for direct and reactive dyes. It does not affect the shade and light fastness. |
| Lamfix PA/TR | Fixing agent to improve the wet fastness of acid dyes on polyamide fabrics, dyed or printed and polyamide yarns. Retarding agent in dyeing of Polyamide/cellulosic blends with direct dyes. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a dye special resin agent. Suitable dye special resin agents are known to those of skill in the art. Exemplary, non-limiting examples of dye special resin agents from a representative supplier, Lamberti SPA, are given in the following table.

| | |
|---|---|
| Denifast TC | Special resin for cationization of cellulose fibers to obtain special effects ("DENIFAST system" and "DENISOL system"). |
| Cobral DD/50 | Special resin for cationization of cellulose fibers to obtain special effect ("DENIFAST system" and "DENISOL system"). |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a dye anti-reducing agent. Suitable dye anti-reducing agents are known to those of skill in the art. Exemplary, non-limiting examples of dye anti-reducing agents from a representative supplier, Lamberti SPA, are given in the following table.

| | |
|---|---|
| Lamberti Redox L2S gra | Anti-reducing agent in grain form. 100% active content. |
| Lamberti Redox L2S liq. | Anti-reducing agent in liquid form for automatic dosage. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a pigment dye system anti-migrating agent. Suitable pigment dye system anti-migrating agents are known to those of skill in the art. Exemplary, non-limiting examples of pigment dye system anti-migrating agents from a representative supplier, Lamberti SPA, are given in the following table.

| | |
|---|---|
| Neopat Compound 96/m conc. | Compound, developed as migration inhibitor for continuous dyeing process with pigments (pad-dry process). |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a pigment dye system binder. Suitable pigment dye system binders are known to those of skill in the art. Exemplary, non-limiting examples of pigment dye system binders from a representative supplier, Lamberti SPA, are given in the following table.

| | |
|---|---|
| Neopat Binder PM/S conc. | Concentrated version of a specific binder used to prepare pad-liquor for dyeing with pigments (pad-dry process). |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a pigment dye system binder and anti-migrating agent combination. Suitable pigment dye system binder and anti-migrating agent combinations are known to those of skill in the art. Exemplary, non-limiting examples of pigment dye system binder and anti-migrating agent combinations from a representative supplier, Lamberti SPA, are given in the following table.

| | |
|---|---|
| Neopat Compound PK1 | Highly concentrated all-in-one product specifically developed as migration inhibitor with specific binder for continuous dyeing process with pigments (pad-dry process). |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is treated with a delave agent. Suitable delave agents are known to those of skill in the art. Exemplary, non-limiting examples of delave agents from a representative supplier, Lamberti SPA, are given in the following table.

| | |
|---|---|
| Neopat compound FTN | Highly concentrated compound of surfactants and polymers specifically developed for pigment dyeing and pigment-reactive dyeing process; especially for medium/dark shades for wash off effect. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is traditionally finished with a wrinkle free treatment. Suitable wrinkle free treatments are known to those of skill in the art. Exemplary, non-limiting examples of wrinkle free treatments from a representative supplier, Lamberti SPA, are given in the following table.

| | |
|---|---|
| Cellofix ULF conc. | Anti-crease modified glyoxalic resin for finishing of cottons, cellulosics and blends with synthetics fibers. |
| Poliflex PO 40 | Polyethilenic resin for waxy, full and slippy handle by foulard applications. |
| Rolflex WF | Aliphatic waterborne Nano-PU dispersion used as extender for wrinkle free treatments. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is traditionally finished with a softener. Suitable softeners are known to those of skill in the art. Exemplary, non-limiting examples of softeners from a representative supplier, Lamberti SPA, are given in the following table.

| | |
|---|---|
| Texamina C/FPN | Cationic softening agent with a very soft handle particularly recommended for application by exhaustion for all kind of fabrics. Suitable also for cone application. |
| Texamina C SAL flakes | 100% cationic softening agent in flakes form for all type of fabrics. Dispersible at room temperature. |
| Texamina CL LIQ. | Anphoteric softening agent for all types of fabrics. Not yellowing. |
| Texamina HVO | Anphoteric softening agent for woven and knitted fabrics of cotton, other cellulosics and blends. Provides a soft, smooth and dry handle. Applied by padding. |
| Texamina SIL | Nonionic silicon dispersion in water. Excellent softening, lubricating and anti-static properties for all fibre types by padding. |

| | |
|---|---|
| Texamina SILK | Special cationic softener with silk protein inside. Provides a "swollen touch" particularly suitable for cellulosic, wool, silk. |
| Lamfinish LW | All-in compound based on special polymeric hydrophilic softeners; by coating, foulard, and exhaustion. |
| Elastolam E50 | General purpose mono-component silicone elastomeric softener for textile finishing. |
| Elastolam EC 100 | Modified polysiloxane micro-emulsion which gives a permanent finishing, with extremely soft and silky handle. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is traditionally finished with a handle modifier. Suitable handle modifiers are known to those of skill in the art. Exemplary, non-limiting examples of handle modifiers from a representative supplier, Lamberti SPA, are given in the following table.

| | |
|---|---|
| Poliflex CSW | Cationic anti-slipping agent. |
| Poliflex R 75 | Parafine finishing agent to give waxy handle. |
| Poliflex s | Compound specifically developed for special writing effects. |
| Poliflex m | Compound for special dry-waxy handle. |
| Lamsoft SW 24 | Compound for special slippy handle specifically developed for coating application. |
| Lamfinish SLIPPY | All-in-one compound to get a slippy touch; by coating. |
| Lamfinish GUMMY | All-in-one compound to get a gummy touch; by coating. |
| Lamfinish OLDRY | All-in-one compound to get dry-sandy touch especially suitable for vintage effects; by coating. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is traditionally finished with a waterborne polyurethane (PU) dispersion. Suitable waterborne polyurethane dispersions for traditional finishing are known to those of skill in the art. Exemplary, non-limiting examples of waterborne polyurethane dispersions for traditional finishing from a representative supplier, Lamberti SPA, are given in the following table.

| | |
|---|---|
| Rolflex LB 2 | Aliphatic waterborne PU dispersion particularly suggested for the formulation of textile coatings where bright and rigid top finish is required. It is particularly suitable as a finishing agent for organza touch on silk fabrics. Transparent and shiny. |
| Rolflex HP 51 | Aliphatic waterborne PU dispersion particularly suggested for the formulation of textile coatings for outwear, luggage, technical articles especially where hard and flexible touch is required. Transparent and shiny. |
| Rolflex PU 879 | Aliphatic waterborne PU dispersion particularly suggested for the formulation of textile coatings for outwear, luggage, technical articles where a medium-hard and flexible touch is required. |
| Rolflex ALM | Aliphatic waterborne PU dispersion particularly suggested for the formulation of textile coatings for outwear, luggage, technical articles where a soft and flexible touch is required. Can be also suitable for printing application. |
| Rolflex AP | Aliphatic waterborne PU dispersion particularly suggested for the formulation of textile coatings for outwear, fashion where a soft and gummy touch is required. |
| Rolflex W4 | Aliphatic waterborne PU dispersion particularly suggested for the formulation of textile coatings for clothing, outwear where a full, soft and non sticky touch is required. |
| Rolflex ZB7 | Aliphatic waterborne PU dispersion particularly suggested for the formulation of textile coatings for clothing, outwear, sportswear, fashion and technical articles for industrial applications. The product has a very high charge digestion properties, electrolytes stability and excellent mechanical and tear resistance. Can be also suitable for foam coating and printing application. |
| Rolflex BZ 78 | Aliphatic waterborne PU dispersion particularly suggested for the formulation of textile coatings for clothing, outwear, sportswear, fashion and technical articles for industrial applications. The product has an excellent hydrolysis resistance, a very high charge digestion and electrolytes stability and an excellent mechanical and tear resistance. Can be also suitable for foam coating and printing application. |
| Rolflex K 110 | Gives to the coated fabric a full, soft, and slightly sticky handle with excellent fastness on all types of fabrics. |
| Rolflex OP 80 | Aliphatic waterborne PU dispersion particularly suggested for the formulation of textile coatings for outwear, luggage and fashion finishes where an opaque non writing effect is desired. |
| Rolflex NBC | Aliphatic waterborne PU dispersion generally used by padding application as a filling and zero formaldehyde sizing agent. Can be used for outwear and fashion finishing where a full, elastic and non-sticky touch is required. |
| Rolflex PAD | Aliphatic waterborne PU dispersion specifically designed for padding application for outwear, sportswear and fashion applications where a full, elastic and non sticky touch is required. Excellent washing and dry cleaning fastness as well as good bath stability. |

| | |
|---|---|
| Rolflex PN | Aliphatic waterborne PU dispersion generally applied by padding application for outerwear and fashion high quality applications where strong, elastic non sticky finishes are required. |
| Elafix PV 4 | Aliphatic blocked isocyanate nano-dispersion used in order to give anti-felting and anti-pilling properties to pure wool fabrics and his blend. |
| Rolflex SW3 | Aliphatic waterborne PU dispersion particularly suggested to be used by padding application for the finishing of outwear, sportswear and fashion where a slippery and elastic touch is required. It is also a good anti-pilling agent. Excellent in wool application. |
| Rolflex C 86 | Aliphatic cationic waterborne PU dispersion particularly suggested for the formulation of textile coatings for clothing, outwear, fashion where medium-soft and pleasant full touch is required. Fabrics treated with the product can be dyed with a selection of dyes, to get double-color effects of different intensity. |
| Rolflex CN 29 | Aliphatic cationic waterborne PU dispersion particularly suggested for the formulation of textile coatings for clothing, outwear, fashion where soft and pleasant full touch is required. Fabrics treated with the product can be dyed with a selection of dyes, to get double-color effects of different intensity. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is traditionally finished with a finishing resin. Suitable finishing resins are known to those of skill in the art. Exemplary, non-limiting examples of finishing resins from a representative supplier, Lamberti SPA, are given in the following table.

| | |
|---|---|
| Textol 110 | Handle modifier with very soft handle for coating finishes |
| Textol RGD | Water emulsion of acrylic copolymer for textile coating, with very rigid handle. |
| Textol SB 21 | Butadienic resin for finishing and binder for textile printing |
| Appretto PV/CC | Vinylacetate water dispersion for rigid stiffening |
| Amisolo B | CMS water dispersion for textile finishing as stiffening agent |
| Lamovil RP | PVOH stabilized solution as stiffening agent |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is technically finished with a waterborne polyurethane dispersion. Suitable waterborne polyurethane dispersions for technical finishing are known to those of skill in the art. Exemplary, non-limiting examples of waterborne polyurethane dispersions for technical finishing from a representative supplier, Lamberti SPA, are given in the following table.

| | |
|---|---|
| Rolflex AFP | Aliphatic polyether polyurethane dispersion in water. The product has high hydrolysis resistance, good breaking load resistance and excellent tear resistance. |
| Rolflex ACF | Aliphatic polycarbonate polyurethane dispersion in water. The product shows good PU and PVC bonding properties, excellent abrasion resistance as well as chemical resistance, included alcohol. |
| Rolflex V 13 | Aliphatic polyether/acrylic copolymer polyurethane dispersion in water. The product has good thermoadhesive properties and good adhesion properties on PVC. |
| Rolflex K 80 | Aliphatic polyether/acrylic copolymer polyurethane dispersion in water. ROLFLEX K 80 is specifically designed as a high performing adhesive for textile lamination. The product has excellent perchloroethylene and water fastness. |
| Rolflex ABC | Aliphatic polyether polyurethane dispersion in water. Particularly, the product presents very high water column, excellent electrolyte resistance, high LOI index, high resistance to multiple bending. |
| Rolflex ADH | Aliphatic polyether polyurethane dispersion in water. The product has a very high water column resistance. |
| Rolflex W4 | Aliphatic waterborne PU dispersion particularly suggested for the formulation of textile coatings for clothing, outwear where a full, soft and non-sticky touch is required. |
| Rolflex ZB7 | Aliphatic waterborne PU dispersion particularly suggested for the formulation of textile coatings for clothing, outwear, sportswear, fashion and technical articles for industrial |

| | |
|---|---|
| | applications. The product has a very high charge digestion properties, electrolytes stability and excellent mechanical and tear resistance. Can be also suitable for foam coating and printing application. |
| Rolflex BZ 78 | Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application. |
| Rolflex PU 147 | Aliphatic polyether polyurethane dispersion in water. This product shows good film forming properties at room temperature. It has high fastness to light and ultraviolet radiation and good resistance to water, solvent and chemical agents, as well as mechanical resistance. |
| Rolflex SG | Aliphatic polyether polyurethane dispersion in water. Due to its thermoplastic properties it is suggested to formulate heat activated adhesives at low temperatures. |
| Elafix PV 4 | Aliphatic blocked isocyanate nano-dispersion used in order to give antifelting and antipilling properties to pure wool fabrics and his blend. |
| Rolflex C 86 | Aliphatic cationic waterborne PU dispersion particularly suggested for the formulation of textile coatings for clothing, outwear, fashion where medium-soft and pleasant full touch is required. Fabrics treated with the product can be dyed with a selection of dyes, to get double-color effects of different intensity. |
| Rolflex CN 29 | Aliphatic cationic waterborne PU dispersion particularly suggested for the formulation of textile coatings for clothing, outwear, fashion where soft and pleasant full touch is required. Fabrics treated with the product can be dyed with a selection of dyes, to get double-color effects of different intensity. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is technically finished with an oil or water repellant. Suitable oil or water repellants for technical finishing are known to those of skill in the art. Exemplary, non-limiting examples of oil or water repellants for technical finishing from a representative supplier, Lamberti SPA, are given in the following table.

| | |
|---|---|
| Lamgard FT 60 | General purpose fluorocarbon resin for water and oil repellency; by padding application. |
| Lamgard 48 | High performance fluorocarbon resin for water and oil repellency; by padding application. High rubbing fastness. |
| Imbitex NRW3 | Wetting agent for water-and oil repellent finishing. |
| Lamgard EXT | Crosslinker for fluorocarbon resins to improve washing fastness. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is technically finished with a flame retardant. Suitable flame retardants for technical finishing are known to those of skill in the art. Exemplary, non-limiting examples of flame retardants for technical finishing from a representative supplier, Lamberti SPA, are given in the following table.

| | |
|---|---|
| Piroflam 712 | Non-permanent flame retardant compound for padding and spray application. |
| Piroflam ECO | Alogen free flame retardant compound for back coating application for all kind of fibers. |
| Piroflam UBC | Flame retardant compound for back coating application for all kind of fibers. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is technically finished with a crosslinker. Suitable crosslinkers for technical finishing are known to those of skill in the art. Exemplary, non-limiting examples of crosslinkers for technical finishing from a representative supplier, Lamberti SPA, are given in the following table.

| | |
|---|---|
| Rolflex BK8 | Aromatic blocked polyisocyanate in water dispersion. It is suggested as a cross-linking agent in coating pastes based of polyurethane resins to improve washing fastness. |
| Fissativo 05 | Water dispersible aliphatic polyisocyanate suitable as crosslinking agent for acrylic and polyurethane dispersions to improve adhesion and wet and dry scrub resistance. |
| Resina MEL | Melammine-formaldheyde resin. |
| Cellofix VLF | Low formaldheyde malammine resin. |

In an embodiment, the invention provides an article comprising a fiber or yarn having a coating, wherein the coating comprises silk based proteins or fragments thereof having a weight average molecular weight range of about 5 kDa to about 144 kDa, wherein the article is a fabric, and wherein the fabric is technically finished with a thickener for technical finishing. Suitable thickeners for technical finishing are known to those of skill in the art. Exemplary, non-limiting examples of thickeners for technical finishing from a representative supplier, Lamberti SPA, are given in the following table.

| | |
|---|---|
| Lambicol CL 60 | Fully neutralised synthetic thickener for pigment printing in oil/water emulsion; medium viscosity type |
| Viscolam PU conc. | Nonionic polyurethane based thickener with pseudoplastic behavior. |
| Viscolam 115 new | Acrylic thickener; not neutralised. |
| Viscolam PS 202 | Nonionic polyurethane based thickener with newtonian behavior. |
| Viscolam 1022 | Nonionic polyurethane based thickener with moderate pseudoplastic behavior. |

In any of the foregoing textile or leather embodiments, the coating comprises silk based proteins or fragments thereof having a weight average molecular weight range of about 5 kDa to about 144 kDa. In any of the foregoing textile or leather embodiments, the coating comprises silk based proteins or fragments thereof having a weight average molecular weight range of about 6 kDa to about 17 kDa. In any of the foregoing textile or leather embodiments, the coating comprises silk based proteins or fragments thereof having a weight average molecular weight range of about 17 kDa to about 39 kDa. In any of the foregoing textile or leather embodiments, the coating comprises silk based proteins or fragments thereof having a weight average molecular weight range of about 39 kDa to about 80 kDa.

In any of the foregoing textile or leather embodiments, the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and optionally wherein the proteins or protein fragments, prior to coating the fabric, do not spontaneously or gradually gelate and do not visibly change in color or turbidity when in a solution for at least 10 days.

Other Materials Coated with Silk Fibroin-Based Protein Fragments

In an embodiment, the invention provides a material coated with silk fibroin-based proteins or fragments thereof. The material may be any material suitable for coating, including plastics (e.g., vinyl), foams (e.g., for use in padding and cushioning), and various natural or synthetic products.

In an embodiment, the invention provides an automobile component coated with silk fibroin-based proteins or fragments thereof having a weight average molecular weight range of about 5 kDa to about 144 kDa. In an embodiment, the invention provides an automobile component coated with silk fibroin-based proteins or fragments thereof having a weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and optionally wherein the proteins or protein fragments, prior to coating the fabric, do not spontaneously or gradually gelate and do not visibly change in color or turbidity when in a solution for at least 10 days. In an embodiment, the invention provides an automobile component coated with silk fibroin-based proteins or fragments thereof, wherein the automobile component exhibits an improved property relative to an uncoated automobile component. In an embodiment, the invention provides an automobile component coated with silk fibroin-based proteins or fragments thereof, wherein the automobile component exhibits an improved property relative to an uncoated automobile component, and wherein the automobile component is selected from the group consisting of an upholstery fabric, a headliner, a seat, a headrest, a transmission control, a floor mat, a carpet fabric, a dashboard, a steering wheel, a trim, a wiring harness, an airbag cover, an airbag, a sunvisor, a seat belt, a headrest, an armrest, and a children's car seat. In an embodiment, the invention provides an electrical component insulated with a coating comprising silk fibroin-based proteins or fragments thereof.

In an embodiment, the invention provides a foam coated with silk fibroin-based proteins or fragments thereof having a weight average molecular weight range of about 5 kDa to about 144 kDa. In an embodiment, the invention provides a foam coated with silk fibroin-based proteins or fragments thereof having a weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and optionally wherein the proteins or protein fragments, prior to coating the fabric, do not spontaneously or gradually gelate and do not visibly change in color or turbidity when in a solution for at least 10 days. In an embodiment, the invention provides a foam coated with silk fibroin-based proteins or fragments thereof, wherein the foam exhibits an improved property relative to an uncoated foam, and wherein the foam is selected from the group consisting of a polyurethane foam, an ethylene-vinyl acetate copolymer foam, a low density polyethylene foam, a low density polyethylene foam, a high density polyethylene foam, a polypropylene copolymer foam, a linear low density polyethylene foam, a natural rubber foam, a latex foam, and combinations thereof.

In any of the foregoing embodiments, the material coating comprises silk based proteins or fragments thereof having a weight average molecular weight range of about 5 kDa to about 144 kDa. In any of the foregoing embodiments, the material coating comprises silk based proteins or fragments thereof having a weight average molecular weight range of about 6 kDa to about 17 kDa. In any of the foregoing embodiments, the material coating comprises silk based proteins or fragments thereof having a weight average molecular weight range of about 17 kDa to about 39 kDa. In any of the foregoing embodiments, the material coating comprises silk based proteins or fragments thereof having a weight average molecular weight range of about 39 kDa to about 80 kDa.

In any of the foregoing embodiments, the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and wherein the proteins or protein fragments, prior to coating the fabric, do not spontaneously or gradually gelate and do not visibly change in color or turbidity when in a solution for at least 10 days.

Processes for Coating Textiles and Leathers with Silk Fibroin-Based Protein Fragments In an embodiment, a method for silk coating a textile, leather, or other material (such as a foam) includes immersion of the textile, leather, or other material in any of the aqueous solutions of pure silk fibroin-based protein fragments of the present disclosure. In an embodiment, a method for coating a textile, leather, or other material (such as a foam) includes spraying. In an embodiment, a method for coating a textile, leather, or other material (such as a foam) includes chemical vapor deposition. In an embodiment, a method for silk coating a textile, leather, or other material (such as a foam) includes electrochemical coating. In an embodiment, a method for silk coating a textile, leather, or other material (such as a foam) includes knife coating to spread any of the aqueous solutions of pure silk fibroin-based protein fragments of the present disclosure onto the fabric. The coated article may then be air dried, dried under heat/air flow, or cross-linked to the fabric surface. In an embodiment, a drying process includes curing with additives, irradiation (e.g., using UV light), heat (e.g., microwave or radiofrequency irradiation), and/or drying at ambient condition. In an embodiment, the invention provides a method of coating a textile, leather, or other material (such as a foam) comprising the step of applying a coating, wherein the coating comprises a solution of silk based proteins or fragments thereof having a weight average molecular weight range of about 1 kDa to about 350 kDa, or about 5 kDa to about 144 kDa, wherein the coating is applied to at least one side of the textile, leather, or other material using a method selected from the group consisting of a bath coating process, a spray coating process, a stencil (i.e., screen) process, a silk-foam based process, a roller-based process, a magnetic roller process, a knife process, a transfer process, a foam process, a lacquering process, a supercritical fluid impregnation process, and a printing process.

In an embodiment, the invention provides a method of coating a textile or leather comprising a step selected from the group consisting of providing an unwinding device used to unroll the fabric supply in a roll configuration, providing a feeding system used to control the feed rate of fabric, providing a material compensator used to maintain consistent the fabric tension, providing a coating machine to apply the silk solution (i.e., silk fibroin-based protein fragments) in different state (liquid or foam) to the fabric, providing a measuring system used to control the amount of silk solution applied, providing a dryer used to cure or dry the silk solution on the fabric, providing a cooling station used to bring the fabric temperature close to room value, providing a steering frame used to guide the fabric to the rewinding device and maintain straight edges, providing a rewinding step used to collect the coated fabric in roll, providing UV irradiation for curing of silk and/or other fabric additives (e.g., in a chemical cross-linking step), providing radiofrequency (RF) irradiation (e.g., using microwave irradiation) for drying and chemical cross-linking, and combinations thereof. Chemical and enzymatic cross-linking steps suitable for use with the compositions, articles, and methods of the invention include any method known to those of skill in the art, including but not limited to N-hydroxysuccinimide ester crosslinking, imidoester crosslinking, carbodiimide crosslinking, dicyclohexyl carbodiimide crosslinking, maleimide crosslinking, haloacetyl crosslinking, pyridyl disulfide crosslinking, hydrazide crosslinking, alkoxyamine crosslinking, reductive amination crosslink, aryl azide crosslinking, diazirine crosslinking, azide-phosphine crosslinking, transferase crosslinking, hydrolase crosslinking, transglutaminase crosslinking, peptidase crosslinking (e.g., sortase SrtA from *Staphylococcus aureus*), oxidoreductase crosslinking, tyrosinase crosslinking, laccase crosslinking, peroxidase crosslinking (e.g., horseradish peroxidase), lysyl oxidase crosslinking, and combinations thereof.

In an embodiment, the invention provides a method of coating a textile or leather comprising the step of applying a coating, wherein the coating comprises a solution of silk based proteins or fragments thereof having a weight average molecular weight range of about 1 kDa to about 350 kDa, or about 5 kDa to about 144 kDa, and wherein the coating is applied to at least one side of the textile or leather using a supercritical fluid impregnation process. The supercritical fluid impregnation process may use $CO_2$ as the supercritical fluid to solubilize and impregnate silk based proteins or fragments thereof into a textile or leather, wherein the supercritical $CO_2$ may include optional organic modifiers known in the art (e.g., methanol) and may further include additional agents described herein, such as dyes.

In an embodiment, the invention provides a method of coating a textile or leather comprising the step of applying a coating, wherein the coating comprises a solution of silk based proteins or fragments thereof having a weight average molecular weight range of about 1 kDa to about 350 kDa, or about 5 kDa to about 144 kDa, using a handheld aerosol spray suitable for consumer use or an aerosol spray system suitable for use by a professional cleaner (e.g., a dry cleaner).

In an embodiment, the invention provides a method of coating a textile or leather comprising the step of applying a coating, wherein the coating comprises a solution of silk based proteins or fragments thereof having a weight average molecular weight range of about 1 kDa to about 350 kDa, or about 5 kDa to about 144 kDa, using a home washing machine.

In an embodiment, the invention provides a method of coating a fabric comprising the steps of:
(a) applying a pretreatment selected from the group consisting of a wetting agent, a detergent, a sequestering or dispersing agent, an enzyme, a bleaching agent, an antifoaming agent, an anti-creasing agent, a dye dispersing agent, a dye leveling agent, a dye fixing agent, a dye special resin agent, a dye anti-reducing agent, a pigment dye system anti-migrating agent, a pigment dye system binder, a delave agent, a wrinkle free treatment, a softener, a handle modifier, a waterborne polyurethane dispersion, a finishing resin, an oil or water repellant, a flame retardant, a crosslinker, a thickener for technical finishing, or any combination thereof;
(b) applying a coating comprising a solution of silk based proteins or fragments thereof having a weight average molecular weight range of about 1 kDa to about 350 kDa, or about 5 kDa to about 144 kDa, using a spray, screen, or stencil coating process; and
(c) drying and optionally curing the coating.

In any of the foregoing embodiments of methods, the silk based proteins or protein fragments thereof may have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.0 and about 5.0, or about 1.5 and about 3.0, and optionally wherein the proteins or protein fragments, prior to coating the fabric, do not spontaneously or gradually gelate and do not visibly change in color or turbidity when in a solution for at least 10 days.

Additives for Silk Fibroin-Based Protein Fragments and Solutions Thereof

In an embodiment, a solution of the present disclosure is contacted with an additive, such as a therapeutic agent and/or a molecule. In an embodiment, molecules include, but are not limited to, antioxidants and enzymes. In an embodiment, molecules include, but are not limited to, ceramics, ceramic particles, metals, metal particles, polymer particles, aldehydes, luminescent molecules, phosphorescent molecules, fluorescent molecules, inorganic particles, organic particles, selenium, ubiquinone derivatives, thiol-based antioxidants, saccharide-containing antioxidants, polyphenols, botanical extracts, caffeic acid, apigenin, pycnogenol, resveratrol, folic acid, vitamin B12, vitamin B6, vitamin B3, vitamin E, vitamin C and derivatives thereof, vitamin D, vitamin A, astaxathin, Lutein, lycopene, essential fatty acids (omegas 3 and 6), iron, zinc, magnesium, flavonoids (soy, Curcumin, Silymarin, Pycnongeol), growth factors, aloe, hyaluronic acid, extracellular matrix proteins, cells, nucleic acids, biomarkers, biological reagents, zinc oxide, benzoyl peroxide, retinoids, titanium, allergens in a known dose (for sensitization treatment), essential oils including, but not limited to, lemongrass or rosemary oil, and fragrances. Therapeutic agents include, but are not limited to, small molecules, drugs, proteins, peptides and nucleic acids. In an embodiment, a solution of the present disclosure is contacted with an allergen of known quantity prior to forming the article. Allergens include but are not limited to milk, eggs, peanuts, tree nuts, fish, shellfish, soy and wheat. Known doses of allergen loaded within a silk article can be released at a known rate for controlled exposure allergy study, tests and sensitization treatment.

In an embodiment, silk fibroin-based protein fragments and solutions thereof may be combined with other soluble and insoluble additives coated onto textiles and leather as described herein, wherein the silk fibroin-based protein fragments and solutions functions as a binder or a dispersion medium for the additives. Additives described herein and those known of ordinary skill in the art for use with coating textiles and leather may be used. The combinations of silk fibroin-based protein fragments and solutions thereof with other soluble and insoluble additives may exhibit improved properties as described herein. The property that is improved may be selected from the group consisting of color retention, resistance to microbial growth, resistance to bacterial growth, resistance to fungal growth, resistance to the buildup of static electrical charge, resistance to the growth of mildew, transparency of the coating, resistance to freeze-thaw cycle damage, resistance from abrasion, blocking of ultraviolet (UV) radiation, regulation of the body temperature of a wearer, resistance to tearing, elasticity of the article, rebound dampening, tendency to cause itching in the wearer, thermal insulation of the wearer, wrinkle resistance, stain resistance, stickiness to skin, flame resistance, and combinations thereof. For example, silk fibroin-based protein fragments and solutions thereof may be combined with insoluble ceramic particles as a suspension, and subsequently coated onto a textile using any of the methods described herein to provide further thermal insulation for the wearer and/or to provide improved flame resistance, or to provide other improved properties.

In an embodiment, a solution of the present disclosure is used to create an article with microneedles by standard methods known to one in the art for controlled delivery of molecules or therapeutic agents to or through the skin.

Processes for Production of Silk Fibroin-Based Protein Fragments and Solutions Thereof As used herein, the term "fibroin" includes silkworm fibroin and insect or spider silk protein. In an embodiment, fibroin is obtained from *Bombyx mori*. In an embodiment, the spider silk protein is selected from the group consisting of swathing silk (Achniform gland silk), egg sac silk (Cylindriform gland silk), egg case silk (Tubuliform silk), non-sticky dragline silk (Ampullate gland silk), attaching thread silk (Pyriform gland silk), sticky silk core fibers (Flagelliform gland silk), and sticky silk outer fibers (Aggregate gland silk).

A silk fragment-water solution of the present disclosure can be sterilized following standard methods in the art not limited to filtration, heat, radiation or e-beam. It is anticipated that the silk protein fragment mixture, because of its shorter protein polymer length, will withstand sterilization better than intact silk protein solutions described in the art. Additionally, silk articles created from the SPF mixtures described herein may be sterilized as appropriate to application.

In an embodiment, the above-described SPF mixture solutions may be utilized to coat at least a portion of a fabric which can be used to create a textile. In an embodiment, the above-described SPF mixture solutions may be weaved into yarn that can be used as a fabric in a textile.

Methods and processes for making silk fibroin-based protein fragments and solutions thereof are generally described by U.S. Pat. Nos. 9,187,538, 9,522,107, 9,517,191, 9,522,108, 9,511,012, and 9,545,369, U.S. Patent Application Publications Nos. 20160022559, 20150094269, 20160222579, and 20160281294, and International Patent Application Publications Nos. WO 2015048805 and WO 2016090055, the entirety of each are incorporated herein by reference. Briefly, heat-treated or non-heat-treated silk worm cocoons, silk fibers, silk powder, or spider silk can be used as the silk source. If starting from raw silk cocoons from *Bombyx mori*, the cocoons can be cut into small pieces. The raw silk is then extracted and rinsed to remove any sericin, which results in substantially sericin free raw silk. In an embodiment, water is heated, and a salt is added, for example a carbonate. The raw silk is added to the boiling water/salt, and submerged for a period of time. In some embodiments, boiling for a longer time results in smaller silk protein fragments. Subsequently, the solution is drained, and excess water/salt is removed from the silk fibroin fibers (e.g., ring out the fibroin extract by hand, spin cycle using a machine, etc.). The resulting silk fibroin extract is rinsed with warm to hot water to remove any remaining adsorbed sericin or contaminate. The resulting silk fibroin extract is a substantially sericin-depleted silk fibroin. In some embodiments, it may be advantageous to agitate, turn or circulate the rinse water to maximize the rinse effect. After rinsing, excess water is removed from the extracted silk fibroin fibers (e.g., ring out fibroin extract by hand or using a machine). Alternatively, methods known to one skilled in the art such as pressure, temperature, or other reagents or combinations thereof may be used for the purpose of sericin extraction. The extracted fibroin fibers are then allowed to dry. Once dry, the extracted silk fibroin is dissolved using a solvent added to the silk fibroin at a temperature between ambient and boiling. In an embodiment, the solvent is a solution of a different salt. Alternatively, the extracted fibroin fibers are not dried but wet and placed in the solvent; solvent concentration can then be varied to achieve similar concentrations as to when adding dried silk to the solvent. Complete dissolution of the extracted fibroin fibers can be achieved by varying the treatment time and temperature along with the concentration of dissolving solvent. To ensure complete dissolution, the silk fibers should be fully immersed within the already heated solvent solution and then maintained at various temperatures. The temperature at which the silk fibroin extract is added to the salt solution (or vice versa) has an effect on the time required to completely dissolve the fibroin and on the resulting molecular weight and polydispersity of the final SPF mixture solution. In addition, agitation during introduction or dissolution may be used to facilitate dissolution at varying temperatures and concentrations. Alternatively, whole cocoons may be placed directly into a solvent, bypassing extraction. This requires subsequent filtration of silk worm particles from the silk and solvent solution and sericin removal using methods know in the art for separating hydrophobic and hydrophilic proteins such as a column separation and/or chromatography, ion exchange, chemical precipitation with salt and/or pH, and or enzymatic digestion and filtration or extraction, all methods are common examples and without limitation for standard protein separation methods. Non-heat treated cocoons with the silkworm removed, may alternatively be placed into a solvent, bypassing extraction. The methods described above may be used for sericin separation, with the advantage that non-heat treated cocoons will contain significantly less worm debris. Dialysis may be used to remove the dissolution solvent from the resulting dissolved fibroin protein fragment solution by dialyzing the solution against a volume of water. Pre-filtration prior to dialysis is helpful to remove any debris (i.e., silk worm remnants) from the silk and salt solution. The result of dissolution at the desired time and temperate filtration is a generally translucent particle-free room temperature shelf-stable silk protein fragment-salt solution. After dialysis, the final silk solution maybe further filtered to remove any remaining debris (i.e., silk worm remnants). Alternatively, Tangential Flow Filtration (TFF), which is a rapid and efficient method for the separation and purification of biomolecules, may be used to remove the solvent from the resulting dissolved fibroin solution. TFF offers a highly pure aqueous silk protein fragment solution and enables scalability of the process in order to produce large volumes of the solution in a controlled and repeatable manner.

Following are non-limiting examples of suitable ranges for various parameters in and for preparation of the silk solutions of the present disclosure. The silk solutions of the present disclosure may include one or more, but not necessarily all, of these parameters and may be prepared using various combinations of ranges of such parameters.

In an embodiment, the percent silk in the solution is less than 30%. In an embodiment, the percent silk in the solution is less than 25%. In an embodiment, the percent silk in the solution is less than 20%. In an embodiment, the percent silk in the solution is less than 19%. In an embodiment, the percent silk in the solution is less than 18%. In an embodiment, the percent silk in the solution is less than 17%. In an embodiment, the percent silk in the solution is less than 16%. In an embodiment, the percent silk in the solution is less than 15%. In an embodiment, the percent silk in the solution is less than 14%. In an embodiment, the percent silk in the solution is less than 13%. In an embodiment, the percent silk in the solution is less than 12%. In an embodiment, the percent silk in the solution is less than 11%. In an embodiment, the percent silk in the solution is less than 10%. In an embodiment, the percent silk in the solution is less than 9%. In an embodiment, the percent silk in the solution is less than 8%. In an embodiment, the percent silk in the solution is less than 7%. In an embodiment, the percent silk in the solution is less than 6%. In an embodiment, the percent silk in the solution is less than 5%. In an embodiment, the percent silk in the solution is less than 4%. In an embodiment, the percent silk in the solution is less than 3%. In an embodiment, the percent silk in the solution is less than 2%. In an embodiment, the percent silk in the solution is less than 1%. In an embodiment, the percent silk in the solution is less than 0.9%. In an embodiment, the percent silk in the solution is less than 0.8%. In an embodiment, the percent silk in the solution is less than 0.7%. In an embodiment, the percent silk in the solution is less than 0.6%. In an embodiment, the percent silk in the solution is less than 0.5%. In an embodiment, the percent silk in the solution is less than 0.4%. In an embodiment, the percent silk in the solution is less than 0.3%. In an embodiment, the percent silk in the solution is less than 0.2%. In an embodiment, the percent silk in the solution is less than 0.1%. In an embodiment, the percent silk in the solution is greater than 0.1%. In an embodiment, the percent silk in the solution is greater than 0.2%. In an embodiment, the percent silk in the solution is greater than 0.3%. In an embodiment, the percent silk in the solution is greater than 0.4%. In an embodiment, the percent silk in the solution is greater than 0.5%. In an embodiment, the percent silk in the solution is greater than 0.6%. In an embodiment, the percent silk in the solution is greater than 0.7%. In an embodiment, the percent silk in the solution is greater than 0.8%. In an embodiment, the percent silk in the solution is greater than 0.9%. In an embodiment, the percent silk in the solution is greater than 1%. In an embodiment, the percent silk in the solution is greater than 2%. In an embodiment, the percent silk in the solution is greater than 3%. In an embodiment, the percent silk in the solution is greater than 4%. In an embodiment, the percent silk in the solution is greater than 5%. In an embodiment, the percent silk in the solution is greater than 6%. In an embodiment, the percent silk in the solution is greater than 7%. In an embodiment, the percent silk in the solution is greater than 8%. In an embodiment, the percent silk in the solution is greater than 9%. In an embodiment, the percent silk in the solution is greater than 10%. In an embodiment, the percent silk in the solution is greater than 11%. In an embodiment, the percent silk in the solution is greater than 12%. In an embodiment, the percent silk in the solution is greater than 13%. In an embodiment, the percent silk in the solution is greater than 14%. In an embodiment, the percent silk in the solution is greater than 15%. In an embodiment, the percent silk in the solution is greater than 16%. In an embodiment, the percent silk in the solution is greater than 17%. In an embodiment, the percent silk in the solution is greater than 18%. In an embodiment, the percent silk in the solution is greater than 19%. In an embodiment, the percent silk in the solution is greater than 20%. In an embodiment, the percent silk in the solution is greater than 25%. In an embodiment, the percent silk in the solution is between 0.1% and 30%. In an embodiment, the percent silk in the solution is between 0.1% and 25%. In an embodiment, the percent silk in the solution is between 0.1% and 20%. In an embodiment, the percent silk in the solution is between 0.1% and 15%. In an embodiment, the percent silk in the solution is between 0.1% and 10%. In an embodiment, the percent silk in the solution is between 0.1% and 9%. In an embodiment, the percent silk in the solution is between 0.1% and 8%. In an embodiment, the percent silk in the solution is between 0.1% and 7%. In an embodiment, the percent silk in the solution is between 0.1% and 6.5%. In an embodiment, the percent silk in the solution is between 0.1% and 6%. In an embodiment, the percent silk in the solution is between 0.1% and 5.5%. In an embodiment, the percent silk in the solution is between 0.1% and 5%. In an embodiment, the percent silk in the solution is between 0.1% and 4.5%. In an embodiment, the percent silk in the solution is between 0.1% and 4%. In an embodiment, the percent silk in the solution is between 0.1% and 3.5%. In an embodiment, the percent silk in the solution is between 0.1% and 3%. In an embodiment, the percent silk in the solution is between 0.1% and 2.5%. In an embodiment, the percent silk in the solution is between 0.1% and 2.0%. In an embodiment, the percent silk in the solution is between 0.1% and 2.4%. In an embodiment, the percent silk in the solution is between 0.5% and 5%. In an embodiment, the percent silk in the solution is between 0.5% and 4.5%. In an embodiment, the percent silk in the solution is between 0.5% and 4%. In an embodiment, the percent silk in the solution is between 0.5% and 3.5%. In an embodiment, the percent silk in the solution is between 0.5% and 3%. In an embodiment, the percent silk in the solution is between 0.5% and 2.5%. In an embodiment, the percent silk in the solution is between 1 and 4%. In an embodiment, the percent silk in the solution is between 1 and 3.5%. In an embodiment, the percent silk in the solution is between 1 and 3%. In an embodiment, the percent silk in the solution is between 1 and 2.5%. In an embodiment, the percent silk in the solution is between 1 and 2.4%. In an embodiment, the percent silk in the solution is between 1 and 2%. In an embodiment, the percent silk in the solution is between 20% and 30%. In an embodiment, the percent silk in the solution is between 0.1% and 6%. In an embodiment, the percent silk in the solution is between 6% and 10%. In an embodiment, the percent silk in the solution is between 6% and 8%. In an embodiment, the percent silk in the solution is between 6% and 9%. In an embodiment, the percent silk in the solution is between 10% and 20%. In an embodiment, the percent silk in the solution is between 11% and 19%. In an embodiment, the percent silk in the solution is between 12% and 18%. In an embodiment, the percent silk in the solution is between 13% and 17%. In an embodiment, the percent silk in the solution is between 14% and 16%. In an embodiment, the percent silk in the solution is 2.4%. In an embodiment, the percent silk in the solution is 2.0%.

In an embodiment, the percent sericin in the solution is non-detectable to 30%. In an embodiment, the percent sericin in the solution is non-detectable to 5%. In an embodiment, the percent sericin in the solution is 1%. In an embodiment, the percent sericin in the solution is 2%. In an embodiment, the percent sericin in the solution is 3%. In an embodiment, the percent sericin in the solution is 4%. In an embodiment, the percent sericin in the solution is 5%. In an embodiment, the percent sericin in the solution is 10%. In an embodiment, the percent sericin in the solution is 30%.

In an embodiment, the stability of the LiBr-silk fragment solution is 0 to 1 year. In an embodiment, the stability of the LiBr-silk fragment solution is 0 to 2 years. In an embodiment, the stability of the LiBr-silk fragment solution is 0 to 3 years. In an embodiment, the stability of the LiBr-silk fragment solution is 0 to 4 years. In an embodiment, the stability of the LiBr-silk fragment solution is 0 to 5 years. In an embodiment, the stability of the LiBr-silk fragment solution is 1 to 2 years. In an embodiment, the stability of the LiBr-silk fragment solution is 1 to 3 years. In an embodiment, the stability of the LiBr-silk fragment solution is 1 to 4 years. In an embodiment, the stability of the LiBr-silk fragment solution is 1 to 5 years. In an embodiment, the stability of the LiBr-silk fragment solution is 2 to 3 years. In an embodiment, the stability of the LiBr-silk fragment solution is 2 to 4 years. In an embodiment, the stability of the LiBr-silk fragment solution is 2 to 5 years. In an embodiment, the stability of the LiBr-silk fragment solution is 3 to 4 years. In an embodiment, the stability of the LiBr-silk fragment solution is 3 to 5 years. In an embodiment, the stability of the LiBr-silk fragment solution is 4 to 5 years.

In an embodiment, the stability of a composition of the present disclosure is 10 days to 6 months. In an embodiment, the stability of a composition of the present disclosure is 6 months to 12 months. In an embodiment, the stability of a composition of the present disclosure is 12 months to 18 months. In an embodiment, the stability of a composition of the present disclosure is 18 months to 24 months. In an embodiment, the stability of a composition of the present disclosure is 24 months to 30 months. In an embodiment, the stability of a composition of the present disclosure is 30 months to 36 months. In an embodiment, the stability of a composition of the present disclosure is 36 months to 48 months. In an embodiment, the stability of a composition of the present disclosure is 48 months to 60 months.

In an embodiment, a composition of the present disclosure includes pure silk fibroin-based protein fragments having an average weight average molecular weight ranging from 5 kDa to 144 kDa. In an embodiment, a composition of the present disclosure includes pure silk fibroin-based protein fragments having an average weight average molecular weight ranging from 6 kDa to 17 kDa. In an embodiment, a composition of the present disclosure includes pure silk fibroin-based protein fragments having an average weight average molecular weight ranging from 17 kDa to 39 kDa. In an embodiment, a composition of the present disclosure includes pure silk fibroin-based protein fragments having an average weight average molecular weight ranging from 39 kDa to 80 kDa. In an embodiment, a composition of the present disclosure includes pure silk fibroin-based protein fragments having an average weight average molecular weight ranging from 39 kDa to 144 kDa.

In an embodiment, a composition of the present disclosure includes pure silk fibroin-based protein fragments having an average weight average molecular weight of about 1 kDa to about 350 kDa, or about 1 kDa to about 300 kDa, or about 1 kDa to about 250 kDa, or about 1 kDa to about 200 kDa, or about 1 kDa to about 150 kDa, or about 1 kDa to about 100 kDa, or about 1 kDa to about 50 kDa, or about 1 kDa to about 25 kDa.

In an embodiment, a composition of the present disclosure includes pure silk fibroin-based protein fragments having an average weight average molecular weight ranging from 1 to 5 kDa. In an embodiment, a composition of the present disclosure includes pure silk fibroin-based protein fragments having an average weight average molecular weight ranging from 5 to 10 kDa. In an embodiment, a composition of the present disclosure includes pure silk fibroin-based protein fragments having an average weight average molecular weight ranging from 10 to 15 kDa. In an embodiment, a composition of the present disclosure includes pure silk fibroin-based protein fragments having an average weight average molecular weight ranging from 15 to 20 kDa. In an embodiment, a composition of the present disclosure includes pure silk fibroin-based protein fragments having an average weight average molecular weight ranging from 20 to 25 kDa. In an embodiment, a composition of the present disclosure includes pure silk fibroin-based protein fragments having an average weight average molecular weight ranging from 25 to 30 kDa. In an embodiment, a composition of the present disclosure includes pure silk fibroin-based protein fragments having an average weight average molecular weight ranging from 30 to 35 kDa. In an embodiment, a composition of the present disclosure includes pure silk fibroin-based protein fragments having an average weight average molecular weight ranging from 35 to 40 kDa. In an embodiment, a composition of the present disclosure includes pure silk fibroin-based protein fragments having an average weight average molecular weight ranging from 40 to 45 kDa. In an embodiment, a composition of the present disclosure includes pure silk fibroin-based protein fragments having an average weight average molecular weight ranging from 45 to 50 kDa. In an embodiment, a composition of the present disclosure includes pure silk fibroin-based protein fragments having an average weight average molecular weight ranging from 50 to 55 kDa. In an embodiment, a composition of the present disclosure includes pure silk fibroin-based protein fragments having an average weight average molecular weight ranging from 55 to 60 kDa. In an embodiment, a composition of the present disclosure includes pure silk fibroin-based protein fragments having an average weight average molecular weight ranging from 60 to 65 kDa. In an embodiment, a composition of the present disclosure includes pure silk fibroin-based protein fragments having an average weight average molecular weight ranging from 65 to 70 kDa. In an embodiment, a composition of the present disclosure includes pure silk fibroin-based protein fragments having an average weight average molecular weight ranging from 70 to 75 kDa. In an embodiment, a composition of the present disclosure includes pure silk fibroin-based protein fragments having an average weight average molecular weight ranging from 75 to 80 kDa. In an embodiment, a composition of the present disclosure includes pure silk fibroin-based protein fragments having an average weight average molecular weight ranging from 80 to 85 kDa. In an embodiment, a composition of the present disclosure includes pure silk fibroin-based protein fragments having an average weight average molecular weight ranging from 85 to 90 kDa. In an embodiment, a composition of the present disclosure includes pure silk fibroin-based protein fragments having an average weight average molecular weight ranging from 90 to 95 kDa. In an embodiment, a composition of the present disclosure includes pure silk fibroin-based protein fragments having an average weight average molecular weight ranging from 95 to 100 kDa. In an embodiment, a composition of the present disclosure includes pure silk fibroin-based protein fragments having an average weight average molecular weight ranging from 100 to 105 kDa. In an embodiment, a composition of the present disclosure includes pure silk fibroin-based protein fragments having an average weight average molecular weight ranging from 105 to 110 kDa. In an embodiment, a composition of the present disclosure includes pure silk fibroin-based protein fragments having an average weight average molecular weight ranging from 110 to 115 kDa. In an embodiment, a composition of the present disclosure includes pure silk fibroin-based protein fragments having an average weight average molecular weight ranging from 115 to 120 kDa. In an embodiment, a composition of the present disclosure includes pure silk fibroin-based protein fragments having an average weight average molecular weight ranging from 120 to 125 kDa. In an embodiment, a composition of the present disclosure includes pure silk fibroin-based protein fragments having an average weight average molecular weight ranging from 125 to 130 kDa. In an embodiment, a composition of the present disclosure includes pure silk fibroin-based protein fragments having an average weight average molecular weight ranging from 130 to 135 kDa. In an embodiment, a composition of the present disclosure includes pure silk fibroin-based protein fragments having an average weight average molecular weight ranging from 135 to 140 kDa. In an embodiment, a composition of the present disclosure includes pure silk fibroin-based protein fragments having an average weight average molecular weight ranging from 140 to 145 kDa. In an embodiment, a composition of the present disclosure includes pure silk fibroin-based protein fragments having an average weight average molecular weight ranging from 145 to 150 kDa. In an embodiment, a composition of the present disclosure includes pure silk fibroin-based protein fragments having an average weight average molecular weight ranging from 150 to 155 kDa. In an embodiment, a composition of the present disclosure includes pure silk fibroin-based protein fragments having an average weight average molecular weight ranging from 155 to 160 kDa. In an embodiment, a composition of the present disclosure includes pure silk fibroin-based protein fragments having an average weight average molecular weight ranging from 160 to 165 kDa. I In an embodiment, a composition of the present disclosure includes pure silk fibroin-based protein fragments having an average weight average molecular weight ranging from 165 to 170 kDa. In an embodiment, a composition of the present disclosure includes pure silk fibroin-based protein fragments having an average weight average molecular weight ranging from 170 to 175 kDa. In an embodiment, a composition of the present disclosure includes pure silk fibroin-based protein fragments having an average weight average molecular weight ranging from 175 to 180 kDa. In an embodiment, a composition of the present disclosure includes pure silk fibroin-based protein fragments having an average weight average molecular weight ranging from 180 to 185 kDa. In an embodiment, a composition of the present disclosure includes pure silk fibroin-based protein fragments having an average weight average molecular weight ranging from 185 to 190 kDa. In an embodiment, a composition of the present disclosure includes pure silk fibroin-based protein fragments having an average weight average molecular weight ranging from 190 to 195 kDa. In an embodiment, a composition of the present disclosure includes pure silk fibroin-based protein fragments having an average weight average molecular weight ranging from 195 to 200 kDa. In an embodiment, a composition of the present disclosure includes pure silk fibroin-based protein fragments having an average weight average molecular weight ranging from 200 to 205 kDa. In an embodiment, a composition of the present disclosure includes pure silk fibroin-based protein fragments having an average weight average molecular weight ranging from 205 to 210 kDa. In an embodiment, a composition of the present disclosure includes pure silk fibroin-based protein fragments having an average weight average molecular weight ranging from 210 to 215 kDa. In an embodiment, a composition of the present disclosure includes pure silk fibroin-based protein fragments having an average weight average molecular weight ranging from 215 to 220 kDa. In an embodiment, a composition of the present disclosure includes pure silk fibroin-based protein fragments having an average weight average molecular weight ranging from 220 to 225 kDa. In an embodiment, a composition of the present disclosure includes pure silk fibroin-based protein fragments having an average weight average molecular weight ranging from 225 to 230 kDa. In an embodiment, a composition of the present disclosure includes pure silk fibroin-based protein fragments having an average weight average molecular weight ranging from 230 to 235 kDa. In an embodiment, a composition of the present disclosure includes pure silk fibroin-based protein fragments having an average weight average molecular weight ranging from 235 to 240 kDa. In an embodiment, a composition of the present disclosure includes pure silk fibroin-based protein fragments having an average weight average molecular weight ranging from 240 to 245 kDa. In an embodiment, a composition of the present disclosure includes pure silk fibroin-based protein fragments having an average weight average molecular weight ranging from 245 to 250 kDa. In an embodiment, a composition of the present disclosure includes pure silk fibroin-based protein fragments having an average weight average molecular weight ranging from 250 to 255 kDa. In an embodiment, a composition of the present disclosure includes pure silk fibroin-based protein fragments having an average weight average molecular weight ranging from 255 to 260 kDa. In an embodiment, a composition of the present disclosure includes pure silk fibroin-based protein fragments having an average weight average molecular weight ranging from 260 to 265 kDa. In an embodiment, a composition of the present disclosure includes pure silk fibroin-based protein fragments having an average weight average molecular weight ranging from 265 to 270 kDa. In an embodiment, a composition of the present disclosure includes pure silk fibroin-based protein fragments having an average weight average molecular weight ranging from 270 to 275 kDa. In an embodiment, a composition of the present disclosure includes pure silk fibroin-based protein fragments having an average weight average molecular weight ranging from 275 to 280 kDa. In an embodiment, a composition of the present disclosure includes pure silk fibroin-based protein fragments having an average weight average molecular weight ranging from 280 to 285 kDa. In an embodiment, a composition of the present disclosure includes pure silk fibroin-based protein fragments having an average weight average molecular weight ranging from 285 to 290 kDa. In an embodiment, a composition of the present disclosure includes pure silk fibroin-based protein fragments having an average weight average molecular weight ranging from 290 to 295 kDa. In an embodiment, a composition of the present disclosure includes pure silk fibroin-based protein fragments having an average weight average molecular weight ranging from 295 to 300 kDa. In an embodiment, a composition of the present disclosure includes pure silk fibroin-based protein fragments having an average weight average molecular weight ranging from 300 to 305 kDa. In an embodiment, a composition of the present disclosure includes pure silk fibroin-based protein fragments having an average weight average molecular weight ranging from 305 to 310 kDa. In an embodiment, a composition of the present disclosure includes pure silk fibroin-based protein fragments having an average weight average molecular weight ranging from 310 to 315 kDa. In an embodiment, a composition of the present disclosure includes pure silk fibroin-based protein fragments having an average weight average molecular weight ranging from 315 to 320 kDa. In an embodiment, a composition of the present disclosure includes pure silk fibroin-based protein fragments having an average weight average molecular weight ranging from 320 to 325 kDa. In an embodiment, a composition of the present disclosure includes pure silk fibroin-based protein fragments having an average weight average molecular weight ranging from 325 to 330 kDa. In an embodiment, a composition of the present disclosure includes pure silk fibroin-based protein fragments having an average weight average molecular weight ranging from 330 to 335 kDa. In an embodiment, a composition of the present disclosure includes pure silk fibroin-based protein fragments having an average weight average molecular weight ranging from 335 to 340 kDa. In an embodiment, a composition of the present disclosure includes pure silk fibroin-based protein fragments having an average weight average molecular weight ranging from 340 to 345 kDa. In an embodiment, a composition of the present disclosure includes pure silk fibroin-based protein fragments having an average weight average molecular weight ranging from 345 to 350 kDa.

In an embodiment, a composition of the present disclosure includes silk protein fragments having an average weight average molecular weight ranging from 5 kDa to 144 kDa. In an embodiment, a composition of the present disclosure includes silk protein fragments having an average weight average molecular weight ranging from 6 kDa to 17 kDa. In an embodiment, a composition of the present disclosure includes silk protein fragments having an average weight average molecular weight ranging from 17 kDa to 39 kDa. In an embodiment, a composition of the present disclosure includes silk protein fragments having an average weight average molecular weight ranging from 39 kDa to 80 kDa.

In an embodiment, a composition of the present disclosure includes silk protein fragments having an average weight average molecular weight of about 1 kDa to about 350 kDa, or about 1 kDa to about 300 kDa, or about 1 kDa to about 250 kDa, or about 1 kDa to about 200 kDa, or about 1 kDa to about 150 kDa, or about 1 kDa to about 100 kDa, or about 1 kDa to about 50 kDa, or about 1 kDa to about 25 kDa.

In an embodiment, a composition of the present disclosure includes silk protein fragments having a weight average molecular weight ranging from 5 kDa to 144 kDa. In an embodiment, a composition of the present disclosure includes silk protein fragments having a weight average molecular weight ranging from 6 kDa to 17 kDa. In an embodiment, a composition of the present disclosure includes silk protein fragments having a weight average molecular weight ranging from 17 kDa to 39 kDa. In an embodiment, a composition of the present disclosure includes silk protein fragments having a weight average molecular weight ranging from 39 kDa to 80 kDa.

In an embodiment, a composition of the present disclosure includes silk protein fragments having a weight average molecular weight of about 1 kDa to about 350 kDa, or about 1 kDa to about 300 kDa, or about 1 kDa to about 250 kDa, or about 1 kDa to about 200 kDa, or about 1 kDa to about 150 kDa, or about 1 kDa to about 100 kDa, or about 1 kDa to about 50 kDa, or about 1 kDa to about 25 kDa.

In an embodiment, a composition of the present disclosure includes silk protein fragments having an average weight average molecular weight ranging from 1 to 5 kDa. In an embodiment, a composition of the present disclosure includes silk protein fragments having an average weight average molecular weight ranging from 5 to 10 kDa. In an embodiment, a composition of the present disclosure includes silk protein fragments having an average weight average molecular weight ranging from 10 to 15 kDa. In an embodiment, a composition of the present disclosure includes silk protein fragments having an average weight average molecular weight ranging from 15 to 20 kDa. In an embodiment, a composition of the present disclosure includes silk protein fragments having an average weight average molecular weight ranging from 20 to 25 kDa. In an embodiment, a composition of the present disclosure includes silk protein fragments having an average weight average molecular weight ranging from 25 to 30 kDa. In an embodiment, a composition of the present disclosure includes silk protein fragments having an average weight average molecular weight ranging from 30 to 35 kDa. In an embodiment, a composition of the present disclosure includes silk protein fragments having an average weight average molecular weight ranging from 35 to 40 kDa. In an embodiment, a composition of the present disclosure includes silk protein fragments having an average weight average molecular weight ranging from 40 to 45 kDa. In an embodiment, a composition of the present disclosure includes silk protein fragments having an average weight average molecular weight ranging from 45 to 50 kDa. In an embodiment, a composition of the present disclosure includes silk protein fragments having an average weight average molecular weight ranging from 50 to 55 kDa. In an embodiment, a composition of the present disclosure includes silk protein fragments having an average weight average molecular weight ranging from 55 to 60 kDa. In an embodiment, a composition of the present disclosure includes silk protein fragments having an average weight average molecular weight ranging from 60 to 65 kDa. In an embodiment, a composition of the present disclosure includes silk protein fragments having an average weight average molecular weight ranging from 65 to 70 kDa. In an embodiment, a composition of the present disclosure includes silk protein fragments having an average weight average molecular weight ranging from 70 to 75 kDa. In an embodiment, a composition of the present disclosure includes silk protein fragments having an average weight average molecular weight ranging from 75 to 80 kDa. In an embodiment, a composition of the present disclosure includes silk protein fragments having an average weight average molecular weight ranging from 80 to 85 kDa. In an embodiment, a composition of the present disclosure includes silk protein fragments having an average weight average molecular weight ranging from 85 to 90 kDa. In an embodiment, a composition of the present disclosure includes silk protein fragments having an average weight average molecular weight ranging from 90 to 95 kDa. In an embodiment, a composition of the present disclosure includes silk protein fragments having an average weight average molecular weight ranging from 95 to 100 kDa. In an embodiment, a composition of the present disclosure includes silk protein fragments having an average weight average molecular weight ranging from 100 to 105 kDa. In an embodiment, a composition of the present disclosure includes silk protein fragments having an average weight average molecular weight ranging from 105 to 110 kDa. In an embodiment, a composition of the present disclosure includes silk protein fragments having an average weight average molecular weight ranging from 110 to 115 kDa. In an embodiment, a composition of the present disclosure includes silk protein fragments having an average weight average molecular weight ranging from 115 to 120 kDa. In an embodiment, a composition of the present disclosure includes silk protein fragments having an average weight average molecular weight ranging from 120 to 125 kDa. In an embodiment, a composition of the present disclosure includes silk protein fragments having an average weight average molecular weight ranging from 125 to 130 kDa. In an embodiment, a composition of the present disclosure includes silk protein fragments having an average weight average molecular weight ranging from 130 to 135 kDa. In an embodiment, a composition of the present disclosure includes silk protein fragments having an average weight average molecular weight ranging from 135 to 140 kDa. In an embodiment, a composition of the present disclosure includes silk protein fragments having an average weight average molecular weight ranging from 140 to 145 kDa. In an embodiment, a composition of the present disclosure includes silk protein fragments having an average weight average molecular weight ranging from 145 to 150 kDa. In an embodiment, a composition of the present disclosure includes silk protein fragments having an average weight average molecular weight ranging from 150 to 155 kDa. In an embodiment, a composition of the present disclosure includes silk protein fragments having an average weight average molecular weight ranging from 155 to 160 kDa. In an embodiment, a composition of the present disclosure includes silk protein fragments having an average weight average molecular weight ranging from 160 to 165 kDa. I In an embodiment, a composition of the present disclosure includes silk protein fragments having an average weight average molecular weight ranging from 165 to 170 kDa. In an embodiment, a composition of the present disclosure includes silk protein fragments having an average weight average molecular weight ranging from 170 to 175 kDa. In an embodiment, a composition of the present disclosure includes silk protein fragments having an average weight average molecular weight ranging from 175 to 180 kDa. In an embodiment, a composition of the present disclosure includes silk protein fragments having an average weight average molecular weight ranging from 180 to 185 kDa. In an embodiment, a composition of the present disclosure includes silk protein fragments having an average weight average molecular weight ranging from 185 to 190 kDa. In an embodiment, a composition of the present disclosure includes silk protein fragments having an average weight average molecular weight ranging from 190 to 195 kDa. In an embodiment, a composition of the present disclosure includes silk protein fragments having an average weight average molecular weight ranging from 195 to 200 kDa. In an embodiment, a composition of the present disclosure includes silk protein fragments having an average weight average molecular weight ranging from 200 to 205 kDa. In an embodiment, a composition of the present disclosure includes silk protein fragments having an average weight average molecular weight ranging from 205 to 210 kDa. In an embodiment, a composition of the present disclosure includes silk protein fragments having an average weight average molecular weight ranging from 210 to 215 kDa. In an embodiment, a composition of the present disclosure includes silk protein fragments having an average weight average molecular weight ranging from 215 to 220 kDa. In an embodiment, a composition of the present disclosure includes silk protein fragments having an average weight average molecular weight ranging from 220 to 225 kDa. In an embodiment, a composition of the present disclosure includes silk protein fragments having an average weight average molecular weight ranging from 225 to 230 kDa. In an embodiment, a composition of the present disclosure includes silk protein fragments having an average weight average molecular weight ranging from 230 to 235 kDa. In an embodiment, a composition of the present disclosure includes silk protein fragments having an average weight average molecular weight ranging from 235 to 240 kDa. In an embodiment, a composition of the present disclosure includes silk protein fragments having an average weight average molecular weight ranging from 240 to 245 kDa. In an embodiment, a composition of the present disclosure includes silk protein fragments having an average weight average molecular weight ranging from 245 to 250 kDa. In an embodiment, a composition of the present disclosure includes silk protein fragments having an average weight average molecular weight ranging from 250 to 255 kDa. In an embodiment, a composition of the present disclosure includes silk protein fragments having an average weight average molecular weight ranging from 255 to 260 kDa. In an embodiment, a composition of the present disclosure includes silk protein fragments having an average weight average molecular weight ranging from 260 to 265 kDa. In an embodiment, a composition of the present disclosure includes silk protein fragments having an average weight average molecular weight ranging from 265 to 270 kDa. In an embodiment, a composition of the present disclosure includes silk protein fragments having an average weight average molecular weight ranging from 270 to 275 kDa. In an embodiment, a composition of the present disclosure includes silk protein fragments having an average weight average molecular weight ranging from 275 to 280 kDa. In an embodiment, a composition of the present disclosure includes silk protein fragments having an average weight average molecular weight ranging from 280 to 285 kDa. In an embodiment, a composition of the present disclosure includes silk protein fragments having an average weight average molecular weight ranging from 285 to 290 kDa. In an embodiment, a composition of the present disclosure includes silk protein fragments having an average weight average molecular weight ranging from 290 to 295 kDa. In an embodiment, a composition of the present disclosure includes silk protein fragments having an average weight average molecular weight ranging from 295 to 300 kDa. In an embodiment, a composition of the present disclosure includes silk protein fragments having an average weight average molecular weight ranging from 300 to 305 kDa. In an embodiment, a composition of the present disclosure includes silk protein fragments having an average weight average molecular weight ranging from 305 to 310 kDa. In an embodiment, a composition of the present disclosure includes silk protein fragments having an average weight average molecular weight ranging from 310 to 315 kDa. In an embodiment, a composition of the present disclosure includes silk protein fragments having an average weight average molecular weight ranging from 315 to 320 kDa. In an embodiment, a composition of the present disclosure includes silk protein fragments having an average weight average molecular weight ranging from 320 to 325 kDa. In an embodiment, a composition of the present disclosure includes silk protein fragments having an average weight average molecular weight ranging from 325 to 330 kDa. In an embodiment, a composition of the present disclosure includes silk protein fragments having an average weight average molecular weight ranging from 330 to 335 kDa. In an embodiment, a composition of the present disclosure includes silk protein fragments having an average weight average molecular weight ranging from 35 to 340 kDa. In an embodiment, a composition of the present disclosure includes silk protein fragments having an average weight average molecular weight ranging from 340 to 345 kDa. In an embodiment, a composition of the present disclosure includes silk protein fragments having an average weight average molecular weight ranging from 345 to 350 kDa.

In an embodiment, a composition of the present disclosure includes silk fibroin-based protein fragments having one or more of low molecular weight, medium molecular weight, and high molecular weight. In an embodiment, a composition of the present disclosure includes silk fibroin-based protein fragments having low molecular weight and silk fibroin-based protein fragments having medium molecular weight. In an embodiment, a composition of the present disclosure includes silk fibroin-based protein fragments having low molecular weight and silk fibroin-based protein fragments having high molecular weight. In an embodiment, a composition of the present disclosure includes silk fibroin-based protein fragments having medium molecular weight and silk fibroin-based protein fragments having high molecular weight. In an embodiment, a composition of the present disclosure includes silk fibroin-based protein fragments having low molecular weight, silk fibroin-based protein fragments having medium molecular weight, and silk fibroin-based protein fragments having high molecular weight.

In an embodiment, a composition of the present disclosure includes silk fibroin-based protein fragments having low molecular weight and silk fibroin-based protein fragments having medium molecular weight. In some embodiments, the w/w ratio between low molecular weight silk fibroin-based protein fragments and medium molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk fibroin-based protein fragments and medium molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk fibroin-based protein fragments and medium molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. In an embodiment, the w/w ratio between low molecular weight silk fibroin-based protein fragments and medium molecular weight silk fibroin-based protein fragments is about 3:1. In an embodiment, the w/w ratio between low molecular weight silk fibroin-based protein fragments and medium molecular weight silk fibroin-based protein fragments is about 1:3.

In an embodiment, a composition of the present disclosure includes silk fibroin-based protein fragments having low molecular weight and silk fibroin-based protein fragments having high molecular weight. In some embodiments, the w/w ratio between low molecular weight silk fibroin-based protein fragments and high molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk fibroin-based protein fragments and high molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk fibroin-based protein fragments and high molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, a composition of the present disclosure includes silk fibroin-based protein fragments having medium molecular weight and silk fibroin-based protein fragments having high molecular weight. In some embodiments, the w/w ratio between medium molecular weight silk fibroin-based protein fragments and high molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between medium molecular weight silk fibroin-based protein fragments and high molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between medium molecular weight silk fibroin-based protein fragments and high molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, a composition of the present disclosure includes silk fibroin-based protein fragments having low molecular weight, silk fibroin-based protein fragments having medium molecular weight, and silk fibroin-based protein fragments having high molecular weight. In an embodiment, the w/w ratio between low molecular weight silk fibroin-based protein fragments, medium molecular weight silk fibroin-based protein fragments, and high molecular weight silk fibroin-based protein fragments is about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1. In an embodiment, the w/w ratio between low molecular weight silk fibroin-based protein fragments, medium molecular weight silk fibroin-based protein fragments, and high molecular weight silk fibroin-based protein fragments is about 3:0.1:0.9, about 3:0.2:0.8, about 3:0.3:0.7, about 3:0.4:0.6, about 3:0.5:0.5, about 3:0.6:0.4, about 3:0.7:0.3, about 3:0.8:0.2, or about 3:0.9:0.1.

In some embodiments, the silk compositions provided herein may be applied as mixtures to an article to be coated or in stepwise processes to form coating layers on the article. For example, a silk composition that includes low molecular weight silk and medium molecular weight silk may be applied to an article to be coated. Alternatively, a low molecular weight silk composition may be applied to an article to be coated, as provided by the processes described herein, and then a medium or high molecular weight silk may then be applied to the article. The low, medium, and high molecular weight silk compositions may be added in any order or any combination (e.g., low/med, low/high, med/high, low/med/high).

In some embodiments, where multiple layers of silk compositions are applied to an article to be coated, they may have at least one layer, or 1 layer to 1 million layers, or 1 layer to 100,000 layers, or 1 layer to 10,000 layers, or 1 layer to 1,000 layers of such silk compositions, wherein the layers may have the same or different thicknesses. For example, in some embodiments, the layers may have a thickness of from about 1 nm to about 1 mm, or about 1 nm to about 1 μm, or about 1 nm to about 500 nm, or about 1 nm to about 400 nm, or about 1 nm to about 300 nm, or about 1 nm to about 200 nm, or about 1 nm to about 100 nm, or about 1 nm to about 75 nm, or about 1 nm to about 50 nm, or about 1 nm to about 25 nm, or about 1 nm to about 20 nm, or about 1 nm to about 15 nm, or about 1 nm to about 10 nm, or about 1 nm to about 5 nm.

In an embodiment, a composition of the present disclosure having pure silk fibroin-based protein fragments has a polydispersity ranging from about 1 to about 5.0. In an embodiment, a composition of the present disclosure having pure silk fibroin-based protein fragments has a polydispersity ranging from about 1.5 to about 3.0. In an embodiment, a composition of the present disclosure having pure silk fibroin-based protein fragments has a polydispersity ranging from about 1 to about 1.5. In an embodiment, a composition of the present disclosure having pure silk fibroin-based protein fragments has a polydispersity ranging from about 1.5 to about 2.0. In an embodiment, a composition of the present disclosure having pure silk fibroin-based protein fragments has a polydispersity ranging from about 2.0 to about 2.5. In an embodiment, a composition of the present disclosure having pure silk fibroin-based protein fragments, has a polydispersity ranging from about 2.0 to about 3.0. In an embodiment, a composition of the present disclosure having pure silk fibroin-based protein fragments, has a polydispersity ranging from about 2.5 to about 3.0.

In an embodiment, a composition of the present disclosure having silk protein fragments has a polydispersity ranging from about 1 to about 5.0. In an embodiment, a composition of the present disclosure having silk protein fragments has a polydispersity ranging from about 1.5 to about 3.0. In an embodiment, a composition of the present disclosure having silk protein fragments has a polydispersity ranging from about 1 to about 1.5. In an embodiment, a composition of the present disclosure having silk protein fragments has a polydispersity ranging from about 1.5 to about 2.0. In an embodiment, a composition of the present disclosure having silk protein fragments has a polydispersity ranging from about 2.0 to about 2.5. In an embodiment, a composition of the present disclosure having silk protein fragments, has a polydispersity ranging from about is 2.0 to about 3.0. In an embodiment, a composition of the present disclosure having silk protein fragments, has a polydispersity ranging from about is 2.5 to about 3.0.

In some embodiments the polydispersity of low molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments the polydispersity of medium molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments the polydispersity of high molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments, in compositions described herein having combinations of low, medium, and/or high molecular weight silk protein fragments, such low, medium, and/or high molecular weight silk proteins may have the same or different polydispersities.

In an embodiment, a composition of the present disclosure having pure silk fibroin-based protein fragments has non-detectable levels of LiBr residuals. In an embodiment, the amount of the LiBr residuals in a composition of the present disclosure is between 10 ppm and 1000 ppm. In an embodiment, the amount of the LiBr residuals in a composition of the present disclosure is between 10 ppm and 300 ppm. In an embodiment, the amount of the LiBr residuals in a composition of the present disclosure is less than 25 ppm. In an embodiment, the amount of the LiBr residuals in a composition of the present disclosure is less than 50 ppm. In an embodiment, the amount of the LiBr residuals in a composition of the present disclosure is less than 75 ppm. In an embodiment, the amount of the LiBr residuals in a composition of the present disclosure is less than 100 ppm. In an embodiment, the amount of the LiBr residuals in a composition of the present disclosure is less than 200 ppm. In an embodiment, the amount of the LiBr residuals in a composition of the present disclosure is less than 300 ppm. In an embodiment, the amount of the LiBr residuals in a composition of the present disclosure is less than 400 ppm. In an embodiment, the amount of the LiBr residuals in a composition of the present disclosure is less than 500 ppm. In an embodiment, the amount of the LiBr residuals in a composition of the present disclosure is less than 600 ppm. In an embodiment, the amount of the LiBr residuals in a composition of the present disclosure is less than 700 ppm. In an embodiment, the amount of the LiBr residuals in a composition of the present disclosure is less than 800 ppm. In an embodiment, the amount of the LiBr residuals in a composition of the present disclosure is less than 900 ppm. In an embodiment, the amount of the LiBr residuals in a composition of the present disclosure is less than 1000 ppm. In an embodiment, the amount of the LiBr residuals in a composition of the present disclosure is non-detectable to 500 ppm. In an embodiment, the amount of the LiBr residuals in a composition of the present disclosure is non-detectable to 450 ppm. In an embodiment, the amount of the LiBr residuals in a composition of the present disclosure is non-detectable to 400 ppm. In an embodiment, the amount of the LiBr residuals in a composition of the present disclosure is non-detectable to 350 ppm. In an embodiment, the amount of the LiBr residuals in a composition of the present disclosure is non-detectable to 300 ppm. In an embodiment, the amount of the LiBr residuals in a composition of the present disclosure is non-detectable to 250 ppm. In an embodiment, the amount of the LiBr residuals in a composition of the present disclosure is non-detectable to 200 ppm. In an embodiment, the amount of the LiBr residuals in a composition of the present disclosure is non-detectable to 150 ppm. In an embodiment, the amount of the LiBr residuals in a composition of the present disclosure is non-detectable to 100 ppm. In an embodiment, the amount of the LiBr residuals in a composition of the present disclosure is 100 ppm to 200 ppm. In an embodiment, the amount of the LiBr residuals in a composition of the present disclosure is 200 ppm to 300 ppm. In an embodiment, the amount of the LiBr residuals in a composition of the present disclosure is 300 ppm to 400 ppm. In an embodiment, the amount of the LiBr residuals in a composition of the present disclosure is 400 ppm to 500 ppm.

In an embodiment, a composition of the present disclosure having pure silk fibroin-based protein fragments, has non-detectable levels of $Na_2CO_3$ residuals. In an embodiment, the amount of the $Na_2CO_3$ residuals in a composition of the present disclosure is less than 100 ppm. In an embodiment, the amount of the $Na_2CO_3$ residuals in a composition of the present disclosure is less than 200 ppm. In an embodiment, the amount of the $Na_2CO_3$ residuals in a composition of the present disclosure is less than 300 ppm. In an embodiment, the amount of the $Na_2CO_3$ residuals in a composition of the present disclosure is less than 400 ppm. In an embodiment, the amount of the $Na_2CO_3$ residuals in a composition of the present disclosure is less than 500 ppm. In an embodiment, the amount of the $Na_2CO_3$ residuals in a composition of the present disclosure is less than 600 ppm. In an embodiment, the amount of the $Na_2CO_3$ residuals in a composition of the present disclosure is less than 700 ppm. In an embodiment, the amount of the $Na_2CO_3$ residuals in a composition of the present disclosure is less than 800 ppm. In an embodiment, the amount of the $Na_2CO_3$ residuals in a composition of the present disclosure is less than 900 ppm. In an embodiment, the amount of the $Na_2CO_3$ residuals in a composition of the present disclosure is less than 1000 ppm.

In an embodiment, the amount of the $Na_2CO_3$ residuals in a composition of the present disclosure is non-detectable to 500 ppm. In an embodiment, the amount of the $Na_2CO_3$ residuals in a composition of the present disclosure is non-detectable to 450 ppm. In an embodiment, the amount of the $Na_2CO_3$ residuals in a composition of the present disclosure is non-detectable to 400 ppm. In an embodiment, the amount of the $Na_2CO_3$ residuals in a composition of the present disclosure is non-detectable to 350 ppm. In an embodiment, the amount of the $Na_2CO_3$ residuals in a composition of the present disclosure is non-detectable to 300 ppm. In an embodiment, the amount of the $Na_2CO_3$ residuals in a composition of the present disclosure is non-detectable to 250 ppm. In an embodiment, the amount of the $Na_2CO_3$ residuals in a composition of the present disclosure is non-detectable to 200 ppm. In an embodiment, the amount of the $Na_2CO_3$ residuals in a composition of the present disclosure is non-detectable to 150 ppm. In an embodiment, the amount of the $Na_2CO_3$ residuals in a composition of the present disclosure is non-detectable to 100 ppm. In an embodiment, the amount of the $Na_2CO_3$ residuals in a composition of the present disclosure is 100 ppm to 200 ppm. In an embodiment, the amount of the $Na_2CO_3$ residuals in a composition of the present disclosure is 200 ppm to 300 ppm. In an embodiment, the amount of the $Na_2CO_3$ residuals in a composition of the present disclosure is 300 ppm to 400 ppm. In an embodiment, the amount of the $Na_2CO_3$ residuals in a composition of the present disclosure is 400 ppm to 500 ppm.

In an embodiment, the water solubility of pure silk fibroin-based protein fragments of the present disclosure is 50 to 100%. In an embodiment, the water solubility of pure silk fibroin-based protein fragments of the present disclosure is 60 to 100%. In an embodiment, the water solubility of pure silk fibroin-based protein fragments of the present disclosure is 70 to 100%. In an embodiment, the water solubility of pure silk fibroin-based protein fragments of the present disclosure is 80 to 100%. In an embodiment, the water solubility is 90 to 100%. In an embodiment, the silk fibroin-based fragments of the present disclosure are non-soluble in aqueous solutions.

In an embodiment, the solubility of pure silk fibroin-based protein fragments of the present disclosure in organic solutions is 50 to 100%. In an embodiment, the solubility of pure silk fibroin-based protein fragments of the present disclosure in organic solutions is 60 to 100%. In an embodiment, the solubility of pure silk fibroin-based protein fragments of the present disclosure in organic solutions is 70 to 100%. In an embodiment, the solubility of pure silk fibroin-based protein fragments of the present disclosure in organic solutions is 80 to 100%. In an embodiment, the solubility of pure silk fibroin-based protein fragments of the present disclosure in organic solutions is 90 to 100%. In an embodiment, the silk fibroin-based fragments of the present disclosure are non-soluble in organic solutions.

In an embodiment, the extraction temperature during a method of preparing a composition of the present disclosure is greater than 84° C. In an embodiment, the extraction temperature during a method of preparing a composition of the present disclosure is less than 100° C. In an embodiment, the extraction temperature during a method of preparing a composition of the present disclosure is 84° C. to 100° C. In an embodiment, the extraction temperature during a method of preparing a composition of the present disclosure is 84° C. to 94° C. In an embodiment, the extraction temperature during a method of preparing a composition of the present disclosure is 94° C. to 100° C.

Compositions and Processes Including Silk Fibroin-Based Coatings

In an embodiment, the invention may include textiles, such as fibers, yarns, fabrics, or other materials and combinations thereof, that may be coated with an SPF mixture solution (i.e., silk fibroin solution (SFS)) as described herein to produce a coated article. In an embodiment, the coated articles described herein may be treated with additional chemical agents that may enhance the properties of the coated article. In an embodiment, the SFS may include one or more chemical agents that may enhance the properties of the coated article.

In an embodiment, textiles may be flexible materials (woven or non-woven) that include a network of natural and/or man-made fibers, thread, yarn, or a combination thereof. SFS may be applied at any stage of textile processing from individual fibers, to yarn, to fabric, to thread, or a combination thereof.

In an embodiment, fibers may be natural fibers that may include a natural fiber cellulose base, wherein the natural fiber cellulose base may include one or more of: (1) a baste such as flax, hemp, kenaf, jute, linen, and/or ramie; (2) a leaf such as flax, hemp, sisal, abaca, banana, henequen, ramie, sunn, and/or coir; and (3) seed hair such as cotton and/or kapok. In an embodiment, fibers may be natural fibers that may include a natural fiber protein base, wherein the natural fiber protein base may include one or more of: (1) hair such as alpaca, camel, cashmere, llama, mohair, and/or vicuna; (2) wool such as sheep; (3) filament such as silk. In an embodiment, fibers may be natural fibers that may include a natural fiber mineral base, including asbestos. In an embodiment, fibers may be man-made fibers that may include a man-made fiber organic natural polymer base, which may include one or more of: (1) a cellulose base such as bamboo, rayon, lyocell, acetate, and/or triacetate; (2) a protein base such as azlon; (3) an alginate; and (4) rubber. In an embodiment, fibers may be man-made fibers that may include a man-made fiber organic synthetic base, which may include one or more of acrylic, anidex, aramid, fluorocarbon, modacrylic, novoloid, nylon, nytril, olefin, PBI, polycarbonate, polyester, rubber, saran, spandex, vinal vinvon. In an embodiment, fibers may be man-made fibers that may include a man-made fiber inorganic base, which may include one or more of a glass material, metallic material, and carbon material.

In an embodiment, yarn may include natural fibers that may include a natural fiber cellulose base, wherein the natural fiber cellulose base may be from: (1) a baste such as flax, hemp, kenaf, jute, linen, and/or ramie; (2) a leaf such as flax, hemp, sisal, abaca, banana, henequen, ramie, sunn, and/or coir; or (3) seed hair such as cotton and/or kapok. In an embodiment, yarn may include natural fibers that may include a natural fiber protein base, wherein the natural fiber protein base may be from: (1) hair such as alpaca, camel, cashmere, llama, mohair, and/or vicuna; (2) wool such as sheep; or (3) filament such as silk. In an embodiment, yarn may include natural fibers that may include a natural fiber mineral base, including asbestos.

In an embodiment, yarn may include man-made fibers that may include a man-made fiber organic natural polymer base, which may include: (1) a cellulose base such as bamboo, rayon, lyocell, acetate, and/or triacetate; (2) a protein base such as azlon; (3) an alginate; or (4) rubber. In an embodiment, yarn may include man-made fibers that may include a man-made fiber organic synthetic base, which may include acrylic, anidex, aramid, fluorocarbon, modacrylic, novoloid, nylon, nytril, olefin, PBI, polycarbonate, polyester, rubber, saran, spandex, vinal and/or vinvon. In an embodiment, yarn may include man-made fibers that may include a man-made fiber inorganic base, which may include a glass material, metallic material, carbon material, and/or specialty material.

In an embodiment, fabric may include natural fibers and/or yarn that may include a natural fiber protein base, wherein the natural fiber protein base may be from: (1) hair such as alpaca, camel, cashmere, llama, mohair, and/or vicuna; (2) wool such as sheep; or (3) filament such as silk. In an embodiment, fabric may include natural fibers and/or yarn that may include a natural fiber mineral base, including asbestos.

In an embodiment, fabric may include man-made fibers and/or yarn that may include a man-made fiber organic natural polymer base, which may include: (1) a cellulose base such as bamboo, rayon, lyocell, acetate, and/or triacetate; (2) a protein base such as azlon; (3) an alginate; or (4) rubber. In an embodiment, fabric may include man-made fibers and/or yarn that may include a man-made fiber organic synthetic base, which may include acrylic, anidex, aramid, fluorocarbon, modacrylic, novoloid, nylon, nytril, olefin, PBI, polycarbonate, polyester, rubber, saran, spandex, vinal and/or vinvon. In an embodiment, fabric may include man-made fibers and/or yarn that may include a man-made fiber inorganic base, which may include a glass material, metallic material, carbon material, and/or specialty material.

In an embodiment, textiles may be manufactured via one or more of the following processes weaving processes, knitting processes, and non-woven processes. In an embodiment, weaving processes may include plain weaving, twill weaving, and/or satin weaving. In an embodiment, knitting processes may include weft knitting (e.g., circular, flat bed, and/or full fashioned) and/or warp knitting (e.g., tricot, Raschel, and/or crochet). In an embodiment, non-woven processes may include stable fiber (e.g., dry laid and/or wet laid) and/or continuous filament (e.g., spun laid and/or melt blown).

In some embodiments, SFS may be applied to fibers and/or yarn having a diameter of less than about 100 nm, or less than about 200 nm, or less than about 300 nm, or less than about 400 nm, or less than about 500 nm, or less than about 600 nm, or less than about 700 nm, or less than about 800 nm, or less than about 900 nm, or less than about 1000 nm, or less than about 2 µm, or less than about 5 µm, or less than about 10 µm, or less than about 20 µm, or less than about 30 µm, or less than about 40 µm, or less than about 50 µm, or less than about 60 µm, or less than about 70 µm, or less than about 80 µm, or less than about 90 µm, or less than about 100 µm, or less than about 200 µm, or less than about 300 µm, or less than about 400 µm, or less than about 500 µm, or less than about 600 µm, or less than about 700 µm, or less than about 800 µm, or less than about 900 µm, or less than about 1000 µm, or less than about 2 mm, or less than about 3 mm, or less than about 4 mm, or less than about 5 mm, 6 mm, or less than about 7 mm, or less than about 8 mm, or less than about 9 mm, or less than about 10 mm, or less than about 20 mm, or less than about 30 mm, or less than about 40 mm, or less than about 50 mm, or less than about 60 mm, or less than about 70 mm, or less than about 80 mm, or less than about 90 mm, or less than about 100 mm, or less than about 200 mm, or less than about 300 mm, or less than about 400 mm, or less than about 500 mm, or less than about 600 mm, or less than about 700 mm, or less than about 800 mm, or less than about 900 mm, or less than about 1000 mm.

In some embodiments, SFS may be applied to fibers and/or yarn having a diameter of greater than about 100 nm, or greater than about 200 nm, or greater than about 300 nm, or greater than about 400 nm, or greater than about 500 nm, or greater than about 600 nm, or greater than about 700 nm, or greater than about 800 nm, or greater than about 900 nm, or greater than about 1000 nm, or greater than about 2 µm, or greater than about 5 µm, or greater than about 10 µm, or greater than about 20 µm, or greater than about 30 µm, or greater than about 40 µm, or greater than about 50 µm, or greater than about 60 µm, or greater than about 70 µm, or greater than about 80 µm, or greater than about 90 µm, or greater than about 100 µm, or greater than about 200 µm, or greater than about 300 µm, or greater than about 400 µm, or greater than about 500 µm, or greater than about 600 µm, or greater than about 700 µm, or greater than about 800 µm, or greater than about 900 µm, or greater than about 1000 µm, or greater than about 2 mm, or greater than about 3 mm, or greater than about 4 mm, or greater than about 5 mm, 6 mm, or greater than about 7 mm, or greater than about 8 mm, or greater than about 9 mm, or greater than about 10 mm, or greater than about 20 mm, or greater than about 30 mm, or greater than about 40 mm, or greater than about 50 mm, or greater than about 60 mm, or greater than about 70 mm, or greater than about 80 mm, or greater than about 90 mm, or greater than about 100 mm, or greater than about 200 mm, or greater than about 300 mm, or greater than about 400 mm, or greater than about 500 mm, or greater than about 600 mm, or greater than about 700 mm, or greater than about 800 mm, or greater than about 900 mm, or greater than about 1000 mm.

In some embodiments, SFS may be applied to fibers and/or yarn having a length of less than about 100 nm, or less than about 200 nm, or less than about 300 nm, or less than about 400 nm, or less than about 500 nm, or less than about 600 nm, or less than about 700 nm, or less than about 800 nm, or less than about 900 nm, or less than about 1000 nm, or less than about 2 µm, or less than about 5 µm, or less than about 10 µm, or less than about 20 µm, or less than about 30 µm, or less than about 40 µm, or less than about 50 µm, or less than about 60 µm, or less than about 70 µm, or less than about 80 µm, or less than about 90 µm, or less than about 100 µm, or less than about 200 µm, or less than about 300 µm, or less than about 400 µm, or less than about 500 µm, or less than about 600 µm, or less than about 700 µm, or less than about 800 µm, or less than about 900 µm, or less than about 1000 µm, or less than about 2 mm, or less than about 3 mm, or less than about 4 mm, or less than about 5 mm, 6 mm, or less than about 7 mm, or less than about 8 mm, or less than about 9 mm, or less than about 10 mm, or less than about 20 mm, or less than about 30 mm, or less than about 40 mm, or less than about 50 mm, or less than about 60 mm, or less than about 70 mm, or less than about 80 mm, or less than about 90 mm, or less than about 100 mm, or less than about 200 mm, or less than about 300 mm, or less than about 400 mm, or less than about 500 mm, or less than about 600 mm, or less than about 700 mm, or less than about 800 mm, or less than about 900 mm, or less than about 1000 mm.

In some embodiments, SFS may be applied to fibers and/or yarn having a length of greater than about 100 nm, or greater than about 200 nm, or greater than about 300 nm, or greater than about 400 nm, or greater than about 500 nm, or greater than about 600 nm, or greater than about 700 nm, or greater than about 800 nm, or greater than about 900 nm, or greater than about 1000 nm, or greater than about 2 µm, or greater than about 5 µm, or greater than about 10 µm, or greater than about 20 µm, or greater than about 30 µm, or greater than about 40 µm, or greater than about 50 µm, or greater than about 60 µm, or greater than about 70 µm, or greater than about 80 µm, or greater than about 90 µm, or greater than about 100 µm, or greater than about 200 µm, or greater than about 300 µm, or greater than about 400 µm, or greater than about 500 µm, or greater than about 600 µm, or greater than about 700 µm, or greater than about 800 µm, or greater than about 900 µm, or greater than about 1000 µm, or greater than about 2 mm, or greater than about 3 mm, or greater than about 4 mm, or greater than about 5 mm, 6 mm, or greater than about 7 mm, or greater than about 8 mm, or greater than about 9 mm, or greater than about 10 mm, or greater than about 20 mm, or greater than about 30 mm, or greater than about 40 mm, or greater than about 50 mm, or greater than about 60 mm, or greater than about 70 mm, or greater than about 80 mm, or greater than about 90 mm, or greater than about 100 mm, or greater than about 200 mm, or greater than about 300 mm, or greater than about 400 mm, or greater than about 500 mm, or greater than about 600 mm, or greater than about 700 mm, or greater than about 800 mm, or greater than about 900 mm, or greater than about 1000 mm.

In some embodiments, SFS may be applied to fibers and/or yarn having a weight (g/m$^2$) of less than about 1 g/m$^2$, or less than about 2 g/m$^2$, or less than about 3 g/m$^2$, or less than about 4 g/m$^2$, or less than about 5 g/m$^2$, or less than about 6 g/m$^2$, or less than about 7 g/m$^2$, or less than about 8 g/m$^2$, or less than about 9 g/m$^2$, or less than about 10 g/m$^2$, or less than about 20 g/m$^2$, or less than about 30 g/m$^2$, or less than about 40 g/m$^2$, or less than about 50 g/m$^2$, or less than about 60 g/m$^2$, or less than about 70 g/m$^2$, or less than about 80 g/m$^2$, or less than about 90 g/m$^2$, or less than about 100 g/m$^2$, or less than about 200 g/m$^2$, or less than about 300 g/m$^2$, or less than about 400 g/m$^2$, or less than about 500 g/m$^2$.

In some embodiments, SFS may be applied to fibers and/or yarn having a weight (g/m$^2$) of at greater than about 1 g/m$^2$, or greater than about 2 g/m$^2$, or greater than about 3 g/m$^2$, or greater than about 4 g/m$^2$, or greater than about 5 g/m$^2$, or greater than about 6 g/m$^2$, or greater than about 7 g/m$^2$, or greater than about 8 g/m$^2$, or greater than about 9 g/m$^2$, or greater than about 10 g/m$^2$, or greater than about 20 g/m$^2$, or greater than about 30 g/m$^2$, or greater than about 40 g/m$^2$, or greater than about 50 g/m$^2$, or greater than about 60 g/m$^2$, or greater than about 70 g/m$^2$, or greater than about 80 g/m$^2$, or greater than about 90 g/m$^2$, or greater than about 100 g/m$^2$, or greater than about 200 g/m$^2$, or greater than about 300 g/m$^2$, or greater than about 400 g/m$^2$, or greater than about 500 g/m$^2$.

In some embodiments, SFS may be applied to fabric having a thickness of less than about 100 nm, or less than about 200 nm, or less than about 300 nm, or less than about 400 nm, or less than about 500 nm, or less than about 600 nm, or less than about 700 nm, or less than about 800 nm, or less than about 900 nm, or less than about 1000 nm, or less than about 2 µm, or less than about 5 µm, or less than about 10 µm, or less than about 20 µm, or less than about 30 µm, or less than about 40 µm, or less than about 50 µm, or less than about 60 µm, or less than about 70 µm, or less than about 80 µm, or less than about 90 µm, or less than about 100 µm, or less than about 200 µm, or less than about 300 µm, or less than about 400 µm, or less than about 500 µm, or less than about 600 µm, or less than about 700 µm, or less than about 800 µm, or less than about 900 µm, or less than about 1000 µm, or less than about 2 mm, or less than about 3 mm, or less than about 4 mm, or less than about 5 mm, 6 mm, or less than about 7 mm, or less than about 8 mm, or less than about 9 mm, or less than about 10 mm.

In some embodiments, SFS may be applied to fabric having a thickness of greater than about 100 nm, or greater than about 200 nm, or greater than about 300 nm, or greater than about 400 nm, or greater than about 500 nm, or greater than about 600 nm, or greater than about 700 nm, or greater than about 800 nm, or greater than about 900 nm, or greater than about 1000 nm, or greater than about 2 µm, or greater than about 5 µm, or greater than about 10 µm, or greater than about 20 µm, or greater than about 30 µm, or greater than about 40 µm, or greater than about 50 µm, or greater than about 60 µm, or greater than about 70 µm, or greater than about 80 µm, or greater than about 90 µm, or greater than about 100 µm, or greater than about 200 µm, or greater than about 300 µm, or greater than about 400 µm, or greater than about 500 µm, or greater than about 600 µm, or greater than about 700 µm, or greater than about 800 µm, or greater than about 900 µm, or greater than about 1000 µm, or greater than about 2 mm, or greater than about 3 mm, or greater than about 4 mm, or greater than about 5 mm, 6 mm, or greater than about 7 mm, or greater than about 8 mm, or greater than about 9 mm, or greater than about 10 mm.

In some embodiments, SFS may be applied to fabric having a width of less than about 100 nm, or less than about 200 nm, or less than about 300 nm, or less than about 400 nm, or less than about 500 nm, or less than about 600 nm, or less than about 700 nm, or less than about 800 nm, or less than about 900 nm, or less than about 1000 nm, or less than about 2 µm, or less than about 5 µm, or less than about 10 µm, or less than about 20 µm, or less than about 30 µm, or less than about 40 µm, or less than about 50 µm, or less than about 60 µm, or less than about 70 µm, or less than about 80 µm, or less than about 90 µm, or less than about 100 µm, or less than about 200 µm, or less than about 300 µm, or less than about 400 µm, or less than about 500 µm, or less than about 600 µm, or less than about 700 µm, or less than about 800 µm, or less than about 900 µm, or less than about 1000 µm, or less than about 2 mm, or less than about 3 mm, or less than about 4 mm, or less than about 5 mm, 6 mm, or less than about 7 mm, or less than about 8 mm, or less than about 9 mm, or less than about 10 mm, or less than about 20 mm, or less than about 30 mm, or less than about 40 mm, or less than about 50 mm, or less than about 60 mm, or less than about 70 mm, or less than about 80 mm, or less than about 90 mm, or less than about 100 mm, or less than about 200 mm, or less than about 300 mm, or less than about 400 mm, or less than about 500 mm, or less than about 600 mm, or less than about 700 mm, or less than about 800 mm, or less than about 900 mm, or less than about 1000 mm, or less than about 2 m, or less than about 3 m, or less than about 4 m, or less than about 5 m.

In some embodiments, SFS may be applied to fabric having a width of greater than about 100 nm, or greater than about 200 nm, or greater than about 300 nm, or greater than about 400 nm, or greater than about 500 nm, or greater than about 600 nm, or greater than about 700 nm, or greater than about 800 nm, or greater than about 900 nm, or greater than about 1000 nm, or greater than about 2 µm, or greater than about 5 µm, or greater than about 10 µm, or greater than about 20 µm, or greater than about 30 µm, or greater than about 40 µm, or greater than about 50 µm, or greater than about 60 µm, or greater than about 70 µm, or greater than about 80 µm, or greater than about 90 µm, or greater than about 100 µm, or greater than about 200 µm, or greater than about 300 µm, or greater than about 400 µm, or greater than about 500 µm, or greater than about 600 µm, or greater than about 700 µm, or greater than about 800 µm, or greater than about 900 µm, or greater than about 1000 µm, or greater than about 2 mm, or greater than about 3 mm, or greater than about 4 mm, or greater than about 5 mm, 6 mm, or greater than about 7 mm, or greater than about 8 mm, or greater than about 9 mm, or greater than about 10 mm, or greater than about 20 mm, or greater than about 30 mm, or greater than about 40 mm, or greater than about 50 mm, or greater than about 60 mm, or greater than about 70 mm, or greater than about 80 mm, or greater than about 90 mm, or greater than about 100 mm, or greater than about 200 mm, or greater than about 300 mm, or greater than about 400 mm, or greater than about 500 mm, or greater than about 600 mm, or greater than about 700 mm, or greater than about 800 mm, or greater than about 900 mm, or greater than about 1000 mm, or greater than about 2 m, or greater than about 3 m, or greater than about 4 m, or greater than about 5 m.

In some embodiments, SFS may be applied to fabric having a length of less than about 100 nm, or less than about 200 nm, or less than about 300 nm, or less than about 400 nm, or less than about 500 nm, or less than about 600 nm, or less than about 700 nm, or less than about 800 nm, or less than about 900 nm, or less than about 1000 nm, or less than about 2 µm, or less than about 5 µm, or less than about 10 µm, or less than about 20 µm, or less than about 30 µm, or less than about 40 µm, or less than about 50 µm, or less than about 60 µm, or less than about 70 µm, or less than about 80 µm, or less than about 90 µm, or less than about 100 µm, or less than about 200 µm, or less than about 300 µm, or less than about 400 µm, or less than about 500 µm, or less than about 600 µm, or less than about 700 µm, or less than about 800 µm, or less than about 900 µm, or less than about 1000 µm, or less than about 2 mm, or less than about 3 mm, or less than about 4 mm, or less than about 5 mm, 6 mm, or less than about 7 mm, or less than about 8 mm, or less than about 9 mm, or less than about 10 mm, or less than about 20 mm, or less than about 30 mm, or less than about 40 mm, or less than about 50 mm, or less than about 60 mm, or less than about 70 mm, or less than about 80 mm, or less than about 90 mm, or less than about 100 mm, or less than about 200 mm, or less than about 300 mm, or less than about 400 mm, or less than about 500 mm, or less than about 600 mm, or less than about 700 mm, or less than about 800 mm, or less than about 900 mm, or less than about 1000 mm.

In some embodiments, SFS may be applied to fabric having a length of greater than about 100 nm, or greater than about 200 nm, or greater than about 300 nm, or greater than about 400 nm, or greater than about 500 nm, or greater than about 600 nm, or greater than about 700 nm, or greater than about 800 nm, or greater than about 900 nm, or greater than about 1000 nm, or greater than about 2 µm, or greater than about 5 µm, or greater than about 10 µm, or greater than about 20 µm, or greater than about 30 µm, or greater than about 40 µm, or greater than about 50 µm, or greater than about 60 µm, or greater than about 70 µm, or greater than about 80 µm, or greater than about 90 µm, or greater than about 100 µm, or greater than about 200 µm, or greater than about 300 µm, or greater than about 400 µm, or greater than about 500 µm, or greater than about 600 µm, or greater than about 700 µm, or greater than about 800 µm, or greater than about 900 µm, or greater than about 1000 µm, or greater than about 2 mm, or greater than about 3 mm, or greater than about 4 mm, or greater than about 5 mm, 6 mm, or greater than about 7 mm, or greater than about 8 mm, or greater than about 9 mm, or greater than about 10 mm, or greater than about 20 mm, or greater than about 30 mm, or greater than about 40 mm, or greater than about 50 mm, or greater than about 60 mm, or greater than about 70 mm, or greater than about 80 mm, or greater than about 90 mm, or greater than about 100 mm, or greater than about 200 mm, or greater than about 300 mm, or greater than about 400 mm, or greater than about 500 mm, or greater than about 600 mm, or greater than about 700 mm, or greater than about 800 mm, or greater than about 900 mm, or greater than about 1000 mm.

In some embodiments, SFS may be applied to fabric having a stretch percentage of less than about 1%, or less than about 2%, or less than about 3%, or less than about 4%, or less than about 5%, or less than about 6%, or less than about 7%, or less than about 8%, or less than about 9%, or less than about 10%, or less than about 20%, or less than about 30%, or less than about 40%, or less than about 50%, or less than about 60%, or less than about 70%, or less than about 80%, or less than about 90%, or less than about 100, or less than about 110%, or less than about 120%, or less than about 130%, or less than about 140%, or less than about 150%, or less than about 160%, or less than about 170%, or less than about 180%, or less than about 190%, or less than about 200%. Stretch percentage may be determined for a fabric having an unstretched width and stretching the fabric to a stretched width, then subtracting the unstretched width from the stretched width to yield the net stretched width, then dividing the net stretched width and multiplying the quotient by 100 to find the stretch percentage (%):

$$\text{Stretch Percentage} = \frac{(\text{Stretched Width} - \text{Unstretched Width})}{\text{Unstretched Width}} * 100$$

In some embodiments, SFS may be applied to fabric having a stretch percentage of greater than about 1%, or greater than about 2%, or greater than about 3%, or greater than about 4%, or greater than about 5%, or greater than about 6%, or greater than about 7%, or greater than about 8%, or greater than about 9%, or greater than about 10%, or greater than about 20%, or greater than about 30%, or greater than about 40%, or greater than about 50%, or greater than about 60%, or greater than about 70%, or greater than about 80%, or greater than about 90%, or greater than about 100, or greater than about 110%, or greater than about 120%, or greater than about 130%, or greater than about 140%, or greater than about 150%, or greater than about 160%, or greater than about 170%, or greater than about 180%, or greater than about 190%, or greater than about 200%

In some embodiments, SFS may be applied to fabric having a tensile energy (N/cm$^2$) of less than about 1 cN/cm$^2$, or less than about 2 cN/cm$^2$, or less than about 3 cN/cm$^2$, or less than about 4 cN/cm$^2$, or less than about 5 cN/cm$^2$, or less than about 5 cN/cm$^2$, or less than about 6 cN/cm$^2$, or less than about 7 cN/cm$^2$, or less than about 8 cN/cm$^2$, or less than about 9 cN/cm$^2$, or less than about 10 cN/cm$^2$, or less than about 20 cN/cm$^2$, or less than about 30 cN/cm$^2$, or less than about 40 cN/cm$^2$, or less than about 50 cN/cm$^2$, or less than about 60 cN/cm$^2$, or less than about 70 cN/cm$^2$, or less than about 80 cN/cm$^2$, or less than about 90 cN/cm$^2$, or less than about 100 cN/cm$^2$, or less than about 2 N/cm$^2$, or less than about 3 N/cm$^2$, or less than about 4 N/cm$^2$, or less than about 5 N/cm$^2$, or less than about 6 N/cm$^2$, or less than about 7 N/cm$^2$, or less than about 8 N/cm$^2$, or less than about 9 N/cm$^2$, or less than about 10 N/cm$^2$, or less than about 20 N/cm$^2$, or less than about 30 N/cm$^2$, or less than about 40 N/cm$^2$, or less than about 50 N/cm$^2$, or less than about 60 N/cm$^2$, or less than about 70 N/cm$^2$, or less than about 80

N/cm², or less than about 90 N/cm², or less than about 100 N/cm², or less than about 150 N/cm², or less than about 200 N/cm².

In some embodiments, SFS may be applied to fabric having a tensile energy (N/cm²) of greater than about 1 cN/cm², or greater than about 2 cN/cm², or greater than about 3 cN/cm², or greater than about 4 cN/cm², or greater than about 5 cN/cm², or greater than about 5 cN/cm², or greater than about 6 cN/cm², or greater than about 7 cN/cm², or greater than about 8 cN/cm², or greater than about 9 cN/cm², or greater than about 10 cN/cm², or greater than about 20 cN/cm², or greater than about 30 cN/cm², or greater than about 40 cN/cm², or greater than about 50 cN/cm², or greater than about 60 cN/cm², or greater than about 70 cN/cm², or greater than about 80 cN/cm², or greater than about 90 cN/cm², or greater than about 100 cN/cm², or greater than about 2 N/cm², or greater than about 3 N/cm², or greater than about 4 N/cm², or greater than about 5 N/cm², or greater than about 6 N/cm², or greater than about 7 N/cm², or greater than about 8 N/cm², or greater than about 9 N/cm², or greater than about 10 N/cm², or greater than about 20 N/cm², or greater than about 30 N/cm², or greater than about 40 N/cm², or greater than about 50 N/cm², or greater than about 60 N/cm², or greater than about 70 N/cm², or greater than about 80 N/cm², or greater than about 90 N/cm², or greater than about 100 N/cm², or greater than about 150 N/cm², or greater than about 200 N/cm².

In some embodiments, SFS may be applied to fabric having a shear rigidity (N/cm-degree) of less than about 1 cN/cm-degree, or less than about 2 cN/cm-degree, or less than about 3 cN/cm-degree, or less than about 4 cN/cm-degree, or less than about 5 cN/cm-degree, or less than about 5 cN/cm-degree, or less than about 6 cN/cm-degree, or less than about 7 cN/cm-degree, or less than about 8 cN/cm-degree, or less than about 9 cN/cm-degree, or less than about 10 cN/cm-degree, or less than about 20 cN/cm-degree, or less than about 30 cN/cm-degree, or less than about 40 cN/cm-degree, or less than about 50 cN/cm-degree, or less than about 60 cN/cm-degree, or less than about 70 cN/cm-degree, or less than about 80 cN/cm-degree, or less than about 90 cN/cm-degree, or less than about 100 cN/cm-degree, or less than about 2 N/cm-degree, or less than about 3 N/cm-degree, or less than about 4 N/cm-degree, or less than about 5 N/cm-degree, or less than about 6 N/cm-degree, or less than about 7 N/cm-degree, or less than about 8 N/cm-degree, or less than about 9 N/cm-degree, or less than about 10 N/cm-degree, or less than about 20 N/cm-degree, or less than about 30 N/cm-degree, or less than about 40 N/cm-degree, or less than about 50 N/cm-degree, or less than about 60 N/cm-degree, or less than about 70 N/cm-degree, or less than about 80 N/cm-degree, or less than about 90 N/cm-degree, or less than about 100 N/cm-degree, or less than about 150 N/cm-degree, or less than about 200 N/cm-degree.

In some embodiments, SFS may be applied to fabric having a shear rigidity (N/cm-degree) of greater than about 1 cN/cm-degree, or greater than about 2 cN/cm-degree, or greater than about 3 cN/cm-degree, or greater than about 4 cN/cm-degree, or greater than about 5 cN/cm-degree, or greater than about 5 cN/cm-degree, or greater than about 6 cN/cm-degree, or greater than about 7 cN/cm-degree, or greater than about 8 cN/cm-degree, or greater than about 9 cN/cm-degree, or greater than about 10 cN/cm-degree, or greater than about 20 cN/cm-degree, or greater than about 30 cN/cm-degree, or greater than about 40 cN/cm-degree, or greater than about 50 cN/cm-degree, or greater than about 60 cN/cm-degree, or greater than about 70 cN/cm-degree, or greater than about 80 cN/cm-degree, or greater than about 90 cN/cm-degree, or greater than about 100 cN/cm-degree, or greater than about 2 N/cm-degree, or greater than about 3 N/cm-degree, or greater than about 4 N/cm-degree, or greater than about 5 N/cm-degree, or greater than about 6 N/cm-degree, or greater than about 7 N/cm-degree, or greater than about 8 N/cm-degree, or greater than about 9 N/cm-degree, or greater than about 10 N/cm-degree, or greater than about 20 N/cm-degree, or greater than about 30 N/cm-degree, or greater than about 40 N/cm-degree, or greater than about 50 N/cm-degree, or greater than about 60 N/cm-degree, or greater than about 70 N/cm-degree, or greater than about 80 N/cm-degree, or greater than about 90 N/cm-degree, or greater than about 100 N/cm-degree, or greater than about 150 N/cm-degree, or greater than about 200 N/cm-degree.

In some embodiments, SFS may be applied to fabric having a bending rigidity (N·cm²/cm) of less than about 1 cN·cm²/cm, or less than about 2 cN·cm²/cm, or less than about 3 cN·cm²/cm, or less than about 4 cN·cm²/cm, or less than about 5 cN·cm²/cm, or less than about 5 cN·cm²/cm, or less than about 6 cN·cm²/cm, or less than about 7 cN·cm²/cm, or less than about 8 cN·cm²/cm, or less than about 9 cN·cm²/cm, or less than about 10 cN·cm²/cm, or less than about 20 cN·cm²/cm, or less than about 30 cN·cm²/cm, or less than about 40 cN·cm²/cm, or less than about 50 cN·cm²/cm, or less than about 60 cN·cm²/cm, or less than about 70 cN·cm²/cm, or less than about 80 cN·cm²/cm, or less than about 90 cN·cm²/cm, or less than about 100 cN·cm²/cm, or less than about 2 N·cm²/cm, or less than about 3 N·cm²/cm, or less than about 4 N·cm²/cm, or less than about 5 N·cm²/cm, or less than about 6 N·cm²/cm, or less than about 7 N·cm²/cm, or less than about 8 N·cm²/cm, or less than about 9 N·cm²/cm, or less than about 10 N·cm²/cm, or less than about 20 N·cm²/cm, or less than about 30 N·cm²/cm, or less than about 40 N·cm²/cm, or less than about 50 N·cm²/cm, or less than about 60 N·cm²/cm, or less than about 70 N·cm²/cm, or less than about 80 N·cm²/cm, or less than about 90 N·cm²/cm, or less than about 100 N·cm²/cm, or less than about 150 N·cm²/cm, or less than about 200 N·cm²/cm.

In some embodiments, SFS may be applied to fabric having a bending rigidity (N·cm²/cm) of greater than about 1 cN·cm²/cm, or greater than about 2 cN·cm²/cm, or greater than about 3 cN·cm²/cm, or greater than about 4 cN·cm²/cm, or greater than about 5 cN·cm²/cm, or greater than about 5 cN·cm²/cm, or greater than about 6 cN·cm²/cm, or greater than about 7 cN·cm²/cm, or greater than about 8 cN·cm²/cm, or greater than about 9 cN·cm²/cm, or greater than about 10 cN·cm²/cm, or greater than about 20 cN·cm²/cm, or greater than about 30 cN·cm²/cm, or greater than about 40 cN·cm²/cm, or greater than about 50 cN·cm²/cm, or greater than about 60 cN·cm²/cm, or greater than about 70 cN·cm²/cm, or greater than about 80 cN·cm²/cm, or greater than about 90 cN·cm²/cm, or greater than about 100 cN·cm²/cm, or greater than about 2 N·cm²/cm, or greater than about 3 N·cm²/cm, or greater than about 4 N·cm²/cm, or greater than about 5 N·cm²/cm, or greater than about 6 N·cm²/cm, or greater than about 7 N·cm²/cm, or greater than about 8 N·cm²/cm, or greater than about 9 N·cm²/cm, or greater than about 10 N·cm²/cm, or greater than about 20 N·cm²/cm, or greater than about 30 N·cm²/cm, or greater than about 40 N·cm²/cm, or greater than about 50 N·cm²/cm, or greater than about 60 N·cm²/cm, or greater than about 70 N·cm²/cm, or greater than about 80 N·cm²/cm, or greater than about 90 N·cm²/cm, or greater than about 100 N·cm²/cm, or greater than about 150 N·cm²/cm, or greater than about 200 N·cm²/cm.

In some embodiments, SFS may be applied to fabric having a compression energy (N·cm/cm$^2$) of less than about 1 cN·cm/cm$^2$, or less than about 2 cN·cm/cm$^2$, or less than about 3 cN·cm/cm$^2$, or less than about 4 cN·cm/cm$^2$, or less than about 5 c N·cm/cm$^2$, or less than about 5 cN·cm/cm$^2$, or less than about 6 cN·cm/cm$^2$, or less than about 7 cN·cm/cm$^2$, or less than about 8 cN·cm/cm$^2$, or less than about 9 cN·cm/cm$^2$, or less than about 10 cN·cm/cm$^2$, or less than about 20 cN·cm/cm$^2$, or less than about 30 cN·cm/cm$^2$, or less than about 40 cN·cm/cm$^2$, or less than about 50 cN·cm/cm$^2$, or less than about 60 cN·cm/cm$^2$, or less than about 70 cN·cm/cm$^2$, or less than about 80 cN·cm/cm$^2$, or less than about 90 cN·cm/cm$^2$, or less than about 100 cN·cm/cm$^2$, or less than about 2 N·cm/cm$^2$, or less than about 3 N·cm/cm$^2$, or less than about 4 N·cm/cm$^2$, or less than about 5 N·cm/cm$^2$, or less than about 6 N·cm/cm$^2$, or less than about 7 N·cm/cm$^2$, or less than about 8 N·cm/cm$^2$, or less than about 9 N·cm/cm$^2$, or less than about 10 N·cm/cm$^2$, or less than about 20 N·cm/cm$^2$, or less than about 30 N·cm/cm$^2$, or less than about 40 N·cm/cm$^2$, or less than about 50 N·cm/cm$^2$, or less than about 60 N·cm/cm$^2$, or less than about 70 N·cm/cm$^2$, or less than about 80 N·cm/cm$^2$, or less than about 90 N·cm/cm$^2$, or less than about 100 N·cm/cm$^2$, or less than about 150 N·cm/cm$^2$, or less than about 200 N·cm/cm$^2$.

In some embodiments, SFS may be applied to fabric having a compression energy (N·cm/cm$^2$) of greater than about 1 cN·cm/cm$^2$, or greater than about 2 cN·cm/cm$^2$, or greater than about 3 cN·cm/cm$^2$, or greater than about 4 cN·cm/cm$^2$, or greater than about 5 cN·cm/cm$^2$, or greater than about 5 cN·cm/cm$^2$, or greater than about 6 cN·cm/cm$^2$, or greater than about 7 cN·cm/cm$^2$, or greater than about 8 cN·cm/cm$^2$, or greater than about 9 cN·cm/cm$^2$, or greater than about 10 cN·cm/cm$^2$, or greater than about 20 cN·cm/cm$^2$, or greater than about 30 cN·cm/cm$^2$, or greater than about 40 cN·cm/cm$^2$, or greater than about 50 cN·cm/cm$^2$, or greater than about 60 cN·cm/cm$^2$, or greater than about 70 cN·cm/cm$^2$, or greater than about 80 cN·cm/cm$^2$, or greater than about 90 cN·cm/cm$^2$, or greater than about 100 cN·cm/cm$^2$, or greater than about 2 N·cm/cm$^2$, or greater than about 3 N·cm/cm$^2$, or greater than about 4 N·cm/cm$^2$, or greater than about 5 N·cm/cm$^2$, or greater than about 6 N·cm/cm$^2$, or greater than about 7 N·cm/cm$^2$, or greater than about 8 N·cm/cm$^2$, or greater than about 9 N·cm/cm$^2$, or greater than about 10 N·cm/cm$^2$, or greater than about 20 N·cm/cm$^2$, or greater than about 30 N·cm/cm$^2$, or greater than about 40 N·cm/cm$^2$, or greater than about 50 N·cm/cm$^2$, or greater than about 60 N·cm/cm$^2$, or greater than about 70 N·cm/cm$^2$, or greater than about 80 N·cm/cm$^2$, or greater than about 90 N·cm/cm$^2$, or greater than about 100 N·cm/cm$^2$, or greater than about 150 N·cm/cm$^2$, or greater than about 200 N·cm/cm$^2$.

In some embodiments, SFS may be applied to fabric having a coefficient of friction of less than about 0.04, or less than about 0.05, or less than about 0.06, or less than about 0.07, or less than about 0.08, or less than about 0.09, or less than about 0.10, or less than about 0.10, or less than about 0.15, or less than about 0.20, or less than about 0.25, or less than about 0.30, or less than about 0.35, or less than about 0.40, or less than about 0.45, or less than about 0.50, or less than about 0.55, or less than about 0.60, or less than about 0.65, or less than about 0.70, or less than about 0.75, or less than about 0.80, or less than about 0.85, or less than about 0.90, or less than about 0.95, or less than about 1.00, or less than about 1.05.

In some embodiments, SFS may be applied to fabric having a coefficient of friction of greater than about 0.04, or greater than about 0.05, or greater than about 0.06, or greater than about 0.07, or greater than about 0.08, or greater than about 0.09, or greater than about 0.10, or greater than about 0.10, or greater than about 0.15, or greater than about 0.20, or greater than about 0.25, or greater than about 0.30, or greater than about 0.35, or greater than about 0.40, or greater than about 0.45, or greater than about 0.50, or greater than about 0.55, or greater than about 0.60, or greater than about 0.65, or greater than about 0.70, or greater than about 0.75, or greater than about 0.80, or greater than about 0.85, or greater than about 0.90, or greater than about 0.95, or greater than about 1.00, or greater than about 1.05.

In some embodiments, chemical finishes may be applied to textiles before or after such textiles are coated with SFS. In an embodiment, chemical finishing may be intended as the application of chemical agents and/or SFS to textiles, including fibers, yarn, and fabric, or to garments that are prepared by such fibers, yarn, and fabric to modify the original textile's or garment's properties and achieve properties in the textile or garment that would be otherwise absent. With chemical finishes, textiles treated with such chemical finishes may act as surface treatments and/or the treatments may modify the elemental analysis of treated textile base polymers.

In an embodiment, a type of chemical finishing may include the application of certain silk-fibroin based solutions to textiles. For example, SFS may be applied to a fabric after it is dyed, but there are also scenarios that may require the application of SFS during processing, during dyeing, or after a garment is assembled from a selected textile or fabric, thread, or yarn. In some embodiments, after its application, SFS may be dried with the use of heat. SFS may then be fixed to the surface of the textile in a processing step called curing.

In some embodiments, SFS may be supplied in a concentrated form suspended in water. In some embodiments, SFS may have a concentration by weight (% w/w or % w/v) or by volume (v/v) of less than about 50%, or less than about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%, or less than about 1%, or less than about 0.1%, or less than about 0.01%, or less than about 0.001%, or less than about 0.0001%, or less than about 0.00001%. In some embodiments, SFS may have a concentration by weight (% w/w or % w/v) or by volume (v/v) of greater than about 50%, or greater than about 45%, or greater than about 40%, or greater than about 35%, or greater than about 30%, or greater than about 25%, or greater than about 20%, or greater than about 15%, or greater than about 10%, or greater than about 5%, or greater than about 4%, or greater than about 3%, or greater than about 2%, or greater than about 1%, or greater than about 0.1%, or greater than about 0.01%, or greater than about 0.001%, or greater than about 0.0001%, or greater than about 0.00001%.

In some embodiments, the solution concentration and the wet pick of the material determines the amount of silk fibroin solution (SFS), which may include silk-based proteins or fragments thereof, that may be fixed or otherwise adhered to the textile being coated. The wet pick up may be expressed by the following formula:

$$\text{wet pick up (\%)} = \frac{\text{weight of } SFS \text{ applied} \times 100}{\text{weight of dry textile material}}.$$

The total amount of SFS added to the textile material may be expressed by the following formula:

$$SFS \text{ added } (\%) = \frac{\text{weight of dry } SFS \text{ coated textile material} \times 100}{\text{weight of dry textile material before coating}}.$$

Regarding methods for applying SFS to textiles more broadly, SFS may be applied to textiles through a pad or roller application on process, a saturation and removal process, and/or a topical application process. Moreover, the methods of silk application (i.e., SFS application or coating) may include bath coating, kiss rolling, spray coating, and/or two-sided rolling. In some embodiments, the coating processes (e.g., bath coating, kiss rolling, spray coating, two-sided rolling, roller application, saturation and removal application, and/or topical application), drying processes, and curing processes may be varied as described herein to modify one or more selected textile (e.g., fabric) properties of the resulting coated textile wherein such properties include, but are not limited to wetting time, absorption rate, spreading speed, accumulative one-way transport, and/or overall moisture management capability. In some embodiments, the aforementioned selected properties may be enhanced by varying one or more of the coating processes, drying processes, and curing processes as described herein.

In some embodiments, the silk compositions provided herein may be applied in a wet process or a dry process, such as by applying the silk compositions to a wet textile or a dry textile.

In an embodiment, the padder application may be used on dry or wet textile. For example, it may be applied on fabric after the dyeing process. The fabric may be fed into a water bath solution and may reach saturation. The fabric to be coated may then pass through a set of rollers that, based on multiple variables, extract the bath solution in excess to the desired wet pick up %. The variables that affect the wet pick up % are the roller pressure and materials, the fabric composition and construction, and the SFS viscosity. An exemplary padder roller configuration is shown in FIG. 183.

In an embodiment, the padder application on wet textile may be used to reduce the cost of drying the fabric post dyeing. The fabric exiting the pad rollers may maintain a higher weight % than the incoming fabric to maintain a SFS deposit on the fabric; and the SFS solution may need to account for any dilution taking place due to water present on the incoming fabric.

In an embodiment, the saturation and removal application is a low wet pick up method that may, for example, solve some of the issues associated with removing large amounts of water during drying processes. Since fabric may dry in an oven from the outside surface towards the inside, water may move from the inside to the outside resulting in a higher coating concentration on the outside surface. With less water content, migration may be reduced due to a higher viscosity in the solution. However, decreased wet pick up may result in an uneven solution deposit.

In an embodiment, vacuum extraction may be used as a method for low wet pick up. Saturated fabric may be subject to a vacuum that pulls solution out of the fabric and returns it to an application loop. Air jet ejection may be a method for providing low wet pick up. The saturated fabric may be subjected to high pressure steam that removes solution out of the fabric and returns it to an application loop.

In an embodiment, a porous bowl method may be used for low wet pick up. Solid pad rollers may be substituted with rubber coated fiber rollers. Saturated fabric may be subjected to the pressure of the roller since the porosity of the rollers may allow for more solution to be squeezed from the fabric.

In an embodiment, a transfer padding method may be used for low wet pick up. Saturated fabric may be passed through two continuous dry non-woven fabrics and may be pressed at low pressure. The non-woven fabrics may extract excess solution from the fabric being treated.

In an embodiment, topical application may be used as a low wet pick up method of application that deposits the desired amount of SFS to the fabric without removing any excess material. The methods described above may be used for one-sided coating applications, but there are variations that may allow for two-sided coating.

In an embodiment, kiss rolling may be used as a topical method of application that transfers the SFS from a roller (i.e., a kiss roller) to one side of the fabric. The solution viscosity, roller surface finish, speed of the roller, speed of the fabric, contact angle of the fabric on the roller and properties of the fabric are parameters that control the amount of solution deposited on the fabric. An exemplary kiss roller is depicted in FIG. 184.

In an embodiment, a variation to the kiss roller technique may be the Triatex MA system that uses two moisture content sensors to determine the solution pick up at the kiss roller and adjust the kiss roller controllable variable to maintain consistent the solution deposit onto the fabric.

In an embodiment, a loop transfer application may be used as a topical method of application that transfers the SFS from a saturated loop fabric to the fabric to be coated between low pressure pad rollers. There is a two rollers version that may allow for minimum contact with the fabric and a three rollers version that allows for greater contact with the fabric.

In an embodiment, an engrave roller application may be used as a topical method of application that may transfer a metered amount of SFS onto the fabric. This may be achieved by engraving a pattern on the surface of the roller with precise depth and design that contains a controlled amount of SFS. A blade may be used to remove any solution that is deposited on the surface of the roller in order to maintain a consistent transfer of solution to the fabric to be coated.

In an embodiment, rotary screen printing may be used as a topical method of application that may deposit SFS onto the fabric by seeping the solution through a roller screen. The solution may be contained in the screen print roller core at a set level while a blade may be used to remove any excess solution from the interior roller wall, providing a clean surface for the next revolution of the screen printer roller.

In an embodiment, magnetic roller coating may be used as a topical method of application that may deposit SFS from a kiss roller onto the fabric to be coated. The kiss roller is semi-submersed in a bath solution while a magnetic field created in the fabric driving roller determines the amount of pressure applied by the kiss roller, controlling the solution pick up rate.

In an embodiment, spraying may be used as a topical method of application that may transfer SFS onto the fabric by nebulizing the solution. The spray pattern may be controlled by the nozzle pattern, size, and the air flow. Spray application may be used for one side application or also two sided applications.

In an embodiment, foam application may be used a topical method of application that may transfer SFS onto the fabric. Foam may be made by substituting part of the water in the solution with air therefore reducing the amount of water to be applied to the fabric. Foam application may be used for one-sided application or two-sided application where the same foam may be deposited through a squeeze roller or different foam solutions may be provided through transfer rolls or through a slot applicator.

In an embodiment, the application of SFS may take place after a garment is assembled. In an embodiment, the process may take place in a washing and dyeing machine or in a spray booth. For example, a washing and dyeing machine may be similar in shape to a household front loader washing machine, it allows the process to take place at exhaustion post dyeing or with an independent processing cycle. In an embodiment, a spray booth machine may include a manual or a fully automated process. For example, a garment may be held by a mannequin while an operator or an anthropomorphic robot may spray the solution onto the fabric.

In an embodiment, SFS may be a water based solution that, after its application to the textile, may require thermal vaporization to infuse the SFS onto the textile. Thermal vaporization may be applied by heat transfer through radiation with equipment such as infrared or radio frequency dryer.

In an embodiment, thermal vaporization may be applied by convection through heated air circulating in an oven to the required temperature, while the fabric is clamped and is transported by a conveyor. This allows full control on fabric width dimension.

In an embodiment, thermal vaporization may be applied by conduction through contacting the textile with heated cylinder or calendar cylinder. Since the fabric is not clamp there is minimal control on fabric width.

In an embodiment, curing of the SFS on the textile may be completed with the same equipment used for the thermal vaporization in a continuous cycle or in a separate cycle.

In an embodiment, curing time temperature may be dependent the textile polymer content and the binding method of preference for the SFS with the specific polymer. The curing process may not start until the thermal vaporization is completed.

In some embodiments, sensor may be used to monitor SFS deposition on the textile and the drying and curing steps.

In some embodiments, for monitoring the deposition of SFS, a contactless sensor, like the one supplied by Pleva model AF120 based on microwave absorption of water, may be used. Measurement of the material moisture may be based on microwave absorption by water. A semiconductor oscillator transmits microwave energy through the web. The non-absorbed part of the energy may be received on the opposite side by a microwave receiver. The amount of absorption is a measurement of the absolute moisture content. The microwave sensor is capable of detecting and measuring water content from a minimum of 0 up to 2000 g $H_2O/m^2$.

In some embodiments, for wide fabric processing multiple sensor may be paired side by side, delivering the data analysis to a centralized control system loop capable to add more solution in the area of the fabric that is low.

In some embodiments, another sensor may be used that is based on microwave technology, such as Aqualot by Mahlo. The sensor may evaluate the shift in the resonant frequency of the two standing waves with respect to each other rather than the attenuation of the microwaves by the quantity of water molecules in the measuring gap.

In some embodiments, another contactless sensor for SFS may be the IR-3000 by MoistTech based on near infrared sensing technology. The sensor measures the amount of near infrared energy reflected at a given wavelength that is inversely proportional to the quantity of absorbing molecules in the fabric.

In some embodiments, the residual moister at the end of the curing process may be measured to further confirm the drying and curing process. In addition to the above sensor, a contact sensor such as the Textometer RMS by Mahlo may be used for measuring moister through conductivity.

In some embodiments, monitoring the end of the drying process phase may be achieved by measuring the fabric temperature with a contactless temperature sensor. When wet product enters the dryer, it first heats up to the cooling limit temperature. In some embodiments, when the water content drops to residual moisture levels, the product temperature may begin to rise again. The closer the product temperature approaches the circulation air temperature in the dryer, the slower the temperature continues to rise. In some embodiments, at a certain temperature threshold (called the fixing temperature) the temperature necessary for processing, fixing, or condensing is reached.

In some embodiments, to determine the dwell time for a desired product temperature, the surface temperature of the product may be measured without contact at several locations in the dryer using high-temperature resistant infrared pyrometers. Mahlo Permaset VMT is an infrarem Pyrometer that may be assembled in multiple units to monitors temperature through the dryer. Setex is another manufacturer offering fabric temperature sensors for use in dryers and oven like the models WTM V11, V21, and V41.

In some embodiments, SFS may be applied to a textile during exhaust dyeing. In some embodiments, the process may involve loading fabric into a bath, originally known as a batch, and allowing it to come into equilibrium with the solution. Exhaust dyeing may be the ability of the silk fibroin molecules to move from the solution onto the fibers or thread of a textile (substantivity). The substantivity of the silk fibroin may be influenced by temperature or additives, such as salt.

In some embodiments, an exhaust dyeing process may take anywhere from a few minutes to a few hours. When the fabric has been absorbed, or fixed, as much silk fibroin as it can, the bath may be emptied and the fabric may be rinsed to remove any excess solution.

In some embodiments, an important parameter in exhaust dyeing may be what is known as the specific liquor ratio. This describes the ratio of the mass of the fabric to the volume of the SFS bath and determines the amount of silk fibroin deposited on a textile.

In some embodiments, SFS can be applied to a textile during jet dyeing processes. A jet dyeing machine may formed by closed tubular system where the fabric is placed. For transporting the fabric through the tube, a jet of dye liquor is supplied through a venturi. The jet may create turbulence. This may help in SFS penetration along with preventing the fabric from touching the walls of the tube. For example, as the fabric is often exposed to comparatively higher concentrations of liquor within the transport tube, a small SFS bath is needed in the bottom of the vessel. This arrangement may be enough for the smooth movement from rear to front of the vessel.

In some embodiments, SFS may be applied during Paddle dyeing. Paddle dyeing machines may be generally used to many forms of textiles but the method best suits to garments. Heat may be generated through steam injection directly into the coating bath. In an embodiment, a paddle dyeing machine operates through a paddle that circulates both the bath and garments in a perforated central island. It is here that the SFS, water, and steam for heat are added. The overhead paddle machine may be described as a vat with a paddle that has blades of full width. The blades may generally dip a few centimeters into the vat. This action may stir the bath and push garments to be died down, thus keeping them submerged in the dye liquor.

In some embodiments, the processing methods set forth herein may be used to apply SFS to textiles with one or more of the following parameters including, but not limited to, fabric speed, solution viscosity, solution added to fabric, fabric range width, drying temperature, drying time, curing time, fabric tension, padder pressure, padder roller shore hardness, stenter temperature, and common drying and curing temperatures. In an embodiment, the processing method parameters may also include a condensation temperature, which may vary depending upon the chemical recipe used to apply the SFS to the textiles.

In an embodiment, the fabric speed for the processes of the invention may be less than about 0.1 m/min, or less than about 0.2 m/min, or less than about 0.3 m/min, or less than about 0.4 m/min, or less than about 0.5 m/min, or less than about 0.6 m/min, or less than about 0.7 m/min, or less than about 0.8 m/min, or less than about 0.9 m/min, or less than about 1 m/min, or less than about 2 m/min, or less than about 3 m/min, or less than about 4 m/min, or less than about 5 m/min, or less than about 6 m/min, or less than about 7 m/min, or less than about 8 m/min, or less than about 9 m/min, or less than about 10 m/min, or less than about 20 m/min, or less than about 30 m/min, or less than about 40 m/min, or less than about 50 m/min, or less than about 60 m/min.

In an embodiment, the fabric speed for the processes of the invention may be greater than about 0.1 m/min, or greater than about 0.2 m/min, or greater than about 0.3 m/min, or greater than about 0.4 m/min, or greater than about 0.5 m/min, or greater than about 0.6 m/min, or greater than about 0.7 m/min, or greater than about 0.8 m/min, or greater than about 0.9 m/min, or greater than about 1 m/min, or greater than about 2 m/min, or greater than about 3 m/min, or greater than about 4 m/min, or greater than about 5 m/min, or greater than about 6 m/min, or greater than about 7 m/min, or greater than about 8 m/min, or greater than about 9 m/min, or greater than about 10 m/min, or greater than about 20 m/min, or greater than about 30 m/min, or greater than about 40 m/min, or greater than about 50 m/min, or greater than about 60 m/min.

In an embodiment, the solution viscosity for the processes of the invention may be less than about 1000 mPas, or less than about 1500 mPas, or less than about 2000 mPas, or less than about 2500, or less than about 3000 mPas, or less than about 4000 mPas, or less than about 4500 mPas, or less than about 5000 mPas, or less than about 5500 mPas, or less than about 6000 mPas, or less than about 6500 mPas, or less than about 7000 mPas, or less than about 7500 mPas, or less than about 8000 mPas, or less than about 8500 mPas, or less than about 9000 mPas, or less than about 9500 mPas, or less than about 10000 mPas, or less than about 10500 mPas, or less than about 11000 mPas, or less than about 11500 mPas, or less than about 12000 mPas.

In an embodiment, the solution viscosity for the processes of the invention may be greater than about 1000 mPas, or greater than about 1500 mPas, or greater than about 2000 mPas, or greater than about 2500 mPas, or greater than about 3000 mPas, or greater than about 4000 mPas, or greater than about 4500 mPas, or greater than about 5000 mPas, or greater than about 5500 mPas, or greater than about 6000 mPas, or greater than about 6500 mPas, or greater than about 7000 mPas, or greater than about 7500 mPas, or greater than about 8000 mPas, or greater than about 8500 mPas, or greater than about 9000 mPas, or greater than about 9500 mPas, or greater than about 10000 mPas, or greater than about 10500 mPas, or greater than about 11000 mPas, or greater than about 11500 mPas, or greater than about 12000 mPas.

In an embodiment, the solution may be added to a textile (e.g., fabric) for the processes of the invention in less than about 0.01 g/m$^2$, or less than about 0.02 g/m$^2$, or less than about 0.03 g/m$^2$, or less than about 0.04 g/m$^2$, or less than about 0.05 g/m$^2$, or less than about 0.06 g/m$^2$, or less than about 0.07 g/m$^2$, or less than about 0.08 g/m$^2$, or less than about 0.09 g/m$^2$, or less than about 0.10 g/m$^2$, or less than about 0.2 g/m$^2$, or less than about 0.3 g/m$^2$, or less than about 0.4 g/m$^2$, or less than about 0.5 g/m$^2$, or less than about 0.6 g/m$^2$, or less than about 0.7 g/m$^2$, or less than about 0.8 g/m$^2$, or less than about 0.9 g/m$^2$, or less than about 1 g/m$^2$, or less than about 2 g/m$^2$, or less than about 3 g/m$^2$, or less than about 4 g/m$^2$, or less than about 5 g/m$^2$, or less than about 6 g/m$^2$, or less than about 7 g/m$^2$, or less than about 8 g/m$^2$, or less than about 9 g/m$^2$, or less than about 10 g/m$^2$, or less than about 20 g/m$^2$, or less than about 30 g/m$^2$, or less than about 40 g/m$^2$, or less than about 50 g/m$^2$, or less than about 60 g/m$^2$, or less than about 70 g/m$^2$, or less than about 80 g/m$^2$, or less than about 90 g/m$^2$, or less than about 100 g/m$^2$.

In an embodiment, the solution may be added to a textile (e.g., fabric) for the processes of the invention in greater than about 0.01 g/m$^2$, or greater than about 0.02 g/m$^2$, or greater than about 0.03 g/m$^2$, or greater than about 0.04 g/m$^2$, or greater than about 0.05 g/m$^2$, or greater than about 0.06 g/m$^2$, or greater than about 0.07 g/m$^2$, or greater than about 0.08 g/m$^2$, or greater than about 0.09 g/m$^2$, or greater than about 0.10 g/m$^2$, or greater than about 0.2 g/m$^2$, or greater than about 0.3 g/m$^2$, or greater than about 0.4 g/m$^2$, or greater than about 0.5 g/m$^2$, or greater than about 0.6 g/m$^2$, or greater than about 0.7 g/m$^2$, or greater than about 0.8 g/m$^2$, or greater than about 0.9 g/m$^2$, or greater than about 1 g/m$^2$, or greater than about 2 g/m$^2$, or greater than about 3 g/m$^2$, or greater than about 4 g/m$^2$, or greater than about 5 g/m$^2$, or greater than about 6 g/m$^2$ or greater than about 7 g/m$^2$, or greater than about 8 g/m$^2$, or greater than about 9 g/m$^2$ or greater than about 10 g/m$^2$, or greater than about 20 g/m$^2$, or greater than about 30 g/m$^2$, or greater than about 40 g/m$^2$, or greater than about 50 g/m$^2$, or greater than about 60 g/m$^2$, or greater than about 70 g/m$^2$, or greater than about 80 g/m$^2$, or greater than about 90 g/m$^2$, or greater than about 100 g/m$^2$.

In an embodiment, the fabric range width for the processes of the invention may be less than about 1 mm, or less than about 2 mm, or less than about 3 mm, or less than about 4 mm, or less than about 5 mm, or less than about 6 mm, or less than about 7 mm, or less than about 8 mm, or less than about 9, or less than about 10 mm, or less than about 20 mm, or less than about 30 mm, or less than about 40 mm, or less than about 50 mm, or less than about 60 mm, or less than about 70 mm, or less than about 80 mm, or less than about 90 mm, or less than about 100 mm, or less than about 200, or less than about 300 mm, or less than about 400 mm, or less than about 500 mm, or less than about 600 mm, or less than about 700 mm, or less than about 800 mm, or less than about 900 mm, or less than about 1000 mm, or less than about 2000 mm, or less than about 2000 mm, or less than about 3000 mm, or less than about 4000 mm, or less than about 5000 mm.

In an embodiment, the fabric range width for the processes of the invention may be greater than about 1 mm, or greater than about 2 mm, or greater than about 3 mm, or greater than about 4 mm, or greater than about 5 mm, or greater than about 6 mm, or greater than about 7 mm, or greater than about 8 mm, or greater than about 9, or greater than about 10 mm, or greater than about 20 mm, or greater than about 30 mm, or greater than about 40 mm, or greater than about 50 mm, or greater than about 60 mm, or greater than about 70 mm, or greater than about 80 mm, or greater than about 90 mm, or greater than about 100 mm, or greater than about 200, or greater than about 300 mm, or greater than about 400 mm, or greater than about 500 mm, or greater than about 600 mm, or greater than about 700 mm, or greater than about 800 mm, or greater than about 900 mm, or greater than about 1000 mm, or greater than about 2000 mm, or greater than about 2000 mm, or greater than about 3000 mm, or greater than about 4000 mm, or greater than about 5000 mm.

In an embodiment, the drying and/or curing temperature for the processes of the invention may be less than about 70° C., or less than about 75° C., or less than about 80° C., or less than about 85° C., or less than about 90° C., or less than about 95° C., or less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C., or less than about 230° C.

In an embodiment, the drying and/or curing temperature for the processes of the invention may be greater than about 70° C., or greater than about 75° C., or greater than about 80° C., or greater than about 85° C., or greater than about 90° C., or greater than about 95° C., or greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C., or greater than about 230° C.

In an embodiment, the drying time for the processes of the invention may be less than about 10 seconds, or less than about 20 seconds, or less than about 30 seconds, or less than about 40 seconds, or less than about 50 seconds, or less than about 60 seconds, or less than about 2 minutes, or less than about, 3 minutes, or less than about 4 minutes, or less than about 5 minutes, or less than about 6 minutes, or less than about 7 minutes, or less than about 8 minutes, or less than about 9 minutes, or less than about 10 minutes, or less than about 20 minutes, or less than about 30 minutes, or less than about 40 minutes, or less than about 50 minutes, or less than about 60 minutes.

In an embodiment, the drying time for the processes of the invention may be greater than about 10 seconds, or greater than about 20 seconds, or greater than about 30 seconds, or greater than about 40 seconds, or greater than about 50 seconds, or greater than about 60 seconds, or greater than about 2 minutes, or greater than about, 3 minutes, or greater than about 4 minutes, or greater than about 5 minutes, or greater than about 6 minutes, or greater than about 7 minutes, or greater than about 8 minutes, or greater than about 9 minutes, or greater than about 10 minutes, or greater than about 20 minutes, or greater than about 30 minutes, or greater than about 40 minutes, or greater than about 50 minutes, or greater than about 60 minutes.

In an embodiment, the curing time for the processes of the invention may be less than about 1 second, or less than about 2 seconds, or less than about 3 seconds, or less than about 4 seconds, or less than about 5 seconds, or less than about 6 seconds, or less than about 7 seconds, or less than about 8 seconds, or less than about 9 seconds, or less than about 10 seconds, or less than about 20 seconds, or less than about 30 seconds, or less than about 40 seconds, or less than about 50 seconds, or less than about 60 seconds, or less than about 2 minutes, or less than about 3 minutes, or less than about 4 minutes, or less than about 5 minutes, or less than about 6 minutes, or less than about 7 minutes, or less than about 8 minutes, or less than about 9 minutes, or less than about 10 minutes, or less than about 20 minutes, or less than about 30 minutes, or less than about 40 minutes, or less than about 50 minutes, or less than about 60 minutes.

In an embodiment, the curing time for the processes of the invention may be greater than about 1 second, or greater than about 2 seconds, or greater than about 3 seconds, or greater than about 4 seconds, or greater than about 5 seconds, or greater than about 6 seconds, or greater than about 7 seconds, or greater than about 8 seconds, or greater than about 9 seconds, or greater than about 10 seconds, or greater than about 20 seconds, or greater than about 30 seconds, or greater than about 40 seconds, or greater than about 50 seconds, or greater than about 60 seconds, or greater than about 2 minutes, or greater than about 3 minutes, or greater than about 4 minutes, or greater than about 5 minutes, or greater than about 6 minutes, or greater than about 7 minutes, or greater than about 8 minutes, or greater than about 9 minutes, or greater than about 10 minutes, or greater than about 20 minutes, or greater than about 30 minutes, or greater than about 40 minutes, or greater than about 50 minutes, or greater than about 60 minutes.

In an embodiment, the fabric tension for the processes of the invention may be less than about 1 N, or less than about 2 N, or less than about 3 N, or less than about 4 N, or less than about 5 N, or less than about 6 N, or less than about 7 N, or less than about 8 N, or less than about 9 N, or less than about 10 N, or less than about 20 N, or less than about 30 N, or less than about 40 N, or less than about 50 N, or less than about 60 N, or less than about 70 N, or less than about 80 N, or less than about 90 N, or less than about 100 N, or less than about 150 N, or less than about 200 N, or less than about 250 N, or less than about 300 N.

In an embodiment, the fabric tension for the processes of the invention may be greater than about 1 N, or greater than about 2 N, or greater than about 3 N, or greater than about 4 N, or greater than about 5 N, or greater than about 6 N, or greater than about 7 N, or greater than about 8 N, or greater than about 9 N, or greater than about 10 N, or greater than about 20 N, or greater than about 30 N, or greater than about 40 N, or greater than about 50 N, or greater than about 60 N, or greater than about 70 N, or greater than about 80 N, or greater than about 90 N, or greater than about 100 N, or greater than about 150 N, or greater than about 200 N, or greater than about 250 N, or greater than about 300 N.

In an embodiment, the padder pressure for the processes of the invention may be less than about 1 N/mm, or less than about 2 N/mm, or less than about 3 N/mm, or less than about 4 N/mm, or less than about 4 N/mm, or less than about 5 N/mm, or less than about 6 N/mm, or less than about 7 N/mm, or less than about 8 N/mm, or less than about 9 N/mm, or less than about 10 N/mm, or less than about 20 N/mm, or less than about 30 N/mm, or less than about 40 N/mm, or less than about 50 N/mm, or less than about 60 N/mm, or less than about 70 N/mm, or less than about 80 N/mm, or less than about 90 N/mm.

In an embodiment, the padder pressure for the processes of the invention may be greater than about 1 N/mm, or greater than about 2 N/mm, or greater than about 3 N/mm, or greater than about 4 N/mm, or greater than about 4 N/mm, or greater than about 5 N/mm, or greater than about 6 N/mm, or greater than about 7 N/mm, or greater than about 8 N/mm, or greater than about 9 N/mm, or greater than about 10 N/mm, or greater than about 20 N/mm, or greater than about 30 N/mm, or greater than about 40 N/mm, or greater than about 50 N/mm, or greater than about 60 N/mm, or greater than about 70 N/mm, or greater than about 80 N/mm, or greater than about 90 N/mm.

In an embodiment, the padder roller shore hardness for the processes of the invention may be less than about 70 shore A, or less than about 75 shore A, or less than about 80 shore A, or less than about 85 shore A, or less than about 90 shore A, or less than about 95 shore A, or less than about 100 shore A.

In an embodiment, the padder roller shore hardness for the processes of the invention may be greater than about 70 shore A, or greater than about 75 shore A, or greater than about 80 shore A, or greater than about 85 shore A, or greater than about 90 shore A, or greater than about 95 shore A, or greater than about 100 shore A.

In an embodiment, the stenter temperature for the processes of the invention may be less than about 70° C., or less than about 75° C., or less than about 80° C., or less than about 85° C., or less than about 90° C., or less than about 95° C., or less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C., or less than about 230° C.

In an embodiment, the stenter temperature for the processes of the invention may be greater than about 70° C., or greater than about 75° C., or greater than about 80° C., or greater than about 85° C., or greater than about 90° C., or greater than about 95° C., or greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C., or greater than about 230° C.

In an embodiment, the common drying temperatures for the processes of the invention may be less than about 110° C., or less than about 115° C., or less than about 120° C., or less than about 125° C., or less than about 130° C., or less than about 135° C., or less than about 140° C., or less than about 145° C., or less than about 150° C.

In an embodiment, the common drying temperatures for the processes of the invention may be greater than about 110° C., or greater than about 115° C., or greater than about 120° C., or greater than about 125° C., or greater than about 130° C., or greater than about 135° C., or greater than about 140° C., or greater than about 145° C., or greater than about 150° C.

In some embodiments, a silk fibroin coated material (e.g., fabric) may be heat resistant to a selected temperature where the selected temperature is chosen for drying, curing, and/or heat setting a dye that may be applied to the material (e.g., LYCRA). As used herein, a "heat resistant" may refer to a property of the silk fibroin coating deposited on the material where the silk fibroin coating and/or silk fibroin protein does not exhibit a substantial modification (i.e., "substantially modifying") in silk fibroin coating performance as compared to a control material having a comparable silk fibroin coating that was not subjected to the selected temperature for drying, curing, wash cycling, and/or heat setting purposes. In some embodiments, the selected temperature is the glass transition temperature (Tg) for the material upon which the silk fibroin coating is applied. In some embodiments, the selected temperature is greater than about 65° C., or greater than about 70° C., or greater than about 80° C., or greater than about 90° C., or greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C. In some embodiments, the selected temperature is less than about 65° C., or less than about 70° C., or less than about 80° C., or less than about 90° C., or less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C.

In an embodiment, "substantially modifying" silk fibroin coating performance may be a decrease in a selected property of silk fibroin coating, such as wetting time, absorption rate, spreading speed, accumulative one-way transport, or overall moisture management capability as compared to a control silk fibroin coating that was not subjected to the selected temperature for drying, curing, wash cycling, and/or heat setting purposes, where such decrease is less than about a 1% decrease, or less than about a 2% decrease, or less than about a 3% decrease, or less than about a 4% decrease, or less than about a 5% decrease, or less than about a 6% decrease, or less than about a 7% decrease, or less than about an 8% decrease, or less than about a 9% decrease, or less than about a 10% decrease, or less than about a 15% decrease, or less than about a 20% decrease, or less than about a 25% decrease, or less than about a 30% decrease, or less than about a 35% decrease, or less than about a 40% decrease, or less than about a 45% decrease, or less than about a 50% decrease, or less than about a 60% decrease, or less than about a 70% decrease, or less than about a 80% decrease, or less than about a 90% decrease, or less than about 100% decrease in wetting time, absorption rate, spreading speed, accumulative one-way transport, or overall moisture management capability as compared to a control silk fibroin coating that was not subjected to the selected temperature for drying, curing, wash cycling, and/or heat setting purposes. In some embodiments, "wash cycling" may refer to at least one wash cycle, or at least two wash cycles, or at least three wash cycles, or at least four wash cycles, or at least five wash cycles.

In an embodiment, "substantially modifying" silk fibroin coating performance may be an increase in a selected property of silk fibroin coating, such as wetting time, absorption rate, spreading speed, accumulative one-way transport, or overall moisture management capability as compared to a control silk fibroin coating that was not subjected to the selected temperature for drying, curing, wash cycling, and/or heat setting purposes, where such increase is less than about a 1% increase, or less than about a 2% increase, or less than about a 3% increase, or less than about a 4% increase, or less than about a 5% increase, or less than about a 6% increase, or less than about a 7% increase, or less than about an 8% increase, or less than about a 9% increase, or less than about a 10% increase, or less than about a 15% increase, or less than about a 20% increase, or less than about a 25% increase, or less than about a 30% increase, or less than about a 35% increase, or less than about a 40% increase, or less than about a 45% increase, or less than about a 50% increase, or less than about a 60% increase, or less than about a 70% increase, or less than about a 80% increase, or less than about a 90% increase, or less than about 100% increase in wetting time, absorption rate, spreading speed, accumulative one-way transport, or overall moisture management capability as compared to a control silk fibroin coating that was not subjected to the selected temperature for drying, curing, wash cycling, and/or heat setting purposes. In some embodiments, "wash cycling" may refer to at least one wash cycle, or at least two wash cycles, or at least three wash cycles, or at least four wash cycles, or at least five wash cycles.

In some embodiments, the SFS coated article may be subjected to heat setting in order to set one or more dyes that may be applied to the SFS coated article in order to permanently set the one or more dyes on the SFS coated article. In some embodiments, the SFS coated article may be heat setting resistant, wherein the SFS coating on the SFS coated article may resist a heat setting temperature of greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C. In some embodiments, the selected temperature is less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C.

In an embodiment, a material coated by the silk fibroin coating as described herein may partially dissolved or otherwise partially incorporated within a portion of the material after the silk fibroin coated material is subjected to heating and/or curing as described herein. Without being limited to any one theory of the invention, where the silk fibroin coated material is heated to greater than about the glass transition temperature (Tg) for the material that is coated, the silk fibroin coating may become partially dissolved or otherwise partially incorporated within a portion of the material.

In some embodiments, a material coated by the silk fibroin coating as described herein may be sterile or may be sterilized to provide a sterilized silk fibroin coated material. Alternatively, or in addition thereto, the methods described herein may include a sterile SFS prepared from sterile silk fibroin.

In some embodiments, the fabric constructions that are compatible with the processes of the invention include woven fabrics, knitted fabrics, and non-woven fabrics.

In some embodiments, the coating pattern provided by the processes of the invention include one side coating, two side coating, and/or throughout coating.

In some embodiments, the equipment manufacturers that are capable of producing equipment configured to continuously coat SFS on textiles include, but are not limited to, Aigle, Amba Projex, Bombi, Bruckner, Cavitec, Crosta, Dienes Apparatebau, Eastsign, Europlasma, Fermor, Fontanet, Gaston Systems, Hansa Mixer, Harish, Has Group, Icomatex, Idealtech, Interspare, Isotex, Klieverik, KTP, M P, Mageba, Mahr Feinpruef, Matex, Mathis, Menzel LP, Meyer, Monforts, Morrison Textile, Mtex, Muller Frick, Muratex Textile, Reliant Machinery, Rollmac, Salvade, Sandvik Tps, Santex, Chmitt-Machinen, Schott & Meissner, Sellers, Sicam, Siltex, Starlinger, Swatik Group India, Techfull, TMT Manenti, Unitech Textile Machinery, Weko, Willy, Wumag Texroll, Yamuna, Zappa, and Zimmer Austria.

In some embodiments, the equipment manufactures that are capable of producing equipment configured to dry SFS coated on textiles include, but are not limited to, Alea, Alkan Makina, Anglada, Atac Makina, Bianco, Bruckner, Campen, CHTC, CTMTC, Dilmenler, Elteksmak, Erbatech, Fontanet, Harish, Icomatex, Ilsung, Inspiron, Interspare, Master, Mathis, Monfongs, Monforts, Salvade, Schmitt-Maschinen, Sellers, Sicam, Siltex, Swastik Group India, Tacome, Tubetex, Turbang, Unitech Textile Machinery, and Yamuna.

In some embodiments, SFS may be used in combination with chemical agents. In some embodiments, SFS may include a chemical agent. In some embodiments, a chemical agent may be applied to a textile to be coated prior to providing an SFS coating. In some embodiments, a chemical agent may be applied to a textile after such textile has been coated with an SFS coating. In some embodiments, a chemical agent may be applied to a textile to be coated simultaneously with providing an SFS coating. One or more chemical agents may be applied, as set forth above, and may include a first chemical agent, second chemical agent, third chemical agent, and the like, where the chemical agents may be the same or a combination of two or more of the chemical agents described herein. In some embodiments, chemical agents may provide selected properties to coated textile (e.g., fabric) including, but not limited to, an antimicrobial property, an antiodor property, a water repellant property, an oil repellant property, a coloring property, a flame retardant property, a fabric softening property, a pH adjusting property, an anticrocking property, an antipilling property, and/or an antifelting property. In some embodiments, chemical agents may include, but are not limited to, an antimicrobial agent, acidic agents (e.g., Brønsted acids, citric acid, acetic acid, etc.), a softener, a water repellant agent, an oil repellant agent, a dye, a flame retardant, a fabric softener, a pH adjusting agent (e.g., an acidic agent), an anticrocking agent, an antipilling agent, and/or an antifelting agent. Such chemical agents may include, but are not limited to, softeners (e.g., chemical fabric softeners), acidic agents, antimicrobials, dyes, finishing agents including monomers (e.g., melted polyester), and combinations thereof.

In some embodiments, SFS may be used in combination with a dye. In some embodiments, SFS may include a dye. In some embodiments, a dye may be applied to a fabric, yarn, textile, or garment to be coated prior to providing an SFS coating. In some embodiments, a dye may be applied to a fabric, yarn, textile, or garment after such fabric, yarn, textile, or garment has been coated with an SFS coating. In some embodiments, a dye may be applied to a fabric, yarn, textile, or garment to be coated simultaneously with SFS coating the fabric, yarn, textile, or garment.

Absorption rate, spreading speed, accumulative one-way transport, flame retardant properties, coloring properties, fabric softening properties, a pH adjusting property, an antifelting property, and overall moisture management capability.

In some embodiments, SFS may be used in an SFS coating, where such coating includes one or more chemical agents (e.g., a silicone). SFS may be provided in such an SFS coating at a concentration by weight (% w/w or % w/v) or by volume (v/v) of less than about 25%, or less than about 20%, or less than about 15%, or less than about 10%, or less than about 9%, or less than about 8%, or less than about 7%, or less than about 6%, or less than about 5%, or less than about 4%, or less than about 3%, or less than about 2%, or less than about 1%, or less than about 0.9%, or less than about 0.8%, or less than about 0.7%, or less than about 0.6%, or less than about 0.5%, or less than about 0.4%, or less than about 0.3%, or less than about 0.2%, or less than about 0.1%, or less than about 0.01%, or less than about 0.001%. In some embodiments, SFS may be provided in such an SFS coating at a concentration by weight (% w/w or % w/v) or by volume (v/v) of greater than about 25%, or greater than about 20%, or greater than about 15%, or greater than about 10%, or greater than about 9%, or greater than about 8%, or greater than about 7%, or greater than about 6%, or greater than about 5%, or greater than about 4%, or greater than about 3%, or greater than about 2%, or greater than about 1%, or greater than about 0.9%, or greater than about 0.8%, or greater than about 0.7%, or greater than about 0.6%, or greater than about 0.5%, or greater than about 0.4%, or greater than about 0.3%, or greater than about 0.2%, or greater than about 0.1%, or greater than about 0.01%, or greater than about 0.001%.

In some embodiments, chemical fabric softeners may include silicones as described herein.

In some embodiments, the chemical agents may include the following, which are supplied by CHT Bezema and are associated with certain selected textile (e.g., fabric) properties, which may be used to strengthen SFS binding on coated surfaces and/or SFS may be used for enhancing the following chemical agents' properties:

ALPAPRINT CLEAR
  Silicone printing and coating
  Component B is mentioned in the technical leaflet
  Dry handle
  Good rubbing fastness
  Good washfastness
ALPAPRINT ELASTIC ADD
  Silicone printing and coating
  Component B is mentioned in the technical leaflet
  Good rubbing fastness
  Good washfastness
  Suited for yardage printing
ALPAPRINT WHITE
  Silicone printing and coating
  Component B is mentioned in the technical leaflet
  Dry handle
  Good rubbing fastness
  Good washfastness
ALPATEC 30142 A
  Textile finishing
  Coating
  Silicone printing and coating
  Component B is mentioned in the technical leaflet
  Suitable for narrow ribbon coating
  Good rubbing fastness
  Good washfastness
ALPATEC 30143 A
  Silicone printing and coating
  Component B is mentioned in the technical leaflet
  Good rubbing fastness
  Good washfastness
  Suited for yardage printing
ALPATEC 30191 A
  Silicone printing and coating
  Component B is mentioned in the technical leaflet
  Suitable for narrow ribbon coating
  High transparency
  Coating
ALPATEC 30203 A
  Silicone printing and coating
  Component B is mentioned in the technical leaflet
  Suitable for narrow ribbon coating
  High transparency
  Coating
ALPATEC 3040 LSR KOMP. A
  Functional coatings, Silicone printing and coating
  Component B is mentioned in the technical leaflet
  High abrasion resistance
  High transparency
  Coating
ALPATEC 3060 LSR KOMP. A
  Functional coatings, Silicone printing and coating
  Component B is mentioned in the technical leaflet
  High abrasion resistance
  High transparency
  Coating
ALPATEC 530
  Silicone printing and coating
  Suitable for narrow ribbon coating
  High transparency
  Coating
  One component system
ALPATEC 540
  Silicone printing and coating
  Suitable for narrow ribbon coating
  High transparency
  Coating
  One component system
ALPATEC 545
  Silicone printing and coating
  Suitable for narrow ribbon coating
  High transparency
  Coating
  One component system
ALPATEC 550
  Silicone printing and coating
  Suitable for narrow ribbon coating
  High transparency
  Coating
  One component system
ALPATEC 730
  Silicone printing and coating
  Suitable for narrow ribbon coating
  Good washfastness
  High abrasion resistance
  High transparency
ALPATEC 740
  Silicone printing and coating
  Suitable for narrow ribbon coating
  Good washfastness
  High abrasion resistance
  High transparency
ALPATEC 745
  Silicone printing and coating
  Suitable for narrow ribbon coating
  Good washfastness
  High abrasion resistance
  High transparency ALPATEC 750
  Silicone printing and coating
  Suitable for narrow ribbon coating
  Good washfastness
  High abrasion resistance
  High transparency
ALPATEC BANDAGE A
  Silicone printing and coating
  Component B is mentioned in the technical leaflet
  Suitable for narrow ribbon coating
  Coating
  Two component system
APYROL BASE2 E
  Flame retardants
  Liquid
  Soft handle
  For BS 5852/1+2
  Suited for paste coating
APYROL FCR-2
  Water repellency/oil repellency
  Cationic
  High effectiveness
  Water-based
  Liquid
APYROL FFD E
  Flame retardants
  Liquid
  Suited for polyester
  Suited for polyamide
  Flame inhibiting filler
APYROL FR CONC E
  Flame retardants, Functional coatings
  Liquid
  Suited for polyester
  Suited for polyamide
  Flame inhibiting filler
APYROL GBO-E
  Flame retardants, Functional coatings
  Suited for polyester
  Black-out coating
  For DIN 4102/B1
  Containing halogen
APYROL LV 21
  Flame retardants, Functional coatings
  For DIN 4102/B1
  Suited for paste coating
  Suited for backcoating of black-out vertical blinds and roller blinds
  Containing halogen
APYROL PP 31
  Flame retardants
  Liquid
  Free from antimony
  Flame inhibiting filler
  For BS 5852/1+2
APYROL PP 46
  Flame retardants
  Powder
  Free from antimony
  Flame inhibiting filler
  Suited for paste coating
APYROL PREM E
  Flame retardants
  Soft handle
  For BS 5852/1+2
  Containing halogen
  Semi-permanent
APYROL PREM2 E
  Flame retardants
  Soft handle
  For BS 5852/1+2
  Containing halogen
  Semi-permanent
COLORDUR 005 WHITE
  Flock adhesives, Functional coatings, Silicone printing and coating
  Based on silicone
  Dyestuff pigment suspension
COLORDUR 105 LEMON
  Flock adhesives, Functional coatings, Silicone printing and coating
  Based on silicone
  Dyestuff pigment suspension
COLORDUR 115 GOLDEN YELLOW
  Flock adhesives, Functional coatings, Silicone printing and coating
  Based on silicone
  Dyestuff pigment suspension
COLORDUR 185 ORANGE
  Flock adhesives, Functional coatings, Silicone printing and coating
  Based on silicone
  Dyestuff pigment suspension
COLORDUR 215 RED
  Flock adhesives, Functional coatings, Silicone printing and coating
  Based on silicone
  Dyestuff pigment suspension
COLORDUR 225 DARK RED
  Flock adhesives, Functional coatings, Silicone printing and coating
  Based on silicone
  Dyestuff pigment suspension
COLORDUR 285 VIOLET
  Flock adhesives, Functional coatings, Silicone printing and coating
  Based on silicone
  Dyestuff pigment suspension
COLORDUR 305 BLUE
  Flock adhesives, Functional coatings, Silicone printing and coating
  Based on silicone
  Dyestuff pigment suspension
COLORDUR 355 MARINE
  Flock adhesives, Functional coatings, Silicone printing and coating
  Based on silicone
  Dyestuff pigment suspension
COLORDUR 405 GREEN
  Flock adhesives, Functional coatings, Silicone printing and coating
  Based on silicone
  Dyestuff pigment suspension
COLORDUR 465 OLIVE GREEN
  Flock adhesives, Functional coatings, Silicone printing and coating
  Based on silicone
  Dyestuff pigment suspension
COLORDUR 705 BLACK
  Flock adhesives, Functional coatings, Silicone printing and coating
  Based on silicone
  Dyestuff pigment suspension COLORDUR AM ADDITIVE
  Flock adhesives, Silicone printing and coating
  Based on silicone
  Migration prevention
  Dyestuff pigment suspension
COLORDUR FL 1015 YELLOW
  Flock adhesives, Functional coatings, Silicone printing and coating
  Based on silicone
  Dyestuff pigment suspension
COLORDUR FL 1815 ORANGE
  Flock adhesives, Functional coatings, Silicone printing and coating
  Based on silicone
  Dyestuff pigment suspension
COLORDUR FL 2415 PINK
  Flock adhesives, Functional coatings, Silicone printing and coating
  Based on silicone
  Dyestuff pigment suspension
COLORDUR FL 4015 GREEN
  Flock adhesives, Functional coatings, Silicone printing and coating
  Based on silicone
  Dyestuff pigment suspension
ECOPERL 1
  Water repellency/oil repellency
  Washfast
  Sprayable
  Based on special functionalised polymers/waxes
  Cationic
ECOPERL ACTIVE
  Water repellency/oil repellency
  Washfast
  Based on special functionalised polymers/waxes
  Cationic
  High effectiveness
LAMETHAN 1 ET 25 BR 160
  Functional coatings, Lamination
  Washfast
  Transparent
  25 µm strong
  Film based on polyester urethane
LAMETHAN ADH-1
  Functional coatings, Lamination
  Breathable
  Suited for dry laminating
  Good stability to washing at 40° C.
  Stable foam adhesive
LAMETHAN ADH-L
  Functional coatings, Lamination
  Washfast
  Transparent
  Suited for paste coating
  Suited for wet laminating
LAMETHAN ALF-K
  Functional coatings, Lamination
  Adhesive additive for bondings
  Suited for dry laminating
  Stable foam adhesive
  Suited for stable foam coating
LAMETHAN LB 15-T BR 152DK
  Functional coatings, Lamination
  Transparent
  15 µm strong
  Breathable
  Suited for dry laminating
LAMETHAN LB 25 BR 155
  Functional coatings, Lamination
  Transparent
  25 µm strong
  Suited for dry laminating
  Good stability to washing at 40° C.
LAMETHAN LB 25 W BR 152
  Lamination
  25 µm strong
  Breathable
  Suited for dry laminating
  Good stability to washing at 40° C.
LAMETHAN TAPE DE 80
  Functional coatings, Lamination
  Polymer base: polyurethane
  Transparent
  Good stability to washing at 40° C.
  Tape for seam sealing
LAMETHAN TAPE ME 160
  Functional coatings, Lamination
  Polymer base: polyurethane
  Transparent
  Good stability to washing at 40° C.
  Tape for seam sealing
LAMETHAN VL-H920 O BR150
  Functional coatings, Lamination
  Two coats with membrane and PES charmeuse
  Breathable
  Suited for dry laminating
  Good stability to washing at 40° C.
LAMETHAN VL-H920 S BR 150
  Functional coatings, Lamination
  Two coats with membrane and PES charmeuse
  Breathable
  Suited for dry laminating
  Good stability to washing at 40° C.
LAMETHAN VL-H920 W BR150
  Functional coatings, Lamination
  Two coats with membrane and PES charmeuse
  Breathable
  Suited for dry laminating
  Good stability to washing at 40° C.
TUBICOAT A 12 E
  Binders, Functional coatings
  Anionic
  Liquid
  Formaldehyde-free
  Polymer base: polyacrylate
TUBICOAT A 17
  Binders, Functional coatings
  Suitable for tablecloth coating
  Anionic
  Liquid
  Self-crosslinking
TUBICOAT A 19
  Binders, Functional coatings
  Washfast
  Anionic
  Formaldehyde-free
  Good stability to washing
TUBICOAT A 22
  Binders, Functional coatings
  Washfast
  Medium-hard film
  Anionic
  Liquid TUBIJET NWA
  Ink jet printing preparation
TUBICOAT A 23
  Binders
  Medium-hard film
  Anionic
  Liquid
  Application for varying the handle
TUBICOAT A 28
  Binders, Functional coatings
  Anionic
  Liquid
  Formaldehyde-free
TUBIJET PUS
  Ink jet printing preparation
  Film forming
  Good stability to washing
TUBICOAT A 36
  Binders, Functional coatings
  Washfast
  Anionic
  Liquid
  Low formaldehyde
TUBICOAT A 37
  Binders, Functional coatings
  Washfast
  Suitable for tablecloth coating
  Anionic
  Liquid
TUBICOAT A 41
  Binders, Functional coatings
  Anionic
  Liquid
  Self-crosslinking
  Good fastnesses
TUBICOAT A 61
  Binders, Functional coatings
  Suitable for tablecloth coating
  Liquid
  Non-ionic
  Self-crosslinking
TUBICOAT A 94
  Binders, Functional coatings
  Anionic
  Liquid
  Self-crosslinking
  Good fastnesses
TUBICOAT AIB 20
  Fashion coatings
  Transparent
  Suited for foam coating
  Pearl Gloss Finish
TUBICOAT AOS
  Foaming auxiliaries
  Non-ionic
  Foaming
  Suited for the fluorocarbon finishing
TUBICOAT ASK
  Functional coatings, Lamination
  Adhesive additive for bondings
  Transparent
  Suited for paste coating
  Suited for dry laminating
TUBICOAT B-H
  Binders, Functional coatings
  Polymer base: Styrene butadiene
  Anionic
  Liquid
  Formaldehyde-free
TUBIJET VDK
  Ink jet printing preparation
TUBICOAT B 45
  Binders, Functional coatings
  Washfast
  Polymer base: Styrene butadiene
  Anionic
  Liquid
TUBICOAT BO-NB
  Functional coatings
  Medium hard
  Suited for black-out coating
  Good flexibility at low temperatures
  Suited for stable foam coating
TUBICOAT BO-W
  Functional coatings
  Suited for black-out coating
  Impermeable for light
  Suited for stable foam coating
  Water vapour permeable
TUBICOAT BOS
  Foaming auxiliaries
  Anionic
  Foaming
  Foam stabilizer
TUBICOAT DW-FI
  Functional coatings, Special products
  Anionic
  Suited for coating pastes
  Suited for stable foam
  Foamable
TUBICOAT E 4
  Binders
  Anionic
  Self-crosslinking
  Low formaldehyde
  Polymer base: polyethylene vinyl acetate
TUBICOAT ELC
  Functional coatings
  Suited for paste coating
  Black
  Electrically conductive
  Soft
TUBICOAT EMULGATOR HF
  Functional coatings, Special products
  Anionic
  Dispersing
  Suited for coating pastes
  Suited for stable foam
TUBICOAT ENTSCHÄUMER N
  Defoamers and deaerators
  Liquid
  Non-ionic
  Silicone-free
  Suited for coating pastes
TUBICOAT FIX FC
  Fixing agents
  Cationic
  Water-based
  Liquid
  Formaldehyde-free
TUBICOAT FIX ICB CONC.
  Fixing agents
  Liquid
  Non-ionic Formaldehyde-free
Suited for crosslinking
TUBICOAT FIXIERER AZ
  Fixing agents
  Liquid
  Suited for crosslinking
  Based on polyaziridin
  Unblocked
TUBICOAT FIXIERER FA
  Fixing agents
  Anionic
  Water-based
  Liquid
  Low formaldehyde
TUBICOAT FIXIERER H 24
  Fixing agents
  Anionic
  Water-based
  Liquid
  Formaldehyde-free
TUBICOAT FIXIERER HT
  Fixing agents
  Water-based
  Liquid
  Non-ionic
  Suited for crosslinking
TUBICOAT FOAMER NY
  Foaming auxiliaries
  Non-ionic
  Foaming
  Suited for the fluorocarbon finishing
  Non-yellowing
TUBICOAT GC PU
  Fashion coatings
  Washfast
  Soft handle
  Polymer base: polyurethane
  Transparent
TUBICOAT GRIP
  Functional coatings
  Slip resistant
  Suited for stable foam coating
  Soft
TUBICOAT HEC
  Thickeners
  Powder
  Non-ionic
  Stable to electrolytes
  Stable to shear forces
TUBICOAT HOP-S
  Special products
  Anionic
  Suited for coating pastes
  Coating
  Adhesion promoter
TUBICOAT HS 8
  Binders
  Anionic
  Liquid
  Formaldehyde-free
  Hard film
TUBICOAT HWS-1
  Functional coatings
  Suited for paste coating
  Water-proof
  Suited for giant umbrellas and tents
TUBICOAT KL-TOP F
  Fashion coatings, Functional coatings
  Washfast
  Polymer base: polyurethane
  Transparent
  Suited for paste coating
TUBICOAT KLS-M
  Fashion coatings, Functional coatings
  Washfast
  Soft handle
  Polymer base: polyurethane
  Breathable
TUBICOAT MAF
  Fashion coatings
  Washfast
  Matrix effect
TUBIJET WET
  Ink jet printing preparation
  Without impact on Improves the rubbing fastnesses
  Soft handle
TUBICOAT MD TC 70
  Fashion coatings
  Vintage wax
  Suited for foam coating
  Suited for topcoats
TUBICOAT MEA
  Functional coatings
  Washfast
  Polymer base: polyurethane
  Suited for paste coating
  Suited for topcoat coatings
TUBICOAT MG-R
  Fashion coatings
  Washfast
  Soft handle
  Suited for paste coating
  Duo Leather Finish
TUBICOAT MOP NEU
  Functional coatings, Special products
  Washfast
  Anionic
  Foamable
  Finish
TUBICOAT MP-D
  Fashion coatings, Functional coatings
  Washfast
  Soft handle
  Medium hard
  Breathable
TUBICOAT MP-W
  Functional coatings
  Washfast
  Polymer base: polyurethane
  Breathable
  Water-proof
TUBICOAT NTC-SG
  Functional coatings
  Washfast
  Transparent
  Suited for paste coating
  Medium hard
TUBICOAT PERL A22-20
  Fashion coatings
  Suited for paste coating
  Suited for foam coating
  Pearl Gloss Finish TUBICOAT PERL HS-1
  Functional coatings
  Suited for paste coating
  Suited for black-out coating
  Suited for pearlescent coating
  Suited for topcoat coatings
TUBICOAT PERL PU SOFT
  Fashion coatings
  Washfast
  Scarabaeus effect
  Soft handle
  Polymer base: polyurethane
TUBICOAT PERL VC CONC.
  Fashion coatings, Functional coatings
  Soft handle
  Polymer base: polyurethane
  Suited for paste coating
  Suited for black-out coating
TUBICOAT PHV
  Functional coatings
  Medium hard
  Suited for three-dimensional dot coating
TUBICOAT PSA 1731
  Functional coatings, Lamination
  Transparent
  Suited for paste coating
  Suited for dry laminating
  Non-breathable
TUBICOAT PU-UV
  Binders
  Anionic
  Liquid
  Formaldehyde-free
  Good fastnesses
TUBICOAT PU 60
  Binders
  Anionic
  Liquid
  Application for varying the handle
  Formaldehyde-free In some embodiments, the chemical agents of the invention may include the following inkjet printing dyes, which are supplied by CHT Bezema and are associated with certain selected textile (e.g., fabric) properties, which may be used in combination with SFS:

BEZAFLUOR BLUE BB
  Pigments
  High Performance
  BEZAFLUOR (fluorescent pigments)
BEZAFLUOR GREEN BT
  Pigments
  High Performance
  BEZAFLUOR (fluorescent pigments)
BEZAFLUOR ORANGE R
  Pigments
  High Performance
  BEZAFLUOR (fluorescent pigments)
BEZAFLUOR PINK BB
  Pigments
  High Performance
  BEZAFLUOR (fluorescent pigments)
BEZAFLUOR RED R
  Pigments
  High Performance
  BEZAFLUOR (fluorescent pigments)
BEZAFLUOR VIOLET BR
  Pigments
  High Performance
  BEZAFLUOR (fluorescent pigments)
BEZAFLUOR YELLOW BA
  Pigments
  High Performance
  BEZAFLUOR (fluorescent pigments)
BEZAPRINT BLACK BDC
  Pigments
  Advanced
  BEZAPRINT (classic pigments)
BEZAPRINT BLACK DT
  Pigments
  Advanced
  BEZAPRINT (classic pigments)
BEZAPRINT BLACK DW
  Pigments
  Advanced
  BEZAPRINT (classic pigments)
BEZAPRINT BLACK GOT
  Pigments
  High Performance
  BEZAKTIV GOT (GOTS)
BEZAPRINT BLUE BN
  Pigments
  Advanced
  BEZAPRINT (classic pigments)
BEZAPRINT BLUE BT
  Pigments
  Advanced
  BEZAPRINT (classic pigments)
BEZAPRINT BLUE GOT
  Pigments
  High Performance
  BEZAKTIV GOT (GOTS)
BEZAPRINT BLUE RR
  Pigments
  Advanced
  BEZAPRINT (classic pigments)
BEZAPRINT BLUE RT
  Pigments
  Advanced
  BEZAPRINT (classic pigments)
BEZAPRINT BLUE RTM
  Pigments
  Advanced
  BEZAPRINT (classic pigments)
BEZAPRINT BLUE TB
  Pigments
  Advanced
  BEZAPRINT (classic pigments)
BEZAPRINT BORDEAUX K2R
  Pigments
  Advanced
  BEZAPRINT (classic pigments)
BEZAPRINT BROWN RP
  Pigments
  Advanced
  BEZAPRINT (classic pigments)
BEZAPRINT BROWN TM
  Pigments
  Advanced
  BEZAPRINT (classic pigments)

BEZAPRINT CITRON 10G
  Pigments
  Advanced
  BEZAPRINT (classic pigments)
BEZAPRINT CITRON GOT
  Pigments
  High Performance
  BEZAKTIV GOT (GOTS)
BEZAPRINT GREEN 2B
  Pigments
  Advanced
  BEZAPRINT (classic pigments)
BEZAPRINT GREEN BS
  Pigments
  Advanced
  BEZAPRINT (classic pigments)
BEZAPRINT GREEN BT
  Pigments
  Advanced
  BEZAPRINT (classic pigments)
BEZAPRINT GREY BB
  Pigments
  Advanced
  BEZAPRINT (classic pigments)
BEZAPRINT NAVY GOT
  Pigments
  High Performance
  BEZAKTIV GOT (GOTS)
BEZAPRINT NAVY RRM
  Pigments
  Advanced
  BEZAPRINT (classic pigments)
BEZAPRINT NAVY TR
  Pigments
  Advanced
  BEZAPRINT (classic pigments)
BEZAPRINT OLIVE GREEN BT
  Pigments
  Advanced
  BEZAPRINT (classic pigments)
BEZAPRINT ORANGE 2G
  Pigments
  Advanced
  BEZAPRINT (classic pigments)
BEZAPRINT ORANGE GOT
  Pigments
  High Performance
  BEZAKTIV GOT (GOTS)
BEZAPRINT ORANGE GT
  Pigments
  Advanced
  BEZAPRINT (classic pigments)
BEZAPRINT ORANGE RG
  Pigments
  Advanced
  BEZAPRINT (classic pigments)
BEZAPRINT PINK BW
  Pigments
  Advanced
  BEZAPRINT (classic pigments)
BEZAPRINT RED 2BN
  Pigments
  Advanced
  BEZAPRINT (classic pigments)
BEZAPRINT RED GOT
  Pigments
  High Performance
  BEZAKTIV GOT (GOTS)
BEZAPRINT RED KF
  Pigments
  Advanced
  BEZAPRINT (classic pigments)
BEZAPRINT RED KGC
  Pigments
  Advanced
  BEZAPRINT (classic pigments)
BEZAPRINT SCARLET GRL
  Pigments
  Advanced
  BEZAPRINT (classic pigments)
BEZAPRINT SCARLET RR
  Pigments
  Advanced
  BEZAPRINT (classic pigments)
BEZAPRINT TURQUOISE GT
  Pigments
  Advanced
  BEZAPRINT (classic pigments)
BEZAPRINT VIOLET FB
  Pigments
  Advanced
  BEZAPRINT (classic pigments)
BEZAPRINT VIOLET KB
  Pigments
  Advanced
  BEZAPRINT (classic pigments)
BEZAPRINT VIOLET R
  Pigments
  Advanced
  BEZAPRINT (classic pigments)
BEZAPRINT VIOLET TN
  Pigments
  Advanced
  BEZAPRINT (classic pigments)
BEZAPRINT YELLOW 2GN
  Pigments
  Advanced
  BEZAPRINT (classic pigments)
BEZAPRINT YELLOW 3GT
  Pigments
  Advanced
  BEZAPRINT (classic pigments)
BEZAPRINT YELLOW 4RM
  Pigments
  Advanced
  BEZAPRINT (classic pigments)
BEZAPRINT YELLOW GOT
  Pigments
  High Performance
  BEZAKTIV GOT (GOTS)
BEZAPRINT YELLOW RR
  Pigments
  Advanced
  BEZAPRINT (classic pigments)

In some embodiments, the chemical agents of the invention may include the following, which are supplied by Lamberti SPA and are associated with certain selected textile (e.g., fabric) properties, which may be used to strengthen SFS binding on coated surfaces or SFS may be used for enhancing such chemical agent properties:

Pre Treatment:
Waterborne Polyurethanes Dispersions
Rolflex AFP.
Aliphatic polyether polyurethane dispersion in water. The product has high hydrolysis resistance, good breaking load resistance and excellent tear resistance.
Rolflex ACF.
Aliphatic polycarbonate polyurethane dispersion in water. The product shows good PU and PVC bonding properties, excellent abrasion resistance as well as chemical resistance, included alcohol.
Rolflex V 13.
Aliphatic polyether/acrylic copolymer polyurethane dispersion in water. The product has good thermoadhesive properties and good adhesion properties on PVC.
Rolflex K 80.
Aliphatic polyether/acrylic copolymer polyurethane dispersion in water. ROLFLEX K 80 is specifically designed as a high performing adhesive for textile lamination. The product has excellent perchloroethylene and water fastness.
Rolflex ABC.
Aliphatic polyether polyurethane dispersion in water. Particularly, the product presents very high water column, excellent electrolytes resistance, high LOI index, high resistance to multiple bending.
Rolflex ADH.
Aliphatic polyether polyurethane dispersion in water. The product has a very high water column resistance.
Rolflex W4.
Aliphatic waterborned PU dispersion particularly suggested for the formulation of textile coatings for clothing, outwear where a full, soft and non sticky touch is required.
Rolflex ZB7.
Aliphatic waterborned PU dispersion particularly suggested for the formulation of textile coatings for clothing, outwear, sportswear, fashion and technical articles for industrial applications. The product has a very high charge digestion properties, electrolytes stability and excellent mechanical and tear resistance.
TUBICOAT PU 80
Binders, Functional coatings
Washfast
Anionic
Liquid
Can be washed off
TUBICOAT PUH-BI
Binders
Anionic
Liquid
Formaldehyde-free
Hard film
TUBICOAT PUL
Functional coatings
Polymer base: polyurethane
Suited for paste coating
Rolflex BZ 78.
Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application.
Rolflex PU 147.
Aliphatic polyether polyurethane dispersion in water. This product shows good film forming properties at room temperature. It has high fastness to light and ultraviolet radiation and good resistance to water, solvent and chemical agents, as well as mechanical resistance.
Rolflex SG.
Aliphatic polyether polyurethane dispersion in water. Due to its thermoplastic properties it is suggested to formulate heat activated adhesives at low temperatures.
Elafix PV 4.
Aliphatic blocked isocyanate Nano-dispersion used in order to give antifelting and antipilling properties to pure wool fabrics and his blend.
Rolflex C 86.
Aliphatic cationic waterborned PU dispersion particularly suggested for the formulation of textile coatings for clothing, outwear, fashion where medium-soft and pleasant full touch is required. Fabrics treated with the product can be dyed with a selection of dyes, to get double-color effects of different intensity.
Rolflex CN 29.
Aliphatic cationic waterborned PU dispersion particularly suggested for the formulation of textile coatings for clothing, outwear, fashion where soft and pleasant full touch is required. Fabrics treated with the product can be dyed with a selection of dyes, to get double-color effects of different intensity.
Oil and water repellents
Lamgard FT 60.
General purpose fluorocarbon resin for water and oil repellency; by padding application.
Lamgard 48.
High performance fluorocarbon resin for water and oil repellency; by padding application. High rubbing fastness.
Imbitex NRW3
Wetting agent for water-and oil repellent finishing.
Lamgard EXT.
Crosslinker for fluorocarbon resins to improve washing fastness.
Flame retardants
Piroflam 712.
Non-permanent flame retardant compound for padding and spray application.
Piroflam ECO.
Alogen free flame retardant compound for back coating application for all kind of fibers.
Piroflam UBC.
Flame retardant compound for back coating application for all kind of fibers.
Crosslinkers
Rolflex BK8.
Aromatic blocked polyisocyanate in water dispersion. It is suggested as a cross-linking agent in coating pastes based of polyurethane resins to improve washing fastness.

Fissativo 05.
Water dispersible aliphatic polyisocyanate suitable as crosslinking agent for acrylic and polyurethane dispersions to improve adhesion and wet and dry scrub resistance.

Resina MEL.
Melammine-formaldheyde resin.

Cellofix VLF.
Low formaldehyde melamine resin.

Lambicol CL 60.
Fully neutralized synthetic thickener for pigment printing in oil/water emulsion; medium viscosity type Viscolam PU conc.
Nonionic polyurethane based thickener with pseudoplastic behavior Viscolam 115 new.
Acrylic thickener not neutralized Viscolam PS 202.
Nonionic polyurethane based thickener with newtonian behavior Viscolam 1022.
Nonionic polyurethane based thickener with moderate pseudoplastic behavior.

Dyeing
  Dispersing Agents
    Lamegal BO.
      dispersing agent non ionic, suitable for direct, reactive, disperse dyeing and PES stripping
    Lamegal DSP.
      Dispersing/anti back-staining agent in preparation, dyeing and soaping of dyed and printed materials. Antioligomer agent.
    Lamegal 619.
      Effective low foam dispersing leveling agent for dyeing of PES
    Lamegal TL5.
      Multi-purpose sequestring and dispersing agent for all kind of textile process
  Levelling Agents
    Lamegal A 12.
      Leveling agent for dyeing on wool, polyamide and its blends with acid or metalcomplex dyes
    Lamfix L.
      Fixing agent for direct and reactive dyestuffs, containing formaldheyde
    Lamfix LU conc.
      Formaldehyde free cationic fixing agent for direct and reactive dyes. It does not affect the shade and light fastness.
    Lamfix PA/TR.
      Fixing agent to improve the wet fastness of acid dyes on polyamide fabrics, dyed or printed and polyamide yarns. Retarding agent in dyeing of Polyamide/cellulosic blends with direct dyes.
  Special Resins
    Denifast TC.
      Special resin for cationization of cellulose fibers to obtain special effects ("DENIFAST system" and "DENISOL system").
    Cobral DD/50.
      Special resin for cationization of cellulose fibers to obtain special effect ("DENIFAST system" and "DENISOL system").
  Antireducing Agents
    Lamberti Redox L2S gra.
      Anti-reducing agent in grain form. 100% active content
    Lamberti Redox L2S liq.
      Anti-reducing agent in liquid form for automatic dosage.
  Anticreasing Agent
    Lubisol AM.
      Lubricating and anti creasing agent for rope wet operation on all kind of fibers and machines.

Pigment Dye
  Antimigrating agent
    Neopat Compound 96/m conc.
      Compound, developed as migration inhibitor for continuous dyeing process with pigments (pad-dry process).
  Binding agent
    Neopat Binder PM/S conc.
      Concentrated version of a specific binder used to prepare pad-liquor for dyeing with pigments (pad-dry process).
  All in One agent
    Neopat Compound PK1.
      High concentrated compound specifically developed as migration inhibitor with specific binder for continuous dyeing process with pigments (pad-dry process) all in one
  Delavè agent
    Neopat compound FTN.
      High concentrated compound of surfactants and polymers specifically developed for pigment dyeing and pigment-reactive dyeing process; especially for medium/dark shades for wash off effect Traditional Finishing Agents
  Wrinkle free treatment
    Cellofix ULF conc.
      Anti-crease modified glyoxalic resin for finishing of cottons, cellulosics and blend with synthetics fibers.
    Poliflex PO 40.
      Polyethilenic resin for waxy, full and slippy handle by foulard applications.
    Rolflex WF.
      Aliphatic waterborned Nano-PU dispersion used as extender for wrinkle free treatments.
  Softeners
    Texamina C/FPN.
      softening agent with a very soft handle particularly recommended for application by exhaustion for all kind of fabrics. Suitable also for cone application.
    Texamina C SAL flakes.
      100% cationic softening agent in flakes form for all type of fabrics. at room temperature.
    Texamina CL LIQ.
      Anphoteric softening agent for all types of fabrics. Not yellowing.
    Texamina HVO.
      Anphoteric softening agent for woven and knitted fabrics of cotton, other cellulosics and blends. Gives a soft, smooth and dry handle. Applied by padding.
    Texamina SIL.
      Nonionic silicon dispersion in water. Excellent softening, lubricating and anti-static properties for all fibre types by padding.

Texamina SILK.
  Special cationic softener with silk protein inside. Gives a "swollen touch" particularly suitable for cellulosic, wool, silk.
Lamfinish LW.
  All-in compound based on special polymeric hydrophilic softeners; by coating, foulard, and exhaustion.
Elastolam E50.
  General purpose mono-component silicone elastomeric softener for textile finishing.
Elastolam EC 100.
  Modified polysiloxane micro-emulsion which gives a permanent finishing, with extremely soft and silky handle.
Handle modifier
  Poliflex CSW.
    anti-slipping agent.
  Poliflex R 75.
    Parafine finishing agent to give waxy handle.
  Poliflex s.
    Compound specifically developed for special writing effects.
  Poliflex m.
    Compound for special dry-waxy handle.
  Lamsoft SW 24.
    Compound for special slippy handle specifically developed for coating application.
  Lamfinish SLIPPY.
    All-in compound to get a slippy touch; by coating.
  Lamfinish GUMMY.
    All-in compound to get a gummy touch; by coating.
  Lamfinish OLDRY.
    All-in compound to get dry-sandy touch especially suitable for vintage effects; by coating
Waterborne Polyurethanes Dispersions
  Rolflex LB 2.
    Aliphatic waterborned PU dispersion particularly suggested for the formulation of textile coatings where bright and rigid top finish is required. It is particularly suitable as a finishing agent for organza touch on silk fabrics. and shiny.
  RolflexSuited for three-dimensional dot coating
  Slip resistant
TUBICOAT PUS
  Binders, Functional coatings
  Anionic
  Liquid
  Formaldehyde-free
  Polymer base: polyurethane
TUBICOAT PUW-M
  Binders
  Medium-hard film
  Anionic
  Liquid
  Formaldehyde-free
TUBICOAT PUW-S
  Binders
  Anionic
  Liquid
  Formaldehyde-free
  Good stability to washing
TUBICOAT PW 14
  Binders, Functional coatings
  Anionic
  Formaldehyde-free
  Heat-sealable
  Not wetting
TUBICOAT SA-M
  Functional coatings
  Washfast
  Suited for paste coating
  Suited for three-dimensional dot coating
TUBICOAT SCHAUMER HP
  Foaming auxiliaries, Functional coatings
  Non-ionic
  Foaming
  Suited for the fluorocarbon finishing
TUBICOAT SF-BASE
  Fashion coatings
  Washfast
  Soft handle
  Suited for foam coating
  Silk gloss effect
TUBICOAT SHM
  Foaming auxiliaries
  Anionic
  Foam stabilizer
TUBICOAT SI 55
  Special products
  Pseudo-cationic
  Suited for coating pastes
  Foamable
  Coating
TUBICOAT STABILISATOR RP
  Foaming auxiliaries
  Anionic
  Foam stabilizer
TUBICOAT STC 100
  Fashion coatings, Functional coatings
  Transparent
  Breathable
  Suited for stable foam coating
TUBICOAT STC 150
  Fashion coatings, Functional coatings
  Washfast
  Soft handle
  Transparent
  Breathable
TUBICOAT STL
  Functional coatings
  Washfast
  Slip resistant
  Suited for stable foam coating
  Soft
TUBICOAT TCT
  Fashion coatings, Functional coatings
  Washfast
  Polymer base: polyurethane
  Transparent
  Suited for paste coating
TUBICOAT VA 10
  Binders
  Anionic
  Liquid
  Formaldehyde-free
  Hard film
TUBICOAT VCP
  Functional coatings
  Suited for paste coating
  Medium hard
  Suited for black-out coating TUBICOAT VERDICKER 17
  Thickeners
  Anionic
  High efficiency
TUBICOAT VERDICKER ASD
  Thickeners
  Anionic
  Quick swelling
  Stable to shear forces
  Pseudoplastic
TUBICOAT VERDICKER LP
  Thickeners
  Anionic
  Stable to shear forces
  Pseudoplastic
  Dispersible
TUBICOAT VERDICKER PRA
  Thickeners
  Anionic
  Liquid
  Stable to electrolytes
  Rheological additive
TUBICOAT WBH 36
  Special products
  Finish
  Application for preventing roller deposits
TUBICOAT WBV
  Special products
  Non-ionic
  Finish
  Application for preventing roller deposits
TUBICOAT WEISS EU
  Functional coatings, Special products
  Suited for coating pastes
  Suited for stable foam
  Suited for topcoat coatings
  Titanium dioxide paste
TUBICOAT WLI-LT KONZ
  Functional coatings
  Washfast
  Suited for paste coating
  Slip resistant
  Soft
TUBICOAT WLI
  Fashion coatings, Functional coatings
  Washfast
  Scarabaeus effect
  Soft handle
  Suited for paste coating
TUBICOAT WOT
  Fashion coatings
  Washfast
  Soft handle
  Suited for paste coating
  Wash-out effect
TUBICOAT WX-TCA 70
  Fashion coatings, Functional coatings
  Vintage wax
  Suited for paste coating
  Suited for topcoat coatings
TUBICOAT WX BASE
  Fashion coatings
  Vintage wax
  Soft handle
  Suited for paste coating
  Application in the prime coat
TUBICOAT ZP NEU
  Water repellency/oil repellency
  Zircon-paraffine base
  Suited for aqueous systems
  Cationic
  Foamable
  Liquid
TUBIGUARD 21
  Water repellency/oil repellency
  Washfast
  Cationic
  High effectiveness
  Water-based
TUBIGUARD 25-F
  Water repellency/oil repellency
  Washfast
  Sprayable
  Cationic
  High effectiveness
TUBIGUARD 270
  Functional coatings, Water repellency/oil repellency
  Washfast
  Cationic
  High effectiveness
  Liquid
TUBIGUARD 30-F
  Water repellency/oil repellency
  Washfast
  Sprayable
  Cationic
  High effectiveness
TUBIGUARD 44 N
  Water repellency/oil repellency
  Washfast
  Sprayable
  Suited for aqueous systems
  Liquid
TUBIGUARD 44N-F
  Water repellency/oil repellency
  Suited for aqueous systems
  Non-ionic
  Suited for polyester
  Foamable
TUBIGUARD 66
  Water repellency/oil repellency
  Washfast
  Sprayable
  High effectiveness
  Liquid
TUBIGUARD 90-F
  Water repellency/oil repellency
  Washfast
  Cationic
  High effectiveness
  Liquid
TUBIGUARD AN-F
  Water repellency/oil repellency
  Washfast
  Sprayable
  Cationic
  High effectiveness
TUBIGUARD FA2-F
  Water repellency/oil repellency
  Sprayable
  Cationic
  Suited for polyester
  Foamable TUBIGUARD PC3-F
  Functional coatings, Water repellency/oil repellency
  Washfast
  Cationic
  Liquid
  Paste
TUBIGUARD SR 2010-F W
  Water repellency/oil repellency
  Cationic
  High effectiveness
  Foamable
  Based on C6 fluorocarbon
TUBIGUARD 10-F
  Water repellency/oil repellency
  Washfast
  Sprayable
    CationicAliphatic waterborned PU dispersion particularly suggested for the formulation of textile coatings for outwear, luggage, technical articles especially where hard and flexible touch is required. and shiny.
Rolflex PU 879.
  Aliphatic waterborned PU dispersion particularly suggested for the formulation of textile coatings for outwear, luggage, technical articles where a medium-hard and flexible touch is required.
Rolflex ALM.
  Aliphatic waterborned PU dispersion particularly suggested for the formulation of textile coatings for outwear, luggage, technical articles where a soft and flexible touch is required. Can be also suitable for printing application.
Rolflex AP.
  Aliphatic waterborned PU dispersion particularly suggested for the formulation of textile coatings for outwear, fashion where a soft and gummy touch is required.
Rolflex W4.
  Aliphatic waterborned PU dispersion particularly suggested for the formulation of textile coatings for clothing, outwear where a full, soft and non sticky touch is required.
Rolflex ZB7.
  Aliphatic waterborned PU dispersion particularly suggested for the formulation of textile coatings for clothing, outwear, sportswear, fashion and technical articles for industrial applications. The product has a very high charge digestion properties, electrolites stability and excellent mechanical and tear resistance. Can be also suitable for foam coating and printing application.
Rolflex BZ 78.
  Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application.
Rolflex K 110.
  Gives to the coated fabric a full, soft, and slightly sticky handle with excellent fastness on all types of fabrics.
Rolflex OP 80.
  Aliphatic waterborned PU dispersion particularly suggested for the formulation of textile coatings for outwear, luggage and fashion finishes where an opaque non writing effect is desired.
Rolflex NBC.
  Aliphatic waterborned PU dispersion generally used by padding application as a filling and zero formaldheyde sizing agent. Can be used for outwear and fashion finishings where a full, elastic and non sticky touch is required.
Rolflex PAD.
  Aliphatic waterborned PU dispersion specifically designed for padding application for outwear, sportswear and fashion applications where a full, elastic and non sticky touch is required. Excellent washing and dry cleaning fastness as well as good bath stability.
Rolflex PN.
  Aliphatic waterborned PU dispersion generally applied by padding application for outerwear and fashion high quality applications where strong, elastic non sticky finishes are required.
Elafix PV 4.
  Aliphatic blocked isocyanate Nano-dispersion used in order to give antifelting and antipilling properties to pure wool fabrics and his blend.
Rolflex SW3.
  Aliphatic waterborned PU dispersion particularly suggested to be used by padding application for the finishing of outwear, sportswear and fashion where a slippery and elastic touch is required. It is also a good antipilling agent. Excellent in wool application.
Rolflex C 86.
  Aliphatic cationic waterborned PU dispersion particularly suggested for the formulation of textile coatings for clothing, outwear, fashion where medium-soft and pleasant full touch is required. Fabrics treated with the product can be dyed with a selection of dyes, to get double-color effects of different intensity.
Rolflex CN 29.
  Aliphatic cationic waterborned PU dispersion particularly suggested for the formulation of textile coatings for clothing, outwear, fashion where soft and pleasant full touch is required. Fabrics treated with the product can be dyed with a selection of dyes, to get double-color effects of different intensity.
Other resins
  Textol 110.
    Handle modifier with very soft handle for coating finishes
  Textol RGD.
    Water emulsion of acrylic copolymer for textile coating, with very rigid handle.
  Textol SB 21.
    Butadienic resin for finishing and binder for textile printing
  Appretto PV/CC.
    Vinylacetate water dispersion for rigid stiffening
  Amisolo B.
    CMS water dispersion for textile finishing as stiffening agent
  Lamovil RP.
    PVOH stabilized solution as stiffening agent Technical Finishing Agents
  Waterborne Polyurethanes Dispersions
    Rolflex AFP.
      Aliphatic polyether polyurethane dispersion in water. The product has high hydrolysis resistance, good breaking load resistance and excellent tear resistance.
    Rolflex ACF.
      Aliphatic polycarbonate polyurethane dispersion in water. The product shows good PU and PVC bonding properties, excellent abrasion resistance as well as chemical resistance, included alcohol.
    Rolflex V 13.
      Aliphatic polyether/acrylic copolymer polyurethane dispersion in water. The product has good thermoadhesive properties and good adhesion properties on PVC.
    Rolflex K 80.
      Aliphatic polyether/acrylic copolymer polyurethane dispersion in water. ROLFLEX K 80 is specifically designed as a high performing adhesive for textile lamination. The product has excellent perchloroethylene and water fastness.
    Rolflex ABC.
      Aliphatic polyether polyurethane dispersion in water. Particularly, the product presents very high water column, excellent electrolytes resistance, high LOI index, high resistance to multiple bending.
    Rolflex ADH.
      Aliphatic polyether polyurethane dispersion in water. The product has a very high water column resistance.
    Rolflex W4.
      Aliphatic waterborned PU dispersion particularly suggested for the formulation of textile coatings for clothing, outwear where a full, soft and non sticky touch is required.
    Rolflex ZB7.
      Aliphatic waterborned PU dispersion particularly suggested for the formulation of textile coatings for clothing, outwear, sportswear, fashion and technical articles for industrial applications. The product has a very high charge digestion properties, electrolites stability and excellent mechanical and tear resistance. Can be also suitable for foam coating and printing application.
    Rolflex BZ 78.
      Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application.
    Rolflex PU 147.
      Aliphatic polyether polyurethane dispersion in water. This product shows good film forming properties at room temperature. It has high fastness to light and ultraviolet radiation and good resistance to water, solvent and chemical agents, as well as mechanical resistance.
    Rolflex SG.
      Aliphatic polyether polyurethane dispersion in water. Due to its thermoplastic properties it is suggested to formulate heat activated adhesives at low temperatures.
    Elafix PV 4.
      Aliphatic blocked isocyanate Nano-dispersion used in order to give antifelting and antipilling properties to pure wool fabrics and his blend.
    Rolflex C 86.
      Aliphatic cationic waterborned PU dispersion particularly suggested for the formulation of textile coatings for clothing, outwear, fashion where medium-soft and pleasant full touch is required. Fabrics treated with the product can be dyed with a selection of dyes, to get double-color effects of different intensity.
    Rolflex CN 29.
      Aliphatic cationic waterborned PU dispersion particularly suggested for the formulation of textile coatings for clothing, outwear, fashion where soft and pleasant full touch is required. Fabrics treated with the product can be dyed with a selection of dyes, to get double-color effects of different intensity.
  Oil and water repellents
    Lamgard FT 60.
      General purpose fluorocarbon resin for water and oil repellency; by padding application.
    Lamgard 48.
      High performance fluorocarbon resin for water and oil repellency; by padding application. High rubbing fastness.
    Imbitex NRW3.
      Wetting agent for water-and oil repellent finishing.
    Lamgard EXT.
      Crosslinker for fluorocarbon resins to improve washing fastness.
  Flame retardants
    Piroflam 712.
      Non-permanent flame retardant compound for padding and spray application.
    Piroflam ECO.
      Alogen free flame retardant compound for back coating application for all kind of fibers.
    Piroflam UBC.
      Flame retardant compound for back coating application for all kind of fibers.
  Crosslinkers
    Rolflex BK8.
      Aromatic blocked polyisocyanate in water dispersion. It is suggested as a cross-linking agent in coating pastes based of polyurethane resins to improve washing fastness.
    Fissativo 05.
      Water dispersible aliphatic polyisocyanate suitable as crosslinking agent for acrylic and polyurethane dispersions to improve adhesion and wet and dry scrub resistance.
    Resina MEL.
      Melammine-formaldheyde resin.
    Cellofix VLF.
      Low formaldehyde melamine resin.
  Thickeners
    Lambicol CL 60.
      Fully neutralized synthetic thickener for pigment printing in oil/water emulsion; medium viscosity type Viscolam PU conc.
  Nonionic polyurethane based thickener with pseudoplastic behavior
Viscolam 115 new.
  Acrylic thickener not neutralized
Viscolam PS 202.
  Nonionic polyurethane based thickener with newtonian behavior
Viscolam 1022.
  Nonionic polyurethane based thickener with moderate pseudoplastic behavior.

In some embodiments, the chemical agent may include one or more of a silicone, an acidic agent, a dyeing agent, a pigment dye, a traditional finishing agent, and a technical finishing agent. The dyeing agent may include one or more of a dispersing agent, a levelling agent, a fixing agent, a special resin, an antireducing agent, and an anticreasing agent. The pigment dye may include one or more of an antimigrating agent, a binding agent, an all in one agent, and a delave agent. The traditional finishing agent may include one or more of a wrinkle free treatment, a softener, a handle modifier, a waterborne polyurethanes dispersion, and other resins. The technical finishing agent may include one or more of a waterborne polyurethanes dispersion, an oil repellant, a water repellant, a crosslinker, and a thickener.

In some embodiments, certain chemical agents of the invention may be provided by one or more of the following chemical suppliers: Adrasa, AcHitex Minerva, Akkim, Archroma, Asutex, Avocet dyes, BCC India, Bozzetto group, CHT, Clearity, Dilube, Dystar, Eksoy, Erca group, Genkim, Giovannelli e Figli, Graf Chemie, Huntsman, KDN Bio, Lamberti, U Specialties, Marlateks, Montegauno, Protex, Pulcra Chemicals, Ran Chemicals, Fratelli Ricci, Ronkimya, Sarex, Setas, Silitex, Soko Chimica, Tanatex Chemicals, Zaitex, Zetaesseti, and Z Schimmer.

In some embodiments, the chemical agent may include an acidic agent. Accordingly, in some embodiments, SFS may include an acidic agent. In some embodiments, an acidic agent may be a Bronsted acid. In an embodiment, the acidic agent includes one or more of citric acid and acetic acid. In an embodiment, the acidic agent aids the deposition and coating of SPF mixtures (i.e., SFS coating) on the textile to be coated as compared to the absence of such acidic agent. In an embodiment, the acidic agent improves crystallization of the SPF mixtures at the textile to be coated.

In an embodiment, the acidic agent is added at a concentration by weight (% w/w or % w/v) or by volume (v/v) of greater than about 0.001%, or greater than about 0.002%, or greater than about 0.003%, or greater than about 0.004%, or greater than about 0.005%, or greater than about 0.006%, or greater than about 0.007%, or greater than about 0.008%, or greater than about 0.009%, or greater than about 0.01%, or greater than about 0.02%, or greater than about 0.03%, or greater than about 0.04%, or greater than about 0.05%, or greater than about 0.06%, or greater than about 0.07%, or greater than about 0.08%, or greater than about 0.09%, or greater than about 0.1%, or greater than about 0.2%, or greater than about 0.3%, or greater than about 0.4%, or greater than about 0.5%, or greater than about 0.6%, or greater than about 0.7%, or greater than about 0.8%, or greater than about 0.9%, or greater than about 1.0% or greater than about 2.0%, or greater than about 3.0%, or greater than about 4.0%, or greater than about 5.0%.

In an embodiment, the acidic agent is added at a concentration by weight (% w/w or % w/v) or by volume (v/v) of less than about 0.001%, or less than about 0.002%, or less than about 0.003%, or less than about 0.004%, or less than about 0.005%, or less than about 0.006%, or less than about 0.007%, or less than about 0.008%, or less than about 0.009%, or less than about 0.01%, or less than about 0.02%, or less than about 0.03%, or less than about 0.04%, or less than about 0.05%, or less than about 0.06%, or less than about 0.07%, or less than about 0.08%, or less than about 0.09%, or less than about 0.1%, or less than about 0.2%, or less than about 0.3%, or less than about 0.4%, or less than about 0.5%, or less than about 0.6%, or less than about 0.7%, or less than about 0.8%, or less than about 0.9%, or less than about 1.0% or less than about 2.0%, or less than about 3.0%, or less than about 4.0%, or less than about 5.0%.

In an embodiment, the chemical agent may include silicone. In some embodiments, a SFS may include silicone. In some embodiments, silicone may include a silicone emulsion. The term "silicone," may generally refer to a broad family of synthetic polymers, mixtures of polymers, and/or emulsions thereof, that have a repeating silicon-oxygen backbone including, but not limited to, polysiloxanes. For example, a silicone may include ULTRATEX® CSP, which is a commercially available (Huntsman International LLC) silicone emulsion that may be used as a softening agent and which may also increase fabric resilience, elasticity of knitted fabrics, and fiber lubrication and also improve sewability. A silicone may also include ULTRATEX® CI, which is a commercially available silicone composition (Huntsman International LLC) that may be used as a fabric softening agent. In some embodiments, a silicone may include any silicone species disclosed herein.

Describing the compositions and coatings more broadly, silicone may be used, for example to improve fabric hand, but may also increase the water repellency (or reduce water transport properties) of a fabric coated with silicone. Silicone may be used in combination with SFS to counteract the water repellant (water transport) properties of silicone.

In some embodiments, SFS may include silicone in a concentration by weight (% w/w or % w/v) or by volume (v/v) of less than about 25%, or less than about 20%, or less than about 15%, or less than about 10%, or less than about 9%, or less than about 8%, or less than about 7%, or less than about 6%, or less than about 5%, or less than about 4%, or less than about 3%, or less than about 2%, or less than about 1%, or less than about 0.9%, or less than about 0.8%, or less than about 0.7%, or less than about 0.6%, or less than about 0.5%, or less than about 0.4%, or less than about 0.3%, or less than about 0.2%, or less than about 0.1%, or less than about 0.01%, or less than about 0.001%.

In some embodiments, SFS may include silicone in a concentration by weight (% w/w or % w/v) or by volume (v/v) of greater than about 25%, or greater than about 20%, or greater than about 15%, or greater than about 10%, or greater than about 9%, or greater than about 8%, or greater than about 7%, or greater than about 6%, or greater than about 5%, or greater than about 4%, or greater than about 3%, or greater than about 2%, or greater than about 1%, or greater than about 0.9%, or greater than about 0.8%, or greater than about 0.7%, or greater than about 0.6%, or greater than about 0.5%, or greater than about 0.4%, or greater than about 0.3%, or greater than about 0.2%, or greater than about 0.1%, or greater than about 0.01%, or greater than about 0.001%.

In some embodiments, SFS may be supplied in a concentrated form suspended in water. In some embodiments, SFS may have a pH of less than about 9, or less than about 8. In some embodiments, SFS may have a concentration by weight (% w/w or % w/v) or by volume (v/v) of less than about 50%, or less than about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%, or less than about 1%, or less than about 0.1%, or less than about 0.01%, or less than about 0.001%, or less than about 0.0001%, or less than about 0.00001%. In some embodiments, SFS may have a concentration by weight (% w/w or % w/v) or by volume (v/v) of greater than about 50%, or greater than about 45%, or greater than about 40%, or greater than about 35%, or greater than about 30%, or greater than about 25%, or greater than about 20%, or greater than about 15%, or greater than about 10%, or greater than about 5%, or greater than about 4%, or greater than about 3%, or greater than about 2%, or greater than about 1%, or greater than about 0.1%, or greater than about 0.01%, or greater than about 0.001%, or greater than about 0.0001%, or greater than about 0.00001%.

In some embodiments, SFS may include an acidic agent, and may have a pH of less than about 9, or less than about 8.5, or less than about 8, or less than about 7.5, or less than about 7, or less than about 6.5, or less than about 6, or less than about 5.5, or less than about 5, or less than about 4.5, or less than about 4, or greater than about 3.5, or greater than about 4, or greater than about 4.5, or greater than about 5, or greater than about 5.5, or greater than about 6, or greater than about 6.5, or greater than about 7, or greater than about 7.5, or greater than about 8, or greater than about 8.5.

In some embodiments, an SFS coating may include SFS, as described herein. In some embodiments, SFS may include a silicone and/or an acidic agent. In some embodiments, SFS may include a silicone and an acidic agent. In some embodiments, the SFS may include a silicone, an acidic agent, and/or an additional chemical agent, wherein the additional chemical agent may be one or more of the chemical agents described herein. In some embodiments, SFS may include a silicone emulsion and an acidic agent, such as acetic acid or citric acid.

In some embodiments, the coating processes of the invention may include a finishing step for the resulting coated textiles. In some embodiments, the finishing or final finishing of the textiles (e.g., fabrics) that are coated with SFS under the processes of the invention may include sueding, steaming, brushing, polishing, compacting, raising, tigering, shearing, heatsetting, waxing, air jet, calendaring, pressing, shrinking, treatment with polymerizer, coating, lamination, and/or laser etching. In some embodiments, finishing of the SFS coated textiles may include treatment of the textiles with an AIRO® 24 dryer that may be used for continuous and open-width tumbling treatments of woven, non-woven, and knitted fabrics.

In some embodiments, a coated textile (e.g., a fabric) may be prepared by unrolling a fabric roll (FIG. 185) to prepare a piece of fabric. The perimeter of such fabric may be processed. For example, fabric (FIG. 186) may have dimensions of 35 cm×35 cm (13.5 inch×13.5 inch) with a tolerance of +/−1 cm (+/−0.4 inch). In some embodiments, every fabric sample may be massed on analytical balance by folding the fabric sample multiple times until it may be contained by a weighing boat on a balance. Each measurement may be recorded. In some embodiments, a coating process may be initiated by preparing a curing oven by setting a selected temperature therein. A padder laboratory unit may be turned on and the speed of said padder unit may be set to a selected velocity and the roller pressure may be adjusted to a selected pressure by operating a cam lever system and locking it in place once the desired pressure is achieved. A silk solution (i.e., SFS) may be poured into a bath (e.g., a stainless steel bath) (FIG. 187). After a fabric sample is submerged in the bath, it may be allowed to reach saturation, and the fabric sample may then be removed from the bath and laid between two rollers of the padder unit (FIG. 188). The fabric sample as it is transported through the rollers it may be squeezed of excessive fluid as determined by the rollers' pressure. The fabric sample may then exit to the opposite side of the rollers. The resulting fabric sample may then be placed on top of the curing frame and may then be gently pushed one edge at a time to engage the fabric edges with frame pins (see FIGS. 189 and 190). The frame may be placed in the drying and curing oven, with the door of said oven secured and kept closed for the drying and curing time (FIG. 191). A timer may be started to alert when the drying and curing time has elapsed. When the timer signals completion of the curing process, the oven door is opened and a temperature sensor (e.g., an IR temperature sensor) may be used to measure the fabric sample surface temperature. The frame bearing the fabric sample may then be removed from the oven and placed on a cooling rack (FIG. 192). The sample fabric may then be removed from the frame and weighed.

In some embodiments, the SFS coated textiles (e.g., fabrics) described herein may meet or exceed requirements established by the following Test Methods:

| Test Description | Test Method | Requirements |
|---|---|---|
| Dimensional Stability to Laundering | AATCC 135 | Maximum, Length: −3%, Width: −3% Maximum, Length: −3%, Width: −5%, for twoway Stretch Fabrics Maximum, Length: −5%, Width: −5%, for fourway Stretch Fabrics No Growth |
| Dimensional Stability to Dry Cleaning | AATCC 158 | Maximum, Length: −3%, Width: −3% Maximum, Length: −3%, Width: −5%, for twoway Stretch Fabrics Maximum, Length: −5%, Width: −5%, for fourway Stretch Fabrics No Growth |
| Pilling Resistance | ASTM D 3512 | Minimum 3.0 |
| Abrasion Resistance | ASTM D 4966 | No rupture to 10,000 cycles (plain fabrics up to 7.5 oz/yd$^2$; or no rupture to 15,000 cycles (plain fabrics over 7.5 oz/yd$^2$) |

-continued

| Test Description | Test Method | Requirements |
| --- | --- | --- |
| Tearing Strength | ASTM D 1424 | Shorts, Pants, Jeans, Jackets, All Plus Size Styles: 2.5 Lbs Minimum; or Blouse, Skirt Dress, Lining, excluding plus size styles: 1.5 Lbs Minimum; or Intimate: <3 oz/yd$^2$: Minimum 1.5 lbs 3~6 oz/yd$^2$: Minimum 2.0 lbs >6 oz/yd$^2$: Minimum 2.5 lbs |
| Colorfastness to Laundering/ Colorfastness to Washing | AATCC 61, 2A | Color Change: Minimum 4.0 Staining: Minimum 3.0 |
| Colorfastness to Dry Cleaning | AATCC 132 | Color Change: Minimum 4.0 Staining: Minimum 3.0 |
| Colorfastness to Crocking/ Colorfastness to Rubbing | AATCC 8 | All except below-Dry: Minimum 4.0; Wet: Minimum 3.0; or Dark Shades (black, red, navy)-Dry: Minimum 4.0; Wet: Minimum 2.5; or Indigos-Dry: Minimum 3.0; Wet: Minimum 2.0; or Pigments-Dry: Minimum 3.5; Wet: Minimum 2.5. |
| Colorfastness to Water | AATCC 107 | Color Change: Minimum 4.0; Staining: Minimum 3.0 |
| Colorfastness to Perspiration | AATCC 15 | Color Change: Minimum 4.0; Staining: Minimum 3 |
| Colorfastness to Light | AATCC 16/20 AFU AATCC 16/5 AFU | Color Change: Minimum 4.0 |
| pH Value | AATCC 81 | 4.0~8.5 or 4.0~7.5 (children < 36 months) |
| Antimicrobial | AATCC 147 | Original: 0% Bacterial Growth 20 Washes: 0% Bacterial Growth |
| | AATCC 100 | Minimum 99.9% Reduction |
| | ASTM E 2149 | Original: Minimum 99.9% Reduction 20 Washes: Minimum 80% Reduction |
| Wicking | AATCC 79 | 1.0 second or less |
| Water Repellency- Spray Test | AATCC 22 | Original: 100 Rating After 3x Washes: Minimum 70 Rating |
| Water Resistance- Rain Test | AATCC 35 | Maximum 1 gram on original and after 3 x washes |
| Dimensional Stability to Laundering (Yoga Garment) | AATCC 150 | Maximum, Length = −3%, Width = −3% Maximum, Length = −3%, Width = −5% for two-way Stretch Fabrics Maximum, Length = −5%, Width = −5% for four-way Stretch fabrics No Distortion Between Components No Growth |
| Dimensional Stability to Dry Cleaning (Yoga Garment) | AATCC 158 | Maximum, Length = −3%, Width = −3% Maximum, Length= −3%, Width= −5%, for two-way Stretch Fabrics Maximum, Length= −5%, Width= −5%, for four-way Stretch Fabrics No Distortion Between Components No Growth |
| Pilling Resistance (Yoga Garment) | ASM D 3512 | Minimum 3.0 |
| Colorfastness to Laundering/ Colorfastness to Washing (Yoga Garment) | AATCC 61, 2A | Color Change: Minimum 4.0 Staining: Minimum 3.0 |

| Test Description | Test Method | Requirements |
| --- | --- | --- |
| Colorfastness Crocking/ Colorfastness to Rubbing (Yoga Garment) | AATCC 8 | General: Dry: Minimum 4.0; Wet: Minimum 3.0; For Dark Colors (Black, Red, Navy): Wet: Minimum 2.5 Pigment: Dry: Minimum 3.5; Wet: Minimum 2.5 Indigos: Dry: Minimum 3.0; Wet: Minimum 2.0 |
| Colorfastness to Water (Yoga Garment) | AATCC 107 | Color Change: Minimum 4.0 Staining: Minimum 3.0 |
| Colorfastness to Perspiration (Yoga Garment) | AATCC 15 | Color Change: 4.0 or better Staining: 3.0 or better |
| Colorfastness to Light (Yoga Garment) | AATCC 16, 20 AFU/5 AFU | Minimum 4.0, All, Except Silk/ Minimum 4.0, Silk |
| pH Value (Yoga Garment) | AATCC 81 | Children (>36 months) & Adults: 4.0~8.5 Children (< 36 months): 4.0~7.5 |

In some embodiments, the SFS coated textiles (e.g., fabrics) described herein may meet requirements established by the foregoing Test Methods. In some embodiments, the SFS coated textiles (e.g., fabrics) described herein may exceed the requirements established by the foregoing Test Methods.

In some embodiments, the SFS coated textiles (e.g., fabrics) may have antiodor activity due to the SFS coating.

In some embodiments, the SFS coated textiles (e.g., fabrics) may have antimicrobial activity (e.g., antifungal and/or antibacterial activity) due to the SFS coating. In an embodiment, antibacterial activity may be determined by the ability of bacteria on the SFS coated textile's surface to be washed away from the SFS coated textile surface following one or more wash cycles, or two or more wash cycles, or three or more wash cycles, or four or more wash cycles, or five or more wash cycles, where the bacteria do not adhere to the surface of the SFS coated textile. In an embodiment, antibacterial activity may be determined by the ability of the SFS coating to reduce the quantity of the bacteria deposited on a surface of the SFS coated textile, wherein the SFS coating may reduce the quantity of the bacteria by greater than about 1%, or greater than about 2%, or greater than about 3%, or greater than about 4%, or greater than about 5%, or greater than about 10%, or greater than about 20%, or greater than about 30%, or greater than about 40%, or greater than about 50%, or greater than about 60%, or greater than about 70%, or greater than about 80%, or greater than about 90%, or greater than about 95%, or greater than about 96%, or greater than about 97%, or greater than about 98%, or greater than about 99%, or by about 100%. In an embodiment, antibacterial activity of the SFS coating on the coated textile may be determined by fluorescent activity (see, e.g., U.S. Pat. Nos. 5,089,395 and 5,968,762, the entirety of which are incorporated herein by reference). In an embodiment, antibacterial activity for an SFS coating may be determined by the ability of the SFS coating on a coated textile to break up colonies of bacteria that may be deposited on a surface of the coated textile. In an embodiment, antibacterial activity for an SFS coating may be determined by the ability of the SFS coating on a coated textile to: (a) prevent the formation of a bacterial biofilm on the coated textile; and/or (b) reduce the size of a bacterial biofilm on the coated textile.

In some embodiments, SFS may be coated upon a textile or other material having antimicrobial (e.g., antibacterial and/or antifungal) properties without interfering with such properties or otherwise inhibiting such properties.

In an embodiment, a textile may be coated with SFS to provide an SFS coated article. In some embodiments, the textile may include one or more of polyester, polyamide, polyaramid, polytetrafluoroethylene, polyethylene, polypropylene, polyurethane, silicone, mixtures of polyurethane and polyethyleneglycol, ultrahigh molecular weight polyethylene, high-performance polyethylene, nylon, and LYCRA (polyester-polyurethane copolymer, also known as SPANDEX and elastomer). In some embodiments, the textile may include LYCRA.

In some embodiments, the SFS coated article may have a crocking value of greater than 4 as determined by AATCC 8. In some embodiments, the SFS coated article may have a crocking value of greater than 4 as determined by AATCC 8, wherein the SFS coated article includes one or more of a silicone and an acidic agent. In some embodiments, the SFS coated article may have a crocking value of greater than 4 as determined by AATCC 8, wherein the SFS coated article includes a silicone.

In some embodiments, the SFS coated article may have an overall moisture management capability (OMMC) of greater than 0.3. In some embodiments, the SFS coated article may have an overall moisture management capability (OMMC) of greater than 0.3, wherein the SFS coated article includes one or more of a silicone and an acidic agent. In some embodiments, the SFS coated article may have an overall moisture management capability (OMMC) of greater than 0.3, wherein the SFS coated article includes a silicone.

In some embodiments, the SFS coated article may contain no sites for bacterial adhesion. In some embodiments, the SFS coated article may contain no sites for bacterial adhesion after heat treatment. In some embodiments, the SFS coated article may contain no sites for bacterial adhesion following a wash cycle with non-chlorinated bleach. In some embodiments, the SFS coated article may contain no bacteria after washing.

EXAMPLES

The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

A) Silk Molecular Weight Determination

The following equipment and material are used in determination of Silk Molecular weight: Agilent 1100 with chemstation software ver. 10.01; Refractive Index Detector (RID); analytical balance; volumetric flasks (1000 mL, 10 mL and 5 mL); HPLC grade water; ACS grade sodium chloride; ACS grade sodium phosphate dibasic heptahydrate; phosphoric acid; dextran MW Standards-Nominal Molecular Weights of 5 kDa, 11.6 kDa, 23.8 kDa, 48.6 kDa, and 148 kDa; 50 mL PET or polypropylene disposable centrifuge tubes; graduated pipettes; amber glass HPLC vials with Teflon caps; Phenomenex PolySep GFC P-4000 column (size: 7.8 mm×300 mm).

Procedure:

I) Preparation of 1 L Mobile Phase (0.1 M Sodium Chloride Solution in 0.0125 M Sodium Phosphate Buffer)

Take a 250 mL clean and dry beaker, place it on the balance and tare the weight. Add about 3.3509 g of sodium phosphate dibasic heptahydrate to the beaker. Note down the exact weight of sodium phosphate dibasic weighed. Dissolve the weighed sodium phosphate by adding 100 mL of HPLC water into the beaker. Take care not to spill any of the content of the beaker. Transfer the solution carefully into a clean and dry 1000 mL volumetric flask. Rinse the beaker and transfer the rinse into the volumetric flask. Repeat the rinse 4-5 times. In a separate clean and dry 250 mL beaker weigh exactly about 5.8440 g of sodium chloride. Dissolve the weighed sodium chloride in 50 mL of water and transfer the solution to the sodium phosphate solution in the volumetric flask. Rinse the beaker and transfer the rinse into the volumetric flask. Adjust the pH of the solution to 7.0±0.2 with phosphoric acid. Make up the volume in volumetric flask with HPLC water to 1000 mL and shake it vigorously to homogeneously mix the solution. Filter the solution through 0.45 μm polyamide membrane filter. Transfer the solution to a clean and dry solvent bottle and label the bottle. The volume of the solution can be varied to the requirement by correspondingly varying the amount of sodium phosphate dibasic heptahydrate and sodium chloride.

II) Preparation of Dextran Molecular Weight Standard Solutions

At least five different molecular weight standards are used for each batch of samples that are run so that the expected value of the sample to be tested is bracketed by the value of the standard used. Label six 20 mL scintillation glass vials respective to the molecular weight standards. Weigh accurately about 5 mg of each of dextran molecular weight standards and record the weights. Dissolve the dextran molecular weight standards in 5 mL of mobile phase to make a 1 mg/mL standard solution.

III) Preparation of Sample Solutions

When preparing sample solutions, if there are limitations on how much sample is available, the preparations may be scaled as long as the ratios are maintained. Depending on sample type and silk protein content in sample weigh enough sample in a 50 mL disposable centrifuge tube on an analytical balance to make a 1 mg/mL sample solution for analysis. Dissolve the sample in equivalent volume of mobile phase make a 1 mg/mL solution. Tightly cap the tubes and mix the samples (in solution). Leave the sample solution for 30 minutes at room temperature. Gently mix the sample solution again for 1 minute and centrifuge at 4000 RPM for 10 minutes.

IV) HPLC Analysis of the Samples

Transfer 1.0 mL of all the standards and sample solutions into individual HPLC vials. Inject the molecular weight standards (one injection each) and each sample in duplicate. Analyze all the standards and sample solutions using the following HPLC conditions:

Column PolySep GFC P-4000 (7.8×300 mm)
Column Temperature 25° C.
Detector Refractive Index Detector (Temperature @35° C.)
Injection Volume 25.0 μL
Mobile Phase 0.1 M Sodium Chloride solution in 0.0125 M sodium phosphate buffer
Flow Rate 1.0 mL/min
Run Time 20.0 min V) Data Analysis and Calculations—Calculation of Average Molecular Weight Using Cirrus Software Upload the chromatography data files of the standards and the analytical samples into Cirrus SEC data collection and molecular weight analysis software. Calculate the weight average molecular weight ($M_w$), number average molecular weight ($M_n$), peak average molecular weight ($M_p$), and polydispersity for each injection of the sample. Average the results for duplicate injections for each sample (Table 1).

TABLE 1

Exemplary Medium and Low Molecular Weight Values, and Polydispersity Values

| Sample ID (MW Group) | Injection # | Mn (Da) | Average Mn (Da) | Mw (Da) | Average Mw (Da) | Polydispersity |
|---|---|---|---|---|---|---|
| 1 ("Mid") | 1 | 13702 | 13535 | 41010 | 41576 | 3.07 |
|  | 2 | 13368 |  | 42141 |  |  |
| 2 ("Mid") | 1 | 13635 | 13641 | 40948 | 41268 | 3.03 |
|  | 2 | 13646 |  | 41588 |  |  |
| 3 ("Mid") | 1 | 14131 | 14069 | 41403 | 41964 | 2.98 |
|  | 2 | 14006 |  | 42524 |  |  |
| 4 ("Mid") | 1 | 13702 | 13780 | 42031 | 42314 | 3.07 |
|  | 2 | 13857 |  | 42596 |  |  |
| 5 ("Mid") | 1 | 15837 | 15710 | 42482 | 42981 | 2.74 |
|  | 2 | 15583 |  | 43480 |  |  |
| 6 ("Mid") | 1 | 16051 | 16034 | 45027 | 45322 | 2.83 |
|  | 2 | 16016 |  | 45616 |  |  |
| 7 ("Mid") | 1 | 15404 | 15516 | 42176 | 42421 | 2.73 |
|  | 2 | 15627 |  | 42666 |  |  |
| 8 ("Mid") | 1 | 19106 | 19138 | 37656 | 37960 | 1.98 |
|  | 2 | 19170 |  | 38263 |  |  |
| 9 ("Mid") | 1 | 19350 | 19445 | 39328 | 39676 | 2.04 |
|  | 2 | 19540 |  | 40023 |  |  |
| 10 ("Mid") | 1 | 19557 | 19620 | 40541 | 40310 | 2.05 |
|  | 2 | 19682 |  | 40079 |  |  |
| 11 ("Mid") | 1 | 19999 | 20061 | 41351 | 41676 | 2.08 |
|  | 2 | 20122 |  | 42000 |  |  |
| 12 ("Mid") | 1 | 20013 | 19985 | 41719 | 41600 | 2.08 |
|  | 2 | 19956 |  | 41481 |  |  |
| 13 ("Mid") | 1 | 20218 | 20194 | 42835 | 42788 | 2.12 |
|  | 2 | 20170 |  | 42740 |  |  |
| 14 ("Mid") | 1 | 19602 | 19659 | 40037 | 40667 | 2.07 |
|  | 2 | 19715 |  | 41296 |  |  |

TABLE 1-continued

Exemplary Medium and Low Molecular Weight Values, and Polydispersity Values

| Sample ID (MW Group) | Injection # | Mn (Da) | Average Mn (Da) | Mw (Da) | Average Mw (Da) | Polydispersity |
|---|---|---|---|---|---|---|
| 15 ("Mid") | 1 | 19823 | 19895 | 42235 | 42276 | 2.12 |
|  | 2 | 19967 |  | 42317 |  |  |
| 16 ("Mid") | 1 | 19765 | 19801 | 41713 | 41899 | 2.12 |
|  | 2 | 19837 |  | 42084 |  |  |
| 17 ("Mid") | 1 | 18485 | 18400 | 37995 | 37666 | 2.05 |
|  | 2 | 18314 |  | 37336 |  |  |
| 18 ("Mid") | 1 | 18327 | 18377 | 37111 | 37158 | 2.02 |
|  | 2 | 18427 |  | 37204 |  |  |
| 19 ("Mid") | 1 | 18243 | 18343 | 37201 | 37830 | 2.06 |
|  | 2 | 18443 |  | 38459 |  |  |
| 20 ("Mid") | 1 | 19468 | 19467 | 41560 | 41880 | 2.15 |
|  | 2 | 19466 |  | 42199 |  |  |
| 21 ("Mid") | 1 | 19328 | 19391 | 41512 | 41761 | 2.15 |
|  | 2 | 19454 |  | 42010 |  |  |
| 22 ("Mid") | 1 | 19529 | 19550 | 42245 | 42447 | 2.17 |
|  | 2 | 19570 |  | 42649 |  |  |
| 23 ("Mid") | 1 | 19732 | 19678 | 43015 | 42706 | 2.17 |
|  | 2 | 19624 |  | 42396 |  |  |
| 24 ("Mid") | 1 | 19686 | 19802 | 42838 | 42862 | 2.16 |
|  | 2 | 19918 |  | 42886 |  |  |
| 25 ("Mid") | 1 | 19689 | 19696 | 42608 | 42850 | 2.18 |
|  | 2 | 19703 |  | 43092 |  |  |
| 26 ("Mid") | 1 | 14303 | 14923 | 40498 | 40640 | 2.73 |
|  | 2 | 15543 |  | 40782 |  |  |
| 27 ("Mid") | 1 | 14654 | 14582 | 38546 | 38558 | 2.64 |
|  | 2 | 14509 |  | 38569 |  |  |
| 28 ("Mid") | 1 | 14303 | 14242 | 35937 | 35847 | 2.52 |
|  | 2 | 14180 |  | 35756 |  |  |
| 29 ("Low") | 1 | 3318 | 3427 | 10508 | 10939 | 3.19 |
|  | 2 | 3536 |  | 11369 |  |  |
| 30 ("Low") | 1 | 3616 | 3647 | 8340 | 8450 | 2.32 |
|  | 2 | 3678 |  | 8559 |  |  |
| 31 ("Low") | 1 | 4709 | 4778 | 13104 | 13297 | 2.78 |
|  | 2 | 4846 |  | 13489 |  |  |
| 32 ("Low") | 1 | 4237 | 4506 | 12232 | 13042 | 2.89 |
|  | 2 | 4774 |  | 13851 |  |  |
| 33 ("Low") | 1 | 4696 | 4783 | 12754 | 12986 | 2.71 |
|  | 2 | 4870 |  | 13217 |  |  |

B) Wool Coating

Wool Raw Material:
  Tube A: 100% wool tubular fabric made with NeW 1/42.8 with 18.9 μm wool fibers (4 inches diameter tubes by 14 inches long supplied by MSC) non superwashed supplied by Kentwool in Greenville SC;
  Tube B: 100% wool tubular fabric made with NeW 1/30 with 21.0 μm Australian wool fibers (4 inches diameter tubes by 14 inches long supplied by MSC) non superwashed supplied by Kentwool in Greenville SC;
  Tube C: 100% wool tubular fabric made with NeW 27/1 with 23.0 μm Australian wool fibers (4 inches diameter tubes by 14 inches long supplied by MSC) superwashed supplied by Kentwool in Greenville SC;
  Tube D: 100% wool tubular fabric made with NeW 60/2 with 18.5 μm Australian wool fibers (4 inches diameter tubes by 14 inches long supplied by MSC) superwashed supplied by Kentwool in Greenville SC.

Equipment:
  Werner Mathis MA0881 padder/coater;
  Curing frame 13×13 inches;
  Across International oven FO-19140;
  Magnetic stirrer hot plate JoanLab SH-2;
  Stirrer bar;
  Large tweezers;
  Balance Veritas M314-AI;
  Universal plastic PH test strip;
  Glassware.

Processes (by Number of Processing Steps):
  4 steps process: pre-treatment, silk treatment, post treatment, and final treatment;
  3 steps process: pre-treatment, silk treatment, and post treatment;
  2 steps process: pre-treatment, and silk treatment;
  1 step process: silk treatment.

Processing Steps and Sub-Steps:
  Wool tubes A, B, C, and D are massed before any processing (see Table 2 for wool samples cross-reference numbers);
  Control samples of each fabric A, B, C, and D are not processed;
  A pretreatment bath at 20:1 ratio liquor to fabric with tap water with 5% citric acid to a pH of 3-4 is maintained at a temperature of 70° C. with a hot plate and is recirculated with a stirrer bar. The silk tube fabrics (N=4) are immersed for 60 minutes;
  The wool tube fabrics are removed from the bath and are padded at 50 pressure on the padder and 3 m/min followed by a 10 min drying cycle at 80° C. in the oven;
  The dried wool tube fabrics are immersed in the same pretreatment bath after the addition of 0.375% low MW and 0.125% medium MW silk solutions based on the liquor volume resulting in a pH of 4-5 and is maintained at 70° C. with a hot plate for 30 minutes with liquor recirculating through a stirrer bar;
  The wool tube fabrics are removed from the bath and are padded at 20 pressure setting and 3 m/min followed by a 10 min drying cycle at 80° C. in the oven;
  The dried wool tube fabrics are immersed in a new bath with 20:1 ratio liquor to fabric with tap water and 0.25% citric acid to a pH of 3-4 at room temperature. The silk tube fabrics are immersed for 3 minutes;
  The wool tube fabrics are removed from the bath and are padded at 50 pressure setting and 3 m/min followed by a 10 min drying cycle at 80° C. in the oven;
  The dried wool tube fabrics are immersed in a new 100 ml bath with 80 methanol and 2000 deionized water at room temperature for 10 minutes;
  The wool tube fabrics are removed from the bath and are padded at 50 pressure setting and 3 in/min followed by a 10 min drying cycle at 80° C. in the oven.

TABLE 2

| | Wool Samples Cross-reference |
|---|---|
| 17042001 | wool tube NeW 1/27 23.5 micron superwashed, control post knitting |
| 17042002 | wool tube NeW 2/60 18.5 micron superwashed, control post knitting |
| 17050901 | wool tube NeW 1/42.8 with 18.9 micron non superwashed post knitting |
| 17050902 | wool tube NeW 1/30 with 21.0 micron non superwashed, post knitting |
| 17051001 | wool tube 17050901 NeW 1/42.8 with 18.9 micron with 0.5% silk 3L1M |

TABLE 2-continued

| | Wool Samples Cross-reference |
|---|---|
| 17051002 | wool tube 17050902 NeW 1/30 with 21.0 micron with 0.5% silk 3L1M |
| 17051003 | wool tube 17042002 NeW 2/60 with 18.5 micron with 0.5% silk 3L1M |
| 17051101 | wool tube 17042001 NeW 1/27 with 23.5 micron with 0.5% silk 3L1M |
| 17060105 | wool tube 17050901 NeW 1/42.8 with 18.9 micron, 0.2% citric acid |
| 17060106 | wool tube 17050901 NeW 1/42.8 with 18.9 micron, 80% methanol |
| 17060107 | wool tube 17050902 NeW 1/30 with 21.0 micron, 0.2% citric acid |
| 17060108 | wool tube 17050902 NeW 1/30 with 21.0 micron, 80% methanol |
| 17060201 | wool tube 17042001 NeW 1/27 with 23.5 micron, 0.2% citric acid |
| 17060202 | wool tube 17042001 NeW 1/27 with 23.5 micron, 80% methanol |
| 17060203 | wool tube 17042002 NeW 2/60 with 18.5 micron, 0.2% citric acid |
| 17060204 | wool tube 17042002 NeW 2/60 with 18.5 micron, 80% methanol |

3L1M: 3:1 low MW silk to medium MW silk

C) Synthetic Materials Coating Method

The following equipment and material are used in coating experiments: medium molecular weight silk fragments solution at 60%; low molecular weight silk fragments solution at 6%; citric acid; Ultratex CSP (Huntsman); M Dohmen Domosil RWAF; Ultratex SI (Huntsman); permanent marker; fabric style #6606D2 nylon/spandex; fabric style #6608D2B polyester/spandex.

The coating processing includes two separate coating steps. Each coating step may be followed by a drying step.

First Coating Step: the total liquor solution prepared and individual ingredient quantities are prepared. The sequence for mixing includes: loading tap water in a mixing tank; adding citric acid 50% in water, followed by mixing for 2-3 minutes; measuring and confirming that the pH is between 4-5; adding low molecular weight silk solution to the mixing tank, and mixing for 1-2 minutes; adding medium molecular weight silk solution to the mixing tank, and mixing for 1-2 minutes; transferring the liquor to the pad bath; processing the fabric with a pick-up rate of 35-70%, with a drying time as required by the fabric material and construction.

Second Coating Step: the total liquor solution prepared and individual ingredient quantities are prepared. The sequence for mixing includes: loading tap water in the mixing tank; adding citric acid 50% in water, and mixing for 2-3 minutes; measuring and confirming that the pH is between 4-5; adding silicone solution to the liquor, and mixing for 2-3 minutes; transferring the liquor to the pad bath; fabrics processed with the first coating step are processed through the frame; fabric is processed with a pick-up rate of 35-70% with a drying time as required by the fabric material and construction.

Example 1: Silk Coating Wool, Including a Citric Acid Pretreatment and Methanol Post Treatment—Water Drop Tested and Hand Evaluated This experiment includes application of silk fibroin solution on wool fabrics after a pretreatment of citric acid and followed by a methanol bath (variables described in Table 3). The application takes place in a sequence of baths and pads application with multiple drying steps.

TABLE 3

| | Coating Experimental Variables | | | | |
|---|---|---|---|---|---|
| Wool type | Pre treatment | Silk coating | Post treatment | Final treatment | Dry/cure temperature ° F. (° C.) |
| Tube C NeW 1/27 23 μm Australian wool | 0.200% citric acid for 60 min at 70° C. | 0.375% low MW + 0.125% medium MW 0.200% citric acid for 30 min at 70 C. | 0.250% citric acid for 10 min at room temp | 80% methanol, 20% di water for 10 min at room temp | 176 (80) for 10 min |
| Tube C NeW 1/27 23 μm Australian wool | 0.200% citric acid for 60 min at 70° C. | 0.375% low MW+ 0.125% medium MW 0.200% citric acid for 30 min at 70 C. | 0.250% citric acid for 10 min at room temp | N/A | 176 (80) for 10 min |
| Tube C NeW 1/27 23 μm Australian wool | 0.200% citric acid for 60 min at 70° C. | 0.375% low MW + 0.125% medium MW 0.200% citric acid for 30 min at 70 C. | N/A | 80% methanol, 20% di water for 10 min at room temp | 176 (80) for 10 min |
| Tube C NeW 1/27 23 μm Australian wool | 0.200% citric acid for 60 min at 70° C. | 0.375% low MW + 0.125% medium MW 0.200% citric acid for 30 min at 70 C. | N/A | N/A | 176 (80) for 10 min |
| Tube C NeW 1/27 23 μm Australian wool | N/A | 0.375% low MW + 0.125% medium MW 0.200% citric acid for 30 min at 70 C. | 0.250% citric acid for 10 min at room temp | 80% methanol, 20% di water for 10 min at room temp | N/A |
| Tube D NeW 2/60 18.5 μm Australian wool | N/A | N/A | N/A | N/A | 176 (80) for 10 min |
| Tube D NeW 2/60 18.5 μm Australian wool | 0.200% citric acid for 60 min at 70° C. | 0.375% low MW + 0.125% medium MW 0.200% citric acid for 30 min at 70 C. | 0.250% citric acid for 10 min at room temp | 80% methanol, 20% di water for 10 min at room temp | 176 (80) for 10 min |

TABLE 3-continued

Coating Experimental Variables

| Wool type | Pre treatment | Silk coating | Post treatment | Final treatment | Dry/cure temperature °F. (°C.) |
|---|---|---|---|---|---|
| Tube D NeW 2/60 18.5 µm Australian wool | 0.200% citric acid for 60 min at 70° C. | 0.375% low MW + 0.125% medium MW 0.200% citric acid for 30 min at 70 C. | 0.250% citric acid for 10 min at room temp | N/A | 176 (80) for 10 min |
| Tube D NeW 2/60 18.5 µm Australian wool | 0.200% citric acid for 60 min at 70° C. | 0.375% low MW + 0.125% medium MW 0.200% citric acid for 30 min at 70 C. | N/A | 80% methanol, 20% di water for 10 min at room temp | 176 (80) for 10 min |
| Tube D NeW 2/60 18.5 µm Australian wool | 0.200% citric acid for 60 min at 70° C. | 0.3711% low m + 0.125% medium MW 0.200% citric acid for 30 min at 70 C. | N/A | N/A | 176 (80) for 10 min |
| Tube D NeW 2/60 18.5 µm Australian wool | N/A | 0.375% low MW + 0.125% medium MW 0.200% citric acid for 30 min at 70 C. | 0.250% citric acid for 10 min at room temp | 80% methanol, 20% di water for 10 min at room temp | N/A |
| Tube D NeW 2/60 18.5 µm Australian wool | N/A | N/A | N/A | N/A | 176 (80) for 10 min |

Water drop test (Table 4) and hand evaluation (Tables 5 and 6) are used to characterize the fabrics, as follows:

Samples are conditioned at ambient condition for 24 hrs;

A 7 cm diameter round metal hoop is inserted in the wool fabric tube and is placed on the drapability jig. A RODI water drop is dispensed with an eye dropper from approximately 3 cm above the fabric. A video imaging recording capture the time from the water drop contacting the fabric until its full absorption or up to 30 seconds;

The wool fabric tubes are scored for hand against a non treated control. Scoring are made from more softest to rougher and any additional perceived difference.

TABLE 4

Water Drop Test

| Sample # | Description | Average | test 1 | test 2 | test 3 |
|---|---|---|---|---|---|
| 17042001 | NeW 1/27 23.5 micron control post knitting | 8 | 7 | 7 | 11 |
| 17042403 | NeW 1/27 23.5 micron water only | 15 | 25 | 5 | 14 |
| 17042103 | NeW 1/27 23.5 micron pre-treatment, silk coating | 15 | 7 | 14 | 25 |
| 17042002 | NeW 2/60 18.5 micron, control post knitting | 30 | 30 | 30 | 30 |

TABLE 4-continued

Water Drop Test

| Sample # | Description | Average | test 1 | test 2 | test 3 |
|---|---|---|---|---|---|
| 17042101 | NeW 1/27 23.5 micron pre-treatment, silk coating, post treatment | 30 | 30 | 30 | 30 |
| 17042102 | NeW 2/60 18.5 micron, pre-treatment, silk coating, post treatment | 30 | 30 | 30 | 30 |
| 17042104 | NeW 2/60 18.5 micron, pre-treatment, silk coating | 30 | 30 | 30 | 30 |
| 17042105 | NeW 2/60 18.5 micron, pre-treatment, silk coating, post treatment, final treatment | 30 | 30 | 30 | 30 |
| 17042106 | NeW 1/27 23.5 micron pre-treatment, silk coating, post treatment, final treatment | 30 | 30 | 30 | 30 |
| 17042107 | NeW 2/60 18.5 micron, pre-treatment, silk coating, final treatment | 30 | 30 | 30 | 30 |
| 17042108 | NeW 1/27 23.5 micron pre-treatment, silk coating, final treatment | 30 | 30 | 30 | 30 |
| 17042401 | NeW 1/27 23.5 micron silk coating, post treatment, final treatment | 30 | 30 | 30 | 30 |
| 17042402 | NeW 2/60 18.5 micron, silk coating, post treatment, final treatment | 30 | 30 | 30 | 30 |
| 17042404 | NeW 2/60 18.5 micron, water only | 30 | 30 | 30 | 30 |

TABLE 5

Hand Scores for Softness

| Sample #2 | Description | Score |
|---|---|---|
| 17042107 | NeW 2/60 18.5 micron, pre-treatment, silk coating, final treatment | 25 |
| 17042105 | NeW 2/60 18.5 micron, pre-treatment, silk coating, post treatment, final treatment | 24 |
| 17042102 | NeW 2/60 18.5 micron, pre-treatment, silk coating, post treatment | 24 |
| 17042104 | NeW 2/60 18.5 micron, pre-treatment, silk coating | 24 |
| 17042402 | NeW 2/60 18.5 micron, silk coating, post treatment, final treatment | 23 |
| 17042404 | NeW 2/60 18.5 micron, water only | 18 |
| 17042106 | NeW 1/27 23.5 micron pre-treatment, silk coating, post treatment, final treatment | 13 |
| 17042101 | NeW 1/27 23.5 micron pre-treatment, silk coating, post treatment | 13 |
| 17042403 | NeW 1/27 23.5 micron water only | 11 |
| 17042002 | NeW 2/60 18.5 micron, control post knitting | 11 |
| 17042108 | NeW 1/27 23.5 micron pre-treatment, silk coating, final treatment | 10 |
| 17042103 | NeW 1/27 23.5 micron pre-treatment, silk coating | 8 |
| 17042401 | NeW 1/27 23.5 micron silk coating, post treatment, final treatment | 4 |
| 17042001 | NeW 1/27 23.5 micron control post knitting | 2 |

TABLE 6

Hand Scores Identified Perceived Cool/Wet Feeling

| Sample #2 | Description | Score |
|---|---|---|
| 17042105 | NeW 2/60 18.5 micron, pre-treatment, silk coating, post treatment, final treatment | 5 |
| 17042102 | NeW 2/60 18.5 micron, pre-treatment, silk coating, post treatment | 5 |

TABLE 6-continued

Hand Scores Identified Perceived Cool/Wet Feeling

| Sample #2 | Description | Score |
|---|---|---|
| 17042402 | NeW 2/60 18.5 micron, silk coating, post treatment, final treatment | 5 |
| 17042107 | NeW 2/60 18.5 micron, pre-treatment, silk coating, final treatment | 4 |
| 17042106 | NeW 1/27 23.5 micron pre-treatment, silk coating, post treatment, final treatment | 1 |

Example 2: Silk Coating Wool, Including a Citric Acid Pretreatment and Methanol Post Treatment—Tested for Dimensional Changes after Laundering, Perceived Hand, and Fiber Morphology by SEM Analysis Silk fibroin solution is applied on wool fabrics after a pretreatment of citric acid and, followed by a methanol bath (Table 7). The application takes place in a sequence of baths and pads application with multiple drying steps. The samples are tested for dimensional changes after laundering, perceived hand, and fiber morphology with SEM analysis (Tables 8-11).

TABLE 7

Coating Experimental Variables

| Wool type | Pre treatment | Silk coating | Post treatment | Final treatment | Dry/cure temperature °F. (°C.) |
|---|---|---|---|---|---|
| NeW 1/42.8 18.9 µm Australian wool | 0.200% citric acid for 60 min at 70° C. | 0.375% low mw + 0.125% medium mw 0.200% citric acid for 30 min at 70° C. | 0.250% citric acid for 10 min at room temp | 80% methanol, 20% di water for 10 min at room temp | 176 (80) for 10 min |
| NeW 1/30 21.0 lam Australian wool | 0.200% citric acid for 60 min at 70° C. | 0.375% low mw + 0.125% medium mw 0.200% citric acid for 30 min at 70° C. | 0.250% citric acid for 10 min at room temp | 80% methanol, 20% di water for 10 min at room temp | 176 (80) for 10 min |
| NeW 1/27 23 lam Australian wool | 0.200% citric acid for 60 min at 70° C. | 0.375% low mw + 0.125% medium mw 0.200% citric acid for 30 min at 70° C. | 0.250% citric acid for 10 min at room temp | 80% methanol, 20% di water for 10 min at room temp | 176 (80) for 10 min |
| NeW 2/60 18.5 lam Australian wool | 0.200% citric acid for 60 min at 70° C. | 0.375% low mw + 0.125% medium mw 0.200% citric acid for 30 min at 70° C. | 0.250% citric acid for 10 min at room temp | 80% methanol, 20% di water for 10 min at room temp | 176 (80) for 10 min |

Samples are conditioned at ambient condition for 24 hrs before a massing post coating. The percentage change is calculated based on the following formula:

$$\text{Mass change \%} = \frac{\text{mass post coating} - \text{mass before coating}}{\text{mass before coating}} \times 100$$

Samples are delivered to the MSC lab for dimensional changes post laundering analysis based on Woolmark Company TM31-May 2000 and AATCC Test Method 135-2015. Samples are tested after t=1 and t=4 laundering cycle for the Woolmark test and at t=0 and t=3 for the AATCC test.

After the dimensional analysis test, the wool fabric tubes are scored for hand against a non-treated control. Scoring are made for softness and any additional perceived difference. After the hand test is completed the samples are subjected to SEM analysis.

TABLE 8

Processing recording and mass percentage change post treatment sample 17051001
fabric'A' 17050901'NeW'1/42.8"NSW'with'18.9'r17051001 t = 0'hr t = 24'hr pre'treatment

| | | | | | |
|---|---|---|---|---|---|
| starting'citric'acid'solution'(ml) | 2.26 | calculation mass'fabric | A1 | 11.3526 gr | 11.4499 gr |
| citric'acid'concentration'(%) | 100.000% | input | A2 | 11.2096 gr | 11.3027 gr |
| required'Dl'(ml) | 902.19 | calculation | A3 | 11.3446 gr | 11.4552 gr |
| required'citric'acid'concentration'(%) | 0.250% | input | A4 | 11.3158 gr | 11.4229 gr |
| final'solution'(ml) | 904.45 | input | tot | 45.2226 gr | 45.6307 gr |
| | | | liquor'ratio 20 | 1 | percentage'change 0.9% |
| | | | total'liquor | 904.452 | | coating

| | | | | |
|---|---|---|---|---|
| final'solution'(ml) | 904.45 | input total'liquor | 904.452 ml | |
| required'Dl'(ml) | 827.27 | calculation | | |
| required'solution'silk'low'mw'(ml) | 56.53 | calculation | | |
| concentration'silk'low'mw'(%) | 6.000% | input | | |
| required'silk'concentration'low'mw'(%) | 0.375% | input | | |
| required'silk'solution'medium'mw'(ml) | 18.84 | calculation | | |
| concentration'silk'medium'mw'(%) | 6.000% | input | | |

TABLE 8-continued

Processing recording and mass percentage change
post treatment sample 17051001
fabric'A' 17050901'NeW'1/42.8"NSW'with'18.9'r17051001 t = 0'hr t = 24'hr

| | | | | | |
|---|---|---|---|---|---|
| required'silk'concentration'medium'mw'(%) | 0.125% | input | | | |
| required'citric'acid'(ml) | 1.81 | calculation | | | |
| citric'acid'(%) | 100.000% | input | | | |
| required'citric'acid'concentration'(%) | 0.200% | input | | | |
| post treatment | | | | | |
| starting'citric'acid'solution'(ml) | 2.26 | calculation total | 45.2226 gr | | |
| citric'acid'concentration'(%) | 100.000% | input | liquor'ratio 20 | 1 | |
| required'Dl'(ml) | 902.19 | calculation | total'liquor | 904.452 ml | |
| required'citric'acid'concentration'(%) | 0.250% | input | | | |
| final'solution'(ml) | 904.45 | input | | | |
| final'treatment | | | | | |
| starting'methanol'solution'(ml) | 361.78 | tot | 45.2226 gr | | |
| methanol'concentration'(%) | 100.000% | liquor'ratio 10 | 1 | | |
| required'Dl'(ml) | 90.45 | total'liquor | 452.226 ml | | |
| required'methanol'concentration'(%) | 80.000% | | | | |
| final'solution'(ml) | 452.23 | | | | |

TABLE 9

Processing recording and mass percentage change
post treatment sample 17051002
fabric'B 17050902'NeW'1/30"NSW'with'21.0'mi 17051002

| | | | | | | |
|---|---|---|---|---|---|---|
| pre'treatment | | | | | | |
| starting'citric'acid'solution'(ml) | 2.81 | calculation mass'fabric | B1 | 13.9581 gr | 14.1793 gr | |
| citric'acid'concentration'(%) | 100.000% | input | B2 | 13.9988 gr | 14.2136 gr | |
| required'Dl'(ml) | 1122.46 | calculation | B3 | 14.2023 gr | 14.4415 gr | |
| required'citric'acid'concentration'(%) | 0.250% | input | B4 | 14.1045 gr | 14.3433 gr | |
| final'solution'(ml) | 1125.27 | input | tot | 56.2637 gr | 57.1777 gr | |
| | | | liquor'ratio 20 | 1 | | percentage'change 1.6% |
| | | | total'liquor | 1125.274 ml | | |
| coating | | | | | | |
| final'solution'(ml) | 1125.27 | input total'liquor | 1125.274 ml | | | |
| required'Dl'(ml) | 1029.25 | calculation | | | | |
| required'solution'silk'low'mw'(ml) | 70.33 | calculation | | | | |
| concentration'silk'low'mw'(%) | 6.000% | input | | | | |
| required'silk'concentration'low'mw'(%) | 0.375% | input | | | | |
| required'silk'solution'medium'mw'(ml) | 23.44 | calculation | | | | |
| concentration'silk'medium'mw'(%) | 6.000% | input | | | | |
| required'silk'concentration'medium'mw'(%) | 0.125% | input | | | | |
| required'citric'acid'(ml) | 2.25 | calculation | | | | |
| citric'acid'(%) | 100.000% | input | | | | |
| required'citric'acid'concentration'(%) | 0.200% | input | | | | |
| post treatment | | | | | | |
| starting'citric'acid'solution'(ml) | 2.81 | calculation total | 56.2637 gr | | | |
| citric'acid'concentration'(%) | 100.000% | input | liquor'ratio 20 | 1 | | |
| required'Dl'(ml) | 1122.46 | calculation | total'liquor | 1125.274 ml | | |
| required'citric'acid'concentration'(%) | 0.250% | input | | | | |
| final'solution'(ml) | 1125.27 | input | | | | |
| final'treatment | | | | | | |
| starting'methanol'solution'(ml) | 450.11 | tot | 56.2637 gr | | | |
| methanol'concentration'(%) | 100.000% | liquor'ratio 10 | 1 | | | |
| required'Dl'(ml) | 112.53 | total'liquor | 562.637 ml | | | |
| required'methanol'concentration'(%) | 80.000% | | | | | |
| final'solution'(ml) | 562.64 | | | | | |

TABLE 10

Processing recording and mass percentage change
post treatment sample 17051003
fabric'C 17042002'NeW'2/60"SW'with'18.5'micron 17051003 pre'treatment

| | | | | | |
|---|---|---|---|---|---|
| starting'citric'acid'solution'(ml) | 2.35 | calculation mass'fabric | C1 | 11.7501 gr | 11.8427 gr |
| citric'acid'concentration'(%) | 100.000% | input | C2 | 11.7615 gr | 11.8588 gr |
| required'Dl'(ml) | 938.72 | calculation | C3 | 11.8146 gr | 11.9135 gr |
| required'citric'acid'concentration'(%) | 0.250% | input | C4 | 11.7273 gr | 11.8197 gr |
| final'solution'(ml) | 941.07 | input | tot | 47.0535 gr | 47.4347 gr |
| | | | liquor'ratio 20 | 1 | percentage'change 0.8% |
| | | | total'liquor | 941.07 ml | | coating

| | | | |
|---|---|---|---|
| final'solution'(ml) | 941.07 | input total'liquor | 941.07 ml |
| required'Dl'(ml) | 860.77 | calculation | |
| required'solution'silk'low'mw'(ml) | 58.82 | calculation | |
| concentration'silk'low'mw'(%) | 6.000% | input | |
| required'silk'concentration'low'mw'(%) | 0.375% | input | |
| required'silk'solution'medium'mw'(ml) | 19.61 | calculation | |
| concentration'silk'medium'mw'(%) | 6.000% | input | |
| required'silk'concentration'medium'mw'(%) | 0.125% | input | |
| required'citric'acid'(ml) | 1.88 | calculation | |
| citric'acid'(%) | 100.000% | input | |
| required'citric'acid'concentration'(%) | 0.200% | input | | post treatment

| | | | | |
|---|---|---|---|---|
| starting'citric'acid'solution'(ml) | 2.35 | calculation tot | 47.0535 gr | |
| citric'acid'concentration'(%) | 100.000% | input | liquor'ratio 20 | 1 |
| required'Dl'(ml) | 938.72 | calculation | total'liquor | 941.07 ml |
| required'citric'acid'concentration'(%) | 0.250% | input | | |
| final'solution'(ml) | 941.07 | input | | | final'treatment

| | | | |
|---|---|---|---|
| starting'methanol'solution'(ml) | 376.43 | tot | 47.0535 gr |
| methanol'concentration'(%) | 100.000% | liquor'ratio 10 | 1 |
| required'Dl'(ml) | 94.11 | total'liquor | 470.535 ml |
| required'methanol'concentration'(%) | 80.000% | | |
| final'solution'(ml) | 470.54 | | |

TABLE 11

Processing recording and mass percentage change
post treatment sample 17051101
fabric'C 17042001'NeW'1/27"SW'with'23.5'micr17051101 t = 0 t = 24 hrs pre'treatment

| | | | | | |
|---|---|---|---|---|---|
| starting'citric'acid'solution'(ml) | 2.76 | calculation mass'fabric | D1 | 14.0077 gr | 14.0646 gr |
| citric'acid'concentration'(%) | 100.000% | input | D2 | 13.8871 gr | 13.9252 gr |
| required'Dl'(ml) | 1102.77 | calculation | D3 | 16.6637 gr | 13.7137 gr |
| required'citric'acid'concentration'(%) | 0.250% | input | D4 | 13.7184 gr | 13.7276 gr |
| final'solution'(ml) | 1105.54 | input | tot | 55.2769 gr | 55.4311 gr |
| | | | liquor'ratio 20 | 1 | percentage'change 0.3% |
| | | | total'liquor | 1105.538 ml | | coating

| | | | |
|---|---|---|---|
| final'solution'(ml) | 1105.54 | input total'liquor | 1105.538 ml |
| required'Dl'(ml) | 1011.20 | calculation | |
| required'solution'silk'low'mw'(ml) | 69.10 | calculation | |
| concentration'silk'low'mw'(%) | 6.000% | input | |
| required'silk'concentration'low'mw'(%) | 0.375% | input | |
| required'silk'solution'medium'mw'(ml) | 23.03 | calculation | |
| concentration'silk'medium'mw'(%) | 6.000% | input | |
| required'silk'concentration'medium'mw'(%) | 0.125% | input | |
| required'citric'acid'(ml) | 2.21 | calculation | |
| citric'acid'(%) | 100.000% | input | |
| required'citric'acid'concentration'(%) | 0.200% | input | | post treatment

| | | | | |
|---|---|---|---|---|
| starting'citric'acid'solution'(ml) | 2.76 | calculation tot | 55.2769 gr | |
| citric'acid'concentration'(%) | 100.000% | input | liquor'ratio 20 | 1 |
| required'Dl'(ml) | 1102.77 | calculation | total'liquor | 1105.538 ml |
| required'citric'acid'concentration'(%) | 0.250% | input | | |
| final'solution'(ml) | 1105.54 | input | | |

TABLE 11-continued

Processing recording and mass percentage change
post treatment sample 17051101
fabric'C 17042001'NeW'1/27"SW'with'23.5'micr17051101 t = 0 t = 24 hrs final'treatment

| | | | | |
|---|---|---|---|---|
| starting'methanol'solution'(ml) | 442.22 | tot | 55.2769 gr | |
| methanol'concentration'(%) | 100.000% | liquor'ratio 10 | 1 | |
| required'DI'(ml) | 110.55 | total'liquor | 552.769 ml | |
| required'methanol'concentration'(%) | 80.000% | | | |
| final'solution'(ml) | 552.77 | | | |

The following tables (Tables 12 to 36) include testing data for assessing the dimensional stability to laundering using the Woolmark method (Woolmark test method: Washing of Wool Textile Products—The Woolmark Company TM31-May 2000, incorporated by reference herein in its entirety), and the AATCC method (Dimensional Changes of Fabrics after Home Laundering—AATCC Test Method 135-2015, incorporated by reference herein in its entirety). Unless specified otherwise, the sample type is knitted fabric, the sample form is tube, and the sample color is greige.

Testing Information: Home Laundered, times using AATCC TM 150 Table II; Laundry Test Conditions: load size=1.8 kg (4 lbs); Launder Right Side Out; Top Loading Machine Wash (2) Delicate, using 66±1 g 1993 AATCC Standard Reference Detergent WOB; (A) Tumble Dry ii Delicate; Ballast Wash Load Type 3—50/50 polyester/cotton bleached plain weave; (−) indicates shrinkage and (+) indicates growth; fabrics were not hand ironed or restored; evaluation conditions: 21° C. (±2° C.) and 65% RH (±5% RH).

TABLE 12

Reference TS 131863/17051001 Coated

| | Length | | Width | |
|---|---|---|---|---|
| | Specimen 1 | Specimen 2 | Specimen 1 | Specimen 2 |
| Original State | 20.0 cm | 20.1 cm | 6.4 cm | 6.3 cm |
| After 1X wash | 17.9 cm | 17.7 cm | 6.3 cm | 6.3 cm |
| shrinkage/growth | −2.1 cm | −2.4 cm | −0.1 cm | 0.0 cm |
| Dimensional Change | −10.5% | −11.9% | −1.6% | 0.0% |
| Original State | 20.0 cm | 20.1 cm | 6.4 cm | 6.3 cm |
| After 2X wash | 17.1 cm | 17.2 cm | 6.4 cm | 6.4 cm |
| shrinkage/growth | −2.9 cm | −2.9 cm | 0.0 cm | 0.1 cm |
| Dimensional Change | −14.5% | −14.4% | 0.0% | 1.6% |
| After 1X wash | 17.9 cm | 17.7 cm | 6.3 cm | 6.3 cm |
| After 2X wash | 17.1 cm | 17.2 cm | 6.4 cm | 6.4 cm |
| shrinkage/growth | −0.8 cm | −0.5 cm | 0.1 cm | 0.1 cm |
| Dimensional Change | −4.5% | −2.8% | 1.6% | 1.6% |
| Original State | 20.0 cm | 20.1 cm | 6.4 cm | 6.3 cm |
| After 3X wash | 16.2 cm | 16.6 cm | 6.2 cm | 6.3 cm |
| shrinkage/growth | −3.8 cm | −3.5 cm | −0.2 cm | 0.0 cm |
| Dimensional Change | −19.0% | −17.4% | −3.1% | 0.0% |
| After 1X wash | 17.9 cm | 17.7 cm | 6.3 cm | 6.3 cm |
| After 3X wash | 16.2 cm | 16.6 cm | 6.2 cm | 6.3 cm |
| shrinkage/growth | −1.7 cm | −1.1 cm | −0.1 cm | 0.0 cm |
| Dimensional Change | −9.5% | −6.2% | −1.6% | 0.0% |
| Original State | 20.0 cm | 20.1 cm | 6.4 cm | 6.3 cm |
| After 4X wash | 15.1 cm | 15.7 cm | 6.2 cm | 6.1 cm |
| shrinkage/growth | −4.9 cm | −4.4 cm | −0.2 cm | −0.2 cm |
| Dimensional Change | −24.5% | −21.9% | −3.1% | −3.2% |

TABLE 12-continued

Reference TS 131863/17051001 Coated

| | Length | | Width | |
|---|---|---|---|---|
| | Specimen 1 | Specimen 2 | Specimen 1 | Specimen 2 |
| After 1X wash | 17.9 cm | 17.7 cm | 6.3 cm | 6.3 cm |
| After 4X wash | 15.1 cm | 15.7 cm | 6.2 cm | 6.1 cm |
| shrinkage/growth | −2.8 cm | −2.0 cm | −0.1 cm | −0.2 cm |
| Dimensional Change | −15.6% | −11.3% | −1.6% | −3.2% |

TABLE 13

Reference 131864/17051002 Coated

| | Length | | Width | |
|---|---|---|---|---|
| | Specimen 1 | Specimen 2 | Specimen 1 | Specimen 2 |
| Original State | 19.6 cm | 19.7 cm | 5.6 cm | 6.3 cm |
| After 1X wash | 17.9 cm | 18.2 cm | 5.6 cm | 6.4 cm |
| shrinkage/growth | −1.7 cm | −1.5 cm | 0.0 cm | 0.1 cm |
| Dimensional Change | −8.7% | −7.6% | 0.0% | 1.6% |
| Original State | 19.6 cm | 19.7 cm | 5.6 cm | 6.3 cm |
| After 2X wash | 17.4 cm | 17.4 cm | 5.7 cm | 6.3 cm |
| shrinkage/growth | −2.2 cm | −2.3 cm | 0.1 cm | 0.0 cm |
| Dimensional Change | −11.2% | −11.7% | 1.8% | 0.0% |
| After 1X wash | 17.9 cm | 18.2 cm | 5.6 cm | 6.4 cm |
| After 2X wash | 17.4 cm | 17.4 cm | 5.7 cm | 6.3 cm |
| shrinkage/growth | −0.5 cm | −0.8 cm | 0.1 cm | −0.1 cm |
| Dimensional Change | −2.8% | −4.4% | 1.8% | −1.6% |
| Original State | 19.6 cm | 19.7 cm | 5.6 cm | 6.3 cm |
| After 3X wash | 16.9 cm | 16.9 cm | 5.7 cm | 6.3 cm |
| shrinkage/growth | −2.7 cm | −2.8 cm | 0.1 cm | 0.0 cm |
| Dimensional Change | −13.8% | −14.2% | 1.8% | 0.0% |
| After 1X wash | 17.9 cm | 18.2 cm | 5.6 cm | 6.4 cm |
| After 3X wash | 16.9 cm | 16.9 cm | 5.7 cm | 6.3 cm |
| shrinkage/growth | −1.0 cm | −1.3 cm | 0.1 cm | −0.1 cm |
| Dimensional Change | −5.6% | −7.1% | 1.8% | −1.6% |
| Original State | 19.6 cm | 19.7 cm | 5.6 cm | 6.3 cm |
| After 4X wash | 16.7 cm | 16.5 cm | 5.7 cm | 6.2 cm |
| shrinkage/growth | −2.9 cm | −3.2 cm | 0.1 cm | −0.1 cm |
| Dimensional Change | −14.8% | −16.2% | 1.8% | −1.6% |
| After 1X wash | 17.9 cm | 18.2 cm | 5.6 cm | 6.4 cm |
| After 4X wash | 16.7 cm | 16.5 cm | 5.7 cm | 6.2 cm |
| shrinkage/growth | −1.2 cm | −1.7 cm | 0.1 cm | −0.2 cm |
| Dimensional Change | −6.7% | −9.3% | 1.8% | −3.1% |

TABLE 14

Reference 131865/17051003 Coated

|  | Length | | Width | |
|---|---|---|---|---|
|  | Specimen 1 | Specimen 2 | Specimen 1 | Specimen 2 |
| Original State | 20.2 cm | 20.2 cm | 6.2 cm | 5.7 cm |
| After 1X wash | 18.9 cm | 19.3 cm | 6.2 cm | 5.6 cm |
| shrinkage/growth | −1.3 cm | −0.9 cm | 0.0 cm | −0.1 cm |
| Dimensional Change | −6.4% | −4.5% | 0.0% | −1.8% |
| Original State | 20.2 cm | 20.2 cm | 6.2 cm | 5.7 cm |
| After 2X wash | 19.2 cm | 19.2 cm | 6.1 cm | 5.7 cm |
| shrinkage/growth | −1.0 cm | −1.0 cm | −0.1 cm | 0.0 cm |
| Dimensional Change | −5.0% | −5.0% | −1.6% | 0.0% |
| After 1X wash | 18.9 cm | 19.3 cm | 6.2 cm | 5.6 cm |
| After 2X wash | 19.2 cm | 19.2 cm | 6.1 cm | 5.7 cm |
| shrinkage/growth | 0.3 cm | −0.1 cm | −0.1 cm | 0.1 cm |
| Dimensional Change | 1.6% | −0.5% | −1.6% | 1.8% |
| Original State | 20.2 cm | 20.2 cm | 6.2 cm | 5.7 cm |
| After 3X wash | 18.9 cm | 19.1 cm | 6.0 cm | 5.6 cm |
| shrinkage/growth | −1.3 cm | −1.1 cm | −0.2 cm | −0.1 cm |
| Dimensional Change | −6.4% | −5.4% | −3.2% | −1.8% |
| After 1X wash | 18.9 cm | 19.3 cm | 6.2 cm | 5.6 cm |
| After 3X wash | 18.9 cm | 19.1 cm | 6.0 cm | 5.6 cm |
| shrinkage/growth | 0.0 cm | −0.2 cm | −0.2 cm | 0.0 cm |
| Dimensional Change | 0.0% | −1.0% | −3.2% | 0.0% |
| Original State | 20.2 cm | 20.2 cm | 6.2 cm | 5.7 cm |
| After 4X wash | 18.9 cm | 19.4 cm | 6.0 cm | 5.7 cm |
| shrinkage/growth | −1.3 cm | −0.8 cm | −0.2 cm | 0.0 cm |
| Dimensional Change | −6.4% | −4.0% | −3.2% | 0.0% |
| After 1X wash | 18.9 cm | 19.3 cm | 6.2 cm | 5.6 cm |
| After 4X wash | 18.9 cm | 19.4 cm | 6.0 cm | 5.7 cm |
| shrinkage/growth | 0.0 cm | 0.1 cm | −0.2 cm | 0.1 cm |
| Dimensional Change | 0.0% | 0.5% | −3.2% | 1.8% |

TABLE 15

Reference 131866/17051101 Coated

|  | Length | | Width | |
|---|---|---|---|---|
|  | Specimen 1 | Specimen 2 | Specimen 1 | Specimen 2 |
| Original State | 20.1 cm | 19.8 cm | 5.9 cm | 5.9 cm |
| After 1X wash | 18.9 cm | 18.9 cm | 5.8 cm | 6.0 cm |
| shrinkage/growth | −1.2 cm | −0.9 cm | −0.1 cm | 0.1 cm |
| Dimensional Change | −6.0% | −4.5% | −1.7% | 1.7% |
| Original State | 20.1 cm | 19.8 cm | 5.9 cm | 5.9 cm |
| After 2X wash | 18.9 cm | 18.7 cm | 5.9 cm | 5.8 cm |
| shrinkage/growth | −1.2 cm | −1.1 cm | 0.0 cm | −0.1 cm |
| Dimensional Change | −6.0% | −5.6% | 0.0% | −1.7% |
| After 1X wash | 18.9 cm | 18.9 cm | 5.8 cm | 6.0 cm |
| After 2X wash | 18.9 cm | 18.7 cm | 5.9 cm | 5.8 cm |
| shrinkage/growth | 0.0 cm | −0.2 cm | 0.1 cm | −0.2 cm |
| Dimensional Change | 0.0% | −1.1% | 1.7% | −3.3% |
| Original State | 20.1 cm | 19.8 cm | 5.9 cm | 5.9 cm |
| After 3X wash | 18.9 cm | 18.7 cm | 5.8 cm | 5.9 cm |
| shrinkage/growth | −1.2 cm | −1.1 cm | −0.1 cm | 0.0 cm |
| Dimensional Change | −6.0% | −5.6% | −1.7% | 0.0% |
| After 1X wash | 18.9 cm | 18.9 cm | 5.8 cm | 6.0 cm |
| After 3X wash | 18.9 cm | 18.7 cm | 5.8 cm | 5.9 cm |
| shrinkage/growth | 0.0 cm | −0.2 cm | 0.0 cm | −0.1 cm |
| Dimensional Change | 0.0% | −1.1% | 0.0% | −1.7% |
| Original State | 20.1 cm | 19.8 cm | 5.9 cm | 5.9 cm |
| After 4X wash | 18.9 cm | 18.9 cm | 5.7 cm | 5.7 cm |
| shrinkage/growth | −1.2 cm | −0.9 cm | −0.2 cm | −0.2 cm |
| Dimensional Change | −6.0% | −4.5% | −3.4% | −3.4% |
| After 1X wash | 18.9 cm | 18.9 cm | 5.8 cm | 6.0 cm |
| After 4X wash | 18.9 cm | 18.9 cm | 5.7 cm | 5.7 cm |
| shrinkage/growth | 0.0 cm | 0.0 cm | −0.1 cm | −0.3 cm |
| Dimensional Change | 0.0% | 0.0% | −1.7% | −5.0% |

TABLE 16

Reference 131867/17042001 Control

|  | Length | | Width | |
|---|---|---|---|---|
|  | Specimen 1 | Specimen 2 | Specimen 1 | Specimen 2 |
| Original State | 20.2 cm | 20.4 cm | 7.5 cm | 7.0 cm |
| After 1X wash | 20.0 cm | 20.4 cm | 6.5 cm | 5.8 cm |
| shrinkage/growth | −0.2 cm | 0.0 cm | −1.0 cm | −1.2 cm |
| Dimensional Change | −1.0% | 0.0% | −13.3% | −17.1% |
| Original State | 20.2 cm | 20.4 cm | 7.5 cm | 7.0 cm |
| After 2X wash | 20.2 cm | 20.2 cm | 6.2 cm | 5.7 cm |
| shrinkage/growth | 0.0 cm | −0.2 cm | −1.3 cm | −1.3 cm |
| Dimensional Change | 0.0% | −1.0% | −17.3% | −18.6% |
| After 1X wash | 20.0 cm | 20.4 cm | 6.5 cm | 5.8 cm |
| After 2X wash | 20.2 cm | 20.2 cm | 6.2 cm | 5.7 cm |
| shrinkage/growth | 0.2 cm | −0.2 cm | −0.3 cm | −0.1 cm |
| Dimensional Change | 1.0% | −1.0% | −4.6% | −1.7% |
| Original State | 20.2 cm | 20.4 cm | 7.5 cm | 7.0 cm |
| After 3X wash | 20.2 cm | 20.0 cm | 6.1 cm | 5.6 cm |
| shrinkage/growth | 0.0 cm | −0.4 cm | −1.4 cm | −1.4 cm |
| Dimensional Change | 0.0% | −2.0% | −18.7% | −20.0% |
| After 1X wash | 20.0 cm | 20.4 cm | 6.5 cm | 5.8 cm |
| After 3X wash | 20.2 cm | 20.0 cm | 6.1 cm | 5.6 cm |
| shrinkage/growth | 0.2 cm | −0.4 cm | −0.4 cm | −0.2 cm |
| Dimensional Change | 1.0% | −2.0% | −6.2% | −3.4% |
| Original State | 20.2 cm | 20.4 cm | 7.5 cm | 7.0 cm |
| After 4X wash | 20.1 cm | 20.1 cm | 6.4 cm | 5.7 cm |
| shrinkage/growth | −0.1 cm | −0.3 cm | −1.1 cm | −1.3 cm |
| Dimensional Change | −0.5% | −1.5% | −14.7% | −18.6% |
| After 1X wash | 20.0 cm | 20.4 cm | 6.5 cm | 5.8 cm |
| After 4X wash | 20.1 cm | 20.1 cm | 6.4 cm | 5.7 cm |
| shrinkage/growth | 0.1 cm | −0.3 cm | −0.1 cm | −0.1 cm |
| Dimensional Change | 0.5% | −1.5% | −1.5% | −1.7% |

Note:
Sample was torqued after wash

TABLE 17

Reference 131868/17042002 Control

|  | Length | | Width | |
|---|---|---|---|---|
|  | Specimen 1 | Specimen 2 | Specimen 1 | Specimen 2 |
| Original State | 20.0 cm | 19.9 cm | 7.0 cm | 6.1 cm |
| After 1X wash | 20.9 cm | 20.7 cm | 6.0 cm | 5.4 cm |
| shrinkage/growth | 0.9 cm | 0.8 cm | −1.0 cm | −0.7 cm |
| Dimensional Change | 4.5% | 4.0% | −14.3% | −11.5% |

TABLE 17-continued

Reference 131868/17042002 Control

|  | Length | | Width | |
|---|---|---|---|---|
|  | Specimen 1 | Specimen 2 | Specimen 1 | Specimen 2 |
| Original State | 20.0 cm | 19.9 cm | 7.0 cm | 6.1 cm |
| After 2X wash | 21.0 cm | 21.2 cm | 5.9 cm | 5.2 cm |
| shrinkage/growth | 1.0 cm | 1.3 cm | −1.1 cm | −0.9 cm |
| Dimensional Change | 5.0% | 6.5% | −15.7% | −14.8% |
| After 1X wash | 20.9 cm | 20.7 cm | 6.0 cm | 5.4 cm |
| After 2X wash | 21.0 cm | 21.2 cm | 5.9 cm | 5.2 cm |
| shrinkage/growth | 0.1 cm | 0.5 cm | −0.1 cm | −0.2 cm |
| Dimensional Change | 0.5% | 2.4% | −1.7% | −3.7% |
| Original State | 20.0 cm | 19.9 cm | 7.0 cm | 6.1 cm |
| After 3X wash | 21.1 cm | 20.7 cm | 5.9 cm | 5.1 cm |
| shrinkage/growth | 1.1 cm | 0.8 cm | −1.1 cm | −1.0 cm |
| Dimensional Change | 5.5% | 4.0% | −15.7% | −16.4% |
| After 1X wash | 20.9 cm | 20.7 cm | 6.0 cm | 5.4 cm |
| After 3X wash | 21.1 cm | 20.7 cm | 5.9 cm | 5.1 cm |
| shrinkage/growth | 0.2 cm | 0.0 cm | −0.1 cm | −0.3 cm |
| Dimensional Change | 1.0% | 0.0% | −1.7% | −5.6% |
| Original State | 20.0 cm | 19.9 cm | 7.0 cm | 6.1 cm |
| After 4X wash | 21.1 cm | 20.7 cm | 5.9 cm | 5.4 cm |
| shrinkage/growth | 1.1 cm | 0.8 cm | −1.1 cm | −0.7 cm |
| Dimensional Change | 5.5% | 4.0% | −15.7% | −11.5% |
| After 1X wash | 20.9 cm | 20.7 cm | 6.0 cm | 5.4 cm |
| After 4X wash | 21.1 cm | 20.7 cm | 5.9 cm | 5.4 cm |
| shrinkage/growth | 0.2 cm | 0.0 cm | −0.1 cm | 0.0 cm |
| Dimensional Change | 1.0% | 0.0% | −1.7% | 0.0% |

Note:
Sample was torqued after wash

TABLE 18

Reference 131869/17050901 Control

|  | Length | | Width | |
|---|---|---|---|---|
|  | Specimen 1 | Specimen 2 | Specimen 1 | Specimen 2 |
| Original State | 20.1 cm | 20.9 cm | 6.5 cm | 6.2 cm |
| After 1X wash | 17.5 cm | 19.9 cm | 5.9 cm | 5.4 cm |
| shrinkage/growth | −2.6 cm | −1.0 cm | −0.6 cm | −0.8 cm |
| Dimensional Change | −12.9% | −4.8% | −9.2% | −12.9% |
| Original State | 20.1 cm | 20.9 cm | 6.5 cm | 6.2 cm |
| After 2X wash | 18.1 cm | 19.7 cm | 5.5 cm | 5.4 cm |
| shrinkage/growth | −2.0 cm | −1.2 cm | −1.0 cm | −0.8 cm |
| Dimensional Change | −10.0% | −5.7% | −15.4% | −12.9% |
| After 1X wash | 17.5 cm | 19.9 cm | 5.9 cm | 5.4 cm |
| After 2X wash | 18.1 cm | 19.7 cm | 5.5 cm | 5.4 cm |
| shrinkage/growth | 0.6 cm | −0.2 cm | −0.4 cm | 0.0 cm |
| Dimensional Change | 3.4% | −1.0% | −6.8% | 0.0% |
| Original State | 20.1 cm | 20.9 cm | 6.5 cm | 6.2 cm |
| After 3X wash | 17.2 cm | 18.5 cm | 5.4 cm | 5.2 cm |
| shrinkage/growth | −2.9 cm | −2.4 cm | −1.1 cm | −1.0 cm |
| Dimensional Change | −14.4% | −11.5% | −16.9% | −16.1% |
| After 1X wash | 17.5 cm | 19.9 cm | 5.9 cm | 5.4 cm |
| After 3X wash | 17.2 cm | 18.5 cm | 5.4 cm | 5.2 cm |
| shrinkage/growth | −0.3 cm | −1.4 cm | −0.5 cm | −0.2 cm |
| Dimensional Change | −1.7% | −7.0% | −8.5% | −3.7% |
| Original State | 20.1 cm | 20.9 cm | 6.5 cm | 6.2 cm |
| After 4X wash | 16.8 cm | 17.4 cm | 5.1 cm | 5.2 cm |
| shrinkage/growth | −3.3 cm | −3.5 cm | −1.4 cm | −1.0 cm |
| Dimensional Change | −16.4% | −16.7% | −21.5% | −16.1% |

TABLE 18-continued

Reference 131869/17050901 Control

|  | Length | | Width | |
|---|---|---|---|---|
|  | Specimen 1 | Specimen 2 | Specimen 1 | Specimen 2 |
| After 1X wash | 17.5 cm | 19.9 cm | 5.9 cm | 5.4 cm |
| After 4X wash | 16.8 cm | 17.4 cm | 5.1 cm | 5.2 cm |
| shrinkage/growth | −0.7 cm | −2.5 cm | −0.8 cm | −0.2 cm |
| Dimensional Change | −4.0% | −12.6% | −13.6% | −3.7% |

Note:
Sample was torqued and wrinkled after wash

TABLE 19

Reference 131870/17050902 Control

|  | Length | | Width | |
|---|---|---|---|---|
|  | Specimen 1 | Specimen 2 | Specimen 1 | Specimen 2 |
| Original State | 20.4 cm | 20.5 cm | 6.5 cm | 6.2 cm |
| After 1X wash | 19.0 cm | 20.0 cm | 5.2 cm | 5.4 cm |
| shrinkage/growth | −1.4 cm | −0.5 cm | −1.3 cm | −0.8 cm |
| Dimensional Change | −6.9% | −2.4% | −20.0% | −12.9% |
| Original State | 20.4 cm | 20.5 cm | 6.5 cm | 6.2 cm |
| After 2X wash | 18.4 cm | 20.2 cm | 5.3 cm | 5.1 cm |
| shrinkage/growth | −2.0 cm | −0.3 cm | −1.2 cm | −1.1 cm |
| Dimensional Change | −9.8% | −1.5% | −18.5% | −17.7% |
| After 1X wash | 19.0 cm | 20.0 cm | 5.2 cm | 5.4 cm |
| After 2X wash | 18.4 cm | 20.2 cm | 5.3 cm | 5.1 cm |
| shrinkage/growth | −0.6 cm | 0.2 cm | 0.1 cm | −0.3 cm |
| Dimensional Change | −3.2% | 1.0% | 1.9% | −5.6% |
| Original State | 20.4 cm | 20.5 cm | 6.5 cm | 6.2 cm |
| After 3X wash | 17.7 cm | 18.1 cm | 5.0 cm | 5.0 cm |
| shrinkage/growth | −2.7 cm | −2.4 cm | −1.5 cm | −1.2 cm |
| Dimensional Change | −13.2% | −11.7% | −23.1% | −19.4% |
| After 1X wash | 19.0 cm | 20.0 cm | 5.2 cm | 5.4 cm |
| After 3X wash | 17.7 cm | 18.1 cm | 5.0 cm | 5.0 cm |
| shrinkage/growth | −1.3 cm | −1.9 cm | −0.2 cm | −0.4 cm |
| Dimensional Change | −6.8% | −9.5% | −3.8% | −7.4% |
| Original State | 20.4 cm | 20.5 cm | 6.5 cm | 6.2 cm |
| After 4X wash | 17.7 cm | 18.2 cm | 5.0 cm | 5.1 cm |
| shrinkage/growth | −2.7 cm | −2.3 cm | −1.5 cm | −1.1 cm |
| Dimensional Change | −13.2% | −11.2% | −23.1% | −17.7% |
| After 1X wash | 19.0 cm | 20.0 cm | 5.2 cm | 5.4 cm |
| After 4X wash | 17.7 cm | 18.2 cm | 5.0 cm | 5.1 cm |
| shrinkage/growth | −1.3 cm | −1.8 cm | −0.2 cm | −0.3 cm |
| Dimensional Change | −6.8% | −9.0% | −3.8% | −5.6% |

Note:
Sample was torqued and wrinkled after wash

TABLE 20

Reference 132484/17060105

|  | Length | | Width | |
|---|---|---|---|---|
|  | Specimen 1 | Specimen 2 | Specimen 1 | Specimen 2 |
| Original State | 19.4 cm | 20.2 cm | 5.2 cm | 5.1 cm |
| After 1X wash | 17.5 cm | 17.9 cm | 5.1 cm | 4.9 cm |
| shrinkage/growth | −1.9 cm | −2.3 cm | −0.1 cm | −0.2 cm |
| Dimensional Change | −9.8% | −11.4% | −1.9% | −3.9% |
| Original State | 19.4 cm | 20.2 cm | 5.2 cm | 5.1 cm |
| After 2X wash | 16.7 cm | 17.0 cm | 5.2 cm | 5.0 cm |

TABLE 20-continued

Reference 132484/17060105

|  | Length | | Width | |
| --- | --- | --- | --- | --- |
|  | Specimen 1 | Specimen 2 | Specimen 1 | Specimen 2 |
| shrinkage/growth | −2.7 cm | −3.2 cm | 0.0 cm | −0.1 cm |
| Dimensional Change | −13.9% | −15.8% | 0.0% | −2.0% |
| After 1X wash | 17.5 cm | 17.9 cm | 5.1 cm | 4.9 cm |
| After 2X wash | 16.7 cm | 17.0 cm | 5.2 cm | 5.0 cm |
| shrinkage/growth | −0.8 cm | −0.9 cm | 0.1 cm | 0.1 cm |
| Dimensional Change | −4.6% | −5.0% | 2.0% | 2.0% |
| Original State | 19.4 cm | 20.2 cm | 5.2 cm | 5.1 cm |
| After 3X wash | 16.0 cm | 16.2 cm | 4.9 cm | 5.0 cm |
| shrinkage/growth | −3.4 cm | −4.0 cm | −0.3 cm | −0.1 cm |
| Dimensional Change | −17.5% | −19.8% | −5.8% | −2.0% |
| After 1X wash | 17.5 cm | 17.9 cm | 5.1 cm | 4.9 cm |
| After 3X wash | 16.0 cm | 16.2 cm | 4.9 cm | 5.0 cm |
| shrinkage/growth | −1.5 cm | −1.7 cm | −0.2 cm | 0.1 cm |
| Dimensional Change | −8.6% | −9.5% | −3.9% | 2.0% |
| Original State | 19.4 cm | 20.2 cm | 5.2 cm | 5.1 cm |
| After 4X wash | 15.4 cm | 15.5 cm | 4.8 cm | 4.8 cm |
| shrinkage/growth | −4.0 cm | −4.7 cm | −0.4 cm | −0.3 cm |
| Dimensional Change | −20.6% | −23.3% | −7.7% | −5.9% |
| After 1X wash | 17.5 cm | 17.9 cm | 5.1 cm | 4.9 cm |
| After 4X wash | 15.4 cm | 15.5 cm | 4.8 cm | 4.8 cm |
| shrinkage/growth | −2.1 cm | −2.4 cm | −0.3 cm | −0.1 cm |
| Dimensional Change | −12.0% | −13.4% | −5.9% | −2.0% |

TABLE 21

Reference 132485/17060106

|  | Length | | Width | |
| --- | --- | --- | --- | --- |
|  | Specimen 1 | Specimen 2 | Specimen 1 | Specimen 2 |
| Original State | 20.1 cm | 20.5 cm | 5.4 cm | 5.2 cm |
| After 1X wash | 18.1 cm | 17.8 cm | 4.8 cm | 4.3 cm |
| shrinkage/growth | −2.0 cm | −2.7 cm | −0.6 cm | −0.9 cm |
| Dimensional Change | −10.0% | −13.2% | −11.1% | −17.3% |
| Original State | 20.1 cm | 20.5 cm | 5.4 cm | 5.2 cm |
| After 2X wash | 16.8 cm | 16.9 cm | 4.6 cm | 4.7 cm |
| shrinkage/growth | −3.3 cm | −3.6 cm | −0.8 cm | −0.5 cm |
| Dimensional Change | −16.4% | −17.6% | −14.8% | −9.6% |
| After 1X wash | 18.1 cm | 17.8 cm | 4.8 cm | 4.3 cm |
| After 2X wash | 16.8 cm | 16.9 cm | 4.6 cm | 4.7 cm |
| shrinkage/growth | −1.3 cm | −0.9 cm | −0.2 cm | 0.4 cm |
| Dimensional Change | −7.2% | −5.1% | −4.2% | 9.3% |
| Original State | 20.1 cm | 20.5 cm | 5.4 cm | 5.2 cm |
| After 3X wash | 16.2 cm | 16.3 cm | 4.4 cm | 4.2 cm |
| shrinkage/growth | −3.9 cm | −4.2 cm | −1.0 cm | −1.0 cm |
| Dimensional Change | −19.4% | −20.5% | −18.5% | −19.2% |
| After 1X wash | 18.1 cm | 17.8 cm | 4.8 cm | 4.3 cm |
| After 3X wash | 16.2 cm | 16.3 cm | 4.4 cm | 4.2 cm |
| shrinkage/growth | −1.9 cm | −1.5 cm | −0.4 cm | −0.1 cm |
| Dimensional Change | −10.5% | −8.4% | −8.3% | −2.3% |
| Original State | 20.1 cm | 20.5 cm | 5.4 cm | 5.2 cm |
| After 4X wash | 15.4 cm | 15.7 cm | 4.5 cm | 4.2 cm |
| shrinkage/growth | −4.7 cm | −4.8 cm | −0.9 cm | −1.0 cm |
| Dimensional Change | −23.4% | −23.4% | −16.7% | −19.2% |
| After 1X wash | 18.1 cm | 17.8 cm | 4.8 cm | 4.3 cm |
| After 4X wash | 15.4 cm | 15.7 cm | 4.5 cm | 4.2 cm |
| shrinkage/growth | −2.7 cm | −2.1 cm | −0.3 cm | −0.1 cm |
| Dimensional Change | −14.9% | −11.8% | −6.3% | −2.3% |

TABLE 22

Reference 132486/17060107

|  | Length | | Width | |
| --- | --- | --- | --- | --- |
|  | Specimen 1 | Specimen 2 | Specimen 1 | Specimen 2 |
| Original State | 20.8 cm | 20.7 cm | 5.5 cm | 5.2 cm |
| After 1X wash | 18.8 cm | 18.6 cm | 5.2 cm | 4.8 cm |
| shrinkage/growth | −2.0 cm | −2.1 cm | −0.3 cm | −0.4 cm |
| Dimensional Change | −9.6% | −10.1% | −5.5% | −7.7% |
| Original State | 20.8 cm | 20.7 cm | 5.5 cm | 5.2 cm |
| After 2X wash | 18.5 cm | 18.1 cm | 5.3 cm | 4.8 cm |
| shrinkage/growth | −2.3 cm | −2.6 cm | −0.2 cm | −0.4 cm |
| Dimensional Change | −11.1% | −12.6% | −3.6% | −7.7% |
| After 1X wash | 18.8 cm | 18.6 cm | 5.2 cm | 4.8 cm |
| After 2X wash | 18.5 cm | 18.1 cm | 5.3 cm | 4.8 cm |
| shrinkage/growth | −0.3 cm | −0.5 cm | 0.1 cm | 0.0 cm |
| Dimensional Change | −1.6% | −2.7% | 1.9% | 0.0% |
| Original State | 20.8 cm | 20.7 cm | 5.5 cm | 5.2 cm |
| After 3X wash | 17.4 cm | 18.1 cm | 5.4 cm | 4.9 cm |
| shrinkage/growth | −3.4 cm | −2.6 cm | −0.1 cm | −0.3 cm |
| Dimensional Change | −16.3% | −12.6% | −1.8% | −5.8% |
| After 1X wash | 18.8 cm | 18.6 cm | 5.2 cm | 4.8 cm |
| After 3X wash | 17.4 cm | 18.1 cm | 5.4 cm | 4.9 cm |
| shrinkage/growth | −1.4 cm | −0.5 cm | 0.2 cm | 0.1 cm |
| Dimensional Change | −7.4% | −2.7% | 3.8% | 2.1% |
| Original State | 20.8 cm | 20.7 cm | 5.5 cm | 5.2 cm |
| After 4X wash | 17.4 cm | 17.7 cm | 5.3 cm | 4.9 cm |
| shrinkage/growth | −3.4 cm | −3.0 cm | −0.2 cm | −0.3 cm |
| Dimensional Change | −16.3% | −14.5% | −3.6% | −5.8% |
| After 1X wash | 18.8 cm | 18.6 cm | 5.2 cm | 4.8 cm |
| After 4X wash | 17.4 cm | 17.7 cm | 5.3 cm | 4.9 cm |
| shrinkage/growth | −1.4 cm | −0.9 cm | 0.1 cm | 0.1 cm |
| Dimensional Change | −7.4% | −4.8% | 1.9% | 2.1% |

TABLE 23

Reference 132487/17060108

|  | Length | | Width | |
| --- | --- | --- | --- | --- |
|  | Specimen 1 | Specimen 2 | Specimen 1 | Specimen 2 |
| Original State | 20.5 cm | 20.5 cm | 5.4 cm | 5.4 cm |
| After 1X wash | 18.6 cm | 18.4 cm | 4.9 cm | 4.9 cm |
| shrinkage/growth | −1.9 cm | −2.1 cm | −0.5 cm | −0.5 cm |
| Dimensional Change | −9.3% | −10.2% | −9.3% | −9.3% |
| Original State | 20.5 cm | 20.5 cm | 5.4 cm | 5.4 cm |
| After 2X wash | 18.5 cm | 18.1 cm | 4.9 cm | 4.8 cm |
| shrinkage/growth | −2.0 cm | −2.4 cm | −0.5 cm | −0.6 cm |
| Dimensional Change | −9.8% | −11.7% | −9.3% | −11.1% |
| After 1X wash | 18.6 cm | 18.4 cm | 4.9 cm | 4.9 cm |
| After 2X wash | 18.5 cm | 18.1 cm | 4.9 cm | 4.8 cm |
| shrinkage/growth | −0.1 cm | −0.3 cm | 0.0 cm | −0.1 cm |

TABLE 23-continued

Reference 132487/17060108

| | Length | | Width | |
|---|---|---|---|---|
| | Specimen 1 | Specimen 2 | Specimen 1 | Specimen 2 |
| Dimensional Change | −0.5% | −1.6% | 0.0% | −2.0% |
| Original State | 20.5 cm | 20.5 cm | 5.4 cm | 5.4 cm |
| After 3X wash | 18.0 cm | 17.7 cm | 4.5 cm | 5.0 cm |
| shrinkage/growth | −2.5 cm | −2.8 cm | −0.9 cm | −0.4 cm |
| Dimensional Change | −12.2% | −13.7% | −16.7% | −7.4% |
| After 1X wash | 18.6 cm | 18.4 cm | 4.9 cm | 4.9 cm |
| After 3X wash | 18.0 cm | 17.7 cm | 4.5 cm | 5.0 cm |
| shrinkage/growth | −0.6 cm | −0.7 cm | −0.4 cm | 0.1 cm |
| Dimensional Change | −3.2% | −3.8% | −8.2% | 2.0% |
| Original State | 20.5 cm | 20.5 cm | 5.4 cm | 5.4 cm |
| After 4X wash | 17.5 cm | 17.7 cm | 4.6 cm | 4.9 cm |
| shrinkage/growth | −3.0 cm | −2.8 cm | −0.8 cm | −0.5 cm |
| Dimensional Change | −14.6% | −13.7% | −14.8% | −9.3% |
| After 1X wash | 18.6 cm | 18.4 cm | 4.9 cm | 4.9 cm |
| After 4X wash | 17.5 cm | 17.7 cm | 4.6 cm | 4.9 cm |
| shrinkage/growth | −1.1 cm | −0.7 cm | −0.3 cm | 0.0 cm |
| Dimensional Change | −5.9% | −3.8% | −6.1% | 0.0% |

TABLE 24

Reference 132488/17060201

| | Length | | Width | |
|---|---|---|---|---|
| | Specimen 1 | Specimen 2 | Specimen 1 | Specimen 2 |
| Original State | 20.2 cm | 20.5 cm | 5.4 cm | 5.3 cm |
| After 1X wash | 18.9 cm | 18.8 cm | 5.1 cm | 5.1 cm |
| shrinkage/growth | −1.3 cm | −1.7 cm | −0.3 cm | −0.2 cm |
| Dimensional Change | −6.4% | −8.3% | −5.6% | −3.8% |
| Original State | 20.2 cm | 20.5 cm | 5.4 cm | 5.3 cm |
| After 2X wash | 18.7 cm | 19.2 cm | 5.2 cm | 5.2 cm |
| shrinkage/growth | −1.5 cm | −1.3 cm | −0.2 cm | −0.1 cm |
| Dimensional Change | −7.4% | −6.3% | −3.7% | −1.9% |
| After 1X wash | 18.9 cm | 18.8 cm | 5.1 cm | 5.1 cm |
| After 2X wash | 18.7 cm | 19.2 cm | 5.2 cm | 5.2 cm |
| shrinkage/growth | −0.2 cm | 0.4 cm | 0.1 cm | 0.1 cm |
| Dimensional Change | −1.1% | 2.1% | 2.0% | 2.0% |
| Original State | 20.2 cm | 20.5 cm | 5.4 cm | 5.3 cm |
| After 3X wash | 18.6 cm | 19.1 cm | 5.0 cm | 5.1 cm |
| shrinkage/growth | −1.6 cm | −1.4 cm | −0.4 cm | −0.2 cm |
| Dimensional Change | −7.9% | −6.8% | −7.4% | −3.8% |
| After 1X wash | 18.9 cm | 18.8 cm | 5.1 cm | 5.1 cm |
| After 3X wash | 18.6 cm | 19.1 cm | 5.0 cm | 5.1 cm |
| shrinkage/growth | −0.3 cm | 0.3 cm | −0.1 cm | 0.0 cm |
| Dimensional Change | −1.6% | 1.6% | −2.0% | 0.0% |
| Original State | 20.2 cm | 20.5 cm | 5.4 cm | 5.3 cm |
| After 4X wash | 18.7 cm | 18.9 cm | 5.1 cm | 5.1 cm |
| shrinkage/growth | −1.5 cm | −1.6 cm | −0.3 cm | −0.2 cm |
| Dimensional Change | −7.4% | −7.8% | −5.6% | −3.8% |
| After 1X wash | 18.9 cm | 18.8 cm | 5.1 cm | 5.1 cm |
| After 4X wash | 18.7 cm | 18.9 cm | 5.1 cm | 5.1 cm |
| shrinkage/growth | −0.2 cm | 0.1 cm | 0.0 cm | 0.0 cm |
| Dimensional Change | −1.1% | 0.5% | 0.0% | 0.0% |

TABLE 25

Reference 132489/17060202

| | Length | | Width | |
|---|---|---|---|---|
| | Specimen 1 | Specimen 2 | Specimen 1 | Specimen 2 |
| Original State | 20.5 cm | 20.4 cm | 5.3 cm | 5.3 cm |
| After 1X wash | 19.7 cm | 19.4 cm | 5.1 cm | 5.0 cm |
| shrinkage/growth | −0.8 cm | −1.0 cm | −0.2 cm | −0.3 cm |
| Dimensional Change | −3.9% | −4.9% | −3.8% | −5.7% |
| Original State | 20.5 cm | 20.4 cm | 5.3 cm | 5.3 cm |
| After 2X wash | 19.5 cm | 19.7 cm | 5.1 cm | 5.0 cm |
| shrinkage/growth | −1.0 cm | −0.7 cm | −0.2 cm | −0.3 cm |
| Dimensional Change | −4.9% | −3.4% | −3.8% | −5.7% |
| After 1X wash | 19.7 cm | 19.4 cm | 5.1 cm | 5.0 cm |
| After 2X wash | 19.5 cm | 19.7 cm | 5.1 cm | 5.0 cm |
| shrinkage/growth | −0.2 cm | 0.3 cm | 0.0 cm | 0.0 cm |
| Dimensional Change | −1.0% | 1.5% | 0.0% | 0.0% |
| Original State | 20.5 cm | 20.4 cm | 5.3 cm | 5.3 cm |
| After 3X wash | 19.4 cm | 19.3 cm | 5.0 cm | 5.0 cm |
| shrinkage/growth | −1.1 cm | −1.1 cm | −0.3 cm | −0.3 cm |
| Dimensional Change | −5.4% | −5.4% | −5.7% | −5.7% |
| After 1X wash | 19.7 cm | 19.4 cm | 5.1 cm | 5.0 cm |
| After 3X wash | 19.4 cm | 19.3 cm | 5.0 cm | 5.0 cm |
| shrinkage/growth | −0.3 cm | −0.1 cm | −0.1 cm | 0.0 cm |
| Dimensional Change | −1.5% | −0.5% | −2.0% | 0.0% |
| Original State | 20.5 cm | 20.4 cm | 5.3 cm | 5.3 cm |
| After 4X wash | 19.4 cm | 19.4 cm | 4.9 cm | 4.9 cm |
| shrinkage/growth | −1.1 cm | −1.0 cm | −0.4 cm | −0.4 cm |
| Dimensional Change | −5.4% | −4.9% | −7.5% | −7.5% |
| After 1X wash | 19.7 cm | 19.4 cm | 5.1 cm | 5.0 cm |
| After 4X wash | 19.4 cm | 19.4 cm | 4.9 cm | 4.9 cm |
| shrinkage/growth | −0.3 cm | 0.0 cm | −0.2 cm | −0.1 cm |
| Dimensional Change | −1.5% | 0.0% | −3.9% | −2.0% |

TABLE 26

Reference 132490/17060203

| | Length | | Width | |
|---|---|---|---|---|
| | Specimen 1 | Specimen 2 | Specimen 1 | Specimen 2 |
| Original State | 20.3 cm | 20.1 cm | 5.3 cm | 5.2 cm |
| After 1X wash | 18.9 cm | 18.1 cm | 5.1 cm | 4.9 cm |
| shrinkage/growth | −1.4 cm | −2.0 cm | −0.2 cm | −0.3 cm |
| Dimensional Change | −6.9% | −10.0% | −3.8% | −5.8% |
| Original State | 20.3 cm | 20.1 cm | 5.3 cm | 5.2 cm |
| After 2X wash | 18.7 cm | 18.2 cm | 5.2 cm | 5.0 cm |
| shrinkage/growth | −1.6 cm | −1.9 cm | −0.1 cm | −0.2 cm |
| Dimensional Change | −7.9% | −9.5% | −1.9% | −3.8% |
| After 1X wash | 18.9 cm | 18.1 cm | 5.1 cm | 4.9 cm |
| After 2X wash | 18.7 cm | 18.2 cm | 5.2 cm | 5.0 cm |
| shrinkage/growth | −0.2 cm | 0.1 cm | 0.1 cm | 0.1 cm |
| Dimensional Change | −1.1% | 0.6% | 2.0% | 2.0% |
| Original State | 20.3 cm | 20.1 cm | 5.3 cm | 5.2 cm |
| After 3X wash | 18.9 cm | 18.3 cm | 5.0 cm | 5.0 cm |
| shrinkage/growth | −1.4 cm | −1.8 cm | −0.3 cm | −0.2 cm |
| Dimensional Change | −6.9% | −9.0% | −5.7% | −3.8% |
| After 1X wash | 18.9 cm | 18.1 cm | 5.1 cm | 4.9 cm |
| After 3X wash | 18.9 cm | 18.3 cm | 5.0 cm | 5.0 cm |
| shrinkage/growth | 0.0 cm | 0.2 cm | −0.1 cm | 0.1 cm |
| Dimensional Change | 0.0% | 1.1% | −2.0% | 2.0% |
| Original State | 20.3 cm | 20.1 cm | 5.3 cm | 5.2 cm |
| After 4X wash | 18.7 cm | 18.1 cm | 5.0 cm | 4.8 cm |

TABLE 26-continued

Reference 132490/17060203

| | Length | | Width | |
|---|---|---|---|---|
| | Specimen 1 | Specimen 2 | Specimen 1 | Specimen 2 |
| shrinkage/growth | −1.6 cm | −2.0 cm | −0.3 cm | −0.4 cm |
| Dimensional Change | −7.9% | −10.0% | −5.7% | −7.7% |
| After 1X wash | 18.9 cm | 18.1 cm | 5.1 cm | 4.9 cm |
| After 4X wash | 18.7 cm | 18.1 cm | 5.0 cm | 4.8 cm |
| shrinkage/growth | −0.2 cm | 0.0 cm | −0.1 cm | −0.1 cm |
| Dimensional Change | −1.1% | 0.0% | −2.0% | −2.0% |

TABLE 27

Reference 132491/17060204

| | Length | | Width | |
|---|---|---|---|---|
| | Specimen 1 | Specimen 2 | Specimen 1 | Specimen 2 |
| Original State | 20.7 cm | 20.8 cm | 5.4 cm | 5.3 cm |
| After 1X wash | 18.4 cm | 18.9 cm | 5.1 cm | 4.9 cm |
| shrinkage/growth | −2.3 cm | −1.9 cm | −0.3 cm | −0.4 cm |
| Dimensional Change | −11.1% | −9.1% | −5.6% | −7.5% |
| Original State | 20.7 cm | 20.8 cm | 5.4 cm | 5.3 cm |
| After 2X wash | 18.2 cm | 19.3 cm | 5.1 cm | 4.9 cm |
| shrinkage/growth | −2.5 cm | −1.5 cm | −0.3 cm | −0.4 cm |
| Dimensional Change | −12.1% | −7.2% | −5.6% | −7.5% |
| After 1X wash | 18.4 cm | 18.9 cm | 5.1 cm | 4.9 cm |
| After 2X wash | 18.2 cm | 19.3 cm | 5.1 cm | 4.9 cm |
| shrinkage/growth | −0.2 cm | 0.4 cm | 0.0 cm | 0.0 cm |
| Dimensional Change | −1.1% | 2.1% | 0.0% | 0.0% |
| Original State | 20.7 cm | 20.8 cm | 5.4 cm | 5.3 cm |
| After 3X wash | 18.4 cm | 19.2 cm | 5.0 cm | 4.9 cm |
| shrinkage/growth | −2.3 cm | −1.6 cm | −0.4 cm | −0.4 cm |
| Dimensional Change | −11.1% | −7.7% | −7.4% | −7.5% |
| After 1X wash | 18.4 cm | 18.9 cm | 5.1 cm | 4.9 cm |
| After 3X wash | 18.4 cm | 19.2 cm | 5.0 cm | 4.9 cm |
| shrinkage/growth | 0.0 cm | 0.3 cm | −0.1 cm | 0.0 cm |
| Dimensional Change | 0.0% | 1.6% | −2.0% | 0.0% |
| Original State | 20.7 cm | 20.8 cm | 5.4 cm | 5.3 cm |
| After 4X wash | 18.3 cm | 19.4 cm | 4.9 cm | 4.8 cm |
| shrinkage/growth | −2.4 cm | −1.4 cm | −0.5 cm | −0.5 cm |
| Dimensional Change | −11.6% | −6.7% | −9.3% | −9.4% |
| After 1X wash | 18.4 cm | 18.9 cm | 5.1 cm | 4.9 cm |
| After 4X wash | 18.3 cm | 19.4 cm | 4.9 cm | 4.8 cm |
| shrinkage/growth | −0.1 cm | 0.5 cm | −0.2 cm | −0.1 cm |
| Dimensional Change | −0.5% | 2.6% | −3.9% | −2.0% |

TABLE 28

Summary Chart

| | Length | | Width | |
|---|---|---|---|---|
| | Specimen 1 | Specimen 2 | Specimen 1 | Specimen 2 |
| 17051001 | | | | |
| Original State | 20.0 cm | 20.1 cm | 6.4 cm | 6.3 cm |
| After 1X wash | 17.9 cm | 17.7 cm | 6.3 cm | 6.3 cm |
| shrinkage/growth | −2.1 cm | −2.4 cm | −0.1 cm | 0.0 cm |
| Dimensional Change | −10.5% | −11.9% | −1.6% | 0.0% |

TABLE 28-continued

Summary Chart

| | Length | | Width | |
|---|---|---|---|---|
| | Specimen 1 | Specimen 2 | Specimen 1 | Specimen 2 |
| wool tube 17050901 NeW 1/42.8 with 18.9 micron with 0.5% silk 3L1M 17050901 | | | | |
| Note: Sample was torqued and wrinkled after wash | | | | |
| Original State | 20.1 cm | 20.9 cm | 6.5 cm | 6.2 cm |
| After 1X wash | 17.5 cm | 19.9 cm | 5.9 cm | 5.4 cm |
| shrinkage/growth | −2.6 cm | −1.0 cm | −0.6 cm | −0.8 cm |
| Dimensional Change | −12.9% | −4.8% | −9.2% | −12.9% |
| NeW 1/42.8 with 18.9 micron 17051002 | | | | |
| Original State | 19.6 cm | 19.7 cm | 5.6 cm | 6.3 cm |
| After 1X wash | 17.9 cm | 18.2 cm | 5.6 cm | 6.4 cm |
| shrinkage/growth | −1.7 cm | −1.5 cm | 0.0 cm | 0.1 cm |
| Dimensional Change | −8.7% | −7.6% | 0.0% | 1.6% |
| wool tube 17050902 NeW 1/30 with 21.0 micron with 0.5% silk 3L1M 17050902 | | | | |
| Note: Sample was torqued and wrinkled after wash | | | | |
| Original State | 20.4 cm | 20.5 cm | 6.5 cm | 6.2 cm |
| After 1X wash | 19.0 cm | 20.0 cm | 5.2 cm | 5.4 cm |
| shrinkage/growth | −1.4 cm | −0.5 cm | −1.3 cm | −0.8 cm |
| Dimensional Change | −6.9% | −2.4% | −20.0% | −12.9% |
| NeW 1/30 with 21.0 micron 17051003 | | | | |
| Original State | 20.2 cm | 20.2 cm | 6.2 cm | 5.7 cm |
| After 1X wash | 18.9 cm | 19.3 cm | 6.2 cm | 5.6 cm |
| shrinkage/growth | −1.3 cm | −0.9 cm | 0.0 cm | −0.1 cm |
| Dimensional Change | −6.4% | −4.5% | 0.0% | −1.8% |
| wool tube 17042002 NeW 2/60 with 18.5 micron with 0.5% silk 3L1M 17042002 | | | | |
| Note: Sample was torqued after wash | | | | |
| Original State | 20.0 cm | 19.9 cm | 7.0 cm | 6.1 cm |
| After 1X wash | 20.9 cm | 20.7 cm | 6.0 cm | 5.4 cm |
| shrinkage/growth | 0.9 cm | 0.8 cm | −1.0 cm | −0.7 cm |
| Dimensional Change | 4.5% | 4.0% | −14.3% | −11.5% |
| superwashed NeW 2/60 with 18.5 micron 17051101 | | | | |
| Original State | 20.1 cm | 19.8 cm | 5.9 cm | 5.9 cm |
| After 1X wash | 18.9 cm | 18.9 cm | 5.8 cm | 6.0 cm |
| shrinkage/growth | −1.2 cm | −0.9 cm | −0.1 cm | 0.1 cm |
| Dimensional Change | −6.0% | −4.5% | −1.7% | 1.7% |
| wool tube 17042001 NeW 1/27 with 23.5 micron with 0.5% silk 3L1M 17042001 | | | | |
| Note: Sample was torqued after wash | | | | |
| Original State | 20.2 cm | 20.4 cm | 7.5 cm | 7.0 cm |
| After 1X wash | 20.0 cm | 20.4 cm | 6.5 cm | 5.8 cm |
| shrinkage/growth | −0.2 cm | 0.0 cm | −1.0 cm | −1.2 cm |
| Dimensional Change | −1.0% | 0.0% | −13.3% | −17.1% |
| superwashed NeW 1/27 with 23.5 micron | | | | |

TABLE 29

NeW1-42.8 with 18.9 micron NS (Woolmark Test Method)

| Dimensional Change | Length Specimen 1 | Length Specimen 2 | Width Specimen 1 | Width Specimen 2 | total dimensional change |
|---|---|---|---|---|---|
| after 1X wash | −4.5% | −2.8% | 1.6% | 1.6% | |
| average | −3.6% | | 1.6% | | −2.1% |
| after 2X wash | −9.5% | −6.2% | −1.6% | 0.0% | |
| average | −7.9% | | −0.8% | | −8.6% |
| after 3X wash | −15.6% | −11.3% | −1.6% | −3.2% | |
| average | −13.5% | | −2.4% | | −15.9% |
| 17051001 | wool tube 17050901 NeW 1/42.8 with 18.9 micron with 0.5% silk 3L1M | | | | |
| after 1X wash | 3.4% | −1.0% | −6.8% | 0.0% | |
| average | 1.2% | | −3.4% | | −2.2% |
| after 2X wash | −1.7% | −7.0% | −8.5% | −3.7% | |
| average | −4.4% | | −6.1% | | −10.5% |
| after 3X wash | −4.0% | −12.6% | −13.6% | −3.7% | |
| average | −8.3% | | −8.6% | | −16.9% |
| 17050901 | NeW 1/42.8 with 18.9 micron | | | | |
| after 1X wash | −4.6% | −5.0% | 2.0% | 2.0% | |
| average | −4.8% | | 2.0% | | −2.8% |
| after 2X wash | −9% | −9% | −4% | 2% | |
| average | −9.0% | | −0.9% | | −10.0% |
| after 3X wash | −12% | −13% | −6% | −2% | |
| average | −12.7% | | −4.0% | | −16.7% |
| 17060105 | NeW 1/42.8 with 18.9 micron 0.2% citric acid | | | | |
| | −12% | −6% | −2% | | |
| after 1X wash | −7% | −5% | −4% | 9% | |
| average | −6.1% | | 2.6% | | −3.6% |
| after 2X wash | −10% | −8% | −8% | −2% | |
| average | −9.5% | | −5.3% | | −14.8% |
| after 3X wash | −15% | −12% | −6% | −2% | |
| average | −13.4% | | −4.3% | | −17.6% |
| 17060106 | NeW 1/42.8 with 18.9 micron, 80% methanol | | | | |

TABLE 30

NeW1-30 with 21.0 micron NS (Woolmark Test Method)

| Dimensional Change | Length Specimen 1 | Length Specimen 2 | Width Specimen 1 | Width Specimen 2 | total dimensional change |
|---|---|---|---|---|---|
| after 1X wash | −2.8% | −4.4% | 1.8% | −1.6% | |
| average | −3.6% | | 0.1% | | −3.5% |
| after 2X wash | −5.6% | −7.1% | 1.8% | −1.6% | |
| average | −6.4% | | 0.1% | | −6.3% |
| after 3X wash | −6.7% | −9.3% | 1.8% | −3.1% | |
| average | −8.0% | | −0.7% | | −8.7% |
| 17051002 | wool tube 17050902 NeW 1/30 with 21.0 micron with 0.5% silk 3L1M | | | | |
| after 1X wash | −3.2% | 1.0% | 1.9% | −5.6% | |
| average | −1.1% | | −1.8% | | −2.9% |
| after 2X wash | −6.8% | −9.5% | −3.8% | −7.4% | |
| average | −8.2% | | −5.6% | | −13.8% |
| after 3X wash | −6.8% | −9.0% | −3.8% | −5.6% | |
| average | −7.9% | | −4.7% | | −12.6% |
| 17050902 | NeW 1/30 with 21.0 micron | | | | |
| after 1X wash | −1.6% | −2.7% | 1.9% | 0.0% | |
| average | −2.1% | | 1.0% | | −1.2% |
| after 2X wash | −7.4% | −2.7% | 3.8% | 2.1% | |
| average | −5.1% | | 3.0% | | −2.1% |
| after 3X wash | −7.4% | −4.8% | 1.9% | 2.1% | |
| average | −6.1% | | 2.0% | | −4.1% |
| 17060107 | NeW 1/30 with 21.0 micron, 0.2% citric acid | | | | |
| after 1X wash | −0.5% | −1.6% | 0.0% | −2.0% | |
| average | −1.1% | | −1.0% | | −2.1% |
| after 2X wash | −3.2% | −3.8% | −8.2% | 2.0% | |
| average | −3.5% | | −3.1% | | −6.6% |
| after 3X wash | −5.9% | −3.8% | −6.1% | 0.0% | |
| average | −4.9% | | −3.1% | | −7.9% |
| 17060108 | NeW 1/30 with 21.0 micron, 80% methanol | | | | |

TABLE 31

NeW2-60 with 18.5 micron SW (Woolmark Test Method)

| Dimensional Change | Length Specimen 1 | Length Specimen 2 | Width Specimen 1 | Width Specimen 2 | total dimensional change |
|---|---|---|---|---|---|
| after 1X wash | 1.6% | −0.5% | −1.6% | 1.8% | |
| average | 0.5% | | 0.1% | | 0.6% |
| after 2X wash | 0.0% | −1.0% | −3.2% | 0.0% | |
| average | −0.5% | | −1.6% | | −2.1% |
| after 3X wash | 0.0% | 0.5% | −3.2% | 1.8% | |
| average | 0.3% | | −0.7% | | −0.5% |
| 17051003 | wool tube 17042002 NeW 2/60 with 18.5 micron with 0.5% silk 3L1M | | | | |
| after 1X wash | 0.5% | 2.4% | −1.7% | −3.7% | |
| average | 1.4% | | −2.7% | | −1.2% |
| after 2X wash | 1.0% | 0.0% | −1.7% | −5.6% | |
| average | 0.5% | | −3.6% | | −3.1% |
| after 3X wash | 1.0% | 0.0% | −1.7% | 0.0% | |
| average | 0.5% | | −0.8% | | −0.4% |
| 17042002 | superwashed NeW 2/60 with 18.5 micron | | | | |
| after 1X wash | −1.1% | 0.6% | 2.0% | 2.0% | |
| average | −0.3% | | 2.0% | | 1.7% |
| after 2X wash | 0.0% | 1.1% | −2.0% | 2.0% | |
| average | 0.6% | | 0.0% | | 0.6% |
| after 3X wash | −1.1% | 0.0% | −2.0% | −2.0% | |
| average | −0.5% | | −2.0% | | −2.5% |
| 17060203 | superwashed NeW 2/60 with 18.5 micron, 0.2% citric acid | | | | |
| after 1X wash | −1.1% | 2.1% | 0.0% | 0.0% | |
| average | 0.5% | | 0.0% | | 0.5% |
| after 2X wash | 0.0% | 1.6% | −2.0% | 0.0% | |
| average | 0.8% | | −1.0% | | −0.2% |
| after 3X wash | −0.5% | 2.6% | −3.9% | −2.0% | |
| average | 1.1% | | −3.0% | | −1.9% |
| 17060204 | superwashed NeW 2/60 with 18.5 micron, 80% methanol | | | | |

TABLE 32

NeW1-27 with 23.5 micron SW (Woolmark Test Method)

| Dimensional Change | Length Specimen 1 | Length Specimen 2 | Width Specimen 1 | Width Specimen 2 | total dimensional change |
|---|---|---|---|---|---|
| after 1X wash | 0.0% | −1.1% | 1.7% | −3.3% | |
| average | −0.5% | | −0.8% | | −1.3% |
| after 2X wash | 0.0% | −1.1% | 0.0% | −1.7% | |
| average | −0.5% | | −0.8% | | −1.4% |
| after 3X wash | 0.0% | 0.0% | −1.7% | −5.0% | |
| average | 0.0% | | −3.4% | | −3.4% |
| 17051101 | wool tube 17042001 NeW 1/27 with 23.5 micron with 0.5% silk 3L1M | | | | |
| after 1X wash | 1.0% | −1.0% | −4.6% | −1.7% | |
| average | 0.0% | | −3.2% | | −3.2% |
| after 2X wash | 1.0% | −2.0% | −6.2% | −3.4% | |
| average | −0.5% | | −4.8% | | −5.3% |
| after 3X wash | 0.5% | −1.5% | −1.5% | −1.7% | |
| average | −0.5% | | −1.6% | | −2.1% |
| 17042001 | superwashed NeW 1/27 with 23.5 micron | | | | |
| after 1X wash | −1.1% | 2.1% | 2.0% | 2.0% | |
| average | 0.5% | | 2.0% | | 2.5% |
| after 2X wash | −1.6% | 1.6% | −2.0% | 0.0% | |
| average | 0.0% | | −1.0% | | −1.0% |
| after 3X wash | −1.1% | 0.5% | 0.0% | 0.0% | |
| average | −0.3% | | 0.0% | | −0.3% |
| 17060201 | superwashed NeW 1/27 with 23.5 micron, 0.2% citric acid | | | | |
| after 1X wash | −1.0% | 1.5% | 0.0% | 0.0% | |
| average | 0.3% | | 0.0% | | 0.3% |
| after 2X wash | −1.5% | −0.5% | −2.0% | 0.0% | |
| average | −1.0% | | −1.0% | | −2.0% |
| after 3X wash | −1.5% | 0.0% | −3.9% | −2.0% | |
| average | −0.8% | | −3.0% | | −3.7% |
| 17060202 | superwashed NeW 1/27 with 23.5 micron, 80% methanol | | | | |

TABLE 33

NeW1-42.8 with 18.9 micron NS (AATCC Test Method)

| Dimensional Change | Length Specimen 1 | Length Specimen 2 | Width Specimen 1 | Width Specimen 2 | total dimensional change |
|---|---|---|---|---|---|
| after 1X wash | −10.5% | −11.9% | −1.6% | 0.0% | |
| average | −11.2% | | −0.8% | | −12.0% |
| after 2X wash | −14.5% | −14.4% | 0.0% | 1.6% | |
| average | −14.5% | | 0.8% | | −13.7% |
| after 3X wash | −19.0% | −17.4% | −3.1% | 0.0% | |
| average | −18.2% | | −1.6% | | −19.8% |
| after 4X wash | −24.5% | −21.9% | −3.1% | −3.2% | |
| average | −23.2% | | −3.1% | | −26.3% |
| 17051001 | wool tube 17050901 NeW 1/42.8 with 18.9 micron with 0.5% silk 3L1M | | | | |
| after 1X wash | −12.9% | −4.8% | −9.2% | −12.9% | |
| average | −8.9% | | −11.1% | | −19.9% |
| after 2X wash | −10.0% | −5.7% | −15.4% | −12.9% | |
| average | −7.8% | | −14.1% | | −22.0% |
| after 3X wash | −14.4% | −11.5% | −16.9% | −16.1% | |
| average | −13.0% | | −16.5% | | −29.5% |
| after 4X wash | −16.4% | −16.7% | −21.5% | −16.1% | |
| average | −16.6% | | −18.8% | | −35.4% |
| 17050901 | NeW 1/42.8 with 18.9 micron | | | | |
| after 1X wash | −9.8% | −11.4% | −1.9% | −3.9% | |
| average | −10.6% | | −2.9% | | −13.5% |
| after 2X wash | −13.9% | −15.8% | 0.0% | −2.0% | |
| average | −14.9% | | −1.0% | | −15.9% |
| after 3X wash | −17.5% | −19.8% | −5.8% | −2.0% | |
| average | −18.7% | | −3.9% | | −22.5% |
| after 4X wash | −20.6% | −23.3% | −7.7% | −5.9% | |
| average | −21.9% | | −6.8% | | −28.7% |
| 17060105 | NeW 1/42.8 with 18.9 micron, 0.2% citric acid | | | | |
| after 1X wash | −10.0% | −13.2% | −11.1% | −17.3% | |
| average | −11.6% | | −14.2% | | −25.8% |
| after 2X wash | −16.4% | −17.6% | −14.8% | −9.6% | |
| average | −17.0% | | −12.2% | | −29.2% |
| after 3X wash | −19.4% | −20.5% | −18.5% | −19.2% | |
| average | −19.9% | | −18.9% | | −38.8% |
| after 4X wash | −23.4% | −23.4% | −16.7% | −19.2% | |
| average | −23.4% | | −17.9% | | −41.3% |
| 17060106 | NeW 1/42.8 with 18.9 micron, 80% methanol | | | | |

TABLE 34

NeW1-30 with 21.0 micron NS (AATCC Test Method)

| Dimensional Change | Length Specimen 1 | Length Specimen 2 | Width Specimen 1 | Width Specimen 2 | total dimensional change |
|---|---|---|---|---|---|
| after 1X wash | −8.7% | −7.6% | 0.0% | 1.6% | |
| average | −8.1% | | 0.8% | | −7.4% |
| after 2X wash | −11.2% | −11.7% | 1.8% | 0.0% | |
| average | −11.4% | | 0.9% | | −10.6% |
| after 3X wash | −13.8% | −14.2% | 1.8% | 0.0% | |
| average | −14.0% | | 0.9% | | −13.1% |
| after 4X wash | −14.8% | −16.2% | 1.8% | −1.6% | |
| average | −15.5% | | 0.1% | | −15.4% |
| 17051002 | wool tube 17050902 NeW 1/30 with 21.0 micron with 0.5% silk 3L1M | | | | |
| after 1X wash | −6.9% | −2.4% | −20.0% | −12.9% | |
| average | −4.7% | | −16.5% | | −21.1% |
| after 2X wash | −9.8% | −1.5% | −18.5% | −17.7% | |
| average | −5.6% | | −18.1% | | −23.7% |
| after 3X wash | −13.2% | −11.7% | −23.1% | −19.4% | |
| average | −12.5% | | −21.2% | | −33.7% |
| after 4X wash | −13.2% | −11.2% | −23.1% | −17.7% | |
| average | −12.2% | | −20.4% | | −32.6% |
| 17050902 | NeW 1/30 with 21.0 micron | | | | |
| after 1X wash | −9.6% | −10.1% | −5.5% | −7.7% | |
| average | −9.9% | | −6.6% | | −16.5% |
| after 2X wash | −11.1% | −12.6% | −3.6% | −7.7% | |
| average | −11.8% | | −5.7% | | −17.5% |
| after 3X wash | −16.3% | −12.6% | −1.8% | −5.8% | |
| average | −14.5% | | −3.8% | | −18.2% |

TABLE 34-continued

NeW1-30 with 21.0 micron NS (AATCC Test Method)

| Dimensional Change | Length Specimen 1 | Length Specimen 2 | Width Specimen 1 | Width Specimen 2 | total dimensional change |
|---|---|---|---|---|---|
| after 4X wash | −16.3% | −14.5% | −3.6% | −5.8% | |
| average | −15.4% | | −4.7% | | −20.1% |
| 17060107 | NeW 1/30 with 21.0 micron, 0.2% citric acid | | | | |
| after 1X wash | −9.3% | −10.2% | −9.3% | −9.3% | |
| average | −9.8% | | −9.3% | | −19.0% |
| after 2X wash | −9.8% | −11.7% | −9.3% | −11.1% | |
| average | −10.7% | | −10.2% | | −20.9% |
| after 3X wash | −12.2% | −13.7% | −16.7% | −7.4% | |
| average | −12.9% | | −12.0% | | −25.0% |
| after 4X wash | −14.6% | −13.7% | −14.8% | −9.3% | |
| average | −14.1% | | −12.0% | | −26.2% |
| 17060108 | NeW 1/30 with 21.0 micron, 80% methanol | | | | |

TABLE 35

NeW2-60 with 18.5 micron SW (AATCC Test Method)

| Dimensional Change | Length Specimen 1 | Length Specimen 2 | Width Specimen 1 | Width Specimen 2 | total dimensional change |
|---|---|---|---|---|---|
| after 1X wash | −6.4% | −4.5% | 0.0% | −1.8% | |
| average | −5.4% | | −0.9% | | −6.3% |
| after 2X wash | −5.0% | −5.0% | −1.6% | 0.0% | |
| average | −5.0% | | −0.8% | | −5.8% |
| after 3X wash | −6.4% | −5.4% | −3.2% | −1.8% | |
| average | −5.9% | | −2.5% | | −8.4% |
| after 4X wash | −6.4% | −4.0% | −3.2% | 0.0% | |
| average | −5.2% | | −1.6% | | −6.8% |
| 17051003 | wool tube 17042002 NeW 2/60 with 18.5 micron with 0.5% silk 3L1M | | | | |
| after 1X wash | 4.5% | 4.0% | −14.3% | −11.5% | |
| average | 4.3% | | −12.9% | | −8.6% |
| after 2X wash | 5.0% | 6.5% | −15.7% | −14.8% | |
| average | 5.8% | | −15.2% | | −9.5% |
| after 3X wash | 5.5% | 4.0% | −15.7% | −16.4% | |
| average | 4.8% | | −16.1% | | −11.3% |
| after 4X wash | 5.5% | 4.0% | −15.7% | −11.5% | |
| average | 4.8% | | −13.6% | | −8.8% |
| 17042002 | superwashed NeW 2/60 with 18.5 micron | | | | |
| after 1X wash | −6.9% | −10.0% | −3.8% | −5.8% | |
| average | −8.4% | | −4.8% | | −13.2% |
| after 2X wash | −7.9% | −9.5% | −1.9% | −3.8% | |
| average | −8.7% | | −2.9% | | −11.5% |
| after 3X wash | −6.9% | −9.0% | −5.7% | −3.8% | |
| average | −7.9% | | −4.8% | | −12.7% |
| after 4X wash | −7.9% | −10.0% | −5.7% | −7.7% | |
| average | −8.9% | | −6.7% | | −15.6% |
| 17060203 | superwashed NeW 2/60 with 18.5 micron, 0.2% citric acid | | | | |
| after 1X wash | −11.1% | −9.1% | −5.6% | −7.5% | |
| average | −10.1% | | −6.6% | | −16.7% |
| after 2X wash | −12.1% | −7.2% | −5.6% | −7.5% | |
| average | −9.6% | | −6.6% | | −16.2% |
| after 3X wash | −11.1% | −7.7% | −7.4% | −7.5% | |
| average | −9.4% | | −7.5% | | −16.9% |
| after 4X wash | −11.6% | −6.7% | −9.3% | −9.4% | |
| average | −9.2% | | −9.3% | | −18.5% |
| 17060204 | superwashed NeW 2/60 with 18.5 micron, 80% methanol | | | | |

TABLE 36

NeW1-27 with 23.5 micron SW (AATCC Test Method)

| Dimensional Change | Length Specimen 1 | Specimen 2 | Width Specimen 1 | Specimen 2 | total dimensional change |
|---|---|---|---|---|---|
| after 1X wash | −6.0% | −4.5% | −1.7% | 1.7% | |
| average | −5.3% | | 0.0% | | −5.3% |
| after 2X wash | −6.0% | −5.6% | 0.0% | −1.7% | |
| average | −5.8% | | −0.8% | | −6.6% |
| after 3X wash | −6.0% | −5.6% | −1.7% | 0.0% | |
| average | −5.8% | | −0.8% | | −6.6% |
| after 4X wash | −6.0% | −4.5% | −3.4% | −3.4% | |
| average | −5.3% | | −3.4% | | −8.6% |
| 17051101 | wool tube 17042001 NeW 1/27 with 23.5 micron with 0.5% silk 3L1M | | | | |
| after 1X wash | −1.0% | 0.0% | −13.3% | −17.1% | |
| average | −0.5% | | −15.2% | | −15.7% |
| after 2X wash | 0.0% | −1.0% | −17.3% | −18.6% | |
| average | −0.5% | | −18.0% | | −18.4% |
| after 3X wash | 0.0% | −2.0% | −18.7% | −20.0% | |
| average | −1.0% | | −19.3% | | −20.3% |
| after 4X wash | −0.5% | −1.5% | −14.7% | −18.6% | |
| average | −1.0% | | −16.6% | | −17.6% |
| 17042001 | superwashed NeW 1/27 with 23.5 micron | | | | |
| after 1X wash | −6.4% | −8.3% | −5.6% | −3.8% | |
| average | −7.4% | | −4.7% | | −12.0% |
| after 2X wash | −7.4% | −6.3% | −3.7% | −1.9% | |
| average | −6.9% | | −2.8% | | −9.7% |
| after 3X wash | −7.9% | −6.8% | −7.4% | −3.8% | |
| average | −7.4% | | −5.6% | | −13.0% |
| after 4X wash | −7.4% | −7.8% | −5.6% | −3.8% | |
| average | −7.6% | | −4.7% | | −12.3% |
| 17060201 | superwashed NeW 1/27 with 23.5 micron, 0.2% citric acid | | | | |
| after 1X wash | −3.9% | −4.9% | −3.8% | −5.7% | |
| average | −4.4% | | −4.7% | | −9.1% |
| after 2X wash | −4.9% | −3.4% | −3.8% | −5.7% | |
| average | −4.2% | | −4.7% | | −8.9% |
| after 3X wash | −5.4% | −5.4% | −5.7% | −5.7% | |
| average | −5.4% | | −5.7% | | −11.0% |
| after 4X wash | −5.4% | −4.9% | −7.5% | −7.5% | |
| average | −5.1% | | −7.5% | | −12.7% |
| 17060202 | superwashed NeW 1/27 with 23.5 micron, 80% methanol | | | | |

Example 3: Silk Coating Wool, Including a Citric Acid Pretreatment and Methanol Post Treatment—Addition of a New Control: Samples Tested for Dimensional Changes after Laundering, Perceived Hand, and Fiber Morphology by SEM Analysis This example adds a new control with no silk coating for evaluating the application of silk fibroin solution on fabrics made with wool fabric tube after a pretreatment of citric acid and followed by a methanol bath. The application takes place in a sequence of baths and pads application with multiple drying steps. The samples were tested for dimensional changes after laundering, perceived hand, and fiber morphology with SEM analysis.

TABLE 37

Coating Experimental Variables

| Wool type | Pre treatment | Silk coating | Post treatment | Final treatment | Dry/cure temperature ° F. (° C.) |
|---|---|---|---|---|---|
| NeW 1/42.8 with 18.9 non superwashed | 0.200% citric acid for 60 min at 70° C. | N/A | N/A | N/A | 176 (80) 10 min |
| NeW 1/42.8 with 18.9 | N/A | N/A | N/A | 80% methanol, | 176 (80) 10 min |

TABLE 37-continued

Coating Experimental Variables

| Wool type | Pre treatment | Silk coating | Post treatment | Final treatment | Dry/cure temperature ° F. (° C.) |
|---|---|---|---|---|---|
| NSW | | | | 20% di water for 10 min at room temp | |
| NeW 1/30 with 21.0 μm Australian wool fibers (NSW) | 0.200% citric acid for 60 min at 70° C. | N/A | N/A | N/A | 176 (80) 10 min |
| NeW 1/30 with 21.0 μm Australian wool fibers (NSW) | N/A | N/A | N/A | 80% methanol, 20% di water for 10 min at room temp | 176 (80) 10 min |
| NeW 27/1 with 23.0 μm Australian wool fibers (SW) | 0.200% citric acid for 60 min at 70° C. | N/A | N/A | N/A | 176 (80) 10 min |
| NeW 27/1 with 23.0 μm Australian wool fibers | N/A | N/A | N/A | 80% methanol, 20% di water for | 176 (80) 10 min |

TABLE 37-continued

Coating Experimental Variables

| Wool type | Pre treatment | Silk coating | Post treatment | Final treatment | Dry/cure temperature ° F. (° C.) |
|---|---|---|---|---|---|
| (SW) | | | | | 10 min at room temp |
| NeW 60/2 with 18.5 μm Australian wool fibers (SW) | 0.200% citric acid for 60 min at 70° C. | N/A | N/A | N/A | 176 (80) 10 min |
| NeW 60/2 with 18.5 μm Australian wool fibers (SW) | N/A | N/A | N/A | 80% methanol, 20% di water for 10 min at room temp | 176 (80) 10 min |

Analysis

Samples are conditioned at ambient condition for 24 hrs before a massing post coating. The percentage change is calculated based on the following formula:

$$\text{Mass change \%} = \frac{\text{mass post coating} - \text{mass before coating}}{\text{mass before coating}} \times 100$$

The dimensional changes of the samples post laundering are analyzed based on Woolmark Company TM31-May 2000 and AATCC Test Method 135-2015. Samples are tested after t=1 and t=4 laundering cycle for the Woolmark test, and at t=0 and t=3 for the AATCC test.

After the dimensional analysis test, the wool fabric tubes are scored for hand against a non treated control. Scoring are made for softness and any additional perceived difference.

After the hand test is completed the samples are analyzed by SEM (FIGS. 7 to 14).

TABLE 38

Processing recording and mass percentage change post treatment for samples 17060105 and 17060106

| 17060105 pre'treatment'only | | | fabric'A' 17050901'NeW'1/42.8"NSW'with'18.9'micron 17060105 citric'only t = 24 hrs | | | |
|---|---|---|---|---|---|---|
| | | | mass'fabric | A1 | 11.1699 gr | 11.3712 gr |
| | | | | A2 | 11.4449 gr | 11.6452 gr |
| starting'citric'acid'solution'(ml) | 4.57 | calculation | | A3 | 11.4702 gr | 11.6595 gr |
| citric'acid'concentration'(%) | 50.000% | input | | A4 | 11.5688 gr | 11.7799 gr |
| required'DI'(ml) | 908.51 | calculation | tot | | 45.6538 gr | 46.4558 gr |
| required'citric'acid'concentration'(%) | 0.250% | input | | | | percentage'change |
| final'solution'(ml) | 913.08 | input | liquor'ratio | 20 | 1 | 1.8% |
| | | | total'liquor | | 913.076 ml | |

| 17060106 final'treatment'only | | | 17050901'NewW'1/42.8"with'18.9'micro 17060106 methanol'only | | | |
|---|---|---|---|---|---|---|
| starting'methanol'solution'(ml) | 359.70 | | | A5 | 11.4029 gr | 11.4062 gr |
| methanol'concentration'(%) | 100.000% | | | A6 | 11.1666 gr | 11.1522 gr |
| required'DI'(ml) | 89.92 | | | A7 | 11.2515 gr | 11.2607 gr |
| required'methanol'concentration'(%) | 80.000% | | | A8 | 11.1413 gr | 11.148 gr |
| final'solution'(ml) | 449.62 | | tot | | 44.9623 gr | 44.9671 gr |
| | | | | | | percentage'change |
| | | | liquor'ratio | 10 | 1 | 0.0% |
| | | | total'liquor | | 449.623 ml | |

TABLE 39

Processing recording and mass percentage change post treatment for samples 17060107 and 17060108

| 17060107 pre'treatment'only | | | fabric'B 17050902'NeW'1/30"NSW'with'21.0'micron 17060107 citric'only t = 24 | | | |
|---|---|---|---|---|---|---|
| | | | mass'fabric | B1 | 14.1824 gr | 14.4437 gr |
| | | | | B2 | 14.028 gr | 14.3154 gr |
| starting'citric'acid'solution'(ml) | 5.65 | calculation | | B3 | 14.0931 gr | 14.411 gr |
| citric'acid'concentration'(%) | 50.000% | input | | B4 | 14.1739 gr | 14.4499 gr |
| required'DI'(ml) | 1123.90 | calculation | tot | | 56.4774 gr | 57.62 gr |
| required'citric'acid'concentration'(%) | 0.250% | input | | | | percentage'change |
| final'solution'(ml) | 1129.55 | input | liquor'ratio | 20 | 1 | 2.0% |
| | | | total'liquor | | 1129.548 ml | |

| 17060108 final'treatment'only | | 17050902'NeW'1/30"with'21.0'micron 17060108 methanol'only t = 24 | | | |
|---|---|---|---|---|---|
| starting'methanol'solution'(ml) | 450.24 | | B5 | 14.1187 gr | 14.1815 gr |
| methanol'concentration'(%) | 100.000% | | B6 | 14.0995 gr | 14.1781 gr |
| required'DI'(ml) | 112.56 | | B7 | 14.0335 gr | 14.1229 gr |

TABLE 39-continued

Processing recording and mass percentage change post treatment for samples 17060107 and 17060108

| | | | | | | |
|---|---|---|---|---|---|---|
| required'methanol'concentration'(%) | 80.000% | | B8 | 14.028 gr | 14.1045 gr | |
| final'solution'(ml) | 562.80 | | tot | 56.2797 gr | 56.587 gr | |
| | | | | | | percentage'change |
| | | | liquor'ratio | 10 | 1 | 0.5% |
| | | | total'liquor | | 562.797 ml | |

TABLE 40

Processing recording and mass percentage change post treatment for samples 17060201 and 17060202

| 17060201 pre'treatment'only | | | | fabric'D 17042002'NeW'2/60"SW'with'18.5'micron 17060201 citric'only t = 24'hr | | | |
|---|---|---|---|---|---|---|---|
| | | | mass'fabric C1 | | 11.6491 gr | 11.8634 gr | |
| | | | C2 | | 11.6829 gr | 11.8955 gr | |
| starting'citric'acid'solution'(ml) | 4.67 | calculation | C3 | | 11.6928 gr | 11.9344 gr | |
| citric'acid'concentration'(%) | 50.000% | input | C4 | | 11.6616 gr | 11.8873 gr | |
| required'DI'(ml) | 929.06 | calculation | tot | | 46.6864 gr | 47.5806 gr | |
| required'citric'acid'concentration'(%) | 0.250% | input | | | | | percentage'change |
| final'solution'(ml) | 933.73 | input | liquor'ratio | 20 | 1 | | 1.9% |
| | | | total'liquor | | 933.728 ml | | |

| 17060202 final'treatment'only | | | 17050902'NeW'1/30"with'21.0'micron 17060202 methanol'only t = 24'hr | | | |
|---|---|---|---|---|---|---|
| starting'methanol'solution'(ml) | 373.56 | | C5 | 11.5935 gr | 11.6135 gr | |
| methanol'concentration'(%) | 100.000% | | C6 | 11.7155 gr | 11.7315 gr | |
| required'DI'(ml) | 93.39 | | C7 | 11.6636 gr | 11.6956 gr | |
| required'methanol'concentration'(%) | 80.000% | | C8 | 11.7219 gr | 11.7374 gr | |
| final'solution'(ml) | 466.95 | | tot | 46.6945 gr | 46.778 gr | |
| | | | | | | percentage'change |
| | | | liquor'ratio | 10 | 1 | 0.2% |
| | | | total'liquor | | 466.945 ml | |

TABLE 41

Processing recording and mass percentage change post treatment for samples 17060203 and 17060204

| 17060107 pre'treatment'only | | | | fabric'C 17042001'NeW'1/27'SW'with'23.5'micron 17060107 citric'only t = 24'hr | | | |
|---|---|---|---|---|---|---|---|
| | | | mass'fabric D1 | | 13.6593 gr | 13.8966 gr | |
| | | | D2 | | 13.7446 gr | 13.9947 gr | |
| starting'citric'acid'solution'(ml) | 5.49 | calculation | D3 | | 13.6889 gr | 13.9228 gr | |
| citric'acid'concentration'(%) | 50.000% | input | D4 | | 13.8554 gr | 14.0869 gr | |
| required'DI'(ml) | 1093.47 | calculation | tot | | 54.9482 gr | 55.901 gr | |
| required'citric'acid'concentration'(%) | 0.250% | input | | | | | percentage'change |
| final'solution'(ml) | 1098.96 | input | liquor'ratio | 20 | 1 | | 1.7% |
| | | | total'liquor | | 1098.964 ml | | |

| 17060108 final'treatment'only | | | 17042001'NewW'1/27"with'23.5'micron 17060204 methanol'only t = 24'hr | | | |
|---|---|---|---|---|---|---|
| starting'methanol'solution'(ml) | 413.21 | | D5 | 10.2721 gr | 10.2781 gr | |
| methanol'concentration'(%) | 100.000% | | D6 | 13.8424 gr | 13.8614 gr | |
| required'DI'(ml) | 103.30 | | D7 | 13.9481 gr | 13.9868 gr | |
| required'methanol'concentration'(%) | 80.000% | | D8 | 13.5886 gr | 13.6192 gr | |
| final'solution'(ml) | 516.51 | | tot | 54.6512 gr | 51.7455 gr | |
| | | | | | | percentage'change |
| | | | liquor'ratio | 10 | 1 | 0.2% |
| | | | total'liquor | | 516.512 ml | |

TABLE 42

Hand score of wool tube

| Sample # | Description | Score |
|---|---|---|
| 17051003 | wool tube 17042002 superwashed, NeW 2/60 with 18.5 micron with 0.5% silk 3L1M | 18 |
| 17060201 | wool tube 17042001 superwashed, NeW 1/27 with 23.5 micron with 0.02% citric acid | 18 |
| 17060202 | wool tube 17042001 superwashed, NeW 1/27 with 23.5 micron with 80% methanol | 18 |
| 17051001 | wool tube 17050901 non superwashed, NeW 1/42.8 with 18.9 micron with 0.5% silk 3L1M | 12 |
| 17061005 | wool tube 17050901 non superwashed, NeW 1/42.8 with 18.9 micron with 0.02% citric acid | 12 |
| 17061006 | wool tube 17050901 non superwashed, NeW 1/42.8 with 18.9 micron with 80% methanol | 12 |
| 17061008 | wool tube 17050902, non superwashed NeW 1/30 with 21.0 micron with 80% methanol | 7 |
| 17060203 | wool tube 17042002 superwashed, NeW 2/60 with 18.5 micron with 0.02% citric acid | 7 |
| 17060204 | wool tube 17042002 superwashed, NeW 2/60 with 18.5 micron with 80% methanol | 4 |
| 17061007 | wool tube 17050902 non superwashed, NeW 1/30 with 21.0 micron with 0.02% citric acid | 2 |

Dimensional Stability to laundering is as described in Tables 12 to 36.

Example 4: Silk Coating a Cashmere Fabric: Improving Pilling Resistance and Water Repellency Materials and Methods A cashmere fabric was used to test for improvements in pilling resistance and water repellency upon silk treatment. The silk coated cashmere sample was obtained with a four bath process: 1) 0.250% Citric Acid; 2) 0.250% Citric Acid, 0.3750% Low MW silk, 0.125% Med MW silk (Total Silk: 0.50% 3L:1M); 3) 0.25% Citric Acid; 4) 80% Methanol.

TABLE 43

Control cashmere fabric sample before Pilling Resistance Test

| Test For | Test Used | Results |
|---|---|---|
| Yarn Size | ASTM D1059 | 2/25.7 worsted count |
| Fiber Identification | AATCC 20A - with moisture | Cashmere: 90.34% 14.6 microns Wool: 9.66% 20.9 microns |

TABLE 44

Control and Silk coated fabric samples after Pilling Resistance Test

| Test For | Test Used | Sample | Yarn Profile* | Results** |
|---|---|---|---|---|
| ICI Pilling Resistance | ISO 12945-1 2 hours, 7,200 cycles, rated per SM54 LAMBSWOOL PHOTO STANDARD | Control CHA-17101902-T001 | 2/27.1 worsted count Cashmere: 90.32%, 14.9 microns (average diameter) Wool: 9.68%, 20.2 microns (average diameter) | Length: 4.0 Width: 3.8 |
| | | Treated CHA-17101902-T002 | 2/25.1 worsted count Cashmere: 90.74%, 14.6 microns (average diameter) Wool: 9.26%, 19.4 microns (average diameter) | Length: 4.5 Width: 4.3 |

*Fiber Identification per AATCC 20A - with moisture; Some of the fibers present in the submitted sample displayed indistinct appearance attributes, primarily stripped scales, rendering classification difficult. These fibers were included with wool.
**Class 5, No change.
Class 4, Slight surface fuzzing and/or partially formed pills.
Class 3, Moderate surface fuzzing and/or moderate pilling. Pills of varying size and density partially covering the specimen surface.
Class 2, Distinct surface fuzzing and/or severe pilling. Pills of varying size and density covering a large proportion of the specimen surface.
Class 1, Dense surface fuzzing and/or severe pilling. Pills of varying size and density covering the whole of the specimen surface.

As shown above, the pilling resistance tests demonstrated that a silk treated sample had a 0.5 improvement in pilling over control for both length and width, improving it from moderate to slight pilling class (on width).

TABLE 45

Dimensional Changes of Cashmere Fabrics after Home Laundering-AATCC Test Method 135-2015; Woolmark Test Method: Washing of Wool Textile Products-The Woolmark Company TM31-May 2000

| | Length CHA-17101902-T001 | CHA-17101902-T002 | Width CHA-17101902-T001 | CHA-17101902-T002 |
|---|---|---|---|---|
| Original State | 20.0 cm | 20.0 cm | 20.0 cm | 20.0 cm |
| After 1X wash | 19.2 cm | 18.5 cm | 19.9 cm | 19.3 cm |
| | −0.8 cm | −1.5 cm | −0.1 cm | −0.7 cm |
| shrinkage/growth Dimensional Change | −4.0% | −7.5% | −0.5% | −3.5% |
| Original State | 20.0 cm | 20.0 cm | 20.0 cm | 20.0 cm |
| After 2X wash | 18.9 cm | 18.3 cm | 19.5 cm | 19.3 cm |
| | −1.1 cm | −1.7 cm | −0.5 cm | −0.7 cm |
| shrinkage/growth Dimensional Change | −5.5% | −8.5% | −2.5% | −3.5% |
| After 1X wash | 19.2 cm | 18.5 cm | 19.9 cm | 19.3 cm |
| After 2X wash | 18.9 cm | 18.3 cm | 19.5 cm | 19.3 cm |
| | −0.3 cm | −0.2 cm | −0.4 cm | 0.0 cm |
| shrinkage/growth Dimensional Change | −1.6% | −1.1% | −2.0% | 0.0% |
| Original State | 20.0 cm | 20.0 cm | 20.0 cm | 20.0 cm |
| After 3X wash | 18.5 cm | 17.8 cm | 19.1 cm | 19.3 cm |
| | −1.5 cm | −2.2 cm | −0.9 cm | −0.7 cm |
| shrinkage/growth Dimensional Change | −7.5% | −11.0% | −4.5% | −3.5% |

TABLE 45-continued

Dimensional Changes of Cashmere Fabrics after Home Laundering-AATCC Test Method 135-2015; Woolmark Test Method: Washing of Wool Textile Products-The Woolmark Company TM31-May 2000

|  | Length CHA-17101902-T001 | CHA-17101902-T002 | Width CHA-17101902-T001 | CHA-17101902-T002 |
|---|---|---|---|---|
| After 1X wash | 19.2 cm | 18.5 cm | 19.9 cm | 19.3 cm |
| After 3X wash | 18.5 cm | 17.8 cm | 19.1 cm | 19.3 cm |
| shrinkage/growth Dimensional Change | −0.7 cm −3.6% | −0.7 cm −3.8% | −0.8 cm −4.0% | 0.0 cm 0.0% |
| Original State | 20.0 cm 18.2 cm | 20.0 cm 17.7 cm | 20.0 cm 19.3 cm | 20.0 cm 19.4 cm |
| After 4X wash shrinkage/growth Dimensional Change | −1.8 cm −9.0% | −2.3 cm −11.5% | −0.7 cm −3.5% | −0.6 cm −3.0% |
| After 1X wash | 19.2 cm 18.2 cm | 18.5 cm 17.7 cm | 19.9 cm 19.3 cm | 19.3 cm 19.4 cm |
| After 4X wash shrinkage/growth Dimensional Change | −1.0 cm −5.2% | −0.8 cm −4.3% | −0.6 cm −3.0% | 0.1 cm 0.5% |

Testing Information:
Home Laundered see above times using AATCC TM 150 Table II Laundry Test Conditions: load size = 1.8 kg (4 lbs.); Launder Right Side Out; Top Loading Machine Wash; (2) Delicate; (III) 105 ± 5° F using 66 ± 1 g 1993 AATCC Standard Reference Detergent WOB; (A) Tumble Dry ii Delicate; Ballast Wash Load Type 3⁵⁰⁄₅₀ polyester/cotton bleached plain weave; a (−) indicates shrinkage and (+) indicates growth; fabrics were not hand ironed or restored; evaluation conditions: 21° C. (±2° C.) and 65% RH (±5% RH) Not Used

TABLE 46

Cashmere Fabric Water Repellency: Spray Test (AATCC 22-2014)

| | Spray Test Rating | |
|---|---|---|
|  | CHA-17101902-T001 | CHA-17101902-T002 |
| Specimen 1 | 0 | 70 |
| Specimen 2 | 0 | 70 |
| Specimen 3 | N/A | N/A |

Testing Information:
Rated the Face of the Specimen - No Average Recorded
Used the Spray Test Rating Chart
Rating of 100 - No Sticking or Wetting of the Specimen Face
Rating of 90 - Slight Random Sticking or Wetting of the Specimen Face
Rating of 80 - Wetting of Specimen Face at Spray Points
Rating of 70 - Partial Wetting of the Specimen Face Beyond the Spray Points
Rating of 50 - Complete Wetting of the Entire Specimen Face Beyond the Spray Points
Rating of 0 - Complete Wetting of the Entire Face of the Specimen

Example 5: Polyester/Lycra and Nylon/Lycra Fabrics Coated with Silk and Silicone: Biocompatibility Evaluation After silk coating (Table 47), samples are ambientally conditioned for 24 hrs., then shipped to a testing lab for cytotoxicity assessment (Table 48).

TABLE 47

Coating Experimental Variables

| Fabric type | Silk solution | Ph correction | Silicone coating | Dry/cure temperature ° F. (° C.)/time |
|---|---|---|---|---|
| 6606D2 | 0.187% low MW + 0.063% medium MW (3:1 ratio) | 0.025% citric acid (50%) or to pH 4-5 | Ultratex CSP | 302 (150) 70 seconds |
|  | 0.187% low MW + 0.063% medium MW (3:1 ratio) | 0.025% citric acid (50%) or to pH 4-5 | Ultratex SI | 302 (150) 70 seconds |
|  | 0.187% low MW + 0.063% medium MW (3:1 ratio) | 0.025% citric acid (50%) or to pH 4-5 | Domosil RWAF | 302 (150) 70 seconds |
| 6608D2B | 0.187% low MW + 0.063% medium MW (3:1 ratio) | 0.025% citric acid (50%) or to pH 4-5 | Ultratex CSP | 350 (177) 60 seconds |
|  | 0.187% low MW + 0.063% medium MW (3:1 ratio) | 0.025% citric acid (50%) or to pH 4-5 | Ultratex SI | 350 (177) 60 seconds |
|  | 0.187% low MW + 0.063% medium MW (3:1 ratio) | 0.025% citric acid (50%) or to pH 4-5 | Domosil RWAF | 350 (177) 60 seconds |

TABLE 48

Summary of Cytotoxicity Tests

| Product Name | Shortened Product | Batch Code Lot | Test Article Name | Results |
|---|---|---|---|---|
| Black Nylon Fabric (16120107) |  | A2701171 | Fabric 11 | No reactivity (passed) |
| 2 step coating Fabric 6606D2, 0.25% Silk 3L1M*, 3% Ultratex CSP, 0.025% citric acid | TexNylonSil | 17042601 | Fabric 1 | Mild reactivity, complete lysis under the test article (passed) |
| 2 step coating Fabric 6606D2, 0.25% Silk 3L1M, 3% Ultratex SI, 0.025% citric acid | TexNylonSil | 17042602 | Fabric 2 | No reactivity (passed) |
| 2 step coating Fabric 6606D2, 0.25% Silk 3L1M, 3% Domosil RWAF, 0.025% citric acid | TexNylonSil | 17042603 | Fabric 3 | Mild reactivity, complete lysis under the test article (passed) |
| 2 step coating Fabric 6608D2B, 0.25% Silk 3L1M, 3% Ultratex CSP, 0.025% citric acid | TexPolySil | 17042604 | Fabric 12 | Mild reactivity, complete lysis under the test article (passed) |
| 2 step coating Fabric 6608D2B, 0.25% Silk 3L1M, 3% Ultratex SI, 0.025% citric acid | TexPolySil | 17042605 | Fabric 13 | Slight reactivity, partial cell lysis under test article (passed) |
| 2 step coating Fabric 6608D2B, 0.25% Silk 3L1M, 3% Domosil RWAF, 0.025% citric acid | TexPolySil | 17042606 | Fabric 14 | Mild reactivity, complete lysis under the test article (passed) |

*3L1M: 3:1 low MW silk to medium MW silk

Example 6: Nylon/Lycra Fabric Coated with Silk and Silicone: Laundering Fastness Evaluation (Hand and Water Drop Absorption)—First Sample Set

TABLE 49

Coating Experimental Variables

| Application steps | Silk solution | pH correction | Silicone coating | pH correction | Dry/cure temperature ° F. (° C.)/time |
|---|---|---|---|---|---|
| 2 | 0.187% low MW + 0.063% medium MW (3:1 ratio) | 0.025% citric acid (50%) or to pH 4-5 | Ultratex CSP | 0.25% citric acid (50%) or to pH 3-4 | 302 (150) 70 seconds |
|   | 0.187% low MW + 0.063% medium MW (3:1 ratio) | 0.025% citric acid (50%) or to pH 4-5 | Domosil RWAF | 0.25% citric acid (50%) or to pH 3-4 | 302 (150) 70 seconds |
| 1 | 0.187% low MW + 0.063% medium MW (3:1 ratio) | 0.025% citric acid (50%) or to pH 4-5 | Domosil RWAF | N/A | 302 (150) 70 seconds |

Analysis: Samples coated as described in Table 49, are conditioned at ambient for 24 hrs before delivering them to testing lab for laundering test. The samples are used for:

N=1 control no laundering

N=1 after 10 laundering cycles

N=1 after 25 laundering cycles

N=1 after 50 laundering cycles

Fabrics are evaluated for hand by two technicians against the control not laundered (Table 50).

Laundering method AATCC Test Method 135-2015 (Table I, "Dimensional Changes of Fabrics after Home Laundering"). Testing Information: Home Laundered 52 times using AATCC TM 150 (Table II); Laundry Test Conditions: load size=1.8 kg (4 lbs), Launder Right Side Out Wash; Normal/CottonSturdy (III) 105±5° F. using 1993 AATCC Standard Reference Detergent WOB; Top Loading Machine; Tumble Dry (i) Cotton Sturdy; Ballast Wash Load Type 3-50/50 polyester/cotton bleached plain weave; Samples removed at 10, 25 and 52 launderings.

After laundering fabrics are evaluated for water drop test (Table 51). The sample fabric is placed on top of a 7 cm diameter positioned on the drapability jig. A RODI water drop is dispensed with an eye dropper from approximately 3 cm above the fabric. A video imaging recording capture the time from the water drop contacting the fabric until its full absorption or up to 60 seconds

TABLE 50

Hand Score of Fabric Results

| Sample # | Description | t = 0 | t = 10 | t = 25 | t = 52 |
|---|---|---|---|---|---|
| 17050303 | 6606D2 nylon/lycra, 0.25% silk 3L1M*, 0.025% citric acid, 3% Domosil RWAF | 5 | 4 | 1 | 1 |
| 17050307 | 6606D2 nylon/lycra, first step 0.25% silk 3L1M, 0.025% citric acid, second step 2% Ultratex CSP, 0.25% citric acid | 5 | 5 | 1 | 1 |
| 17050308 | 6606D2 nylon/lycra, first step 0.25% silk 3L1M, 0.025% citric acid, second step 3% Domosil RWAF, 0.25% citric acid | 5 | 5 | 3 | 3 |
| 17050306 | 6608D2B polyester/lycra, 0.25% silk 3L1M, 0.025% citric acid, 3% Domosil RWAF | 5 | 4 | 3 | 3 |
| 17050309 | 6608D2B polyester/lycra, first step 0.25% silk 3L1M, 0.025% citric acid second step 2% Ultratex CSP, 0.25% citric acid | 5 | 5 | 4 | 4 |
| 17050310 | 6608D2B polyester/lycra, first step 0.25% silk 3L1M, 0.025% citric acid, second step 3% Domosil RWAF, 0.25% citric acid | 5 | 5 | 4 | 4 |

*3L1M: 3:1 low MW silk to medium MW silk

TABLE 51

Water Drop Test Results

| Sample # | Description | | Average water drop absorption time |
|---|---|---|---|
| 17050303 | 6606D2 nylon/lycra, 0.25% silk 3L1M*, 0.025% citric acid, 3% Domosil RWAF | t = 0 | 8.8 |
| | | t = 10 | 60 |
| | | t = 25 | 16 |
| | | t = 52 | 4 |
| 17050307 | 6606D2 nylon/lycra, first step 0.25% silk 3L1M, 0.025% citric acid, second step 2% Ultratex CSP, 0.25% citric acid | t = 0 | 27.4 |
| | | t = 10 | 60 |
| | | t = 25 | 60 |
| | | t = 52 | 17.2 |
| 17050308 | 6606D2 nylon/lycra, first step 0.25% silk 3L1M, 0.025% citric acid, second step 3% Domosil RWAF, 0.25% citric acid | t = 0 | 1 |
| | | t = 10 | 2.6 |
| | | t = 25 | 3.6 |
| | | t = 52 | 2.6 |
| 17050306 | 6608D2B polyester/lycra, 0.25% silk 3L1M, 0.025% citric acid, 3% Domosil RWAF | t = 0 | 2.6 |
| | | t = 10 | 60 |
| | | t = 25 | 60 |
| | | t = 52 | 60 |
| 17050309 | 6608D2B polyester/lycra, first step 0.25% silk 3L1M, 0.025% citric acid, second step 2% Ultratex CSP, 0.25% citric acid | t = 0 | 11.2 |
| | | t = 10 | 60 |
| | | t = 25 | 60 |
| | | t = 52 | 60 |
| 17050310 | 6608D2B polyester/lycra, first step 0.25% silk 3L1M, 0.025% citric acid, second step 3% Domosil RWAF, 0.25% citric acid | t = 0 | 0.8 |
| | | t = 10 | 3.2 |
| | | t = 25 | 7 |
| | | t = 52 | 28.6 |

*3L1M: 3:1 low MW silk to medium MW silk

Note:

end of test 60 seconds

Example 7: Nylon/Lycra Fabric and Polyester/Lycra Fabric Coated with Silk and Silicone: Laundering Fastness Evaluation (Hand and Water Drop Absorption)—Second Sample Set

TABLE 52

Coating Experimental Variables

| Fabric Style # | Silk solution | pH correction | Silicone coating | pH correction | Dry/cure temperature ° F. (° C.)/time |
|---|---|---|---|---|---|
| 6606D2 | 0.187% low MW + 0.063% medium MW (3:1 ratio) | 0.025% citric acid (50%) or to pH 4-5 | N/A | N/A | 302 (150) 70 seconds |
|  | N/A | N/A | Domosil RWAF 3% | 0.025% citric acid (50%) or to pH 4-5 | 302 (150) 70 seconds |
| 6608D2B | 0.187% low MW + 0.063% medium MW (3:1 ratio) | 0.025% citric acid (50%) or to pH 4-5 | N/A | N/A | 350 (177) 60 seconds |
|  | N/A | N/A | Domosil RWAF 3% | 0.025% citric acid (50%) or to pH 4-5 | 350 (177) 60 seconds |

Analysis:

Samples coated as described in Table 52, are conditioned at ambient for 24 hrs before delivering them to testing lab for laundering test. The samples will be used for:

N=1 control no laundering;
N=1 after 10 laundering cycles;
N=1 after 25 laundering cycles;
N=1 after 50 laundering cycles;
Fabrics are evaluated for hand by two technicians against the control not laundered (Table 53).

Laundering method AATCC Test Method 135-2015 (Table I, "Dimensional Changes of Fabrics after Home Laundering"). Testing Information: Home Laundered 52 times using AATCC TM 150 (Table II); Laundry Test Conditions: load size=1.8 kg (4 lbs), Launder Right Side Out Wash; (1) Normal/CottonSturdy (III) 105±5° F. using 1993 AATCC Standard Reference Detergent WOB; Top Loading Machine; Tumble Dry (i) Cotton Sturdy; Ballast Wash Load Type 3—50/50 polyester/cotton bleached plain weave; Samples removed at 10, 25 and 52 launderings.

Figure 1B:
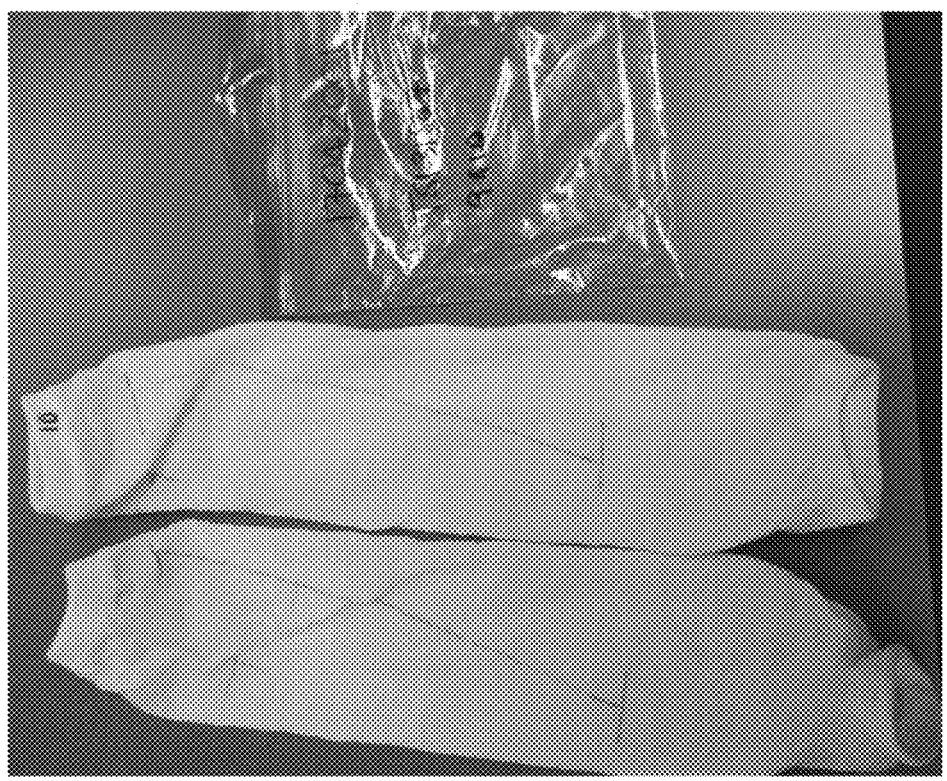
FIG. 1B is a photograph of wool tubular fabric control sample no. 17042001 after one laundering cycle.
Figure 1A:
FIG. 1A is a photograph of wool tubular fabric control sample no. 17056902 after one laundering cycle.
Figure 2B:
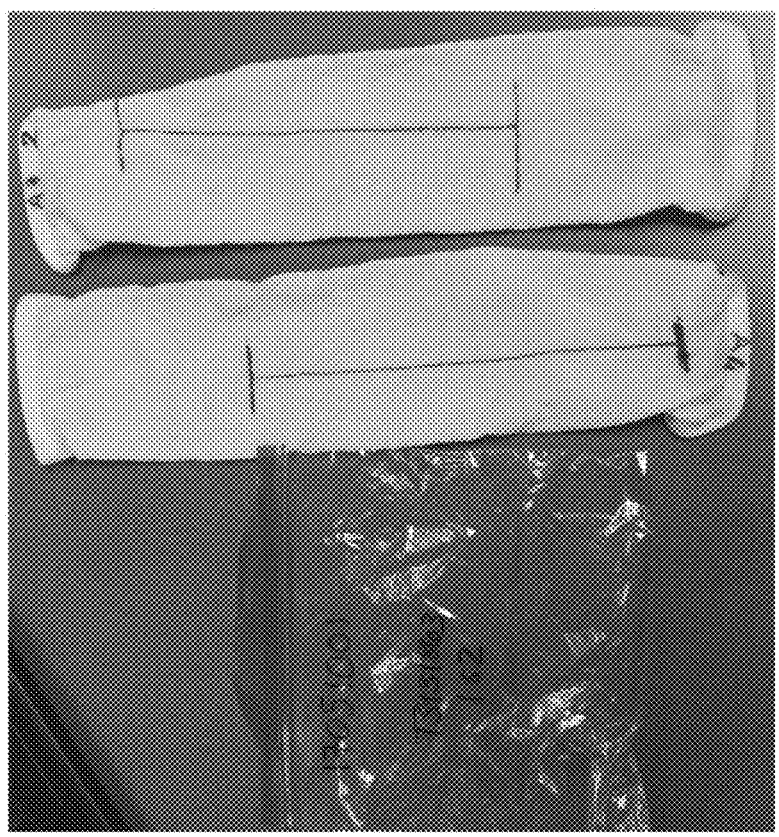
FIG. 2B is a photograph of silk coated wool tubular fabric sample no. 17051001 after one laundering cycle.
Figure 2A:
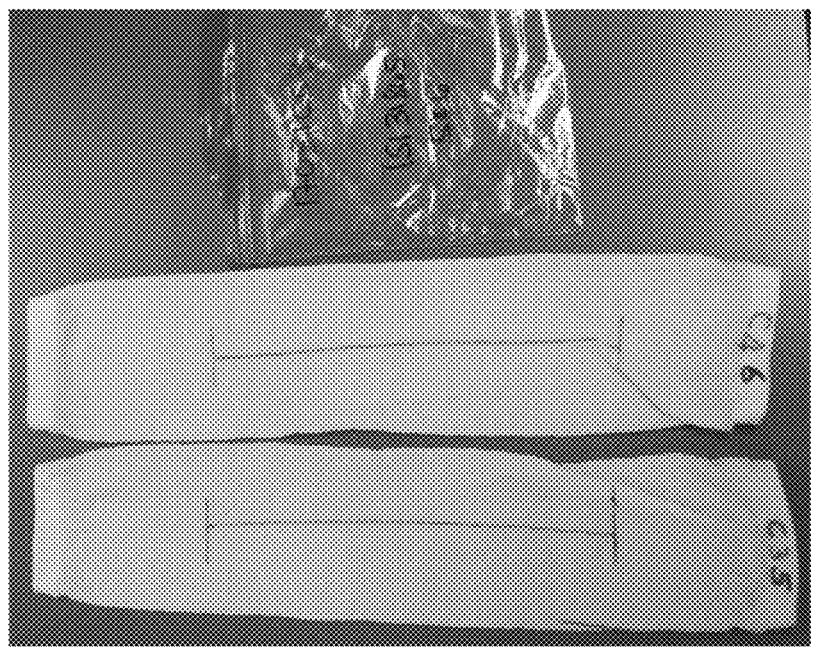
FIG. 2A is a photograph of silk coated wool tubular fabric sample no. 17051003 after one laundering cycle.
Figure 3:
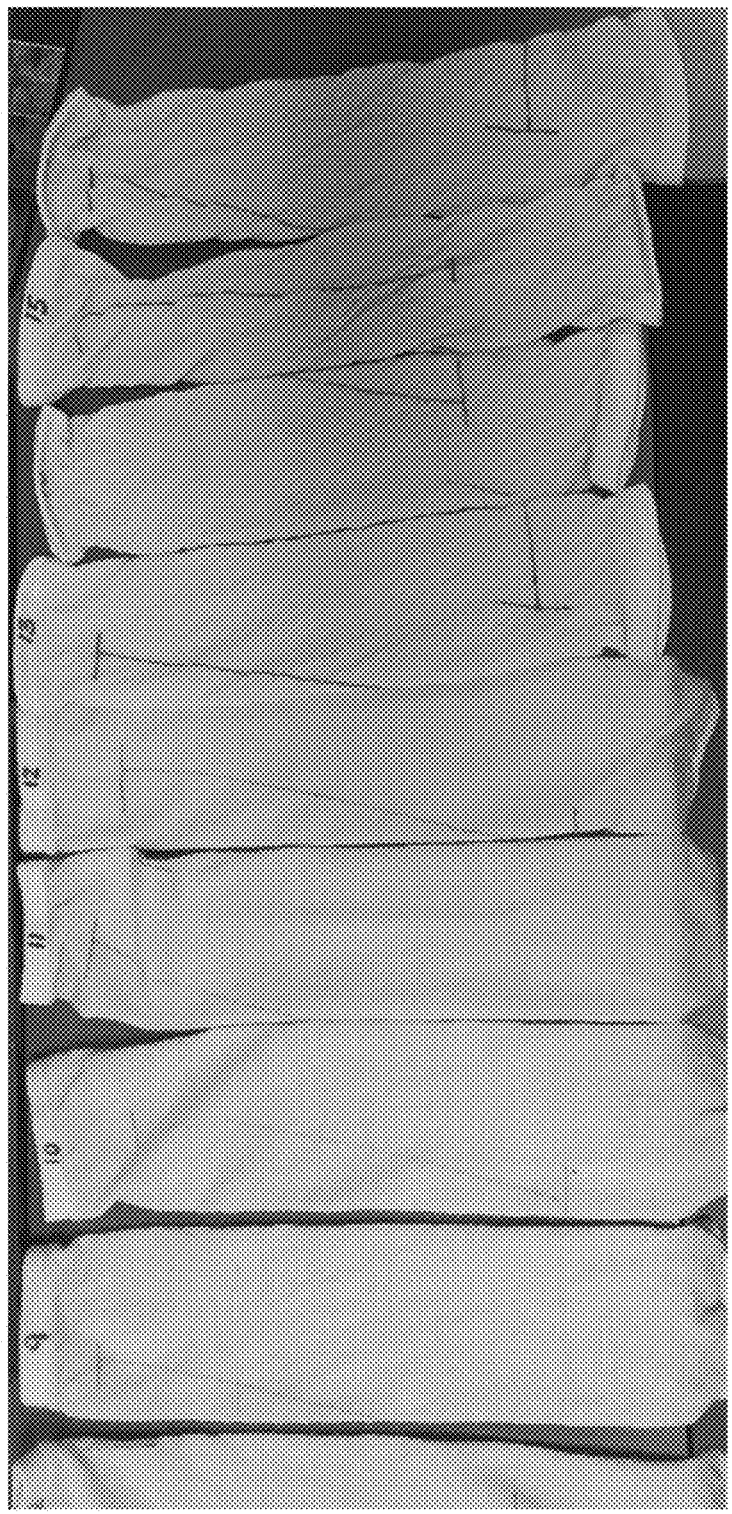
FIG. 3 is a photograph of several wool tubular fabric control samples after two laundering cycles.
Figure 4:
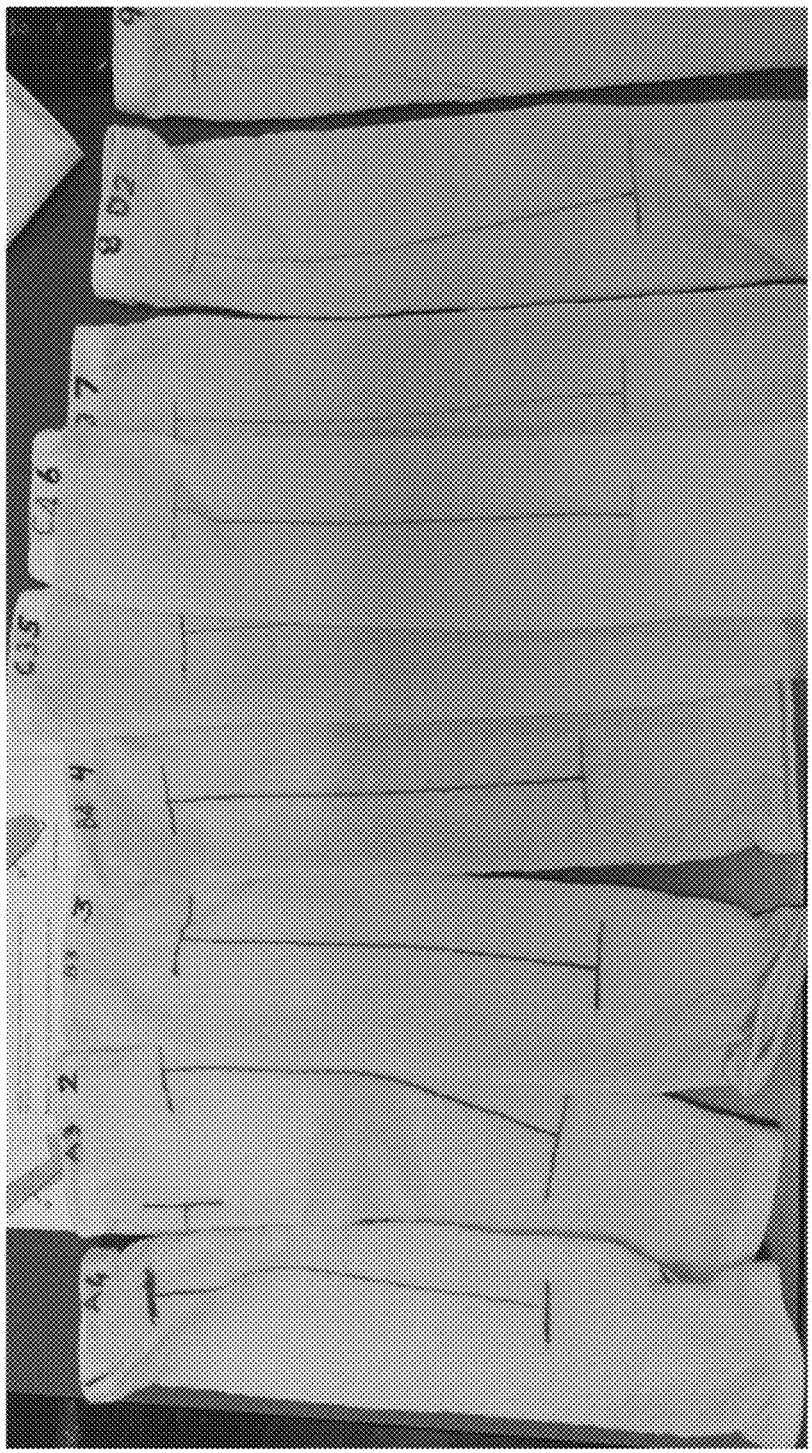
FIG. 4 is a photograph of several silk coated wool tubular fabric samples after two laundering cycles.
Figure 5A:
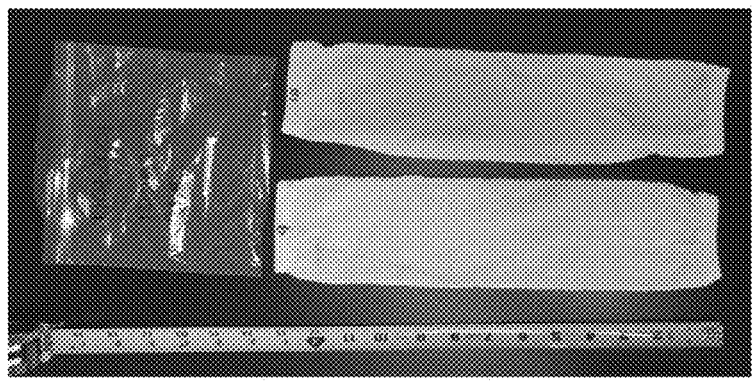
FIG. 5A is a photograph of wool tubular fabric control sample no. 17042001 after five laundering cycles.
Figure 5B:
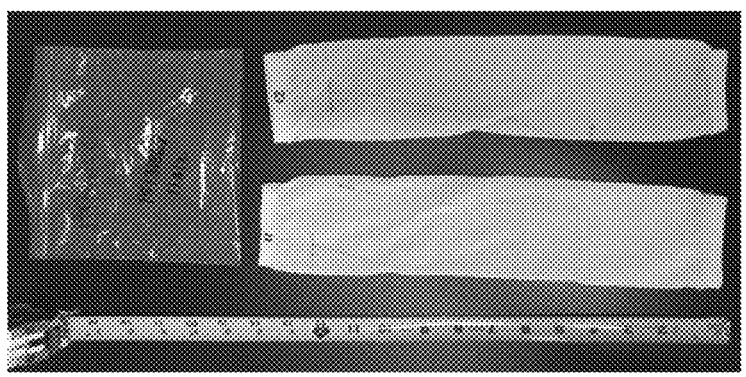
FIG. 5B is a photograph of wool tubular fabric control sample no. 17042002 after five laundering cycles.
Figure 5C:
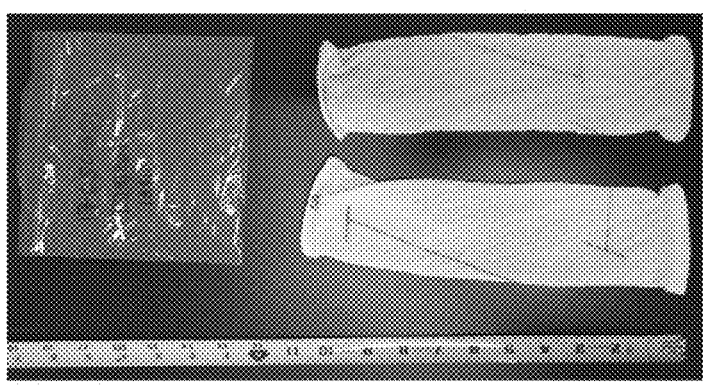
FIG. 5C is a photograph of wool tubular fabric control sample no. 17050901 after five laundering cycles.
Figure 5D:
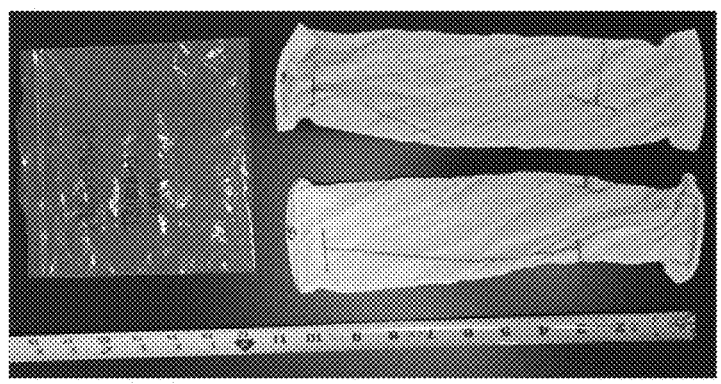
FIG. 5D is a photograph of wool tubular fabric control sample no. 17050902 after five laundering cycles.
Figure 6D:
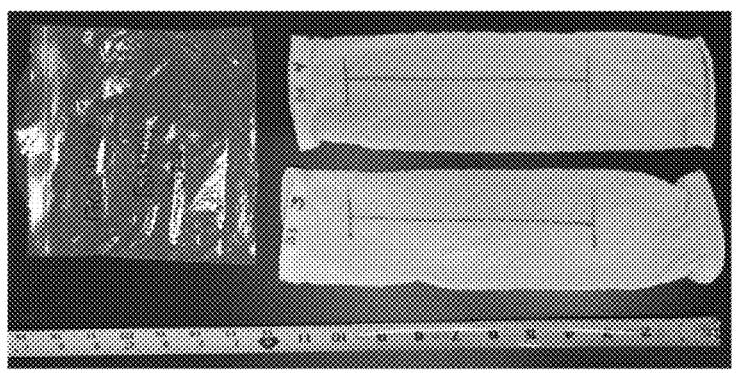
FIG. 6D is a photograph of silk coated wool tubular fabric sample no. 17051002 after five laundering cycles.
Figure 6C:
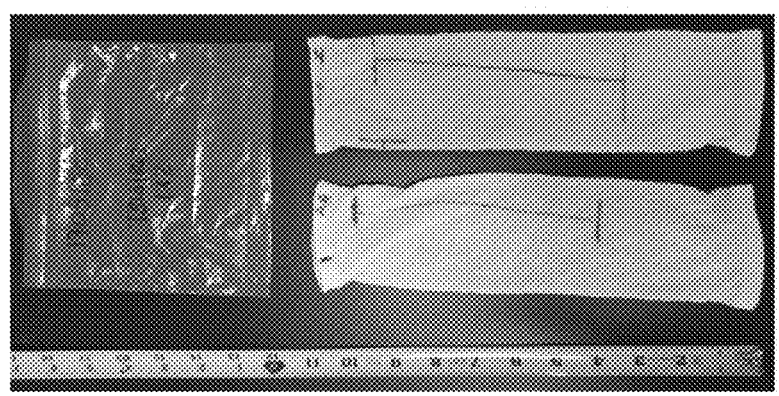
FIG. 6C is a photograph of silk coated wool tubular fabric sample no. 17051001 after five laundering cycles.
Figure 6B:
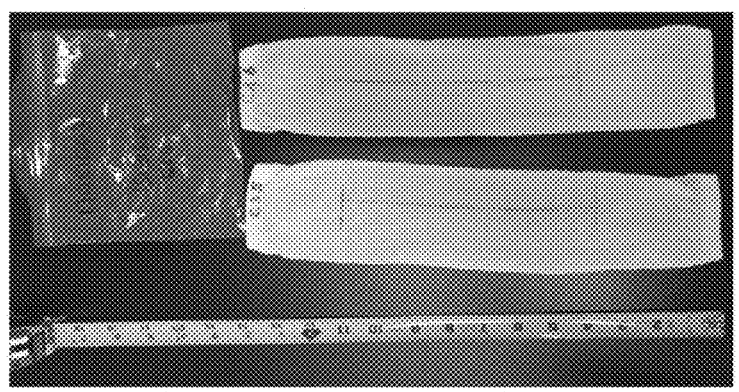
FIG. 6B is a photograph of silk coated wool tubular fabric sample no. 17051003 after five laundering cycles.
Figure 6A:
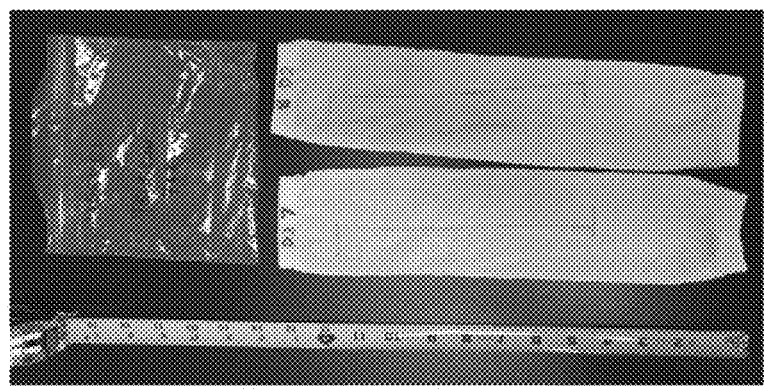
FIG. 6A is a photograph of silk coated wool tubular fabric sample no. 17051101 after five laundering cycles.
Figure 7A:
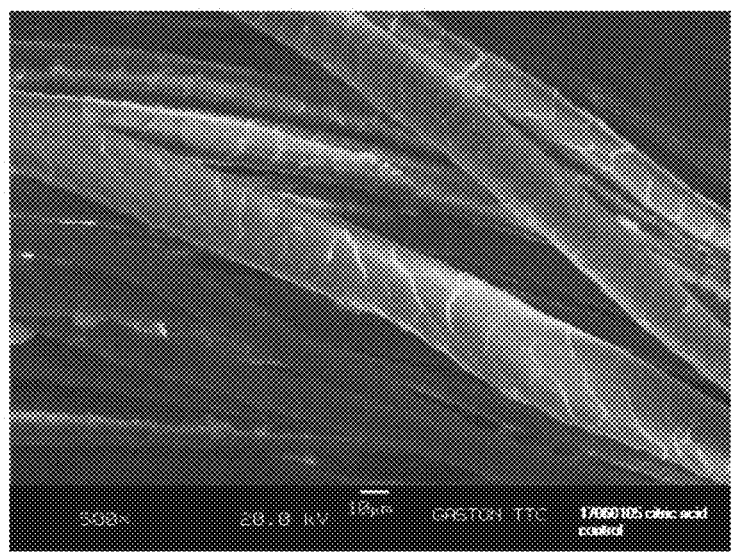
FIG. 7A-7C are a series of SEM photographs of citric acid control wool tubular fabric sample no. 17060105 at 500× and 1000× magnification.
Figure 7B:
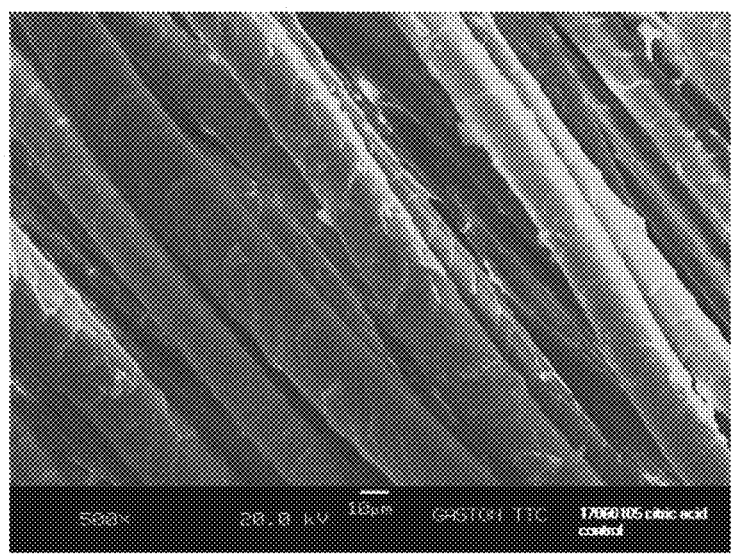
Figure 7C:
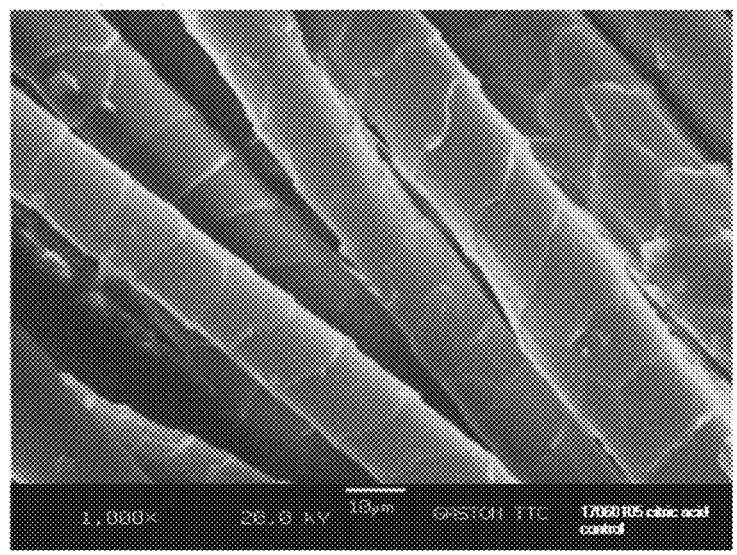
Figure 8A:
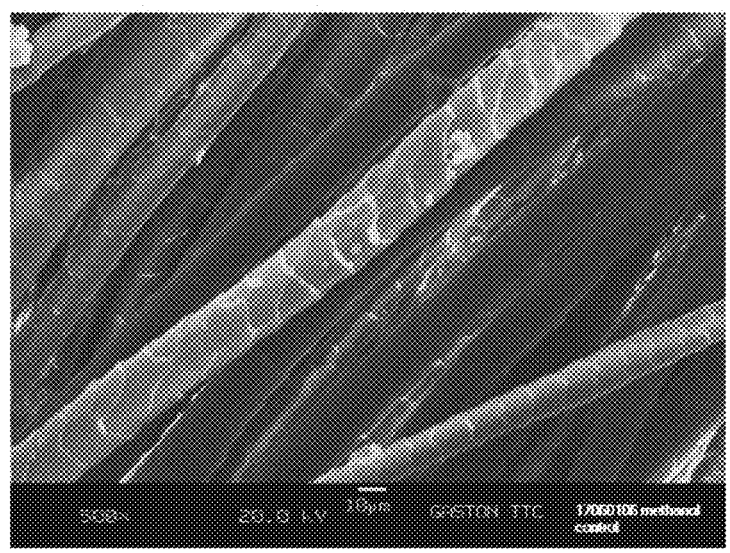
FIG. 8A-8C are a series of SEM photographs of methanol control wool tubular fabric sample no. 17060106 at 500× and 1000× magnification.
Figure 8B:
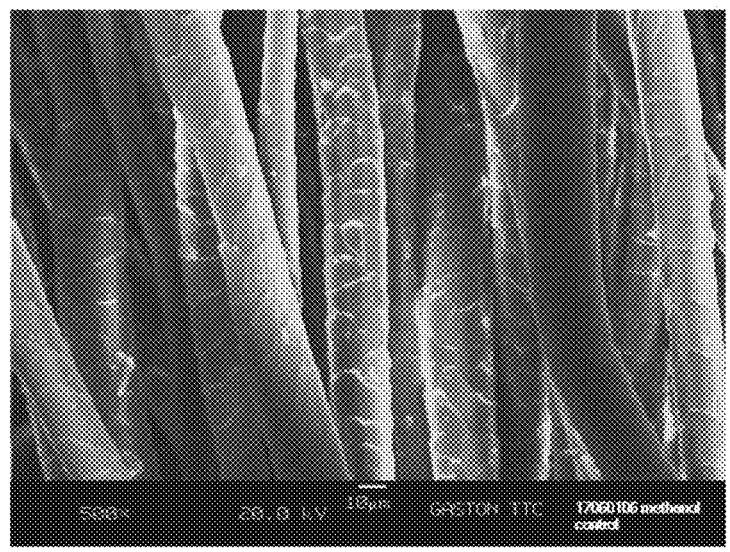
Figure 8C:
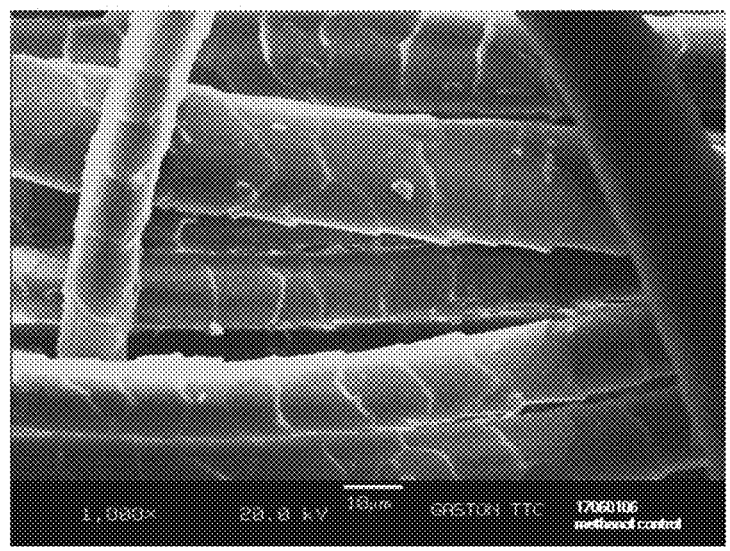
Figure 9A:
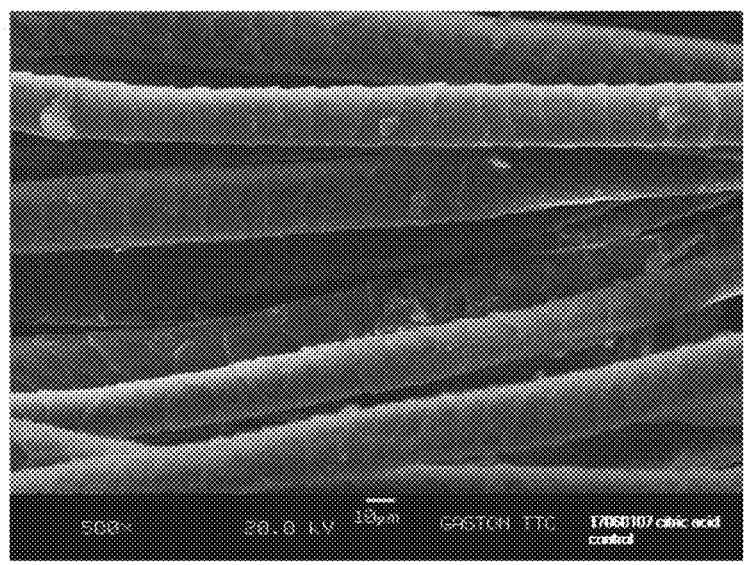
FIG. 9A-9C are a series of SEM photographs of citric acid control wool tubular fabric sample no. 17060107 at 500× and 1000× magnification.
Figure 9B:
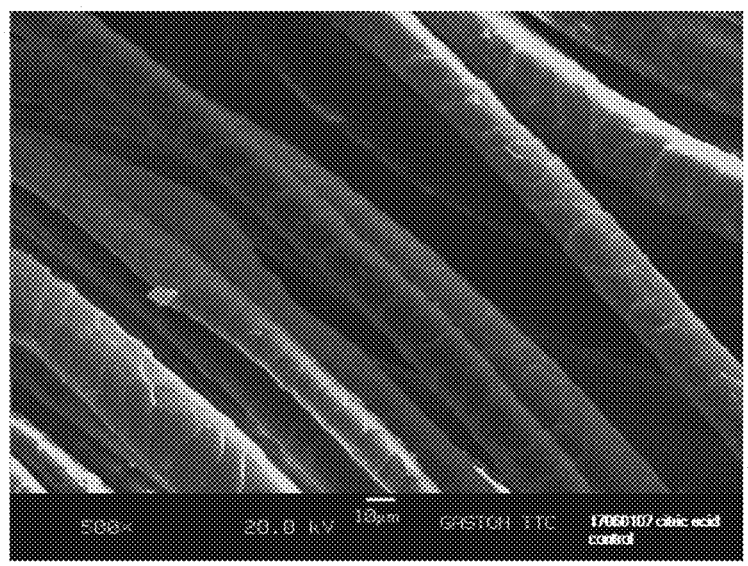
Figure 9C:
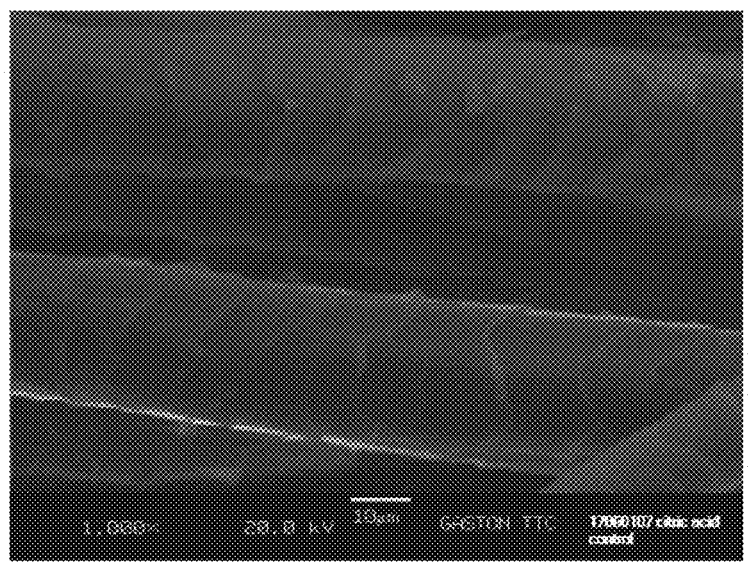
Figure 10A:
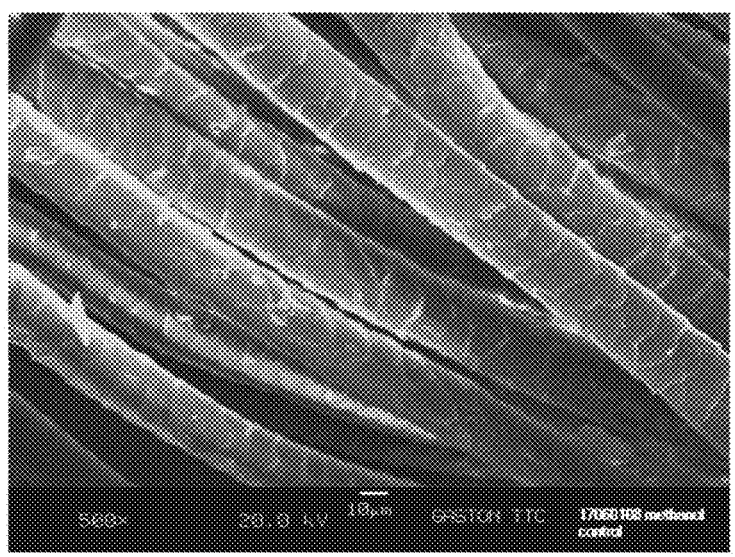
FIG. 10A-10C are a series of SEM photographs of methanol control wool tubular fabric sample no. 17060108 at 500× and 1000× magnification.
Figure 10B:
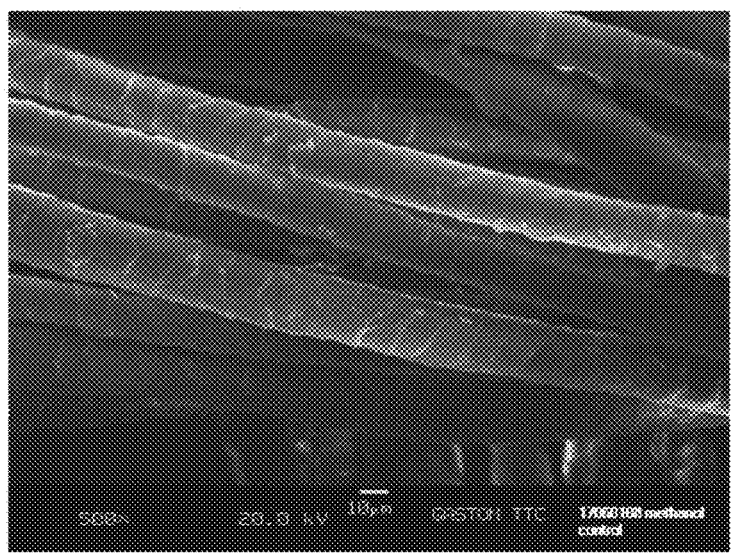
Figure 10C:
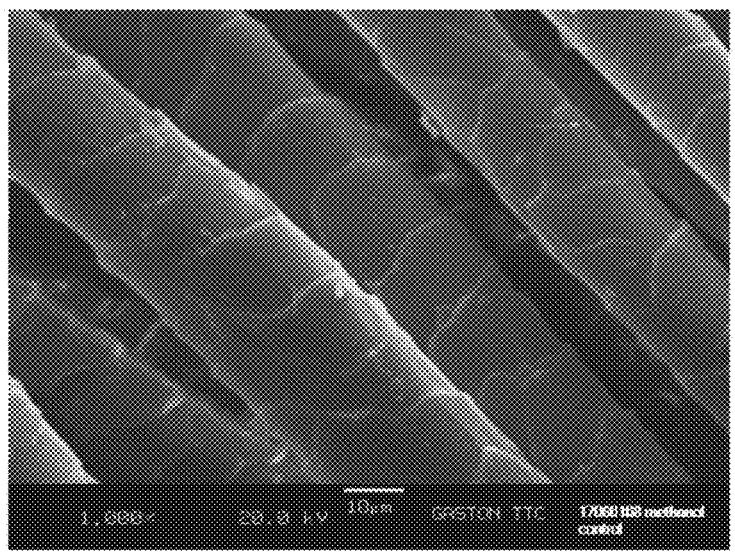
Figure 11A:
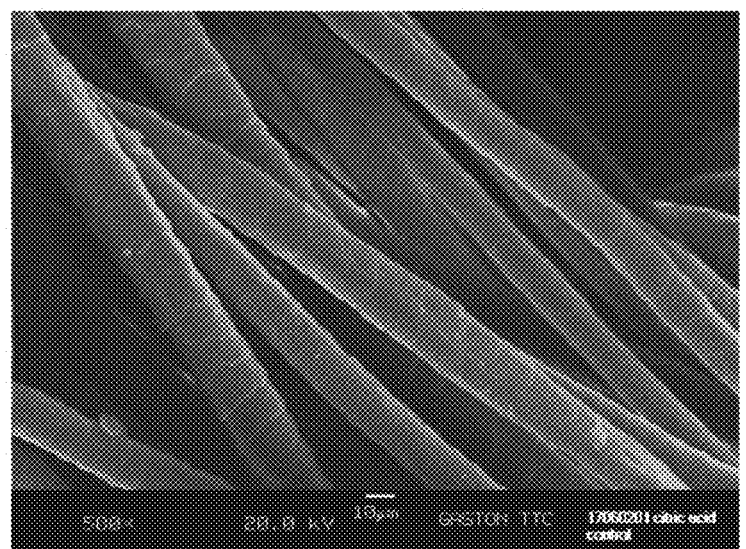
FIG. 11A-11C are a series of SEM photographs of citric acid control wool tubular fabric sample no. 17060201 at 500× and 1000× magnification.
Figure 11B:
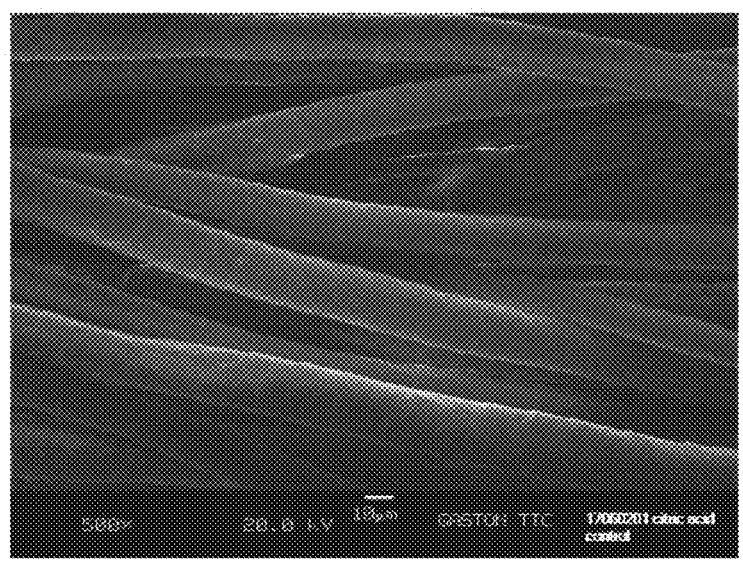
Figure 11C:
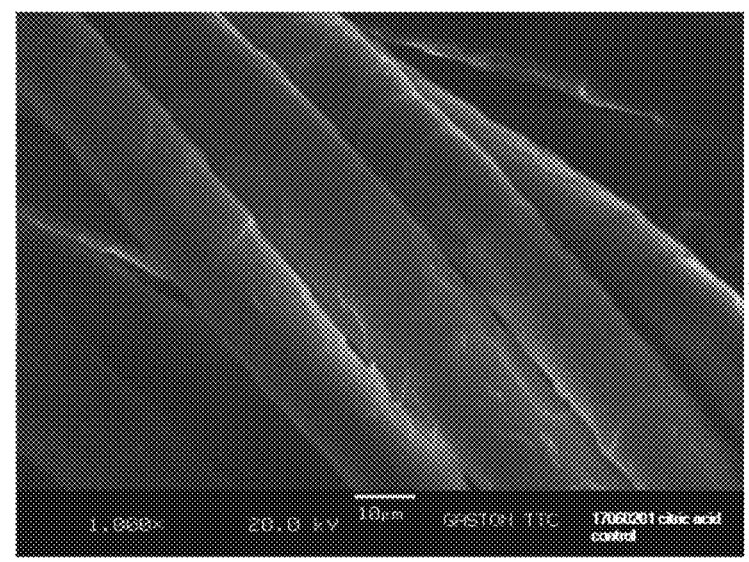
Figure 12A:
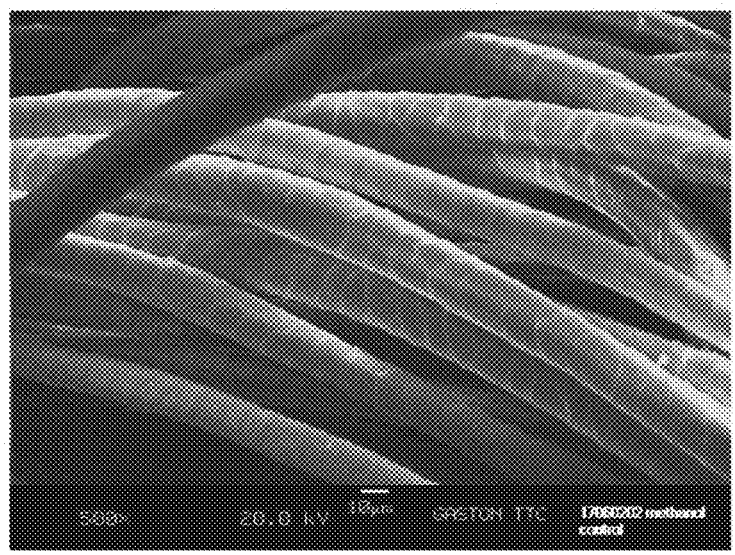
FIG. 12A-12C are a series of SEM photographs of methanol control wool tubular fabric sample no. 17060202 at 500× and 1000× magnification.
Figure 12B:
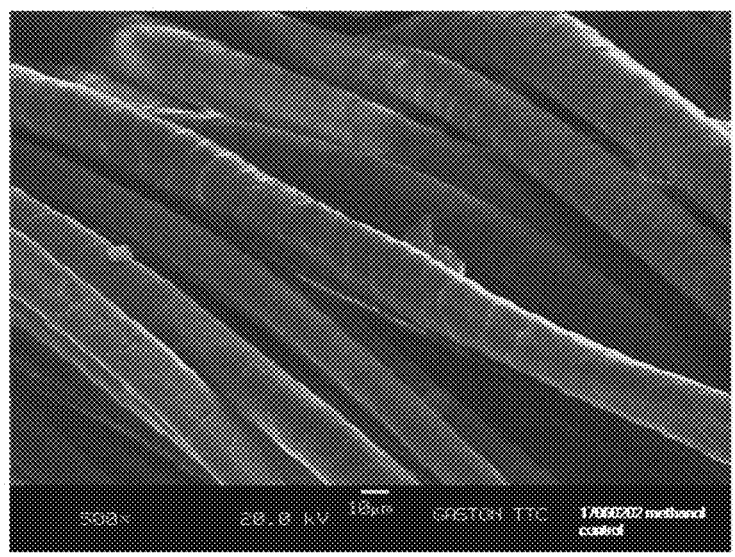
Figure 12C:
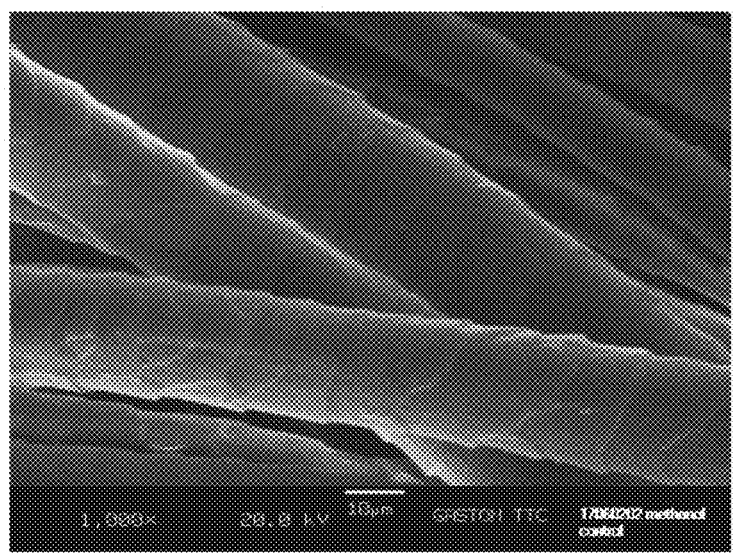
Figure 13A:
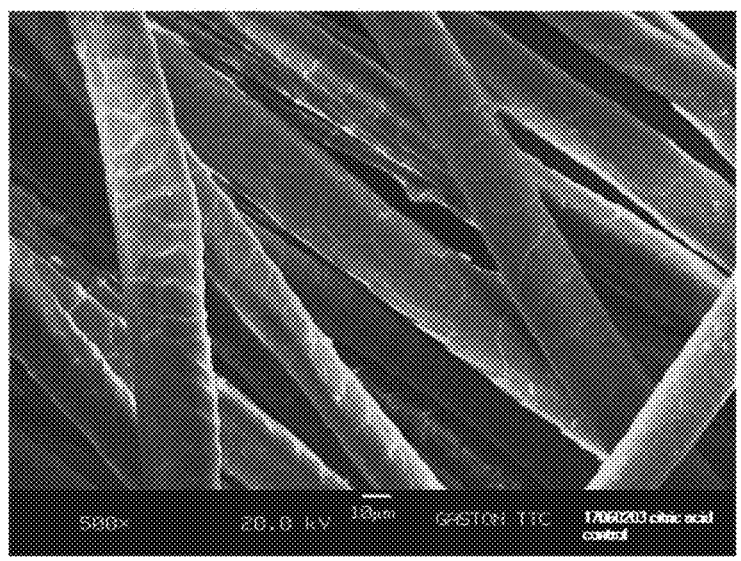
FIG. 13A-13C are a series of SEM photographs of citric acid control wool tubular fabric sample no. 17060203 at 500× and 1000× magnification.
Figure 13B:
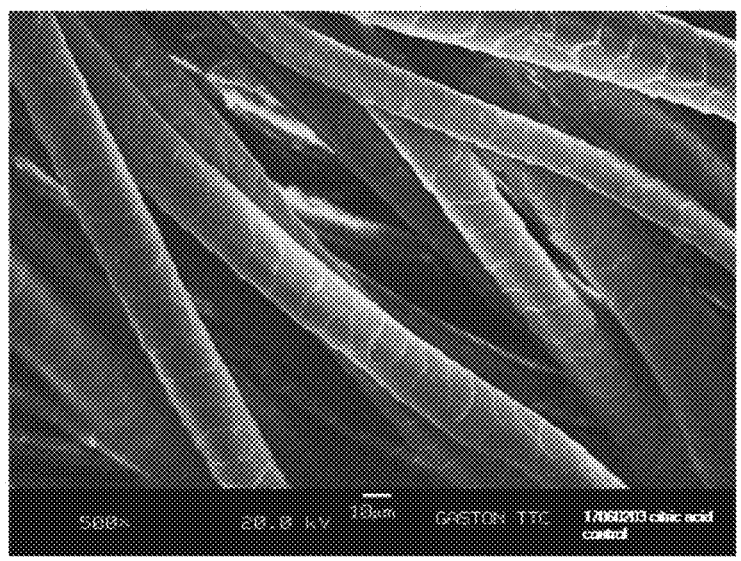
Figure 13C:
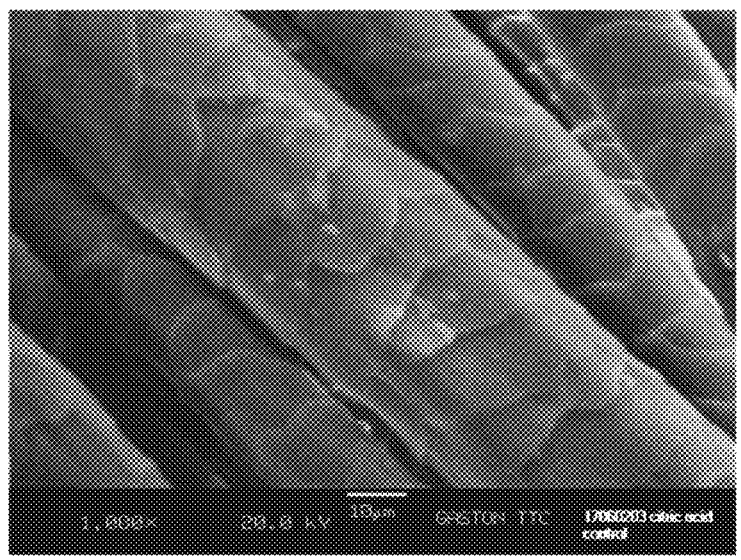
Figure 14A:
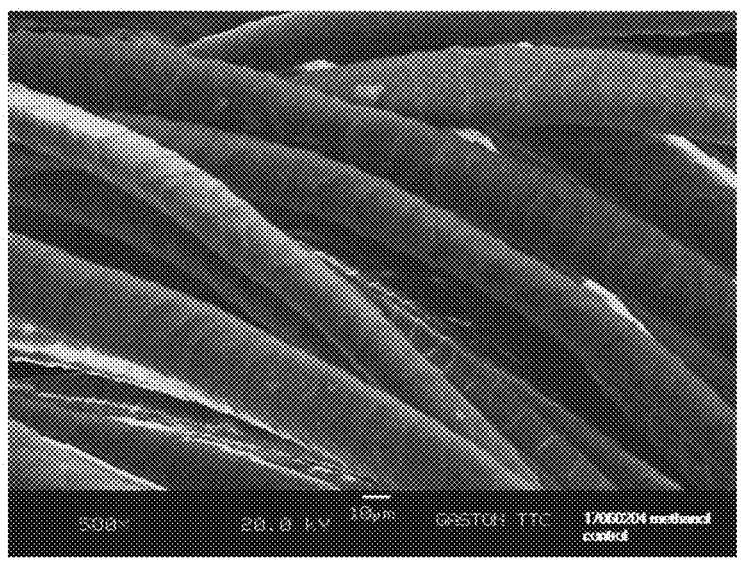
FIG. 14A-14C are a series of SEM photographs of methanol control wool tubular fabric sample no. 17060204 at 500× and 1000× magnification.
Figure 14B:
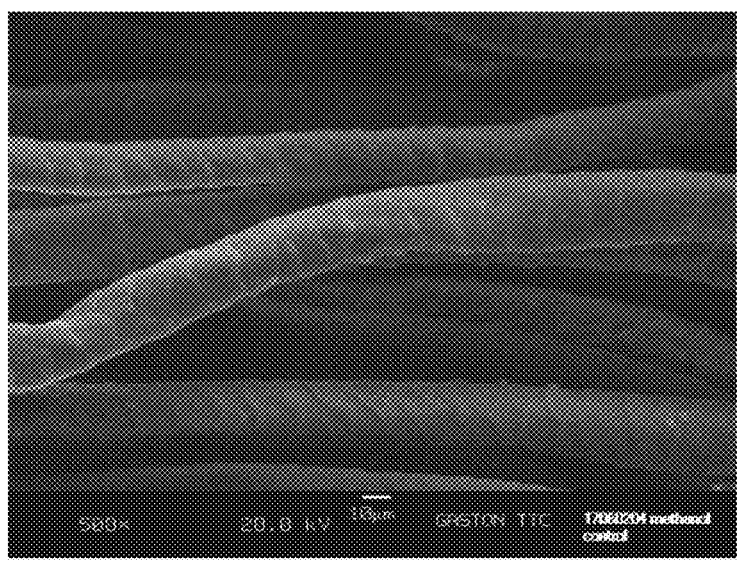
Figure 14C:
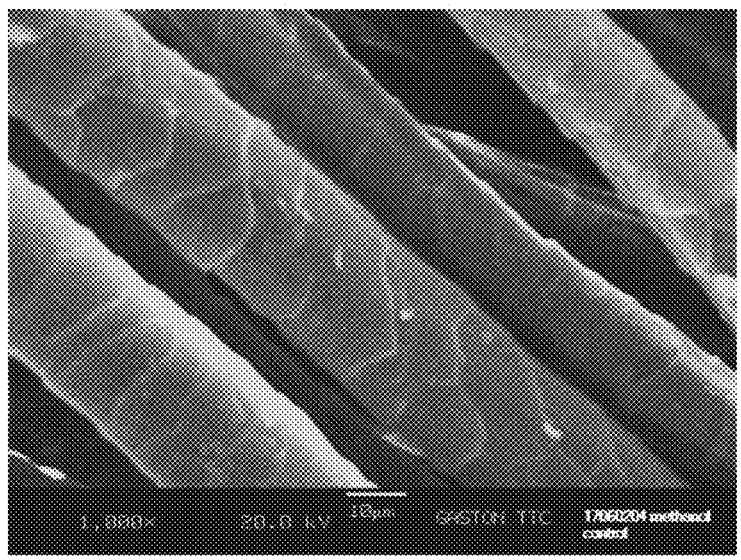
Figure 15A:
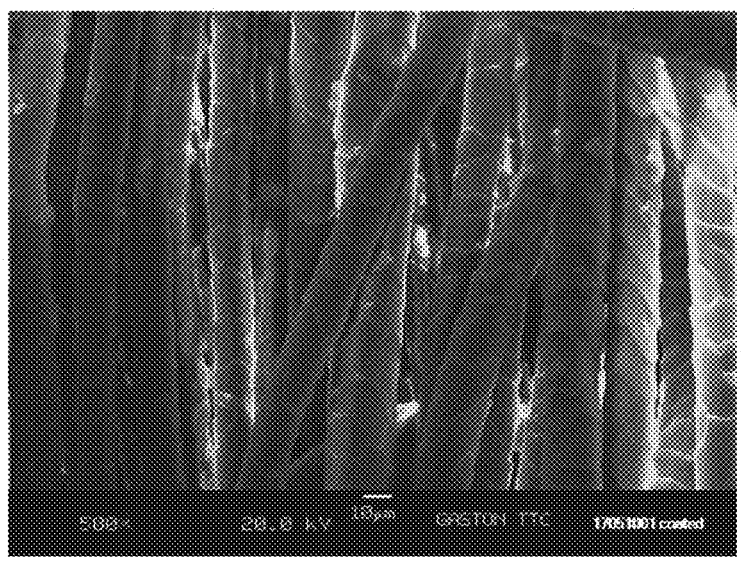
FIG. 15A-15C are a series of SEM photographs of silk coated wool tubular fabric sample no. 17051001 at 500× and 1000× magnification.
Figure 15B:
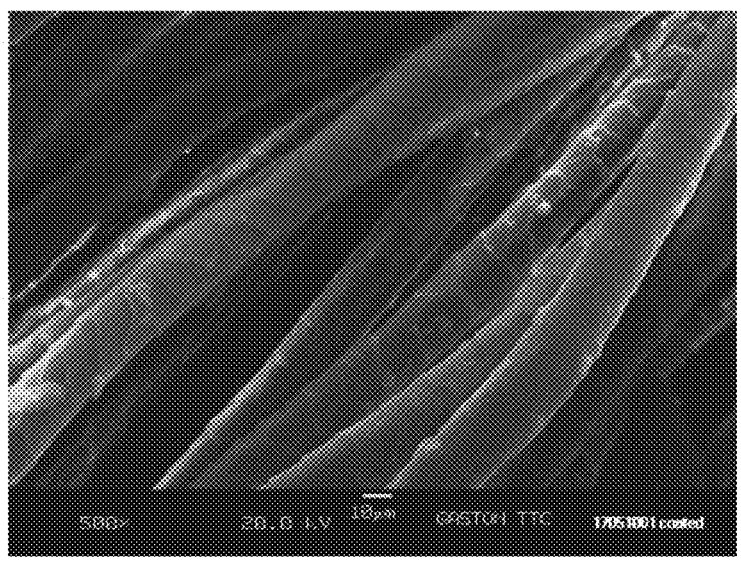
Figure 15C:
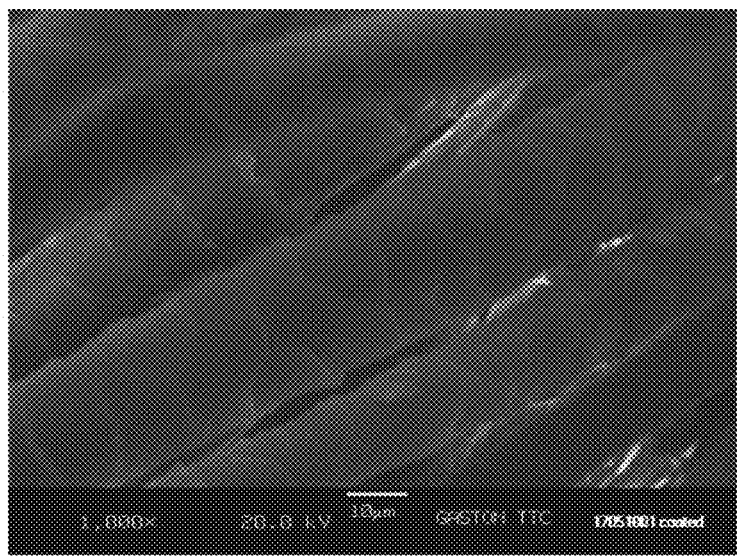
Figure 16A:
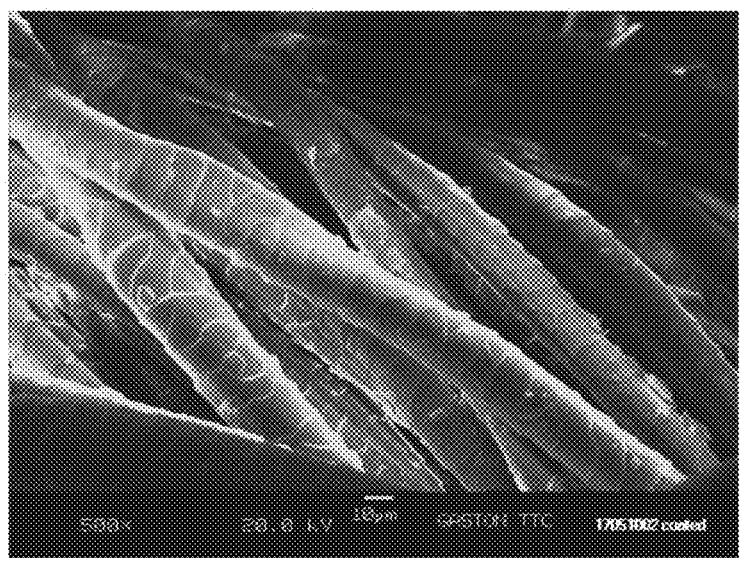
FIG. 16A-16C are a series of SEM photographs of silk coated wool tubular fabric sample no. 17051002 at 500× and 1000× magnification.
Figure 16B:
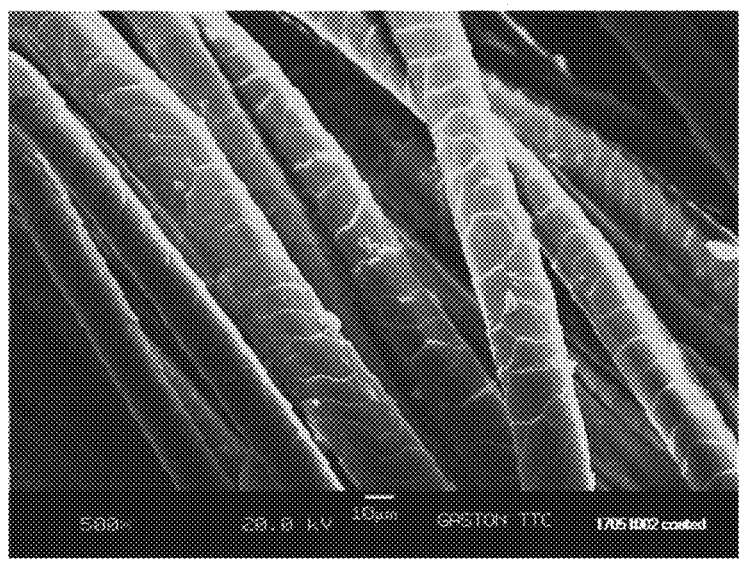
Figure 16C:
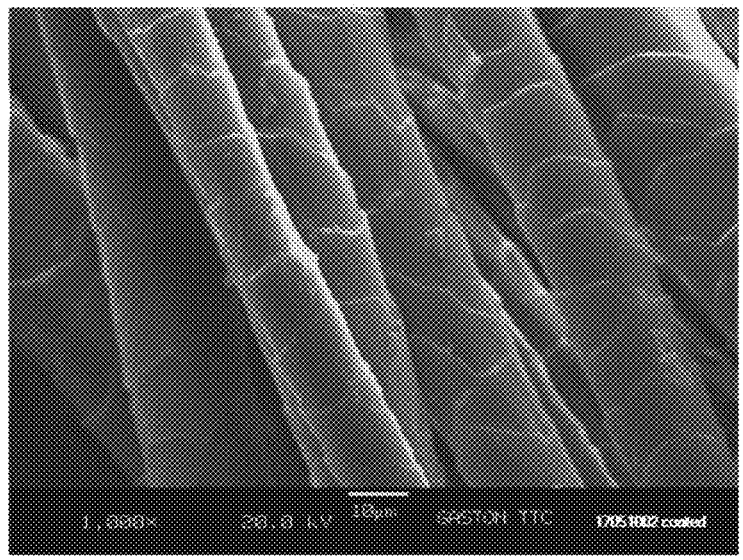
Figure 17A:
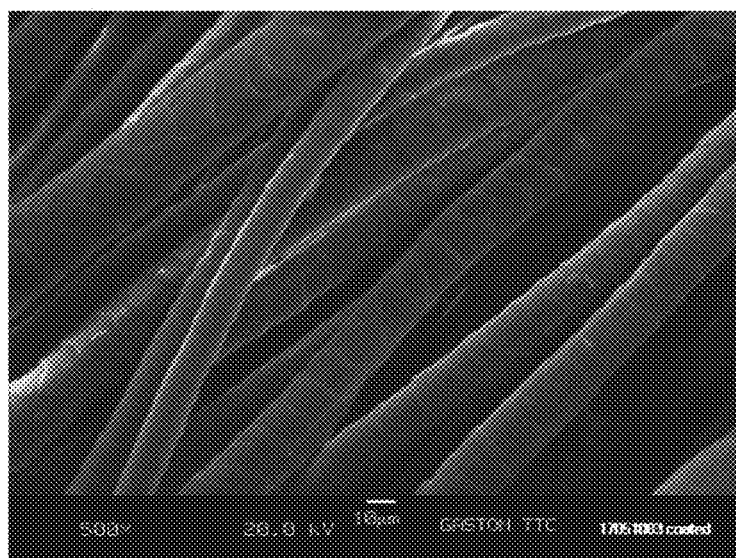
FIG. 17A-17C are a series of SEM photographs of silk coated wool tubular fabric sample no. 17051003 at 500× and 1000× magnification.
Figure 17B:
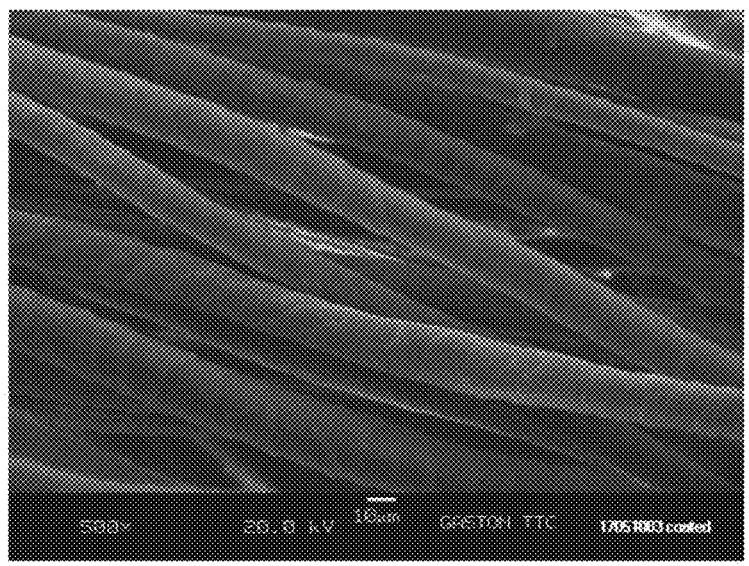
Figure 17C:
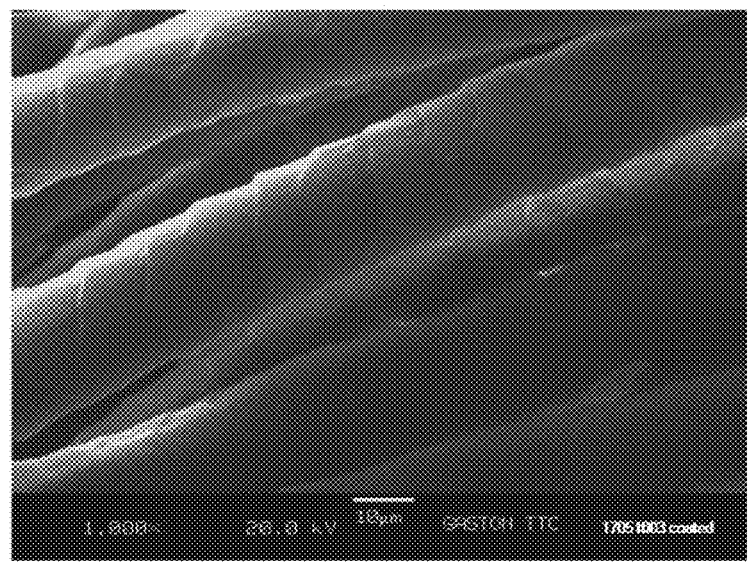
Figure 18A:
FIG. 18A-18C are a series of SEM photographs of silk coated wool tubular fabric sample no. 17051101 at 500× and 1000× magnification.
Figure 18B:
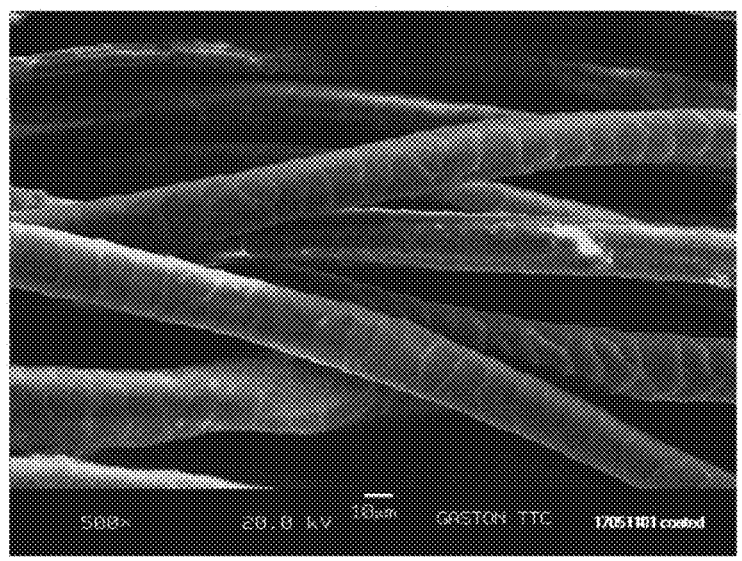
Figure 18C:
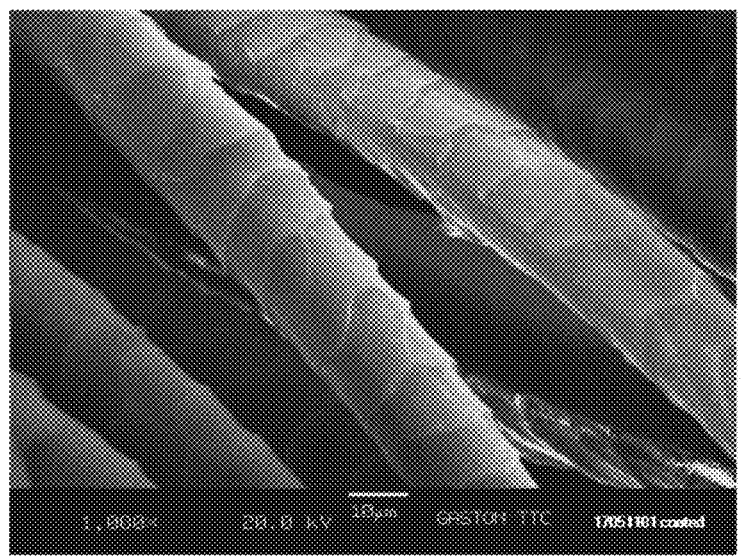
Figure 19A:
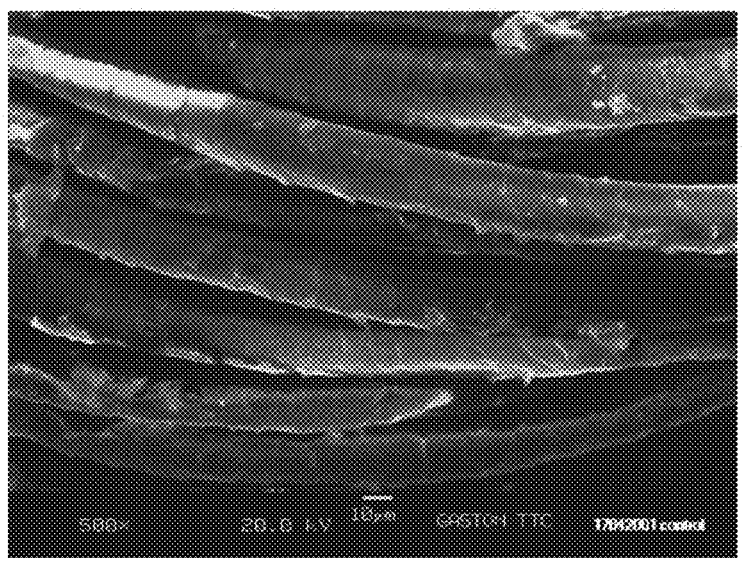
FIG. 19A-19C are a series of SEM photographs of wool tubular fabric control sample no. 17042001 at 500× and 1000× magnification.
Figure 19B:
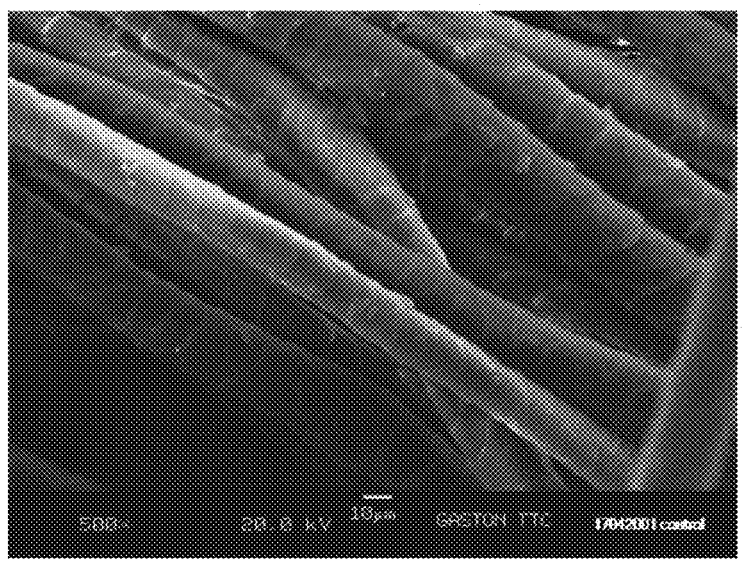
Figure 19C:
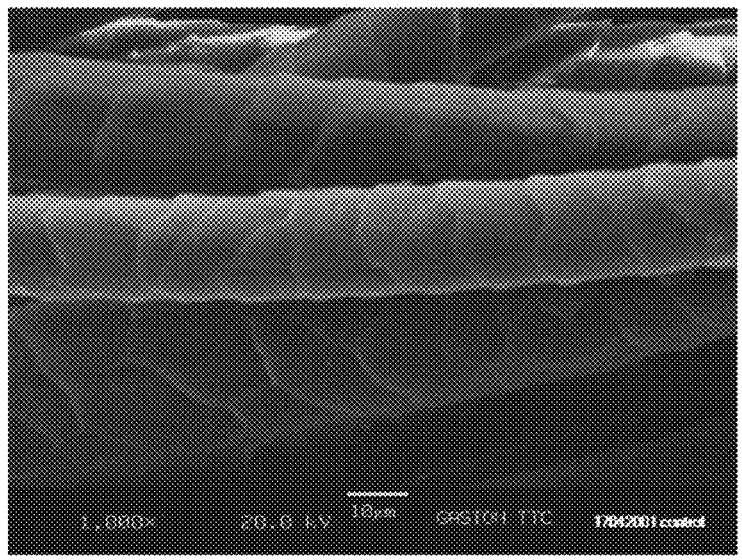
Figure 20A:
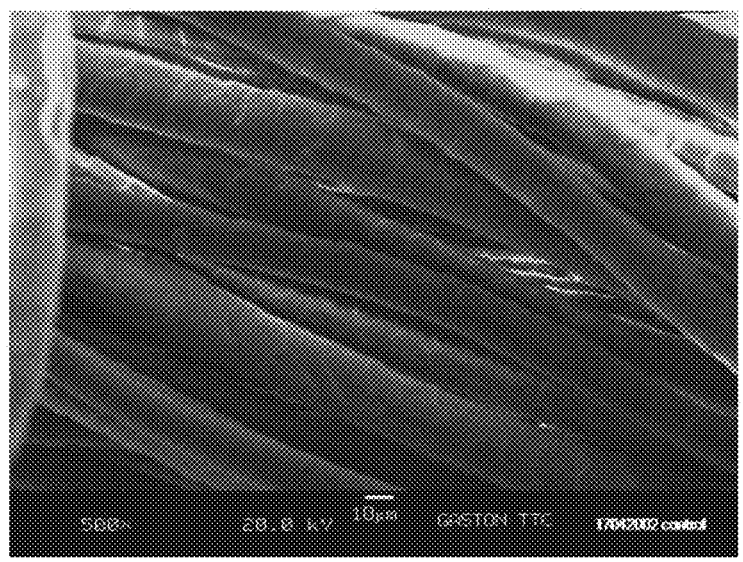
FIG. 20A-20C are a series of SEM photographs of wool tubular fabric control sample no. 17042002 at 500× and 1000× magnification.
Figure 20B:
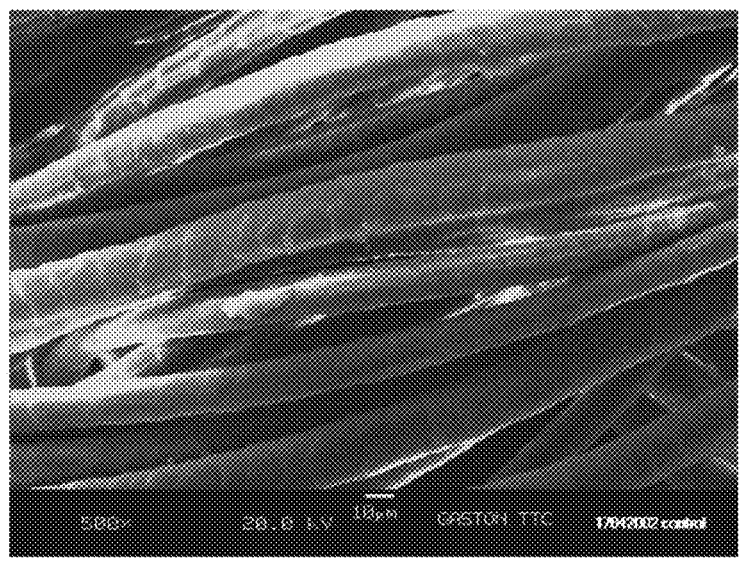
Figure 20C:
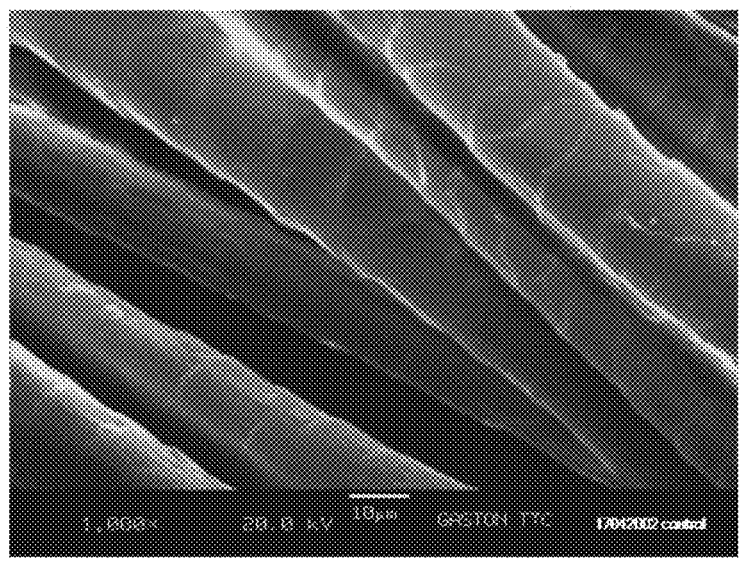
Figure 21A:
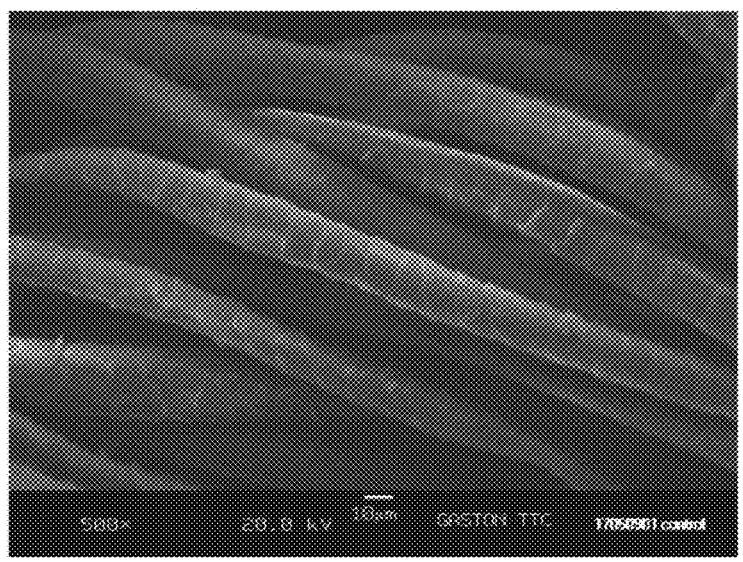
FIG. 21A-21C are a series of SEM photographs of wool tubular fabric control sample no. 17050901 at 500× and 1000× magnification.
Figure 21B:
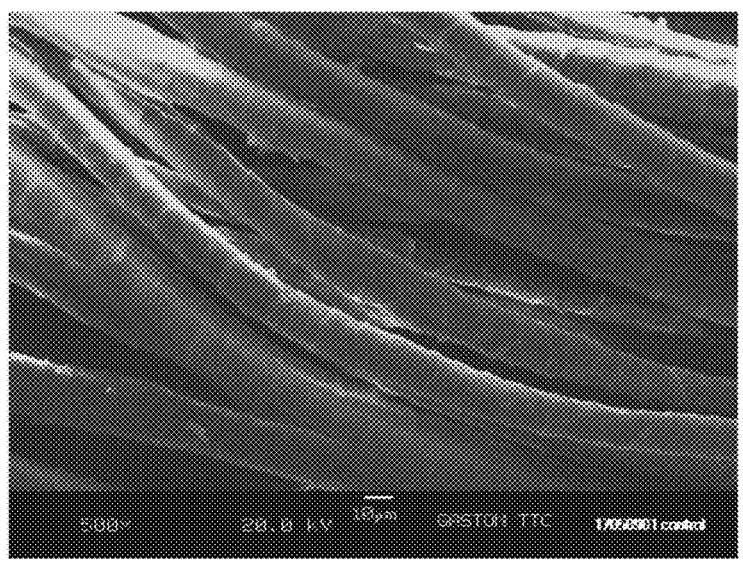
Figure 21C:
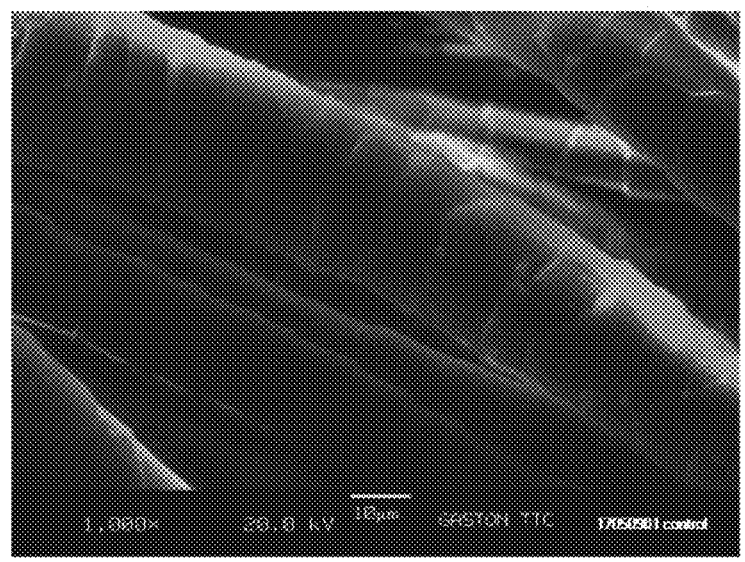
Figure 22A:
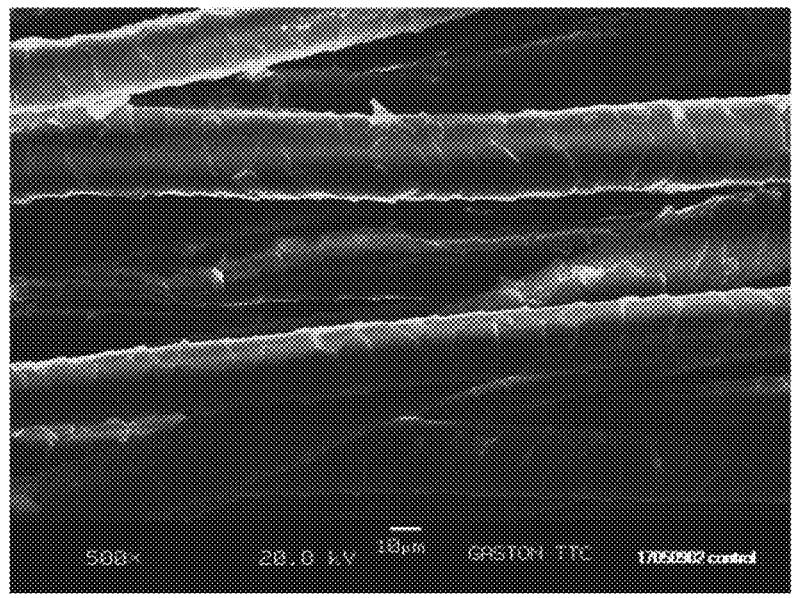
FIGS. 22A and 22B are two SEM photographs of wool tubular fabric control sample no. 17050902 at 500× and 1000× magnification.
Figure 22B:
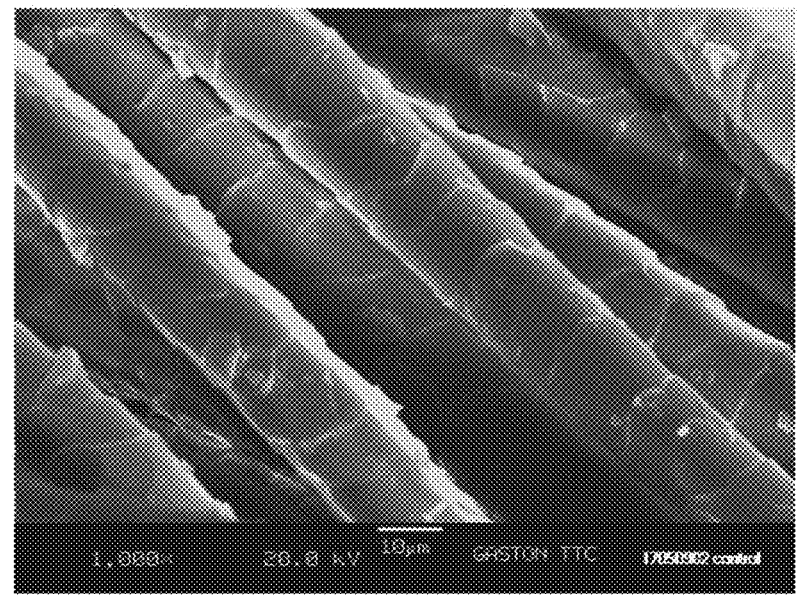
Figure 23:
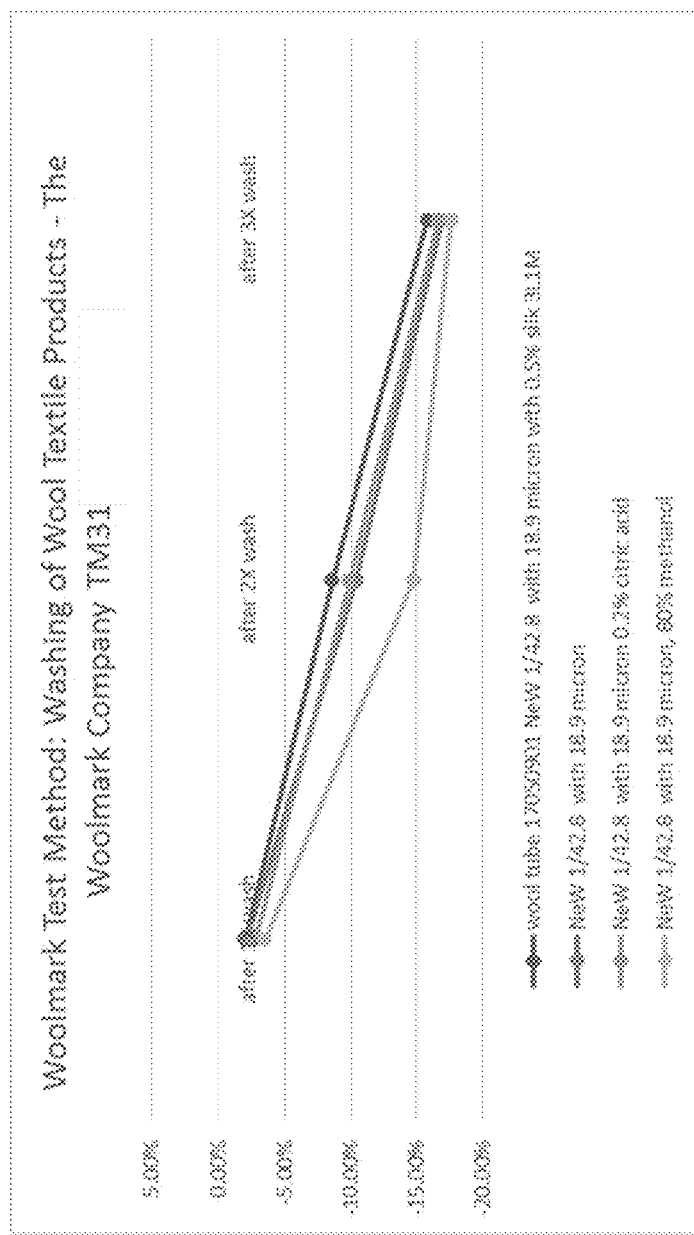
FIG. 23 is a chart summarizing dimensional stability to laundering (Woolmark Test Method) of NeW 1-42.8 with 18.9 micron NS wool samples, including the dimensional stability of a silk coated sample, the dimensional stability of a control sample, the dimensional stability of a citric acid pretreated and silk coated sample, and the dimensional stability of a silk coated and finally treated sample.
Figure 24:
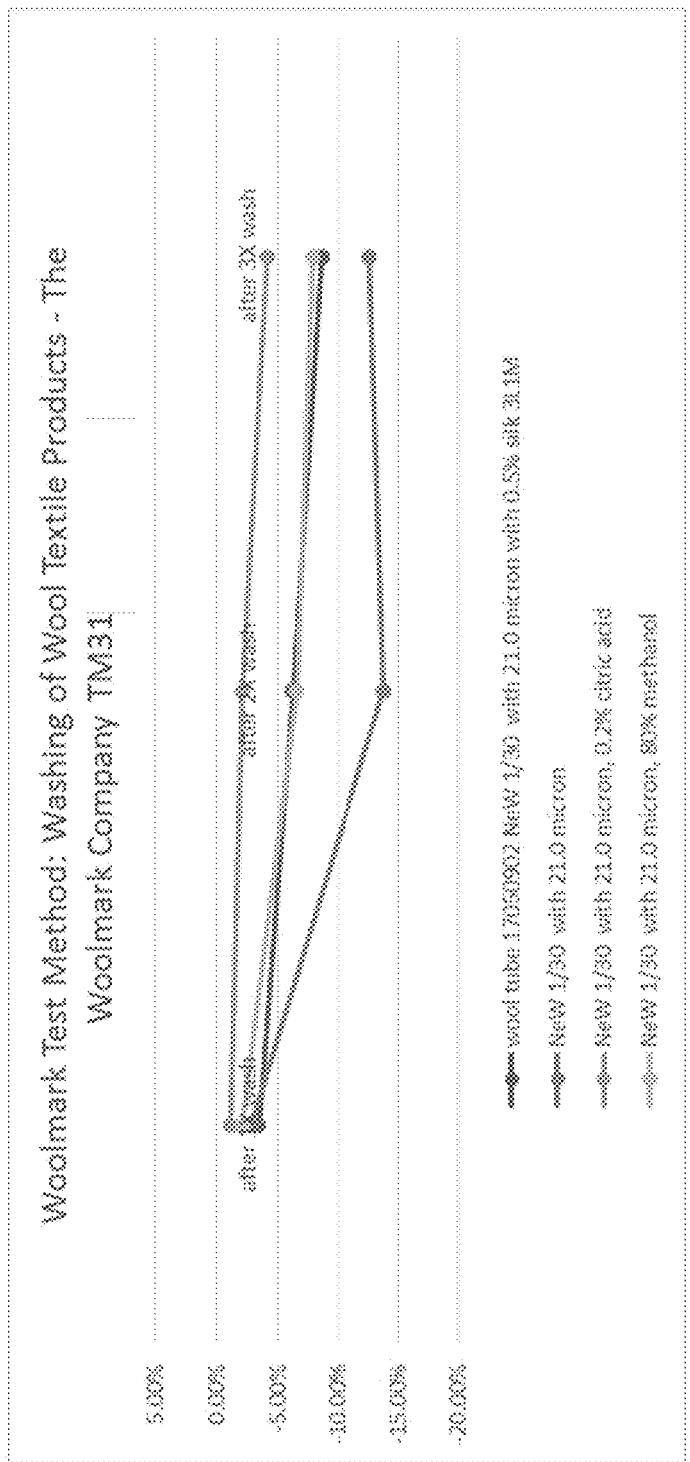
FIG. 24 is a chart summarizing dimensional stability to laundering (Woolmark Test Method) of NeW 1-30 with 21.0 micron NS wool samples, including the dimensional stability of a silk coated sample, the dimensional stability of a control sample, the dimensional stability of a citric acid pretreated and silk coated sample, and the dimensional stability of a silk coated and finally treated sample.
Figure 25:
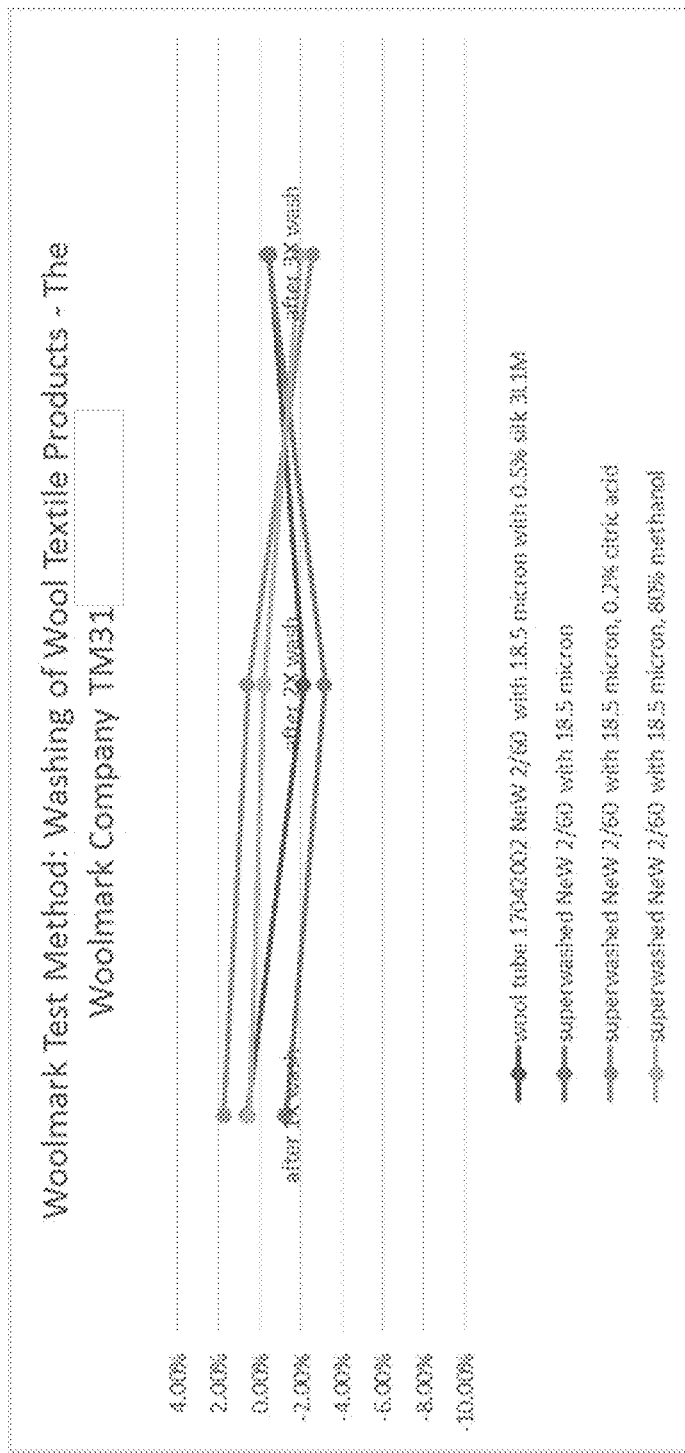
FIG. 25 is a chart summarizing dimensional stability to laundering (Woolmark Test Method) of NeW 2-60 with 18.5 micron SW wool samples, including the dimensional stability of a silk coated sample, the dimensional stability of a control sample, the dimensional stability of a citric acid pretreated and silk coated sample, and the dimensional stability of a silk coated and finally treated sample.
Figure 26:
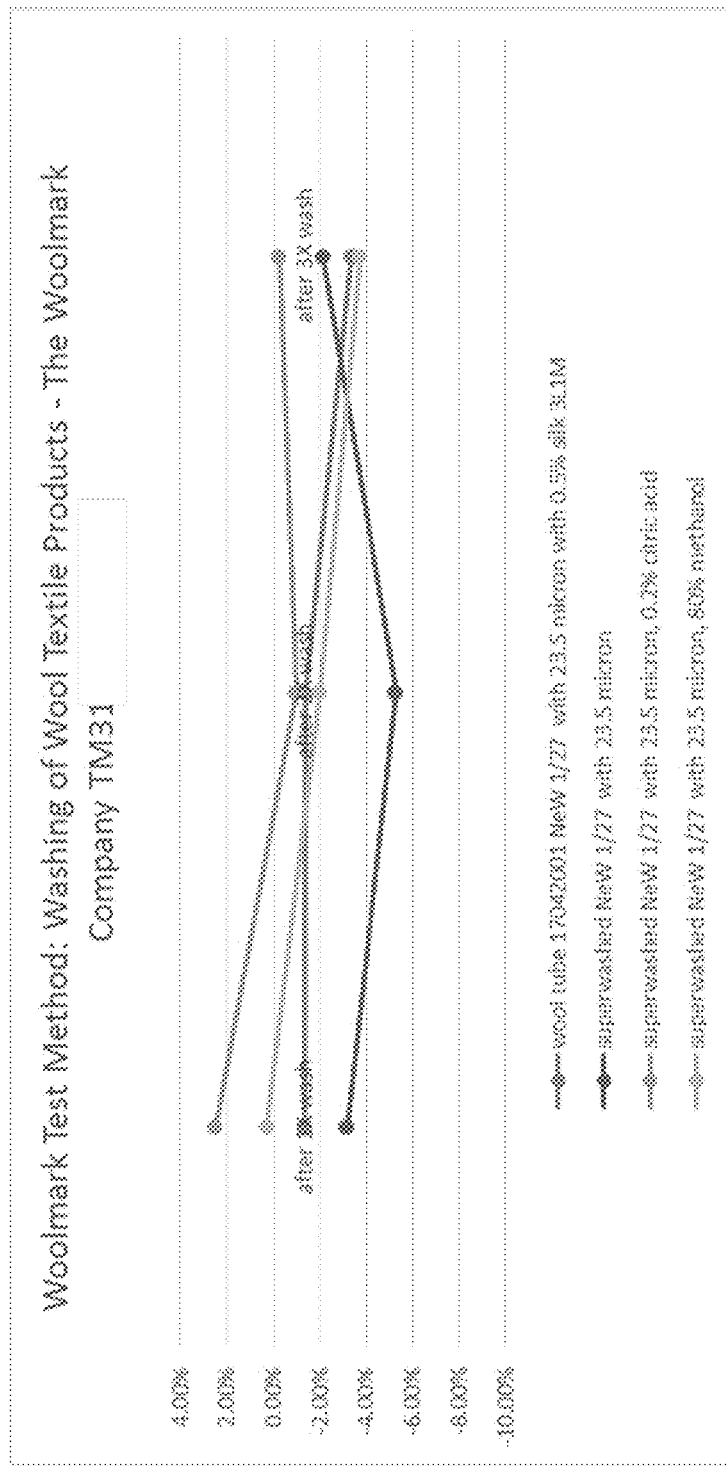
FIG. 26 is a chart summarizing dimensional stability to laundering (Woolmark Test Method) of NeW 1-27 with 23.5 micron SW wool samples, including the dimensional stability of a silk coated sample, the dimensional stability of a control sample, the dimensional stability of a citric acid pretreated and silk coated sample, and the dimensional stability of a silk coated and finally treated sample.
Figure 27:
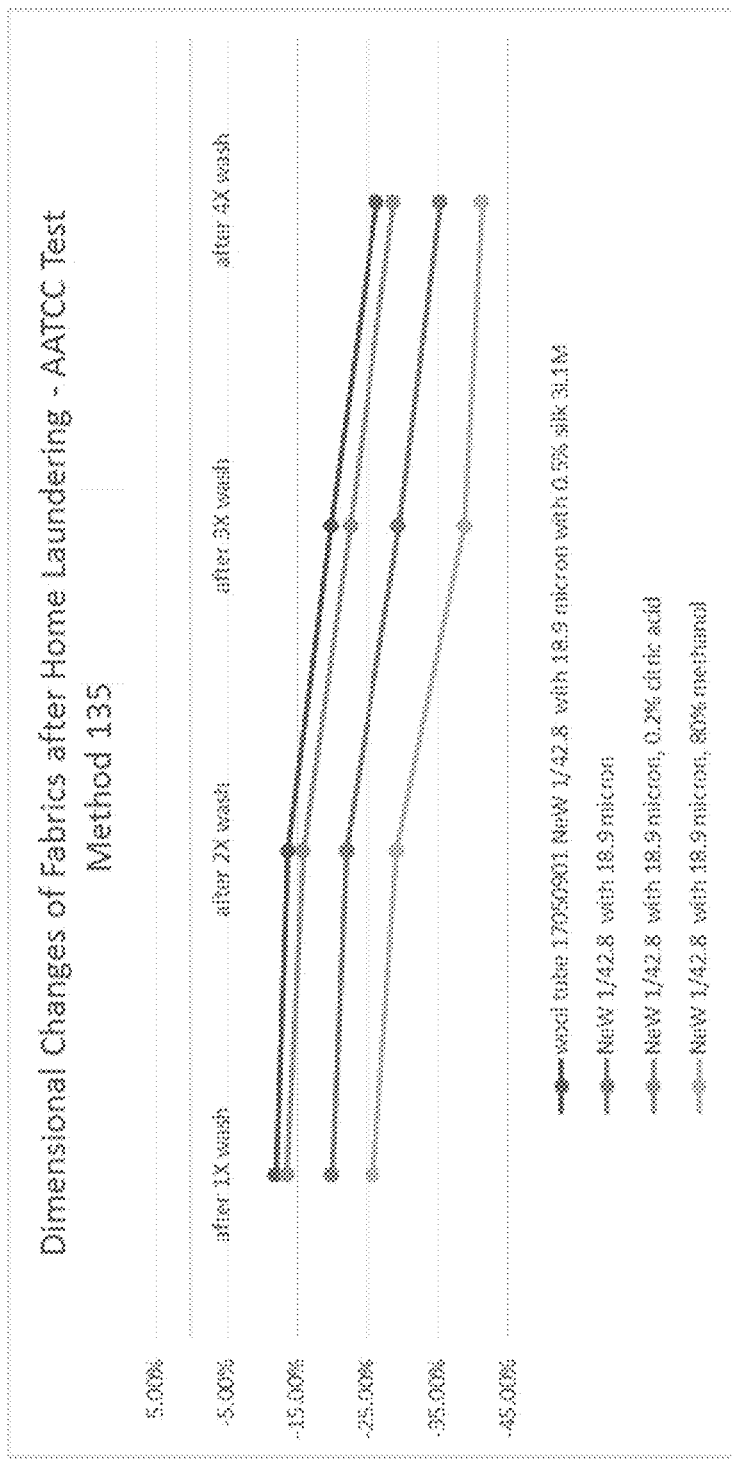
FIG. 27 is a chart summarizing dimensional stability to laundering (AATCC Test Method) of NeW 1-42.8 with 18.9 micron NS wool samples, including the dimensional stability of a silk coated sample, the dimensional stability of a control sample, the dimensional stability of a citric acid pretreated and silk coated sample, and the dimensional stability of a silk coated and finally treated sample.
Figure 28:
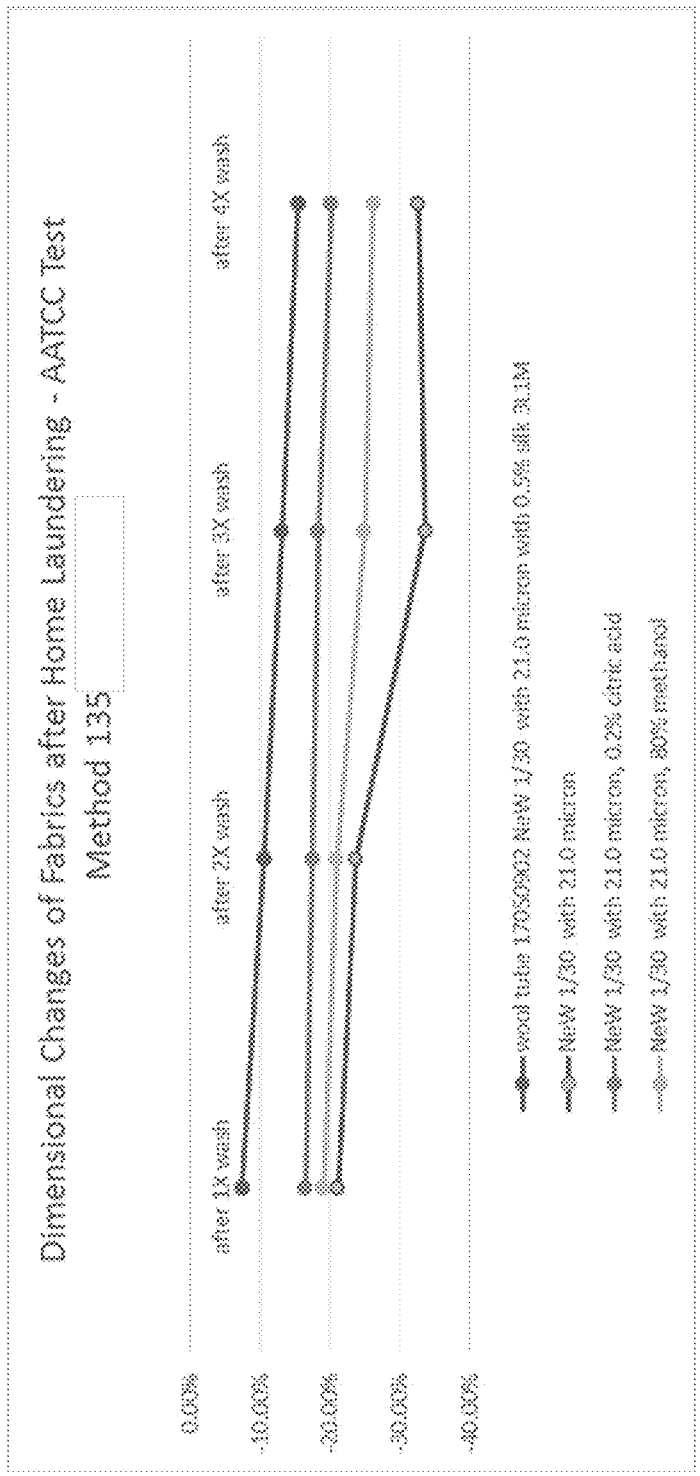
FIG. 28 is a chart summarizing dimensional stability to laundering (AATCC Test Method) of NeW 1-30 with 21.0 micron NS wool samples, including the dimensional stability of a silk coated sample, the dimensional stability of a control sample, the dimensional stability of a citric acid pretreated and silk coated sample, and the dimensional stability of a silk coated and finally treated sample.
Figure 29:
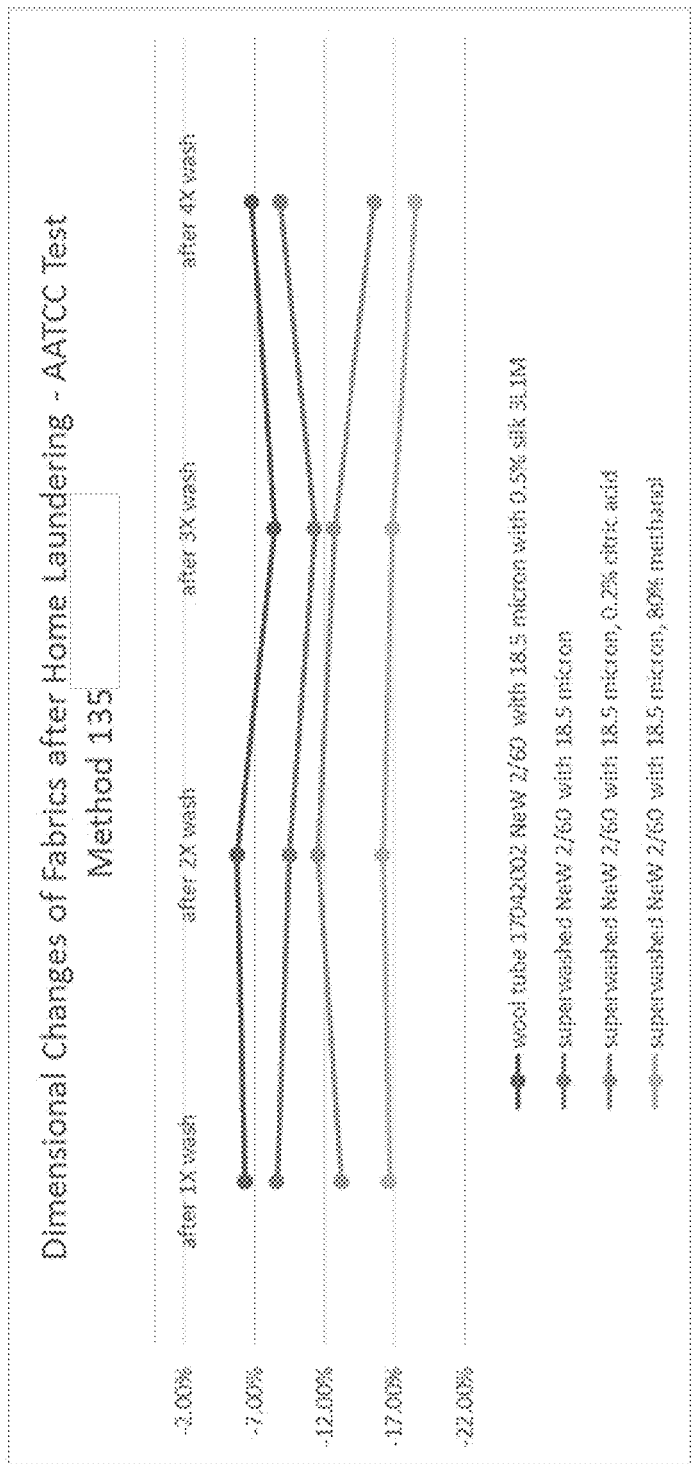
FIG. 29 is a chart summarizing dimensional stability to laundering (AATCC Test Method) of NeW 2-60 with 18.5 micron SW wool samples, including the dimensional stability of a silk coated sample, the dimensional stability of a control sample, the dimensional stability of a citric acid pretreated and silk coated sample, and the dimensional stability of a silk coated and finally treated sample.
Figure 30:
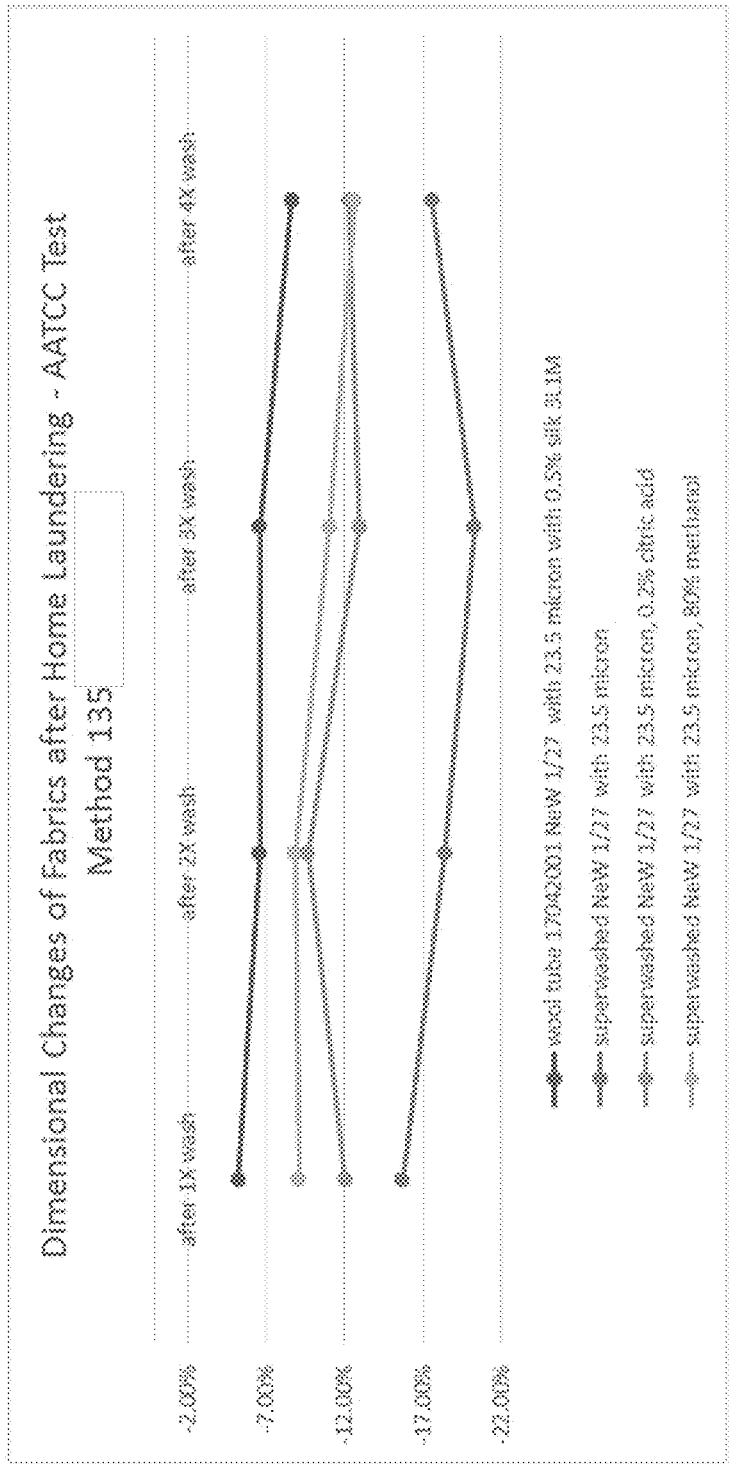
FIG. 30 is a chart summarizing dimensional stability to laundering (AATCC Test Method) of NeW 1-27 with 23.5 micron SW wool samples, including the dimensional stability of a silk coated sample, the dimensional stability of a control sample, the dimensional stability of a citric acid pretreated and silk coated sample, and the dimensional stability of a silk coated and finally treated sample.
Figure 31A:
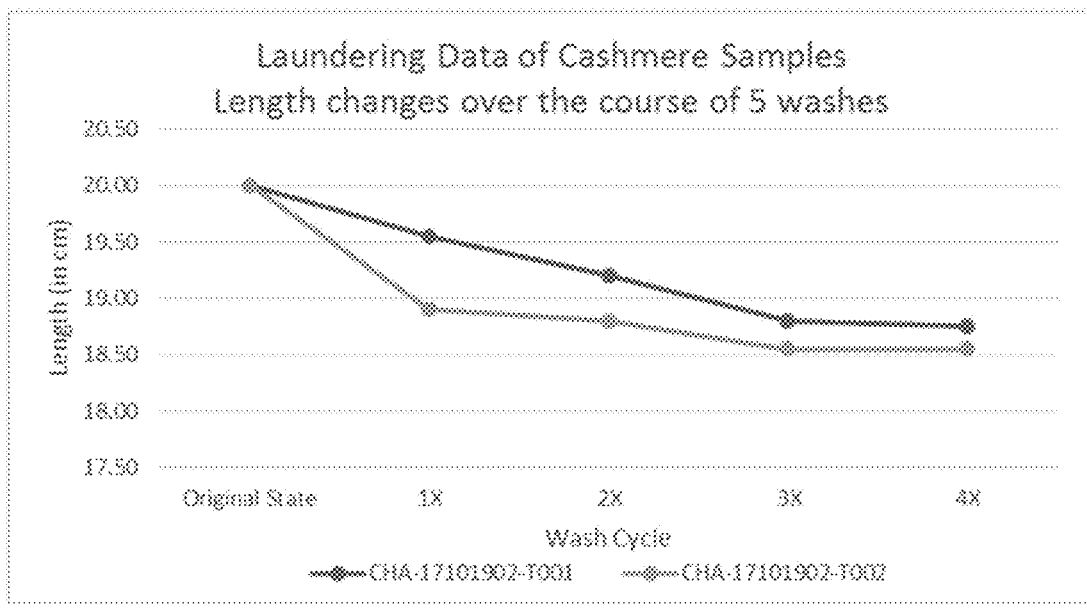
FIG. 31A to FIG. 31D are a series of charts summarizing dimensional stability to laundering (AATCC Test Method 135-2015) of CHA-17101902-T001 (control) and CHA-17101902-T002 (silk coated) cashmere fabric samples, including a chart illustrating the length changes over the course of five washes (FIG. 31A), a chart illustrating the change in average lengths after each wash over the course of four washes (FIG. 31B), a chart illustrating the area dimensional change % through four washes based from the original state lengths (FIG. 31C), and a chart illustrating the area dimensional change % through four washes based from the state lengths after one wash (FIG. 31D).
Figure 31B:
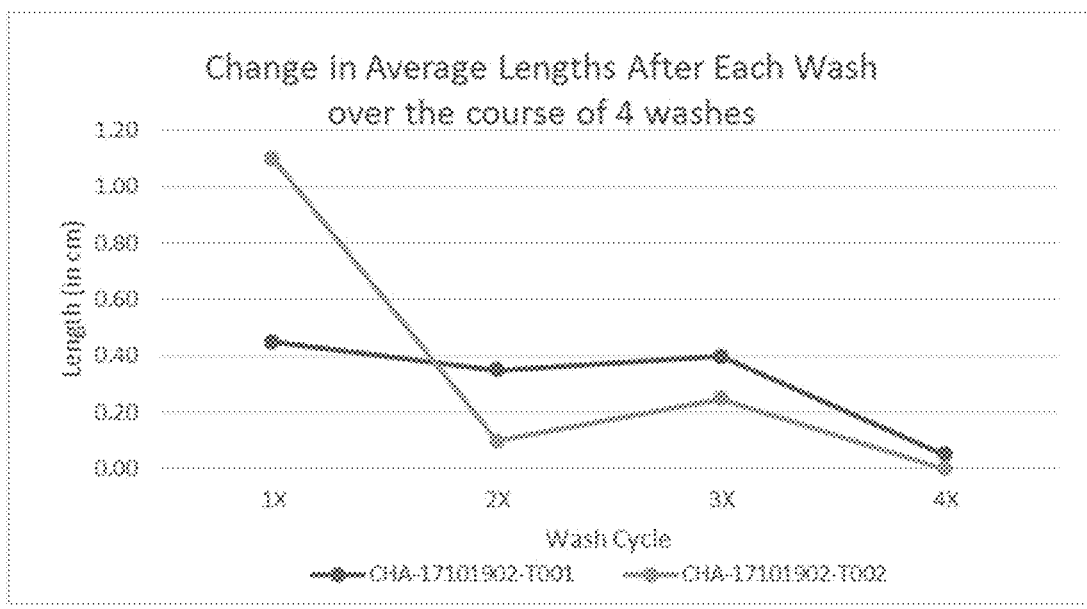
Figure 31C:
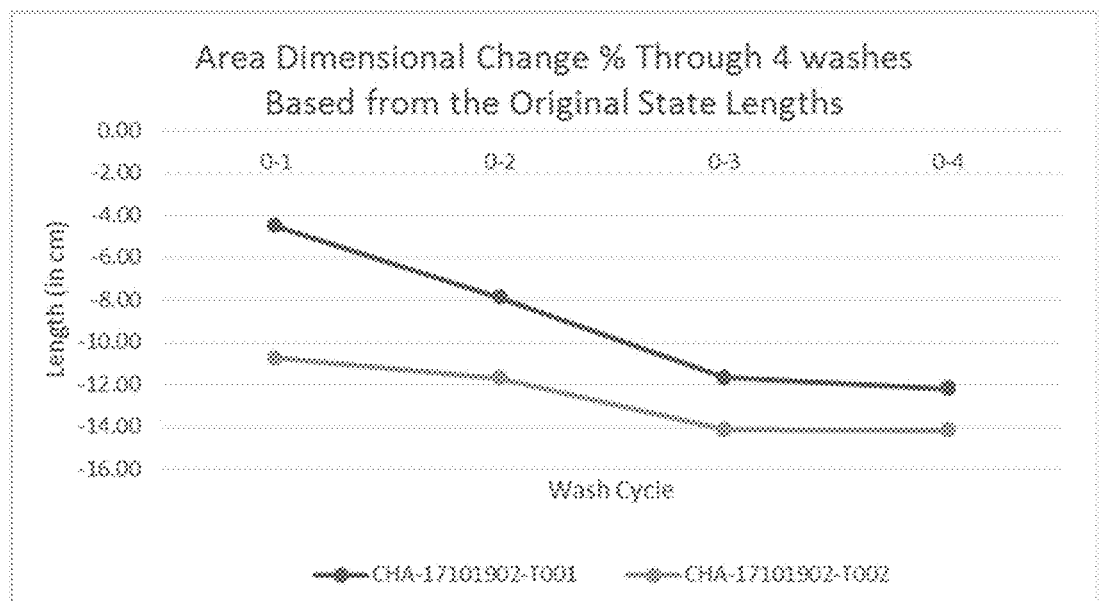
Figure 31D:
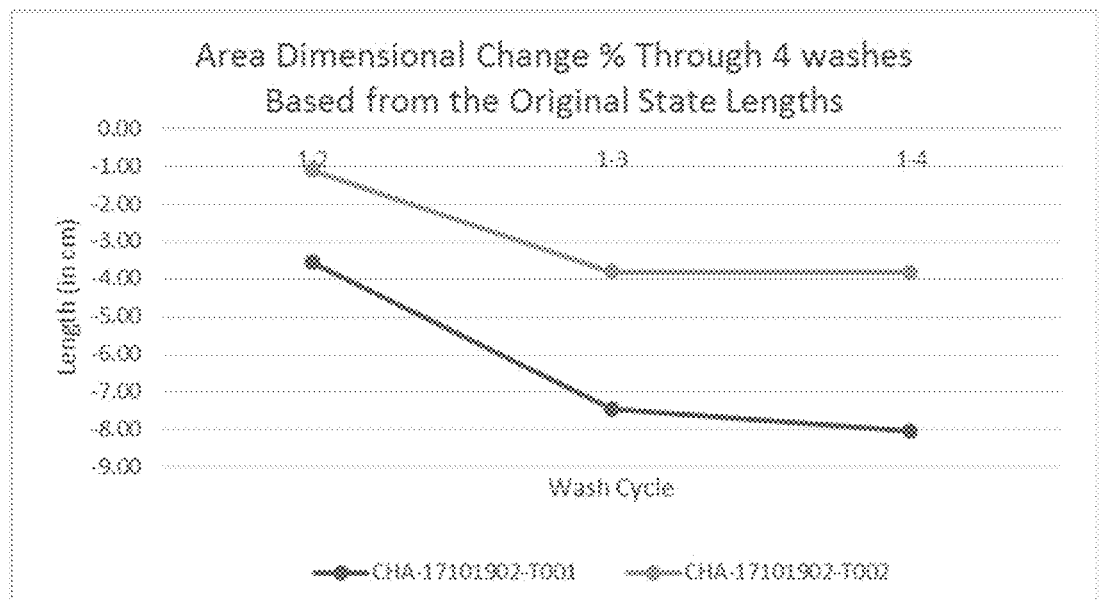
Figure 32:
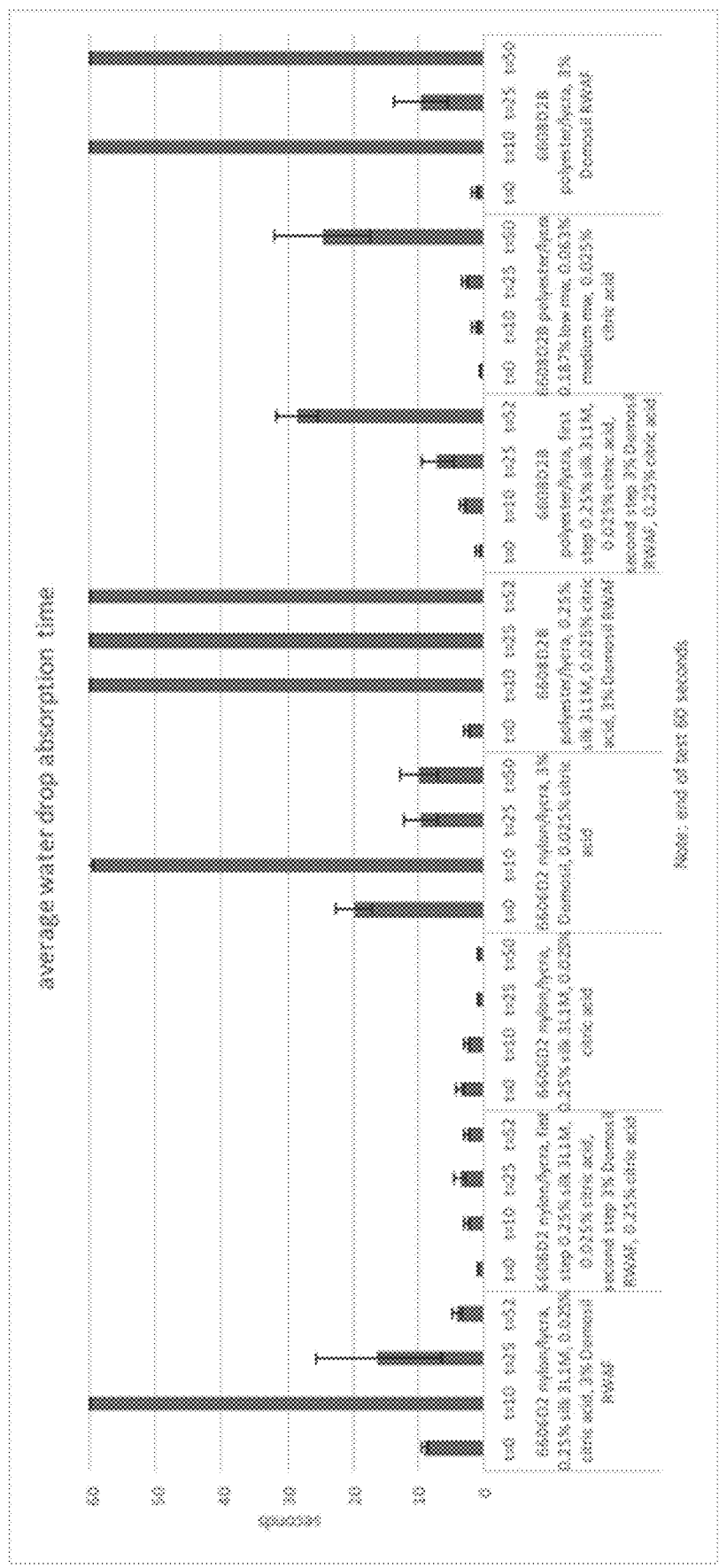
FIG. 32 is a chart illustrating the average water drop absorption times for various silk coated fabric samples before laundering (t=0), and after 10, 25, or 50 laundering cycles.
Figure 33A:
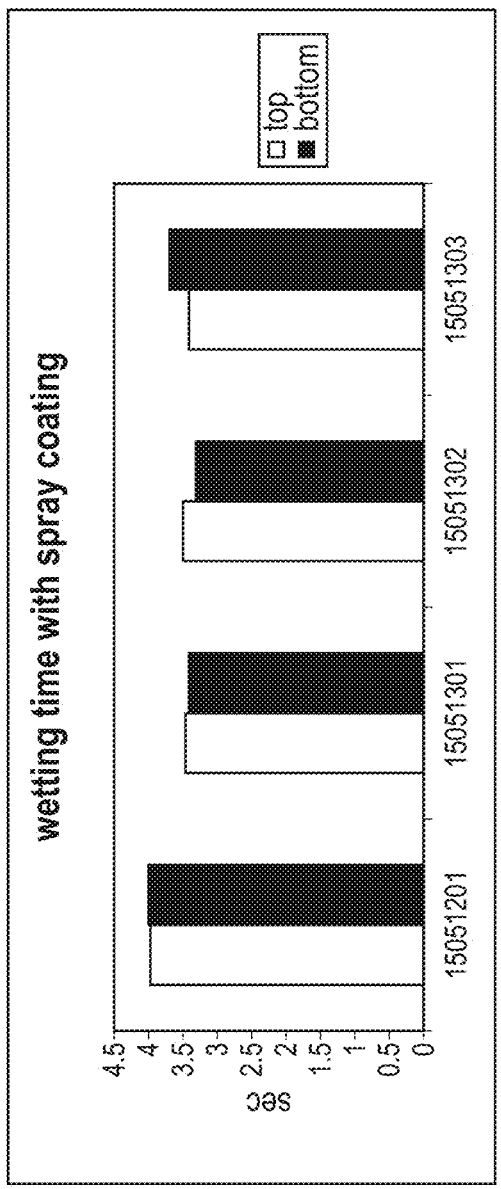
FIG. 33A is a graph illustrating wetting time with spray coating.
Figure 33B:
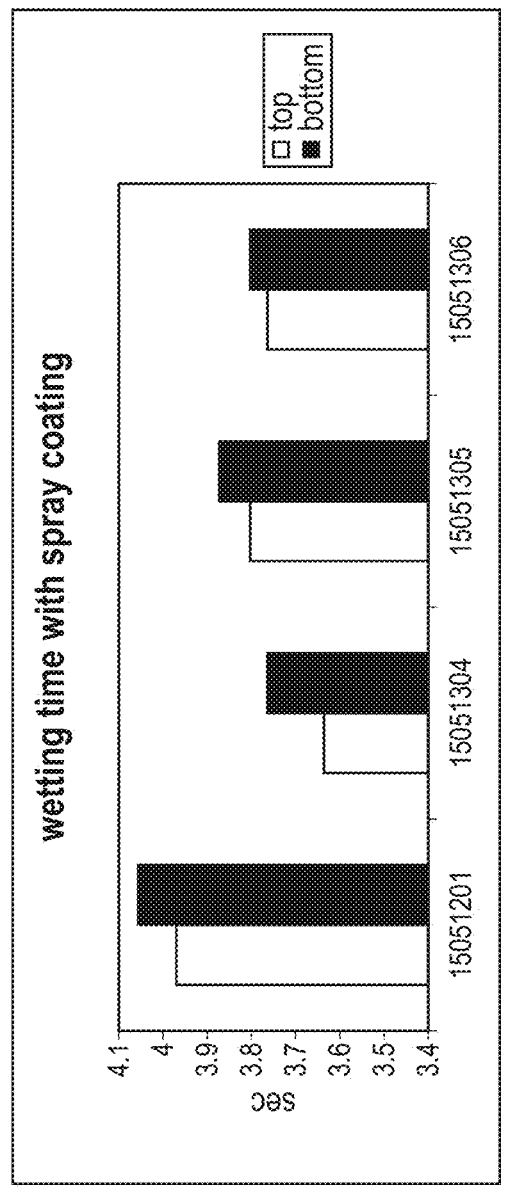
FIG. 33B is a graph illustrating wetting time with stencil coating.
Figure 33C:
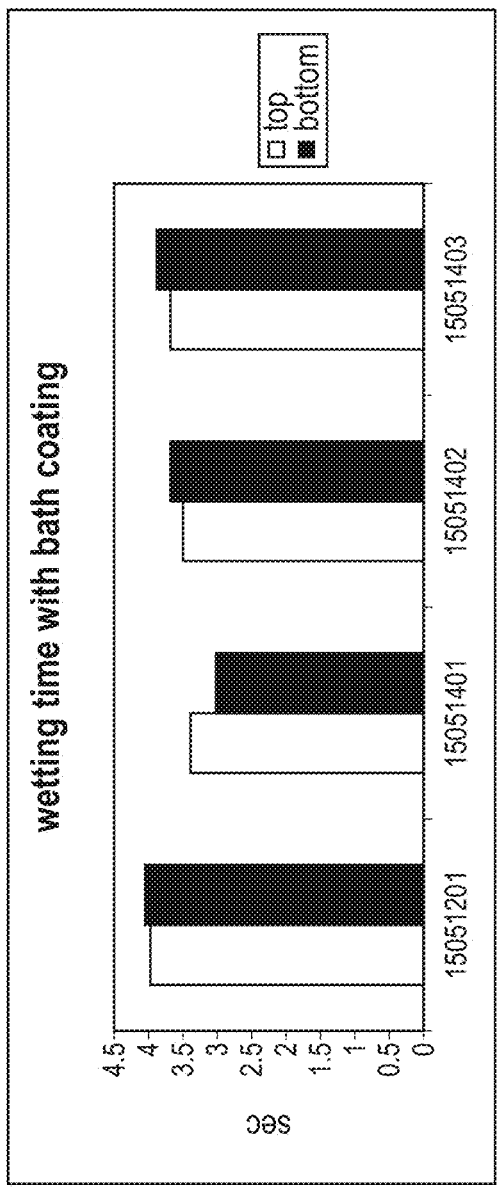
FIG. 33C is a graph illustrating wetting time with bath coating.
Figure 33D:
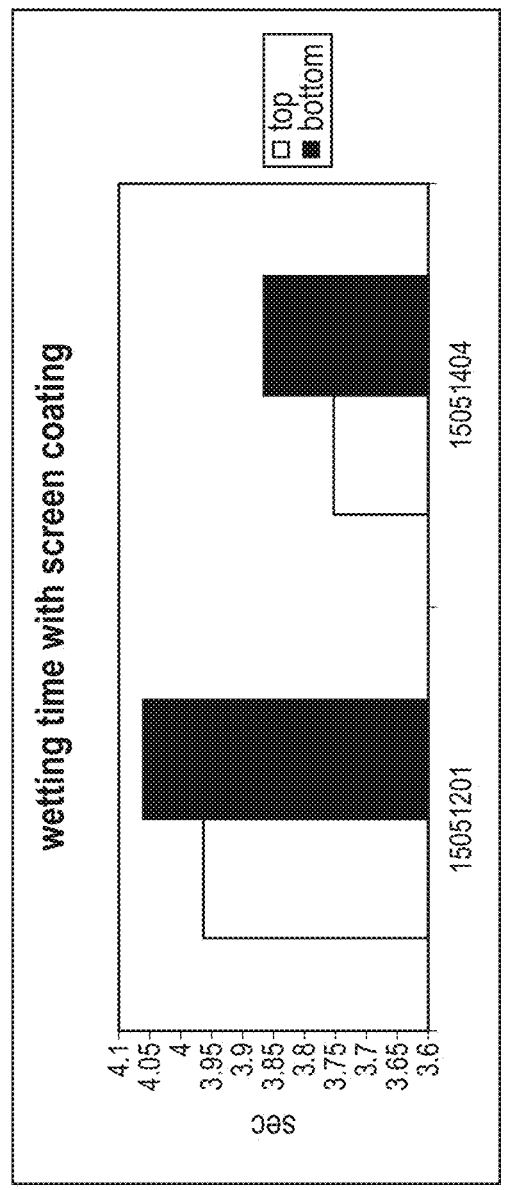
FIG. 33D is a graph illustrating wetting time with screen coating.
Figure 34A:
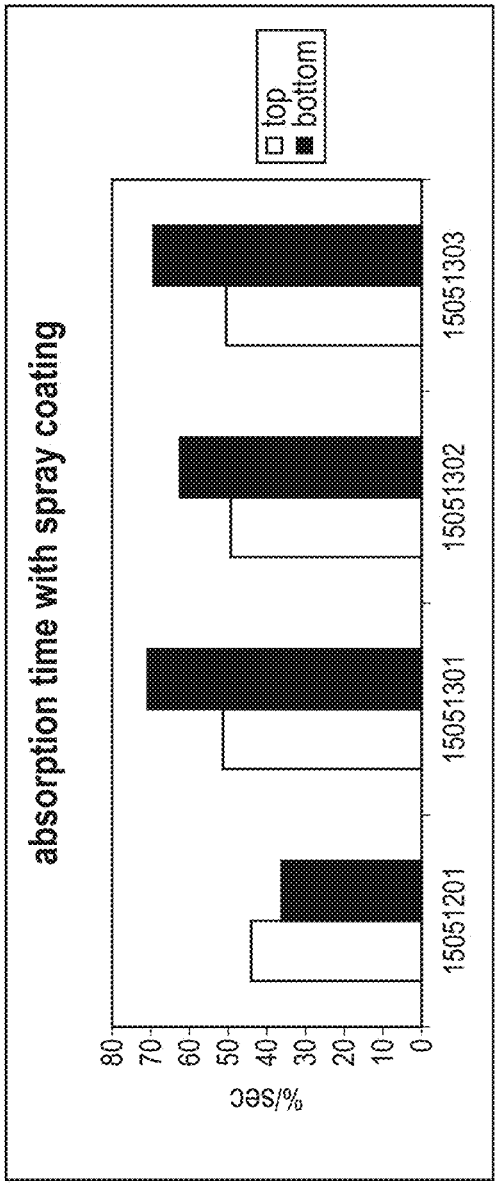
FIG. 34A is a graph illustrating absorption time with spray coating.
Figure 34B:
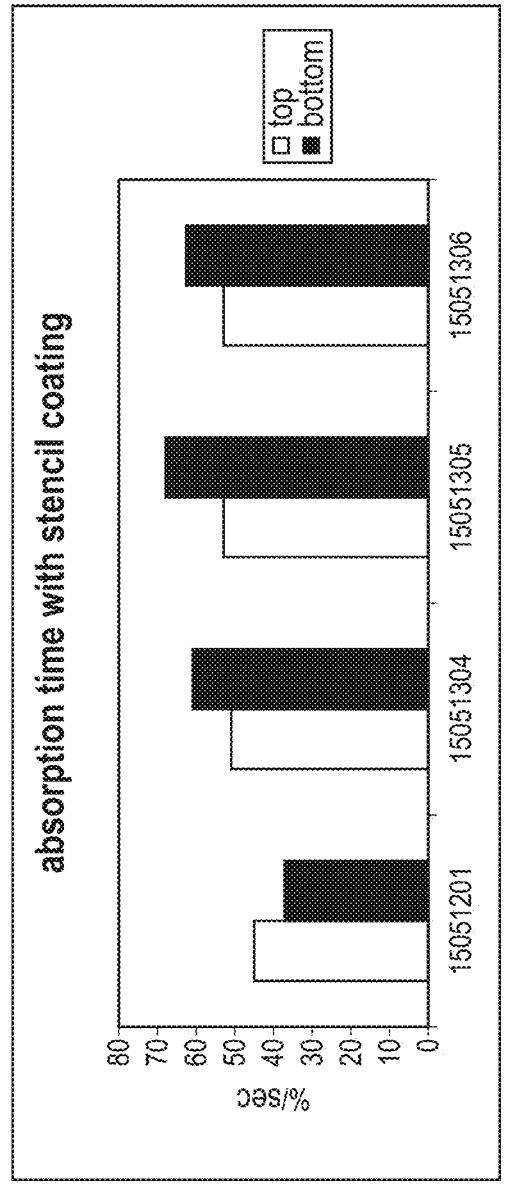
FIG. 34B is a graph illustrating absorption time with stencil coating.
Figure 34C:
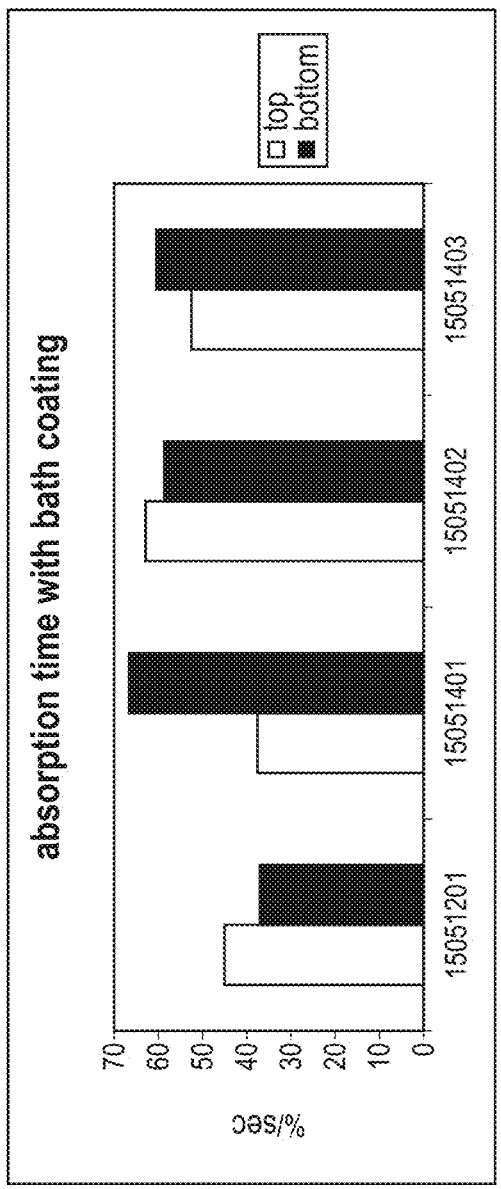
FIG. 34C is a graph illustrating absorption time with bath coating.
Figure 34D:
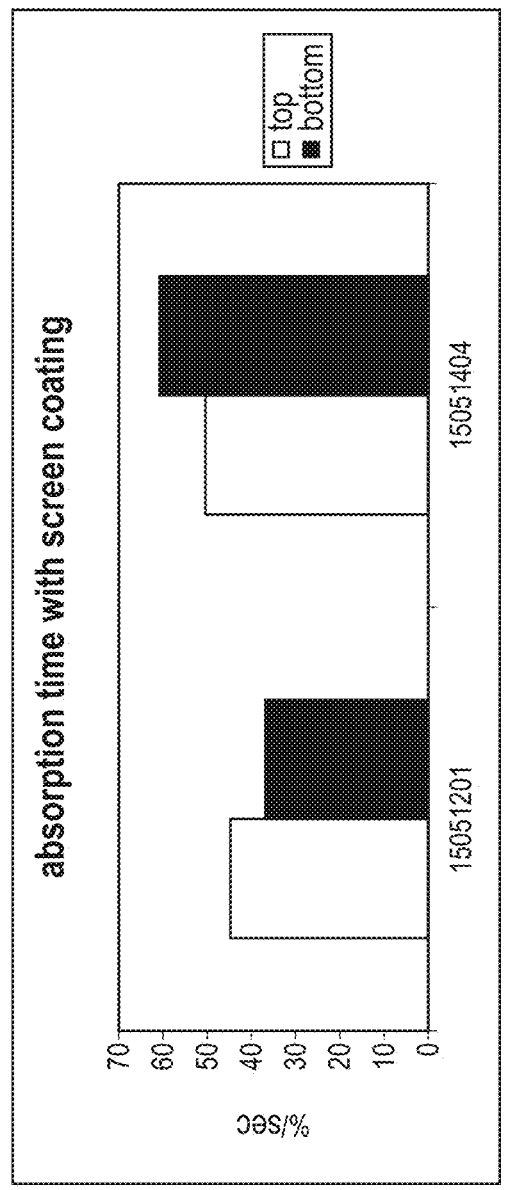
FIG. 34D is a graph illustrating absorption time with screen coating.
Figure 35A:
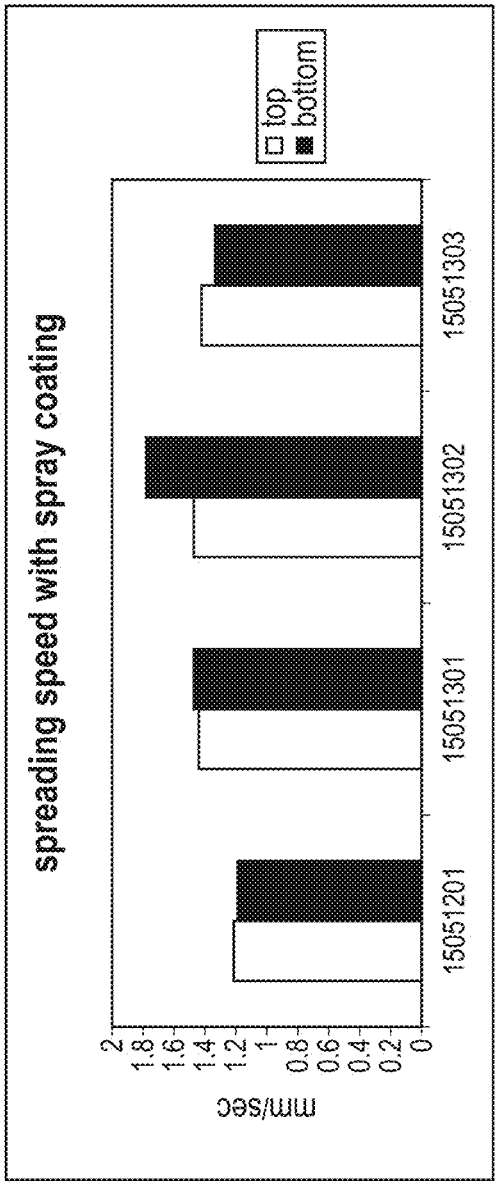
FIG. 35A is a graph illustrating spreading speed with spray coating.
Figure 35B:
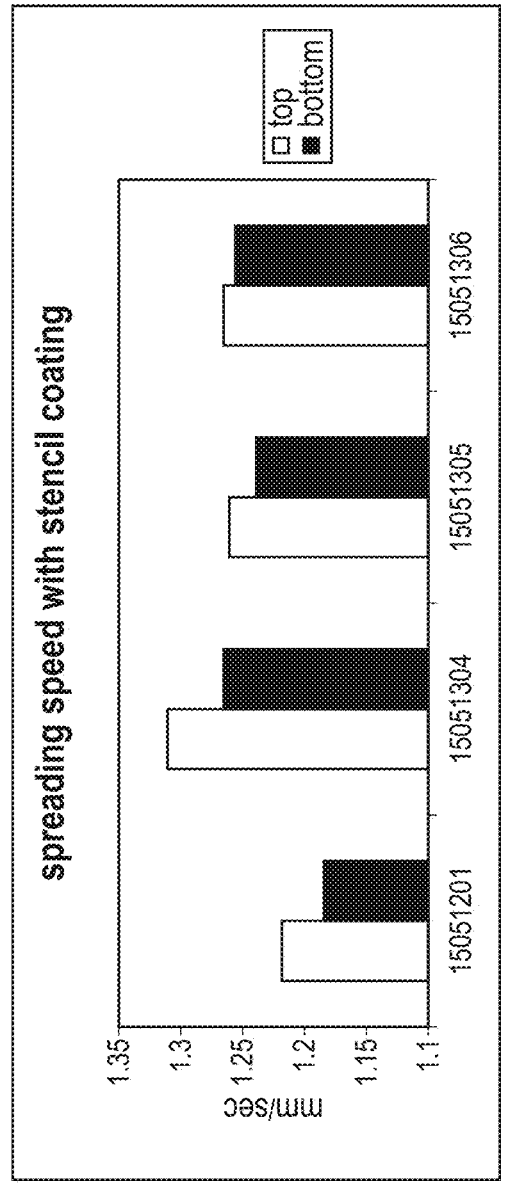
FIG. 35B is a graph illustrating spreading speed with stencil coating.
Figure 35C:
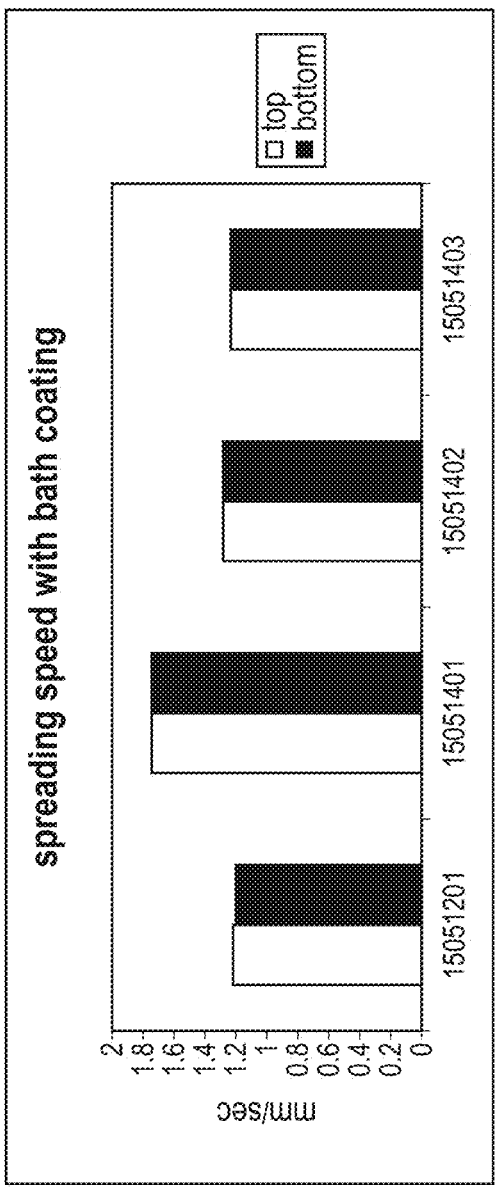
FIG. 35C is a graph illustrating spreading speed with bath coating.
Figure 35D:
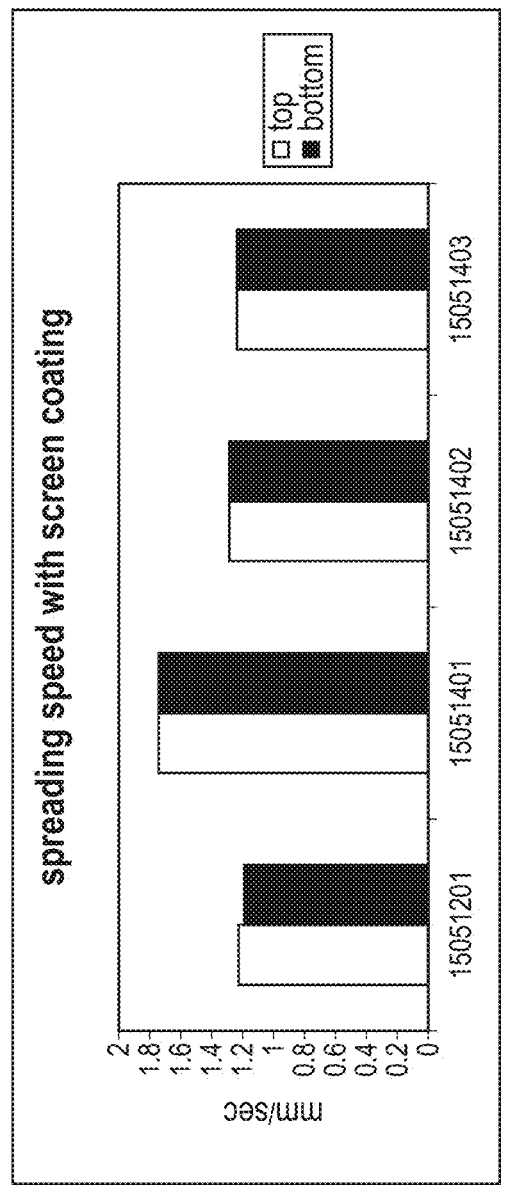
FIG. 35D is a graph illustrating spreading speed with screen coating.
Figure 36A:
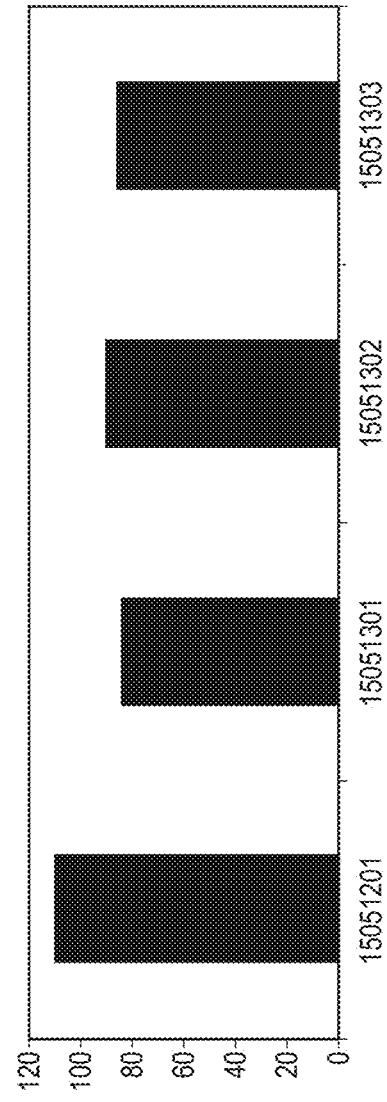
FIG. 36A is a graph illustrating accumulative one-way transport index with spray coating.
Figure 36B:
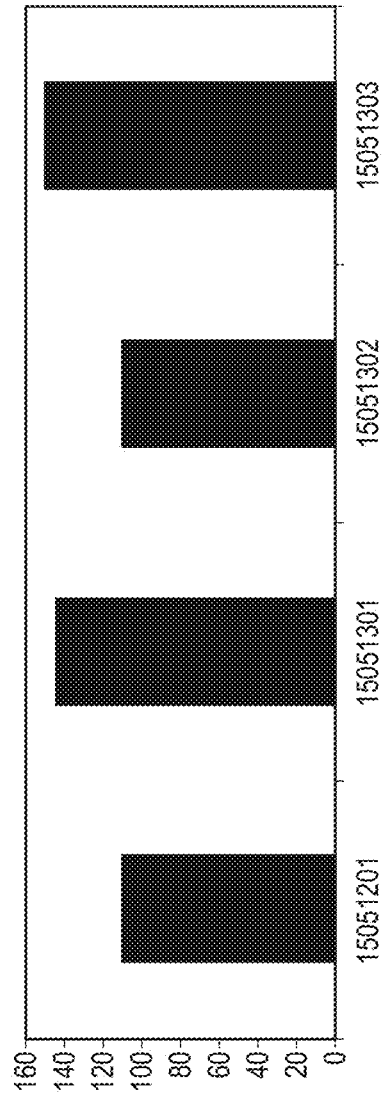
FIG. 36B is a graph illustrating accumulative one-way transport index with stencil coating.
Figure 36C:
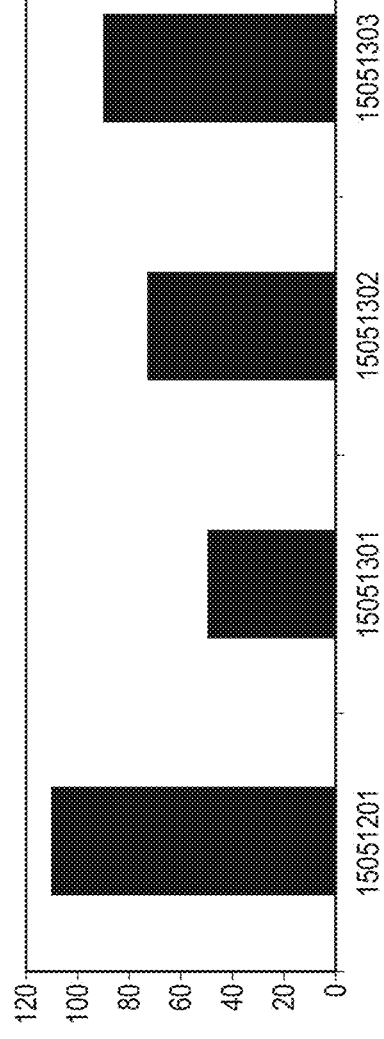
FIG. 36C is a graph illustrating accumulative one-way transport index with bath coating.
Figure 36D:
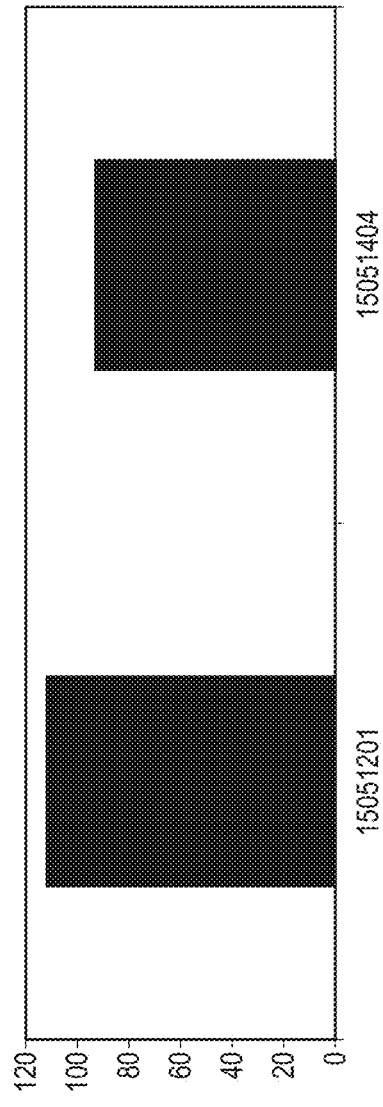
FIG. 36D is a graph illustrating accumulative one-way transport index with screen coating.
Figure 37A:
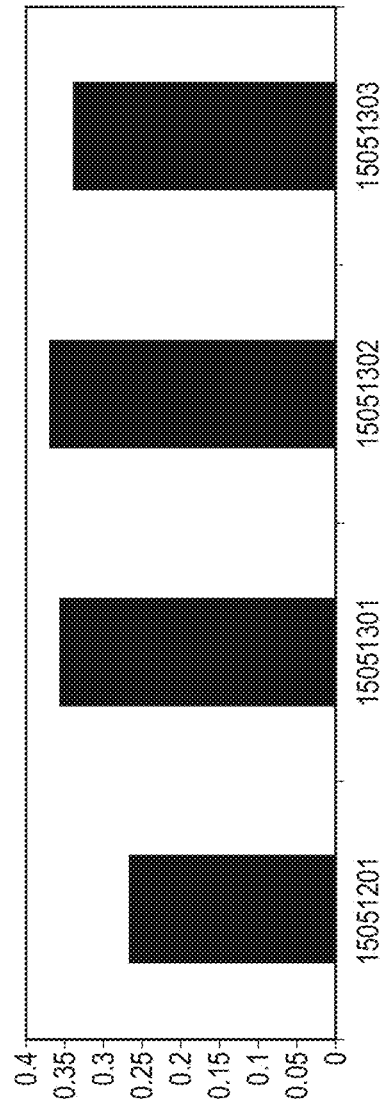
FIG. 37A is a graph illustrating overall moisture management capability with spray coating.
Figure 37B:
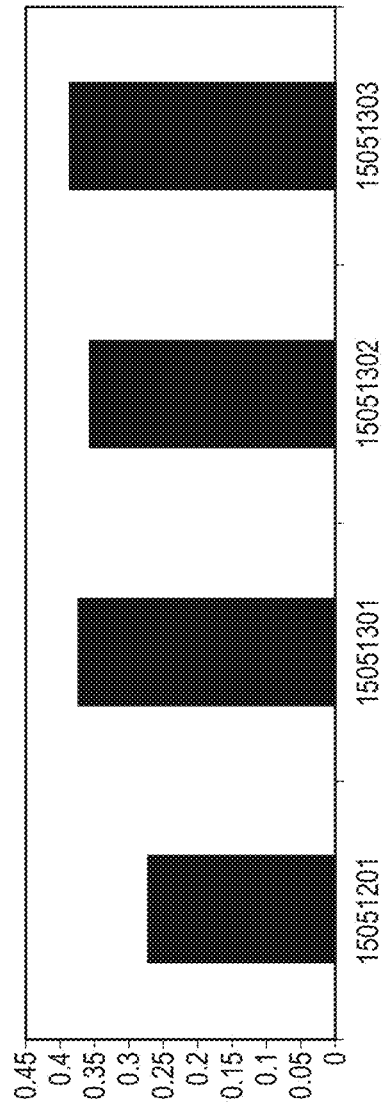
FIG. 37B is a graph illustrating overall moisture management capability with stencil coating.
Figure 37C:

FIG. 37C is a graph illustrating overall moisture management capability with bath coating.
Figure 37D:
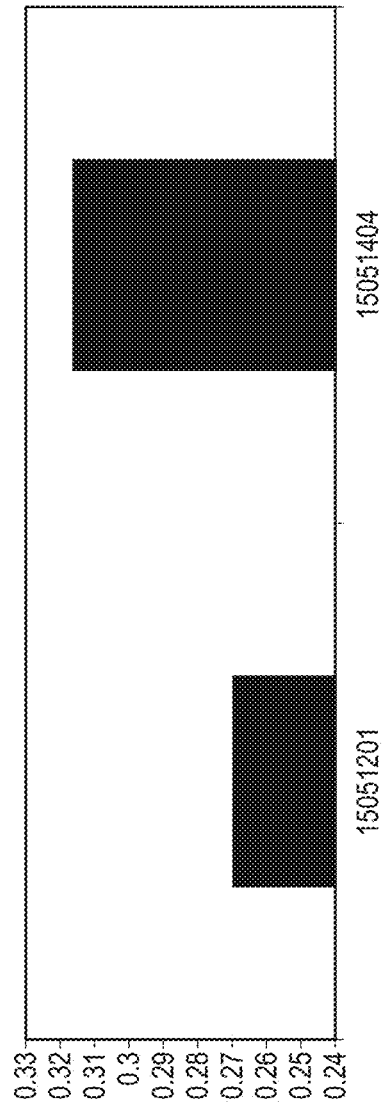
FIG. 37D is a graph illustrating overall moisture management capability with screen coating.
Figure 38A:
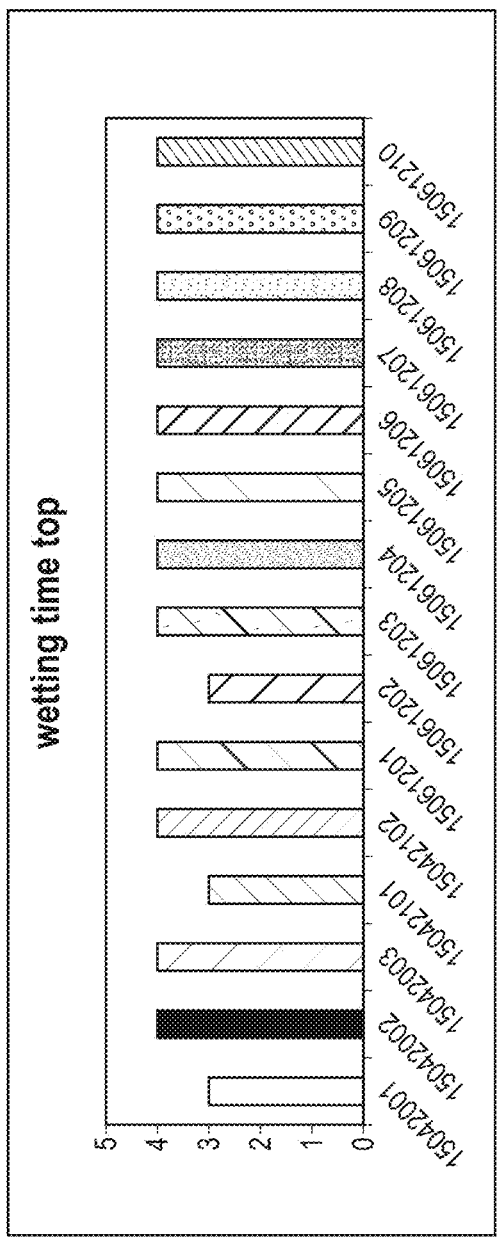
FIG. 38A is a graph illustrating wetting time top.
Figure 38B:
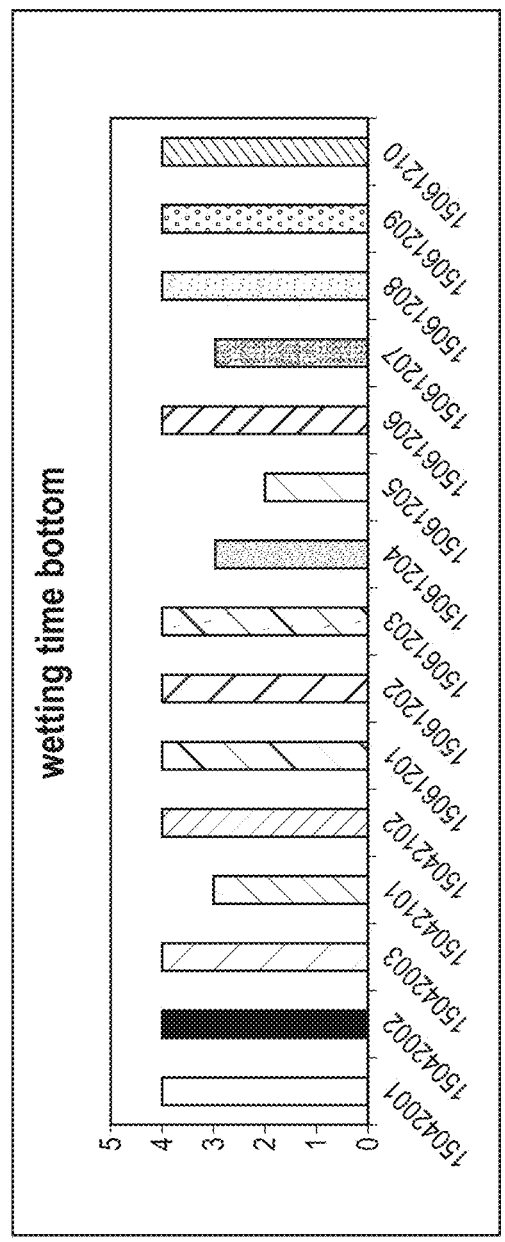
FIG. 38B is a graph illustrating wetting time bottom.
Figure 39A:
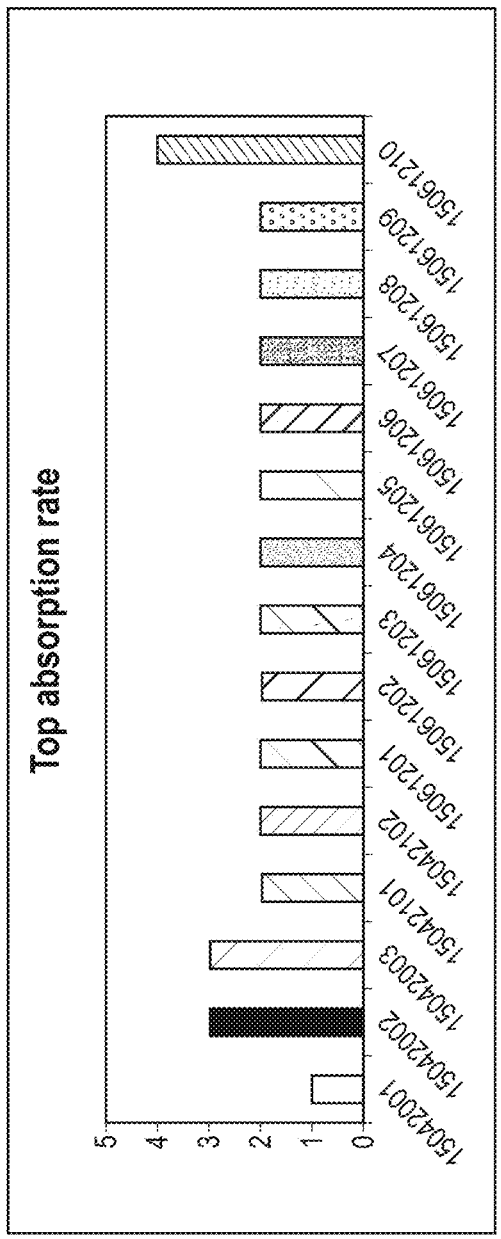
FIG. 39A is a graph illustrating top absorption rate.
Figure 39B:
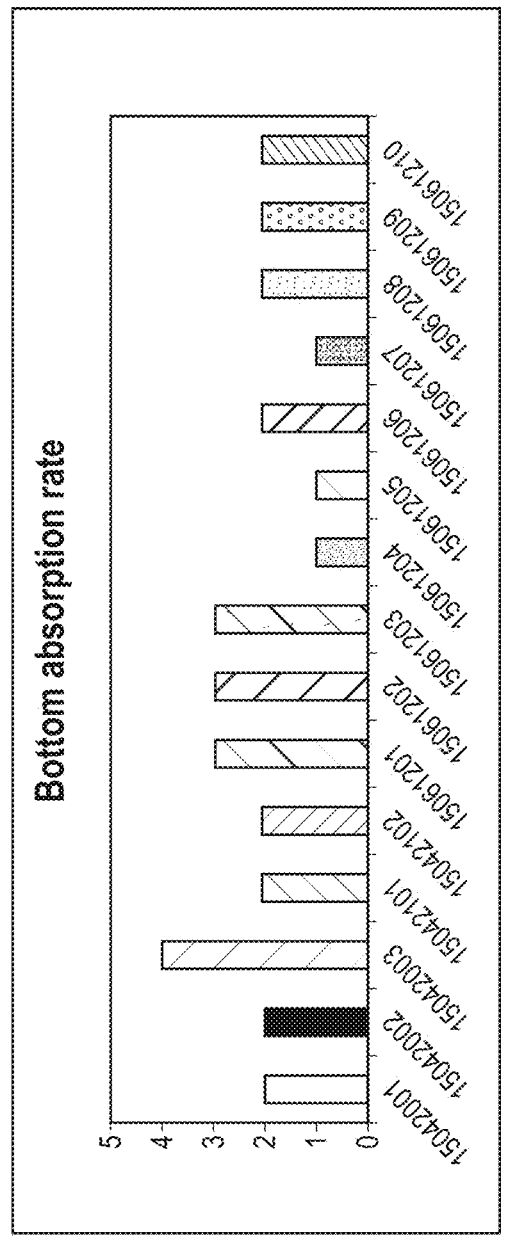
FIG. 39B is a graph illustrating bottom absorption rate.
Figure 40A:
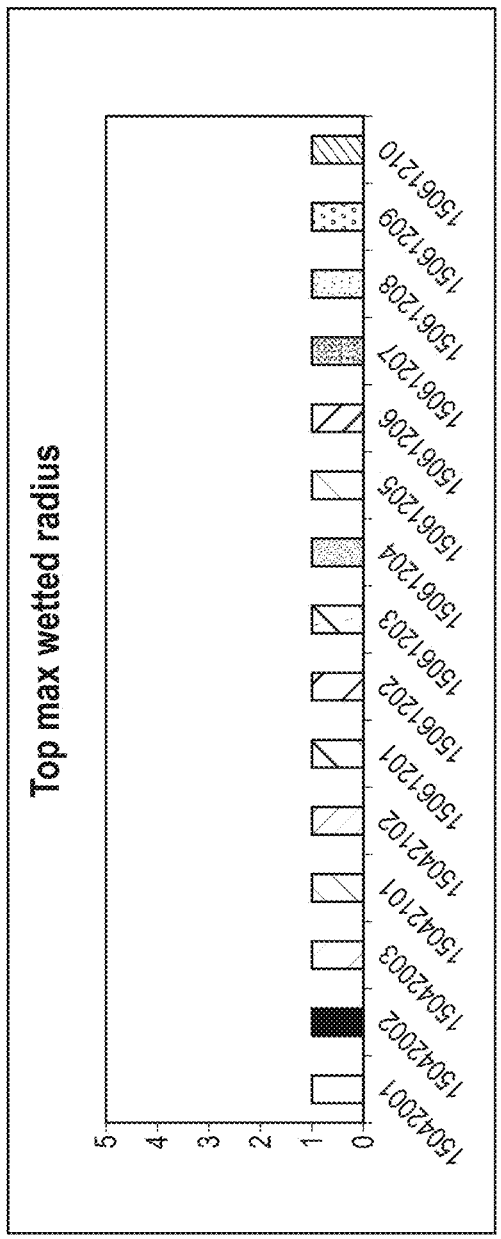
FIG. 40A is a graph illustrating top max wetted radius.
Figure 40B:
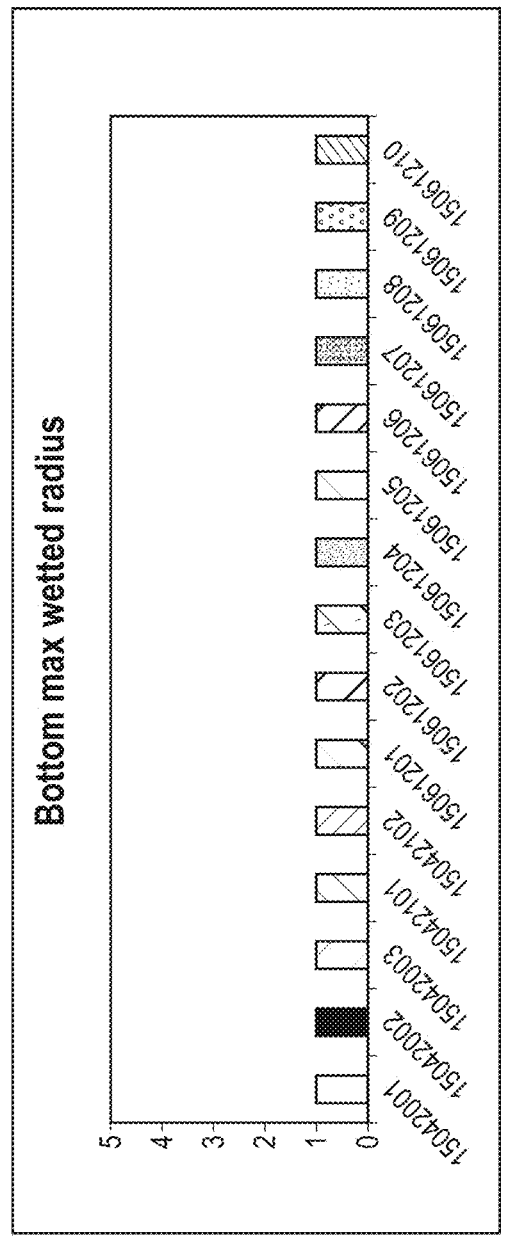
FIG. 40B is a graph illustrating bottom max wetted radius.
Figure 42A:
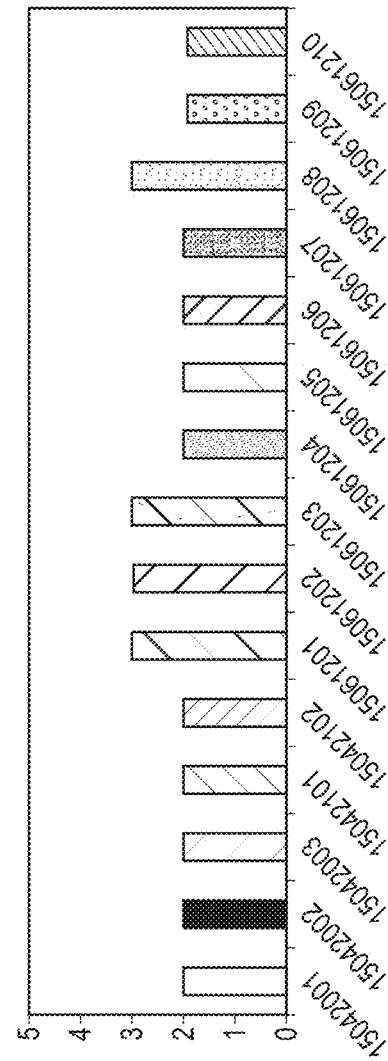
FIG. 42A is a graph illustrating accumulative one-way transport index.
Figure 42B:
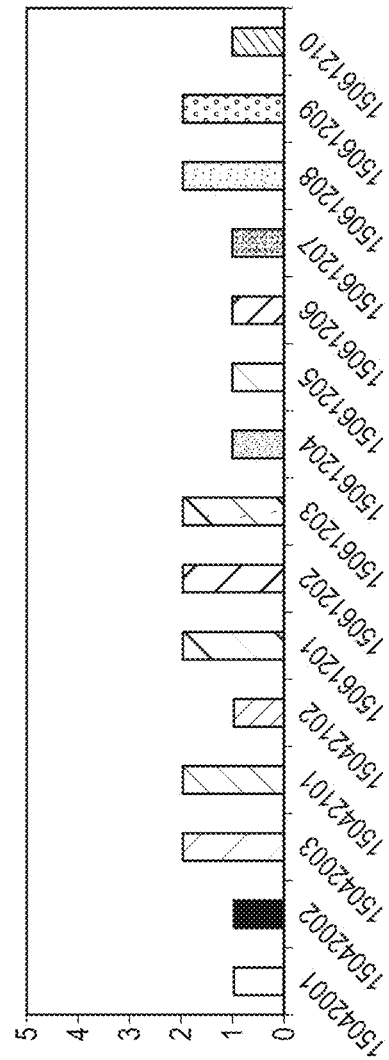
FIG. 42B is a graph illustrating overall moisture management capability.
Figure 45A:
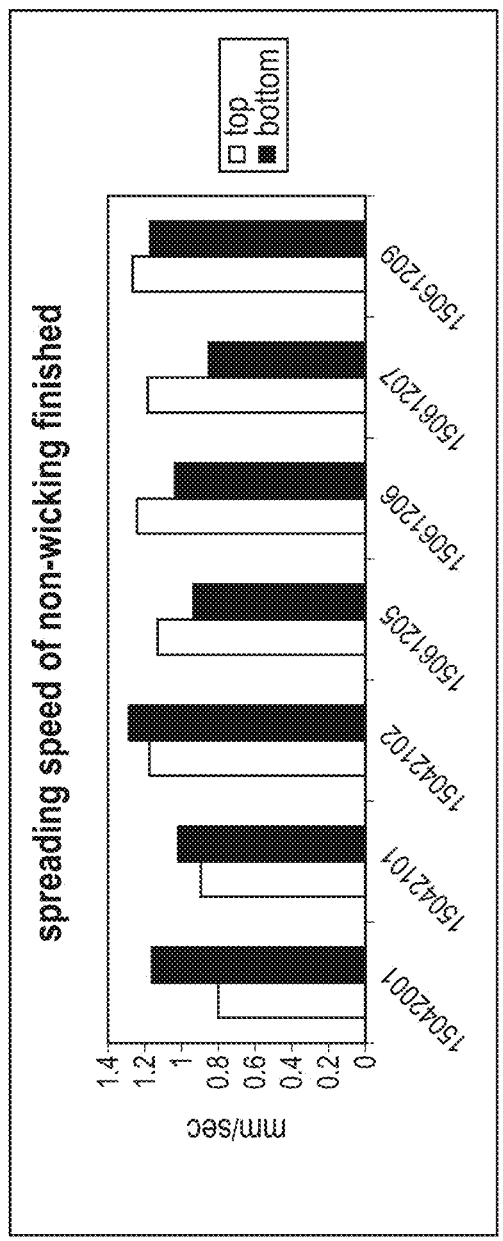
FIG. 45A is a graph illustrating spreading speed of non-wicking finished.
Figure 45B:
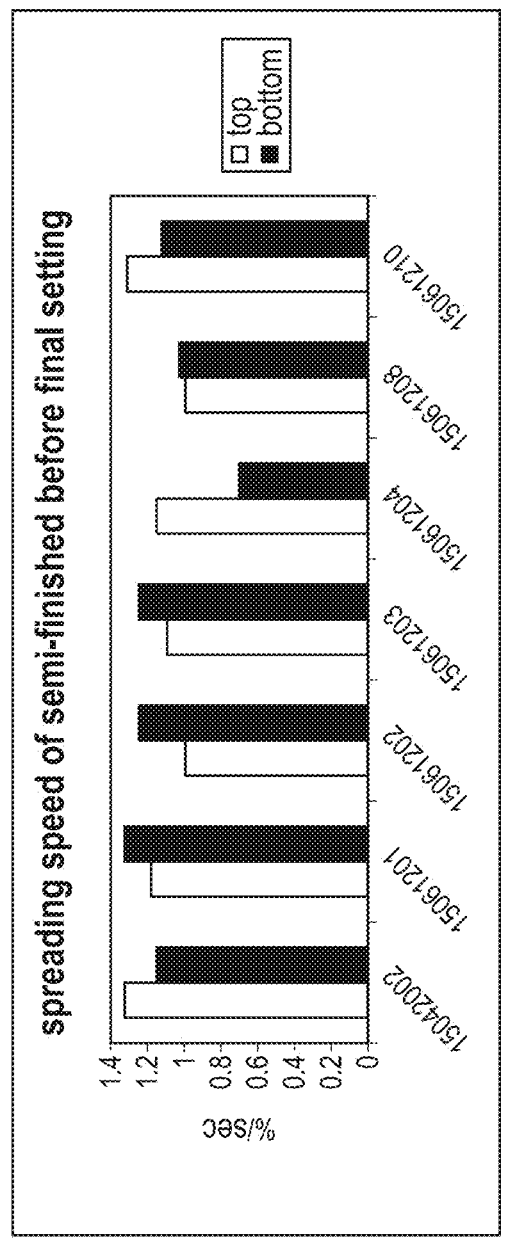
FIG. 45B is a graph illustrating spreading speed of semi-finished before final setting.
Figure 47A:
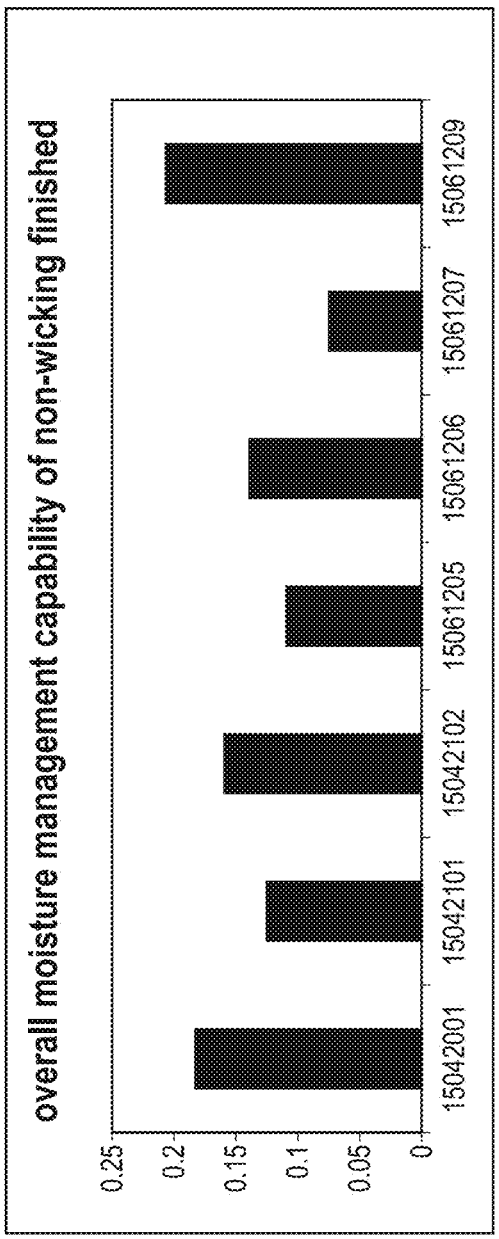
FIG. 47A is a graph illustrating overall moisture management capability of non-wicking finished.
Figure 47B:
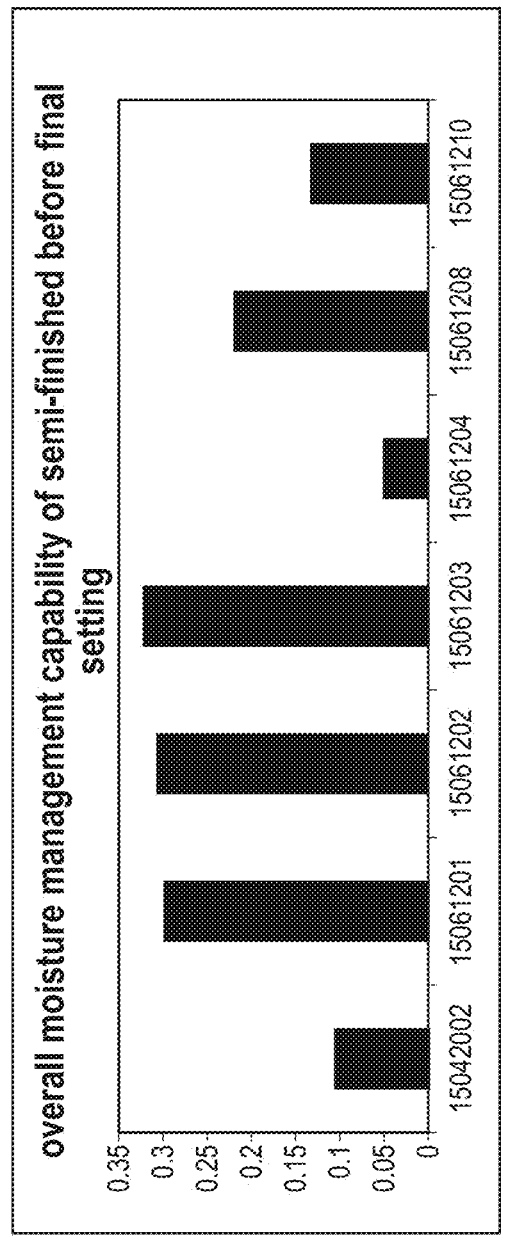
FIG. 47B is a graph illustrating overall moisture management capability of semi-finished before final setting.
Figure 48A:
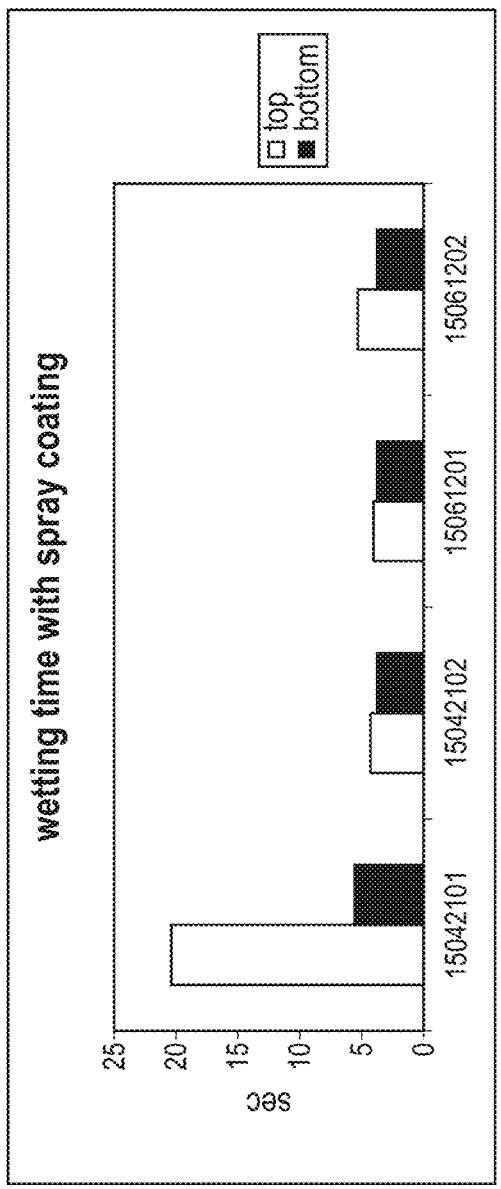
FIG. 48A is a graph illustrating wetting time with spray coating.
Figure 48B:
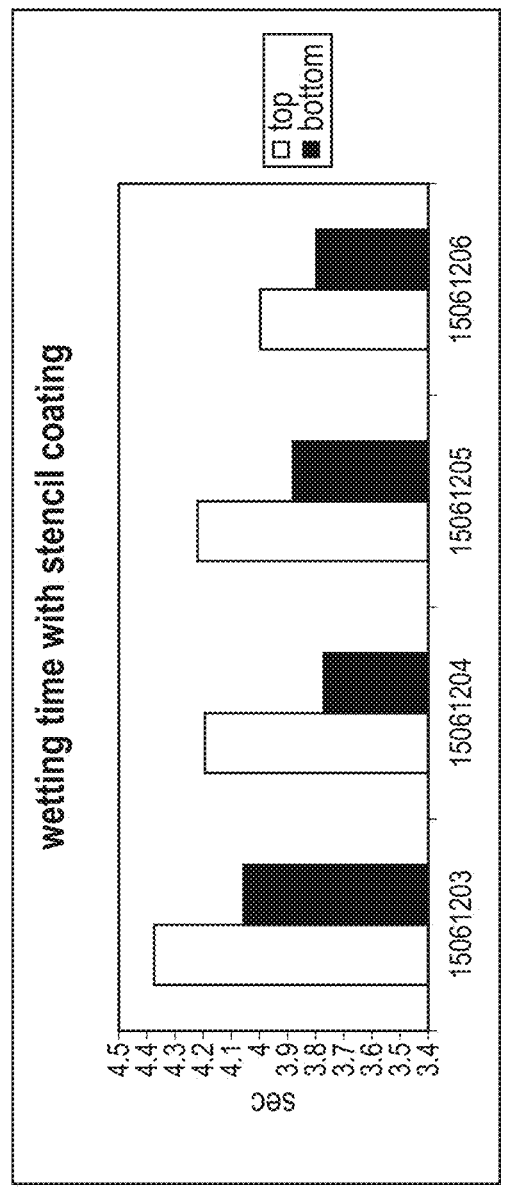
FIG. 48B is a graph illustrating wetting time with stencil coating.
Figure 48C:
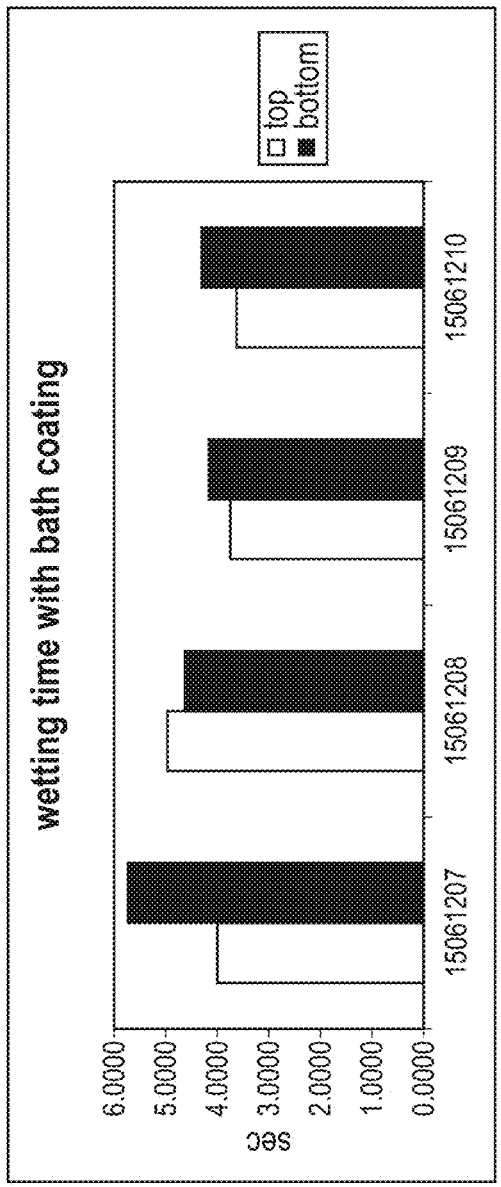
FIG. 48C is a graph illustrating wetting time with bath coating.
Figure 49A:
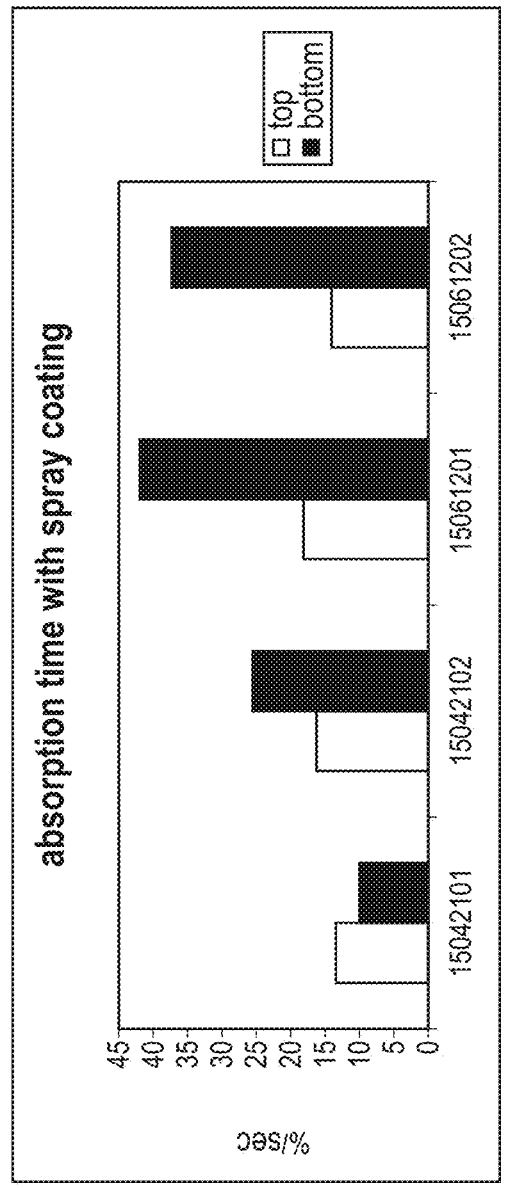
FIG. 49A is a graph illustrating absorption time with spray coating.
Figure 49B:
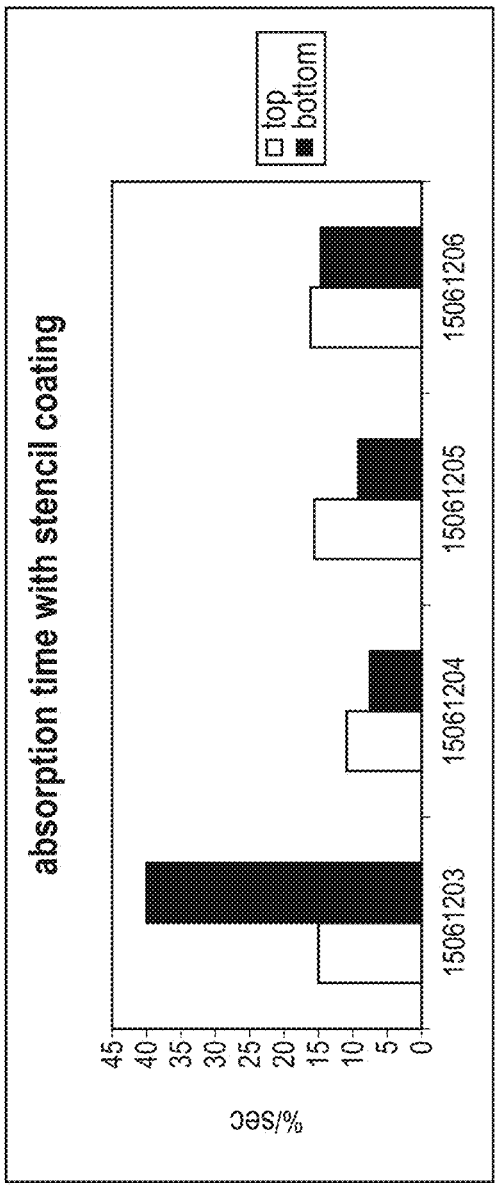
FIG. 49B is a graph illustrating absorption time with stencil coating.
Figure 49C:
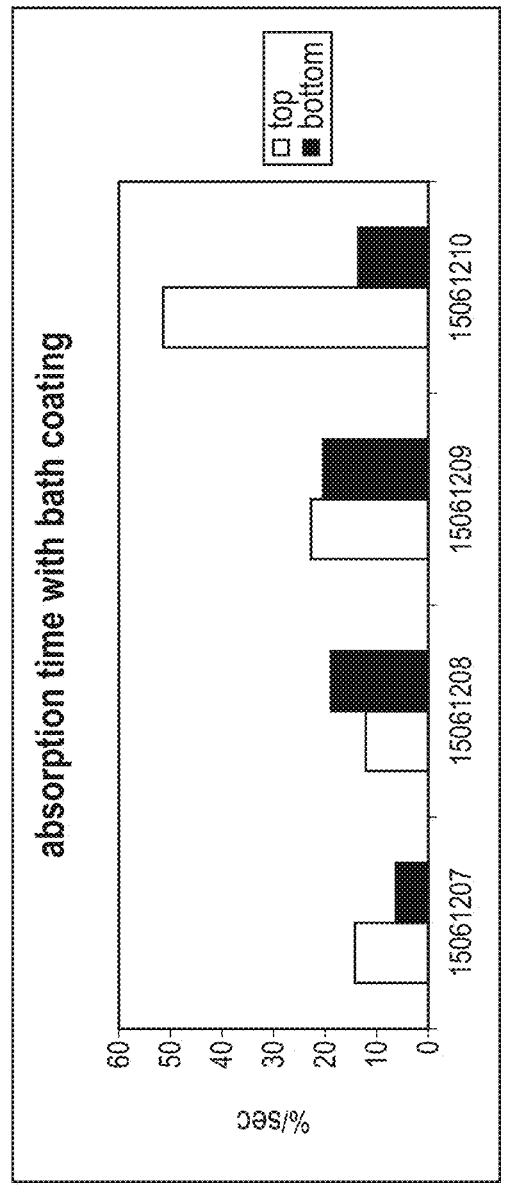
FIG. 49C is a graph illustrating absorption time with bath coating.
Figure 50A:
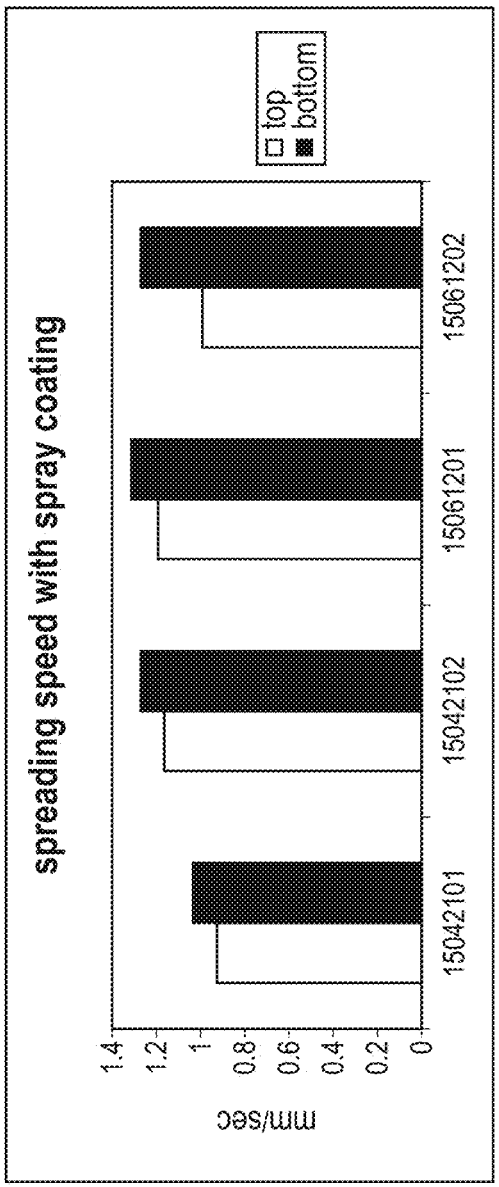
FIG. 50A is a graph illustrating spreading speed with spray coating.
Figure 50B:
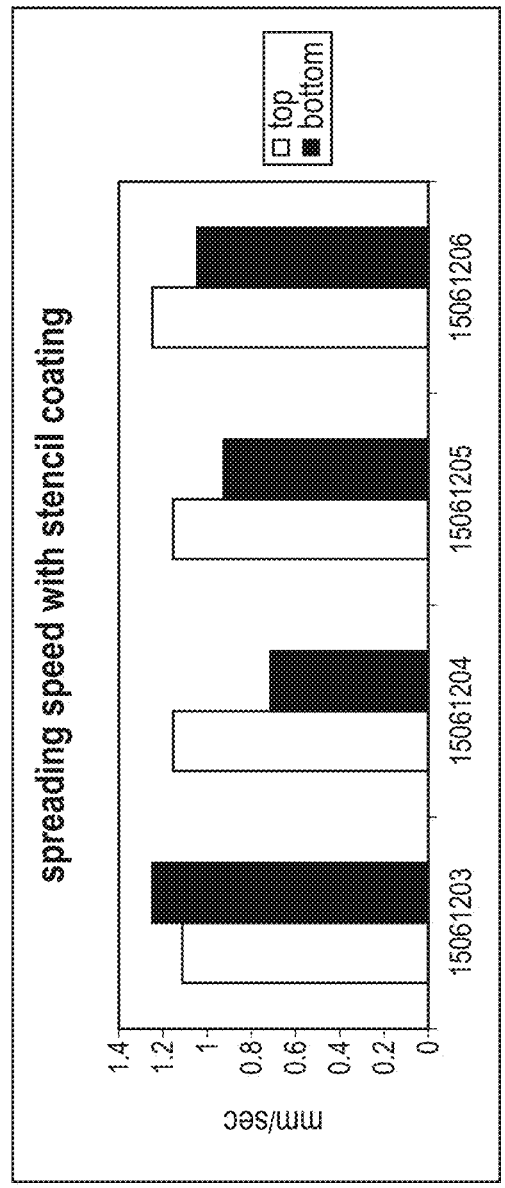
FIG. 50B is a graph illustrating spreading speed with stencil coating.
Figure 50C:
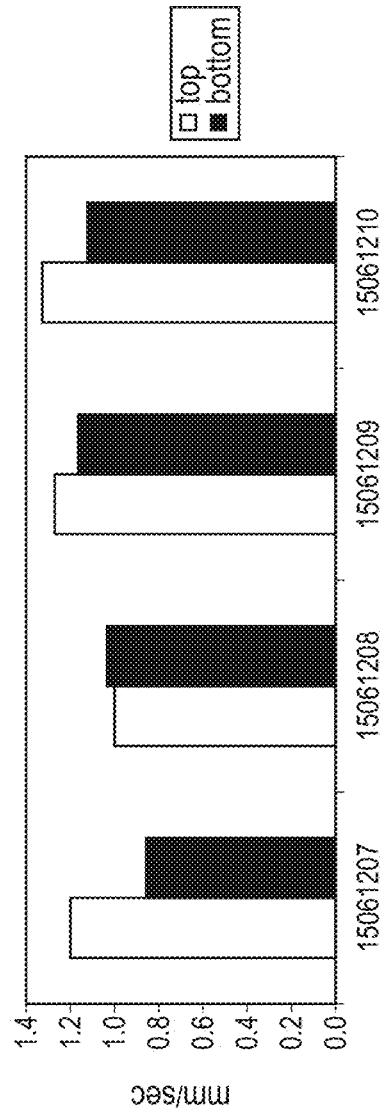
FIG. 50C is a graph illustrating spreading speed with bath coating.
Figure 51A:
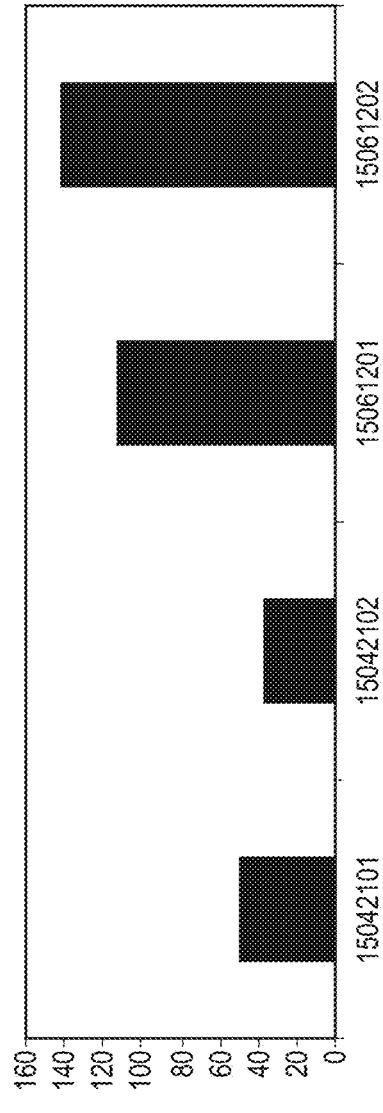
FIG. 51A is a graph illustrating accumulative one-way transport index with spray coating.
Figure 51B:
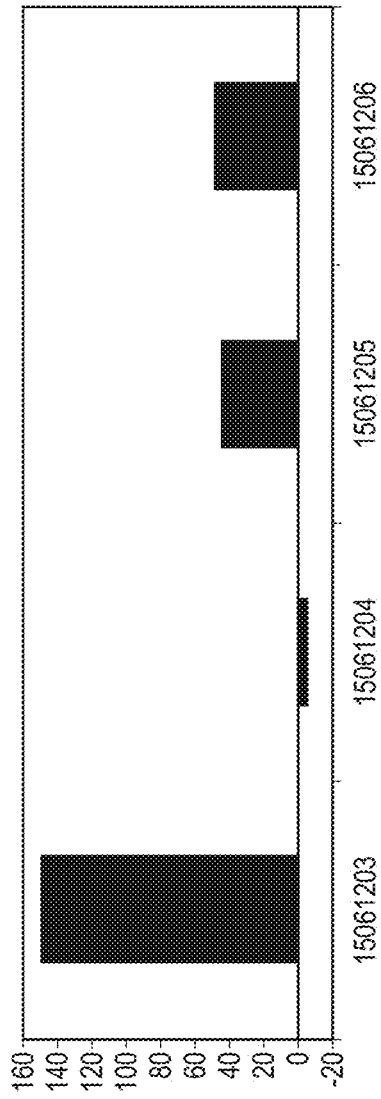
FIG. 51B is a graph illustrating accumulative one-way transport index with stencil coating.
Figure 51C:
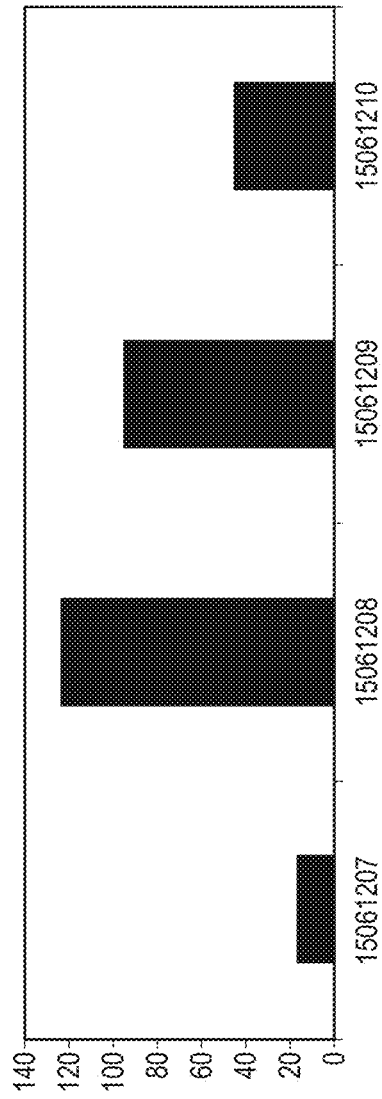
FIG. 51C is a graph illustrating accumulative one-way transport index with bath coating.
Figure 52A:
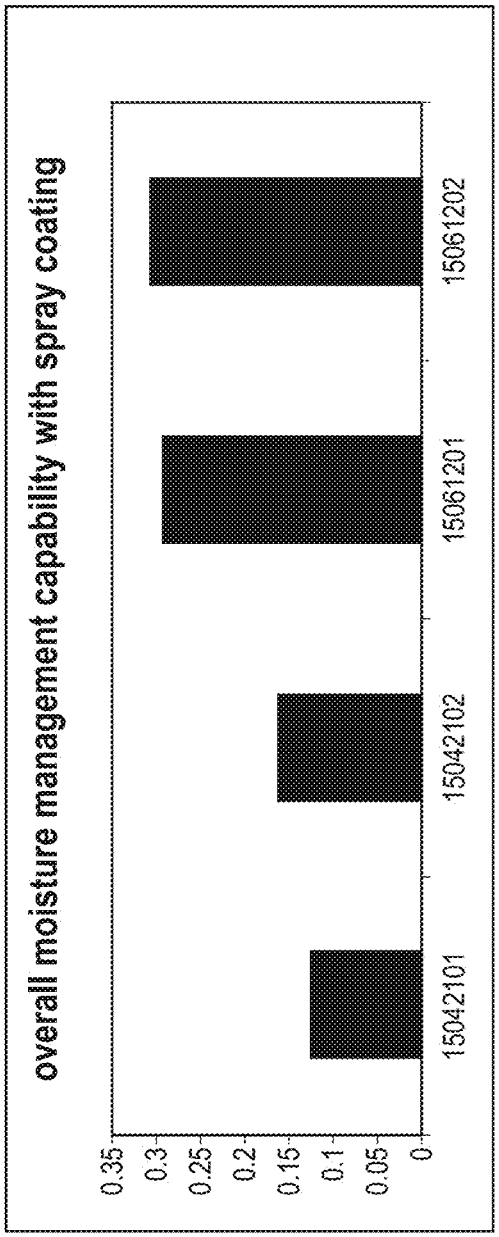
FIG. 52A is a graph illustrating overall moisture management capability with spray coating.
Figure 52B:
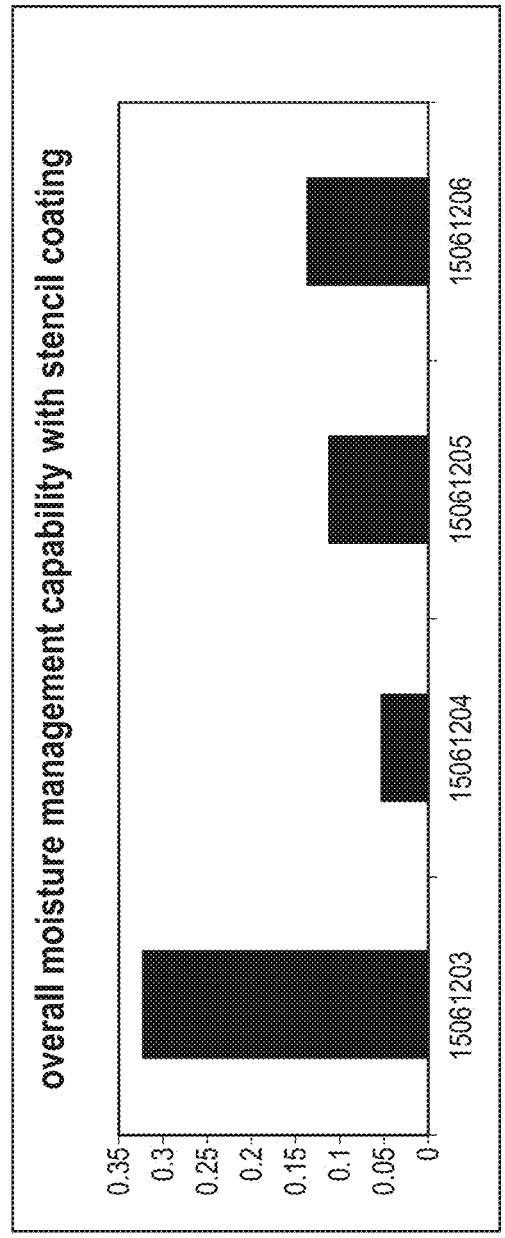
FIG. 52B is a graph illustrating overall moisture management capability with stencil coating.
Figure 52C:
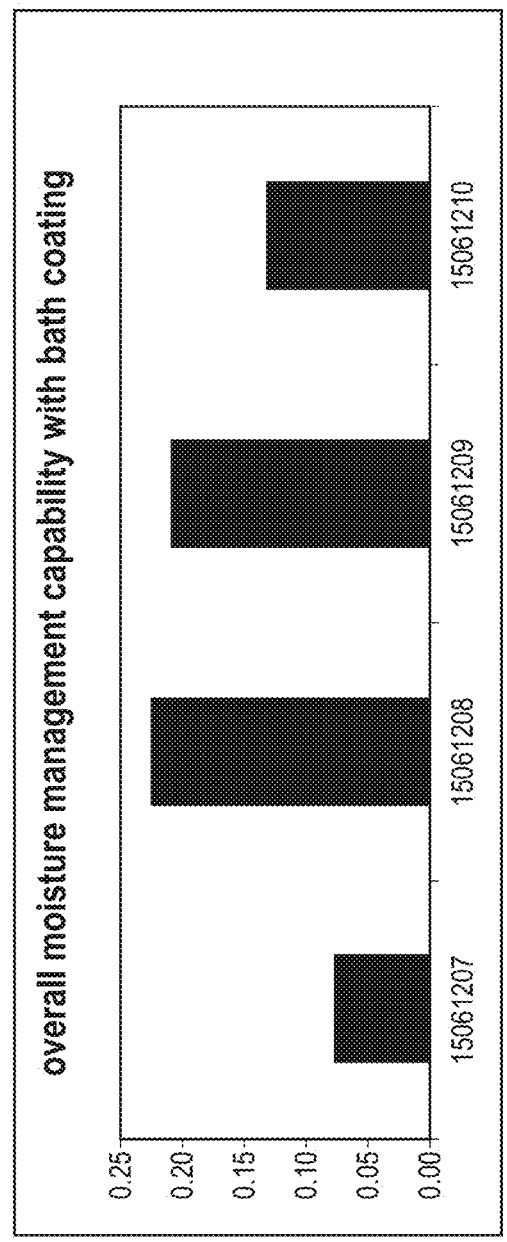
FIG. 52C is a graph illustrating overall moisture management capability with bath coating.
Figure 53A:
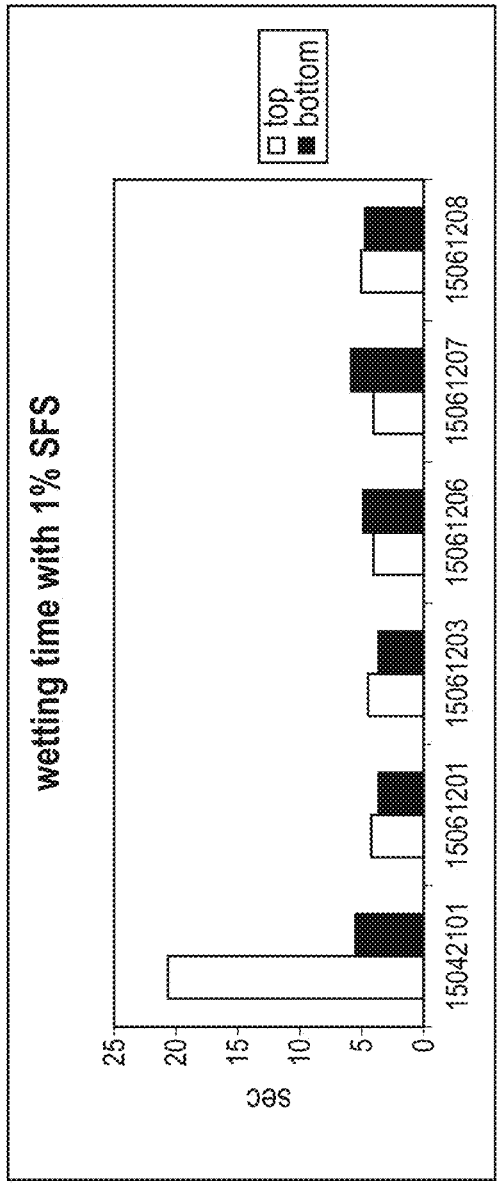
FIG. 53A is a graph illustrating wetting time with 1% SFS.
Figure 53B:
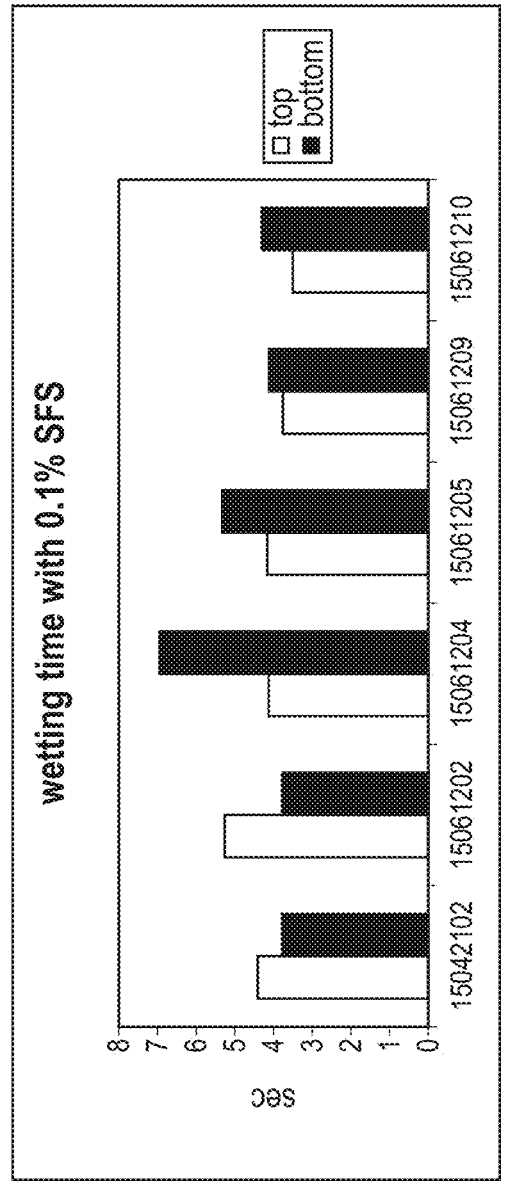
FIG. 53B is a graph illustrating wetting time with 0.1% SFS.
Figure 54A:
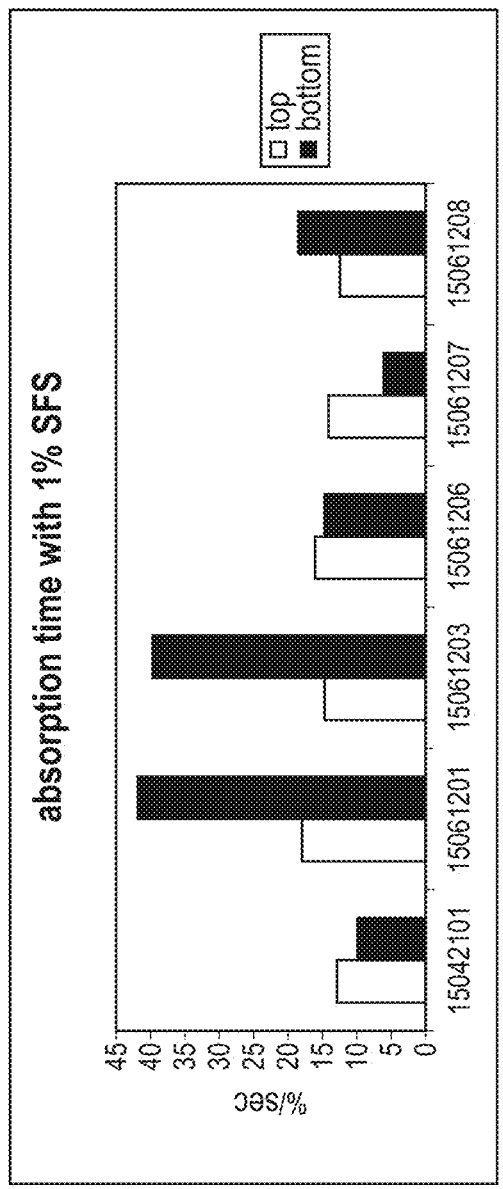
FIG. 54A is a graph illustrating absorption time with 1% SFS.
Figure 54B:
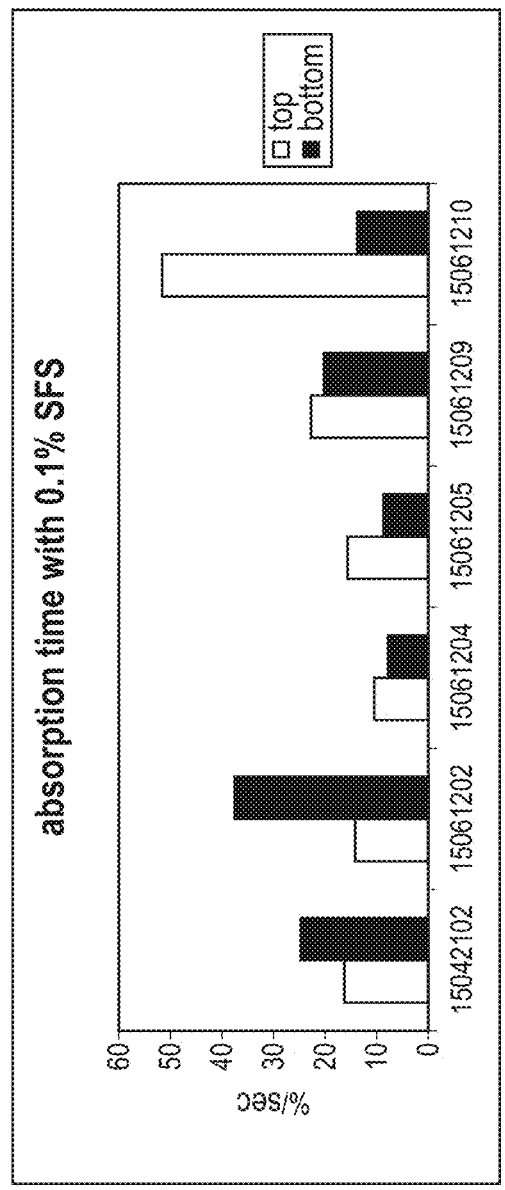
FIG. 54B is a graph illustrating absorption time with 0.1% SFS.
Figure 55A:
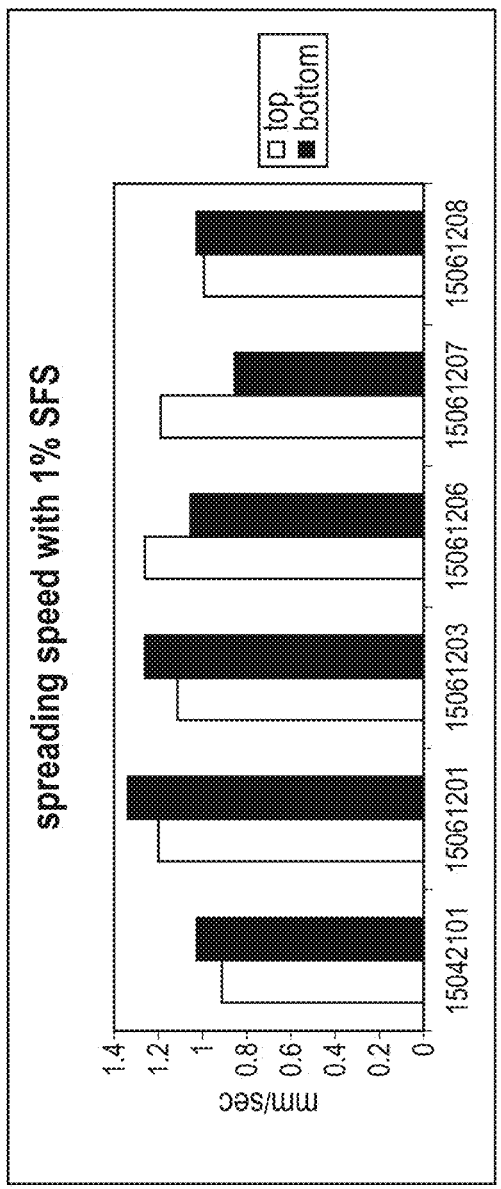
FIG. 55A is a graph illustrating spreading speed with 1% SFS.
Figure 55B:
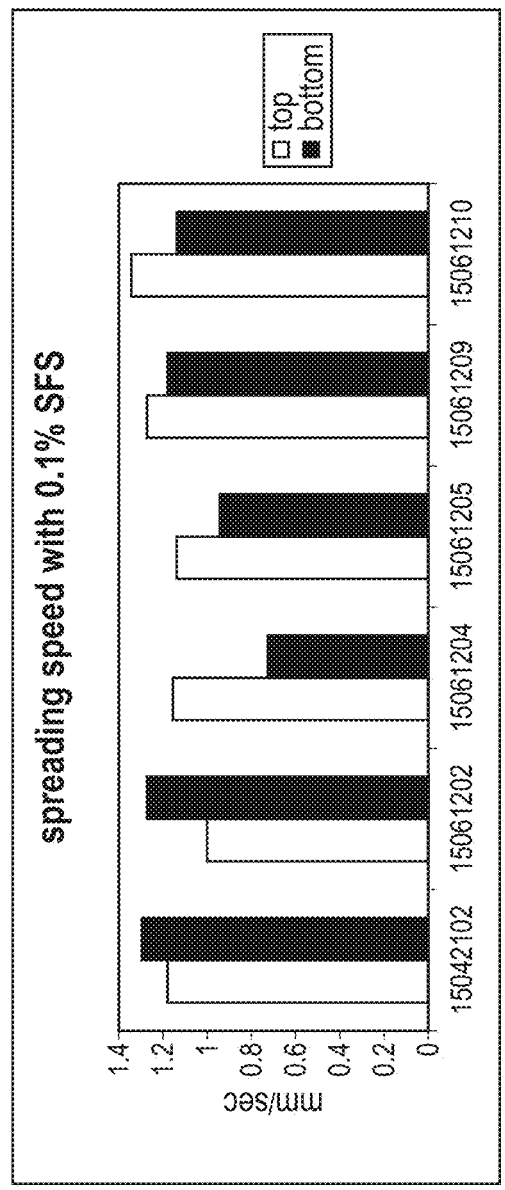
FIG. 55B is a graph illustrating spreading speed with 0.1% SFS.
Figure 56A:
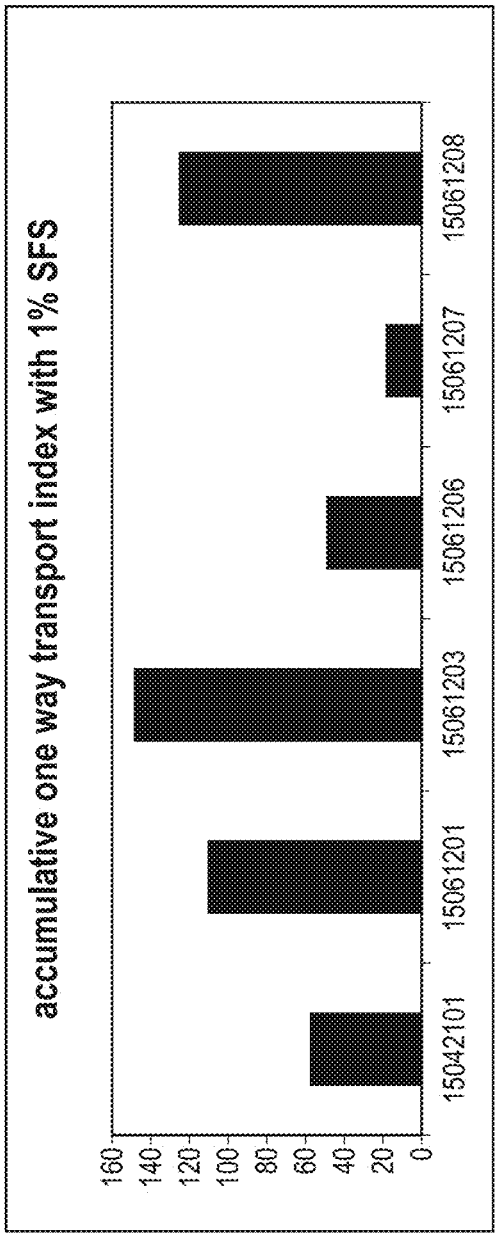
FIG. 56A is a graph illustrating accumulative one-way transport index with 1% SFS.
Figure 56B:
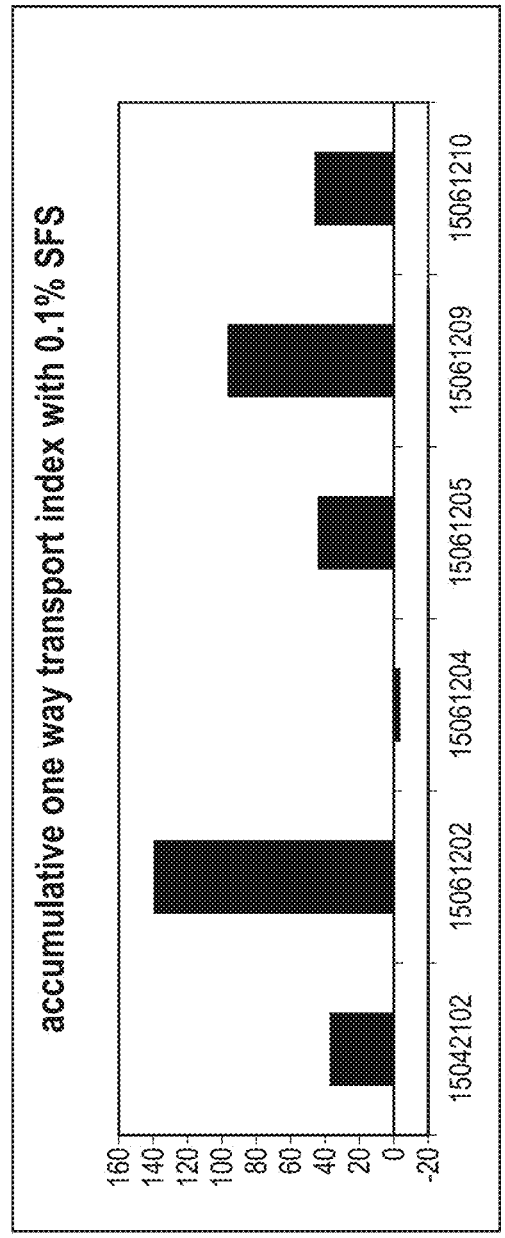
FIG. 56B is a graph illustrating accumulative one-way transport index with 0.1% SFS.
Figure 57A:
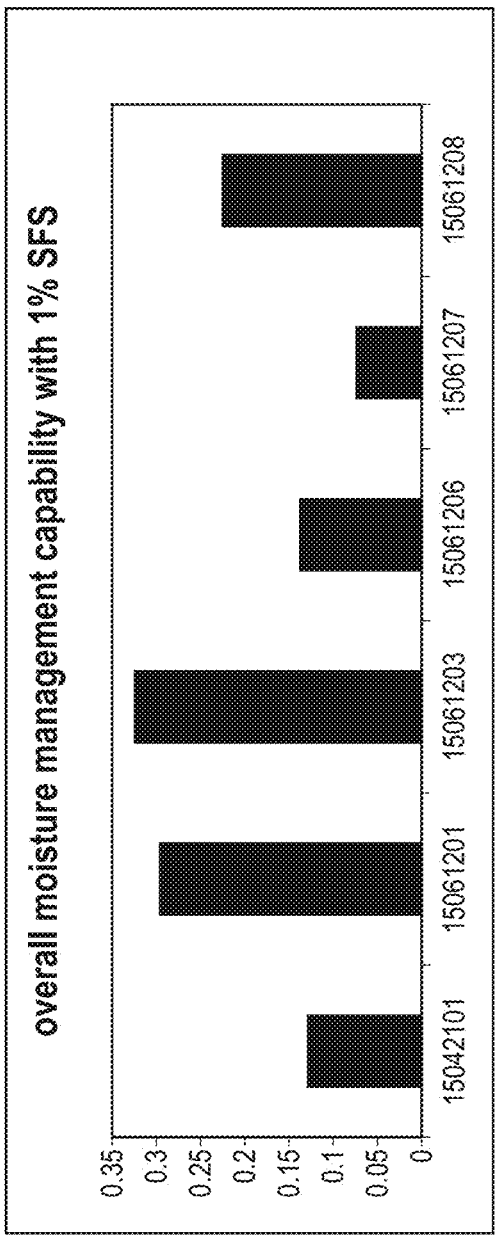
FIG. 57A is a graph illustrating overall moisture management capability with 1% SFS.
Figure 57B:
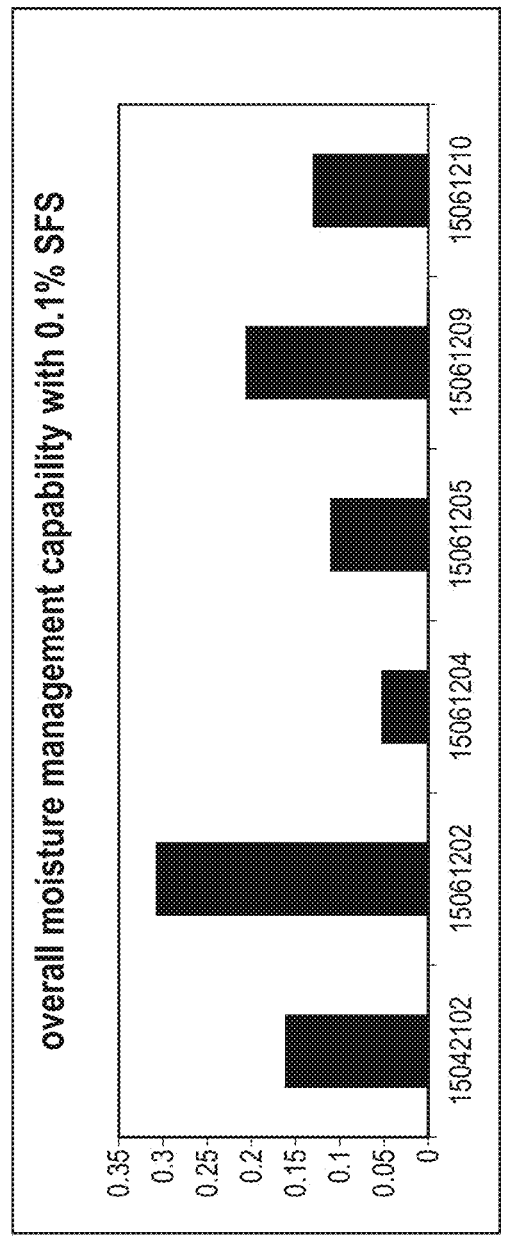
FIG. 57B is a graph illustrating overall moisture management capability with 0.1% SFS.
Figure 58A:
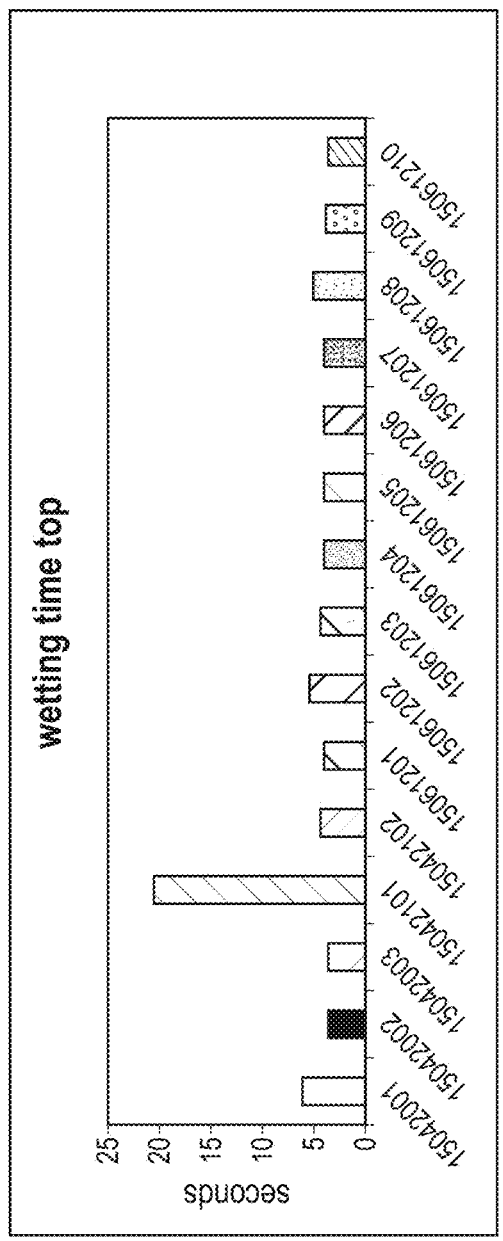
FIG. 58A is a graph illustrating summary of wetting time top.
Figure 58B:
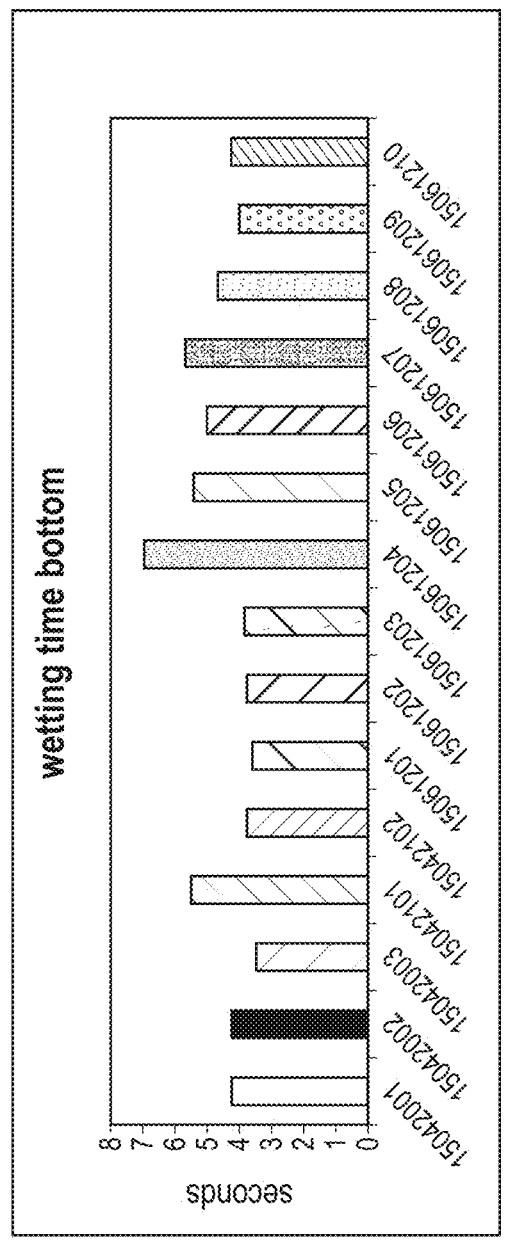
FIG. 58B is a graph illustrating summary of wetting time bottom.
Figure 59A:
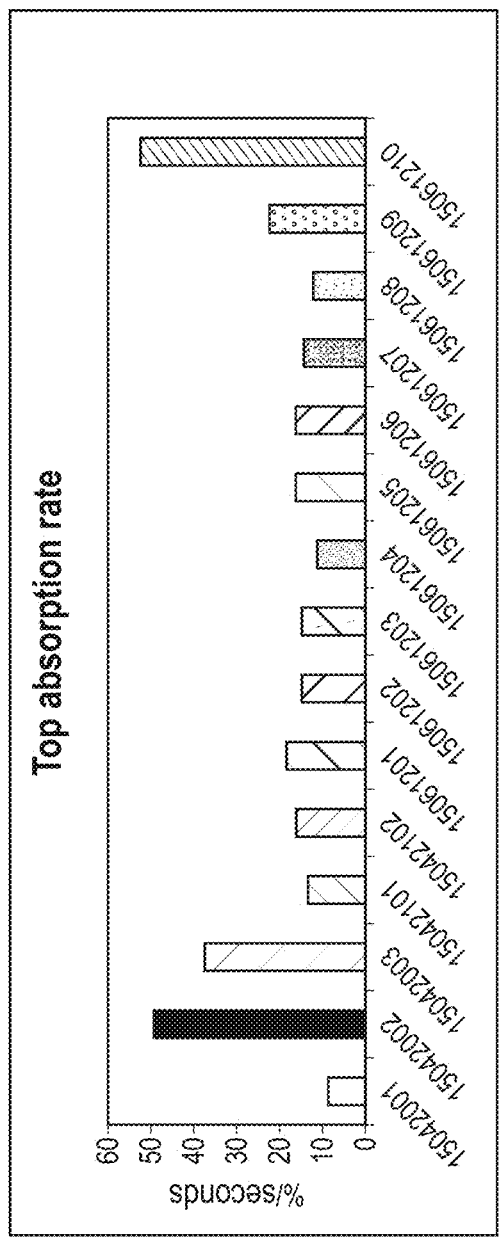
FIG. 59A is a graph illustrating summary of top absorption rate.
Figure 59B:
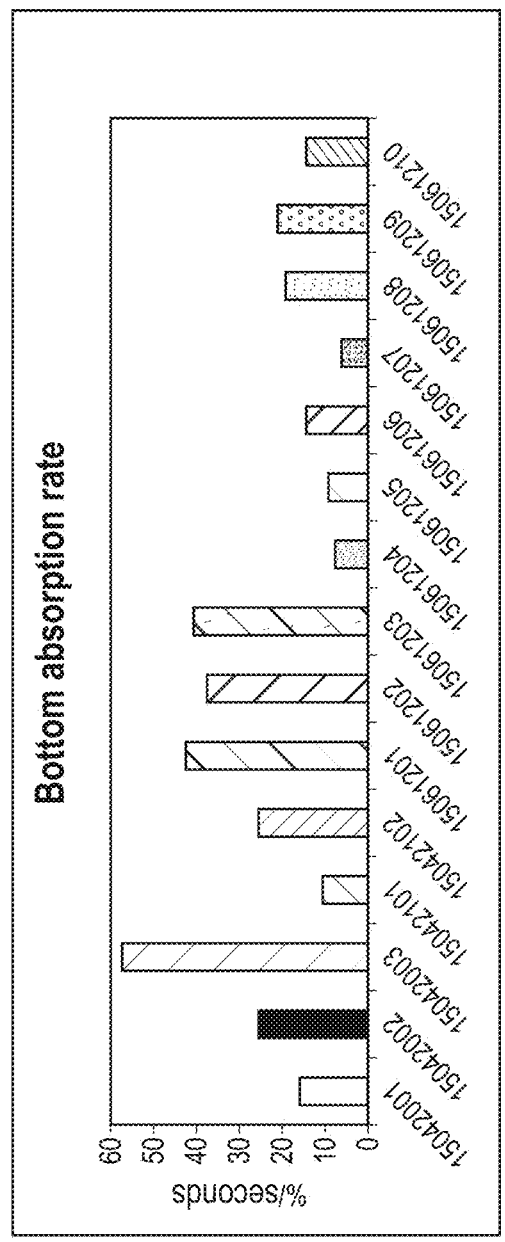
FIG. 59B is a graph illustrating summary of bottom absorption rate.
Figure 60A:
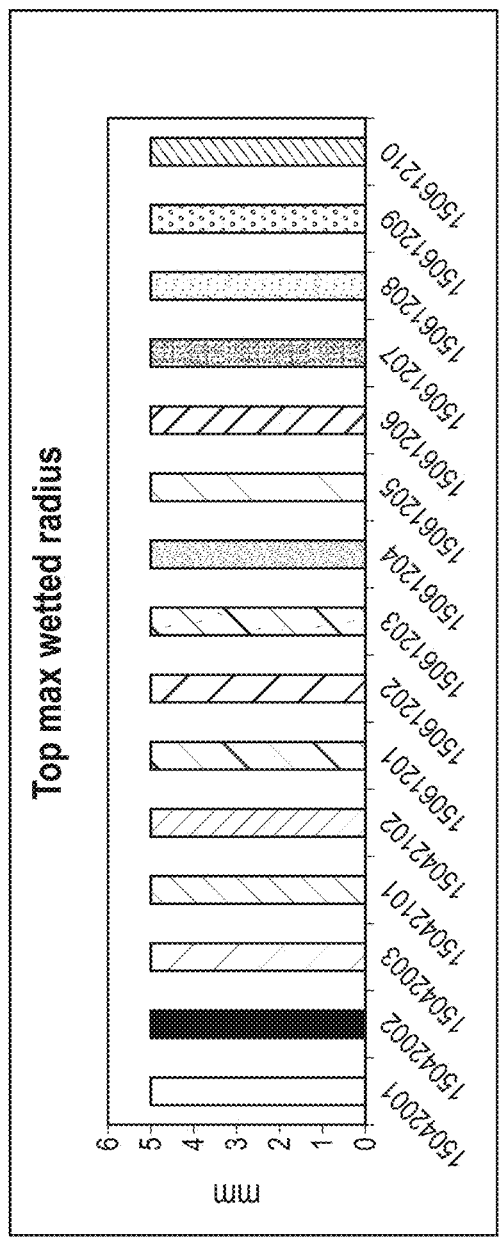
FIG. 60A is a graph illustrating summary of top max wetted radius.
Figure 60B:
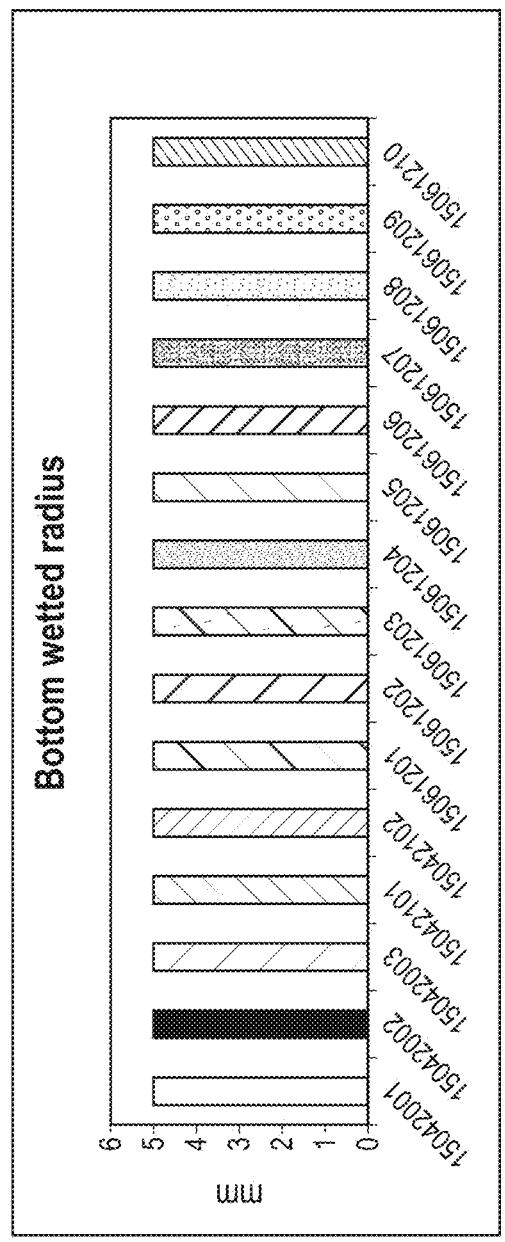
FIG. 60B is a graph illustrating summary of bottom wetted radius.
Figure 62A:
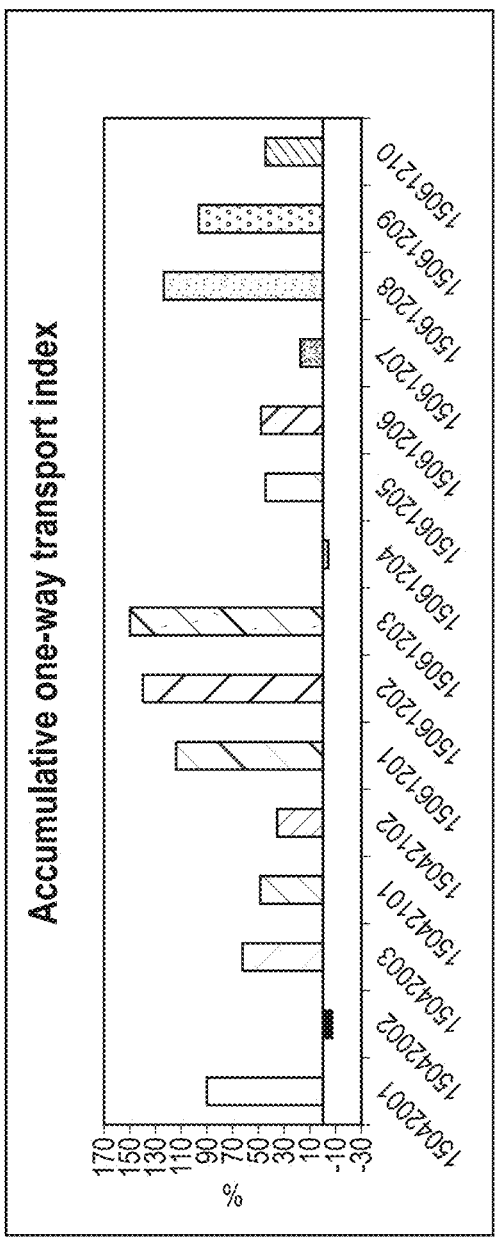
FIG. 62A is a graph illustrating summary of accumulative one-way transport index.
Figure 62B:
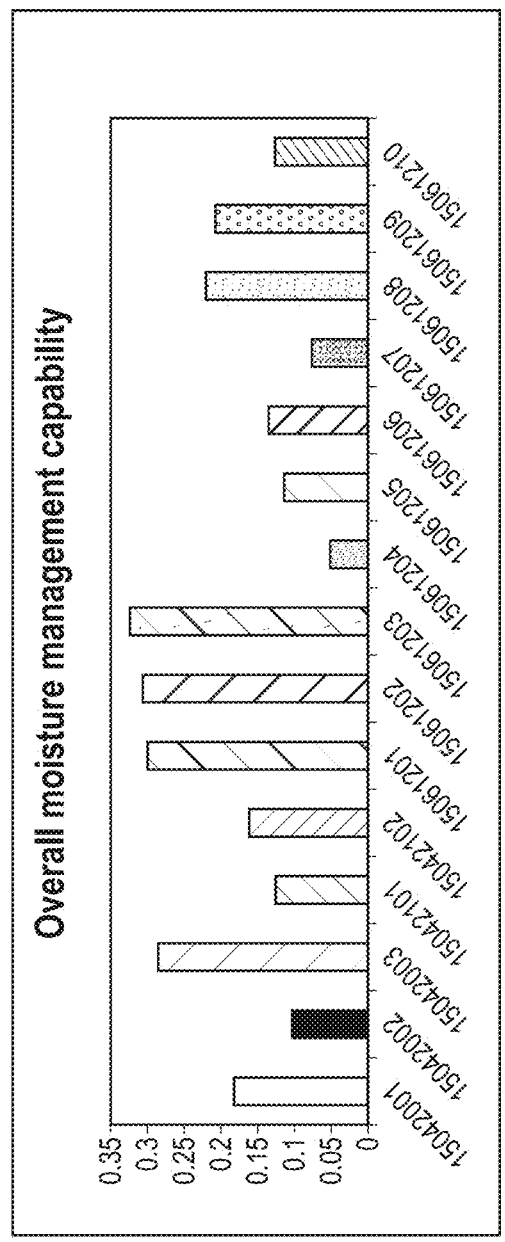
FIG. 62B is a graph illustrating summary of overall moisture management capability.
Figure 63:
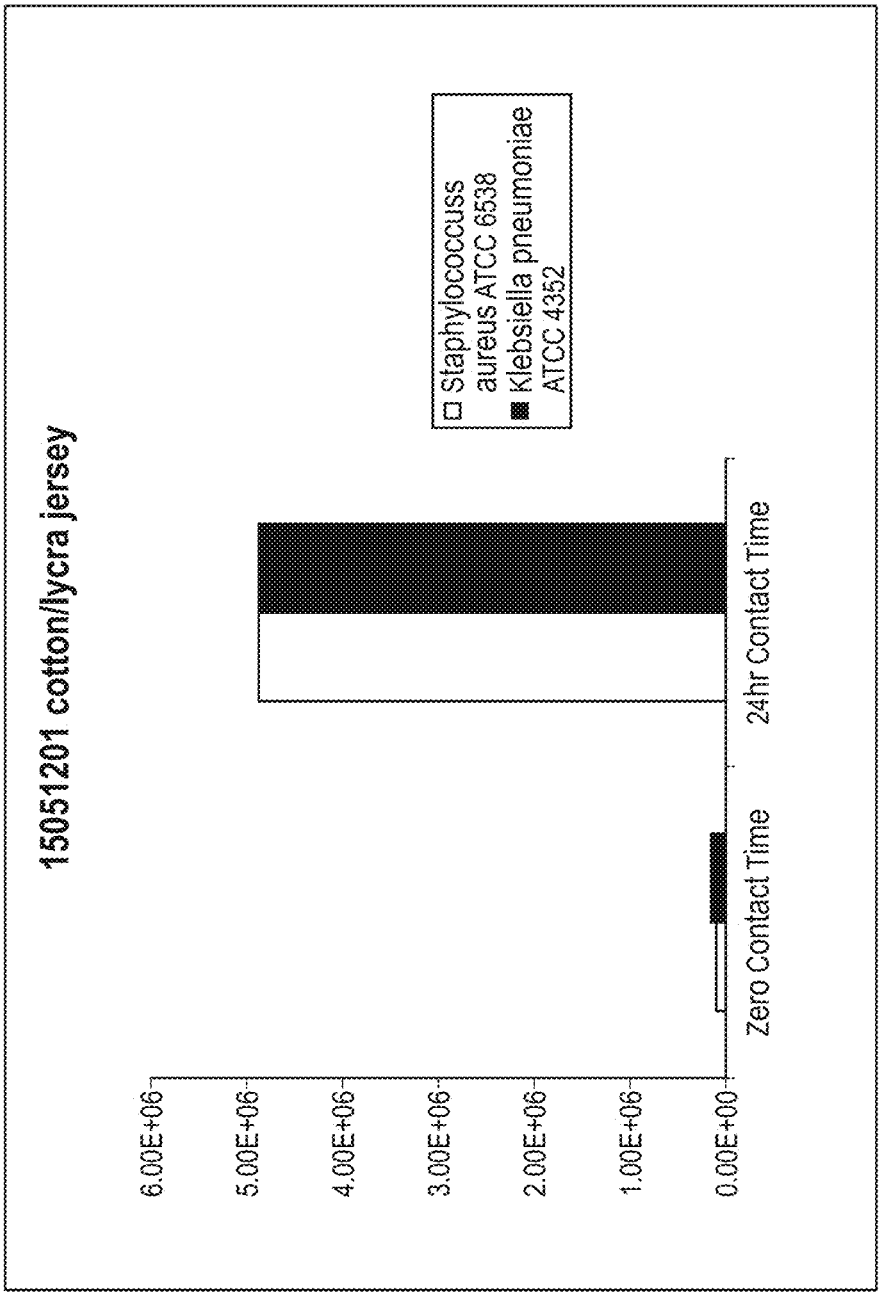
FIG. 63 illustrates bacterial growth results.
Figure 64:
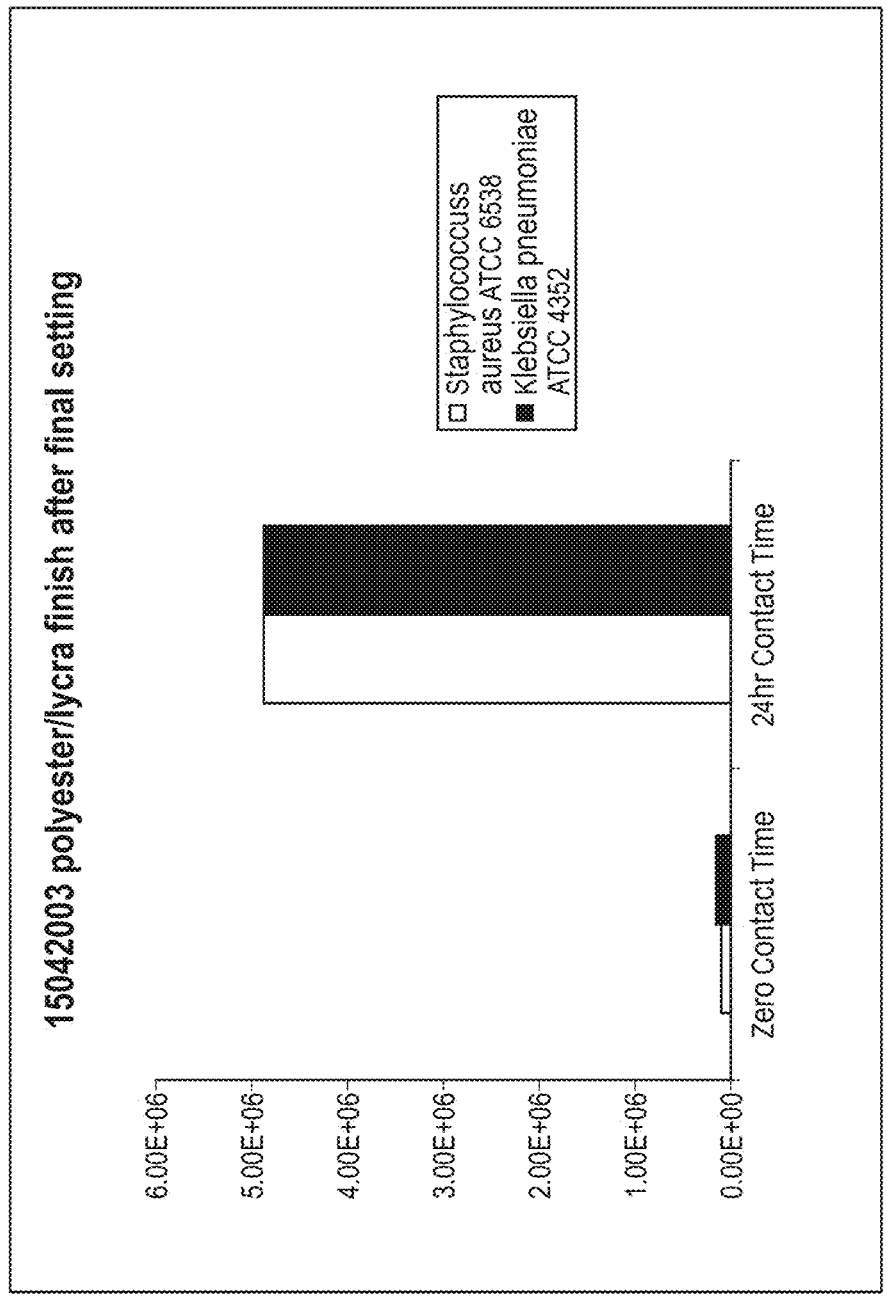
FIG. 64 illustrates bacterial growth results.
Figure 65:
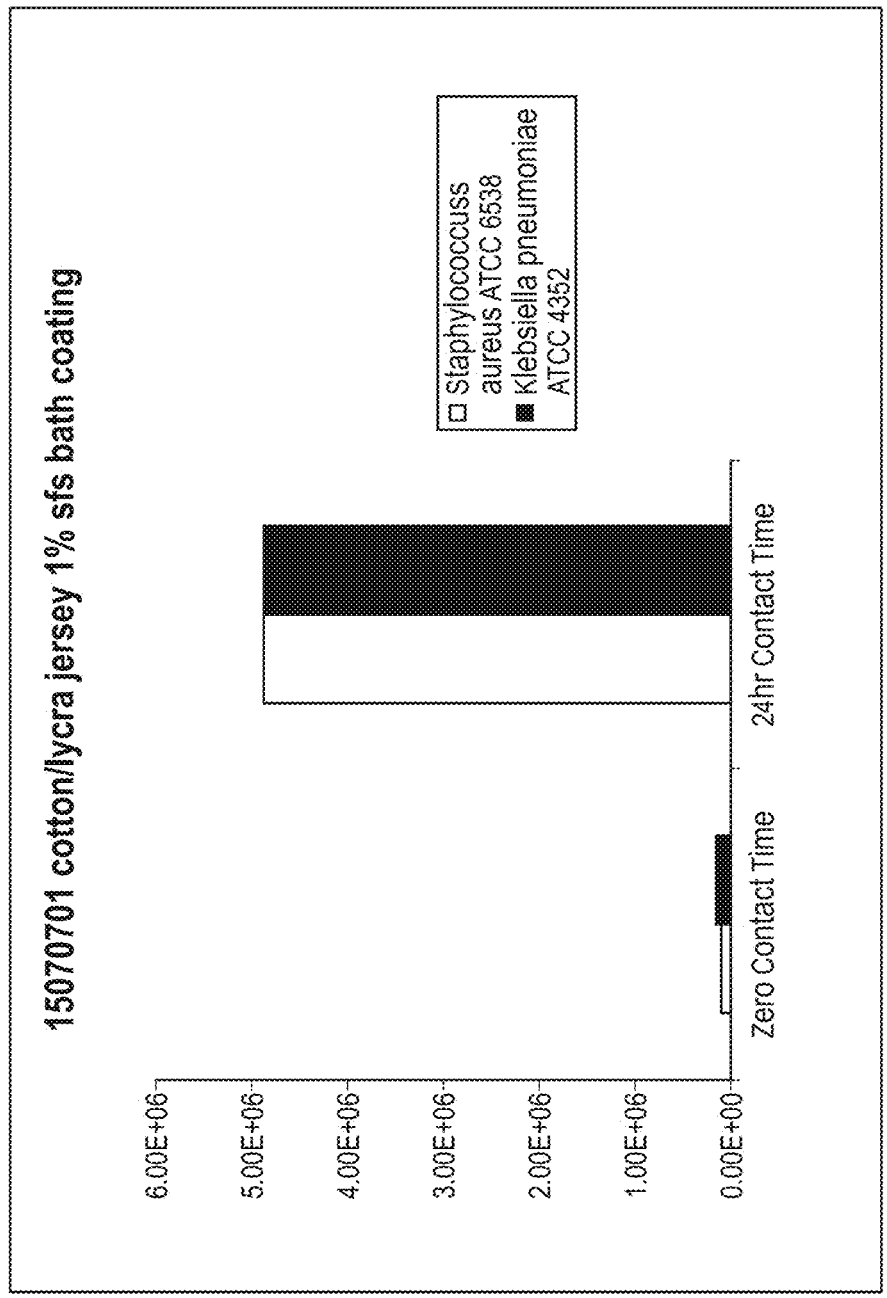
FIG. 65 illustrates bacterial growth results.
Figure 66:
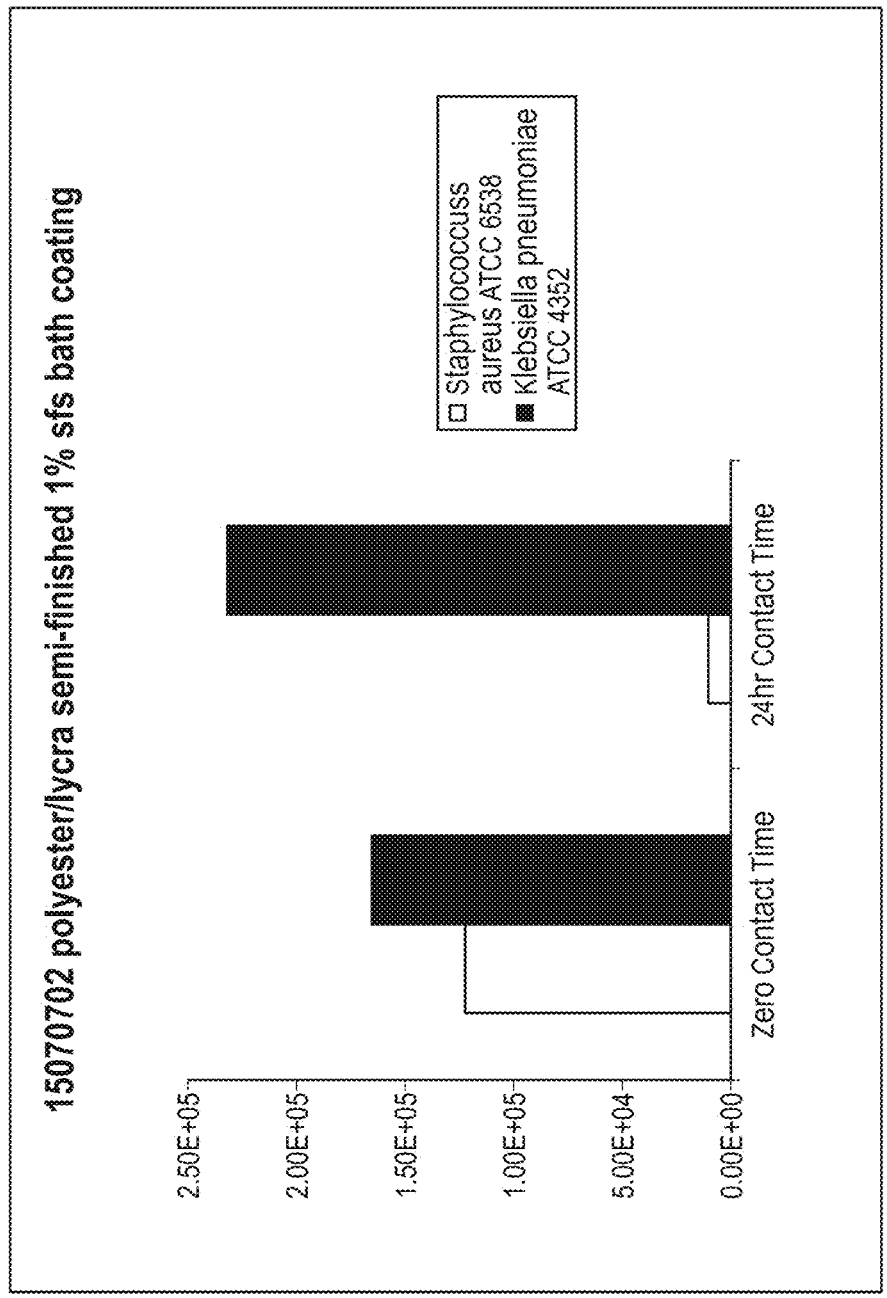
FIG. 66 illustrates bacterial growth results.
Figure 67:
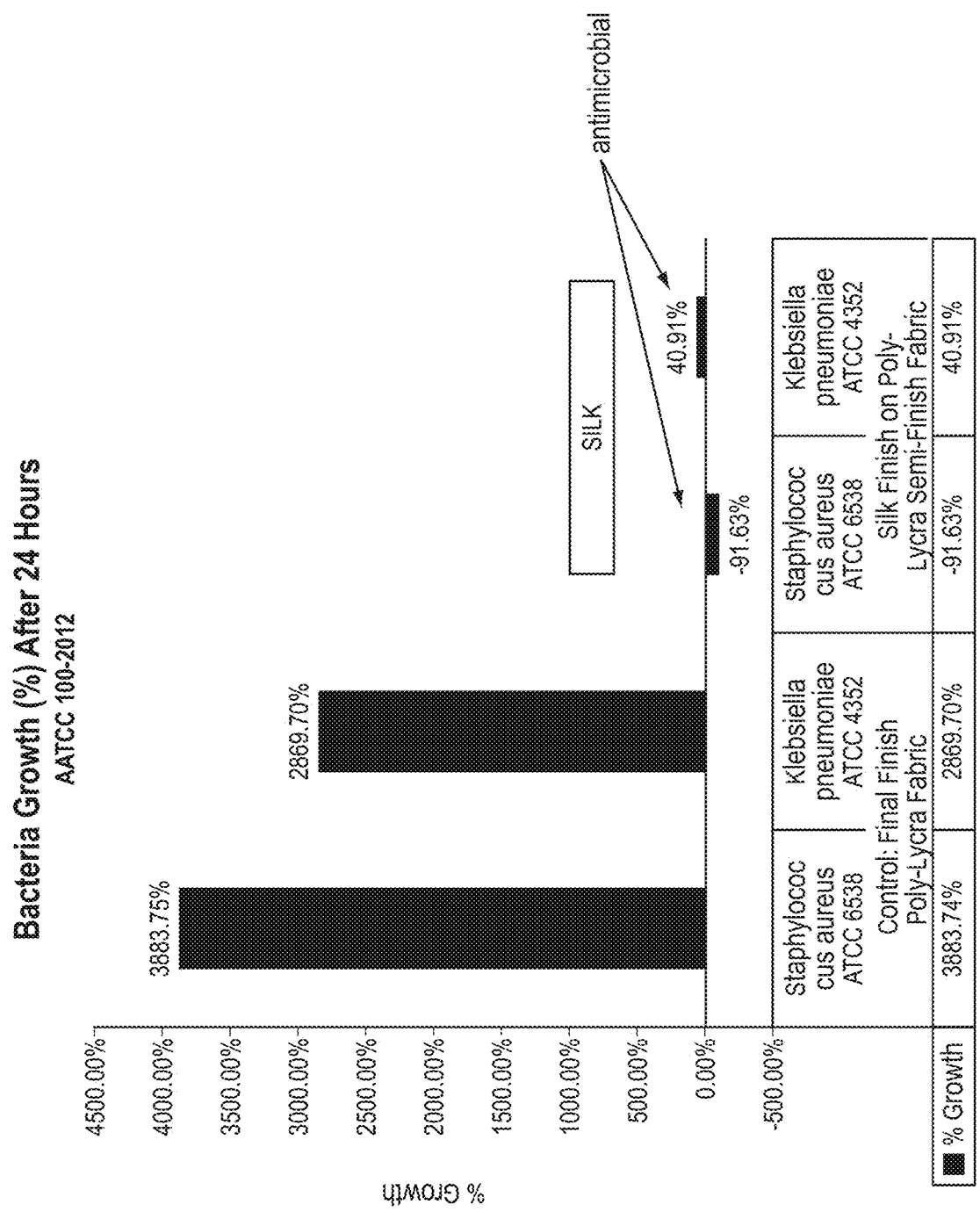
FIG. 67 illustrates bacterial growth results.

After laundering fabrics are evaluated for water drop test (Table 54, and FIG. 32). The sample fabric is placed on top of a 7 cm diameter positioned on the drapability jig. A RODI water drop is dispensed with an eye dropper from approximately 3 cm above the fabric. A video imaging recording capture the time from the water drop contacting the fabric until its full absorption or up to 60 seconds.

TABLE 53

Hand Score of Fabric

| Sample # | Description | t = 0 | t = 10 | t = 25 | t = 52 |
|---|---|---|---|---|---|
| 17050303 | 6606D2 nylon/lycra, 0.25% silk 3L1M*, 0.025% citric acid, 3% Domosil RWAF | 5 | 4 | 1 | 1 |
| 17050308 | 6606D2 nylon/lycra, first step 0.25% silk 3L1M, 0.025% citric acid, second step 3% Domosil RWAF, 0.25% citric acid | 5 | 5 | 3 | 3 |
| 17060101 | 6606D2 nylon/lycra, 0.25% silk 3L1M, 0.025% citric acid | 5 | 6 | 6 | 6 |
| 17060102 | 6606D2 nylon/lycra, 3% Domosil RWAF, 0.25% citric acid | 5 | 4 | 4 | 3 |
| 17050306 | 6608D2B polyester/lycra, 0.25% silk 3L1M, 0.025% citric acid, 3% Domosil RWAF | 5 | 4 | 3 | 3 |
| 17050310 | 6608D2B polyester/lycra, first step 0.25% silk 3L1M, 0.025% citric acid, second step 3% Domosil RWAF, 0.25% citric acid | 5 | 5 | 4 | 4 |
| 17060103 | 6608D2B polyester/lycra, 0.25% silk 3L1M, 0.025% citric acid | 5 | 6 | 4 | 4 |
| 17060104 | 6608D2B polyester/lycra, 3% Domosil RWAF, 0.25% citric acid | 5 | 4 | 4 | 4 |

*3L1M: 3:1 low MW silk to medium MW silk
Sample #17060101 and #17060103 had some scores higher than 5; without being limited to any one theory, it is theorized that there is affinity between silk and silicone and the silicone shedding from the coated fabric recoated the silk only coated variables Sample #17060101 and #17060103 had some scores higher than 5; without being limited to any one theory, it is theorized that there is affinity between silk and silicone and the silicone shedding from the coated fabric recoated the silk only coated variables

TABLE 54

Water Drop Test Results

| Sample# | Description |  | Average water drop absorption time | Standard deviation |
|---|---|---|---|---|
| 17050303 | 6606D2 nylon/lycra, 0.25% silk 3L1M, 0.025% citric acid, 3% Domosil RWAF | t = 0 | 8.8 | 0.447 |
|  |  | t = 10 | 60 | 0.000 |
|  |  | t = 25 | 16 | 9.772 |
|  |  | t = 52 | 4 | 0.707 |
| 17050308 | 6606D2 nylon/lycra, first step 0.25% silk 3L1M, 0.025% citric acid, second step 3% Domosil RWAF, 0.25% citric acid | t = 0 | 1 | 0.000 |
|  |  | t = 10 | 2.6 | 0.548 |
|  |  | t = 25 | 3.6 | 0.894 |
|  |  | t = 52 | 2.6 | 0.548 |
| 17060101 | 6606D2 nylon/lycra, 0.25% silk 3L1M, 0.025% citric acid | t = 0 | 3.6 | 0.548 |
|  |  | t = 10 | 2.6 | 0.548 |
|  |  | t = 25 | 1 | 0.000 |
|  |  | t = 50 | 1 | 0.000 |
| 17060102 | 6606D2 nylon/lycra, 3% Domosil, 0.025% citric acid | t = 0 | 19.8 | 2.775 |
|  |  | t = 10 | 59.8 | 0.447 |
|  |  | t = 25 | 9.6 | 2.608 |
|  |  | t = 50 | 9.8 | 2.950 |
| 17050306 | 6608D2B polyester/lycra, 0.25% silk 3L1M, 0.025% citric acid, 3% Domosil RWAF | t = 0 | 2.6 | 0.548 |
|  |  | t = 10 | 60 | 0.000 |
|  |  | t = 25 | 60 | 0.000 |
|  |  | t = 52 | 60 | 0.000 |
| 17050310 | 6608D2B polyester/lycra, first step 0.25% silk 3L1M, 0.025% citric acid, second step 3% Domosil RWAF, 0.25% citric acid | t = 0 | 0.8 | 0.274 |
|  |  | t = 10 | 3.2 | 0.447 |
|  |  | t = 25 | 7 | 2.345 |
|  |  | t = 52 | 28.6 | 3.130 |
| 17060103 | 6608D2B polyester/lycra 0.187% low MW, 0.063% medium MW, 0.025% citric acid | t = 0 | 0.5 | 0.000 |
|  |  | t = 10 | 1.4 | 0.548 |
|  |  | t = 25 | 2.8 | 0.447 |
|  |  | t = 50 | 24.6 | 7.503 |
|  |  | t = 0 | 1.4 | 0.548 |

TABLE 54-continued

Water Drop Test Results

| Sample# | Description | | Average water drop absorption time | Standard deviation |
|---|---|---|---|---|
| 17060104 | 6608D2B polyester/lycra, 3% Domosil RWAF | t = 10 | 60 | 0.000 |
| | | t = 25 | 9.4 | 4.037 |
| | | t = 50 | 60 | 0.000 |

Example 8: Nylon/Lycra and Polyester/Lycra Fabric Coated with Silk and Silicone: Evaluation of Oil Repellency/Hydrocarbon Resistance, and Soil Repellency

TABLE 55

Coating Experimental Variables

| Fabric type (application steps) | Silk solution | pH correction | Silicone coating | pH correction | Dry/cure temperature °F. (°C.) |
|---|---|---|---|---|---|
| Fabric 6606D2 nylon/lycra (2) | 0.187% low MW + 0.063% medium MW (3:1 ratio) | 0.025% citric acid (50%) or to pH 4-5 | Domosil RWAF | 0.25% citric acid (50%) or to pH 3-4 | 302 (150) 70 seconds |
| Fabric 6608D2B polyester/lycra (2) | 0.187% low MW + 0.063% medium MW (3:1 ratio) | 0.025% citric acid (50%) or to pH 4-5 | Domosil RWAF | 0.25% citric acid (50%) or to pH 3-4 | 350 (150) 60 seconds |
| Fabric 6606D2 nylon/lycra (1) | 0.187% low MW + 0.063% medium MW (3:1 ratio) | 0.025% citric acid (50%) or to pH 4-5 | N/A | N/A | 302 (150) 70 seconds |
| Fabric 6608D2B polyester/lycra (1) | 0.187% low MW + 0.063% medium MW (3:1 ratio) | 0.025% citric acid (50%) or to pH 4-5 | N/A | N/A | 350 (150) 60 seconds |

Analysis:

Samples coated as described in Table 55, are conditioned at ambient for 24 hrs before lab delivery for testing. The samples tested for (Table 56):

AATCC TM118-2013, Oil Repellency: Hydrocarbon Resistance; the scale ranges from zero to eight, with a rating of eight signifying the most repellent surface; testing conditions: 21° C. (2° C.) and 65% RH (±5% RH);

AATCC TM130-2015, Soil Release: Oily Stain Release Method; AATCC Stain Release Replica version 2013 used for grading; washing procedure III (41±3° C. (105±5° F.)); ballast wash load Type 3—92×92 cm (36×36 in) hemmed pieces of 50/50 Poly/Cotton sheeting; 1993 AATCC Standard Reference Detergent WOB containing no phosphate; washer manufacturer: Kenmore, Model #: 110.23902200, or Whirlpool, Model #: GTS9679PW3; dryer manufacturer: Whirlpool, Model #: LEQ9858PW1; a grade of 5 indicates excellent stain removal; a grade of 1 indicates very poor stain removal; testing conditions: 21° C. (±2° C.) and 65% RH (±5% RH).

The sample tested for each method are:
N=1 control no laundering
N=1 Fabric 6606D2, 0.25% silk 3L1M
N=1 Fabric 6606D2, 0.25% silk 3L1M, 3% Domosil RWAF silicone
N=1 Fabric 6608D2B, 0.25% silk 3L1M
N=1 Fabric 6608D2B, 0.25% silk 3L1M, 3% Domosil RWAF silicone

TABLE 56

Oil Repellency and Soil Release

| Sample # | Description | Average Soil Release: Oily Stain Release Method - AATCC 130-2015 | Average Oil Repellency: Hydrocarbon Resistance Test AATCC 118-2013 |
|---|---|---|---|
| 16111801 | 6606D2 nylon/lycra control | 3.8 | 0 |
| 17050308 | 6606D2 nylon/lycra, first step 0.25% silk 3L1M*, 0.025% citric acid, second step 3% Domosil RWAF, 0.25% citric acid | 4.3 | 0 |
| 17050301 | 6606D2 nylon/lycra, 0.25% silk 3L1M, 0.025% citric acid | 4.5 | 0 |
| 16122001 | 6608D2B polyester/lycra control | 4.5 | 0 |
| 17050310 | 6608D2B polyester/lycra, first step 0.25% silk 3L1M, 0.025% citric acid, second step 3% Domosil RWAF, 0.25% citric acid | 3.8 | 0 |
| 17050304 | 6608D2B polyester/lycra, 0.25% silk 3L1M | 4.3 | 0 |

*3L1M: 3:1 low MW silk to medium MW silk

Example 9: Nylon/Lycra and Polyester/Lycra Fabric Coated with Silk and Silicone: Evaluation of Textile Abrasion The experiment includes the determination of the abrasion resistance of textile fabrics using the Martindale abrasion tester. Fabrics of all types may be tested by this method, but difficulties may arise with fabrics with a pile depth greater than 0.08 in (2 mm).

The values stated in inch-pound units are regarded as standard. The values given in parentheses are mathematical conversions to SI units that are provided for information only and are not considered standard.

Materials and Equipment: 66061D2 nylon/lycra sample #16120102-M coated with 0.15% low MW, 0.05% medium MW (ratio 3:1), 0.025% citric acid; silk medium molecular weight solution at 60%; silk low molecular weight solution at 60%; citric acid; unfiltered tap water; fabric sample style 66061D2; Krantz tenter frame; dye machine.

Coating Methods: the fabric is dyed in black with a dyeing machine using the following recipe:
ERIOFAST BLACK M 6%;
Low molecular weight and medium molecular weight silk are diluted using tap water from 6% to the concentration for each of the 3 tests reported in Table 57;
The solution will be prepared for 104 liter pad liquor, with an estimating wet pick up rate of 65-70% for the processed fabric, and reduced by the end of each of the 3 tests to a minimum level of 60 liter (safety factor of 20% from the 50 liter minimum level of bath processing);

When medium molecular weight is used in the coating solution, the solution will be prepared with the following steps: mix low molecular weight, water, and citric acid for 2-3 minutes; add medium molecular weight and mix for additional 2-3 minutes;

When only low molecular weight silk is used, the silk solution is mixed with water and citric acid for 2-5 minutes;

Citric acid is added to the solution to correct the pH to 4-5, not exceeding a 0.25% liquor concentration;

The tenter frame is cleaned from any residue that may have built up on the bath or pad rollers from previous runs;

The approximately 700 yards dyed fabric is split into N=5 sections, N=3 sections of 220 yards each, N=1 section of 35 yards, and N=1 section of 5 yards;

The fabric is processed per Table 1, except for the 5 yards sample that is tested unprocessed for control;

For each test number, a sample of the solution is taken after it is mixed in the mixing tank, at approximately the middle of the fabric processing on the tenter frame and after the fabric is processed on the tenter frame bath; the solution is analyzed to quantify the silk solution concentration and determine any depletion rate at the tenter frame bath for fabric exposure;

During each trial, the first 5 meters of fabric sample are collected for testing, after approximately 110 meter additional 5 meter sample are collected, and the last 5 meter of processed fabric are collected;

After the fabric is cut during the middle of the run to collect the 5 meter sample, the fabric can be rolled on the same core;

All fabric rolls processed are assigned an identification number for traceability.

TABLE 57

Coating Processing Variables

| | Silk solution | Fabric length (yards) | Ph correction | Dry/cure temperature ° F. (° C.) |
|---|---|---|---|---|
| Trial 1 | 0.08% low MW + 0.02% medium MW (1:4 ratio) | 260 | 0.025% citric acid (50%) or to pH 4-5 | 302 (150) 70 seconds |
| Trial 2 | 0.15% low MW + 0.05% medium MW (1:3 ratio) | 268 | 0.025% citric acid (50%) or to pH 4-5 | 302 (150) 70 seconds |
| Trial 3 | 0.5% low MW | 208 | 0.025% citric acid (50%) or to pH 4-5 | 302 (150) 70 seconds |
| Control no finishing (Trial 1) | Control no coating | 5 | N/A | N/A |
| Control (Trial 1) | Control no coating (water bath) | 35 | N/A | 302 (150) 70 seconds |

Abrasion Method:
  Fabric is not laundered;
  Abradand: worsted wool;
  Mass of Weight=9 kPa for apparel fabrics;
  Abrasion cycle for the Martindale Abrasion Tester, 16 rubs required to complete a geometric shape, known as a Lissajous Figure (geometric figure that starts as a straight line, then becomes a widening ellipse, and narrows to again become a straight line; there are 16 rubs in one Lissajous figure); rub=one rotation of the two outer gears of the Martindale Abrasion Tester;
  Testing Conditions: 21° C. (2° C.) and 65% RH (±5% RH);
  End of test confirmed under a microscope for see through hole.
  Interim results: the abrasion test is completed on N=3 samples; sample #1 was voluntary stopped at 1,388,251 cycles; sample #2 was voluntary stopped at 585,696 cycles. For comparative purposes, a sock normally wears at 5,000-10,000 cycles; 25,000 cycles typically represent a 95 percentile result.

Example 10. Preparation of Silk Gels

TABLE 58

Gel Samples - Silk gel formulations including additives, concentration of silk and additive, gelation conditions and gelation times.

| Sample Name | mL 2% silk solution | Mass Vit C (g) | Ratio silk: Vit C | Additive | Amount of additive | Temp/ Treatment | Days to Gelation |
|---|---|---|---|---|---|---|---|
| 1 | 10 | 0.04 | 5:01 | None | None | RT | 8 |
| 2 | 10 | 0.08 | 2.5:1 | None | None | RT | 8 |
| 3 | 10 | 0.2 | 1:01 | None | None | RT | 8 |
| 4 | 10 | 0.4 | 1:02 | None | None | RT | 14 |
| 5 | 10 | 0.8 | 1:04 | None | None | RT | None |
| 6 | 10 | 0.04 | 5:01 | None | None | Fridge | ~39 |
| 7 | 10 | 0.08 | 2.5:1 | None | None | Fridge | ~39 |
| 8 | 10 | 0.2 | 1:01 | None | None | Fridge | ~39 |
| 9 | 10 | 0.4 | 1:02 | None | None | Fridge | None |
| 10 | 10 | 0.8 | 1:04 | None | None | Fridge | None |
| 11 | 10 | 0.2 | 1:01 | None | None | RT/Shake vigorously | 8 |
| O-1 | 10 | 0.04 | 5:01 | None | None | 37° C. Oven | 3 |
| O-2 | 10 | 0.04 | 5:01 | None | None | 50° C. Oven | 2 |
| O-3 | 10 | 0.2 | 1:01 | None | None | 37° C. Oven | 4 |

TABLE 58-continued

Gel Samples - Silk gel formulations including additives, concentration of silk and additive, gelation conditions and gelation times.

| Sample Name | mL 2% silk solution | Mass Vit C (g) | Ratio silk:Vit C | Additive | Amount of additive | Temp/Treatment | Days to Gelation |
|---|---|---|---|---|---|---|---|
| O-4 | 10 | 0.2 | 1:01 | None | None | 50° C. Oven | 3 |
| M | 40 | 0.16 | 5:01 | None | None | RT | 5 |
| D | 40 | 0.16 | 5:01 | None | None | RT | 5 |
| E1 | 10 | 0.04 | 5:01 | Vit E | 1 drop | RT | 7 |
| E2 | 10 | 0.04 | 5:01 | Vit E | 3 drops | RT | 7 |
| E3 | 10 | 0 | None | Vit E | 1 drop | RT | None |
| E4 | 10 | 0 | None | Vit E | 3 drops | RT | None |
| L1 | 10 | 0.04 | 5:01 | Lemon | 300 µL | RT | 6 |
| L2 | 10 | 0.04 | 5:01 | Lemon Juice | 300 µL | RT | 6 |
| L3 | 10 | 0.04 | 5:01 | Lemon Juice | 1000 µL | RT | 5 |
| L4 | 10 | 0 | None | Lemon | 300 µL | RT | 6 |
| L5 | 10 | 0 | None | Lemon Juice | 300 µL | RT | 7 |
| Jar 1 | 20 | 0.08 | 5:01 | Lemon Juice | 2000 µL | RT | 5-7 |
| Jar 2 | 5 | 0.02 | 5:01 | Lemongrass Oil | 1 drop | RT | 2-3 |
| R-1 | 10 | 0.04 | 5:01 | Rosemary Oil | 1 drop | RT | 7 |
| T-1 | 10 | 0.04 | 5:01 | None | None | RT/Tube | 7 |
| RO-1 | 10 | 0.04 | 5:01 | Rose Oil | 1 drop | RT | 6 |
| RO-2 | 10 | None | None | Rose Oil | 1 drop | RT | None |

Ratio of Silk to Vitamin C

Samples 1-10 were used to examine the effect of silk to vitamin C ratio on serum gelation. Samples 1-3 with less vitamin C gelled quicker than samples 4 and 5. All other conditions were kept constant. Samples 6-8 with less vitamin C gelled quicker than samples 9 and 10. All other conditions were kept constant. It is concluded that decreasing the ratio of silk to vitamin C (increasing the amount of vitamin C), will lengthen the time to gel creation. At ratios with small amounts of vitamin C, days to gel creation did not vary greatly.

Physical Stimulation

Samples 3 and 11 were used to examine the effect of physical stimulation on serum gelation. Each sample was prepared under the same conditions. Sample 11 was vigorously shaken for about 3 minutes after addition of vitamin C. Treatment of 3 and 11 was otherwise the same. The shaking resulted in bubbles but did not significantly change gel creation time.

Temperature Treatment

Samples 1, 3, 6, 8, O-1, O-2, O-3, and O-4 were used to examine the effect of temperature treatment on serum gelation time. Samples 1, 6, O-1, and O-2 were identical other than temperature treatment. Samples 3, 8, O-3, and O-4 were identical other than temperature treatment. The two groups differed in silk to vitamin C ratio. Time to serum gelation was directly related to temperature treatment with a higher temperature resulting in quicker serum gelation.

Solution Volume

Samples 1, M and D were used to examine the effect of solution volume on serum gelation time. Samples M and D varied from sample 1 only by an increased solution volume. Samples M and D gelled in 5 days while sample 1 gelled in 8 days. Samples M and D were definitively noticed to be gelled on the day of gelling while sample 1 gelled over a weekend.

Additives

Samples E1, E2, E3, E4, L1, L2, L3, L4, L5, Jar 2, R1, RO-1 and RO-2 were used to examine the effect of additives on serum gelation time. Samples E1-4 contained Vitamin E. Only samples E1 and E2 contained vitamin C and only these two samples gelled. Vitamin E can be added to a solution to become a gel but it appears that another additive may be needed to create a gel. Samples L1-5 contained a form of lemon juice. Samples L1 and L4 had juice directly from a lemon while samples L2, L3 and L5 contained lemon juice from a plastic lemon container. Samples L4 and L5 did not have vitamin C while all others did. All samples gelled showing that lemon juice can create gel on its own. Amount of lemon juice and type of lemon juice had little effect on gelation time. Sample Jar 2 contained lemon grass oil which formed an albumen like substance when initially added. This sample also had vitamin C but gelation time was significantly quicker than with other vitamin C samples. Sample R1 contained rosemary oil, which seemed to be soluble, as well as vitamin C. The sample gelled in a similar time frame to other samples with only vitamin C. Samples RO-1 and RO-2 contained rose oil while only RO-1 had vitamin C. Only RO-1 gelled showing that rose oil will not create a gel quickly on its own. In both cases the rose oil was immiscible and visible as yellow bubbles.

Aqueous silk fibroin-based fragment solution and essential oils are immiscible liquids. In an embodiment, to increase the fragrance of the silk fibroin-based fragment solution, without entrapping oils within the solution, the solution is mixed with the essential oil with the use of a stir bar. The stir bar is rotated at a speed such that some turbulence is observed in the mixture, thus causing contact between the fragrant essential oil and the molecules in solution, adding a scent to the solution. Before casting of product from the solution, mixing may be stopped and the oil allowed to separate to the top of the solution. Dispensing from the bottom fraction of the solution into the final product allows for fragrance without visible essential oil within the final product.

Alternatively, the silk fibroin-based solution and essential oil can be combined with or without additional ingredients and/or an emulsifier to create a composition containing both ingredients.

In an embodiment, mixing of the solution as described above can reduce gelation time if the solution is used to create a gel formulation.

Vessel

Samples T1 and Jar 1 were used to examine the effect of casting vessel on serum gelation time. Jar 1 was cast in a glass jar while T1 was cast in an aluminum tube. Both samples gelled and did not affect serum gel time.

SUMMARY

All treatments of silk solution for gel solution were in a conical tube at room temperature unless otherwise stated. The ratio of silk to vitamin C did affect the ability of a solution to gel as ratios above 1:2 did not gel and a 1:2 ratio took twice as long as other lower ratios (5:1, 2.5:1, 1:1). Temperature affected gel creation time with higher temperatures resulting in quicker gel times. 50° C. treatment gelled in as quick as 2 days, 37° C. treatment gelled in as quick as 3 days, room temperature treatment gelled in 5-8 days and storage in a refrigerator took at least 39 days to gel. The effects of additives on gel creation were dependent on the additive. Vitamin E, Rosemary Oil and Rose Oil all had no effect on gel creation. Each of these additives did not prevent gelation or affect the time to gelation. Each also required the presence of vitamin C to gel. Lemon juice from a fresh lemon, pre-squeezed lemon juice from a plastic lemon container and lemon grass oil did affect gel creation. Without wishing to be bound by theory, it is believed that the lower pH as a result of these additives is the reason the additives had an impact on decreasing gelation time. Both lemon juice types were able to cause gelation without the presence of vitamin C. This occurred in the same number of days as with vitamin C. The lemongrass oil was able to decrease the number of days to gelation to 2-3 days. All additives appeared soluble other than lemongrass oil and rose oil. Rose oil remained in yellow bubbles while the lemongrass oil was partially soluble and formed an albumen like chunk. In an embodiment, oils that are not fully soluble, can still be suspended within the gel as an additive. Physical stimulation by shaking, vessel the solution was cast into and solution volume did not affect gelation time.

TABLE 59

Concentration of vitamin C in various gel formulations.

| Sample Info | Sample Weight (mg) | Concentration of Vitamin C (mg/g) In Sample | Average |
|---|---|---|---|
| Rosemary (Room Temperature storage) | 685.7 | 3.2511 3.2804 | 3.2657 |
| | 638 | 3.3336 3.3332 | 3.3334 |
| Lemongrass (Room Temperature storage) | 646 | 2.8672 2.8868 | 2.877 |
| | 645.5 | 2.9051 2.9052 | 2.9051 |
| Rosemary (Room Temperature; Foil Covered storage) | 645.2 | 3.9063 3.923 | 3.9147 |
| | 649 | 3.9443 3.9305 | 3.9374 |
| Lemongrass (Room Temperature; Foil Covered storage) | 630.1 | 3.8253 3.8295 | 3.8274 |
| | 660.4 | 3.8283 3.8222 | 3.8253 |

TABLE 59-continued

Concentration of vitamin C in various gel formulations.

| Sample Info | Sample Weight (mg) | Concentration of Vitamin C (mg/g) In Sample | Average |
|---|---|---|---|
| Rosemary (Fridge, Foil Covered storage) | 672.4 | 5.1616 5.1352 | 5.1484 |
| | 616.5 | 5.1984 5.2036 | 5.201 |
| Lemongrass (Fridge, Foil Covered storage) | 640.5 | 5.1871 5.1776 | 5.1824 |
| | 627.7 | 5.2098 5.2154 | 5.2126 |

Example 11. Preparation of Silk Gels

Additional gels may be prepared according to Table 60, Table 61, Table 62, and Table 63.

TABLE 60

Lemongrass Gel

| | |
|---|---|
| % Silk Solution | 2% |
| Quantity Vitamin C | 100 mg/15 mL solution |
| Quantity Lemongrass Oil | 20 µL/15 mL solution |

TABLE 61

Rosemary Gel

| | |
|---|---|
| % Silk Solution | 2% |
| Quantity Vitamin C | 100 mg/15 mL solution |
| Quantity Rosemary Oil | 20 µL/50 mL solution |

TABLE 62

Lemongrass Gel (50 mL)

| | |
|---|---|
| % Silk Solution (60 minute boil, 25 kDa) | 2% |
| Quantity Vitamin C (ascorbyl glucoside) | 12.82 mg/mL solution (641 mg total) |
| Quantity Lemongrass Oil | 1.33 µL/mL solution |
| pH | 4 |

TABLE 63

Rosemary Gel (50 mL)

| | |
|---|---|
| % Silk Solution (60 minute boil, 25 kDa) | 2% |
| Quantity Vitamin C (ascorbyl glucoside) | 12.82 mg/mL solution (641 mg total) |
| Quantity Rosemary Oil | 0.8 µL/mL solution |
| pH | 4 |

Gels of the present disclosure can be made with about 0.5% to about 8% silk solutions. Gels of the present disclosure can be made with ascorbyl glucoside at concentrations of about 0.67 to about 5% w/v. Gels of the present disclosure be clear/white in color. Gels of the present disclosure can have a consistency that is easily spread and absorbed by the skin. Gels of the present disclosure can produce no visual residue or oily feel after application. Gels of the present disclosure do not brown over time.

Silk gels with essential oils were prepared by diluting a silk solution of the present disclosure to 2%. Vitamin C was added to the solution and allowed to dissolve. The essential oil was added, stirred and dissolved. The solution was aliquot into jars.

Example 12. Coating Fabrics with Aqueous Silk Solutions

TABLE 64

Silk Solution Characteristics

| Molecular Weight: | 57 kDa | | | |
|---|---|---|---|---|
| Polydispersity: | 1.6 | | | |
| % Silk | 5.0% | 3.0% | 1.0% | 0.5% |
| Process Parameters Extraction | | | | |
| Boil Time: | 30 minutes | | | |
| Boil Temperature: | 100° C. | | | |
| Rinse Temperature: | 60° C. | | | |
| Dissolution | | | | |
| LiBr Temperature: | 100° C. | | | |
| Oven Temperature: | 100° C. | | | |
| Oven Time: | 60 minutes | | | |

Silk Solution and Silk Gel Application to Fabric and Yarn Samples

Three 50 mm diameter fabric samples from each of three different fabric materials, cotton, polyester, and nylon/LYCRA®, were placed in plastic containers. about 0.3 mL of about 5.80 silk fibroin solution was deposited using a 1 mL syringe and 18-gauge needle on two samples of each material, and allowed to sit for about 1 minute. About 0.3 mL of denatured alcohol (containing methanol and ethanol) was then deposited using a 1 mL syringe and 30-gauge needle on one of the silk-coated samples of each material.

In an additional experiment, silk gel with Rosemary Essential Oil (water, silk, ascorbyl glucoside, rosemary essential oil) was collected on a tip and applied to half the length of 2 pieces of 400 μm tencel yarn. One sample was then wetted with about 0.3 mL alcohol.

Silk Solution Dip Test

Polyester fabric samples were dipped in silk fibroin solutions of varying concentration. Samples were placed in incubator with air flow on foil and allowed to dry at about 22.5° C. for about 15.5 hours. Change in mass before and after silk coating was measured.

TABLE 66

Polyester Fabric Samples with Silk Coatings of the Present Disclosure

| Silk Fibroin Concentration (%) | Starting Mass (g) | Mass after coating (g) | Change (%) | Average Change (%) |
|---|---|---|---|---|
| 1 | 0.25 | 0.26 | +4 | -3% |
| | 0.30 | 0.27 | -10 | |
| | 0.24 | 0.24 | 0 | |
| | 0.22 | 0.21 | -5 | |
| 3 | 0.30 | 0.36 | +20 | 15% |
| | 0.28 | 0.31 | +11 | |
| | 0.29 | 0.33 | +14 | |
| | 0.29 | 0.34 | +15 | |
| 5 | 0.25 | 0.29 | +16 | 16% |
| | 0.28 | 0.33 | +18 | |
| | 0.31 | 0.35 | +13 | |
| | 0.27 | 0.31 | +15 | |

Silk Solution Spray Test

A spray test was performed to verify the handle impact of silk fibroin solution sprayed on polyester fabric. About 0.5 silk fibroin solution was applied to a 4 inch by 4 inch square of polyester fabric using a spray gun from a distance of about 10 inches. Three passes were completed from left to right and from right to left (six passes total). Samples were placed in a 50° C. oven on aluminum foil over a water bath for about 1.5 hours. Methods were repeated with a second polyester fabric sample with an about 5.8 silk fibroin solution spray application. No change in material hand was observed in samples sprayed with either 0.50% or 5.8% solutions. Perceived increase in materials smoothness was observed for samples sprayed with either the 0.50 and 5.80 solutions.

Example 13. Optimized Fabric Coating Processes

The coating processes described in Table 67 were used to produce multiple fabric samples for performance testing, as described in more detail below.

TABLE 67

Coating Processes.

| | |
|---|---|
| 1 Spray | |
| 1.1 | Material for coating |
| 1.1.1 | cork board 24" × 36" Hobby Lobby part 132894 |
| 1.1.2 | Covered the cork board with polyester interlock fabric |
| 1.1.3 | Saw horse for support |
| 1.1.4 | Several clamps for holding cork panel to saw horse |
| 1.1.5 | Double filter to remove oil residue from compressor and dehumidificaton salt |
| 1.1.6 | Iwata eclipse MP-CS airbrush |
| 1.1.7 | Husky 30.3 liter tank compression system |
| 1.1.8 | Push pin to hold fabric on cork panel Hobby Lobby part #523456 |
| 1.2 | Material for preparation |
| 1.2.1 | Scissor |
| 1.2.2 | Ruler |
| 1.2.3 | Balance AWS model Pnx-203 |
| 1.3 | Material for drying |
| 1.3.1 | Wolf stove set up at 150° F. maintaining 71-78° C. with fan system. |
| 1.3.2 | Flat baking sheet |
| 1.3.3 | Aluminum foil |
| 1.3.4 | SC 307T thermometer with probe |
| 1.4 | Execution |
| 1.1.1 | lay fabric to be coated on top of cork panel covered with polyester fabric |
| 1.1.2 | secure fabric with pin to the cork panel |
| 1.1.3 | set compressor with oil and humidity filters |
| 1.1.4 | set air pressure supply to 55 psi |
| 1.1.5 | load solution to airbrush gun |
| 1.1.6 | position airbrush gun approximately 10 inches from board |
| 1.1.7 | pull the airbrush gun trigger and over spray 2 inches side to side the fabric to be coated |
| 1.1.8 | remove pin from cork panel and place coated fabric on aluminum foil |
| 1.1.9 | place coated fabric in oven for 30-60 min at 150° C. |
| 2 Stencil/Spray | |
| 2.1 | Material for coating |
| 2.1.1 | cork board 24" × 36" Hobby Lobby part 132894 |
| 2.1.2 | Covered the cork board with polyester interlock fabric |
| 2.1.3 | Saw horse for support |
| 2.1.4 | Several clamps for holding cork panel to saw horse |
| 2.1.5 | Double filter to remove oil residue from compressor and dehumidification salt |
| 2.1.6 | Iwata eclipse MP-CS airbrush |
| 2.1.7 | Husky 30.3 liter tank compression system |
| 2.1.8 | Push pin to hold fabric on cork panel Hobby Lobby part #523456 |
| 2.1.9 | Stencil pattern SKU #75244 Lincaine 12" × 24" × 0.020" Hobby Lobby |

TABLE 67-continued

Coating Processes.

| | | |
|---|---|---|
| 2.2 | Material for preparation | |
| 2.2.1 | Scissor | |
| 2.2.2 | Ruler | |
| 2.2.3 | Balance AWS model Pnx-203 | |
| 2.3 | Material for drying | |
| 2.3.1 | Wolf stove set up at 150° F. maintaining 71-78° C. with fan system. | |
| 2.3.2 | Flat baking sheet | |
| 2.3.3 | Aluminum foil | |
| 2.3.4 | SC 307T thermometer with probe | |
| 2.4 | Execution | |
| 2.4.1 | lay fabric to be coated on top of cork panel covered with polyester fabric | |
| 2.4.2 | lay stencil pattern on top of fabric | |
| 2.4.3 | secure stencil with pin to the cork panel | |
| 2.4.4 | set compressor with oil and humidity filters | |
| 2.4.5 | set air pressure supply to 55 psi | |
| 2.4.6 | load solution to airbrush gun | |
| 2.4.7 | position airbrush gun approximately 10 inches from board | |
| 2.4.8 | pull the airbrush gun trigger and over spray 2 inches side to side the fabric to be coated | |
| 2.4.9 | remove pin from cork panel and place coated fabric on aluminum foil | |
| 2.4.10 | place coated fabric in oven for 30-60 min at 150° C. | |
| 3 Screen print | | |
| 3.1 | Material for coating | |
| 3.1.1 | cork board 24" x 36" Hobby Lobby part 132894 | |
| 3.1.2 | Covered the cork board with polyester interlock fabric | |
| 3.1.3 | Saw horse for support | |
| 3.1.4 | Several clamps for holding cork panel to saw horse | |
| 3.1.5 | screen print frame 12" x 18" part #4710 made by Speed Ball | |
| 3.1.6 | silicon spatula | |
| 3.2 | Material for preparation | |
| 3.2.1 | Scissor | |
| 3.2.2 | Ruler | |
| 3.2.3 | Balance AWS model Pnx-203 | |
| 3.3 | Material for drying | |
| 3.3.1 | Wolf stove set up at 150° F. maintaining 71-78° C. with fan system. | |
| 3.3.2 | Flat baking sheet | |
| 3.3.3 | Aluminum foil | |
| 3.3.4 | SC 307T thermometer with probe | |
| 3.4 | Execution | |
| 3.4.1 | lay fabric to be coated on top of cork panel covered with polyester fabric | |
| 3.4.2 | lay screen print frame on top of fabric | |
| 3.4.3 | load solution to one edge of the screen print frame | |
| 3.4.4 | with a silicon spatula move solution across the screen print frame until the entire fabric to be coated surface is covered | |
| 3.4.5 | remove screen print frame and place coated fabric on aluminum foil | |
| 3.4.6 | place coated fabric in oven for 30-60 min at 150° C. | |
| 4 Bath | | |
| 4.1 | Material for coating | |
| 4.1.1 | cork board 24" x 36" Hobby Lobby part 132894 | |
| 4.1.2 | Covered the cork board with polyester interlock fabric | |
| 4.1.3 | Saw horse for support | |
| 4.1.4 | Several clamps for holding cork panel to saw horse | |
| 4.1.5 | Paint tray liner Item #: 170418 Model #: LOWES0-PK170418 at Lowes Hardware | |
| 4.1.6 | Noodle making machine Imperia model #15-4590 | |
| 4.2 | Material for preparation | |
| 4.2.1 | Scissor | |
| 4.2.2 | Ruler | |
| 4.2.3 | Balance AWS model Pnx-203 | |
| 4.3 | Material for drying | |
| 4.3.1 | Wolf stove set up at 150° F. maintaining 71-78° C. with fans ystem. | |
| 4.3.2 | Flat baking sheet | |
| 4.3.3 | Aluminum foil | |
| 4.3.4 | SC 307T thermometer with probe | |
| 4.4 | Execution | |
| 4.4.1 | load silk solution inside the paint tray liner well | |
| 4.4.2 | immerse the fabric sample to be coated inside the silk solution until it is all saturated | |
| 4.4.3 | pass the saturated fabric between pressure roller (noodle making machine) to remove any excess solution | |
| 4.4.4 | place coated fabric on aluminum foil | |
| 4.4.5 | place coated fabric in oven for 30-60 min at 150° C. | |

The products produced using the coating processes described above were tested for accumulative one-way transport capability (or index) and other properties using Association of Textile, Apparel & Materials Professionals (AATCC) test method 195-2012 for the measurement, evaluation, and classification of liquid moisture management properties of textile fabrics. The details of the test methods are available from AATCC, and a synopsis of the methods and calculations is provided here. The absorption rate (ART) (top surface) and (ARB) (bottom surface) is defined as the average speed of liquid moisture absorption for the top and bottom surfaces of the specimen during the initial change of water content during a test. The accumulative one-way transport capability (R) is defined as the difference between the area of the liquid moisture content curves of the top and bottom surfaces of a specimen with respect to time. The bottom surface (B) is defined for testing purposes as the side of the specimen placed down against the lower electrical sensor which is the side of the fabric that would be the outer exposed surface of a garment when it is worn or product when it is used. The top surface (T) for testing purposes is defined as the side of a specimen that, when the specimen is placed on the lower electrical sensor, is facing the upper sensor. This is the side of the fabric that would come in contact with the skin when a garment is worn or when a product is used. The maximum wetted radius (MWRT) and (MWRB) (mm) is defined as the greatest ring radius measured on the top and bottom surfaces. Moisture management is defined, for liquid moisture management testing, as the engineered or inherent transport of aqueous liquids such as perspiration or water (relates to comfort) and includes both liquid and vapor forms of water. The overall (liquid) moisture management capability (OMMC), an index of the overall capability of a fabric to transport liquid moisture as calculated by combining three measured attributes of performance: the liquid moisture absorption rate on the bottom surface (ARB), the one-way liquid transport capability (R), and the maximum liquid moisture spreading speed on the bottom surface ($SS_B$). The spreading speed ($SS_i$) is defined as the accumulated rate of surface wetting from the center of the specimen where the test solution is dropped to the maximum wetted radius. The total water content (U) (%) is defined as the sum of the percent water content of the top and bottom surfaces. The wetting time (WTT) (top surface) and (WTB) (bottom surface) is defined as the time in seconds when the top and bottom surfaces of the specimen begin to be wetted after the test is started.

A moisture management tester (MMT) is used to perform the test. The accumulative one-way liquid transport capability (R) is calculated as: [Area ($U_B$)–Area ($U_T$)]/total testing time. The OMMC is calculated as: OMMC=$C_1*AR_{B\_ndv}+C_2*R_{nvd}+C_3*SS_{B\_ndv}$, where $C_1$, $C_2$, and $C_3$ are the weighting values * for $AR_{B\_ndv}$, $R_{ndv}$ and $SS_{B\_ndv}$; ($AR_B$)=absorption rate; (R)=one-way transport capability, and ($SS_B$)=spreading speed. Detailed calculations of these parameters, and other parameters of interest, are provided in AATCC test method 195-2012.

A description of the samples used is given in Table 68.

TABLE 68

Description of samples.

| Sample ID | Description |
|---|---|
| 15051201 | no coating (polyester) |
| 15051301 | 1% silk solution spray coating on 15051201 |
| 15051302 | 0.1% silk solution spray coating on 15051201 |
| 15051303 | 0.05% silk solution spray coating on 15051201 |
| 15051304 | 1% silk solution spray stencil coating on 15051201 |
| 15051305 | 0.1% silk solution spray stencil coating on 15051201 |
| 15051306 | 0.05% silk solution spray stencil coating on 15051201 |
| 15051401 | 1% silk solution bath coating on 15051201 |
| 15051402 | 0.1% silk solution bath coating on 15051201 |
| 15051403 | 0.05% silk solution bath coating on 15051201 |
| 15051404 | PureProC screen print on 15051201 |
| 15042001 | non wicking finished |
| 15042002 | semifinished before final setting |
| 15042003 | with wicking finished |
| 15042101 | non wicking finished (15042001) 1% silk solution spray coating |
| 15042102 | non wicking finished (15042001) 0.1% silk solution spray coating |
| 15061206 | non wicking finished (15042001) 1% silk solution stencil coating |
| 15061207 | non wicking finished (15042001) 1% silk solution bath coating |
| 15061205 | non wicking finished (15042001) 0.1% silk solution stencil coating |
| 15061209 | non wicking finished (15042001) 0.1% silk solution bath coating |
| 15061201 | semifinished before final setting (15042002) 1% silk solution spray coating |
| 15061203 | semifinished before final setting (15042002) 1% silk solution stencil coating |
| 15061208 | semifinished before final setting (15042002) 1% silk solution bath coating |
| 15061202 | semifinished before final setting (15042002) 0.1% silk solution spray coating |
| 15061204 | semifinished before final setting (15042002) 0.1% silk solution stencil coating |
| 15061210 | semifinished before final setting (15042002) 0.1% silk solution bath coating |

The results of the tests are depicted in FIG. 33A through FIG. 62B and illustrate the superior performance of silk coated fabric, including superior performance with respect to accumulative one-way transport capability (index) and overall moisture management capability.

Example 14. Antimicrobial Properties of Silk Coatings on Fabrics

The antimicrobial properties of silk coatings were testing on four materials: a cotton/LYCRA jersey (15051201), a cotton/LYCRA jersey with 1% silk fibroin solution (sfs) bath coating (15070701), a polyester/LYCRA finish after final setting (15042003), and a polyester/LYCRA semi-finished 1% sfs bath coating (15070702) (wherein LYCRA is the trade name of a polyester-polyurethane copolymer). AATCC test method 100-2012 for the assessment of antibacterial finishes on textile materials was used. The details of the test method are available from AATCC. Briefly, the tests were performed using tryptic soy broth as a growth medium, a sample size of 4 layers, autoclave sterilization, 100 mL Letheen broth with Tween for neutralization, a target inoculation level of 1-2×10⁵ CFU/mL, 5% nutrient broth as an inoculant carrier and dilution medium, a contact time of 18 to 24 hours, and a temperature of 37+/−2° C.

The results of the tests are summarized in Table 69 and are depicted in FIG. 63 to FIG. 67, and illustrate the superior antimicrobial performance of the silk-coated fabrics.

TABLE 69

Antimicrobial test results.

| | | Results: cfu/sample | | |
|---|---|---|---|---|
| sample # | bacteria | Zero Contact Time | 24 hr Contact Time | Percent Reduction |
| 15051201 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15070701 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15042003 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15070702 | Staphylococcus aureus ATCC 6538 | 1.23E+05 | 1.03E+04 | 91.63% |
| | Klebsiella pneumoniae ATCC 4352 | 1.65E+05 | 2.33E+05 | −40.91% |

Example 15. Methods of Preparing Fabrics with Silk Coatings

A method for preparing an aqueous solution of pure silk fibroin-based protein fragments having an average weight average molecular weight ranging from about 6 kDa to about 17 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 17 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A method for preparing an aqueous solution of pure silk fibroin-based protein fragments having an average weight average molecular weight ranging from about 17 kDa to about 39 kDa includes the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 39 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A method for preparing an aqueous solution of pure silk fibroin-based protein fragments having an average weight average molecular weight ranging from about 39 kDa to about 80 kDa, includes the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

Example 16. Characterization of Silk Coatings on Polyester

Figure 68:
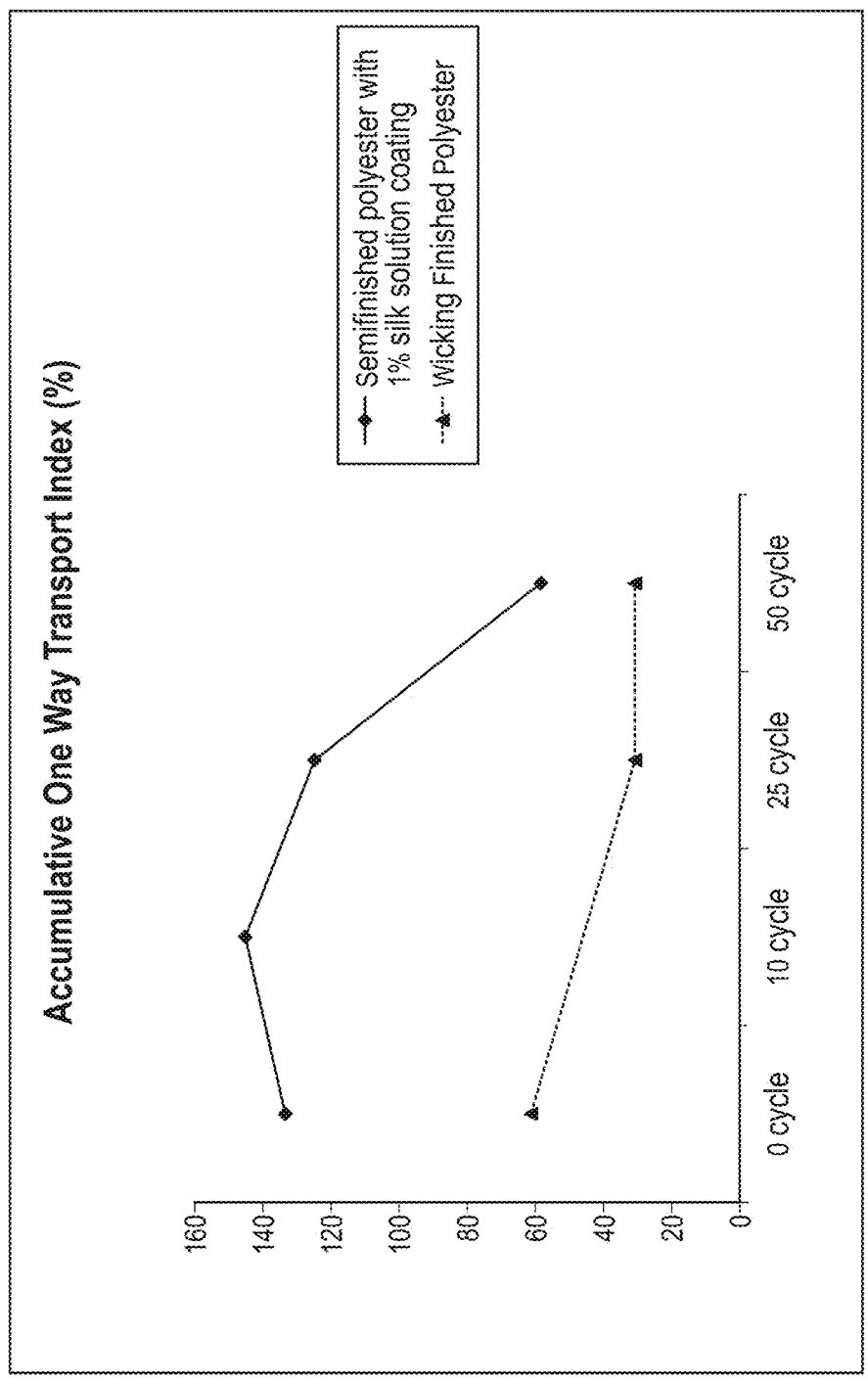
FIG. 68 illustrates accumulative one-way transport index versus fabric washing cycles.
Figure 69:
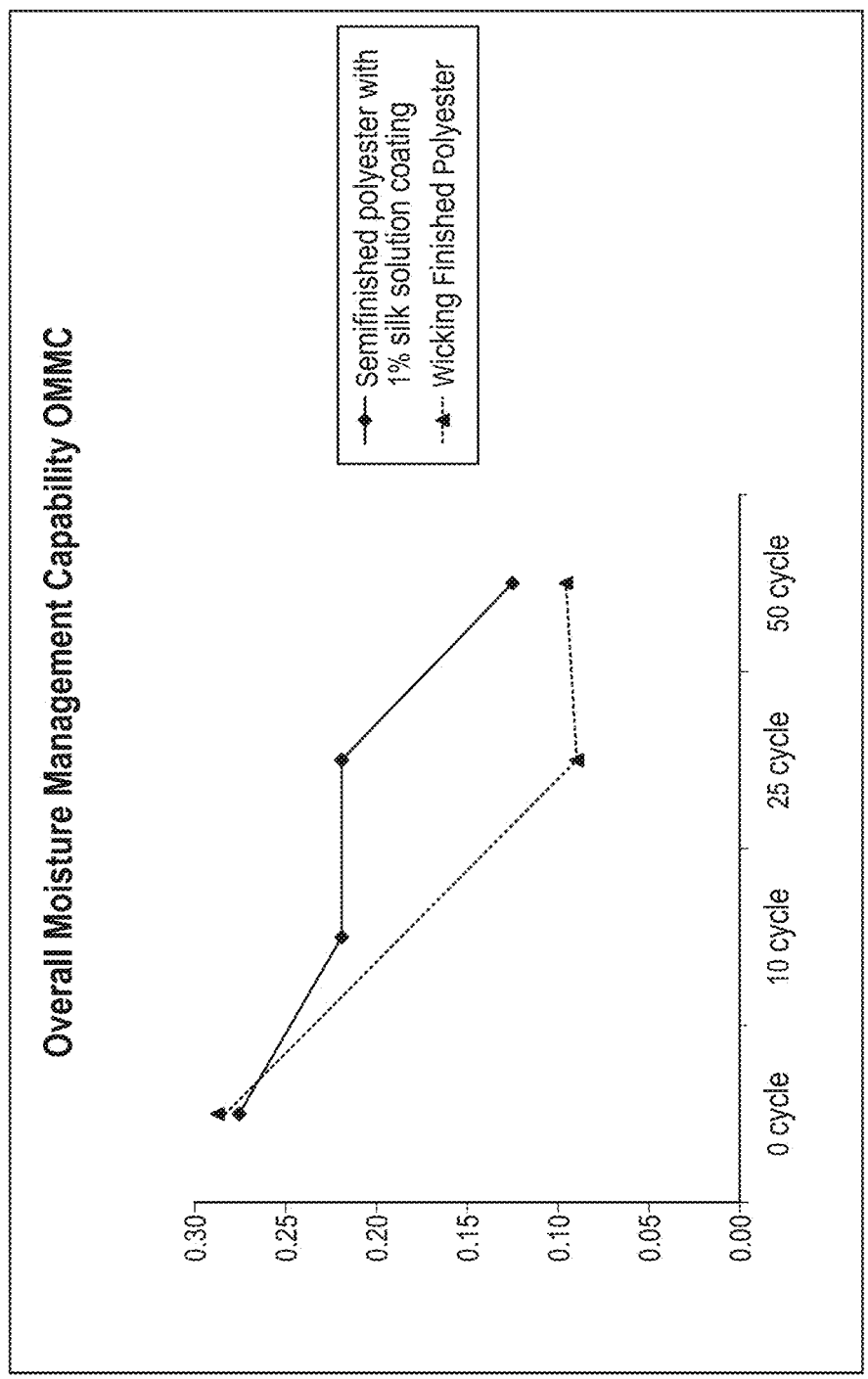
FIG. 69 illustrates overall moisture management capability (OMMC) versus fabric washing cycles.
Figure 70:
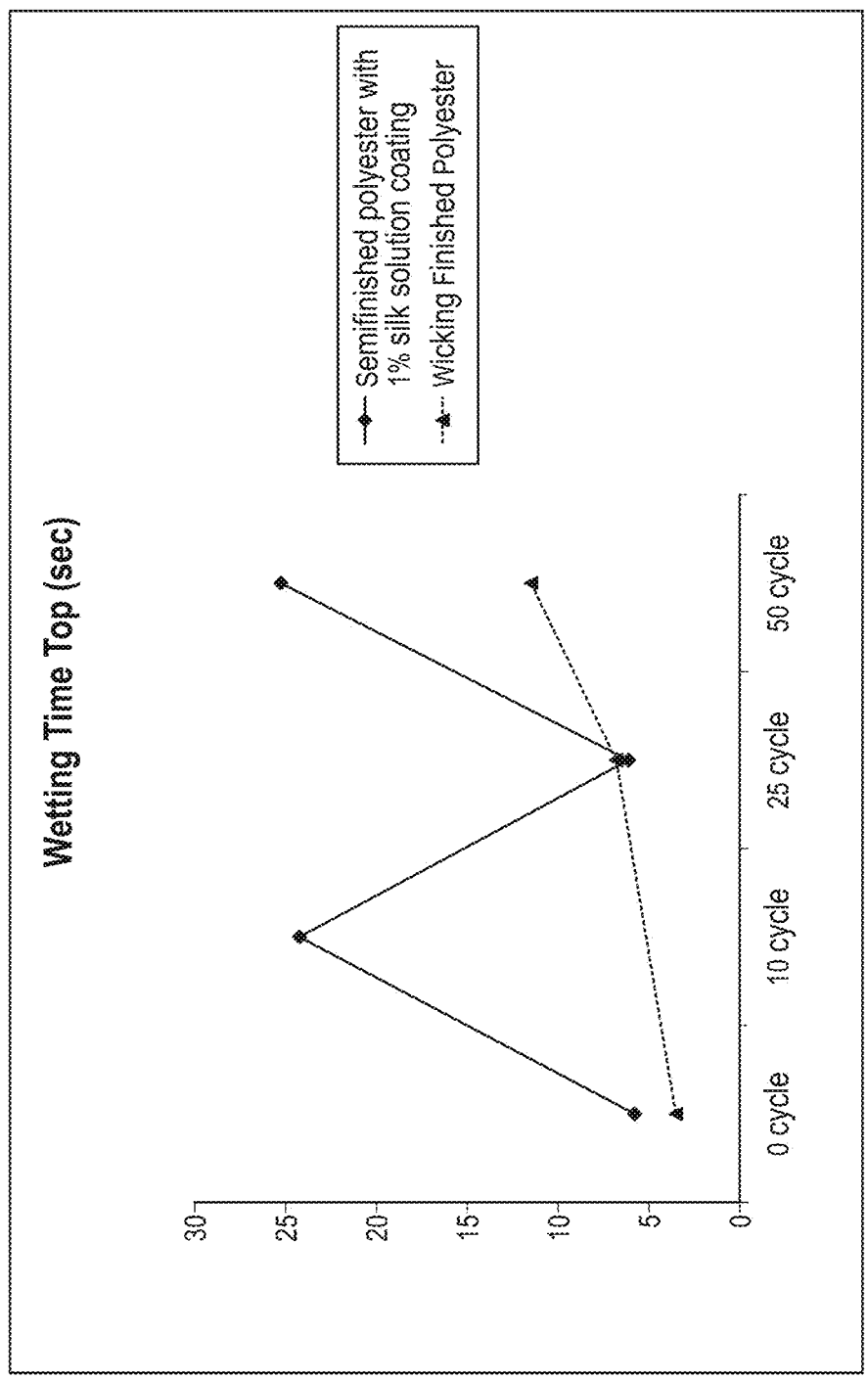
FIG. 70 illustrates wetting time at the top of the fabric versus fabric washing cycles.
Figure 71:
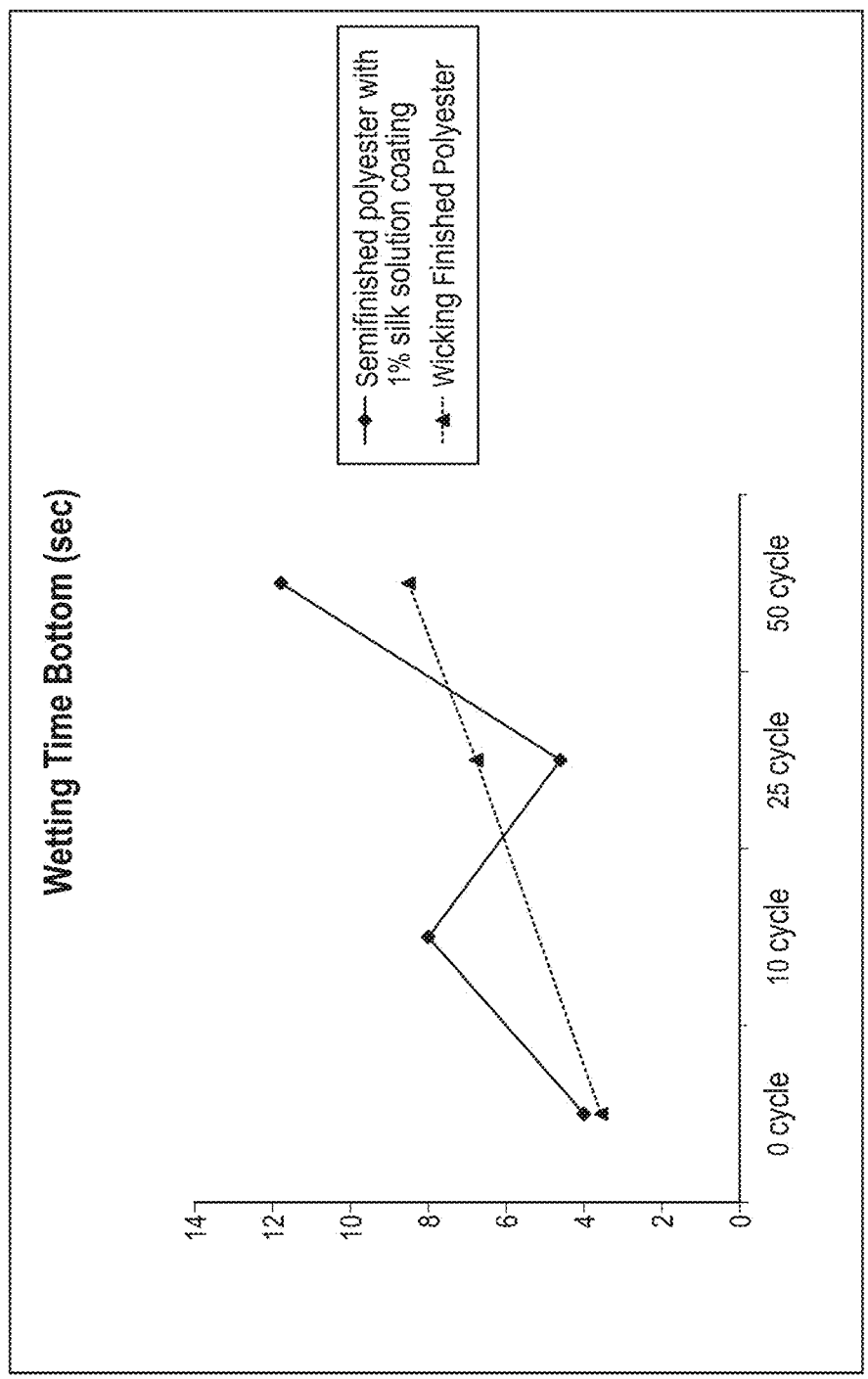
FIG. 71 illustrates wetting time at the bottom of the fabric versus fabric washing cycles.
Figure 72:
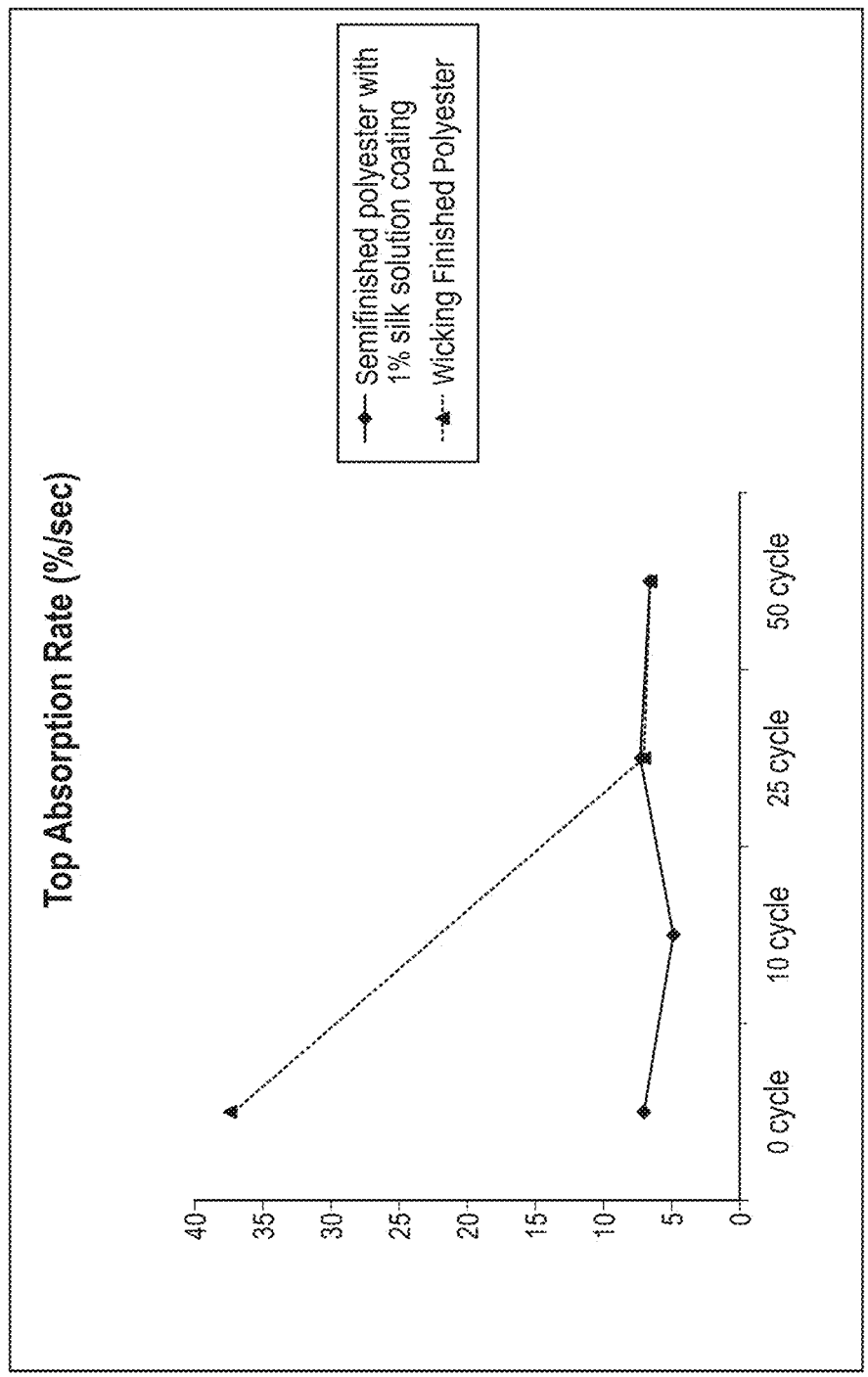
FIG. 72 illustrates absorption rate at the top of the fabric versus fabric washing cycles.
Figure 73:
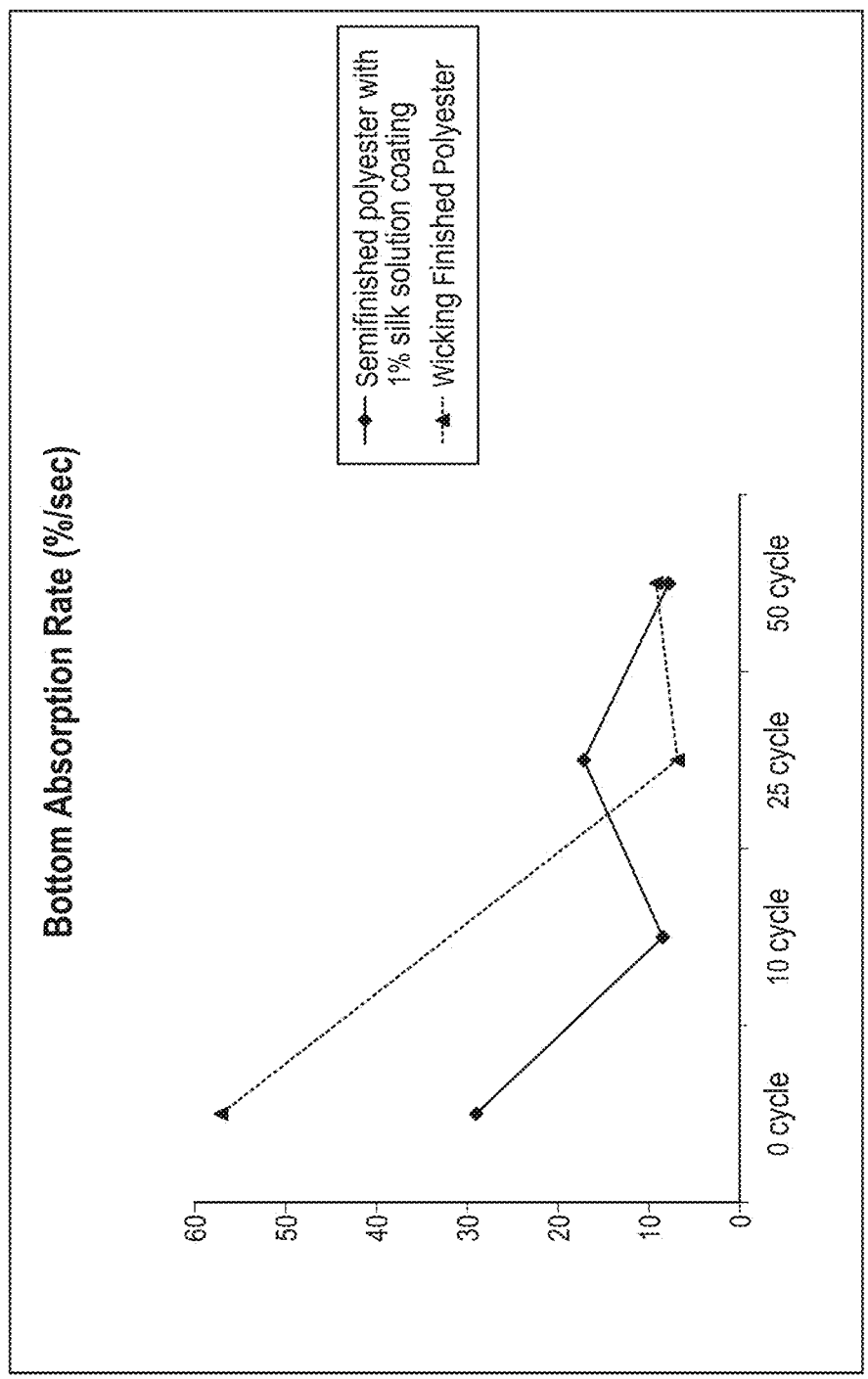
FIG. 73 illustrates absorption rate at the bottom of the fabric versus fabric washing cycles.
Figure 74:
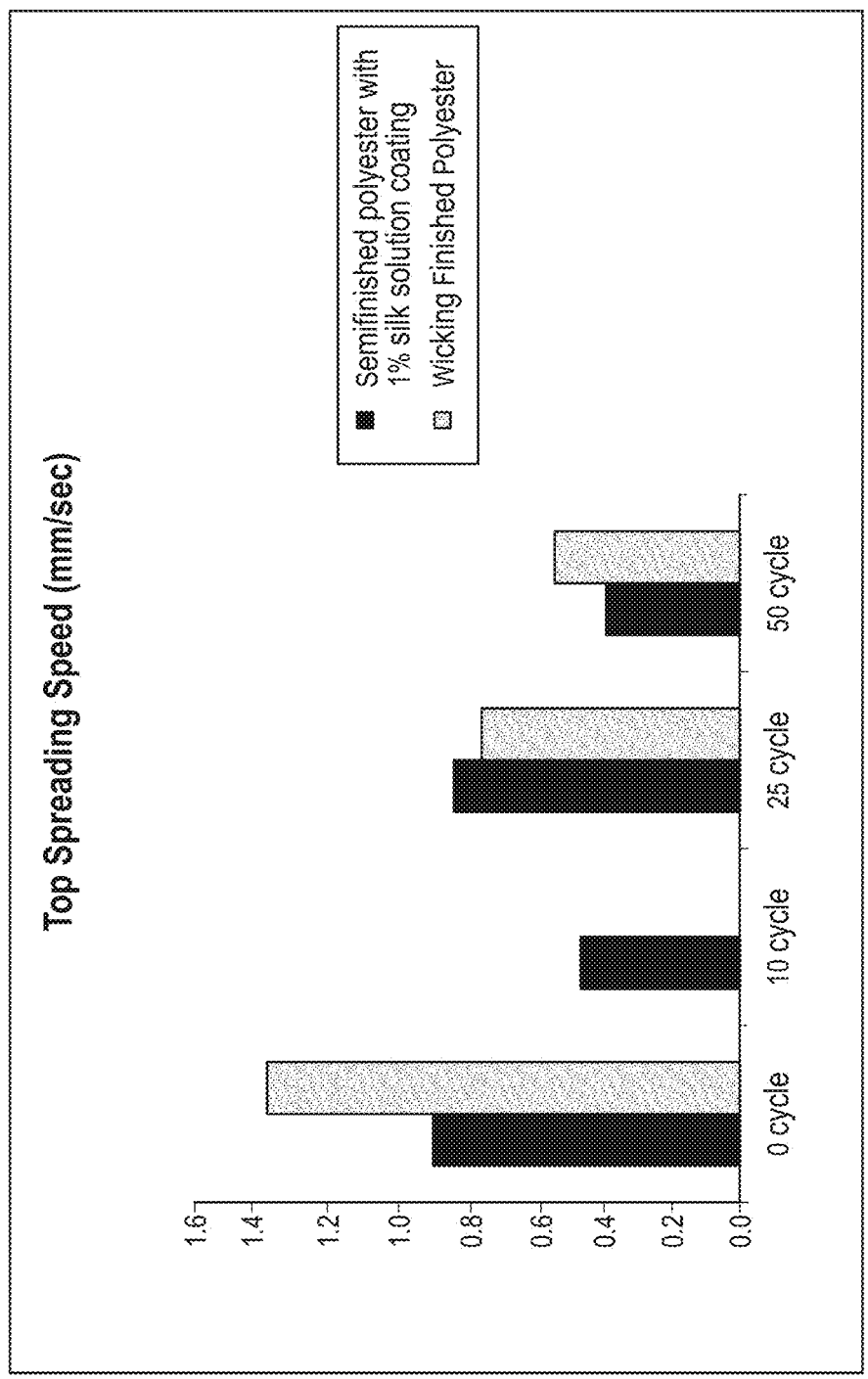
FIG. 74 illustrates spreading speed at the top of the fabric versus fabric washing cycles.
Figure 75:
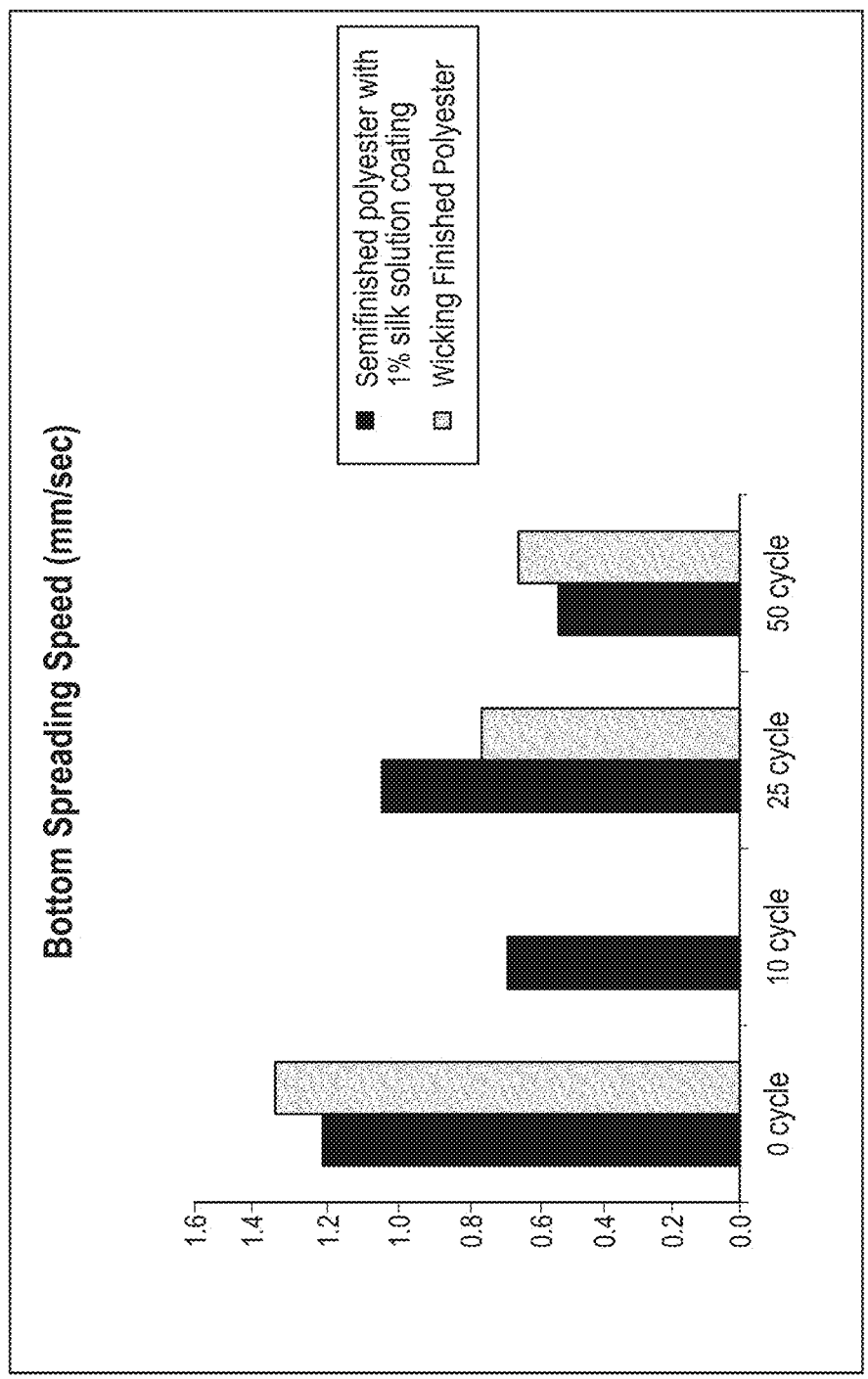
FIG. 75 illustrates spreading speed at the bottom of the fabric versus fabric washing cycles.
Figure 76:
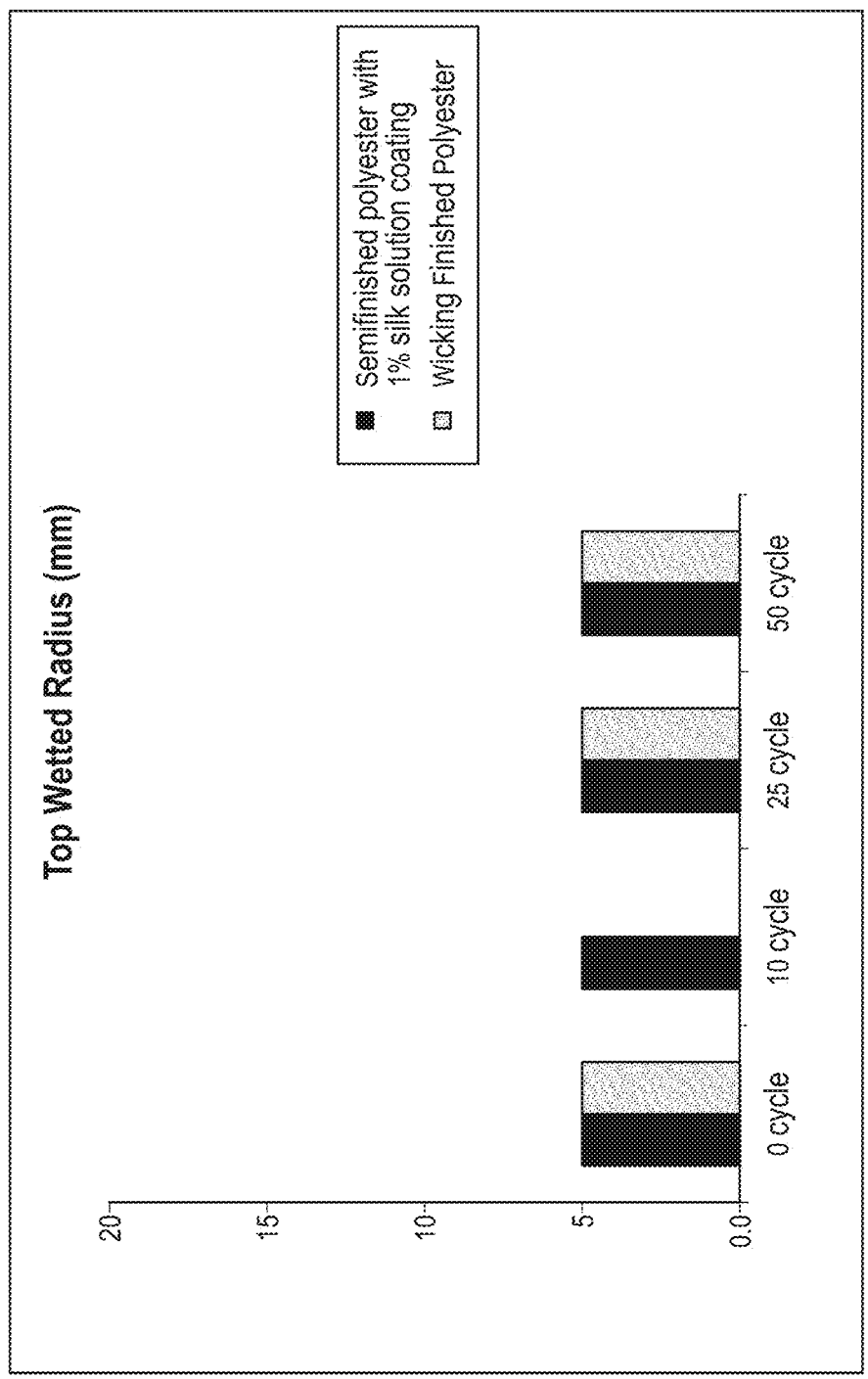
FIG. 76 illustrates wetted radius at the top of the fabric versus fabric washing cycles.
Figure 77:
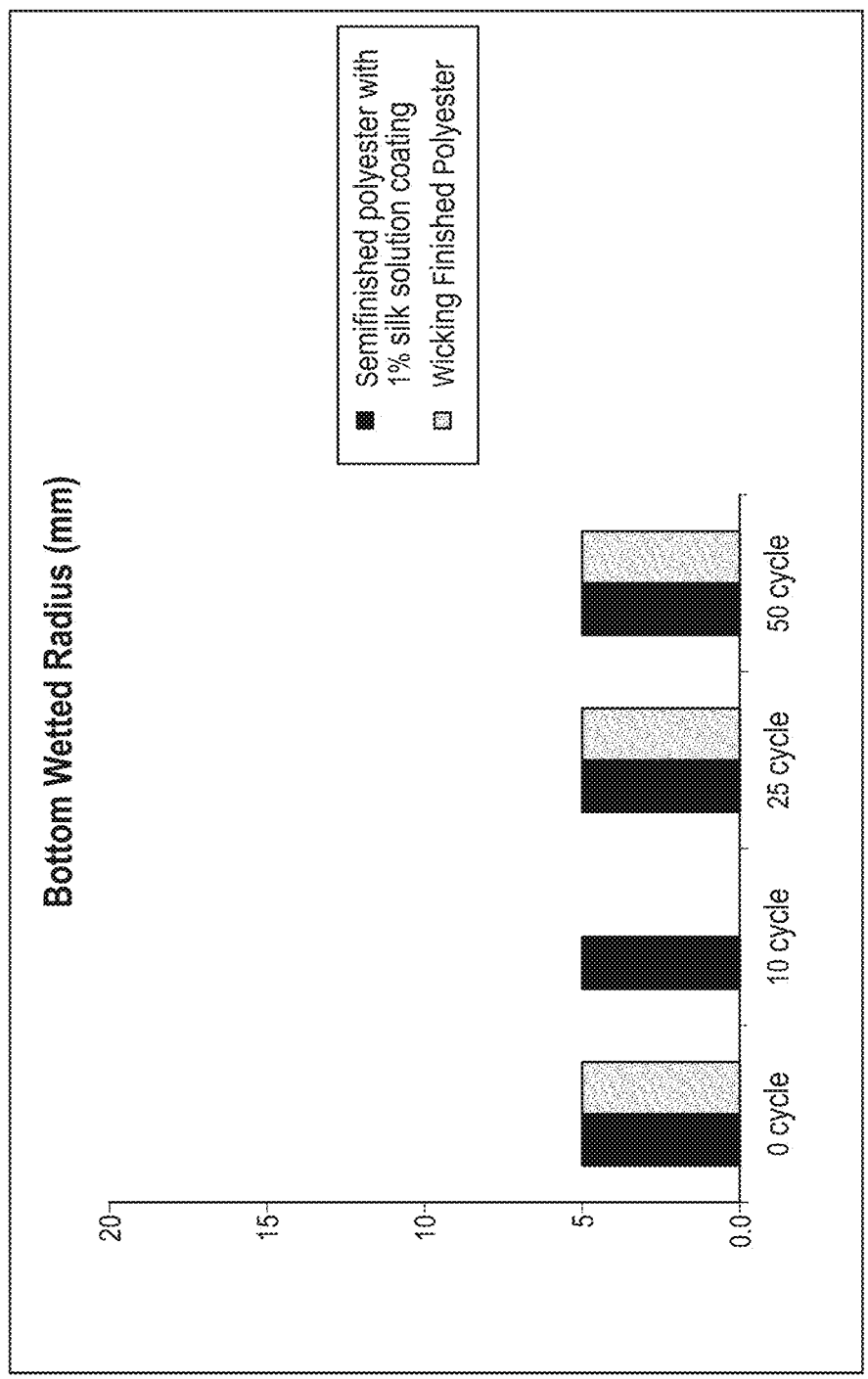
FIG. 77 illustrates wetted radius at the bottom of the fabric versus fabric washing cycles.
Figure 78:
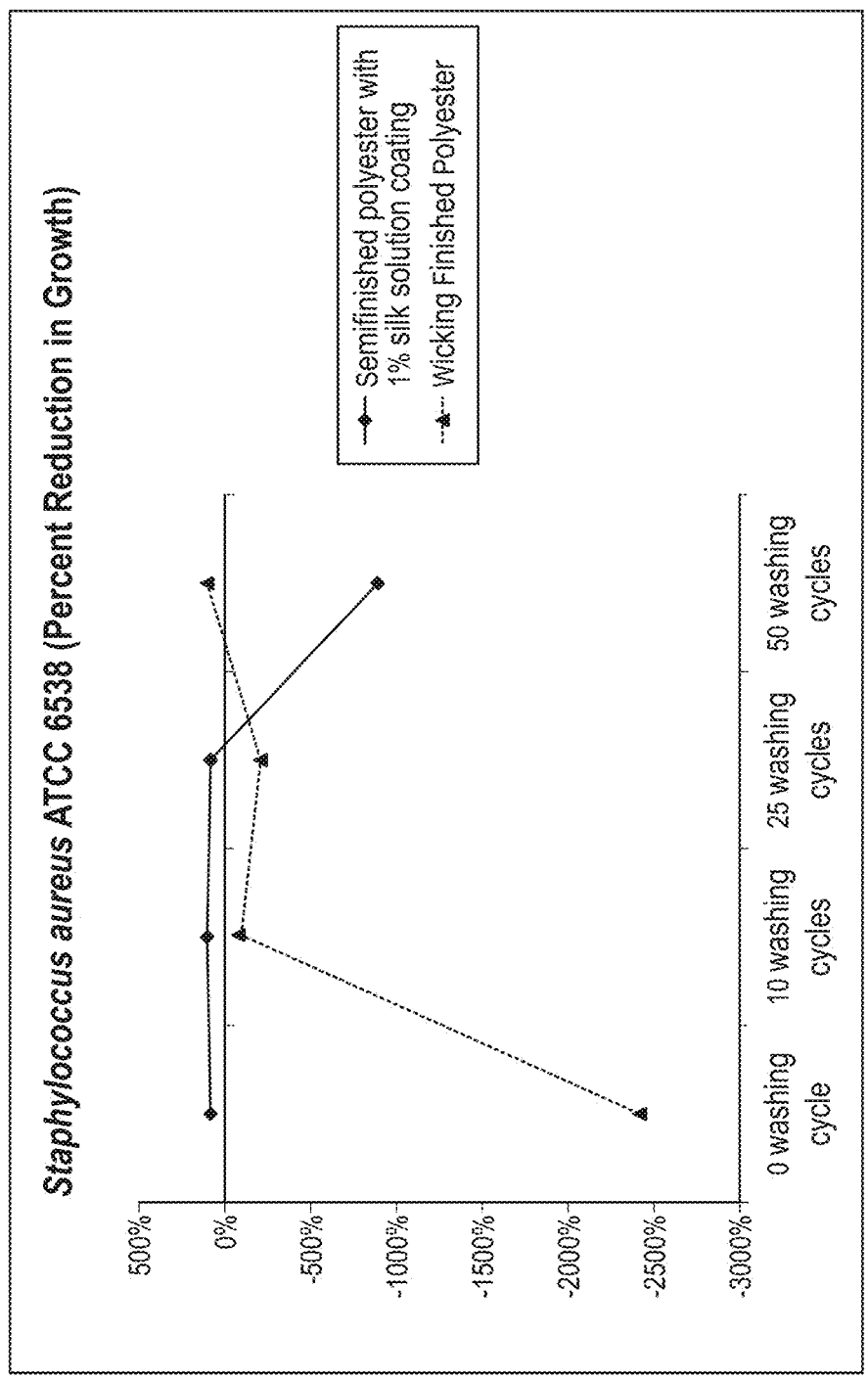
FIG. 78 illustrates percent reduction in growth of *Staphylococcus aureus* ATCC 6538 versus fabric washing cycles.
Figure 79:
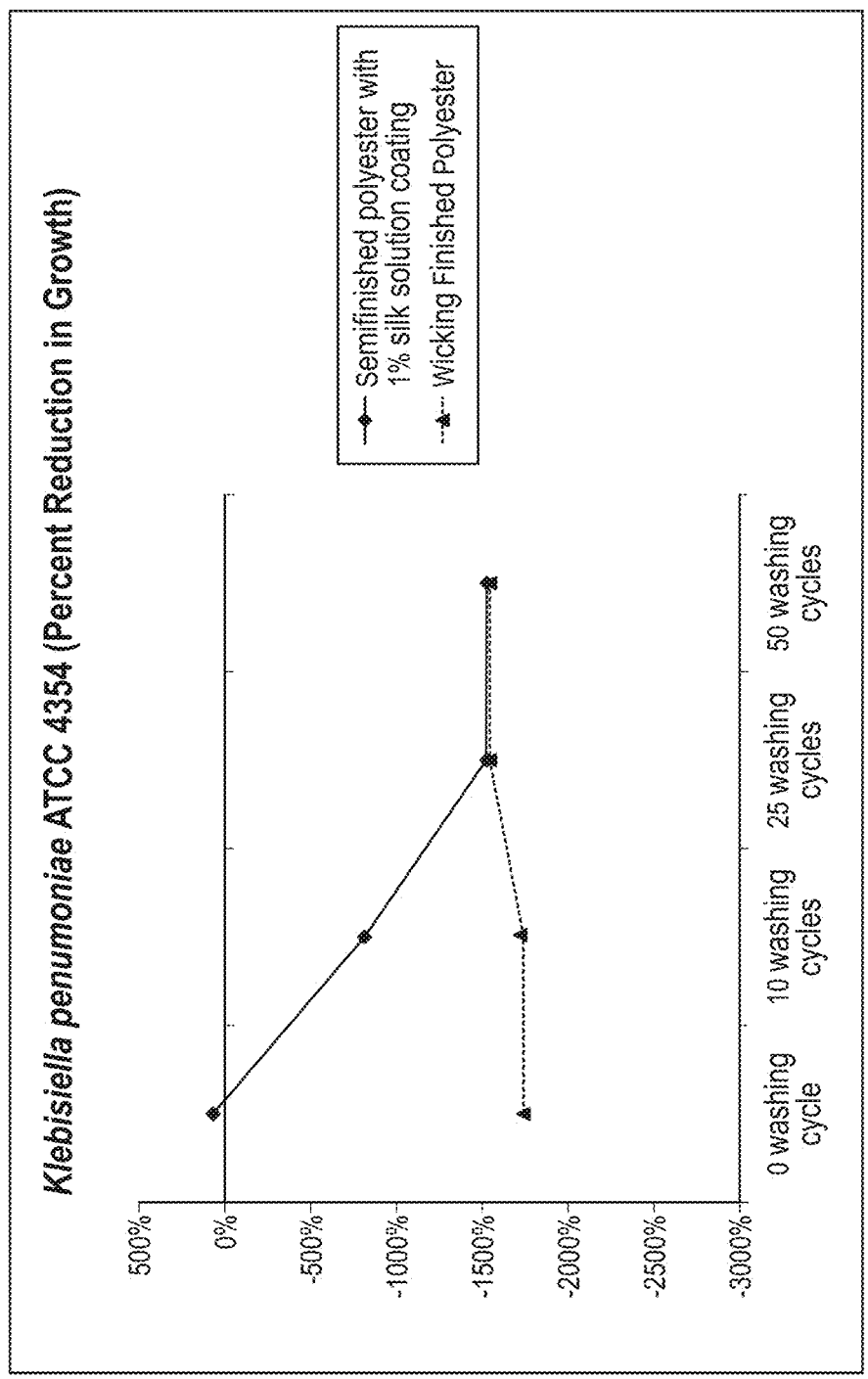
FIG. 79 illustrates percent reduction in growth of *Klebsiella pneumoniae* ATCC 4354 versus fabric washing cycles.
Figure 80:
FIG. 80 illustrates a scanning electron microscopy image of fabric sample FAB-01-BATH-B (first view).
Figure 81:
FIG. 81 illustrates a scanning electron microscopy image of fabric sample FAB-01-BATH-B (third view).
Figure 82:
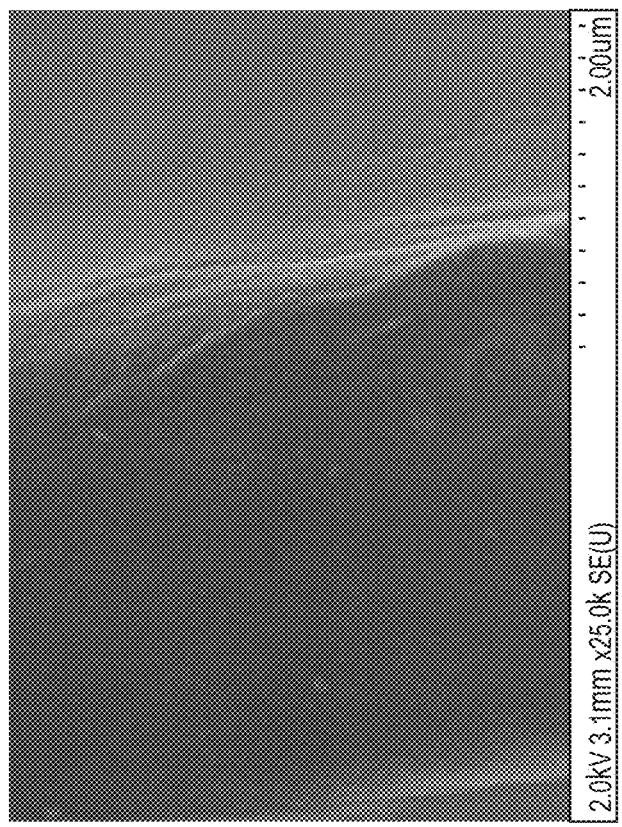
FIG. 82 illustrates a scanning electron microscopy image of fabric sample FAB-01-BATH-B (fourth view).
Figure 83:
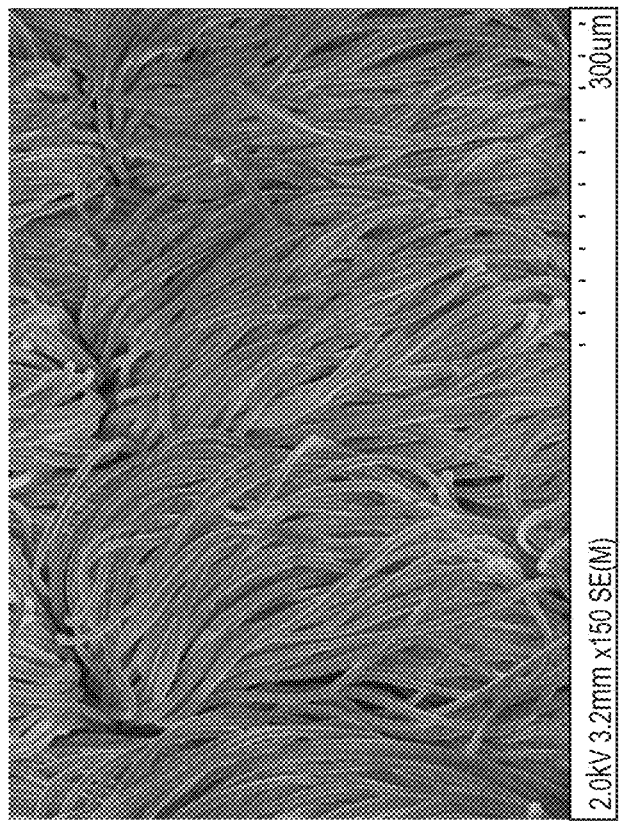
FIG. 83 illustrates a scanning electron microscopy image of fabric sample FAB-01-SPRAY-B (first view).
Figure 84:
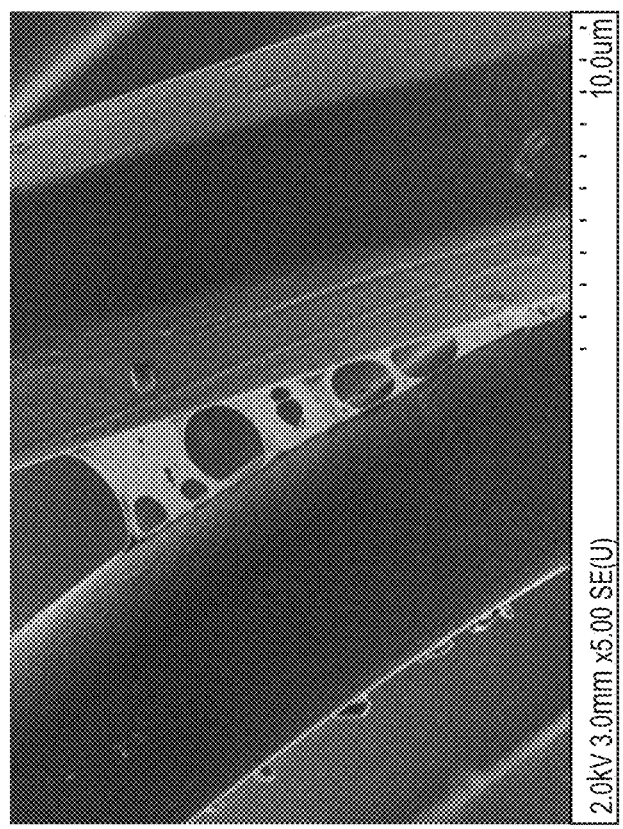
FIG. 84 illustrates a scanning electron microscopy image of fabric sample FAB-01-SPRAY-B (second view).
Figure 85:
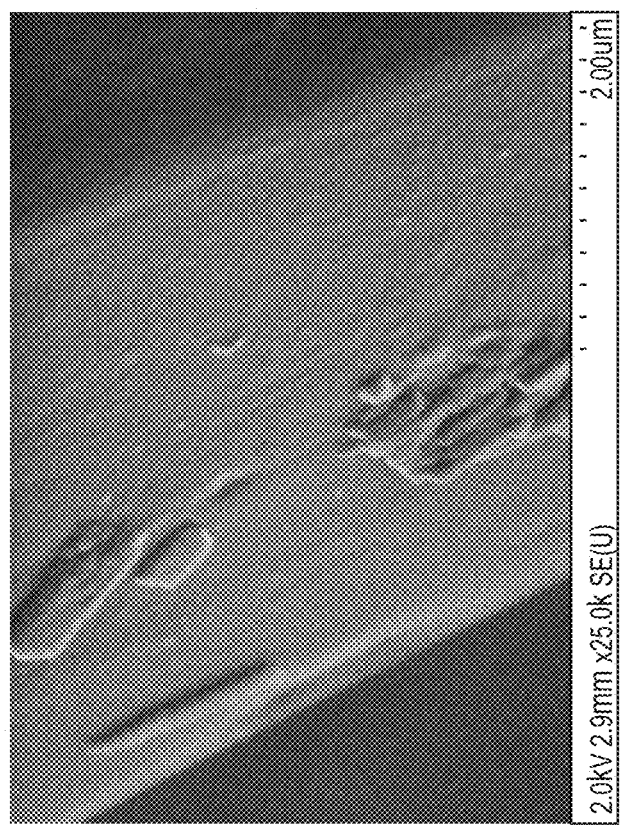
FIG. 85 illustrates a scanning electron microscopy image of fabric sample FAB-01-SPRAY-B (fifth view).
Figure 86:
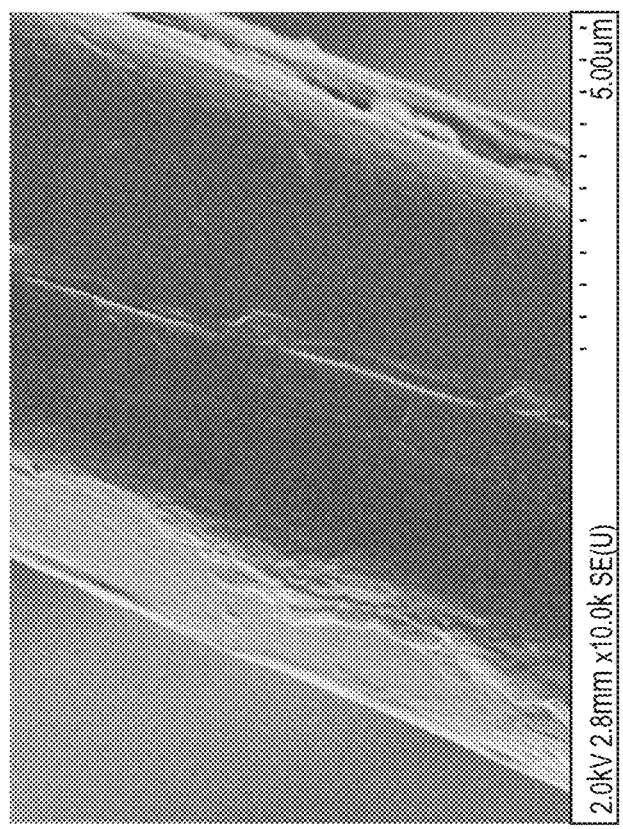
FIG. 86 illustrates a scanning electron microscopy image of fabric sample FAB-01-SPRAY-B (sixth view).
Figure 87:
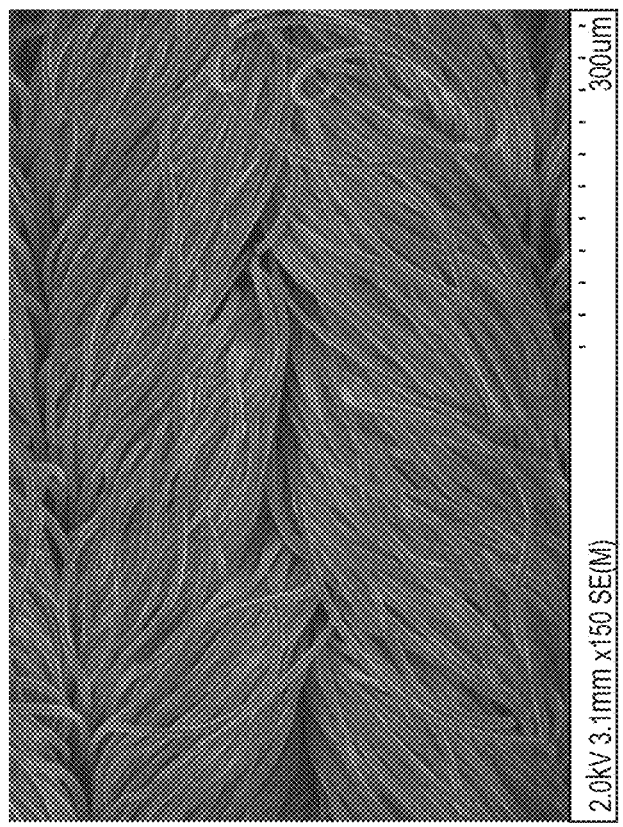
FIG. 87 illustrates a scanning electron microscopy image of fabric sample FAB-01-SPRAY-C (first view).
Figure 88:
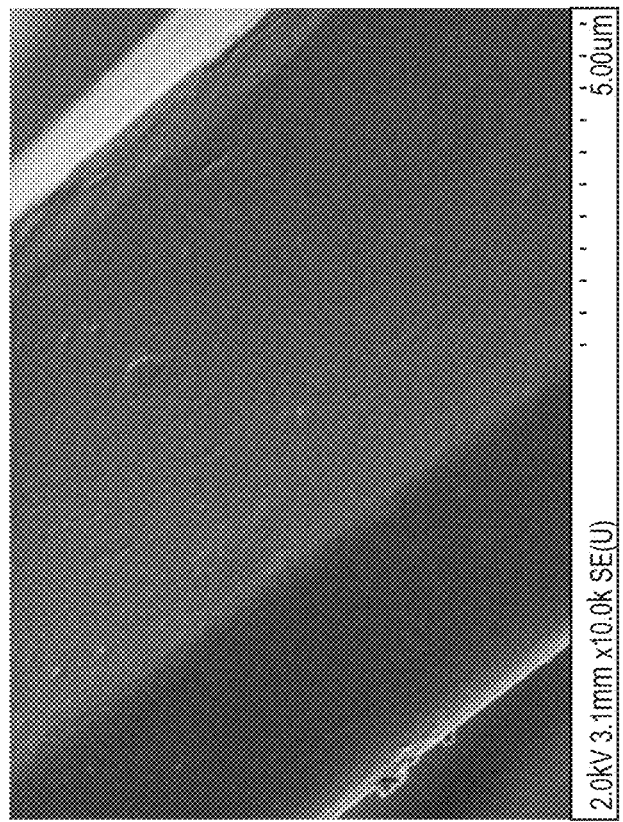
FIG. 88 illustrates a scanning electron microscopy image of fabric sample FAB-01-SPRAY-C (second view).
Figure 89:
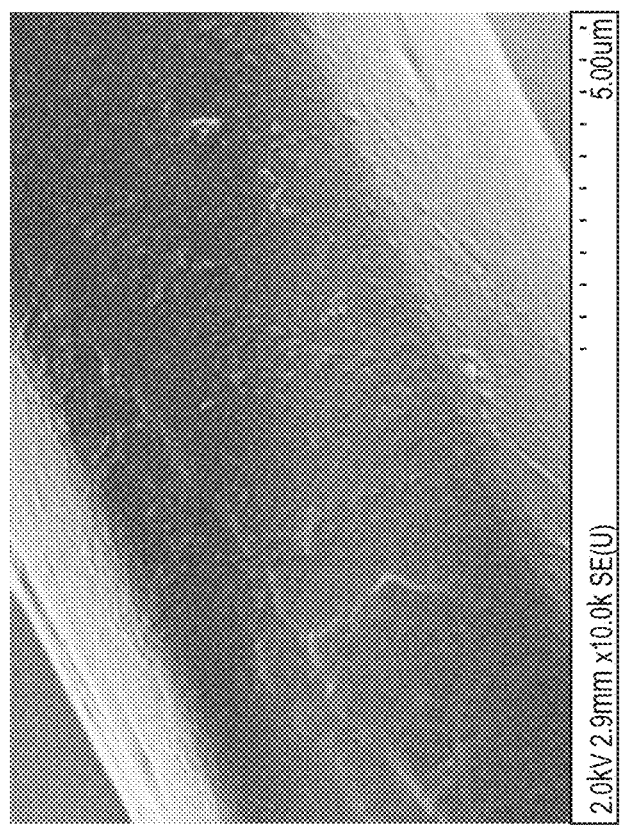
FIG. 89 illustrates a scanning electron microscopy image of fabric sample FAB-01-SPRAY-C (fourth view).
Figure 90:
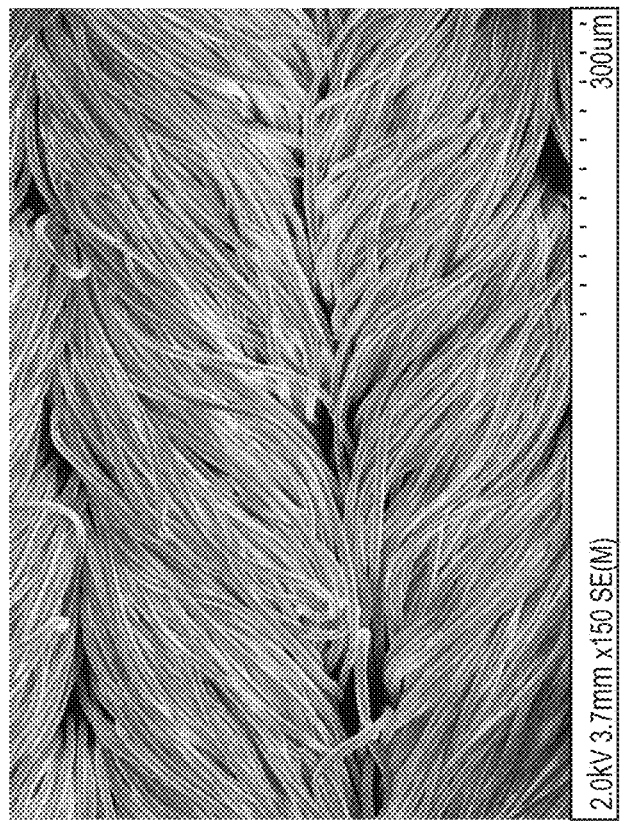
FIG. 90 illustrates a scanning electron microscopy image of fabric sample FAB-01-STEN-C (first view).
Figure 91:
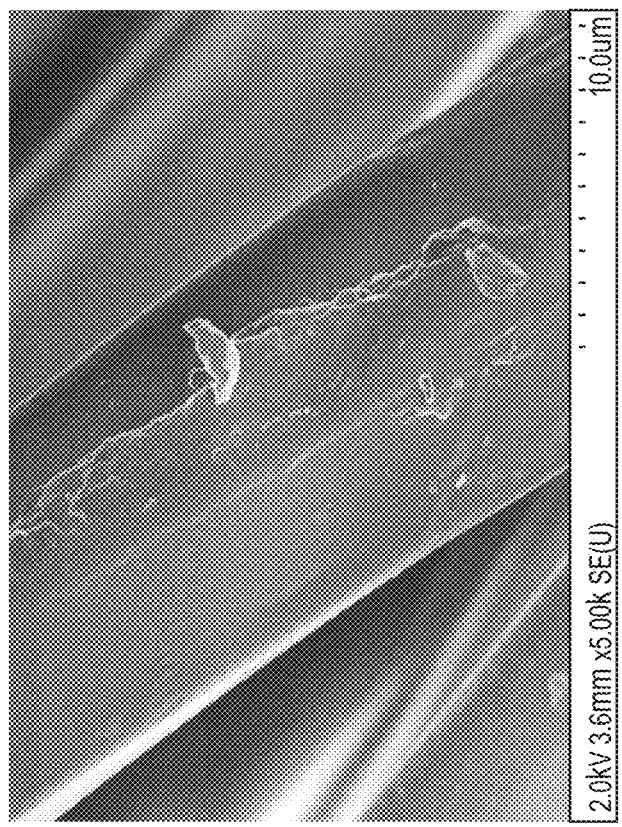
FIG. 91 illustrates a scanning electron microscopy image of fabric sample FAB-01-STEN-C (second view).
Figure 92:
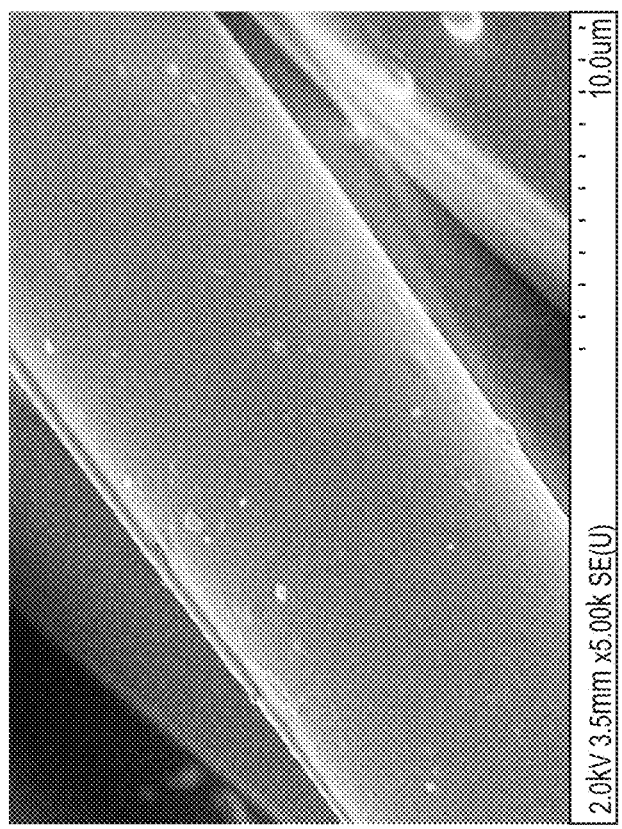
FIG. 92 illustrates a scanning electron microscopy image of fabric sample FAB-01-STEN-C (seventh view).
Figure 93:
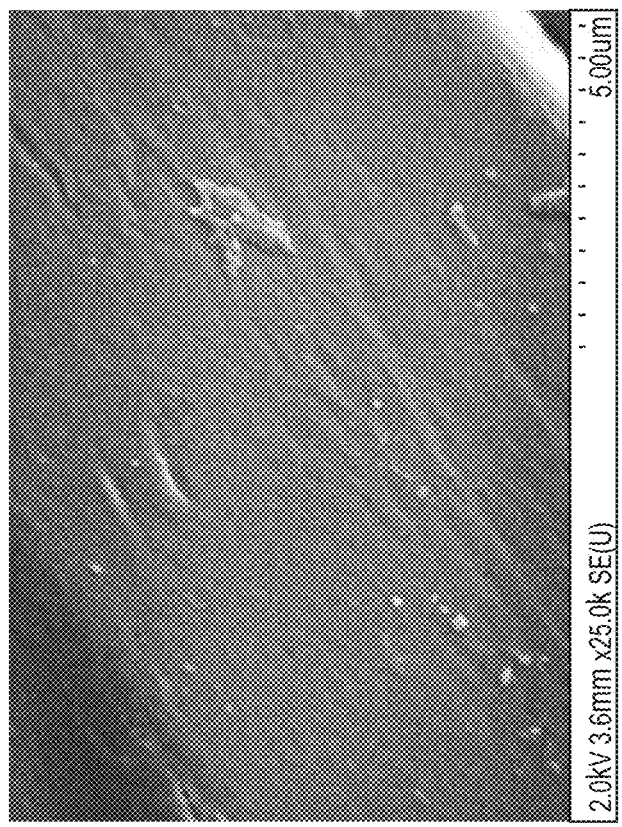
FIG. 93 illustrates a scanning electron microscopy image of fabric sample FAB-01-STEN-C (ninth view).
Figure 94:
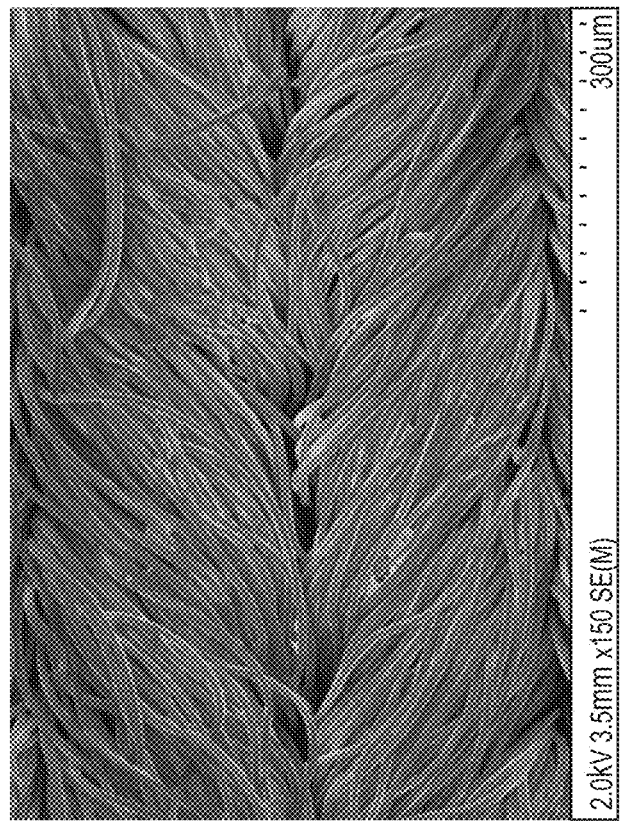
FIG. 94 illustrates a scanning electron microscopy image of fabric sample FAB-10-BATH-B (first view).
Figure 95:
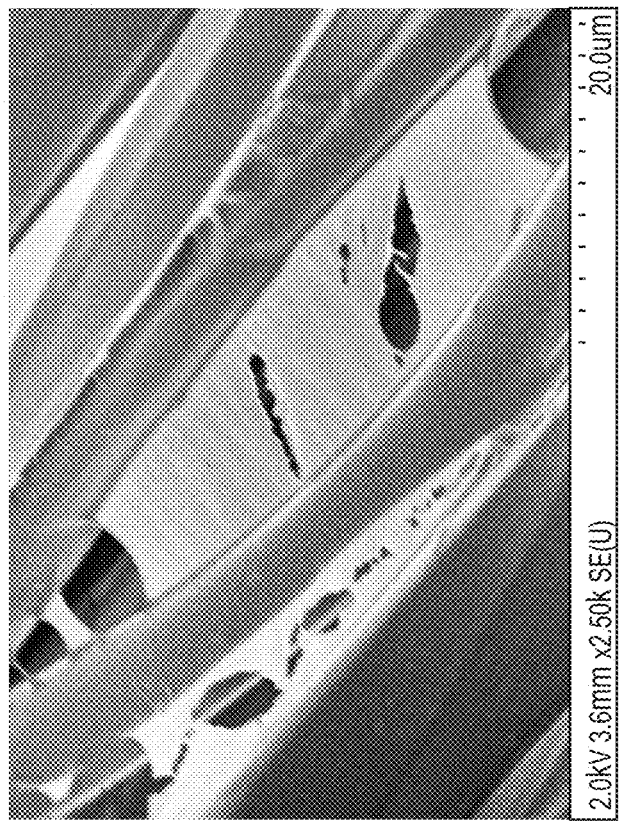
FIG. 95 illustrates a scanning electron microscopy image of fabric sample FAB-10-BATH-B (second view).
Figure 96:
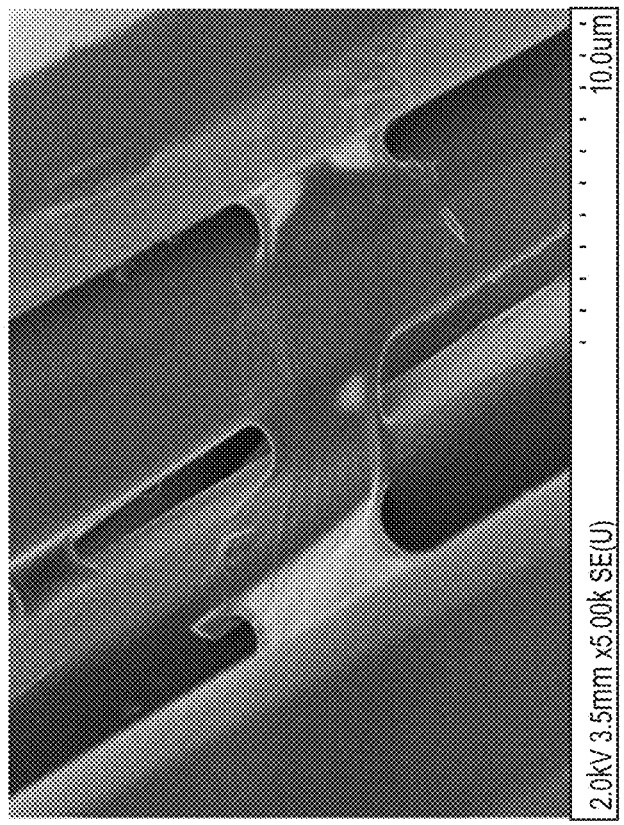
FIG. 96 illustrates a scanning electron microscopy image of fabric sample FAB-10-BATH-B (third view).
Figure 97:
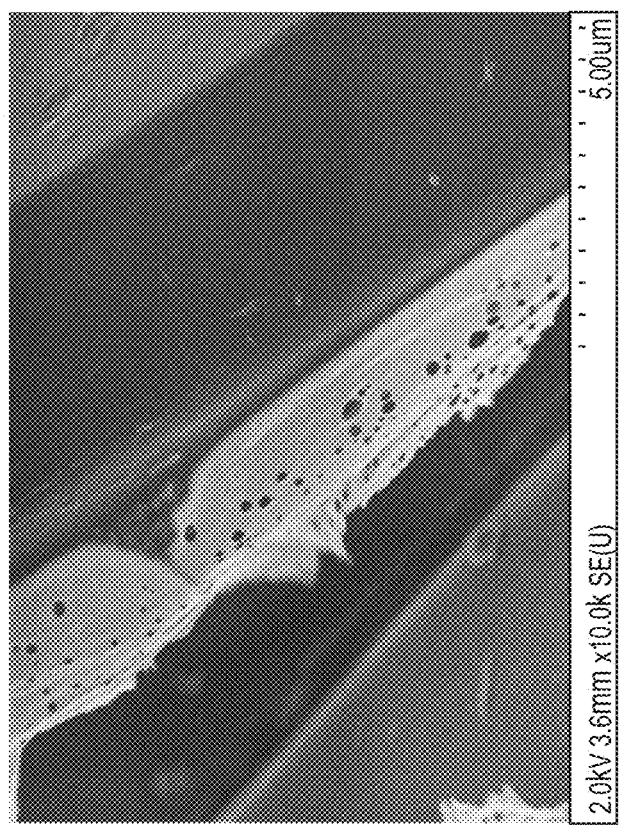
FIG. 97 illustrates a scanning electron microscopy image of fabric sample FAB-10-BATH-B (fourth view).
Figure 98:
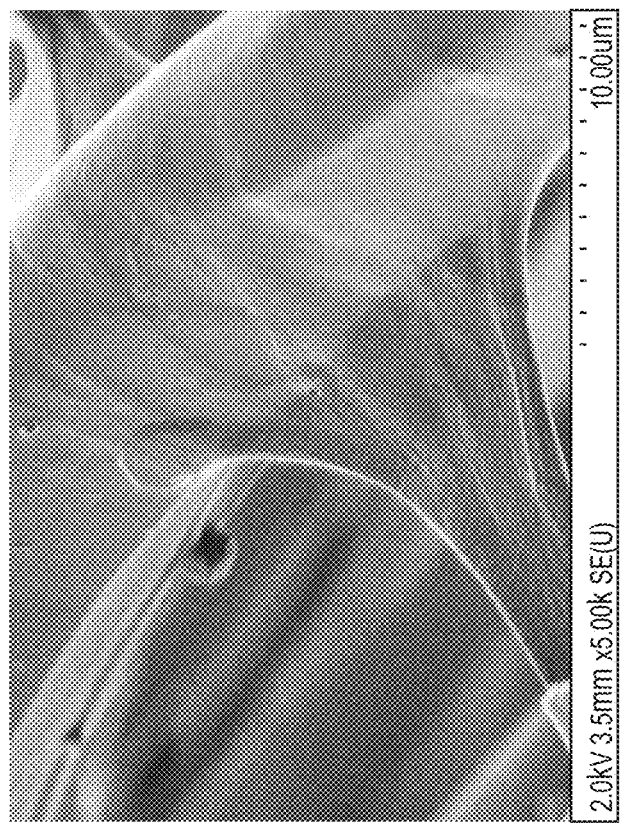
FIG. 98 illustrates a scanning electron microscopy image of fabric sample FAB-10-BATH-B (fifth view).
Figure 99:
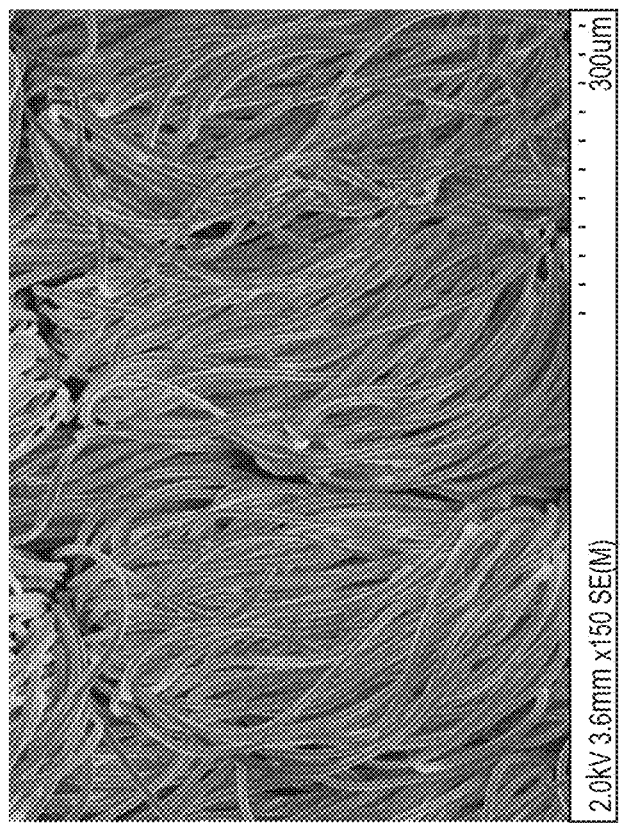
FIG. 99 illustrates a scanning electron microscopy image of fabric sample FAB-10-BATH-C (first view).
Figure 100:
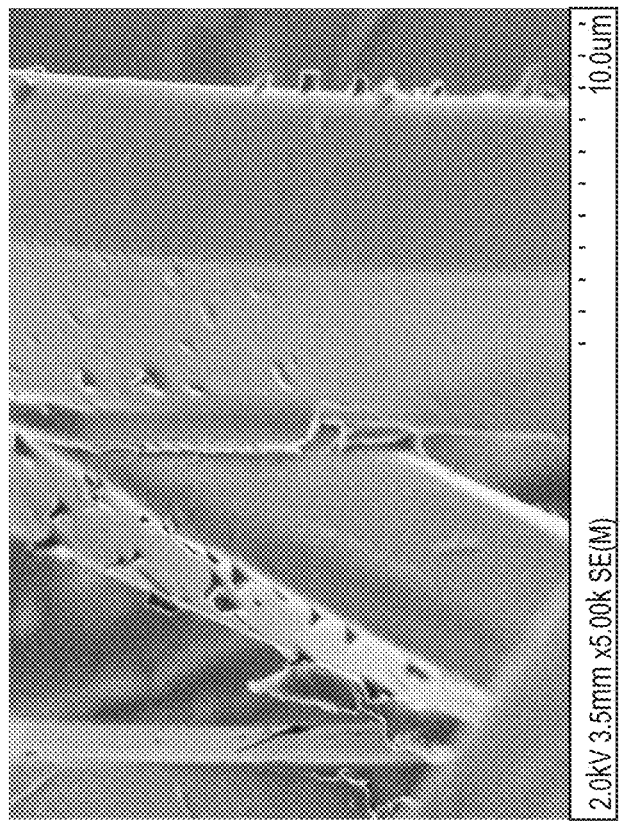
FIG. 100 illustrates a scanning electron microscopy image of fabric sample FAB-10-BATH-C (second view).
Figure 101:
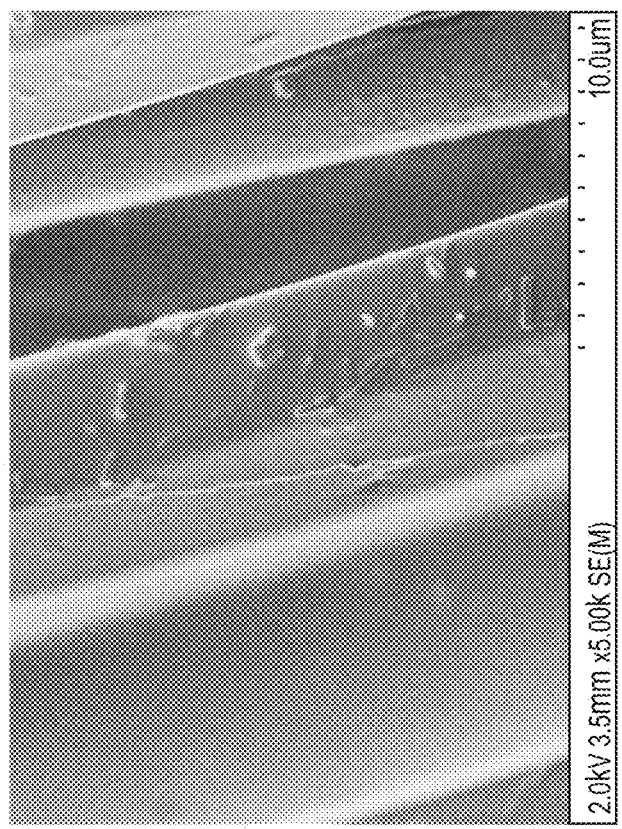
FIG. 101 illustrates a scanning electron microscopy image of fabric sample FAB-10-BATH-C (third view).
Figure 102:
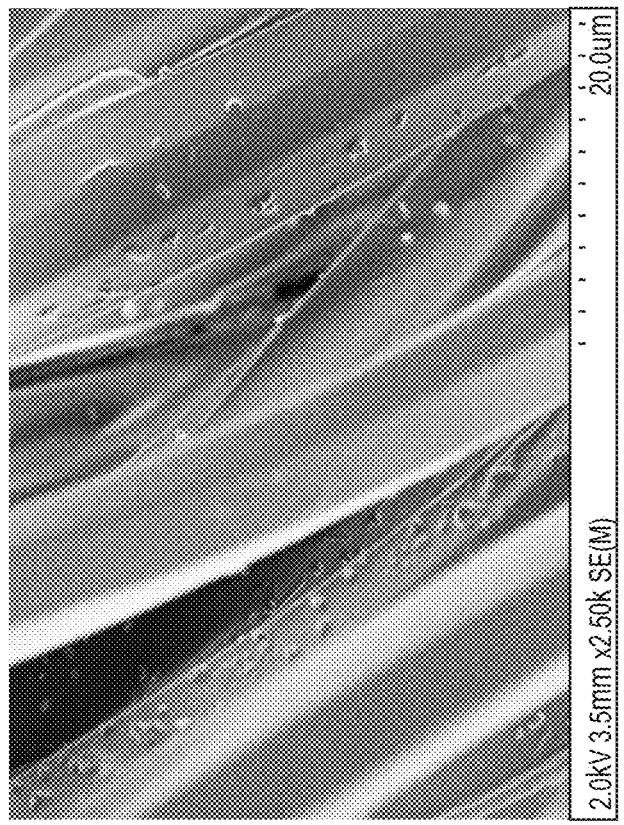
FIG. 102 illustrates a scanning electron microscopy image of fabric sample FAB-10-BATH-C (fourth view).
Figure 103:
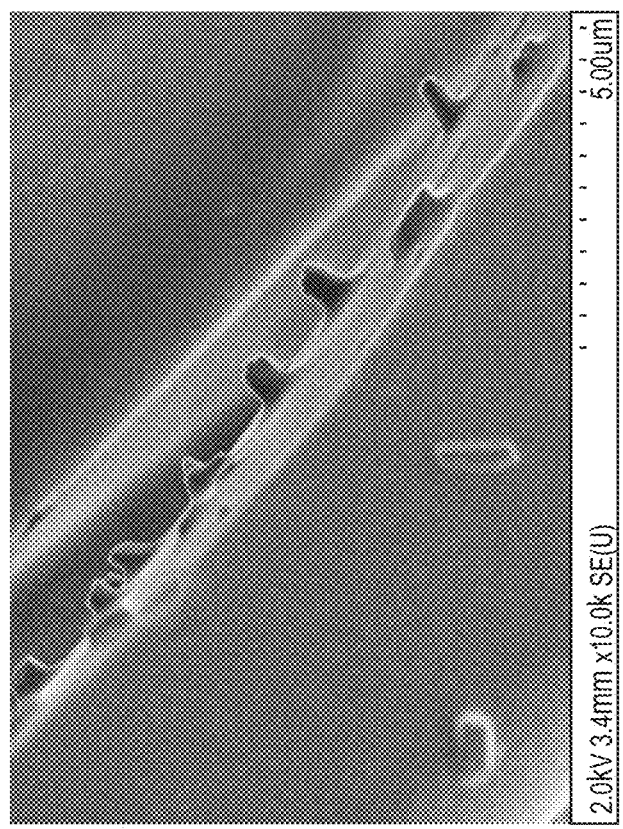
FIG. 103 illustrates a scanning electron microscopy image of fabric sample FAB-10-BATH-C (fifth view).
Figure 104:
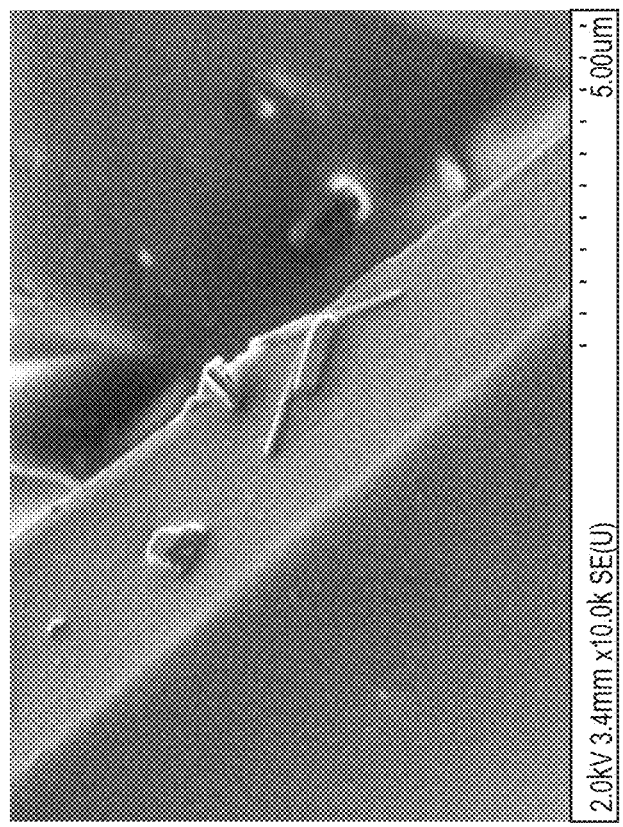
FIG. 104 illustrates a scanning electron microscopy image of fabric sample FAB-10-BATH-C (sixth view).
Figure 105:
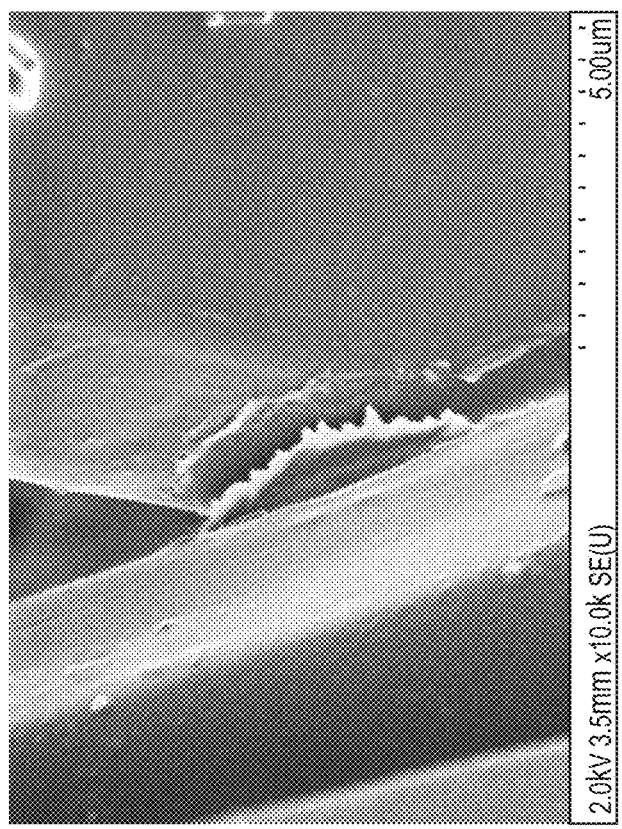
FIG. 105 illustrates a scanning electron microscopy image of fabric sample FAB-10-BATH-C (seventh view).
Figure 106:
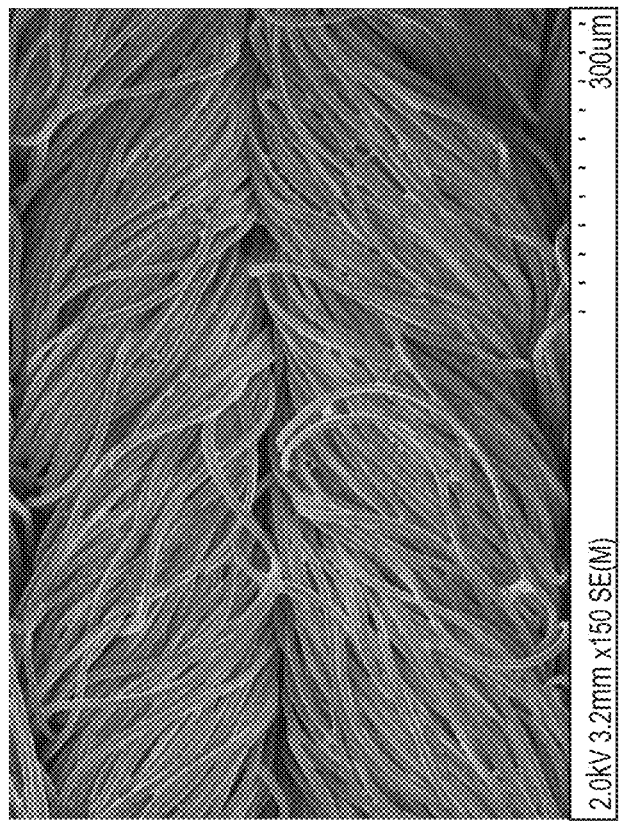
FIG. 106 illustrates a scanning electron microscopy image of fabric sample FAB-10-SPRAY-B (first view).
Figure 107:
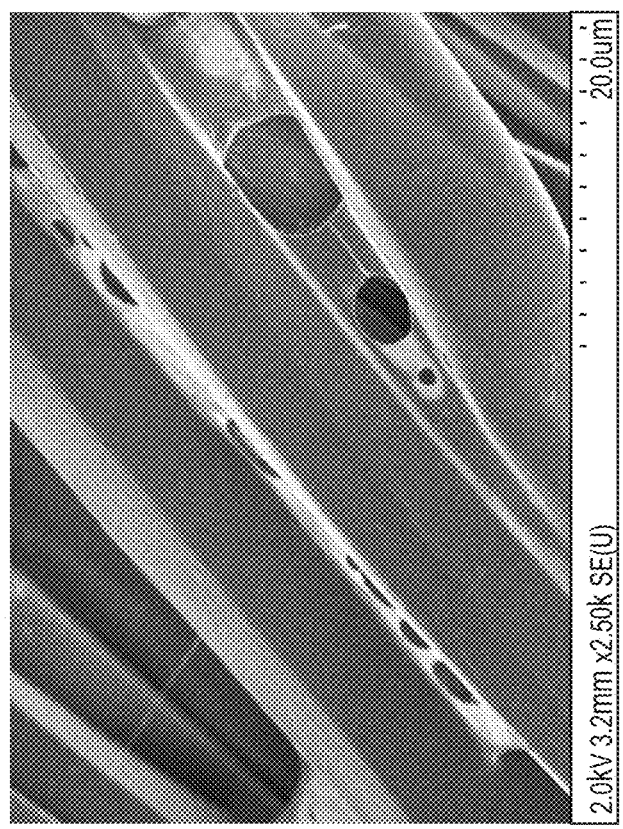
FIG. 107 illustrates a scanning electron microscopy image of fabric sample FAB-10-SPRAY-B (second view).
Figure 108:
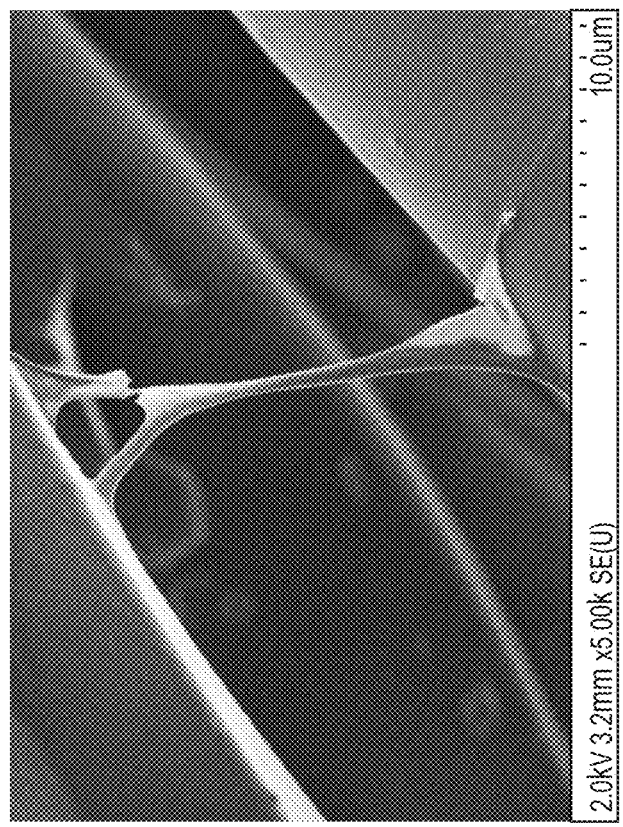
FIG. 108 illustrates a scanning electron microscopy image of fabric sample FAB-10-SPRAY-B (fourth view).
Figure 109:
FIG. 109 illustrates a scanning electron microscopy image of fabric sample FAB-10-SPRAY-B (fifth view).
Figure 110:
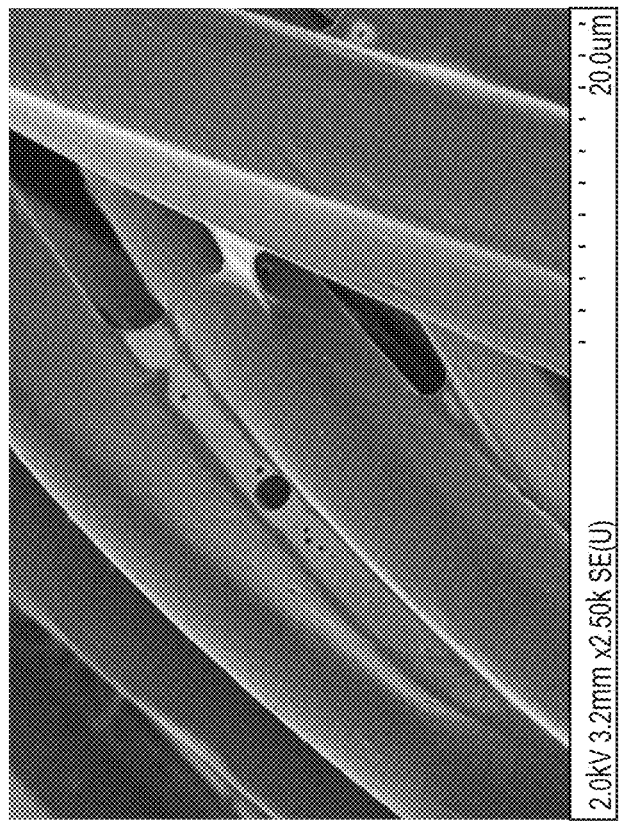
FIG. 110 illustrates a scanning electron microscopy image of fabric sample FAB-10-SPRAY-B (sixth view).
Figure 111:
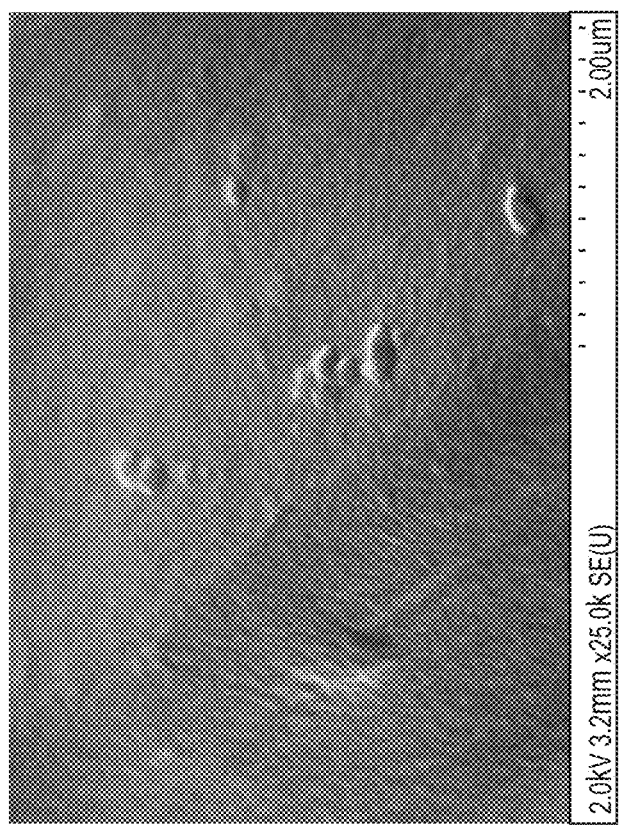
Figure 112:
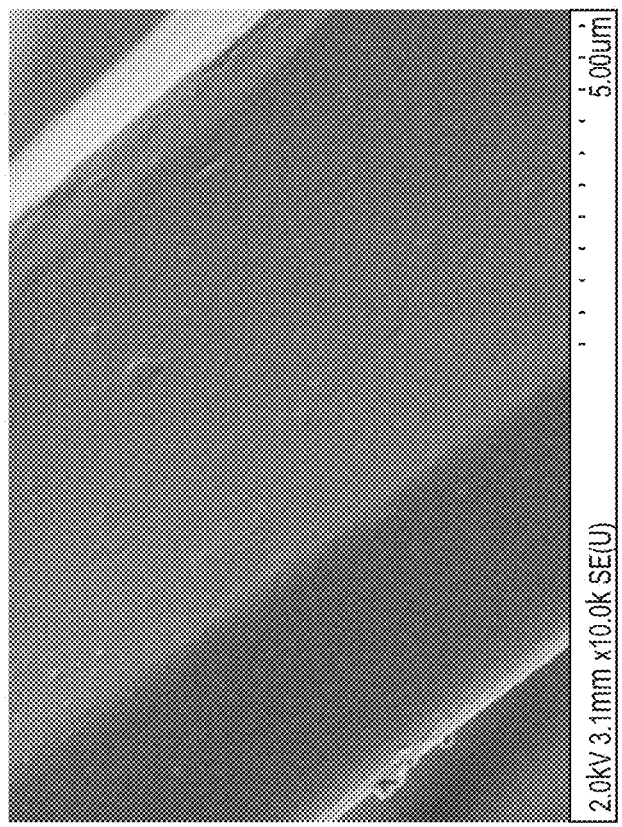
Figure 113:
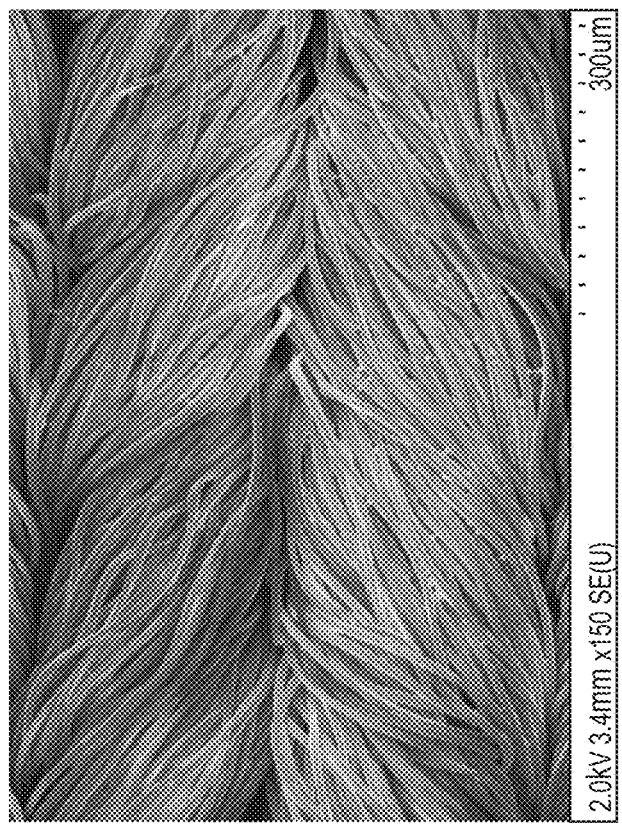
Figure 114:
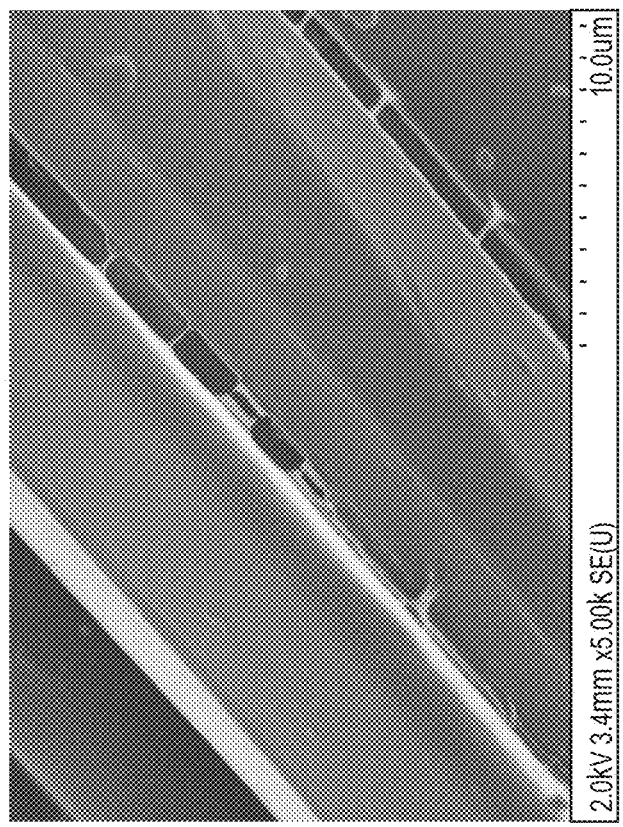
Figure 115:
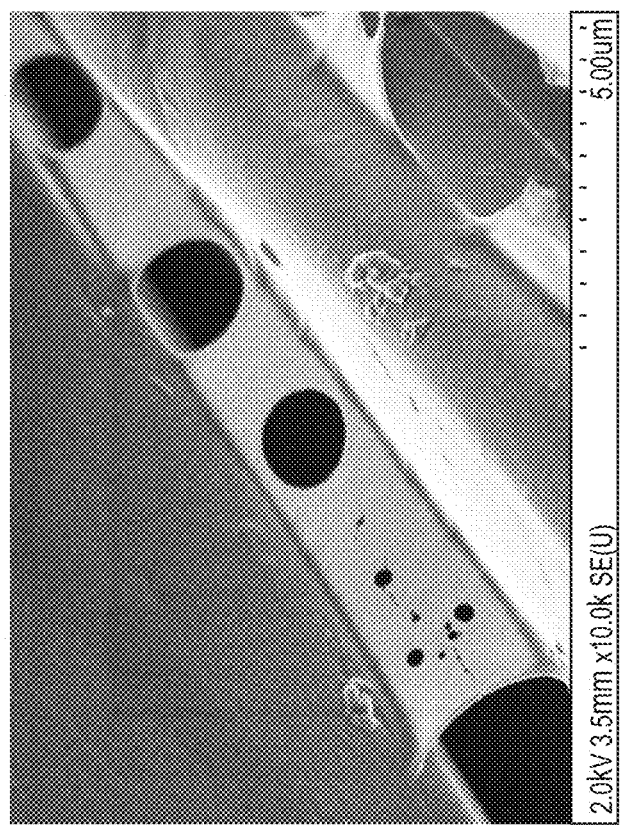
Figure 116:
Figure 117:
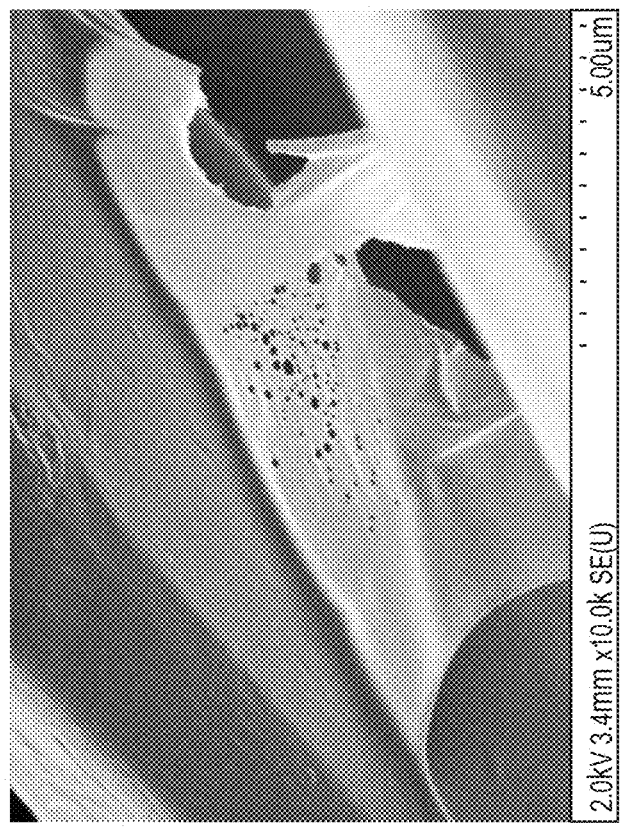
Figure 118:
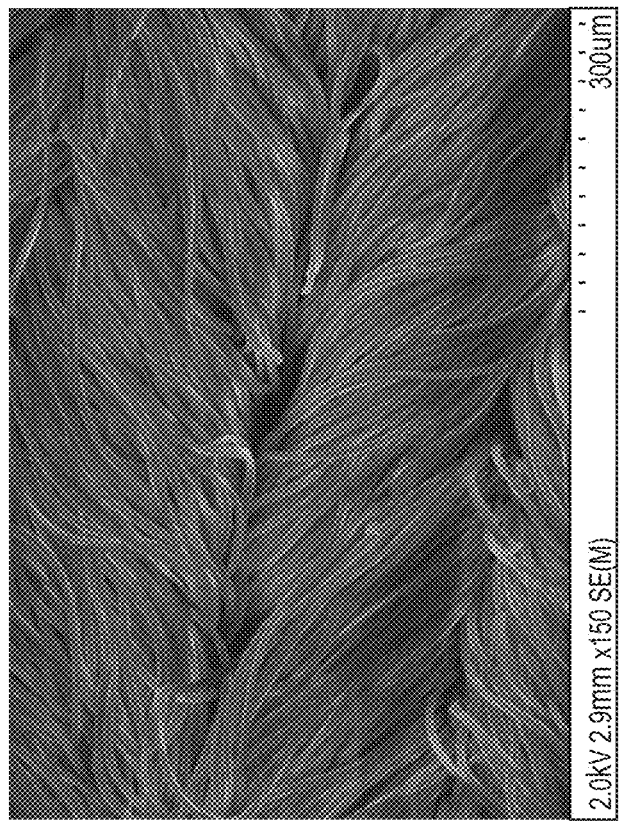
Figure 119:
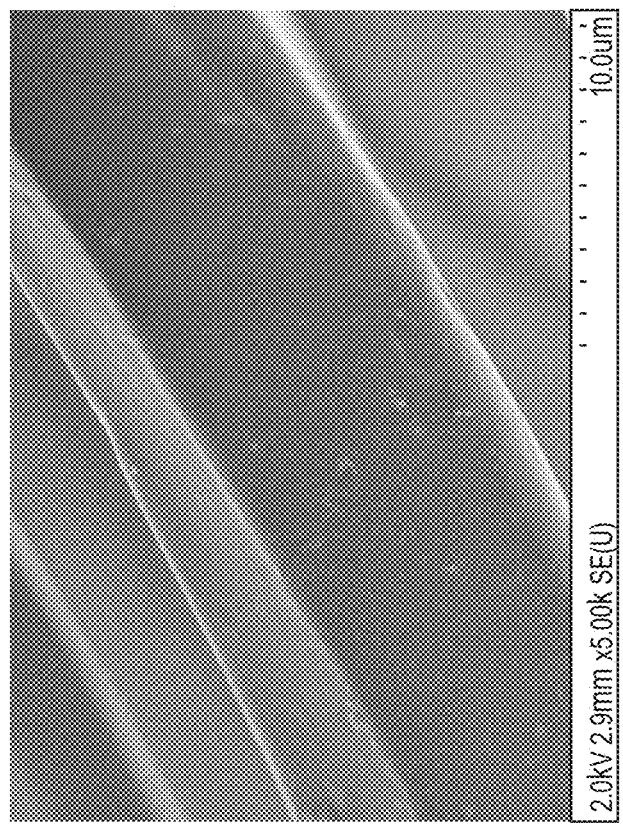
Figure 120:
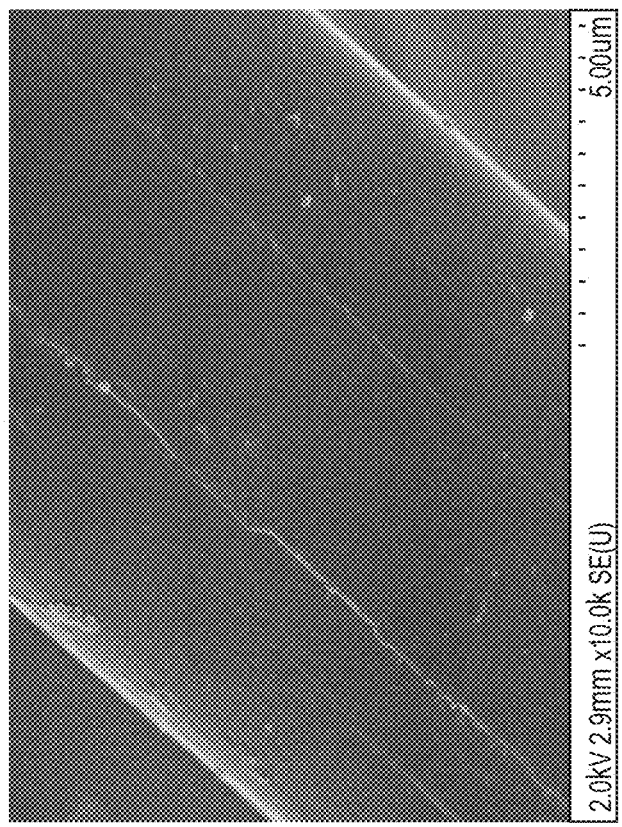
Figure 121:
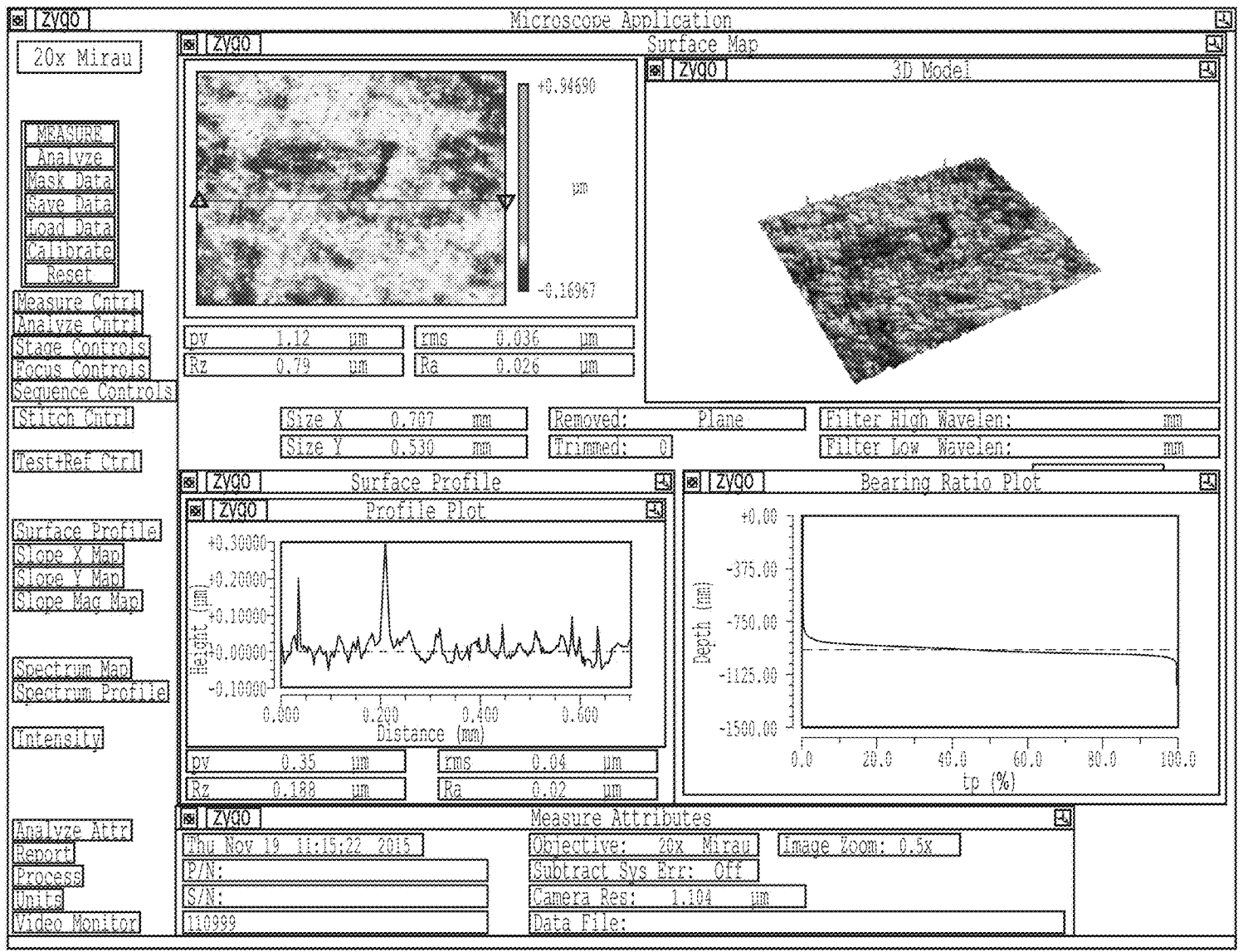
Figure 122:
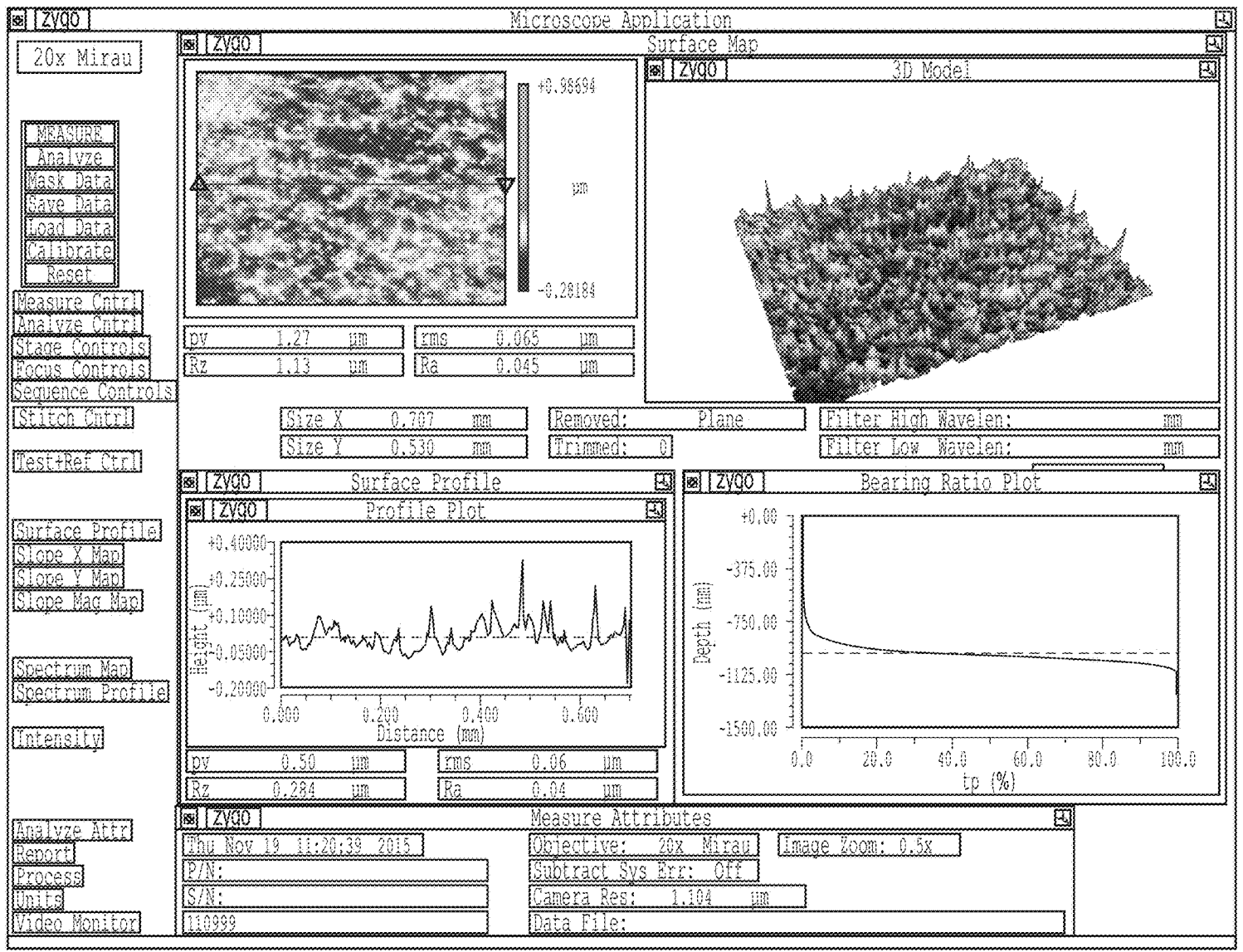

A summary of the results from studies of silk coatings on polyester are given in Table 70 and Table 71. The results shown in FIG. 68 and FIG. 69 illustrate that the accumulative one way transport index and OMMC performance is maintained even at 50 wash cycles. Additional test results are shown in FIG. 70 to FIG. 77. The antimicrobial performance of the silk coated polyester fabrics are maintained to 25 to 50 washing cycles, as shown in FIG. 78 and FIG. 79. The results illustrate the surprising improvement in moisture management properties, as well as the surprising result that the improved properties survive many wash cycles.

TABLE 70

Test results for semifinished polyester with 1% silk solution coating.
Testing Results: Semifinished polyester with 1% silk solution coating

| Number of Washes | Raw Data: | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index (%) | Overall Moisture Management Capability OMMC |
|---|---|---|---|---|---|---|---|---|---|---|---|
| 0 Cycles | Mean | 5.63 | 3.95 | 7.24 | 28.73 | 5 | 5 | 0.90 | 1.22 | 133.26 | 0.27 |
| | S. Deviation | 1.20 | 0.38 | 1.46 | 8.62 | 0 | 0 | 0.20 | 0.12 | 34.81 | 0.06 |
| | CV | 0.21 | 0.10 | 0.20 | 0.30 | 0 | 0 | 0.22 | 0.09 | 0.26 | 0.21 |
| 10 Cycles | Mean | 23.87 | 7.96 | 4.82 | 8.55 | 5 | 5 | 0.46 | 0.68 | 144.84 | 0.22 |
| | S. Deviation | 31.51 | 3.30 | 0.84 | 2.94 | 0 | 0 | 0.28 | 0.23 | 27.71 | 0.03 |
| | CV | 1.32 | 0.41 | 0.17 | 0.34 | 0 | 0 | 0.61 | 0.33 | 0.19 | 0.14 |
| 25 Cycles | Mean | 6.09 | 4.59 | 7.36 | 17.22 | 5 | 5 | 0.83 | 1.05 | 124.05 | 0.22 |
| | S. Deviation | 1.61 | 0.44 | 2.98 | 3.28 | 0 | 0 | 0.17 | 0.09 | 11.70 | 0.02 |
| | CV | 0.26 | 0.10 | 0.40 | 0.19 | 0 | 0 | 0.20 | 0.09 | 0.09 | 0.09 |
| 50 Cycles | Mean | 25.20 | 11.64 | 6.84 | 7.80 | 5 | 5 | 0.39 | 0.53 | 58.81 | 0.13 |
| | S. Deviation | 28.06 | 6.36 | 3.38 | 5.70 | 0 | 0 | 0.30 | 0.27 | 26.56 | 0.03 |
| | CV | 1.11 | 0.55 | 0.49 | 0.73 | 0 | 0 | 0.77 | 0.51 | 0.45 | 0.25 |

TABLE 71

Test results for wicking finished polyester without silk coating.
Testing Results: Wicking Finished Polyester

| Number of Washes | Raw Data: | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index (%) | Overall Moisture Management Capability OMMC |
|---|---|---|---|---|---|---|---|---|---|---|---|
| 0 Cycles | Mean | 3.46 | 3.48 | 37.30 | 56.90 | 5 | 5 | 1.37 | 1.36 | 62.37 | 0.29 |
| | S. Deviation | 0.07 | 0.04 | 12.89 | 10.24 | 0 | 0 | 0.02 | 0.02 | 9.74 | 0.03 |
| | CV | 0.02 | 0.01 | 0.35 | 0.18 | 0 | 0 | 0.02 | 0.01 | 0.16 | 0.12 |
| 25 Cycles | Mean | 6.69 | 6.71 | 7.23 | 6.89 | 5 | 5 | 0.75 | 0.76 | 30.40 | 0.09 |
| | S. Deviation | 1.48 | 1.92 | 1.27 | 2.74 | 0 | 0 | 0.13 | 0.19 | 16.22 | 0.02 |
| | CV | 0.22 | 0.29 | 0.18 | 0.40 | 0 | 0 | 0.17 | 0.25 | 0.53 | 0.20 |
| 50 Cycles | Mean | 11.27 | 8.46 | 6.70 | 9.35 | 5 | 5 | 0.54 | 0.65 | 31.21 | 0.09 |
| | S. Deviation | 6.57 | 3.53 | 1.45 | 5.21 | 0 | 0 | 0.23 | 0.25 | 18.26 | 0.03 |
| | CV | 0.58 | 0.42 | 0.22 | 0.56 | 0 | 0 | 0.44 | 0.38 | 0.59 | 0.30 |

Example 17. Characterization of Silk Coatings on Polyester Fabrics

Scanning electron microscopy (SEM) analysis was performed using a Hitachi S-4800 field-emission SEM (FE-SEM) operated at 2 kV accelerating voltage. Pieces from each sample were sectioned using a razor blade and placed on carbon adhesive tape mounted on aluminum SEM stubs. A coating of iridium approximately 2 nm thick was applied via sputter deposition in order to minimize the buildup of surface charge.

The samples used in the SEM study are described in Table 72. SEM micrographs for fabric samples are shown in FIG. 80 to FIG. 120.

TABLE 72

Fabric samples tested by scanning electron microscopy and optical profilometry.

| Sample ID | Fabric | Silk solution for coating/treatment (average molecular weight, Da) | Silk coating/treatment method using silk fibroin solution (sfs) |
|---|---|---|---|
| FAB-10-SPRAY-B | 15042002 | 41.576 | spray with 1% sfs |
| FAB-01-SPRAY-B | 15042002 | 41.576 | spray with 0.1% sfs |
| FAB-10-STEN-B | 15042002 | 41.576 | stencil spray with 1% sfs |
| FAB-10-BATH-B | 15042002 | 41.576 | bath with 1% sfs |
| FAB-01-BATH-B | 15042002 | 41.576 | bath with 0.1% sfs |
| FAB-01-SPRAY-C | 15042002 | 10.939 | spray with 0.1% sfs |
| FAB-01-STEN-C | 15042002 | 10.939 | stencil spray with 0.1% sfs |
| FAB-10-BATH-C | 15042002 | 10.939 | bath with 1% sfs |

The fabric SEM results show that the silk solution has very clearly been deposited along and between individual polyester fibers. The use of 0.1% silk solution results in less coating than 1.0% silk solution. The use of a bath for 0.1% silk solution, with an average molecular weight of 41 kDa, results in uniform coating along fibers with large, smooth features. The use of a spray with a 0.1% silk solution, with an average molecular weight of 41 kDa, in coating along fibers as well as connected, webbed coating between fibers. The use of a spray for 0.1% silk solution, with an average molecular weight of 11 kDa, results in uniform coating along fibers with small, spotted/ribbed features. The use of a stencil for 0.1% silk solution, with an average molecular weight of 11 kDa, results in coating along fibers that has clear edges and delineation between coated and non coated sides. The use of a bath for 1.0% silk solution, with an average molecular weight of 41 kDa, results in thick coating along fibers as well as thick connected, webbed coating between fibers. The use of a bath for 1.0% silk solution, with an average molecular weight of 11 kDa, results in coating along all sides of individual fibers. Coating appears uniform on surface with many single point extrusions. The use of a spray for 1.0% silk solution, with an average molecular weight of 41 kDa, results in coating along fibers as well as connected, webbed coating between fibers, which was thicker than that observed using 0.1% silk solution. The use of a stencil for 1.0% silk solution, with an average molecular weight of 41 kDa, results in coating along fibers and between fibers, and the coating appears well organized.

The SEM results demonstrate that the silk coating has been applied as an even, thin, uniform coating to the fibers of the fabric. This illustrates the surprising result that the silk coating was applied to the fibers without the use of any additives or cross-linking, using a water based delivery system.

Example 18. Characterization of Silk Coatings on Polyester Films

The film samples are described in Table 73.

The results show that the silk coatings are applied uniformly. Little to no variation is observed in the characteristics or topology of the coated polyester films. Surprisingly, the coating is even, uniform, and thin. Furthermore, surprising, the silk coated the fibers without any additives or cross-linking using a water-based system.

Optical profiling was carried out using a Zygo New View 6200 optical profilometer. Two locations on each sample were randomly selected and measured with 10× magnification. The results are shown in FIG. 121 to FIG. 144. The results indicate that the silk-coated samples have a homogeneous deposition of silk fibroin. Surface roughness features observed in the control are visible after silk coating on Mylar films, which is consistent with the presence of a relatively thin silk film that is forming a conformal coating on Mylar. The results substantiate the uniformity of the coating, and demonstrate that silk can be stenciled into discrete locations.

Contact profilometry was performed and the cross-sectioned samples were examined by SEM. Results are shown in FIG. 145 to FIG. 148. For sample FIL-10-SPRAY-B-10MYL, the thickness ranged from approximately 260 nm to 850 nm in 4 locations analyzed. For sample FIL-10-BATH-B-01MYL, the coating ranged from approximately 140 nm to 400 nm in 4 locations. SEM images from cross-sections show similar trends, with one location on sample FIL-10-SPRAY-B-10MYL having a cross-section that measures approximately 500 nm and one on FIL-10-BATH-B-01MYL measuring approximately 180 nm.

TABLE 73

Film samples tested by scanning electron microscopy and optical profilometry.

| Sample identifier | Polyester substrate material | Silk solution for coating/treatment (average molecular weight, Da) | Silk coating/treatment method using silk fibroin solution (sfs) |
|---|---|---|---|
| FIL-10-SPRAY-B-01MYL | 0.01 Mylar | 41.576 | spray with 1% sfs |
| FIL-01-SPRAY-B-01MYL | 0.01 Mylar | 41.576 | spray with 0.1% sfs |
| FIL-01-SPRAY-B-007MEL | 0.007 Melinex | 41.576 | spray with 0.1% sfs |
| FIL-01-SPRAY-C-01MYL | 0.01 Mylar | 10.939 | spray with 0.1% sfs |
| FIL-01-STEN-B-01MYL | 0.01 Mylar | 41.576 | stencil spray with 0.1% sfs |
| FIL-01-STEN-C-01MYL | 0.01 Mylar | 10.939 | stencil spray with 0.1% sfs |
| FIL-10-BATH-B-01MYL | 0.01 Mylar | 41.576 | bath with 1% sfs |
| FIL-10-BATH-B-007MEL | 0.007 Melinex | 41.576 | bath with 1% sfs |
| FIL-10-BATH-C-01MYL | 0.01 Mylar | 10.939 | bath with 1% sfs |
| FIL-01-BATH-B-01MYL | 0.01 Mylar | 41.576 | bath with 0.1% sfs |

Example 19. Preparation of Silk Fibroin Solutions with Higher Molecular Weights

The preparation of silk fibroin solutions with higher molecular weights is given in Table 74.

TABLE 74

Preparation and properties of silk fibroin solutions.

| Sample Name | Extraction Time (mins) | Extraction Temp (° C.) | LiBr Temp (° C.) | Oven/Sol'n Temp | Average weight average molecular weight (k(Da) | Average polydispersity |
|---|---|---|---|---|---|---|
| Group A TFF | 60 | 100 | 100 | 100° C. oven | 34.7 | 2.94 |
| Group A DIS | 60 | 100 | 100 | 100° C. oven | 44.7 | 3.17 |
| Group B TFF | 60 | 100 | 100 | 100° C. sol'n | 41.6 | 3.07 |
| Group B DIS | 60 | 100 | 100 | 100° C. sol'n | 44.0 | 3.12 |
| Group C TFF | 60 | 100 | 140 | 140° C. sol'n | 10.9 | 3.19 |
| Group C DIS | 60 | 100 | 140 | 140° C. sol'n | | |
| Group D DIS | 30 | 90 | 60 | 60° C. sol'n | 129.7 | 2.56 |
| Group D FIL | 30 | 90 | 60 | 60° C. sol'n | 144.2 | 2.73 |
| Group E DIS | 15 | 100 | RT | 60° C. sol'n | 108.8 | 2.78 |
| Group E FIL | 15 | 100 | RT | 60° C. sol'n | 94.8 | 2.62 |

Example 20. Silk Coatings on Natural Fabrics

The coating of natural fabric with silk fibroin-based protein fragment solutions and the resulting properties are illustrated in Table 75, Table 76, FIG. 149, and FIG. 150. The results demonstrate that silk fibroin solutions can coat cotton-Lycra natural fabrics including LUON and POWER LUXTREME.

TABLE 75

Silk fibroin coated fabrics.

| Legend | Fabric |
|---|---|
| 15072201 | Power Luxtreme RT1211362 |
| 15072202 | Luon RT20602020 |
| 15072301 | Power Luxtreme RT1211362 (15072201) 1% silk solution spray coating |
| 15072302 | Luon RT20602020 (15072202) 1% silk solution spray coating |
| 15072303 | Power Luxtreme RT1211362 (15072201) 0.1% silk solution spray coating |
| 15072304 | Luon RT20602020 (15072202) 0.1% silk solution spray coating |
| 15072305 | Power Luxtreme RT1211362 (15072201) 1% silk solution stencil coating |
| 15072306 | Luon RT20602020 (15072202) 1% silk solution stencil coating |
| 15072307 | Power Luxtreme RT1211362 (15072201) 0.1% silk solution stencil coating |
| 15072308 | Luon RT20602020 (15072202) 0.1% silk solution stencil coating |
| 15072309 | Power Luxtreme RT1211362 (15072201) 1% silk solution bath coating |
| 15072310 | Luon RT20602020 (15072202) 1% silk solution bath coating |
| 15072311 | Power Luxtreme RT1211362 (15072201) 0.1% silk solution bath coating |
| 15072312 | Luon RT20602020 (15072202) 0.1% silk solution bath coating |

TABLE 76

Test results for silk fibroin coated fabrics.

| Raw Data: | | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index (%) | Overall Moisture Management Capability OMMC |
|---|---|---|---|---|---|---|---|---|---|---|---|
| 15072201 | Mean | 64.3786 | 3.4072 | 8.8123 | 8.60494 | 5 | 5 | 0.15038 | 1.41686 | 151.65248 | 0.25898 |
| 15072202 | Mean | 25.1786 | 28.1922 | 5.4636 | 6.195 | 5 | 5 | 0.218 | 0.4244 | 80.9572 | 0.1529 |
| 15072301 | Mean | 16.7172 | 12.2804 | 21.9859 | 33.6196 | 5 | 5 | 0.4304 | 0.4906 | 143.6659 | 0.2808 |
| 15072302 | Mean | 25.8898 | 41.5026 | 6.16512 | 8.70282 | 5 | 5 | 0.23336 | 0.1791 | 44.06124 | 0.10704 |
| 15072303 | Mean | 42.152 | 4.7268 | 7.9114 | 19.3725 | 4 | 5 | 0.3261 | 1.364 | 370.2757 | 0.5297 |
| 15072304 | Mean | 78.4746 | 34.3138 | 5.01486 | 6.63212 | 5 | 5 | 0.0661 | 0.38728 | 94.97976 | 0.16848 |
| 15072305 | Mean | 36.1954 | 17.2038 | 6.27158 | 6.25526 | 5 | 5 | 0.18872 | 0.89046 | 139.73478 | 0.23052 |
| 15072306 | Mean | 78.4746 | 34.3138 | 5.01486 | 6.63212 | 5 | 5 | 0.0661 | 0.38728 | 94.97976 | 0.16848 |
| 15072307 | Mean | 36.195 | 17.2038 | 6.2716 | 6.2553 | 5 | 5 | 0.1887 | 0.8905 | 139.7348 | 0.2305 |
| 15072308 | Mean | 57.335 | 25.7588 | 5.6432 | 6.4437 | 5 | 5 | 0.1274 | 0.6389 | 117.3573 | 0.1995 |
| 15072309 | Mean | 54.1384 | 9.2662 | 4.01594 | 9.11064 | 5 | 5 | 0.09398 | 0.85306 | 267.0755 | 0.36724 |
| 15072310 | Mean | 28.4544 | 13.6658 | 6.8844 | 7.8956 | 5 | 5 | 0.3059 | 0.5111 | 104.5035 | 0.1794 |

TABLE 76-continued

Test results for silk fibroin coated fabrics.

| Raw Data: | | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index (%) | Overall Moisture Management Capability OMMC |
|---|---|---|---|---|---|---|---|---|---|---|---|
| 15072311 | Mean | 5.1292 | 4.4738 | 8.8047 | 13.0277 | 5 | 5 | 0.9486 | 1.1702 | 246.6729 | 0.3597 |
| 15072312 | Mean | 6.8516 | 9.4722 | 11.0684 | 11.7268 | 5 | 5 | 0.7394 | 0.5794 | 73.4005 | 0.1461 |

Example 21. Manufacturing Processes for Silk Coated Textiles and Leathers

Silk coated textiles and leathers may be manufactured on larger scales according to the methods provided herein using standard textile and leather manufacturing equipment with the addition of silk fibroin-based protein fragment coating steps (e.g., via bath, stencil, or spray methods). For example, a tentering and stentering frame, representing a typical process for applying the silk solution in a continuous process, may include the following units:

An unwinding device used to unroll the fabric supply in a roll configuration;
A feeding system used to control the feed rate of fabric;
A material compensator used to maintain consistent the fabric tension;
A coating machine used to apply the silk solution (i.e., silk fibroin-based protein fragments) in different state (liquid or foam) to the fabric;
A measuring system used to control the amount of silk solution applied;
A dryer used to cure or dry the silk solution on the fabric;
A cooling station used to bring the fabric temperature closed to room value;
A steering frame used to guide the fabric to the rewinding device and maintain straight edges; and
A rewinding used to collect the coated fabric in roll.

Frames may also include rollers and sprayers for application of silk fibroin-based protein fragment coating, UV irradiators for curing of silk and/or other fabric additives (e.g., in a chemical cross-linking step), and RF irradiators (e.g., using microwave irradiation) for drying and chemical cross-linking.

Tentering and stentering equipment and other equipment capable of coating silk solutions onto continuous flat fabric or textile material, including leather, according to the above process, is available from the following suppliers: Aigle, Amba Projex, Bombi, Bruckner, Cavitec, Crosta, Dienes Apparatebau, Eastsign, Europlasma, Fermor, Fontanet, Gaston Systems, Hansa Mixer, Harish, Has Group, Icomatex, Idealtech, Interspare, Isotex, Klieverik, KTP, MP, Mageba, Mahr Feinpruef, Matex, Mathis, Menzel LP, Meyer, Monforts, Morrison Textile, Mtex, Muller Frick, Muratex Textile, Reliant Machinery, Rollmac, Salvade, Sandvik Tps, Santex, Chmitt-Machinen, Schott & Meissner, Sellers, Sicam, Siltex, Starlinger, Swatik Group India, Techfull, TMT Manenti, Unitech Textile Machinery, Weko, Willy, Wumag Texroll, Yamuna, Zappa, and Zimmer Austria.

Equipment capable of drying silk solution coatings on fabric or other textile materials, including leather, is available from the following suppliers: Alea, Alkan Makina, Anglada, Atac Makina, Bianco, Bruckner, Campen, CHTC, CTMTC, Dilmenler, Elteksmak, Erbatech, Fontanet, Harish, Icomatex, Ilsung, Inspiron, Interspare, Master, Mathis, Monfongs, Monforts, Salvade, Schmitt-Maschinen, Sellers, Sicam, Siltex, Swastik Group India, Tacome, Tubetex, Turbang, Unitech Textile Machinery, and Yamuna.

Example 22. Flammability Testing for Silk Coated Textiles

Flame resistant testing of textiles and other products of the invention, coated with silk fibroin-based protein fragments prepared using any of the methods disclosed herein may be performed using methods known to those of skill in the art, and may provide results that demonstrate flame resistant property for textiles and other products coated with silk fibroin-based protein fragments relative to uncoated textiles. Flame resistant testing of fabrics coated with silk fibroin-based protein fragments may be determined, for example, using 16 C.F.R. 1615 or 16 C.F.R. 1616 or other suitable versions of flame resistant testing standards known to those of skill in the art. Briefly, a piece of textile coated with silk fibroin-based protein fragments prepared using any of the methods disclosed herein, after 25 washing cycles, is cut into 3.5 inches wide×10 inches long rectangle specimen. One specimen is suspended in a test chamber through a specimen holder. The test chamber should be a steel chamber and at least with dimensions 32.9 cm. (1215/16 in.) wide, 32.9 cm. (12 15/16 in.) deep, and 76.2 cm. (30 in.) long. The specimen is suspended in the test chamber vertically along the length of the specimen, and is lit up by a burner. Then the char length is measured. The testing is repeated for 5 times and average char length is calculated based on the individual result. The same testing is performed with a textile without a silk coating as a control. The specimen after 5, 10, 15, 20, 30, 35, 40, 45, and 50 washing cycles are also tested. The average char length needs to be less than 7 inches (177.8 mm) to be determined as flame resistant. The char length is the value used to evaluate passing grade for sleepwear flammability.

Two representative fabrics were used in the flammability tests. A cotton interlock fabric coated with 1% silk fibroin solution (16021103) was compared to the same fabric without (16021101) coating. A polyester double knit fabric coated with 1% silk fibroin solution (16021104) was compared to the same fabric without coating (16021102) with 1% silk fibroin solution. The SFS used to coat the fabrics in these experiments had a weight average molecular weight range of about 32-44 kDa.

Results for a cotton interlock fabric are shown in FIG. 151 and FIG. 152. The coating with silk fibroin-based protein fragments does not adversely affect the flammability of the fabric. Similarly, the results for a polyester double-knit fabric, shown in FIG. 153 and FIG. 154, also indicate that coating with silk fibroin-based protein fragments does not adversely affect the flammability of the fabric. No significant differences between samples made from same material (cotton or polyester) were observed. The differences between fabric made with the same material for afterglow and after flame time were not significant. Cotton, as expected, was flammable and none of the samples were left after the test.

Example 23. Abrasion Testing for Silk Coated Textiles

Abrasion testing of textiles and other products coated with silk fibroin-based protein fragments prepared using any of the methods disclosed herein may be performed using methods known to those of skill in the art, and may provide results that demonstrate improved resistance to abrasion for textiles and other products coated with silk fibroin-based protein fragments relative to uncoated textiles. Improved resistance to abrasion is useful in applications such as upholstery, including upholstery designed for home, automotive, aircraft, or other uses. Abrasion testing of fabrics coated with silk fibroin-based protein fragments may be determined, for example, using ASTM Method D4966-12 (Standard Test Method for Abrasion Resistance of Textile Fabrics (Martindale Abrasion Tester Method), ASTM, 2013) or other suitable versions of ASTM Method D4966. Briefly, abrasion resistance is measured by subjecting a textile specimen to a rubbing motion that takes the form of a geometric figure, beginning with a straight line, which becomes a gradually widening ellipse until it forms another straight line in the opposite direction, after which the motion reverses repeatedly. The rubbing occurs under known conditions of pressure and abrasive action. A Martindale Abrasion Tester (commercially available from James H. Heal Co., Ltd.) is used for testing. Resistance to abrasion is evaluated.

Four samples were tested using ASTM Method D4966-12. Sample 16021101 was a 100% cotton interlock fabric. Sample 16021102 was a 100% polyester double knit. Sample 16021501 was the 100% cotton interlock fabric after bath coating (as described herein) with 1% silk fibroin solution (SFS). Sample 16021502 was the 100% polyester double knit fabric after bath coating (as described herein) with 1% SFS. The SFS used to coat the fabrics in these experiments had a weight average molecular weight range of about 11 kDa.

| Testing Results: 16021101 | | Testing Results: 16021102 | |
|---|---|---|---|
| Specimen 1 | 943 rubs | Specimen 1 | 2,000 rubs |
| Specimen 2 | 1,253 rubs | Specimen 2 | 1,862 rubs |
| Specimen 3 | 737 rubs | Specimen 3 | 2,637 rubs |
| Average | 978 rubs | Average | 2,166 rubs |
| standard deviation | 260 | standard deviation | 413 |

| Testing Results: 16021501 | | Testing Results: 16021502 | |
|---|---|---|---|
| Specimen 1 | 805 rubs | Specimen 1 | 4,910 rubs |
| Specimen 2 | 897 rubs | Specimen 2 | 3,090 rubs |
| Specimen 3 | 797 rubs | Specimen 3 | 6,000 rubs |
| Average | 833 rubs | Average | 4,667 rubs |
| standard deviation | 56 | standard deviation | 1,470 |

The foregoing results are illustrated in FIG. 155 and FIG. 156, which show the improved abrasion resistance of polyester after coating with a silk fibroin-based solution.

Example 24: Surface Analysis of Coated Fabrics to Demonstrate the Applied Coatings SEM images of the back side of certain coated fabrics disclosed in Table 77 were obtained at various magnifications as shown in FIGS. 157 to 182.

TABLE 77

| Sample No. | Associated SEM Images | Coating Properties |
|---|---|---|
| 16041301 | FIGS. 277 to 281 | no coating, 150 C., 5 min |
| 16041302 | FIGS. 282 to 286 | 1%, low mw silk, 150 C., 5 min |
| 16041303 | FIGS. 287 to 291 | 1%, low mw silk, 200 C., 3 min |
| 16041304 | FIGS. 292 to 296 | no coating, 200 C., 3 min |
| 16041305 | FIGS. 297 to 301 | 1%, medium mw silk, 200 C., 3 min |
| 16041306 | FIGS. 302 to 306 | 1%, medium mw silk, 150 C., 5 min |
| 16040803 | FIGS. 307 to 311 | 0.075%, medium mw silk, 150 C., 5 min |
| 16040808 | FIGS. 312 to 316 | 0.01%, low mw silk, 150 C., 5 min |

Upon examination of the figures, there are some formations visible on top of controls 16041301 and 16041304, they can be identified as cyclic trimer, which may be a polyester byproduct, salt, or excess dye. The low molecular weight coated fibers present broken bridges between fibers. It may be noted that at low concentration the low molecular weight conglomerates in globs; more than at equivalent concentrations with the medium molecular weight. The medium molecular weight fibers have excellent polyester fibers at any concentration and temperature and a network of bridging fibers may be more visible at higher concentrations.

Example 25: Examination of the Effect of Various Parameters on SFS Coatings

This experiment tested the impact of SFS molecular weight with a 1% concentration at 3 different drying and curing temperature with different drying and curing temperature time. The fabrics were characterized by mass and Liquid Moisture Management Properties of Textile Fabrics (MMT) following AATCC Test Method 195-2012 (Tables 78-80).

TABLE 78

| Experimental parameters | Variables | | |
|---|---|---|---|
| silk solution concentration | 1% | | |
| silk solution molecular weight | medium | low | |
| Wet pick up | at 50 setting on padder | | |
| Temperature @ heat setting (C.) | 65 | 150 | 200 |
| Curing time (min) | 10 | 5 | 3 |

This experiment tested the impact of temperature on silk coated fabric.
  Material 15042001—Non-wicking finish—fabric having a composition of 82% polyester and 1800 elastane.
  Material TFF-01-0012/TFF-01-0010—6% silk solution, medium molecular weight.
  Material TFF-01-0013—6% silk solution, low molecular weight.

TABLE 79

| Sample | Sample Preparation |
|---|---|
| 16040101 (Sample 1) | TFF-01-0012 @ 1% silk solution, 50 setting on padders, 65° C. drying temperature, 10 min curing time, temperature on fabric surface at end of curing was 51.6° C. |
| 16040102 (Sample 2) | TFF-01-0012 @ 1% silk solution, 50 setting on padders, 150° C. drying temperature, 5 min curing tie, temperature on fabric surface at end of curing was 125.3° C. |
| 16040103 (Sample 3) | TFF-01-0012 @ 1% silk solution, 50 setting on padders, 200° C. drying temperature, 3 min drying time, temperature on fabric surface at the end of curing was 165.8° C. |

TABLE 79-continued

| Sample | Sample Preparation |
|---|---|
| 16040104 (Sample 4) | TFF-01-0013 @ 1% silk solution, 50 setting on padders, 200° C. drying temperature, 3 min drying time, temperature on fabric surface at the end of curing was 144° C. |
| 106040105 (Sample 5) | TFF-01-0013 @ 1% silk solution, 50 setting on padders, 150° C. drying temperature, 5 min drying time, temperature on fabric at the end of curing was 130.7° C. |
| 106040106 (Sample 6) | TFF-01-0013 @ 1% silk solution, 50 setting on padders, 65° C. drying temperature, 10 min drying time, temperature on fabric surface at the end of curing was 64° C. |

The samples mass recording is reported in the following table for each variable tested.

TABLE 80

| Sample # | Variables | Mass Before Coating | Mass Post Coating | Coating Mass % |
|---|---|---|---|---|
| 16040101 | 1%, medium, 65 C., 10 min | 28.357 | 28.6268 | 0.95% |
| 16040102 | 1%, medium, 150 C., 5 min | 28.2137 | 28.4231 | 0.74% |
| 16040103 | 1%, medium, 200 C., 3 min | 28.2459 | 28.4365 | 0.67% |
| 16040104 | 1%, low, 200 C., 3 min | 28.0225 | 28.1442 | 0.43% |
| 16040105 | 1%, low, 150 C., 5 min | 27.9803 | 28.1203 | 0.50% |
| 16040106 | 1%, low, 65 C., 10 min | 28.5204 | 28.7611 | 0.84% |

The collective results are provided in FIG. 193 for each tested material. However, sample 16040102 did not produce acceptable results and 15042001 is provided as a reference, which is not coated.

The results of these analyses are provided in table form in FIG. 194. Specifically, FIG. 194 describes the grading for each tested sample (medium and low molecular weight samples) in terms of wetting (top and bottom), absorption rate (top and bottom), wetted radius (top max and bottom max), spreading speed (top and bottom), accumulative one-way transport, and overall moisture management capability (OMMC).

From the presented results the SFS coated fabric has an impact on the MMT grading of fabric, significantly improving the accumulative one way transport index from the non-coated standard of grade 2 to the SFS coated grades of 4-5 depending on molecular weight and curing time and temperature. While with the OMMC index the non-coated standard has a grade of 1 compared to the SFS coated grades of 3 independent of tested variables.

Example 26: Impact of SFS Concentration at Low and Medium Molecular Weight Samples This experiment tested the impact of SFS concentration at 2 molecular weights using the same drying and curing temperature time. The fabrics were characterized by mass and Liquid Moisture Management Properties of Textile Fabrics (MMT) following AATCC Test Method 195-2012. The experimental parameters are provided in Table 81.

TABLE 81

| Experimental parameters | Variables | | | | | | | |
|---|---|---|---|---|---|---|---|---|
| silk solution concentration | 0.750% | 0.500% | 0.250% | 0.100% | 0.075% | 0.050% | 0.025% | 0.010% |
| silk solution molecular weight | medium | low | medium | low | medium | low | medium | low |
| Wet pick up | at 50 setting on padder | | | | | | | |
| Temperature @ heat setting ° C. | 150 | | | | | | | |
| Curing time (min) | 5 | | | | | | | |
| Padder speed (m/min) | 3 | | | | | | | |

The samples mass recording is reported in the following table for each variable tested (Table 82).

TABLE 82

| Sample # | Variables | Mass Before Coating | Mass Post Coating | Mass Post 24 hrs Coating | Coating Mass % |
|---|---|---|---|---|---|
| 16040801 | 0.75%, medium mw silk, 150 C., 5 min | 27.7229 | 27.8157 | 27.8731 | 0.54% |
| 16040802 | 0.25%, medium mw silk, 150 C., 5 min | 27.5821 | 27.5660 | 27.6011 | 0.07% |
| 16040803 | 0.075%, medium mw silk, 150 C., 5 min | 27.5871 | 27.5154 | 27.5582 | −0.10% |
| 16040804 | 0.025%, medium mw silk, 150 C., 5 min | 27.7265 | 27.6364 | 27.6771 | −0.18% |
| 16040805 | 0.50%, low mw silk, 150 C., 5 min | 27.9121 | 27.9367 | 27.9646 | 0.19% |
| 16040806 | 0.10%, low mw silk, 150 C., 5 min | 27.6692 | 27.5963 | 27.6298 | −0.14% |
| 16040807 | 0.05%, low mw silk, 150 C., 5 min | 27.8840 | 27.8040 | 27.8389 | −0.16% |
| 16040808 | 0.01%, low mw silk, 150 C., 5 min | 28.1490 | 28.0500 | 28.0755 | −0.26% |

Sample test results for each variable tested are reported in the table set forth in FIG. 195, where sample 15042001 is a non-coated control. Sample test grading for each variable tested are reported in the table provided in FIG. 196.

From the presented results the SFS coated fabric has an impact on the MNMT grading of fabric, significantly improving the accumulative one-way transport index from the non-coated standard of grade 2 to the SFS coated grades of 5 depending on molecular weight (low vs. medium) and SFS concentration. While with the OMMC index the non-coated standard has a grade of 1 compared to the SFS coated grades of 3 independent of tested variables.

Example 27: Tested Impact of Curing Time on Coatings at Two Molecular Weights

This experiment tested the impact of curing time at 150° C. and 200° C. with SFS at 1% concentration at two molecular weights. The fabrics were characterized by mass and Liquid Moisture Management Properties of Textile Fabrics (MMT) following AATCC Test Method 195-2012.

The experimental parameters are provided in Table 83.

TABLE 83

| Experimental Parameters | Variables | |
|---|---|---|
| silk solution concentration | 1.000% | |
| silk solution molecular weight | medium | low |
| Wet pick up | at 50 setting on padder | |
| Temperature @ heat setting° C. | 150 | 200 |
| Curing time (min) | 3 5 10 | |
| Padder speed (m/min) | 3 | 3 |

The samples mass recording is reported in the following table for each variable tested (Table 84).

TABLE 84

| Sample # | Variables | Mass Before Coating | Mass Post Coating | Mass Post 24 hrs Coating | Coating Mass % |
|---|---|---|---|---|---|
| 16041201 | 1% low mw silk, 150 C., 10 min | 28.2130 | 28.2708 | 28.3311 | 0.42% |
| 16041202 | 1% low mw silk, 200 C., 10 min | 28.0331 | 28.0221 | 28.0575 | 0.09% |
| 16041302 | 1%, low mw silk, 150 C., 5 min | 27.7916 | 27.8905 | 27.9608 | 0.61% |
| 16041303 | 1%, low mw silk, 200 C., 3 min | 27.7066 | 27.7484 | 27.7973 | 0.33% |
| 16041203 | 1% medium mw silk, 200 C., 10 min | 27.8510 | 27.8545 | 27.9256 | 0.27% |
| 16041204 | 1% medium mw silk, 150 C., 10 min | 27.0315 | 27.1104 | 27.1567 | 0.46% |
| 16041305 | 1%, medium mw silk, 200 C., 3 min | 28.1509 | 28.2656 | 28.3306 | 0.64% |
| 16041306 | 1%, medium mw silk, 150 C., 5 min | 27.3574 | 27.5165 | 27.5715 | 0.78% |
| 16041301 | no coating, 150 C., 5 min | 26.7848 | 26.6993 | 26.7412 | −0.16% |
| 16041304 | no coating, 200 C., 3 min | 27.8559 | 27.7539 | 27.7896 | −0.24% |

Sample test results for each variable tested are reported in the table set forth in FIG. 197, where samples 16041301 and 16041304 are non-coated fabrics for reference. Sample test grading for each variable tested are reported in the table provided in FIG. 198.

From the presented results the curing temperature time may reduce the MMT grading when 1% SFS coated fabric is exposed between 5-10 minutes at 150° C. or 200° C. At the other curing time tested 3 and 5 minutes at 150° C. or 200° C. there is no apparent impact on accumulative one-way transport or OMMC grades.

Example 28

This experiment tested the impact of temperatures of 65° C., 150° C., and 200° C. at the minimum drying and curing time with 1% SFS at two molecular weights. The fabrics were characterized by mass and Liquid Moisture Management Properties of Textile Fabrics (MMT) following AATCC Test Method 195-2012.

The experimental parameters are provided in Table 85.

TABLE 85

| Experimental Parameters | Variables | |
|---|---|---|
| silk solution concentration | 1% | no solution |
| silk solution molecular weight | medium | low |
| Wet pick up | at 50 setting on padder | |
| Temperature @ heat setting (C.) | 150 | 200 |
| Curing time (min) | 5 | 3 |
| Padder speed (m/min) | 3 | 3 |

The samples mass recording is reported in the following table for each variable tested (Table 86).

TABLE 86

| Sample # | Variables | Mass Before Coating | Mass Post Coating | Mass Post 24 hrs Coating | Coating Mass % |
|---|---|---|---|---|---|
| 16041301 | no coating, 150° C., 5 min | 26.7848 | 26.6993 | 26.7412 | −0.16% |
| 16041302 | 1%, low mw silk, 150° C., 5 min | 27.7916 | 27.8905 | 27.9608 | 0.61% |
| 16041303 | 1%, low mw silk, 200° C., 3 min | 27.7066 | 27.7484 | 27.7973 | 0.33% |
| 16041304 | no coating, 200° C., 3 min | 27.8559 | 27.7539 | 27.7896 | −0.24% |
| 16041305 | 1%, medium mw silk, 200° C., 3 min | 28.1509 | 28.2656 | 28.3306 | 0.64% |
| 16041306 | 1%, medium mw silk, 150° C., 5 min | 27.3574 | 27.5165 | 27.5715 | 0.78% |
| 15042001 | no coating | | | | |
| 16040101 | 1%, medium mw silk, 65° C., 10 min | 28.357 | 28.6268 | | |
| 16040106 | 1%, low mw silk, 65° C., 10 min | 28.5204 | 28.7611 | | |

Sample test results for each variable tested are reported in the table set forth in FIG. 199, where samples 16041301, 16041304, and 15042001 are non-coated fabrics for reference. Sample test grading for each variable tested is reported in the table provided in FIG. 200.

From the presented results the curing temperature of 65° C., 150° C., and 200° C. has limited to no impact on the MMT grading when 1% SFS coated fabric is exposed for respectively 3, 5, and 10 minutes. Medium molecular weight coated fabrics have faster wetting time than low molecular weight coated fabrics or non-coated control fabrics. Low molecular weight coated fabrics exhibit a faster spreading time than medium molecular weight coated fabrics or non-coated control fabrics. Medium molecular weight coated fabrics or low molecular weight coated fabrics perform equal to or better than non-coated control fabrics in terms of Accumulative One Way Transport and OMMC.

Example 29: Listing of Specific Fabrics

Table 87 includes a listing of coated and non-coated fabrics tested in the present Examples and their associated coating process variables.

TABLE 87

| Sample ID | Variables |
|---|---|
| 16040101 | 1% SFS, medium, 65° C., 10 min |
| 16040102 | 1% SFS, medium, 150° C., 5 min |
| 16040103 | 1% SFS, medium, 200° C., 3 min |
| 16040104 | 1% SFS, low, 200° C., 3 min |

TABLE 87-continued

| Sample ID | Variables |
|---|---|
| 16040105 | 1% SFS, low, 150° C., 5 min |
| 16040106 | 1% SFS, low, 65° C., 10 min |
| 16040801 | 0.75% SFS, medium mw silk, 150° C., 5 min |
| 16040802 | 0.25% SFS, medium mw silk, 150° C., 5 min |
| 16040803 | 0.075% SFS, medium mw silk, 150° C., 5 min |
| 16040804 | 0.025% SFS, medium mw silk, 150° C., 5 min |
| 16040805 | 0.50% SFS, low mw silk, 150° C., 5 min |
| 16040806 | 0.10% SFS, low mw silk, 150° C., 5 min |
| 16040807 | 0.05% SFS, low mw silk, 150° C., 5 min |
| 16040808 | 0.01% SFS, low mw silk, 150° C., 5 min |
| 16041201 | 1% SFS, low mw silk, 150° C., 10 min |
| 16041202 | 1% SFS, low mw silk, 200° C., 10 min |
| 16041203 | 1% SFS, medium mw silk, 200° C., 10 min |
| 16041204 | 1% SFS, medium mw silk, 150° C., 10 min |
| 16041301 | no coating, 150° C., 5 min |
| 16041302 | 1% SFS, low mw silk, 150° C., 5 min |
| 16041303 | 1% SFS, low mw silk, 200° C., 3 min |
| 16041304 | no coating, 200° C., 3 min |
| 16041305 | 1% SFS, medium mw silk, 200° C., 3 min |
| 16041306 | 1% SFS, medium mw silk, 150° C., 5 min |
| 16042501 | 0.075% SFS, medium mw silk skin side up |
| 16042502 | 0.075% SFS, medium mw silk skin side down |
| 16042503 | 0.1% SFS, low mw silk skin side up |
| 16042504 | 0.01% SFS, low mw silk skin side down |
| 16050301 | 1% SFS, low mw silk, 200° C. 3 min |
| 16050302 | 0.1% SFS, low mw silk, 200° C., 3 min |
| 16050303 | 1% SFS, medium mw silk, 200° C. 3 min |
| 16050304 | 1% SFS, medium mw silk, 200° C. 3 min |
| 16050305 | 1% SFS, medium mw silk, 200° C. 3 min |
| 16050306 | 0.1% SFS, medium mw silk, 200° C., 3 min |
| 16050307/ 15042001 | non wicking finished, 200° C., 3 min |
| 16050308/ 15042001 | non wicking finished, 200° C., 3 min |
| 16050309/ 15042001 | non wicking finished, 200° C., 3 min |
| 16050310/ 15042001 | non wicking finished, 150° C., 5 min |
| 16050311/ 15042001 | non wicking finished, 150° C., 5 min |
| 16050312/ 15042001 | non wicking finished, 150° C., 5 min |
| 16050401 | 0.1% SFS, medium mw silk, 65° C. 10 min |
| 16050402 | 0.1% SFS, medium mw silk, 150° C. 5 min |
| 16050403 | 0.1% SFS, medium mw silk, 200° C. 3 min |
| 16050404 | 0.25% SFS, medium mw silk, 65° C. 10 min |
| 16050405 | 0.25% SFS, medium mw silk, 150° C. 5 min |
| 16050406 | 0.25% SFS, medium mw silk, 200° C. 3 min |
| 16050407 | 0.1% SFS, low mw silk, 65° C. 10 min |
| 16050408 | 0.1% SFS, low mw silk, 150° C. 5 min |
| 16050409 | 0.1% SFS, low mw silk, 200° C. 3 min |
| 16050410 | 0.25% SFS, low mw silk, 65° C. 10 min |
| 16050411 | 0.25% SFS, low mw silk, 150° C. 5 min |
| 16050412 | 0.25% SFS, low mw silk, 200° C. 3 min |

Example 30: A Map of the Fabric Samples Tested

A number of the coated and non-coated fabrics described herein were tested for anti-microbial activity. Those fabrics, and their identities and process variables, are set forth in Table 88.

TABLE 88

| silk molecular weight | concentration (%) | curing 65 | | | 150 | | | 200 (385° F. = 196° C.) | | | temperature (° C.) time (min) |
|---|---|---|---|---|---|---|---|---|---|---|---|
| | | 3 | 5 | 10 | 3 | 5 | 10 | 3 | 5 | 10 | |
| medium | 1.000 | | | 16040101 | | 16040102 | 16041204 | 16040103 16041305 16050303 16050304 16050305 | | 16041203 | anti microbial |
| | 0.750 | | | | | 16040801 | | | | | |
| | 0.500 | | | | | | | | | | |
| | 0.250 | | | 16050404 | | 16040802 16040802 16050405 | | 16050406 | | | |
| | 0.100 | | | 16050401 | | 16050402 | | 16050403 16050306 | | | |
| | 0.075 | | | | | 16040803 16042503 16042504 | | | | | |
| | 0.050 | | | | | | | | | | |
| | 0.025 | | | | | 16040804 | | | | | |
| | 0.001 | | | | | | | | | | |
| low | 1.000 | | | 16040106 | | 16040105 16041302 16040105 | 16041201 | 16040104 16041303 16050301 | | 16041202 | |
| | 0.750 | | | | | | | | | | |
| | 0.500 | | | | | 16040805 | | | | | |
| | 0.250 | | | 16050410 | | 16050411 | | 16050412 | | | |
| | 0.100 | | | 16050407 | | 16040806 16042501 16042502 16040806 16050408 | | 16050409 16050302 | | | |
| | 0.075 | | | | | | | | | | |
| | 0.050 | | | | | 16040807 | | | | | |
| | 0.025 | | | | | | | | | | |
| | 0.001 | | | | | 16040808 | | | | | |
| control | | | | | | | | | | | |

TABLE 88-continued

| | silk | | | | | | curing | | | temperature |
|---|---|---|---|---|---|---|---|---|---|---|
| molecular weight | concentration (%) | 65 | | | 150 | | 200 (385° F. = 196° C.) | | | (° C.) |
| | | 3 | 5 | 10 | 3 | 5 | 10 | 3 | 5 | 10 | time (min) |
| non-finished | 15042001 | | | | 16041301 16050310 16050311 16050312 | | | 16041304 16050307 16050308 16050309 | | | antimicrobial |
| semi-finished | 15042002 | | | | | | | | | | |
| finished | 15042002 15042003 16042003 | | | | | | | | | | |

Example 31: Results of Liquid Moisture Management Tests

FIG. 201 provides a map of Liquid Moisture Management Test results for various coated fabrics described herein.

Example 32: Silk Fibroin Solution with Silicone Softener

The objective of this study will be to evaluate the impact to the hand of the fabric of two types of silicon softeners in conjunction with silk fibroin solution. In addition, Liquid Moisture Management testing (MMT) according to AATCC 195-2012 will be completed on the samples, and a drapability test according to the drape elevator method modified to accommodate samples dimension.

This study will be performed to evaluate the changes in hand characteristics of a fabric when commercially available silicon softeners are mixed with different percentage and molecular weight of silk fibroin solution followed by a drying and curing process. The fabrics will be characterized for Moisture Management properties and drapability.

Materials and equipment for the study include Silk Therapeutics medium molecular weight solution at 6%, Silk Therapeutics low molecular weight solution at 6%, Huntsman Ultratex CSP, Huntsman Ultratex SI, Acetic acid, Citric acid, RODI water, Fabric sample 15042001 non-wicking finish, a permanent marker, Werner Mathis MA0881 padder/coater, curing frame, Across International Oven FO-19140, Balance Veritas M314-AI, Universal plastic pH test strip, Drape elevator test fixture, and an LG Nexus 5× phone camera.

Silk coated fabric will be prepared following SOP-TEMP-001. Silk solution concentration will be prepared at the desired concentration as reported in the table below and is mixed to the desired concentration of silicon softener as reported in Table 89. The coating solution is applied to the fabric with bath immersion and pad roller pressure setting at 50. After coating the fabric is dry/cure in the oven at 200° C. for 3 minutes.

TABLE 89

| Experiment Variables | | | | |
|---|---|---|---|---|
| Silk solution medium mw silk | Ultratex SI | Ultratex CSP | Acetic acid | Citric acid |
| 1% | 22 gr/liter | | | |
| 1% | | 50 gr/liter | | |
| 1% | 22 gr/liter | | | 0.5 gr/liter |

TABLE 89-continued

| Experiment Variables | | | | |
|---|---|---|---|---|
| Silk solution medium mw silk | Ultratex SI | Ultratex CSP | Acetic acid | Citric acid |
| 1% | | 50 gr/liter | 1 gr/liter | |
| 1% | | | | 1 gr/liter |
| 1% | | | | 0.5 gr/liter |
| No Silk | 22 gr/liter | | | |
| No Silk | | 50 gr/liter | | |
| No Silk | 22 gr/liter | | 0.5 gr/liter | |
| No Silk | | 50 gr/liter | 1 gr/liter | |

Post curing the fabric is left to condition at room temperature for 24 hrs.

Samples are cut to 8 cm by 8 cm square and delivered to MSC lab for MMT testing.

After conditioning the fabric is tested for drapability using the drape elevator test modified to accommodate the MMT sample size dimension. After placing the sample on the testing jig an image is recorded with a camera; the elevator is lowered until no more contact is made with the fabric by the elevator table and a second image is recorded. Image analysis of the fabric area is performed through Photoshop. A drape coefficient is calculated with the following formula:

$$\text{Drape Coefficient} = \frac{Ad - S1}{S2 - S1} * 100,$$

where Ad is the vertical projection of the draping sample, S1 the area of the round sample holder, and S2 is the area of the sample.

Example 33: Antibacterial Study

An experiment is devised for evaluating the antibacterial proliferation on SFS coated fabrics through multiple washing cycles. Specifically, the study will examine whether bacteria will adhere to silk-coated fabric following wash.

The study will mimic the bacterial deposition on textile material during regular exercise and home laundering.

The antibacterial testing will be at 0, 1, 10, and 25 minute cycles using a front loading washer with water at less than 30° C. The fabrics will be air or tumble dried at less than 50° C.

A 13.5×13.5 inch fabric swatch will spotted with eight (8) inoculation sites and tested following washing at the disclosed intervals to determine the presence and quantity of bacteria.

Example 34: Drapability of Exemplary Silk Coated Fabrics

The following coated fabrics were prepared according to the processes described herein and tested for drapability according to the method described in Mizutani, et al., "A New Apparatus for the Study of Fabric Drape." *Textile Research Journal* (2005) 75: 81-87.

The materials in the method include a sample and camera holding fixture, sample holding fixture of 5 cm in diameter, an elevator plane, and a camera. The fabric specimens were 8×8 cm$^2$. The procedure included: (1) cutting the sample to 8×8 cm square (8 cm diameter may be used); (2) placing the specimen at the center of a fixture; (3) elevating the fixture to examine the draping of the specimen; and (4) capture an image of the specimen.

The images were opened in Adobe Photoshop CS5.1 and the lazo function was used to delmit the perimeter of the specimen. The measurement function was then used to count all the pixels within the selected area and such data was saved. This process was repeated for each specimen. A drape coefficient was calculated based on the following formula:

$$\text{Drape Coefficient} = \frac{Ad - S1}{S2 - S1} * 100,$$

where Ad is the vertical projection of the draping sample, S1 is the area of the round sample holder, and S2 is the area of the sample. The data for such analysis is set forth in Table 90 and associated FIG. 202.

TABLE 90

| Sample No. | Sample Properties | Avg. Drapability Coefficient | STDev |
|---|---|---|---|
| 16052001 | 1% medium mw silk solution, + 2.2% ULTRATEX ® SI ("SI") | 80.0 | 1.9 |
| 16052002 | 1% medium mw silk, + 2.2% SI + acetic acid 0.5% | 88.2 | 2.1 |
| 16052003 | 1% medium mw silk solution, + 5% ULTRATEX ® CSP ("CSP") | 81.8 | 3.1 |
| 16052004 | 1% medium mw silk solution, + 5% CSP + acetic acid 1% | 88.2 | 2.9 |
| 16052005 | 1% medium mw silk solution, + 0.1% citric acid | 92.7 | 0.7 |
| 16052006 | 1% medium mw silk solution, + 0.05% citric acid | 89.9 | 0.4 |
| 16051103 | no coating, 200 C., 3 min | 83.2 | 1.4 |
| 16051109 | 0.25%, medium mw silk solution, 200° C. 3 min | 85.7 | 1.7 |
| 16051115 | 0.25%, low mw silk solution, 200° C. 3 min | 89.9 | 2.4 |
| 16052501 | 2.2% SI | 69.1 | 4.4 |
| 16052502 | 2.2% SI + acetic acid 0.5% | 61.7 | 1.9 |
| 16052503 | 5% CSP | 61.6 | 4.8 |
| 16052504 | 5% CSP + acetic acid 1% | 59.5 | 3.5 | the foregoing study, silk solution, drying parameters, and silicone compositions were used to adjust the drapability for a variety of coated fabrics.

Example 35: Effect of Mechanical and Steam Finishing on a Silk Coated Fabric

A sample was prepared as described herein, wherein the sample was a polyester/LYCRA non-finished fabric coated with a 1% SFS (medium molecular weight) that was dried at 200° C. for 3 minutes. In addition, the same fabric was subjected to a 41 minutes dryer cycle at normal setting on medium temperature (mechanical finishing) and to steaming on a steam table for 5 seconds (steam finishing). The resulting samples, after finishing, were examined for drapability as shown in Table 91 and in FIG. 203.

TABLE 91

| Sample No. | Sample Properties | Avg. Drapability Coefficient | STDev |
|---|---|---|---|
| 16041305 | 1% medium mw silk, 200° C. 3 min | 82.1 | 1.2176 |
| 16041305 | post mechanical finish | 80.0 | 2.3692 |
| 16041305 | post steam finish | 91.4 | 2.7572 |

While the mechanical finishing with the dryer reduced the drapability coefficient (i.e., less stiff fabric), the steam finishing increased the drapability coefficient (i.e., stiffer fabric).

Results of experiments measuring solution depletion calculation during coating are shown in FIG. 204, and illustrate the amount of silk fibroin deposited on fabrics.

Additional results of moisture management testing of coated fabrics are given in FIG. 205 to FIG. 210.

Additional results from antimicrobial testing of coated fabrics are given in FIG. 211.

Example 36: Effectiveness of Diluting Silk with Tap Water

The silk compositions described herein are stable and effective when prepared with tap water.

A 1:1 ratio between the silicone and silk gave a softer hand to a resulting fabric with a 20:1 ratio between silk/silicone and citric acid.

The parameters for the study between tap water and reverse-osmosis/deionized (RODI) water are set forth in Table 92.

TABLE 92

| Silk Solution | Water | Softener | pH Correction |
|---|---|---|---|
| 0.25% med mw silk | RODI | | |
| 0.25% med mw silk | RODI | 0.25% Ultratex CSP | 0.02% citric acid (50%) |
| 0.25% low mw silk | RODI | | |
| 0.25% low mw silk | RODI | 0.25% Ultratex CSP | 0.02% citric acid (50%) |
| 0.25% med mw silk | Unfiltered tap | | |
| 0.25% med mw silk | Unfiltered tap | 0.25% Ultratex CSP | 0.02% citric acid (50%) |
| 0.25% low mw silk | Unfiltered tap | | |
| 0.25% low mw silk | Unfiltered tap | 0.25% Ultratex CSP | 0.02% citric acid (50%) |

The parameters for a second study are set forth in Tables 93 and 94. The results of this study are illustrated in FIG. 215. The second study relates to a water drop test on polyester/lycra knitted fabric treated with RODI water and tap water.

TABLE 93

| Experimental Parameters | Variables | | |
|---|---|---|---|
| silk solution concentration | 0.25% | | |
| silk solution molecular weight | medium | low | — |
| water | RODI | tap water | — |
| Wet pick up | at 50 setting on padder | | |
| Temperature @ heat setting (C.) | 200 | | |
| Curing time (min) | 3 | | |
| silicon softener Ultratex CSP | 0.25% | — | — |
| citric acid | 0.0200% | — | — |

TABLE 94

| Sample Number | Description | Time to absorb (sec) |
|---|---|---|
| 16070601 | 0.25% medium mw silk (RODI) | 1 |
| 16070602 | 0.25% medium mw silk, 0.25% Ultratex CSP, 0.02% citric acid (50%) | 25 |
| 16070603 | 0.25% low mw silk | 1 |
| 16070604 | 0.25% low mw silk, 0.25% Ultratex CSP, 0.02% citric acid (50%) | 10 |
| 16070605 | 0.25% medium mw silk (tap water) | 2 |
| 16070606 | 0.25% medium mw silk, 0.25% Ultratex CSP, 0.02% citric acid (50%) | 30 |
| 16070607 | 0.25% low mw silk | 1 |
| 16070608 | 0.25% low mw silk, 0.25% Ultratex CSP, 0.02% citric acid (50%) | 22 |

The results of the foregoing study indicated that there was no difference in the resulting properties of those silk solutions prepared in RODI water as compared to unfiltered tap water. Moreover, the silk solutions did not precipitate with the use of tap water.

Example 37: A Study of Silk Solution as a Wicking Agent

Silk solutions as disclosed herein can be adopted as a wicking agent in common finishing recipes to balance the water repellency of silicone softeners.

The present test is a modification to AATCC-79-2014 that was prepared to accommodate the dimensions of the tested samples (8×8 cm samples), where the AATCC test is designed for a sample of 150 cm in diameter. Here, the samples are cut in 8 cm by 8 cm and placed in a drapability jig suspended on a 7 cm diameter round metal hoop so the back of the fabric has no surface contact. An RODI water drop is dispensed with an eye dropper from approximately 3 cm above the fabric. A video imaging recording captures the time from the water drop contacting the fabric until its full absorption or up to 30 seconds.

Without silk, the water drop stays on the fabric surface up to the test end of 30 seconds; while in the presence of silk the water drop is absorbed in as long as 4 seconds or as fast as 1 second depending on the tested variables.

The parameters for this study are set forth in Table 95 with the results set forth in FIGS. 212 and 213.

TABLE 95

| Sample Number | Description | Time to absorb (sec) |
|---|---|---|
| 16062901 | 0.22% Ultratex SI | 30 |
| 16062902 | 0.5% Ultratex CSP | 30 |
| 16062905 | 0.22% Ultratex SI, 0.025% citric acid | 30 |

TABLE 95-continued

| Sample Number | Description | Time to absorb (sec) |
|---|---|---|
| 16062906 | 0.5% Ultratex CSP, 0.025% citric acid | 30 |
| 16062105 | 0.5% medium mw silk, 0.22 gr/liter Ultatex SI | 3 |
| 16062106 | 0.5% low mw silk, 0.5 gr/liter Ultratex CSP | 1 |
| 16062107 | 0.5% low mw silk, 2.2 gr/liter Ultratex SI, 0.025 gr/liter citric acid | 1 |
| 16062108 | 0.5% medium mw silk, 5 gr/liter Ultratex CSP, 0.025 gr/liter citric acid | 4 |

Example 38: A Study of Dyeing Polyester and Nylon Fabrics Followed by the Application of Silicone and Silk Solution Through Exhaust The objective of this study is to evaluate the application of silk fibroin solution on fabrics made with polyester/spandex and nylon/spandex. The application will take place after dyeing the fabrics at exhaust. In addition, silicon softeners will be added to the silk solution to improve the hand of the fabrics. Liquid Moisture Management testing (MMT) according to AATCC 195-2012, a drapability test according to the drape elevator method modified to accommodate samples dimension, and a water drop test will be used to characterize the fabrics.

This study was performed for research and development purposes to evaluate the feasibility to apply silk fibroin solution at exhaust post dyeing. In addition, commercially available silicon softeners were mixed with different percentage and molecular weight of silk fibroin solution to improve hand and drapability of the fabric.

Materials:
  Silk Therapeutics medium molecular weight solution at 6%;
  Silk Therapeutics low molecular weight solution at 6%;
  Huntsman Ultratex CSP;
  Huntsman Ultratex SI;
  Acetic acid;
  Fabric sample polyester/spandex; and
  Fabric sample nylon/spandex.
Equipment:
  5 pounds paddle dyer by Rome Machine Foundry Co. SN #640115;
  5 pounds pressure dyer by Optidye RS Basic Plus;
  Hydroextractor;
  Balance Veritas M314-AI;
  Universal plastic PH test strip;
  Drape elevator test fixture; and
  5× phone camera.
Methods:
Nylon
  The fabric sample is placed in the 5-pound paddle dryer along with enough dunnage to total 3-pound load. The tub is filled with water. The following wetting and scouring agent are added:
    1.0% wetter D.75 OWG;
    1.0% scour SKB OWG;
    4.0% black 2RSLD OWG;
    acetic acid 56% to reach PH 5.5;
    2.0% softener RWS Hydrophilic OWG; and
    3% fix agent ED 73% OWG.
  The dyer is run at 100 F for 5 minutes. Dye is added and run for 10 minutes. The sample is heated at a rate of 4 F/minute up to 200 F. Acetic acid is added to a pH of 5.5. The sample is allowed to run for 45 more minutes.

A sample color shade is prepared and, if acceptable, the sample is allowed to cool to 160 F.

The solution is dropped and refilled than refilled and run for 5 times, with the entire process repeated 4 times.

Softener is then added (i.e., silicon and silk solution at the concentration reported in Table 96) heat to 160° F. and run for 10 minutes. Drop solution and remove fabric from the machine.

TABLE 96

| Silk solution | Ultratex SI | Ultratex CSP |
|---|---|---|
| 0.1% low mw silk | 1 gr/liter | |
| 0.1% low mw silk | | 2.5 gr/liter |
| 0.5% low mw silk | 1 gr/liter | |
| 0.5% low mw silk | | 2.5 gr/liter |
| 0.1% medium mw silk | 1 gr/liter | |
| 0.1% medium mw silk | | 2.5 gr/liter |
| 0.5% medium mw silk | 1 gr/liter | |
| 0.5% medium mw silk | | 2.5 gr/liter |
| | 1 gr/liter | |
| 0.5% medium mw silk | | 2.5 gr/liter |
| 0.5% low mw silk | | |
| Control (only dye) | Control (only dye) | Control (only dye) |

Polyester

The fabric sample is placed in the 5-pound pressure dryer along with enough dunnage to total 3-pound load. The tub is filled with water. The following wetting and scouring agent are added for pre-scouring process: 1.0% wetter and 2.0% scour.

The solution was heated to 180° F. for 20 minutes. The solution was dropped and rinsed. To the solution was added 1% wetter, acetic acid to pH 5.0, with a leveler used as desired, and heated to 110° F. Dissolved dyes were added and heated to 180° F., with the temperature held for 10 minutes. The solution was then heated to 265° F. at 3° F./minute and held at 265° F. for 90 minutes.

The solution was then cooled to 180° F. and the color shade was sampled. Upon acceptance, the solution was dropped and rinsed three times. The solution was further cooled to 140° F. and hydro was added for 15 minutes. The solution was again dropped and rinsed 2-3 times until clean. The solution was then cooled to 110° F. and softener was added (silicone and silk solution at the concentration reported in Table 96) for 10 minutes. The solution was dropped and the fabric was removed from the machine.

The fabric is dried by first removing excess fluid with Hydroextractor followed by a dryer cycle at normal setting with low temperature. Samples are cut to 8 cm by 8 cm square and delivered to MSC lab for MMT testing. Samples cut in 8 cm by 8 cm that are not tested for MMT are placed in the drapability jig suspended on a 7 cm diameter round metal hoop. A RODI water drop is dispensed with an eye dropper from approximately 3 cm above the fabric. A video image recording captured the time from the water drop contacting the fabric until its full absorption or up to 60 seconds.

After conditioning, the fabric is tested for drapability using the drape elevator test modified to accommodate the MMT sample size dimension. After placing the sample on the testing jig an image is recorded with a camera; the elevator is lowered until no more contact is made with the fabric by the elevator table and a second image is recorded. Image analysis of the fabric area is performed through Photoshop. A drape coefficient is calculated with the following formula:

$$\text{Drape Coefficient} = \frac{Ad - S1}{S2 - S1} * 100$$

where Ad is the vertical projection of the draping sample, S1 the area of the round sample holder, and S2 is the area of the sample. The fabrics with a water drop test <3 seconds and a drapability of <90 were submitted for MMT testing.

Example 39: Bacterial Wash Adherence Study through Washing Machine Cycle

The objective of this study was to evaluate the bacterial proliferation through multiple washing cycles in the laboratory while duplicating the bacterial deposition on textile materials that take place during regular exercise.

Materials. The Following List of Materials were Used for Fabric Sample Preparation and Study Execution:
Polyester/lycra fabric 15042201;
Deionized water;
6% Mid-MW silk provided by Silk Therapeutics, Inc.;
6% Low-MW Silk provided by Silk Therapeutics, Inc.;
Launtry Permanent Marker;
Front loader washing machine LG model WM3370HWA;
AATCC detergent without optical brightener liquid H/E;
*Staphylococcus aureus* subsp. *aureus* RosenbachATCC® 6538;
Inoculum carrier to be 5% Nu-broth;
Letheen broth with tween as neutralizer for enumeration;
BD Difco Leethen broth #268110; and
Concentrated Clorox regular bleach.

Equipment. The Following is a List of Equipment Used from the Fabric Sample Preparation and Study Execution:
Werner Mathis MA-881 padder/coater;
Curing frame;
Across International Oven FO-19140;
Balance Veritas M314-AI;
Universal plastic PH test strip; and
Tempo Filler and Reader from BioMerieux for enumeration.

Methods.

Fabric Sample Preparation. Silk coated fabric is prepared following SOP-TEMP-001. Silk solution concentration at 0.05% is applied to the fabric with bath immersion with the padder's roller pressure setting at 50 and 200 C curing time for 3 minutes. Fabric sample with 13.5 inches by 13.5 inches are divided with a permanent marker to delimit 8 equivalent areas.

Bacteria Inoculation. At the center for each of the 8 areas $2 \times 10^7$ cfu of bacteria solution was inoculated. The total load per washing cycle was expected to be $1$-$2 \times 10^8$ CFU. The inoculated fabric was allowed to air dry for 60 minutes.

Washing Cycle. The inoculated fabric was placed in the washing machine with 1.8 kg of cotton towel as dunnage with 50 mL of detergent. A washing machine cycle at gentle setting with warm water at less than 30 C was completed. The inoculated fabric was removed from the washing machine and allowed to air dry for 120 minutes. After each washing cycle the dunnage was bleached with 120 mL concentrated Clorox regular bleach to eliminate any bacteria transfers from the tested specimen to the dunnage.

Bacteria Enumeration. At preset intervals, from the dried inoculated fabric 2 square samples were cut out and the bacteria count was enumerated following, as a guideline, the enumeration method of AATCC 100.

Study Execution. For the fabric to be inoculated, multiple bacteria inoculation washing cycles and testing for bacteria enumeration at different intervals were executed on each tested fabric. For the fabric with no inoculation, the same washing cycle and testing for bacteria enumeration at the same intervals were used. Since at enumeration swatches of fabric were removed from the fabric, to maintain the total bacteria load per washing cycle, an additional piece of control fabric was added to the dunnage. The additional fabric was inoculated with the balance of bacteria load. For example, after 1 washing cycle the additional fabric received $4 \times 10^7$ of bacteria load.

Methods of Analysis. Analysis was performed to determine antibacterial properties of the fabric following, as guidelines, the enumeration method of AATCC 100: Antibacterial Finishes. The fabric sample is placed in a polypropylene container with 100 mL of Letheem broth and shaken for 60 seconds. The bacteria count as then enumerated with Tempo filler reader. At each tested interval two side by side tested samples are cut out from the fabric and tested with duplicates. After each enumeration the fabric was tested for any odor intensity and for any changes between T=0 and the enumerated tested sample. Odor is evaluated on the following scale: 0=no odor; 1=very weak (odor threshold); 2=weak; 3=distinct; 4=strong; 5=very strong; and 6=intolerable. After each enumeration, high resolution image recording was taken for each sample so enumerated.

The fabric surfaces were also examined during the study for both the coated and non-coated fabrics by taking microscopic images of the coated and non-coated samples prior to washing, after one washing, and after 10 washings. A qualitative analysis of the microscopic images was performed to observe the % foreign matter coverage area on the observable fibers. The coated inoculated fibers displayed little or no foreign matter on their observable surfaces as compared to the non-coated inoculated fibers. The presence of silk does not contribute to increased bacteria adherence on the fabric surface, while any bacteria that may be deposited on the surface it can be removed through a standard home laundering cycle. As described herein, bacteria did not appear to adhere to the coated materials after washing.

Example 40. A Water Drop Study with Silk and Silicone Coated Fabrics

A study was performed to determine the effect of water wicking on fabrics coated with silk and silicone that have been treated with citric acid.

As shown herein, citric acid does not function as a wicking agent. However, with a 1:1 ratio of silk/silicone at 0.250, the water took a longer time to absorb than that observed with previously described water drop studies.

The parameters for a first study are set forth in Table 97 and 98. The results of this study are illustrated in FIGS. 215 and 216.

TABLE 97

| Experimental Parameters | Variables | |
|---|---|---|
| silk solution concentration | | |
| silk solution molecular weight | | |
| Wet pick up | at 50 setting on padder | |
| Temperature @ heat setting (C.) | 200 | |
| Curing time (min) | 3 | |
| silicon softener Ultratex SI | 0.22% | 0.02% |
| silicon softener Ultratex CSP | 0.50% | 0.05% |
| citric acid | 0.0250% | |

TABLE 98

| Sample Number | Description | Time to Absorb (sec) |
|---|---|---|
| 16062901 | 0.22% Ultratex SI | 30 |
| 16062902 | 0.5% Ultratex CSP | 30 |
| 16062905 | 0.22% Ultratex SI, 0.025% citric acid | 30 |
| 16062906 | 0.5% Ultratex CSP, 0.025% citric acid | 30 |
| 16062105 | 0.5% medium mw silk, 0.22 gr/liter Ultratex SI | 3 |
| 16062106 | 0.5% low mw silk, 0.5 gr/liter Ultatex CSP | 1 |
| 16062107 | 0.5% low mw silk, 2.2 gr/liter Ultratex SI, 0.025 gr/liter citric acid | 1 |
| 16062108 | 0.5% medium mw silk, 5 gr/liter Ultratex CSP, 0.025 gr/liter citric acid | 4 |
| 16051103 | no coating, 200 C., 3 min | 1 |
| 16070701 | 0.025% citric acid | 1 |

Example 41. Coating Cotton, Cashmere. and Cashmere/Silk Blends

Example 41a: A knitted and scoured cashmere panel (14"×20") is soaked for 15 minutes in a 0.25 wt % solution of liquid silk (5 L), then spun dry for 10 seconds. The panel is then soaked for 5 minutes in water (5 L) and spun dry for 10 seconds. The panel is then soaked again in water (5 L) for 5 minutes and spun dry for 10 seconds. The panel is dried at 60° C. for 30 minutes. Panels are tested for hand and pilling.

Example 41b: A knitted and scoured cashmere/silk blend panel (4"×4") is soaked for 15 minutes in a solution (500 mL) of silk (0.25 wt %) and glutaraldehyde-sodium bisulfite complex (0.1 wt %), then padded at 20 psi. The panel is then soaked for 5 minutes in water or alcohol solution (500 mL) and padded at 20 psi. The panel is then soaked again in water or alcohol solution (500 mL) for 5 minutes and spun dry for 10 seconds. The panel is dried at 60° C. for 5 minutes. Panels are tested for hand and water absorbency.

FIG. 217A illustrates a silk-coated cotton SEM image; scalebar represents 2 µm. FIG. 217B illustrates a silk-coated cotton SEM image; scalebar represents 10 µm. FIG. 218 illustrates manipulating water absorbency of liquid silk coated fabric. The time needed for a standard water drop to fully absorb into the fabric is recorded, and varies according to the silk treatment. FIG. 219 illustrates various process parameters for coating fabrics. FIG. 220 illustrates that liquid silk application significantly reduces pilling on cashmere; the pilling score of each cashmere panel, as measured according to ISO 12945-1: Score 5=No change; Score 4=Slight surface fuzzing and/or partially formed pills; Score 3=Moderate surface fuzzing and/or moderate pilling, pills of varying size and density partially covering the specimen surface; Score 2=Distinct surface fuzzing and/or severe pilling, pills of varying size and density covering a large proportion of the specimen; Score 1=Dense surface fuzzing and/or severe pilling, pills of varying size and density covering the whole of the specimen surface. Silk Formulation A: 0.05% M Silk; pH unadjusted, STI-18050801-T004. Silk Formulation B: 0.25% M Silk; pH 9.25, STI-18050801-T009. Silk Formulation C: 0.25% 3L1M Silk, pH unadjusted, STI-18050801-T005. FIG. 221A (control) and FIG. 221B (cashmere treated with silk) illustrate cashmere coating coverage by scanning electron microscopy (SEM); as liquid silk and cashmere bond naturally, SEM demonstrates that liquid silk smooths and refines cashmere fibers. FIG. 222A (microscopic image) and FIG. 222B (dye intensity chart) illustrate deposition of FITC labeled silk fragments preferentially on cashmere cuticles; cuticle edges are 15-20 microns apart, and exhibit more fluorescence than the cuticle faces. (20× objective; laser power: 12%; gain: 600; gamma: 0.45). FIG. 223 illustrate silk protein binding and smoothing the "scales" of wool to the core fiber, preventing the "Velcro-like" effect that is responsible for wool's shrinkage and inability to withstand washing; additional data shows wool+ liquid silk is water resistant, stable and shrink-resistant following washing while matching or improving pilling. FIG. 224 illustrates improved washability of wool by area dimensional change on wool tubes finished with liquid silk compared to untreated wool tubes. Liquid silk improves area dimensional change about twofold. FIG. 225A-225D illustrates SEM images of silk coated wool.

Example 42. Coating Synthetic Materials

Example 42a: Polyester Coating—Polyester fabric panels (13"×13") were coated with a 0.1 wt % liquid silk solution using a pad-dry-cure method. The liquid silk solution is comprised of 3 parts Liquid Silk Formulation A and 1 part Liquid Silk Formulation B. The pH is adjusted to the desired range using pH adjusters commonly used in the field. The panels are soaked for 3 seconds and passed through a padder, after which they are transferred to an oven and dried for 90 seconds at 130° C. The samples are allowed to rest overnight, after which they are tested for silk deposition, hand, and performance (moisture management, abrasion resistance, pilling resistance, stain release, odor release, SEM, fluorescence microscopy).

FIG. 226 illustrates the coating coverage of silk fragments on polyester as shown by scanning electron microscopy (SEM); SEM confirms that after application of liquid silk, coating coverage is similar or greater than other commercial coatings for polyester. FIG. 226 A illustrates polyester unfinished control sample, showing fibers with no coating. FIG. 226B illustrates polyester finished with silk, showing coated layers on the polyester fibers. FIG. 227 illustrates EDS Data on Polyester Related Experiments; polyester fabric was coated in 6% silk (FIG. 227C) and energy-dispersive X-ray spectroscopy (EDS) was used to determine chemical content (FIG. 227 A and FIG. 227B); EDS suggests regions between fibers (FIG. 227B) show nitrogen content due to silk depositions regions. FIG. 228 illustrates liquid silk coated polyester absorbency; the results indicate that the coated material exceeds commonly accepted industry criteria for absorbency, and outperformed commercial counterparts after 50 laundering cycles. FIG. 229 illustrates dry rate in polyester samples; in general liquid silk coated polyester dried faster than commercial control before laundering and after multiple laundering cycles; AATCC Test Method 201-1013 Heated Plate Method; higher values indicate faster dry rate (silk+mechanical denotes a second water pass and drying process). FIG. 230 illustrates vertical wicking and abrasion resistance in polyester samples. FIG. 230A: liquid silk coated polyester demonstrated improved wicking at 5 minutes vs. unfinished fabric after 3 laundering cycles. FIG. 230B: liquid silk improves abrasion resistance of polyester fabrics, and outperformed the commercial standard. FIG. 231 illustrates pilling resistance in polyester liquid silk coated fabric which outperforms the commercial standard. FIG. 232A and FIG. 232B illustrates silk-coated Nylon SEM images. FIG. 233 illustrates fluorescence microscopy images for silk-coated vs. control; FIG. 233A: FITC-Silk Coated Nylon; scale bars represent 107 µm. FIG. 233B: Uncoated Nylon Control; scale bars represent 53 µm. Nylon coated in FITC-Silk showed increased fluorescence due to the FITC-silk coating; 5% enhancement. FIG. 234 illustrates coating coverage on Nylon: scanning electron microscopy (SEM) confirms application of liquid silk. FIG. 234A: Nylon unfinished control. FIG. 234B: Nylon with silk finish—coated silk layers also adopt clear surface features. FIG. 235A illustrates absorbency performance of coated Nylon; liquid silk coated nylon exceeded commonly accepted industry criteria for absorbency, and outperformed commercial counterparts after 50 laundering cycles (AATCC Test Method 79-2013; smaller values indicate faster absorbency, silk+mechanical denotes a second water pass and drying process). FIG. 235B illustrates dry rate performance in coated nylon; liquid silk coated nylon dried faster than commercial control before laundering and after multiple laundering cycles (AATCC Test Method 201-1013 Heated Plate Method; higher values indicate faster dry rate; silk+mechanical denotes a second water pass and drying process). FIG. 236A illustrates vertical wicking performance; Nylon liquid silk coated nylon demonstrated improved wicking at 5 minutes vs. commercial finish after 3 laundering cycles (AATCC Test Method 197 (modified); higher values indicate better wicking; silk+mechanical denotes a second water pass and drying process). FIG. 236B illustrates abrasion resistance performance; Nylon liquid silk coated improves abrasion resistance of nylon; liquid silk coated nylon matched the commercial standard Abrasion Resistance—ASTM Standard D4966-12Eε1 (accelerated); testing ended when fabric first demonstrated abrasion or broke, whichever happened first; instead of wool, Trizact was used.

Example 42b: Odor release—Sour milk test (Odor Properties of Textiles Assessment from Pasteurized Cows' Milk). This test method follows IAC Biofouling of Textiles from Pasteurized Cow's Milk, and includes modifications. The general procedure involves souring the milk using citric acid, placing the milk solution on the fabric, and allowing it to sit open for 3 days. Afterwards, the samples were sent out for washing and drying. Following the washing and drying process, the samples were resealed in clean jars. The samples were stored at room temperature for 24 hours. Odor presence was assessed after 24 hours by opening the jars and wafting the samples for presence of odor. The strength of the odor was rated from 1-5, where little to no odor present was rated (1) and pungent odor present was rated (5).

FIG. 237 illustrates the Sour Milk Test Experimental Results; liquid silk coated fabrics reduced odor more than both finished and unfinished fabrics. FIG. 238A and FIG. 238B illustrates Sour Milk Test Experimental Results; liquid silk coated fabrics reduced odor more than both finished and unfinished fabrics. FIG. 239 illustrates biocompatibility of liquid silk coated fabrics (by the FDA standard test to show compatibility for contact with human skin); liquid silk coated fabrics demonstrated no reactivity; multiple commercial performance fabrics failed biocompatibility testing (0=No reactivity around or under specimen (passed); 1=Slight reactivity, some degenerated cell under test article (passed); 2=Mild reactivity, zone limited to area under the test article (passed); 3=Moderate reactivity, zone of lysis extending specimen size up to 1 cm (failed); 4=Severe, zone of lysis extending farther than 1 cm beyond specimen (failed)).

Example 43. Nebulizer Coating

Materials: Omron model NE-U22V vibrating mesh nebulizer; pipette 1 ml; glassware; tap water; silk low MW 6%; silk medium MW 6%; GAP-17120505-L007-02 Powervita.

Procedure: cut N=5 fabric samples to 12 cm×12 cm square; mark fabric samples with a 2 cm diameter circle to delimit the area of application and label with the abbreviation of the experiment Table 99; prepare solution per Table 99; fill nebulizer reservoir with prepare solution and turn on the nebulizer; allow the nebulizer to begin the production of water drops; place the fabric application area on top of the nebulizer nozzle and wait for 5 seconds; place the tested fabric samples in the oven at 300° C. for 1 minute; repeat procedure for all Table 99 experiments.

TABLE 99

| tested variable | silk concentration (%) | oven dry temperature (C.) |
|---|---|---|
| control no treatment | N/A | N/A |
| control water only | N/A | 300° C. |
| low mw | 0.50% | 300° C. |
| medium mw | 0.50% | 300° C. |
| low MW:medium MW 3:1 | 0.50% | 300° C. |

Water drop test: place the tested fabric on the drapability jig, turn on a video recording and drop a water sample with the dropper. Stop recording as the water is fully absorbed by the fabric.

TABLE 100

| tested variable | water drop absorption time (seconds) |
|---|---|
| control no treatment | 36 |
| control water only | 9 |
| low mw | 3 |
| medium mw | 4 |
| low MW:medium mw 3:1 | 3 |

FIGS. 240A-240D illustrate samples of fabric coated with silk formulations using a nebulizer applicator. FIG. 240A: low MW silk; FIG. 240B: medium MW silk; FIG. 240C: low MW to medium MW 3:1; FIG. 240D: control. FIGS. 240E-240H illustrate nebulizers and the silk solutions, and control, respectively.

All patents, patent applications, and published references cited herein are hereby incorporated by reference in their entirety. While the methods of the present disclosure have been described in connection with the specific embodiments thereof, it will be understood that it is capable of further modification. Further, this application is intended to cover any variations, uses, or adaptations of the methods of the present disclosure, including such departures from the present disclosure as come within known or customary practice in the art to which the methods of the present disclosure pertain.

The invention claimed is:

1. A silk fibroin coated article comprising a leather substrate and a coating comprising low molecular weight silk fibroin protein fragments and medium molecular weight silk fibroin protein fragments.

2. The silk fibroin coated article of claim 1, wherein the low molecular weight silk fibroin fragments have an average weight average molecular weight selected from between about 5 kDa to about 20 kDa.

3. The silk fibroin coated article of claim 2, wherein the low molecular weight silk fibroin fragments have a polydispersity from 1 to about 5.

4. The silk fibroin coated article of claim 1, wherein the medium molecular weight silk fibroin fragments have an average weight average molecular weight selected from between about 20 kDa to about 55 kDa.

5. The silk fibroin coated article of claim 4, wherein the medium molecular weight silk fibroin fragments have and a polydispersity from 1 to about 5.

6. The silk fibroin coated article of claim 1, wherein the leather substrate is natural leather or synthetic leather.

7. The silk fibroin coated article of claim 6, wherein the natural leather is selected from chrome-tanned leather, vegetable-tanned leather, aldehyde-tanned leather, brain-tanned leather, formaldehyde-tanned leather, Chamois leather, rose-tanned leather, synthetic-tanned leather, alum-tanned leather, patent leather, Vachetta leather, nubuck leather, rawhide leather, split leather, full-grain leather, top-grain leather, and corrected-grain leather.

8. The silk fibroin coated article of claim 6, wherein the synthetic leather is selected from poromeric imitation leathers, vinyl and polyamide felt fibers, polyurethane, polyvinyl chloride, polyethylene (PE), polypropylene (PP), vinyl acetate copolymer (EVA), polyamide, polyester, textile-polymer composite microfibers, corfan, koskin, leatherette, BIOTHANE®, BIRKIBUC®, BIRKO-FLOR®, CLARINO®, ECOLORICA®, KYDEX®, LORICA®, NAUGAHYDE®, REXINE®, VEGETAN®, and FABRIKOID®.

9. The silk fibroin coated article of claim 1, wherein the w/w ratio between low molecular weight silk fibroin protein fragments and medium molecular weight silk fibroin protein fragments is about 90:10, about 80:20, about 75:25, about 70:30, about 66:34, about 60:40, about 50:50, about 40:60, about 34:66, about 30:70, about 25:75, about 20:80, or about 10:90.

10. The silk fibroin coated article of claim 1, wherein the w/w ratio between low molecular weight silk fibroin protein fragments and medium molecular weight silk fibroin protein fragments is about 3:1.

11. The silk fibroin coated article of claim 1, wherein the coating further comprises a chemical agent.

12. The silk fibroin coated article of claim 11, wherein the chemical agent is selected from a silicone, an antimicrobial agent, an antifungal agent, a softener, a water repellant agent, an oil repellant agent, a dye, a flame retardant, and a pH adjusting agent.

13. The silk fibroin coated article of claim 11, wherein the chemical agent modifies one or more of a first property and second property of the silk fibroin coated article.

14. The silk fibroin coated article of claim 13, wherein the first property comprises one or more of an antimicrobial property, an antiodor property, a water repellant property, an oil repellant property, a flame retardant property, a coloring property, a stain repellant property, and a pH adjusting property.

15. The silk fibroin coated article of claim 1, wherein the leather exhibits a property selected from improved color retention property, improved mildew resistance, improved resistance to freeze-thaw cycle damage, improved resistance to abrasion, improved blocking of ultraviolet (UV) radiation, improved regulation of the body temperature of a wearer, improved tear resistance, improved elasticity, improved rebound dampening, improved anti-itch properties, improved insulation, improved wrinkle resistance, improved stain resistance, and improved stickiness.

* * * * *